(12) United States Patent
Zeng et al.

(10) Patent No.: US 10,357,475 B2
(45) Date of Patent: *Jul. 23, 2019

(54) IRE-1α INHIBITORS

(71) Applicant: FOSUN ORINOVE PHARMATECH, INC., Suzhou (CN)

(72) Inventors: Qingping Zeng, Thousand Oaks, CA (US); Andras Toro, Oxnard, CA (US); John Bruce Patterson, Ventura, CA (US); Warren Stanfield Wade, San Diego, CA (US); Zoltan Zubovics, Budapest (HU); Yun Yang, Tianjin (CN); Zhipeng Wu, Tianjin (CN)

(73) Assignee: Fosun Orinove PharmaTech, Inc., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,728

(22) Filed: Dec. 8, 2017

(65) Prior Publication Data

US 2018/0228765 A1    Aug. 16, 2018

Related U.S. Application Data

(60) Continuation of application No. 15/600,473, filed on May 19, 2017, now Pat. No. 9,867,803, which is a division of application No. 14/594,400, filed on Jan. 12, 2015, now Pat. No. 9,693,992, which is a division of application No. 13/639,734, filed as application No. PCT/US2011/031274 on Apr. 5, 2011, now Pat. No. 9,040,714.

(60) Provisional application No. 61/320,975, filed on Apr. 5, 2010.

(51) Int. Cl.
| | |
|---|---|
| C07D 311/16 | (2006.01) |
| C07D 405/10 | (2006.01) |
| C07D 417/04 | (2006.01) |
| A61K 31/366 | (2006.01) |
| A61K 31/343 | (2006.01) |
| A61K 31/352 | (2006.01) |
| A61K 31/37 | (2006.01) |
| A61K 31/381 | (2006.01) |
| A61K 31/4025 | (2006.01) |
| A61K 31/404 | (2006.01) |
| A61K 31/4045 | (2006.01) |
| A61K 31/415 | (2006.01) |
| A61K 31/4155 | (2006.01) |
| A61K 31/4172 | (2006.01) |
| A61K 31/4184 | (2006.01) |
| A61K 31/423 | (2006.01) |
| A61K 31/427 | (2006.01) |
| A61K 31/4433 | (2006.01) |
| A61K 31/4439 | (2006.01) |
| A61K 31/452 | (2006.01) |
| A61K 31/453 | (2006.01) |
| A61K 31/454 | (2006.01) |
| A61K 31/4545 | (2006.01) |
| A61K 31/496 | (2006.01) |
| A61K 31/5377 | (2006.01) |
| A61K 45/06 | (2006.01) |

(Continued)

(52) U.S. Cl.
CPC .......... *A61K 31/366* (2013.01); *A61K 31/343* (2013.01); *A61K 31/352* (2013.01); *A61K 31/37* (2013.01); *A61K 31/381* (2013.01); *A61K 31/404* (2013.01); *A61K 31/4025* (2013.01); *A61K 31/4045* (2013.01); *A61K 31/415* (2013.01); *A61K 31/4155* (2013.01); *A61K 31/4172* (2013.01); *A61K 31/4184* (2013.01); *A61K 31/423* (2013.01); *A61K 31/427* (2013.01); *A61K 31/4433* (2013.01); *A61K 31/4439* (2013.01); *A61K 31/452* (2013.01); *A61K 31/453* (2013.01); *A61K 31/454* (2013.01); *A61K 31/4545* (2013.01); *A61K 31/496* (2013.01); *A61K 31/5377* (2013.01); *A61K 45/06* (2013.01); *C07D 217/02* (2013.01); *C07D 217/08* (2013.01); *C07D 311/12* (2013.01); *C07D 311/16* (2013.01); *C07D 311/20* (2013.01); *C07D 311/22* (2013.01); *C07D 311/94* (2013.01); *C07D 401/04* (2013.01); *C07D 401/12* (2013.01); *C07D 405/04* (2013.01); *C07D 405/10* (2013.01); *C07D 409/04* (2013.01); *C07D 417/04* (2013.01); *Y02A 50/389* (2018.01); *Y02A 50/393* (2018.01)

(58) Field of Classification Search
CPC ... C07D 311/16; C07D 405/10; C07D 417/04
See application file for complete search history.

(56) References Cited

U.S. PATENT DOCUMENTS

| | | |
|---|---|---|
| 5,843,990 A | 12/1998 | Baker |
| 6,303,652 B1 | 10/2001 | Uckun et al. |

(Continued)

FOREIGN PATENT DOCUMENTS

| | | |
|---|---|---|
| JP | 2004506417 A | 3/2004 |
| JP | 2007-231124 | 9/2007 |

(Continued)

OTHER PUBLICATIONS

Alvey et al., A new synthetic access to furo[3,2-f]chromene analogues of an antimycobacterial. Bioorganic and Medicinal Chemistry, No. 16, vol. 17, pp. 8264-8272 (2008).

(Continued)

*Primary Examiner* — Laura L Stockton
(74) *Attorney, Agent, or Firm* — Panitch Schwarze Belisario & Nadel LLP

(57) ABSTRACT

Compounds which directly inhibit IRE-1α activity in vitro, prodrugs, and pharmaceutically acceptable salts thereof. Such compounds and prodrugs are useful for treating diseases associated with the unfolded protein response or with regulated IRE1-dependent decay (RIDD) and can be used as single agents or in combination therapies.

13 Claims, 8 Drawing Sheets

Specification includes a Sequence Listing.

(51) Int. Cl.
| | |
|---|---|
| C07D 311/20 | (2006.01) |
| C07D 311/94 | (2006.01) |
| C07D 401/04 | (2006.01) |
| C07D 405/04 | (2006.01) |
| C07D 409/04 | (2006.01) |
| C07D 217/02 | (2006.01) |
| C07D 217/08 | (2006.01) |
| C07D 311/12 | (2006.01) |
| C07D 311/22 | (2006.01) |
| C07D 401/12 | (2006.01) |

(56) References Cited

U.S. PATENT DOCUMENTS

| | | | |
|---|---|---|---|
| 6,420,391 | B1 | 7/2002 | Konishi et al. |
| 6,555,555 | B1 | 4/2003 | Konishi et al. |
| 6,559,333 | B1 | 5/2003 | Brunelle et al. |
| 9,040,714 | B2 | 5/2015 | Zeng et al. |
| 9,693,992 | B2 | 7/2017 | Zeng et al. |
| 9,867,803 | B2 | 1/2018 | Zeng et al. |

FOREIGN PATENT DOCUMENTS

| | | |
|---|---|---|
| WO | 1997/014671 | 4/1997 |
| WO | 1999/051587 A1 | 10/1999 |
| WO | 9954286 A2 | 10/1999 |
| WO | 200206316 A2 | 1/2002 |
| WO | 2005/121116 A1 | 12/2005 |
| WO | 2008/154484 A1 | 12/2008 |
| WO | 2011/127070 A2 | 10/2011 |

OTHER PUBLICATIONS

Averbeck D. et al., Photobiological activity in yeast of derivatives of psoralen substituted at the 3,4 and/or the 4', 5' reaction site. Photochemistry and Photobiology, vol. 30, No. 5, pp. 547-555 (1979).
Bastian et al., Recherches sur les derives nitres d'interet biologique. European Journal of Medicinal Chemistry, vol. 16, No. 6, pp. 563-568 (compounds 23 and 27) (1981).
Bender et al., Synthesis and Derivitization of 8-Acetylpsoralens. Acetyl Migrations during Claisen Rearrangement. Journal of Organic Chemistry, vol. 48, No. 16, pp. 2709-2719 (1983).
Berkaew et al., Aurocitrin and related polyketide metabolites from the wood-decay fungus *Hypocrea* sp. BCC 14122. Journal of Natural Products, vol. 71., No. 5, pp. 902-904 (2008).
Chemical Abstracts No. 1028268-82-7, indexed in the Registry file on STN CAS Online Jun. 15, 2008.
Chemical Abstracts No. 2067-86-9, indexed in the Registry file on STN CAS Online Nov. 16, 1984.
Chilin et al., Coumarin as attractive casein kinase 2 (CK2) inhibitor scaffold: an integrate approach to elucidate the putative binding motif and explain structure-activity relationships. Journal of Medicinal Chemistry, vol. 51, No. 4, pp. 752-759 (2008).
De Re et al., Basi di Schiff da 7-idrossi e 7-metossi-8-formilcromoni e flavoni e loro prodotti di riduzione. Annali di Chimica (Rome, Italy), vol. 50, pp. 1642-1650 (p. 1643, compounds Rec 7-0343 and Rec 7-0344) (1990).
Da Re et al., Journal of Medicinal Chemistry, 7(2), pp. 162-166 (1964).
English translation of Office Action dated Mar. 24, 2014 for JP 2013-503848 (6 pages) and Office Action in Japanese (6 pages).
Foster et al., Furano-compounds. Part IV. A Synthesis of alloBergapten. Journal of the Chemical Society, pp. 930-933 (1939).
Goddard et al., Total synthesis of bioactive frustulosin and frustulosinol. Tetrahedron Letters, vol. 47, No. 6, pp. 909-911 (2006).
International Search Report and Written Opinion dated Jan. 26, 2012, for PCT/US2011/031274.
Lee et al., Synthesis and anticancer activity of lavendustin A derivatives containing arylethenylchromone substituents. European Journal of Medicinal Chemistry, vol. 41, No. 8, pp. 991-996 (2006).
Lewis et al., Inhibition of rat hepatic aryl hydrocarbon hydroxylase activity by a series of 7-hydroxy coumarins: QSAR studies. Xenobiotica, vol. 24, No. 9, pp. 829-838 (1994).
McQuaid et al., C—H Bond Functionalization via Hydride Transfer: Synthesis of Dihydrobenzopyrans from ortho-Vinylaryl Akyl Ethers. Organic Letters, vol. 11, No. 14, pp. 2972-2975 (2009).
Moskvina et al., Synthesis of pyrano[2,3-f]chromen-2,8-diones and pyrano[3,2-g]chromen-2,8-diones based on o-hydroxyformyl(acyl)neoflavonoids. Chemistry of Natural Compounds, vol. 44, No. 1, pp. 16-23 (2008).
Naik et al., Formylation of Benzopyrones. II. Formylation of Hydroxycoumarins with N-Methylformanilide. Journal of Organic Chemistry, 22, pp. 1630-1633 (1957).
Pastrorini et al., Methylpyranochromones and Methylbenzodipyranones: New Potential Photoreagents Towards DNA. Gazzetta Chimica Italiana, vol. 119, No. 9, pp. 481-485 (1989).
Pennisi et al., The proteasome inhibitor, bortezomib suppresses primary myeloma and stimulates bone formation in myelomatous and nonmyelomatous bones in vivo. American Journal of Hematology, vol. 84, No. 1, pp. 6-14 (2009).
Raghotham et al., New Entry to 9-Acetyl/Formyl-Substituted 2H,8H-Pyrano[2,3-f]Chromen-2-ones through Baylis-Hillman Reaction. Synthetic Communications, 38(14), pp. 2459-2464 (2008).
Shokol et al., 7-Hydroxy-3-Phenoxy-8-Formylchromones, analogs of Natural Flavonoids. Chemistry of Natural Compounds, vol. 45, No. 3, pp. 350-355 (2009).
Shokol et al., Azaheterocyclic Derivatives of a-Pyrono[2,3-f]Isoflavones. Chemistry of Natural Compounds, vol. 42, No. 6, pp. 668-672 (2006).
Spath et al., Natural Coumarins. CA Document #29:39296 (1935).
Spath and Schmid, Die Konstitution des Sphondiins (LVI, Mitteil, uber naturliche Cumarine). Berichte der Duetshen Chemishen Gellschaft Abteilung) B: Abhandlungen, vol. 74B, pp. 595-598 (compound structures) (1941).
Taniguchi et al., Four coumarins from Heracleum yunngningense. Chemical & Pharmaceutical Bulletin, vol. 53, No. 6, pp. 701-704 (2005).
Troxler F., Praeparative Verwendung Von Mannich-Basen Von Hydroxy-Indolen ALS Alkylierungsmittel 4. Mitteilung Ueber Synthetische Indoi-Verbindungen. Helvetica Chimica ACTA, vol. 51, No. 6, pp. 1214-1224 (1968).
Zhang et al., Docking and 3D-QSAR studies of 7-hydroxycoumarin derivatives as CK2 inhibitors. European Journal of Medicinal Chemistry, vol. 45, No. 1, pp. 292-297 (2010).
Re et al., A series of coumarin derivatives with central stimulating activity. vol. 7, pp. 162-166 (1964), Journal of Medicinal Chemistry.
Extended European Search Report dated Oct. 15, 2018 in EP 1818955.8.
Office Action dated May 23, 2018 in JP Application 2017-157724.

Kidney

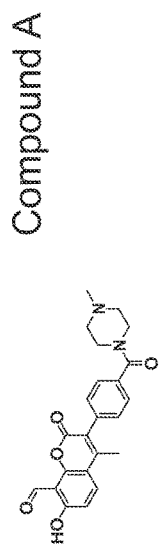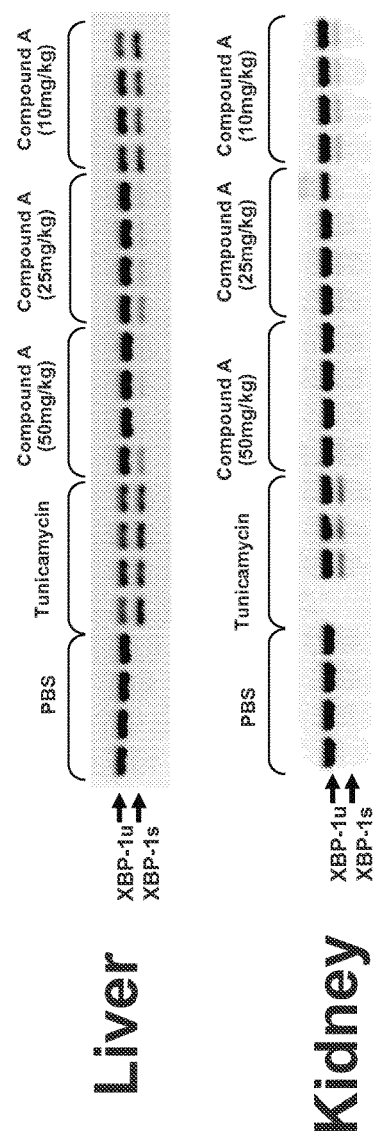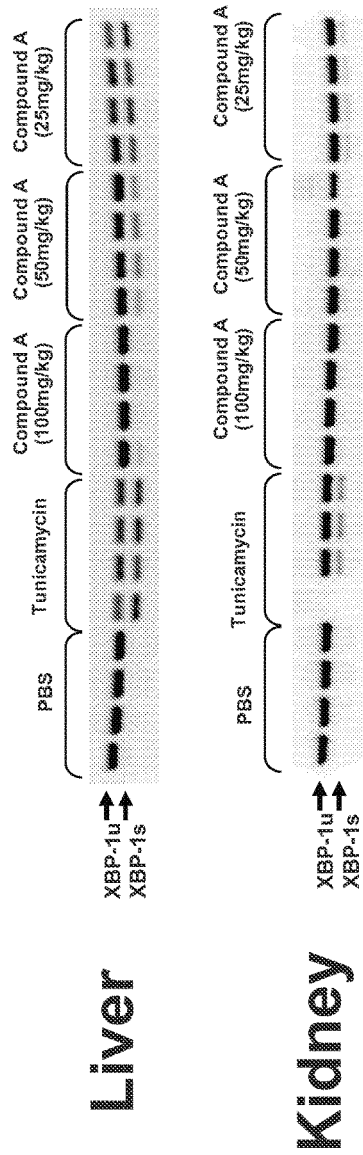
FIG. 4A
FIG. 4B

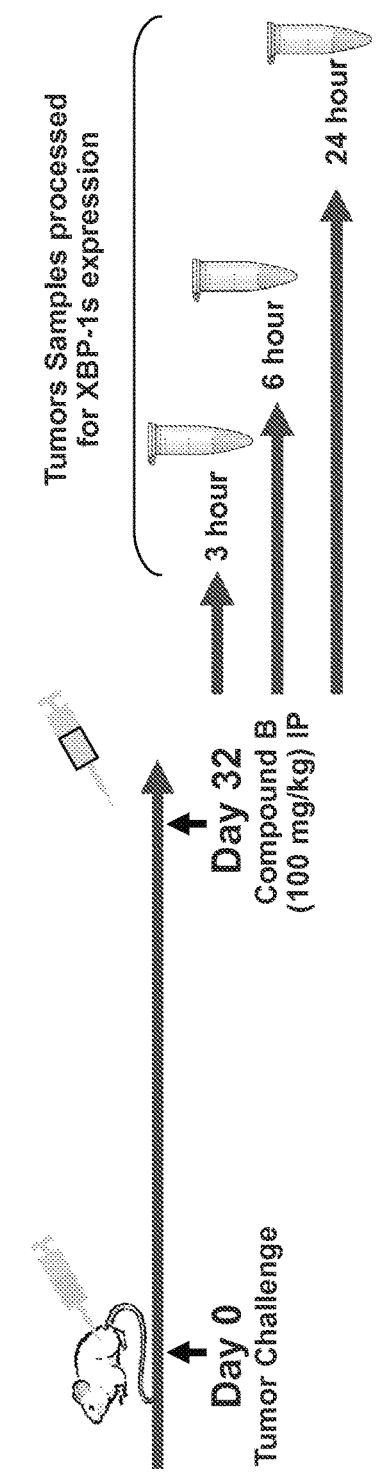
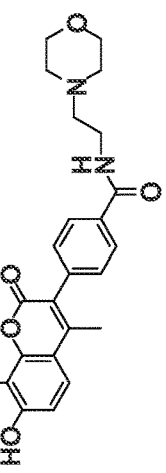
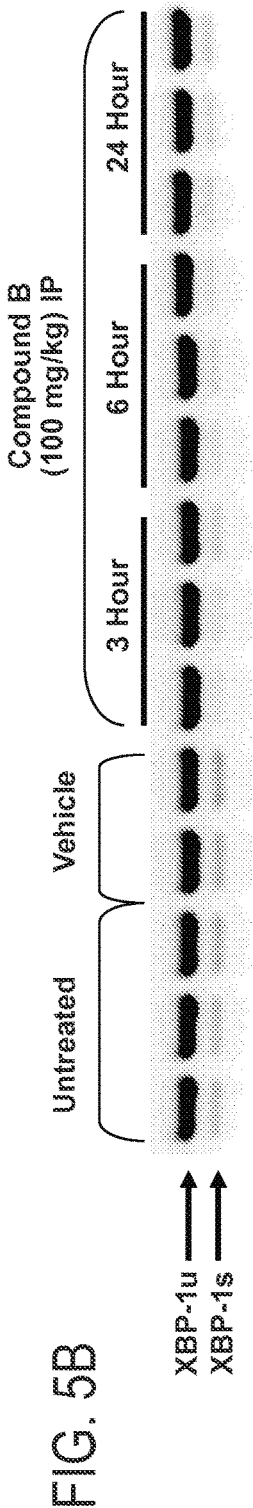
FIG. 5A
FIG. 5B

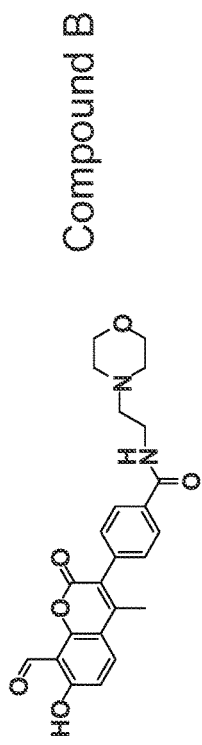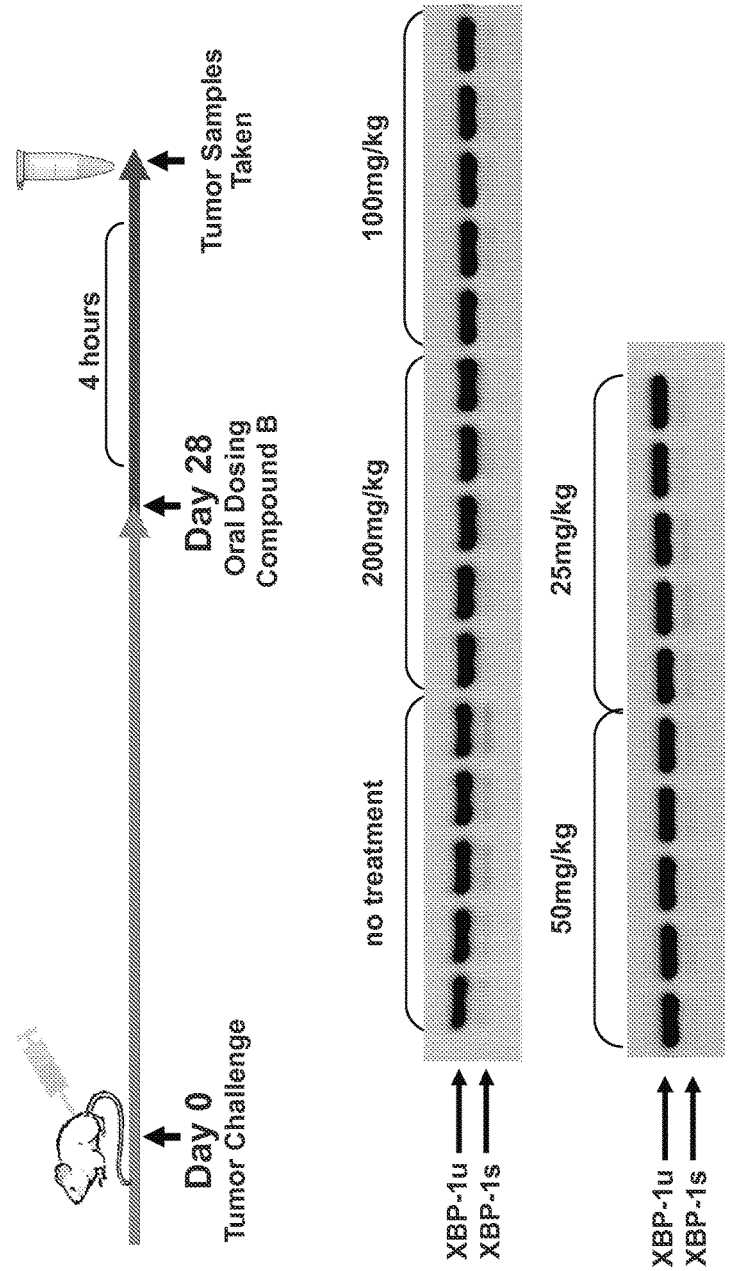
FIG. 6A
FIG. 6B

IRE-1α INHIBITORS

RELATED APPLICATIONS

This application is a Continuation of Ser. No. 15/600,473, filed on May 19, 2017, which is a Division of U.S. patent application Ser. No. 14/594,400, filed on Jan. 12, 2015, now U.S. Pat. No. 9,693,992, issued on Jul. 4, 2017, which is a Division of U.S. patent application Ser. No. 13/639,734, filed on Oct. 24, 2012, now U.S. Pat. No. 9,040,714, issued on May 26, 2015, which is a National Stage Entry of PCT/US2011/031274, filed on Apr. 5, 2011, which claims priority from U.S. Provisional Pat. Appln. No. 61/320,975, filed on Apr. 5, 2010. The entire contents of these applications are herein incorporated by reference.

Each patent, patent application, and reference cited in this disclosure is expressly incorporated herein by reference in its entirety.

SEQUENCE LISTING

This application contains a sequence listing having the filename 1959221-00007_ST25.txt, which is 1,473 bytes in size, and was created on Dec. 6, 2017. The entire content of this sequence listing is herein incorporated by reference.

FIELD OF THE INVENTION

The field of the invention includes IRE-1α inhibitors and their therapeutic uses.

BACKGROUND

Protein folding stress in the endoplasmic reticulum of a cell initiates a signal transduction cascade termed the unfolded protein response or UPR. A key enzyme, inositol requiring enzyme 1 (IRE-1α), relieves protein folding stress by enhancing molecular chaperone activity and therefore protects cells from stress induced apoptosis. Inhibitors of IRE-1α are useful for treating at least B cell autoimmune diseases, certain cancers, and some viral infections.

BRIEF DESCRIPTION OF THE DRAWINGS

FIG. 4A shows results of RT-PCR analysis performed using murine-specific XBP-1 primers from total RNA harvested from specified organs after intravenous treatment with an IRE-1α inhibitor (Example 44).

FIG. 4B shows results of RT-PCR analysis performed using murine-specific XBP-1 primers from total RNA harvested from specified organs after oral treatment with an IRE-1α inhibitor (Example 44).

FIG. 5A shows a time course of experiment described in Example 45.

FIG. 5B shows results of RT-PCR amplification of XBP-1 using human specific primers.

FIG. 6A shows a time course of experiment described in Example 46.

FIG. 6B shows results of RT-PCR amplification of XBP-1 using human specific primers.

DETAILED DESCRIPTION

Figure 1:
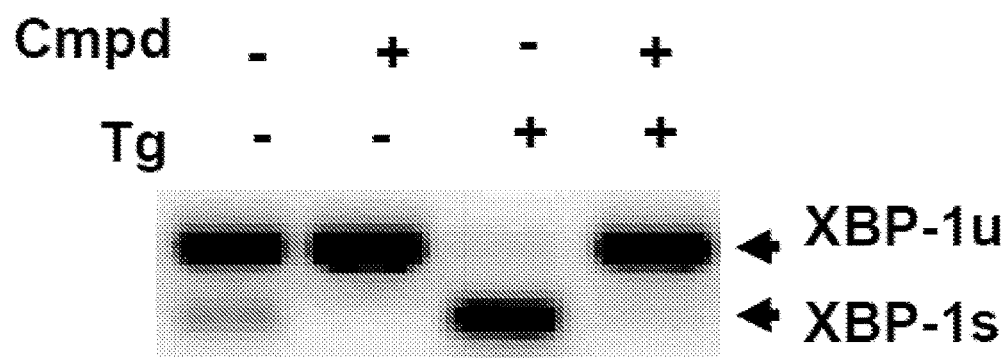
FIG. 1 shows inhibition of endogenous XBP-1 splicing in RPMI 8226 cells using 10 μM IRE-1α endoribonuclease inhibitor (Cmpd) and Thapsigargin (Tg) induced XBP-1s. PCR amplification products were run on a 4% agarose gel and stained with ethidium bromide. The inverse image is shown.

This specification describes IRE-1α inhibitor compounds and prodrugs and pharmaceutically acceptable salts thereof; purified preparations IRE-1α inhibitor compounds and prodrugs and pharmaceutically acceptable salts thereof; pharmaceutical compositions comprising IRE-1α inhibitor compounds and prodrugs and pharmaceutically acceptable salts thereof; and methods of using IRE-1α inhibitor compounds, prodrugs, and pharmaceutically acceptable salts thereof therapeutically to treat disorders associated with the unfolded protein response. Patients who can be treated include those with B cell autoimmune diseases, certain cancers, and some viral infections. In other embodiments IRE-1α inhibitor compounds, prodrugs, or pharmaceutically acceptable salts thereof can be administered to treat disorders associated with regulated IRE1-dependent decay (RIDD). Other embodiments are intermediates of IRE-1α inhibitor compounds and methods of synthesizing IRE-1α inhibitor compounds as set forth in the specific Examples, below.

DEFINITIONS

"Halogen" includes fluorine, chlorine, bromine, and iodine.

Unless otherwise specified, the term "alkyl" as used herein means a saturated monovalent hydrocarbon radical having 1, 2, 3, 4, 5, or 6 carbon atoms ("C1-C6 alkyl") and can be linear, branched, or a combination thereof "C1-C6 alkyl" includes C1-C5 alkyl, C1-C4 alkyl, and C1-C3 alkyl. Examples of C1-C6 alkyls include methyl, ethyl, propyl, isopropyl, sec-butyl, tert-butyl, n-butyl, 2-butyl, pentyl, and hexyl.

"Alkoxy" as used herein means —O-alkyl groups, where "alkyl" is as defined above, and can be linear, branched, or a combination thereof. Examples of C1-C6 alkoxys include, for example, methoxy, ethoxy, propoxy, 2-propoxy, butoxy, sec-butoxy, and tert-butoxy.

The term "perfluoroalkyl" means an alkyl group as defined above in which all of the hydrogen atoms are replaced by fluorine atoms. The term "perfluoroalkoxy" means an alkoxy group in which the alkyl moiety is a perfluoroalkyl group as defined above.

The term "hydroxylalkyl" as used herein means an alkyl group as defined above which is substituted with a hydroxyl group.

The term "alkoxylalkyl" means radicals of the formula $C_aH_{2a+1}$—O—$(CH_2)_b$—, in which a and b independently are 1, 2, 3, 4, 5, or 6.

A "cycloalkyl" is a saturated or partially saturated 3- to 14-membered (i.e., a 3-, 4-, 5-, 6, 7-, 8-, 9-, 10-, 11-, 12-, 13-, or 14-membered) monocyclic or polycyclic ring, such as a 5-, 6-, or 7-membered monocyclic ring or a 10-membered bicyclic ring, in which all of the ring members are carbon atoms. Examples of cycloalkyls include cyclobutyl, cyclopentyl, cyclohexyl, cycloheptyl, and cyclooctyl.

"Aryl," when used alone or as part of another term, means a carbocyclic aromatic ring containing 5 to 14 members (e.g., 5, 6, 7, 8, 9, 10, 11, 12, 13, or 14 members) and can be monocyclic or polycyclic. Examples of aryls include phenyl, naphthyl, anthryl, and phenanthryl.

A "heterocycle," "heterocyclic group," and "heterocyclic ring" is a saturated or a partially saturated 4- to 14-membered (i.e., 4-, 5-, 6-, 7-, 8-, 9-, 10-, 11-, 12-, 13-, or 14-membered) monocyclic or polycyclic (fused) ring, such as a 5-, 6-, or 7-membered monocyclic ring or a 10-membered bicyclic ring which has 1, 2, 3, or 4 heteroatoms selected from nitrogen (N), oxygen (O), and sulfur (S). Any of the nitrogen and sulfur heteroatoms optionally can be oxidized, and any nitrogen heteroatom optionally can be quaternized. A heterocyclic ring can be attached at any suitable heteroatom or carbon atom. Examples of heterocycles include azepinyl, furyl, thienyl, pyrrolyl, pyrazolyl, imidazolyl, pyridyl, pyrazinyl, pyrimidinyl, pyridazinyl, triazolyl, isobenzofuranyl, furazanyl, indolyl, quinolinyl, oxazolyl, imidazolinyl, isoxazolyl, quinolyl, naphthyridinyl, phenoxazinyl, phenanthridinyl, chromenyl, triazinyl, purinyl, benzothienyl, benzimidazolyl, benzopyranyl, benzothiazolyl, benzoazolyl, benzo[b]thienyl, naphtho[2,3-b]-thienyl, isothiazolyl, thiazolyl, isothiazolyl, isoquinolinyl, thiadiazolyl, oxadiazolyl, tetrahydroquinolinyl, indolizinyl, isoindolyl, indazolyl, isoquinolyl, phthalazinyl, tetrahydroquinolinyl, and cinnolinyl.

A "heteroaryl" is a saturated 4- to 14-membered (i.e., 4-, 5-, 6-, 7-, 8-, 9-, 10-, 11-, 12-, 13-, or 14-membered) monocyclic or polycyclic (fused) ring, such as a 5-, 6-, or 7-membered monocyclic ring or a 10-membered bicyclic ring which has 1, 2, 3, or 4 heteroatoms selected from nitrogen (N), oxygen (O), and sulfur (S). Any of the nitrogen and sulfur heteroatoms optionally can be oxidized, and any nitrogen heteroatom optionally can be quaternized. A heteroaryl can be attached at any suitable heteroatom or carbon atom. Examples of heteroaryls include pyridyl, imidazolyl, pyrrolyl, thienyl, furyl, pyranyl, pyrimidinyl, pyridazinyl, indolyl, quinolyl, naphthyridinyl, and isoxazolyl.

IRE-1α Inhibitor Compounds

IRE-1α inhibitor compounds directly inhibit IRE-1α. The compounds are understood to act through inhibition of the RNAse activity of the enzyme. In some embodiments IRE-1α inhibitor compounds form a complex with IRE-1α. In particular embodiments this activity is detected as cleavage of a human mini-XBP-1 mRNA stem-loop substrate 5'-CAGUCCGCAGGACUG-3' (SEQ ID NO:1) by IRE-1α in vitro by 10 to 100%. Other substrates also can be used to detect cleavage. See US 2007/0105123.

IRE-1α inhibitor compounds can meet either or both of the following criteria:

a. Some compounds inhibit IRE-1α in the in vitro assay with an $IC_{50}$ of approximately 0.0005-20 μM. Some of these compounds have an $IC_{50}$ in this assay of approximately 1-20 μM. Others have an $IC_{50}$ in this assay of approximately 0.1-1 μM. Still others have an $IC_{50}$ of approximately 0.0005-0.1 μM.

b. Some compounds inhibit IRE-1α in an in vivo XBP-1 splicing assay (e.g., in myeloma cells) with an $EC_{50}$ in the range of approximately 0.05-80 μM. Some of these compounds have an $EC0_{50}$ in this assay of approximately 10-80 μM. Others have an $EC0_{50}$ in this assay of approximately 1-10 μM. Still others have an $EC0_{50}$ in this assay of approximately 0.05-1 μM.

Compounds fall into one or more of the structural formulae described below. Non-limiting examples of compounds falling within the scope of these structural formulae are provided in Tables 1 and 2 and in the Examples.

Some embodiments specifically include and some embodiments only include compounds which have structural formula (A):

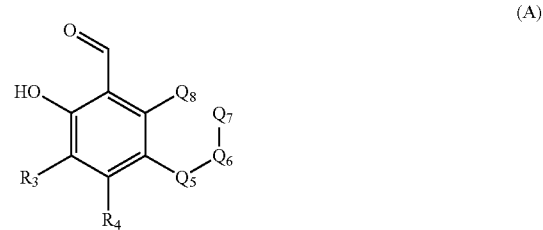

(A)

wherein:

R3 and R4 independently are hydrogen; halogen; hydroxyl; optionally substituted alkyl; or optionally substituted alkoxyl; or optionally substituted alkylamino. Optional substituents for the alkyl or for the alkoxyl and alkylamino are (1) a C1-C6 hydrocarbon chain containing an N or O atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl;

Q5, Q6, Q7 and Q8 (used throughout this specification interchangeably with $Q_5$, $Q_6$, $Q_7$ and $Q_8$), together with the benzene ring to which they are attached, form a benzofused ring. In some embodiments, Q7 is a bond which connects Q6 and Q8. The benzofused ring may or may not be fully aromatic.

Q5 is CR5, CR5R5', N, NR5, NC=OR5, O, S, or C=O;
Q6 is CR6, CR6R6', N, NR6, NC=OR6, O, S, or C=O;
Q7 is CR7, CR7R7', N, NR7, NC=OR7, O, S, C=O, or a bond; and
Q8 is CR8, CR8R8', N, NR8, NC=OR8, O, S, C=O,
PROVIDED THAT: at least one of Q5, Q6, Q7 (when not a bond), and Q8 must be a heteroatom selected from N, S, and O and Q5, Q6, Q7, and Q8 do not form O—O, O—N, O—S, or O=C—C=O bonds.

R5, R5', R6, R6', R7, R7', R8, and R8' are independently hydrogen; R21;

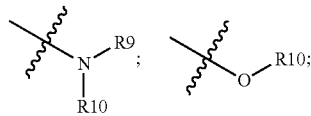

alkenyl, alkynyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

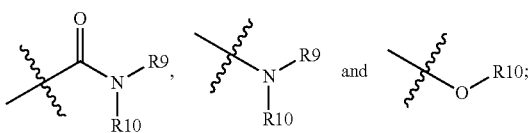

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

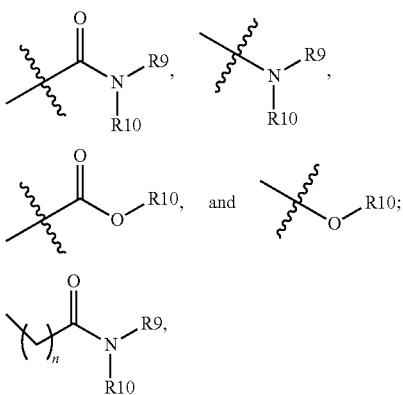

wherein n is 0, 1, or 2;

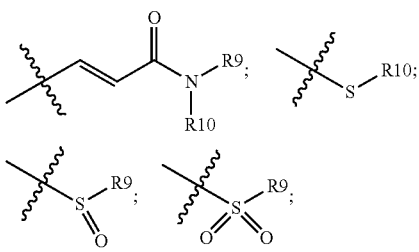

or R5 and R6, together with the carbon atoms to which they are attached, form a 5-membered cycloalkyl, PROVIDED THAT:
1. R5, R5', R6, R6', R7, R7', R8, and R8' are not simultaneously hydrogen;
2. when R5, R5', R6, R6', R7, R7', R8, and R8' are independently

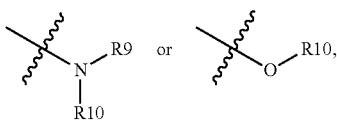

none of Q5, Q6, Q7, and Q8 is N, O, or S; and
3. when R5, R5', R6, R6', R7, R7', R8, and R8' are independently a 5- or 6-membered heteroaryl substituted with 1, 2, or 3 substituents independently selected from

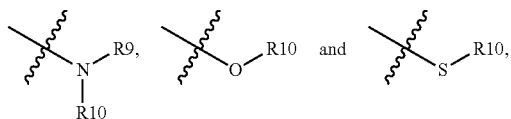

then the

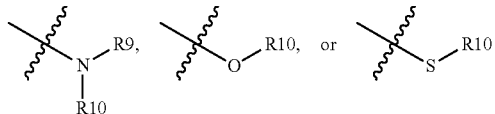

is linked to a carbon atom of the 5- or 6-membered heteroaryl;

R9 and R10 are independently hydrogen; alkyl; alkoxylalkyl; perfluoroalkoxylalkyl; aryl, optionally substituted with 1, 2, or 3 substituents independently selected from R21; a 5- or 6-membered heterocycle, optionally substituted with 1, 2, or 3 substituents independently selected from R21; a 5- or 6-membered heteroaryl, optionally substituted with 1, 2, or 3 substituents independently selected from R21; or

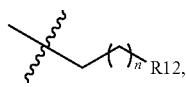

wherein n is 0, 1, 2, or 3; or
R9 and R10, together with the nitrogen atom to which they are attached, form a heterocycle containing 1, 2, 3, or 4 heteroatoms selected from N, O, and S, optionally substituted with 1, 2, or 3 substituents selected independently from R11;
R11 is hydrogen; alkyl; aryl; heteroaryl containing 1 or 2 heteroatoms selected from N, O, and S; arylalkyl; heteroarylalkyl in which the heteroaryl contains 1 or 2 heteroatoms selected from N, O, and S;

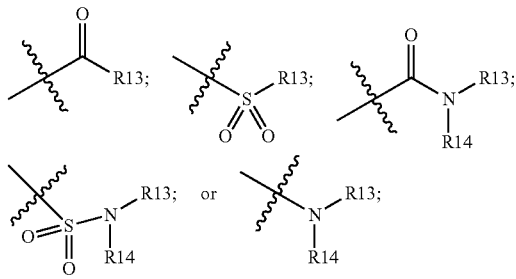

R12 is amino; alkoxy; aryl, optionally substituted with 1, 2, or 3 substituents selected independently from R11; a 5- or 6-membered heterocycle having 1, 2, or 3 heteroatoms selected from N, O, and S and optionally substituted with 1, 2, or 3 substituents selected independently from R11; or a 5- or 6-membered heteroaryl having 1, 2, or 3 heteroatoms selected from N, O, and S and optionally substituted with 1, 2, or 3 substituents selected independently from R11;
R13 is alkyl; alkoxylalkyl; perfluoroalkoxylalkyl; aryl, optionally substituted with 1, 2, or 3 substituents independently selected from R21; a 5- or 6-membered heterocycle, optionally substituted with 1, 2, or 3 substituents independently selected from R21; a 5- or 6-membered heteroaryl, optionally substituted with 1, 2, or 3 substituents independently selected from R21; or

wherein n is 0, 1, 2, or 3; and R14 is hydrogen or R13; or

R13 and R14, together with the nitrogen to which they are attached, form a heterocycle containing 1, 2, or 3 heteroatoms selected independently from N, O, and S, optionally substituted with 1, 2, or 3 substituents selected independently from R16;

R15 is amino; alkoxy; aryl, optionally substituted with 1, 2, or 3 substituents selected independently from R21; a 5- or 6-membered heterocycle having 1, 2, or 3 heteroatoms selected from N, O, and S and optionally substituted with 1, 2, or 3 substituents selected from R21; or a 5- or 6-membered heteroaryl having 1, 2, or 3 heteroatoms selected from N, O, and S and optionally substituted with 1, 2, or 3 substituents selected from R21;

R16 is hydrogen; alkyl; aryl; heteroaryl containing 1 or 2 heteroatoms selected from N, O, and S; arylalkyl; heteroarylalkyl in which the heteroaryl contains 1 or 2 heteroatoms selected from N, O, and S;

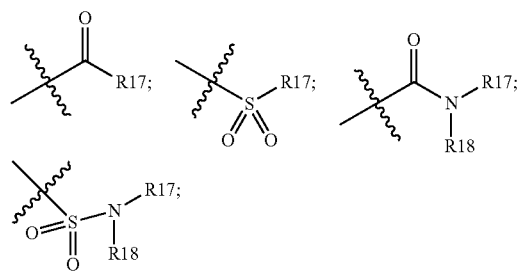

amino; or

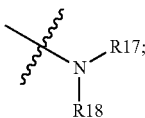

R17 is alkyl; alkoxylalkyl; perfluoroalkoxylalkyl; aryl, optionally substituted with 1, 2, or 3 substituents independently selected from R21; a 5- or 6-membered heterocycle, optionally substituted with 1, 2, or 3 substituents independently selected from R21; a 5- or 6-membered heteroaryl, optionally substituted with 1, 2, or 3 substituents independently selected from R21; or

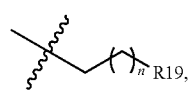

wherein n is 0, 1, 2, or 3; and R18 is hydrogen or R17; or

R17 and R18, together with the nitrogen to which they are attached, form a heterocycle containing 1, 2, 3, or 4 heteroatoms selected independently from N, O, and S, optionally substituted with 1, 2, or 3 substituents selected independently from R20;

R19 is alkoxy; aryl, optionally substituted with 1, 2, or 3 substituents selected independently from R21; a 5- or 6-membered heterocycle, optionally substituted with 1, 2, or 3 substituents independently selected from R21; or a 5- or 6-membered heteroaryl, optionally substituted with 1, 2, or 3 substituents independently selected from R21;

R20 is a 5- or 6-membered heterocycle having 1 or 2 heteroatoms selected from N, O, and S and optionally substituted with 1, 2, or 3 substituents selected independently from R21; a 5- or 6-membered heteroaryl, optionally substituted with 1, 2, or 3 substituents selected independently from R21; or R21; and R21 is halogen, perfluoroalkyl, perfluoroalkoxy, —CN, —CONH$_2$, —CON(CH$_3$)$_2$, alkyl, alkoxy, hydroxylalkyl, or alkoxylalkyl, with the exception of the compounds excluded from structural formulae (A-1), (A-2), (A-3), (A-4), (A-5), (A-6), and (A-7), below.

Non-limiting examples of

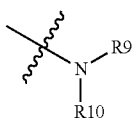

include the following, in which "X" is halogen, —CN, —CONH$_2$, —CON(CH$_3$)$_2$, C1-C4 alkyl, C1-C4 alkoxy, C1-C4 hydroxylalkyl, or C1-C4 alkoxylalkyl:

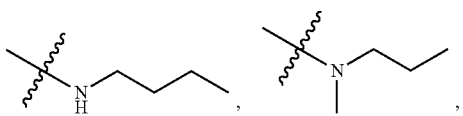

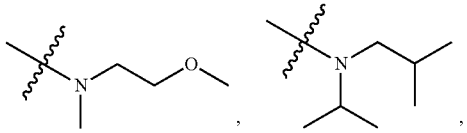

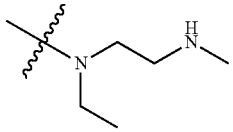

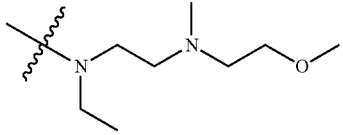

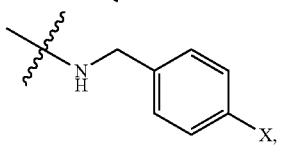

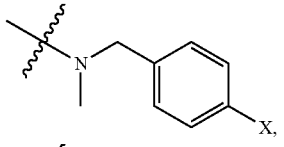

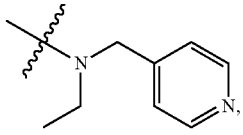

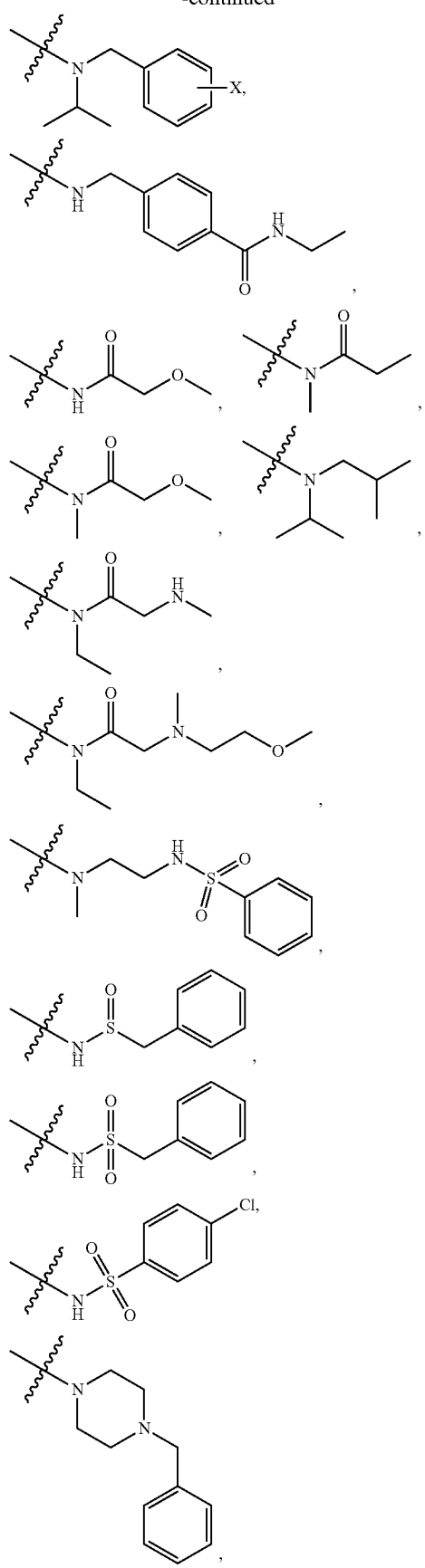
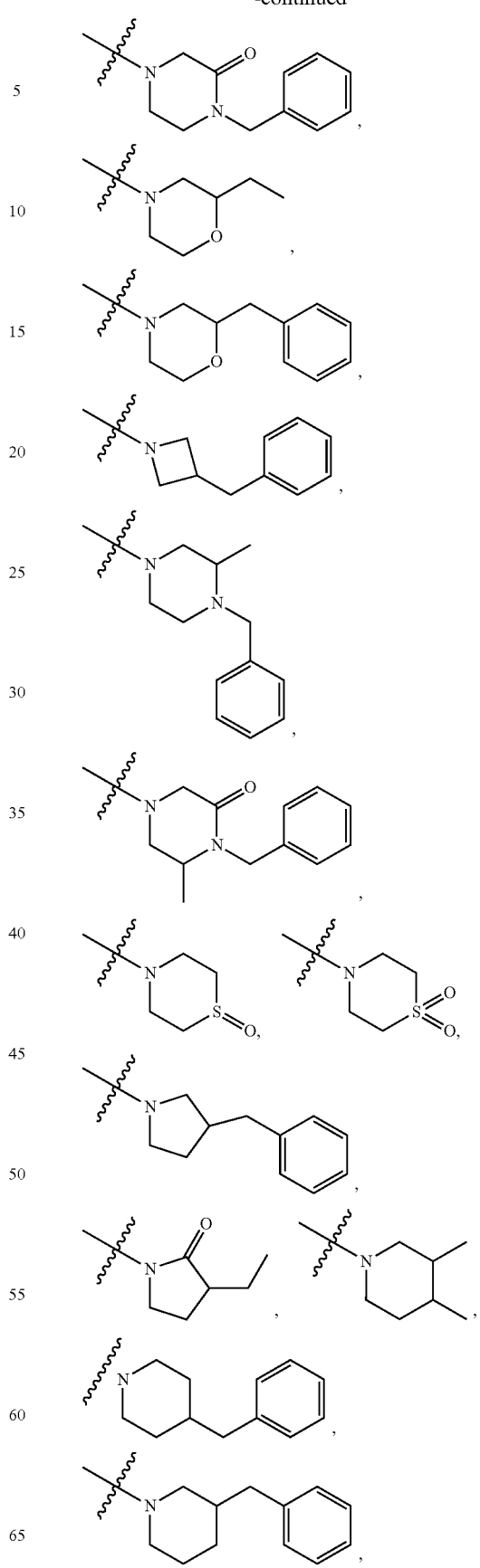

-continued

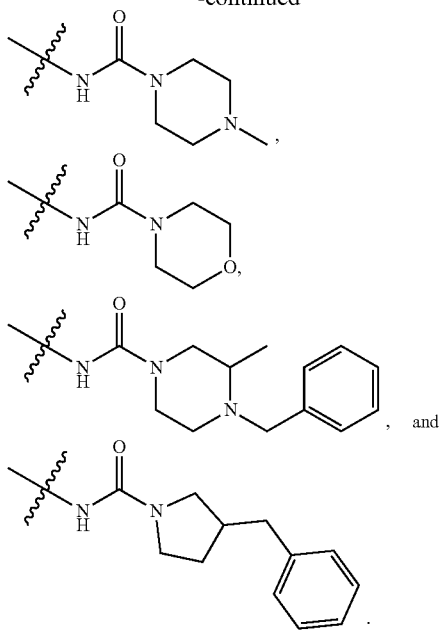

Some embodiments specifically include and some embodiments only include compounds which have structural formula (A-1):

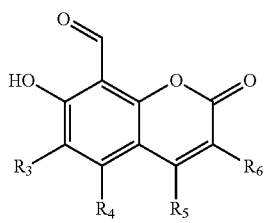

(A-1)

wherein R3, R4, R5, and R6 are as defined in structural formula (A), PROVIDED THAT if R3 and R4 are both hydrogen and R5 is methyl, then R6 cannot be ethyl or unsubstituted phenyl. In other embodiments, such compounds are specifically excluded from structural formula (A).

Structural formula (A-1a). Some embodiments specifically include and some embodiments only include compounds of structural formula (A-1) in which R5 is hydrogen; halogen; —CN; optionally substituted alkyl; or an optionally substituted alkoxyl. Optional substituents for the alkyl and for the alkoxyl are (1) a C1-C6 hydrocarbon chain containing an N or O atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-1).

Structural formula (A-1b). Some embodiments specifically include and some embodiments only include compounds of structural formula (A-1) in which R6 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-1).

Structural formula (A-1c). Some embodiments specifically include and some embodiments only include compounds of structural formula (A-1) in which R6 is alkenyl, alkyne, phenyl, or a 5- or 6-membered heteroaryl, each optionally substituted with 1, 2, or 3 substituents independently selected from the group consisting of

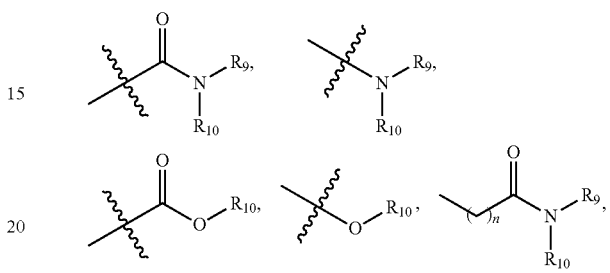

wherein n is 0, 1, or 2;

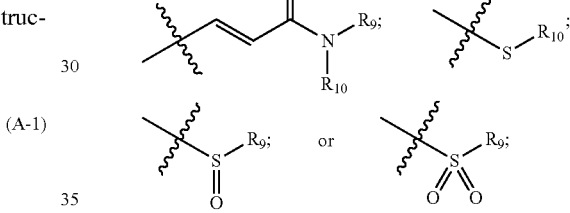

and

R9 and R10 are as defined in connection with structural formula (A). In other embodiments, such compounds are specifically excluded from structural formulae (A) and/or (A-1).

Structural formula (A-id). Some embodiments specifically include and some embodiments only include compounds of structural formula (A-1) in which R4 is hydrogen, alkoxyl, or hydroxyl. In other embodiments, such compounds are specifically excluded from structural formulae (A) and/or (A-1).

Structural formula (A-1e). Some embodiments specifically include and some embodiments only include compounds of structural formula (A-1) in which
  a. R4 is hydrogen, alkoxyl, or hydroxyl, and
  b. R5 is hydrogen, alkyl, alkoxyl, alkylamino, CF$_3$, or, together with R6 and the carbon atoms to which they are attached, forms a five-membered cycloalkyl.

In other embodiments, such compounds are specifically excluded from structural formulae (A) and/or (A-1).

Structural formula (A-1f). Some embodiments specifically include and some embodiments only include compounds of structural formula (A-1) in which
  a. R4 is hydrogen, alkoxyl, or hydroxyl and
  b. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

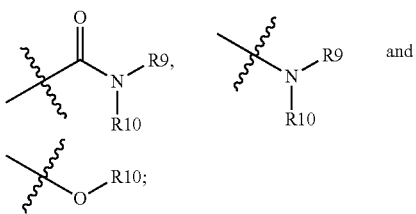

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

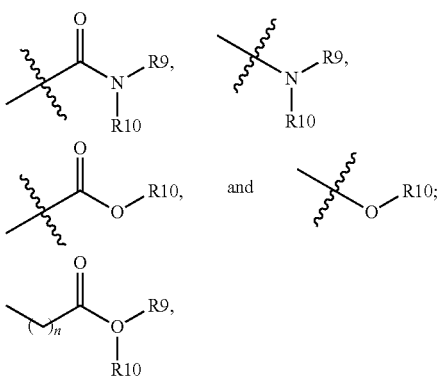

wherein n is 0, 1, or 2;

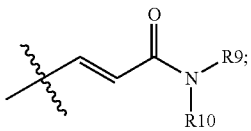

or R5 and R6, together with the carbon atoms to which they are attached, form a 5-membered cycloalkyl.

In other embodiments, such compounds are specifically excluded from structural formulae (A) and/or (A-1).

Structural formula (A-1g). Some embodiments specifically include and some embodiments only include compounds of structural formula (A-1) in which R5 is hydrogen, alkyl, alkoxyl, alkylamino, CF$_3$, or, together with R6 and the carbon atoms to which they are attached, forms a five-membered cycloalkyl. In other embodiments, such compounds are specifically excluded from structural formulae (A) and/or (A-1).

Structural formula (A-1h). Some embodiments specifically include and some embodiments only include compounds include only compounds of structural formula (A-1) in which
  a. R5 is hydrogen, alkyl, alkoxyl, alkylamino, CF$_3$, or, together with R6 and the carbon atoms to which they are attached, forms a five-membered cycloalkyl and
  b. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

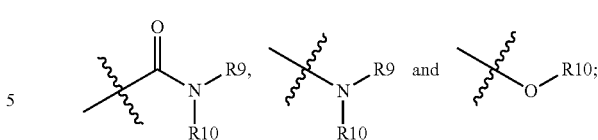

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

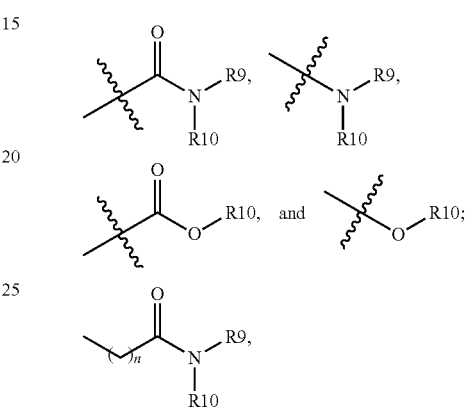

wherein n is 0, 1, or 2;

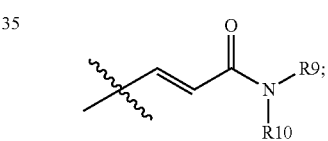

or R5 and R6, together with the carbon atoms to which they are attached, form a 5-membered cycloalkyl.

In other embodiments, such compounds are specifically excluded from structural formulae (A) and/or (A-1).

Structural formula (A-1i). Some embodiments specifically include and some embodiments only include compounds of structural formula (A-1) in which R6 is independently hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

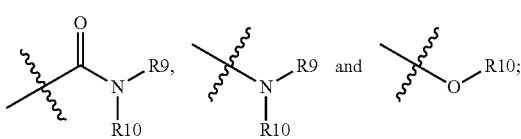

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

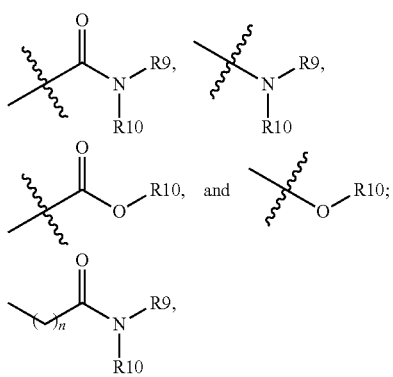

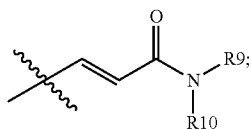

wherein n is 0, 1, or 2;

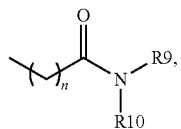

wherein n is 0, 1, or 2;

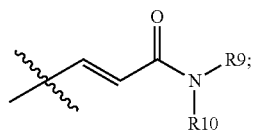

or R5 and R6, together with the carbon atoms to which they are attached, form a 5-membered cycloalkyl.

In other embodiments, such compounds are specifically excluded from structural formulae (A) and/or (A-1).

Structural formula (A-1j). Some embodiments specifically include and some embodiments only include compounds of structural formula (A-1) in which
  a. R4 is hydrogen, alkoxyl, or hydroxyl,
  b. R5 is hydrogen, alkyl, alkoxyl, alkylamino, CF$_3$, or, together with R6 and the carbon atoms to which they are attached, forms a five-membered cycloalkyl, and
  c. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

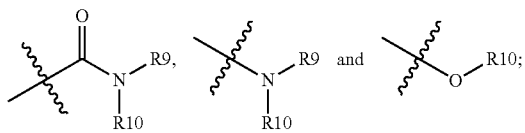

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

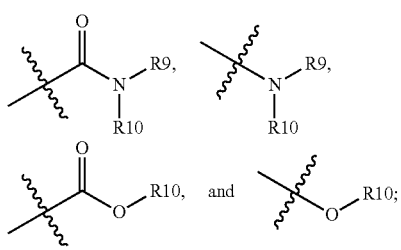

or R5 and R6, together with the carbon atoms to which they are attached, form a 5-membered cycloalkyl.

In other embodiments, such compounds are specifically excluded from structural formulae (A) and/or (A-1).

Structural formula (A-1k). Some embodiments specifically include and some embodiments only include compounds of structural formula (A-1) in which
  a. R4 is hydrogen, alkoxyl, or hydroxyl,
  b. R5 is hydrogen, alkyl, alkoxyl, alkylamino, CF$_3$, or, together with R6 and the carbon atoms to which they are attached, forms a five-membered cycloalkyl, and
  c. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

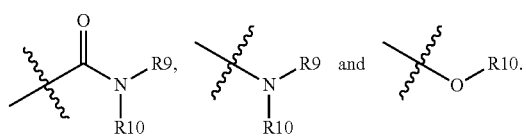

In other embodiments, such compounds are specifically excluded from structural formulae (A) and/or (A-1).

Structural formula (A-1l). Some embodiments specifically include and some embodiments only include compounds of structural formula (A-1) in which
  a. R4 is hydrogen, alkoxyl, or hydroxyl,
  b. R5 is hydrogen, alkyl, alkoxyl, alkylamino, CF$_3$, or, together with R6 and the carbon atoms to which they are attached, forms a five-membered cycloalkyl, and
  c. R6 is a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

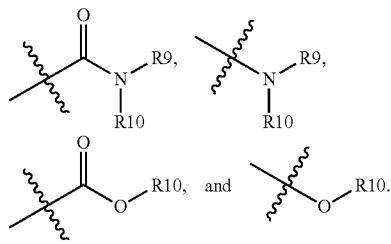

In other embodiments, such compounds are specifically excluded from structural formulae (A) and/or (A-1).

Structural formula (A-1m). Some embodiments specifically include and some embodiments only include compounds of structural formula (A-1) in which
a. R4 is hydrogen, alkoxyl, or hydroxyl,
b. R5 is hydrogen, alkyl, alkoxyl, alkylamino, CF$_3$, or, together with R6 and the carbon atoms to which they are attached, forms a five-membered cycloalkyl, and
c. R6 is

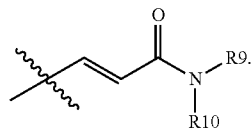

In other embodiments, such compounds are specifically excluded from structural formulae (A) and/or (A-1).

Structural formula (A-1n). Some embodiments specifically include and some embodiments only include compounds of structural formula (A-1) in which
a. R4 is hydrogen,
b. R5 is hydrogen, alkyl, alkoxyl, alkylamino, CF$_3$, or, together with R6 and the carbon atoms to which they are attached, forms a five-membered cycloalkyl, and
c. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

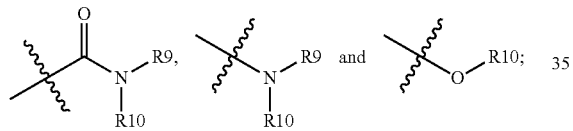

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

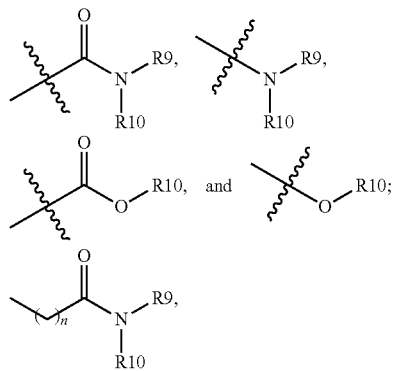

wherein n is 0, 1, or 2;

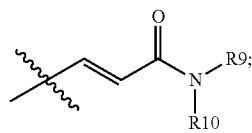

or R5 and R6, together with the carbon atoms to which they are attached, form a 5-membered cycloalkyl.

In other embodiments, such compounds are specifically excluded from structural formulae (A) and/or (A-1).

Structural formula (A-1o). Some embodiments specifically include and some embodiments only include compounds of structural formula (A-1) in which
a. R4 is alkoxyl,
b. R5 is hydrogen, alkyl, alkoxyl, alkylamino, CF$_3$, or, together with R6 and the carbon atoms to which they are attached, forms a five-membered cycloalkyl, and
c. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

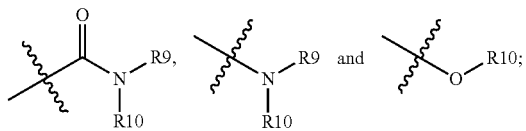

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

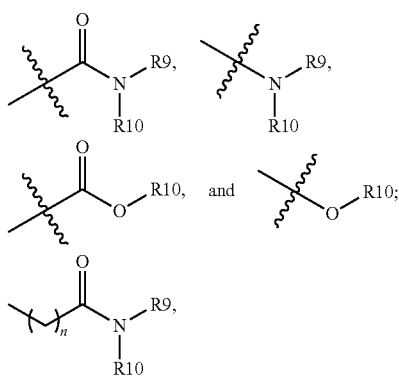

wherein n is 0, 1, or 2;

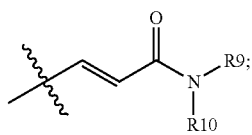

or R5 and R6, together with the carbon atoms to which they are attached, form a 5-membered cycloalkyl.

In other embodiments, such compounds are specifically excluded from structural formulae (A) and/or (A-1).

Structural formula (A-1p). Some embodiments specifically include and some embodiments only include compounds of structural formula (A-1) in which
a. R4 is hydroxyl,
b. R5 is hydrogen, alkyl, alkoxyl, alkylamino, CF$_3$, or, together with R6 and the carbon atoms to which they are attached, forms a five-membered cycloalkyl, and c. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

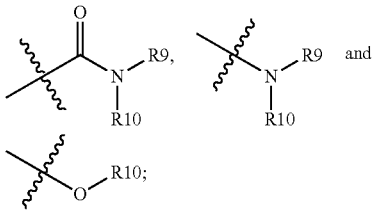

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

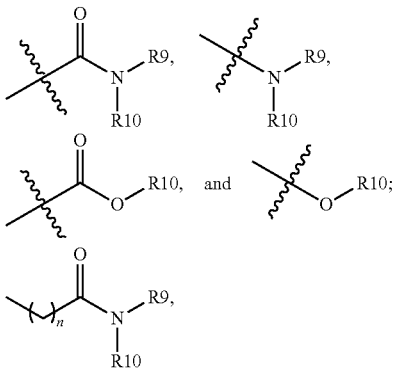

wherein n is 0, 1, or 2;

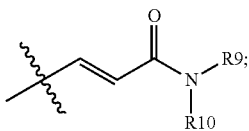

or R5 and R6, together with the carbon atoms to which they are attached, form a 5-membered cycloalkyl.

In other embodiments, such compounds are specifically excluded from structural formulae (A) and/or (A-1).

Structural formula (A-1q). Some embodiments specifically include and some embodiments only include compounds of structural formula (A-1) in which a. R4 is hydrogen, alkoxyl, or hydroxyl,
b. R5 is hydrogen, alkyl, alkoxyl, alkylamino, or CF$_3$, and
c. R6 is hydrogen; alkenyl, alkyl, or phenyl, each optionally substituted with 1, 2, or 3 substituents independently selected from the group consisting of halogen, —CN, alkyl, perfluoroalkyl, alkoxy, hydroxylalkyl, alkoxylalkyl, perfluoroalkoxy,

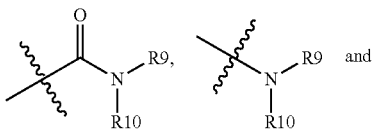

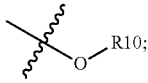

a 5- or 6-membered heteroaryl that is substituted with 1, 2, or 3 substituents independently selected from the group consisting of halogen, —CN, alkyl, perfluoroalkyl, alkoxy, hydroxylalkyl, alkoxylalkyl, perfluoroalkoxyl,

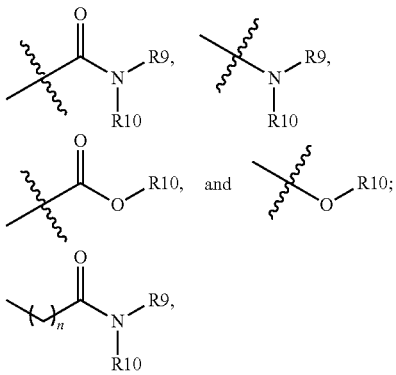

wherein n is 0, 1, or 2;

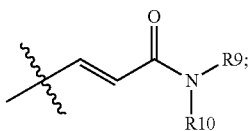

or R5 and R6, together with the carbon atoms to which they are attached, form a 5-membered cycloalkyl.

In other embodiments, such compounds are specifically excluded from structural formulae (A) and/or (A-1).

Some embodiments specifically include and some embodiments only include (1) compounds of structural formula (A-1a) and (2) compounds of any of structural formulae (A-1b), (A-1c), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1).

Some embodiments specifically include and some embodiments only include (1) compounds of structural formula (A-1a) and (2) compounds of up to 16 (e.g., 1, 2, 3, 4, 5, 6, 7, 8, 9, 10, 11, 12, 13, 14, 15, or 16) of structural formulae (A-1b), (A-1c), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1).

Some embodiments specifically include and some embodiments only include (1) compounds of structural formula (A-1a) and (2) compounds of any of structural formulae (A-1b), (A-1c), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1a) and (2) compounds of up to 16 (e.g., 1, 2, 3, 4, 5, 6, 7, 8, 9, 10, 11, 12, 13, 14, 15, or 16) of structural formulae (A-1b), (A-1c), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1b) and (2) compounds of any of structural formulae (A-1a), (A-1c), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1b) and (2) compounds of up to 16 (e.g., 1, 2, 3, 4, 5, 6, 7, 8, 9, 10, 11, 12, 13, 14, 15, or 16) of structural formulae (A-1a), (A-1c), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1c) and (2) compounds of any of structural formulae (A-1a), (A-1b), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1c) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1d), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1d) and (2) compounds of any of structural formulae (A-1a), (A-1b), (A-1c), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1d) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1e), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1e) and (2) compounds of any of structural formulae (A-1a), (A-1b), (A-1c), (A-1d), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1e) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1f), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1f) and (2) compounds of any of structural formulae (A-1a), (A-1b), (A-1c), (A-1d), (A-1e), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1f) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1g), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1g) and (2) compounds of any of structural formulae (A-1a), (A-1b), (A-1c), (A-1d), (A-1e), (A-1f), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1g) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1h), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1h) and (2) compounds of any of structural formulae (A-1a), (A-1b), (A-1c), (A-1d), (A-1e), (A-1f), (A-1g), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1h) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1i), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1i) and (2) compounds of any of structural formulae (A-1a), (A-1b), (A-1c), (A-1d), (A-1e), (A-1f), (A-1g), (A-1h), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1i) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1j), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1j) and (2) compounds of any of structural formulae (A-1a), (A-1b), (A-1c), (A-1d), (A-1e), (A-1f), (A-1g), (A-1h), (A-1i), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1j) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1k), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1k) and (2) compounds of any of structural formulae (A-1a), (A-1b), (A-1c), (A-1d), (A-1e), (A-1f), (A-1g), (A-1h), (A-1i), (A-1j), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1k) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1l), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1l) and (2) compounds of any of structural formulae (A-1a), (A-1b), (A-1c), (A-1d), (A-1e), (A-1f), (A-1g), (A-1h), (A-1i), (A-1j), (A-1k), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1l) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1k), (A-1m), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1m) and (2) compounds of any of structural formulae (A-1a), (A-1b), (A-1c), (A-1d), (A-1e), (A-1f), (A-1g), (A-1h), (A-1i), (A-1j), (A-1k), (A-1l), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1m) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1k), (A-1l), (A-1n), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1n) and (2) compounds of any of structural formulae (A-1a), (A-1b), (A-1c), (A-1d), (A-1e), (A-1f), (A-1g), (A-1h), (A-1i), (A-1j), (A-1k), (A-1l), (A-1m), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1n) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1k), (A-1l), (A-1m), (A-1o), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1o) and (2) compounds of any of structural formulae (A-1a), (A-1b), (A-1c), (A-1d), (A-1e), (A-1f), (A-1g), (A-1h), (A-1i), (A-1j), (A-1k), (A-1l), (A-1m), (A-1n), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1o) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1k), (A-1l), (A-1m), (A-1n), (A-1p), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1p) and (2) compounds of any of structural formulae (A-1a), (A-1b), (A-1c), (A-1d), (A-1e), (A-1f), (A-1g), (A-1h), (A-1i), (A-1j), (A-1k), (A-1l), (A-1m), (A-1n), (A-1o), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1p) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1k), (A-1l), (A-1m), (A-1n), (A-1o), and (A-1q). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1q) and (2) compounds of any of structural formulae (A-1a), (A-1b), (A-1c), (A-1d), (A-1e), (A-1f), (A-1g), (A-1h), (A-1i), (A-1j), (A-1k), (A-1l), (A-1m), (A-1n), (A-1o), and (A-1p). In other embodiments, such compounds are specifically excluded from structural formulae (A) and/or (A-1). Each possible combination is specifically contemplated as if set forth explicitly herein.

Some embodiments specifically include and some embodiments only include (1) compounds of structural formula (A-1q) and (2) compounds of up to 16 (e.g., 1, 2, 3, 4, 5, 6, 7, 8, 9, 10, 11, 12, 13, 14, 15, or 16) of structural formulae (A-1a), (A-1b), (A-1c), (A-1d), (A-1e), (A-1f), (A-1g), (A-1h), (A-1i), (A-1j), (A-1k), (A-1l), (A-1m), (A-1n), (A-1o), and (A-1p). In other embodiments, such compounds are specifically excluded from structural formulae (A) and/or (A-1). Each possible combination is specifically contemplated as if set forth explicitly herein.

Some embodiments specifically include and some embodiments only include compounds which have structural formula (A-2):

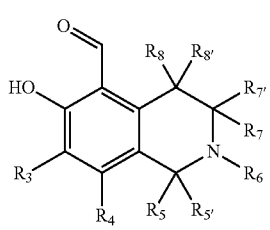

(A-2)

wherein $R_3$, $R_4$, $R_5$, $R_5'$, $R_6$, $R_7$, $R_7'$, $R_8$, and $R_8'$ are as defined in structural formula (A). In other embodiments, such compounds are specifically excluded from structural formula (A).

Structural formula (A-2a). Some embodiments specifically include and some embodiments only include compounds of structural formula (A-2) in which R3, R4, R5, R5', R7, R7', R8, and R8' are hydrogen. In other embodiments, such compounds are specifically excluded from structural formulae (A) and/or (A-2).

Structural formula (A-2b). Some embodiments specifically include and some embodiments only include compounds of structural formula (A-2) in which R6 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-2).

Structural formula (A-2c). Some embodiments specifically include and some embodiments only include compounds of structural formula (A-2) in which R7' is hydrogen and R7 is a side chain selected from the group consisting of alkyl, perfluoroalkyl alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-2).

Structural formula (A-2d). Some embodiments specifically include and some embodiments only include compounds of structural formula (A-2) in which R6 is alkenyl, alkyne, phenyl, or a 5- or 6-membered heteroaryl, each optionally substituted with 1, 2, or 3 substituents independently selected from the group consisting of

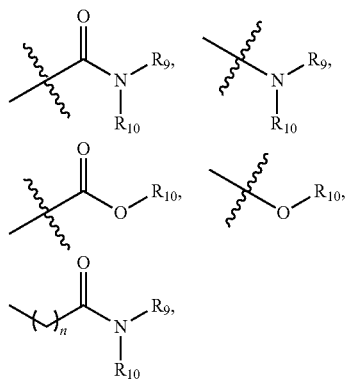

wherein n is 0, 1, or 2;

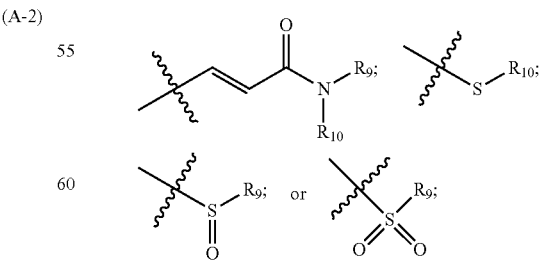

and

R9 and R10 are as defined in connection with structural formula (A).

In other embodiments, such compounds are specifically excluded from structural formulae (A) and/or (A-2).

Some embodiments specifically include and some embodiments only include (1) compounds of structural formula (A-2a) and (2) compounds of any of structural formulae (A-2b), (A-2c), and (A-2d). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2a) and (2) compounds of up to 3 (e.g., 1, 2, or 3) of structural formulae (A-2b), (A-2c), and (A-2d). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2b) and (2) compounds of any of structural formulae (A-2a), (A-2c), and (A-2d). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2b) and (2) compounds of up to 3 (e.g., 1, 2, or 3) of structural formulae (A-2a), (A-2c), and (A-2d). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2c) and (2) compounds of any of structural formulae (A-2a), (A-2b), and (A-2d). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2c) and (2) compounds of up to 3 (e.g., 1, 2, or 3) of structural formulae (A-2a), (A-2b), and (A-2d). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2d) and (2) compounds of any of structural formulae (A-2a), (A-2b), and (A-2c). In other embodiments, such compounds are specifically excluded from structural formulae (A) and/or (A-2). Each possible combination is specifically contemplated as if set forth explicitly herein.

Some embodiments specifically include and some embodiments only include (1) compounds of structural formula (A-2d) and (2) compounds of up to 3 (e.g., 1, 2, or 3) of structural formulae (A-2a), (A-2b), and (A-2c). In other embodiments, such compounds are specifically excluded from structural formulae (A) and/or (A-2). Each possible combination is specifically contemplated as if set forth explicitly herein.

Some embodiments specifically include and some embodiments only include compounds which have structural formula (A-3):

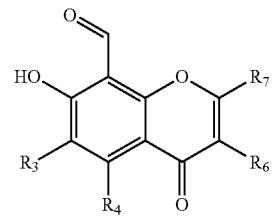

(A-3)

wherein:

R3, R4, R6, and R7 are as defined in structural formula (A), PROVIDED THAT:
   i. if R3 and R4 are hydrogen and R6 is optionally substituted phenyl, then R7 cannot be optionally substituted phenyl, hydrogen, methyl, or $CH_2O(CH_2)_2$;
   ii. if R3 and R4 are hydrogen and R6 is methoxy, then R7 is not methyl or unsubstituted phenyl;
   iii. if R3 is ethyl, R4 is hydrogen, R7 is methyl, then R6 is not fluorophenyl;
   iv. if R3 is halogen and R4 and R7 are hydrogen, then R6 is not bromophenyl; and
   v. R6 and R7 cannot both be methyl if either:
      i. R3 is halogen and R4 is hydrogen; or
      ii. one of R3 and R4 is methyl and the other is hydrogen.

In other embodiments, such compounds are specifically excluded from structural formula (A).

Structural formula (A-3a). Some embodiments specifically include and some embodiments only include compounds of structural formula (A-3) in which R6 is a side chain selected from the group consisting of alkyl, perfluoroalkyl, alkoxyl, hydroxylalkyl, C1-C6 alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-3).

Structural formula (A-3b). Some embodiments specifically include and some embodiments only include compounds of structural formula (A-3) in which R6 is alkenyl, or alkynyl, or phenyl, or a 5- or 6-membered heteroaryl, each optionally substituted with 1, 2, or 3 substituents independently selected from the group consisting of

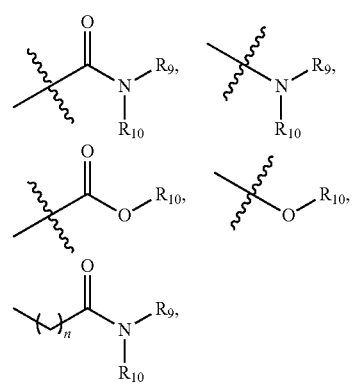

wherein n is 0, 1, or 2;

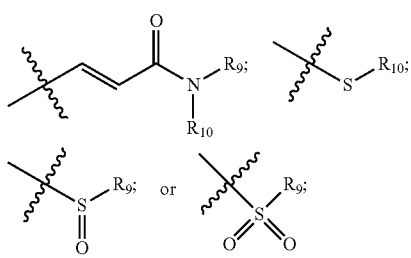

in which R9 and R10 are defined as in structural formula (A). In other embodiments, such compounds are specifically excluded from structural formulae (A) and/or (A-3).

Structural formula (A-3c). Some embodiments specifically include and some embodiments only include compounds of structural formula (A-3) in which R7 is hydrogen; halogen; —CN; optionally substituted alkyl; or optionally substituted alkoxyl. Optional substituents for the alkyl and for the alkoxyl are (1) a C1-C6 hydrocarbon chain containing an N or O atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-3).

Structural formula (A-3d). Some embodiments specifically include and some embodiments only include compounds of structural formula (A-3) in which R9 and R10 are independently hydrogen, C2-C6 alkyl, alkoxylalkyl, perfluoroalkoxylalkyl, aryl, optionally substituted with 1, 2, or 3 substituents independently selected from R21. In other embodiments, such compounds are specifically excluded from structural formulae (A) and/or (A-3).

Structural formula (A-3e). Some embodiments specifically include and some embodiments only include compounds of structural formula (A-3) in which R9 and R10 are independently a 5- or 6-membered heterocycle, optionally substituted with 1, 2, or 3 substituents independently selected from R21. In other embodiments, such compounds are specifically excluded from structural formulae (A) and/or (A-3).

Structural formula (A-3f). Some embodiments specifically include and some embodiments only include compounds of structural formula (A-3) in which R9 and R10 are independently a 5- or 6-membered heteroaryl, optionally substituted with 1, 2, or 3 substituents independently selected from R21; or

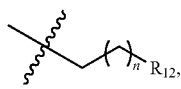

wherein n is 0, 1, 2, or 3 and R12 is as defined in structural formula (A). In other embodiments, such compounds are specifically excluded from structural formulae (A) and/or (A-3).

Structural formula (A-3g). Some embodiments specifically include and some embodiments only include compounds of structural formula (A-3) in which R9 and R10, together with the nitrogen atom to which they are attached, form a heterocycle containing 1, 2, 3, or 4 heteroatoms selected from N, O and S, optionally substituted with 1, 2, or 3 substituents selected independently from R11, wherein R11 is defined as in structural formula (A). In other embodiments, such compounds are specifically excluded from structural formulae (A) and/or (A-3).

Structural formula (A-3h). Some embodiments specifically include and some embodiments only include compounds of structural formula (A-3) which R6 is alkenyl, or alkynyl, or phenyl, or a 5- or 6-membered heteroaryl, each optionally substituted with 1, 2, or 3 substituents independently selected from the group consisting of

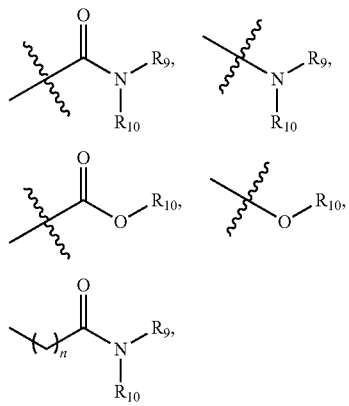

wherein n is 0, 1, or 2;

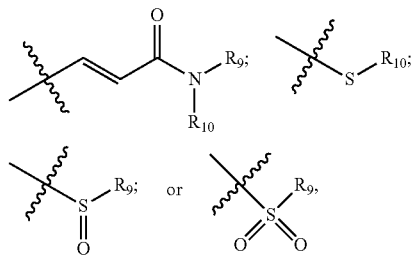

in which R9 and R10 are defined as in structural formula (A). In other embodiments, such compounds are specifically excluded from structural formulae (A) and/or (A-3).

Structural formula (A-3i). Some embodiments specifically include and some embodiments only include compounds of structural formula (A-3) in which R7 is alkyl. In other embodiments, such compounds are specifically excluded from structural formulae (A) and/or (A-3).

Structural formula (A-3j). Some embodiments specifically include and some embodiments only include compounds of structural formula (A-3) in which R7 is methyl. In other embodiments, such compounds are specifically excluded from structural formulae (A) and/or (A-3).

Structural formula (A-3k). Some embodiments specifically include and some embodiments only include compounds of structural formula (A-3) in which a. R7 is alkyl.
b. R6 is alkenyl, or alkynyl, or phenyl, or a 5- or 6-membered heteroaryl, each optionally substituted with 1, 2, or 3 substituents independently selected from the group consisting of

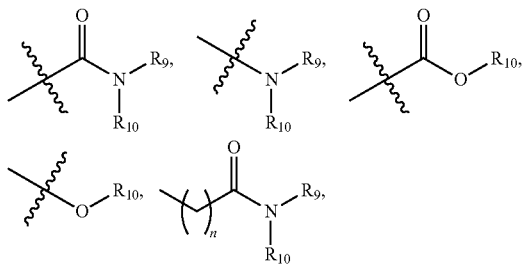

wherein n is 0, 1, or 2;

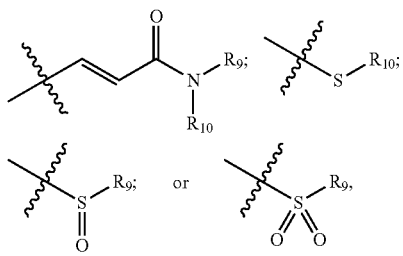

in which R9 and R10 are defined as in structural formula (A).

In other embodiments, such compounds are specifically excluded from structural formulae (A) and/or (A-3).

Structural formula (A-3l). Some embodiments specifically include and some embodiments only include compounds of structural formula (A3) in which R3 is alkoxyl. Some embodiments specifically include and some embodiments only include compounds of structural formula (A-3) in which R3 is methoxy. In other embodiments, such compounds are specifically excluded from structural formulae (A) and/or (A-3).

Structural formula (A-3m). Some embodiments specifically include and some embodiments only include compounds of structural formula (A-3) in which
  a. R7 is methyl and
  b. R3 is alkoxyl.

In other embodiments, such compounds are specifically excluded from structural formulae (A) and/or (A-3).

Structural formula (A-3n). Some embodiments specifically include and some embodiments only include compounds of structural formula (A-3) in which
  a. R7 is methyl;
  b. R3 is alkoxyl; and
  c. R6 is alkenyl, or alkynyl, or phenyl, or a 5- or 6-membered heteroaryl, each optionally substituted with 1, 2, or 3 substituents independently selected from the group consisting of

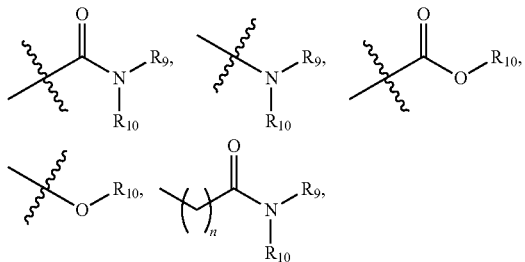

wherein n is 0, 1, or 2;

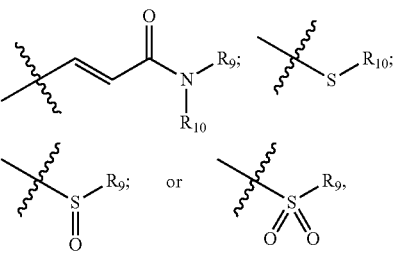

in which R9 and R10 are defined as in structural formula (A).

In other embodiments, such compounds are specifically excluded from structural formulae (A) and/or (A-3).

Structural formula (A-3o). Some embodiments specifically include and some embodiments only include compounds of structural formula (A-3) in which
  a. R7 is methyl and
  b. R3 is methoxy.

In other embodiments, such compounds are specifically excluded from structural formulae (A) and/or (A-3).

Structural formula (A-3p). Some embodiments specifically include and some embodiments only include compounds of structural formula (A-3) in which
  a. R7 is methyl;
  b. R3 is methoxy; and
  c. R6 is alkenyl, or alkynyl, or phenyl, or a 5- or 6-membered heteroaryl, each optionally substituted with 1, 2, or 3 substituents independently selected from the group consisting of

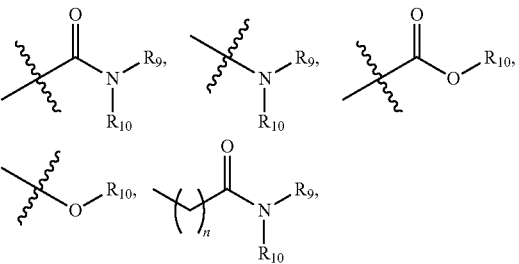

wherein n is 0, 1, or 2;

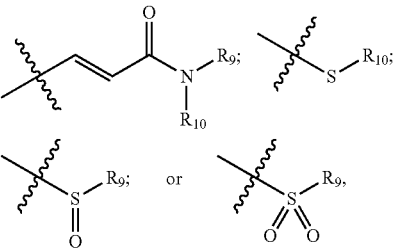

in which R9 and R10 are defined as in structural formula (A).

In other embodiments, such compounds are specifically excluded from structural formulae (A) and/or (A-3).

Structural formula (A-3q). Some embodiments specifically include and some embodiments only include compounds of structural formula (A-3) in which
  a. R7 is alkyl and
  b. R3 is alkoxyl.

In other embodiments, such compounds are specifically excluded from structural formulae (A) and/or (A-3).

Structural formula (A-3r). Some embodiments specifically include and some embodiments only include compounds of structural formula (A-3) in which
a. R7 is alkyl,
b. R3 is alkoxyl, and
c. R6 is alkenyl, or alkynyl, or phenyl, or a 5- or 6-membered heteroaryl, each optionally substituted with 1, 2, or 3 substituents independently selected from the group consisting of

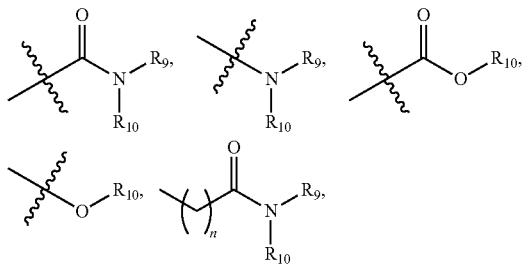

wherein n is 0, 1, or 2;

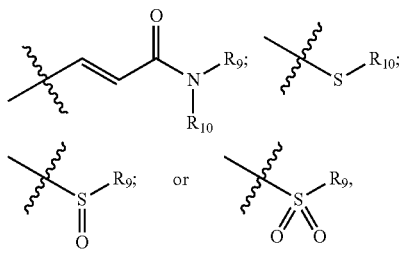

in which R9 and R10 are defined as in structural formula (A).

In other embodiments, such compounds are specifically excluded from structural formulae (A) and/or (A-3).

Structural formula (A-3s). Some embodiments specifically include and some embodiments only include compounds of structural formula (A-3) in which R6 is

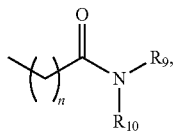

wherein n is 0, 1, or 2, and R9 and R10 are defined as in structural formula (A).

In other embodiments, such compounds are specifically excluded from structural formulae (A) and/or (A-3).

Structural formula (A-3t). Some embodiments specifically include and some embodiments only include compounds of structural formula (A-3) in which R3 is hydrogen. In other embodiments, such compounds are specifically excluded from structural formulae (A) and/or (A-3).

Structural formula (A-3u). Some embodiments specifically include and some embodiments only include compounds of structural formula (A-3) in which R4 is hydrogen. In other embodiments, such compounds are specifically excluded from structural formulae (A) and/or (A-3).

Structural formula (A-3v). Some embodiments specifically include and some embodiments only include compounds of structural formula (A-3) in which R3 and R4 are hydrogen. In other embodiments, such compounds are specifically excluded from structural formulae (A) and/or (A-3).

Structural formula (A-3w). Some embodiments specifically include and some embodiments only include compounds of structural formula (A-3) in which
a. R3 is methoxy and
b. R4 is hydrogen.

In other embodiments, such compounds are specifically excluded from structural formulae (A) and/or (A-3).

Structural formula (A-3x). Some embodiments specifically include and some embodiments only include compounds of structural formula (A-3) in which
a. R3 is methoxy,
b. R4 is hydrogen, and
c. R7 is methyl.

In other embodiments, such compounds are specifically excluded from structural formulae (A) and/or (A-3).

Structural formula (A-3y). Some embodiments specifically include and some embodiments only include compounds of structural formula (A-3) in which
a. R4 is methoxy and
b. R7 is methyl.

In other embodiments, such compounds are specifically excluded from structural formulae (A) and/or (A-3).

Structural formula (A-3z). Some embodiments specifically include and some embodiments only include compounds of structural formula (A-3) in which
a. R3 is hydrogen and
b. R6 is alkenyl, or alkynyl, or phenyl, or a 5- or 6-membered heteroaryl, each optionally substituted with 1, 2, or 3 substituents independently selected from the group consisting of

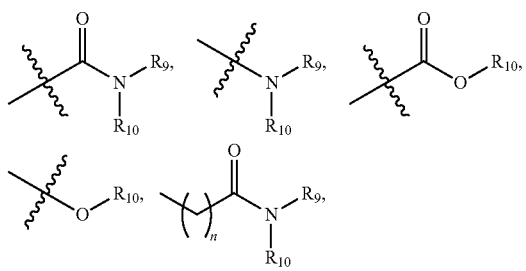

wherein n is 0, 1, or 2;

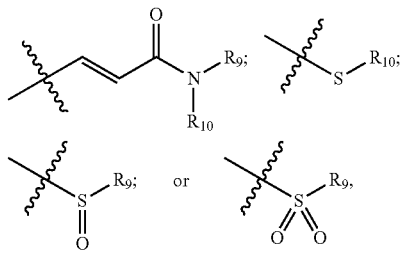

in which R9 and R10 are defined as in structural formula (A).

In other embodiments, such compounds are specifically excluded from structural formulae (A) and/or (A-3).

Structural formula (A-3aa). Some embodiments specifically include and some embodiments only include compounds of structural formula (A-3) in which
  a. R4 is hydrogen and
  b. R6 is alkenyl, or alkynyl, or phenyl, or a 5- or 6-membered heteroaryl, each optionally substituted with 1, 2, or 3 substituents independently selected from the group consisting of

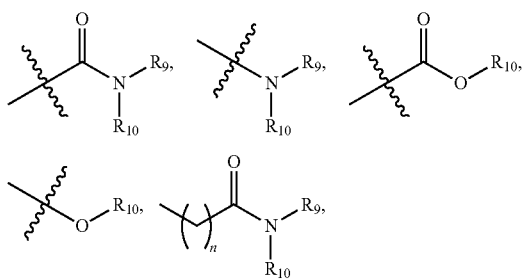

wherein n is 0, 1, or 2;

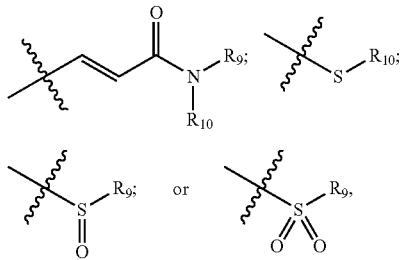

in which R9 and R10 are defined as in structural formula (A).

In other embodiments, such compounds are specifically excluded from structural formulae (A) and/or (A-3).

Structural formula (A-3bb). Some embodiments specifically include and some embodiments only include compounds of structural formula (A-3) in which
  a. R3 and R4 are hydrogen and
  b. R6 is alkenyl, or alkynyl, or phenyl, or a 5- or 6-membered heteroaryl, each optionally substituted with 1, 2, or 3 substituents independently selected from the group consisting of

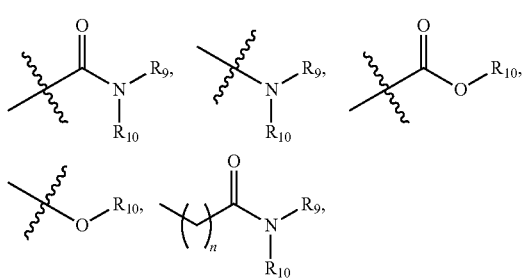

wherein n is 0, 1, or 2;

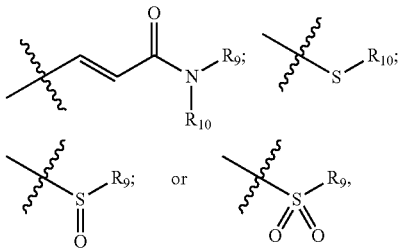

in which R9 and R10 are defined as in structural formula (A).

In other embodiments, such compounds are specifically excluded from structural formulae (A) and/or (A-3).

Structural formula (A-3cc). Some embodiments specifically include and some embodiments only include compounds of structural formula (A-3) in which
  a. R3 is methoxy,
  b. R4 is hydrogen, and
  c. R6 is alkenyl, or alkynyl, or phenyl, or a 5- or 6-membered heteroaryl, each optionally substituted with 1, 2, or 3 substituents independently selected from the group consisting of

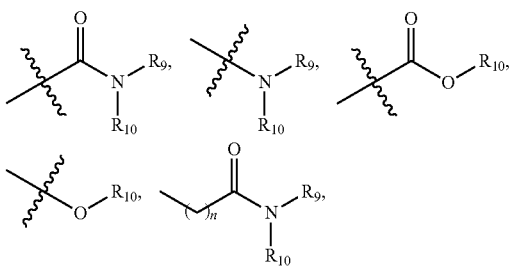

wherein n is 0, 1, or 2;

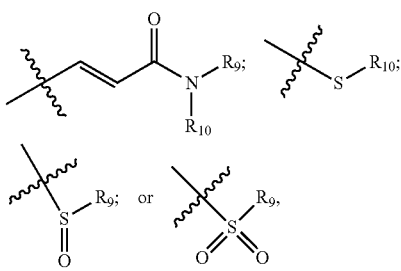

in which R9 and R10 are defined as in structural formula (A).

In other embodiments, such compounds are specifically excluded from structural formulae (A) and/or (A-3).

Structural formula (A-3dd). Some embodiments specifically include and some embodiments only include compounds of structural formula (A-3) in which
  a. R3 is methoxy,
  b. R4 is hydrogen,
  c. R7 is methyl, and
  d. R6 is alkenyl, or alkynyl, or phenyl, or a 5- or 6-membered heteroaryl, each optionally substituted with 1, 2, or 3 substituents independently selected from the group consisting of

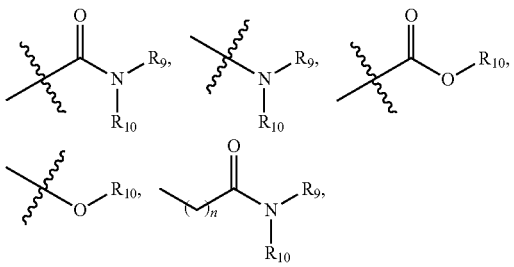

wherein n is 0, 1, or 2;

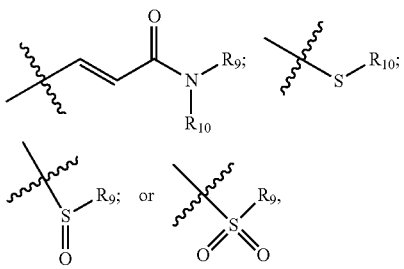

in which R9 and R10 are defined as in structural formula (A).

In other embodiments, such compounds are specifically excluded from structural formulae (A) and/or (A-3).

Structural formula (A-3ee). Some embodiments specifically include and some embodiments only include compounds of structural formula (A-3) in which
a. R4 is methoxy,
b. R7 is methyl, and
c. R6 is alkenyl, or alkynyl, or phenyl, or a 5- or 6-membered heteroaryl, each optionally substituted with 1, 2, or 3 substituents independently selected from the group consisting of

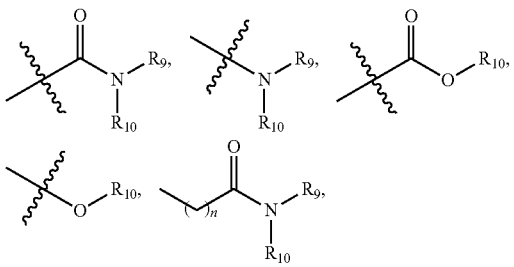

wherein n is 0, 1, or 2;

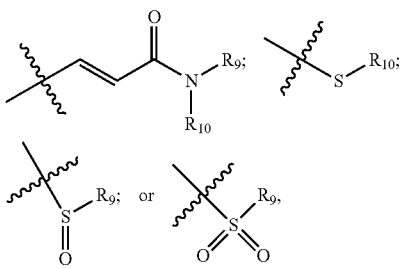

in which R9 and R10 are defined as in structural formula (A).

In other embodiments, such compounds are specifically excluded from structural formulae (A) and/or (A-3).

Some embodiments specifically include and some embodiments only include (1) compounds of structural formula (A-3a) and (2) compounds of any of structural formulae (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3a) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3b) and (2) compounds of any of structural formulae (A-3a), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3b) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3c) and (2) compounds of any of structural formulae (A-3a), (A-3b), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3c) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3d) and (2) compounds of any of structural formulae (A-3a), (A-3b), (A-3c), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3d) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3e) and (2) compounds of any of structural formulae (A-3a), (A-3b), (A-3c), (A-3d), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3e) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3f) and (2) compounds of any of structural formulae (A-3a), (A-3b), (A-3c), (A-3d), (A-3e), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3f) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3g) and (2) compounds of any of structural formulae (A-3a), (A-3b), (A-3c), (A-3d), (A-3e), (A-3f), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3g) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3h) and (2) compounds of any of structural formulae (A-3a), (A-3b), (A-3c), (A-3d), (A-3e), (A-3f), (A-3g), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3h) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3i) and (2) compounds of any of structural formulae (A-3a), (A-3b), (A-3c), (A-3d), (A-3e), (A-3f), (A-3g), (A-3h), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3i) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3j) and (2) compounds of any of structural formulae (A-3a), (A-3b), (A-3c), (A-3d), (A-3e), (A-3f), (A-3g), (A-3h), (A-3i), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3j) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3k) and (2) compounds of any of structural formulae (A-3a), (A-3b), (A-3c), (A-3d), (A-3e), (A-3f), (A-3g), (A-3h), (A-3i), (A-3j), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3k) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3l) and (2) compounds of any of structural formulae (A-3a), (A-3b), (A-3c), (A-3d), (A-3e), (A-3f), (A-3g), (A-3h), (A-3i), (A-3j), (A-3k), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3l) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3m) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3m) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3n) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3n) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3o) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3o) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3p), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3p) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3p) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3q), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3q) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3q) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3r), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3r) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3r) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3s), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3s) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3s) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3t), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3t) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3t) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3u), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3u) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3u) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3v), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3v) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3v) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3w), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3w) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3w) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3x), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3x) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3x) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3y), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3y) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3y) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3z), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3z) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3z) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3aa), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3aa) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3aa) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3bb), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3bb) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3bb) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3cc), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3cc) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3cc) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3dd), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3dd) and (2) compounds of any of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3dd) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), and (A-3ee). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3ee) and (2) compounds of any of structural (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), and (A-3dd). In other embodiments, such compounds are specifically excluded from structural formulae (A) and/or (A-3). Each possible combination is specifically contemplated as if set forth explicitly herein.

Some embodiments specifically include and some embodiments only include (1) compounds of structural formula (A-3ee) and (2) compounds of up to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-3a), (A-3b), (A-3c), (A-3d), (A-3e), (A-3f), (A-3g), (A-3h), (A-3i), (A-3j), (A-3k), (A-3l), (A-3m), (A-3n), (A-3o), (A-3p), (A-3q), (A-3r), (A-3s), (A-3t), (A-3u), (A-3v), (A-3w), (A-3x), (A-3y), (A-3z), (A-3aa), (A-3bb), (A-3cc), and (A-3dd). In other embodiments, such compounds are specifically excluded from structural formulae (A) and/or (A-3). Each possible combination is specifically contemplated as if set forth explicitly herein.

Some embodiments specifically include and some embodiments only include compounds which have structural formula (A-4):

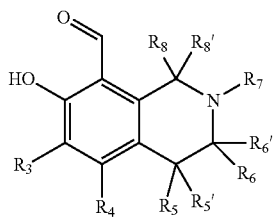

(A-4)

wherein R3, R4, R5, R5', R6, R6', R7, R8, and R8' are as defined in structural formula (A). In other embodiments, such compounds are specifically excluded from structural formula (A).

Structural formula (A-4a). Some embodiments specifically include and some embodiments only include compounds of structural formula (A-4) in which R3, R4, R5, R5', R6, R6', R8, and R8' are hydrogen. In other embodiments, such compounds are specifically excluded from structural formulae (A) and/or (A-4).

Structural formula (A-4b). Some embodiments specifically include and some embodiments only include compounds of structural formula (A-4) in which R7 is hydrogen; halogen; —CN; optionally substituted alkyl; or an optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-4).

Structural formula (A-4c). Some embodiments specifically include and some embodiments only include compounds of structural formula (A-4) in which R7 is alkyl, perfluoroalkyl, alkoxyl, hydroxylalkyl, alkoxylalkyl, or perfluoroalkoxyl. In other embodiments, such compounds are specifically excluded from structural formulae (A) and/or (A-4).

Structural formula (A-4d). Some embodiments specifically include and some embodiments only include compounds of structural formula (A-4) in which R7 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-4).

Structural formula (A-4e). Some embodiments specifically include and some embodiments only include compounds of structural formula (A-4) in which R7 is alkenyl, alkyne, phenyl, or a 5- or 6-membered heteroaryl, each optionally substituted with 1, 2, or 3 substituents independently selected from the group consisting of

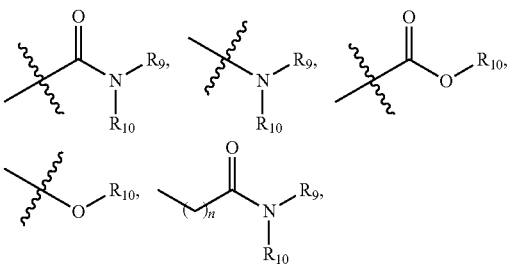

wherein n is 0, 1, or 2;

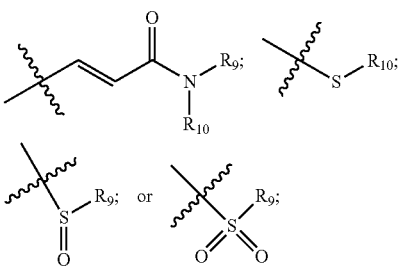

and

R9 and R10 are as defined in connection with structural formula (A). In other embodiments, such compounds are specifically excluded from structural formulae (A) and/or (A-4).

Some embodiments specifically include and some embodiments only include (1) compounds of structural formula (A-4a) and (2) compounds of any of structural formulae (A-4b), (A-4c), (A-4d), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4a) and (2) compounds of up to 4 (e.g., 1, 2, 3, or 4) of structural formulae (A-4b), (A-4c), (A-4d), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4b) and (2) compounds of any of structural formulae (A-4a), (A-4c), (A-4d), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4b) and (2) compounds of up to 4 (e.g., 1, 2, 3, or 4) of structural formulae (A-4a), (A-4c), (A-4d), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4c) and (2) compounds of any of structural formulae (A-4a), (A-4b), (A-4d), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4c) and (2) compounds of up to 4 (e.g., 1, 2, 3, or 4) of structural formulae (A-4a), (A-4b), (A-4d), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4d) and (2) compounds of any of structural formulae (A-4a), (A-4b), (A-4c), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4d) and (2) compounds of up to 4 (e.g., 1, 2, 3, or 4) of structural formulae (A-4a), (A-4b), (A-4c), and (A-4e). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4e) and (2) compounds of any of structural formulae (A-4a), (A-4b), (A-4c), and (A-4d). In other embodiments, such compounds are specifically excluded from structural formulae (A) and/or (A-4). Each possible combination is specifically contemplated as if set forth explicitly herein.

Some embodiments specifically include and some embodiments only include (1) compounds of structural formula (A-4e) and (2) compounds of up to 4 (e.g., 1, 2, 3, or 4) of structural formulae (A-4a), (A-4b), (A-4c), and (A-4d). In other embodiments, such compounds are specifically excluded from structural formulae (A) and/or (A-4). Each possible combination is specifically contemplated as if set forth explicitly herein.

Some embodiments specifically include and some embodiments only include compounds which have structural formula (A-5):

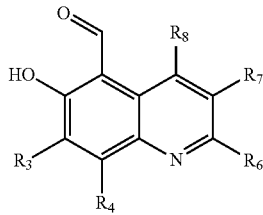

(A-5)

wherein R3, R4, R6, R7, and R8 are as defined in structural formula (A). In other embodiments, such compounds are specifically excluded from structural formula (A).

Structural formula (A-5a). Some embodiments include only those compounds of structural formula (A-5) in which R3 and R4 are hydrogen. In other embodiments, such compounds are specifically excluded from structural formulae (A) and/or (A-5).

Structural formula (A-5b). Some embodiments specifically include and some embodiments only include compounds of structural formula (A-5) in which R6 is alkenyl, alkyne, phenyl, or a 5- or 6-membered heteroaryl, each optionally substituted with 1, 2, or 3 substituents independently selected from the group consisting of

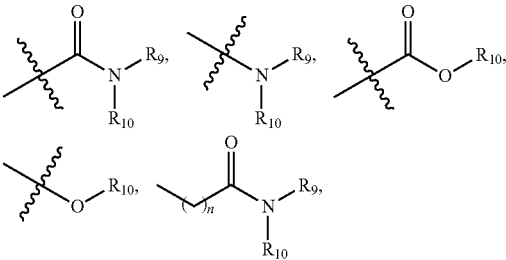

wherein n is 0, 1, or 2;

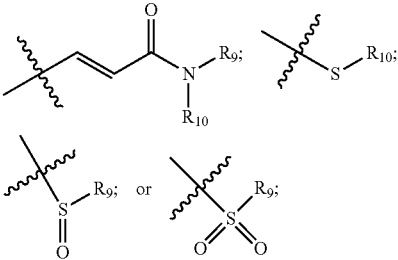

and

R9 and R10 are as defined in connection with structural formula (A). In other embodiments, such compounds are specifically excluded from structural formulae (A) and/or (A-5).

Some embodiments specifically include and some embodiments only include (1) compounds of structural formula (A-5a) and (2) compounds of structural formula (A-5b). In other embodiments, (1) compounds of structural formula (A-5a) and (2) compounds of structural formula (A-5b) compounds are specifically excluded from structural formulae (A) and/or (A-5).

Some embodiments specifically include and some embodiments only include compounds which have structural formula (A-6a):

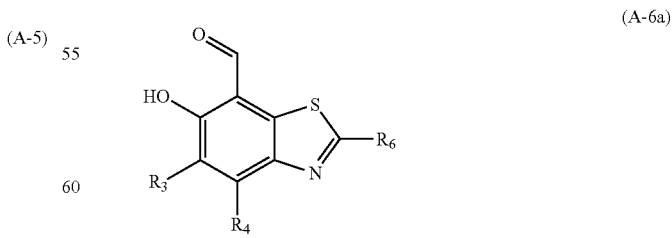

(A-6a)

wherein:
R3, R4, and R6 are as defined in structural formula (A). In other embodiments, such compounds are specifically excluded from structural formula (A).

Structural formula (A-6a1). Some embodiments include only those compounds of structural formula (A-6a) in which R3 is hydrogen. In other embodiments, such compounds are specifically excluded from structural formulae (A) and/or (A-6a).

Structural formula (A-6a2). Some embodiments include only those compounds of structural formula (A-6a) in which R4 is hydrogen. In other embodiments, such compounds are specifically excluded from structural formulae (A) and/or (A-6a).

Structural formula (A-6a3). Some embodiments include only those compounds of structural formula (A-6a) in which R3 and R4 are hydrogen. In other embodiments, such compounds are specifically excluded from structural formulae (A) and/or (A-6a).

Structural formula (A-6a4). Some embodiments specifically include and some embodiments only include compounds of structural formula (A-6a) in which R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-6a).

Structural formula (A-6a5). Some embodiments specifically include and some embodiments only include compounds of structural formula (A-6a) in which R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl. In other embodiments, such compounds are specifically excluded from structural formulae (A) and/or (A-6a).

Structural formula (A-6a6). Some embodiments include only those compounds of structural formula (A-6a) in which
a. R3 is hydrogen and
b. R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl.

In other embodiments, such compounds are specifically excluded from structural formulae (A) and/or (A-6a).

Structural formula (A-6a7). Some embodiments include only those compounds of structural formula (A-6a) in which
a. R4 is hydrogen and
b. R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl.

In other embodiments, such compounds are specifically excluded from structural formulae (A) and/or (A-6a).

Structural formula (A-6a8). Some embodiments include only those compounds of structural formula (A-6a) in which
a. R3 and R4 are hydrogen and
b. R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl.

In other embodiments, such compounds are specifically excluded from structural formulae (A) and/or (A-6a).

Structural formula (A-6a9). Some embodiments include only those compounds of structural formula (A-6a) in which
a. R3 is hydrogen and
b. R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl.

In other embodiments, such compounds are specifically excluded from structural formulae (A) and/or (A-6a).

Structural formula (A-6a10). Some embodiments include only those compounds of structural formula (A-6a) in which
a. R4 is hydrogen and
b. R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl.

In other embodiments, such compounds are specifically excluded from structural formulae (A) and/or (A-6a).

Structural formula (A-6a11). Some embodiments include only those compounds of structural formula (A-6a) in which
a. R3 and R4 are hydrogen and
b. R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl.

In other embodiments, such compounds are specifically excluded from structural formulae (A) and/or (A-6a).

Structural formula (A-6a12). Some embodiments specifically include and some embodiments only include compounds of structural formula (A-6a) in which R6 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-6a).

Structural formula (A-6a13). Some embodiments specifically include and some embodiments only include compounds of structural formula (A-6a) in which R6 is alkenyl, alkyne, phenyl, or a 5- or 6-membered heteroaryl, each optionally substituted with 1, 2, or 3 substituents independently selected from the group consisting of

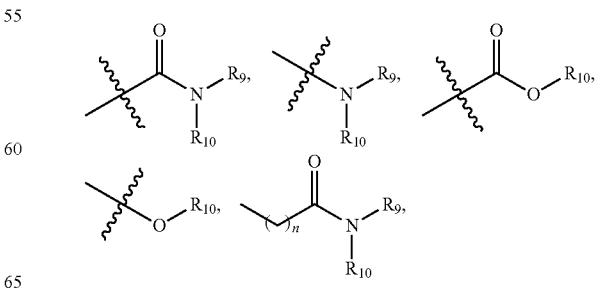

wherein n is 0, 1, or 2;

and

R9 and R10 are as defined in connection with structural formula (A). In other embodiments, such compounds are specifically excluded from structural formulae (A) and/or (A-6a).

Some embodiments specifically include and some embodiments only include (1) compounds of structural formula (A-6a1) and (2) compounds of any of structural formulae (A-6a2), (A-6a3), (A-6a4), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a1) and (2) compounds of up to 12 (e.g., 1, 2, 3, 4, 5, 6, 7, 8, 9, 10, 11, or 12) of structural formulae (A-6a2), (A-6a3), (A-6a4), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a2) and (2) compounds of any of structural formulae (A-6a1), (A-6a3), (A-6a4), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a2) and (2) compounds of up to 12 (e.g., 1, 2, 3, 4, 5, 6, 7, 8, 9, 10, 11, or 12) of structural formulae (A-6a1), (A-6a3), (A-6a4), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a3) and (2) compounds of any of structural formulae (A-6a1), (A-6a2), (A-6a4), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a3) and (2) compounds of up to 12 (e.g., 1, 2, 3, 4, 5, 6, 7, 8, 9, 10, 11 or 12) of structural formulae (A-6a1), (A-6a2), (A-6a4), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a4) and (2) compounds of any of structural formulae (A-6a1), (A-6a2), (A-6a3), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a4) and (2) compounds of up to 12 (e.g., 1, 2, 3, 4, 5, 6, 7, 8, 9, 10, 11, or 12) of structural formulae (A-6a1), (A-6a2), (A-6a3), (A-6a5), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a5) and (2) compounds of any of structural formulae (A-6a1), (A-6a2), (A-6a3), (A-6a4), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a5) and (2) compounds of up to 12 (e.g., 1, 2, 3, 4, 5, 6, 7, 8, 9, 10, 11 or 12) of structural formulae (A-6a1), (A-6a2), (A-6a3), (A-6a4), (A-6a6), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a6) and (2) compounds of any of structural formulae (A-6a1), (A-6a2), (A-6a3), (A-6a4), (A-6a5), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a6) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a7), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a7) and (2) compounds of any of structural formulae (A-6a1), (A-6a2), (A-6a3), (A-6a4), (A-6a5), (A-6a6), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a7) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a8), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a8) and (2) compounds of any of structural formulae (A-6a1), (A-6a2), (A-6a3), (A-6a4), (A-6a5), (A-6a6), (A-6a7), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a8) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a7), (A-6a9), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a9) and (2) compounds of any of structural formulae (A-6a1), (A-6a2), (A-6a3), (A-6a4), (A-6a5), (A-6a6), (A-6a7), (A-6a8), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a9) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a7), (A-6a8), (A-6a10), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a10) and (2) compounds of any of structural formulae (A-6a1), (A-6a2), (A-6a3), (A-6a4), (A-6a5), (A-6a6), (A-6a7), (A-6a8), (A-6a9), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a10) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a7), (A-6a8), (A-6a9), (A-6a11), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a11) and (2) compounds of any of structural formulae (A-6a1), (A-6a2), (A-6a3), (A-6a4), (A-6a5), (A-6a6), (A-6a7), (A-6a8), (A-6a9), (A-6a10), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a11) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a7), (A-6a8), (A-6a9), (A-6a10), (A-6a12), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a12) and (2) compounds of any of structural formulae (A-6a1), (A-6a2), (A-6a3), (A-6a4), (A-6a5), (A-6a6), (A-6a7), (A-6a8), (A-6a9), (A-6a10), (A-6a11), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a12) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a7), (A-6a8), (A-6a9), (A-6a10), (A-6a11), and (A-6a13). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a13) and (2) compounds of any of structural formulae (A-6a1), (A-6a2), (A-6a3), (A-6a4), (A-6a5), (A-6a6), (A-6a7), (A-6a8), (A-6a9), (A-6a10), (A-6a11), and (A-6a12). In other embodiments, such compounds are specifically excluded from structural formulae (A) and/or (A-6a). Each possible combination is specifically contemplated as if set forth explicitly herein.

Some embodiments specifically include and some embodiments only include (1) compounds of structural formula (A-6a13) and (2) compounds of up to 12 (e.g., 1, 2, 3, 4, 5, 6, 7, 8, 9, 10, 11, or 12) of structural formulae (A-6a1), (A-6a2), (A-6a3), (A-6a4), (A-6a5), (A-6a6), (A-6a7), (A-6a8), (A-6a9), (A-6a10), (A-6a11), and (A-6a12). In other embodiments, such compounds are specifically excluded from structural formulae (A) and/or (A-6a). Each possible combination is specifically contemplated as if set forth explicitly herein.

Some embodiments specifically include and some embodiments only include compounds which have structural formula (A-6b):

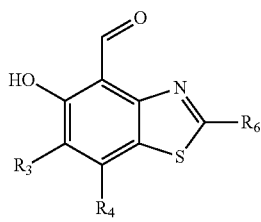
(A-6b)

wherein:

R3, R4, and R6 are as defined in structural formula (A). In other embodiments, such compounds are specifically excluded from structural formula (A).

Structural formula (A-6b1). Some embodiments include only those compounds of structural formula (A-6b) in which R3 is hydrogen. In other embodiments, such compounds are specifically excluded from structural formulae (A) and/or (A-6b).

Structural formula (A-6b2). Some embodiments include only those compounds of structural formula (A-6b) in which R4 is hydrogen. In other embodiments, such compounds are specifically excluded from structural formulae (A) and/or (A-6b).

Structural formula (A-6b3). Some embodiments include only those compounds of structural formula (A-6b) in which R3 and R4 are hydrogen. In other embodiments, such compounds are specifically excluded from structural formulae (A) and/or (A-6b).

Structural formula (A-6b4). Some embodiments specifically include and some embodiments only include compounds of structural formula (A-6b) in which R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-6b).

Structural formula (A-6b5). Some embodiments specifically include and some embodiments only include compounds of structural formula (A-6b) in which R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl. In other embodiments, such compounds are specifically excluded from structural formulae (A) and/or (A-6b).

Structural formula (A-6b6). Some embodiments include only those compounds of structural formula (A-6b) in which
a. R3 is hydrogen and
b. R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl.

In other embodiments, such compounds are specifically excluded from structural formulae (A) and/or (A-6b).

Structural formula (A-6b7). Some embodiments include only those compounds of structural formula (A-6b) in which
a. R4 is hydrogen and
b. R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl.

In other embodiments, such compounds are specifically excluded from structural formulae (A) and/or (A-6b).

Structural formula (A-6b8). Some embodiments include only those compounds of structural formula (A-6b) in which
a. R3 and R4 are hydrogen and
b. R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl.

In other embodiments, such compounds are specifically excluded from structural formulae (A) and/or (A-6b).

Structural formula (A-6b9). Some embodiments include only those compounds of structural formula (A-6b) in which
a. R3 is hydrogen and
b. R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl.

In other embodiments, such compounds are specifically excluded from structural formulae (A) and/or (A-6b).

Structural formula (A-6b10). Some embodiments include only those compounds of structural formula (A-6b) in which
a. R4 is hydrogen and
b. R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl.

In other embodiments, such compounds are specifically excluded from structural formulae (A) and/or (A-6b).

Structural formula (A-6b11). Some embodiments include only those compounds of structural formula (A-6b) in which
a. R3 and R4 are hydrogen and
b. R6 is C1-C6 alkyl, C1-C6 perfluoroalkyl, C1-C6 alkoxyl, C1-C6 hydroxylalkyl, C1-C6 alkoxylalkyl, or C1-C6 perfluoroalkoxyl.

In other embodiments, such compounds are specifically excluded from structural formulae (A) and/or (A-6b).

Structural formula (A-6b12). Some embodiments specifically include and some embodiments only include compounds of structural formula (A-6b) in which R6 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-6b).

Structural formula (A-6b13). Some embodiments specifically include and some embodiments only include compounds of structural formula (A-6b) in which R6 is alkenyl, alkyne, phenyl, or a 5- or 6-membered heteroaryl, each optionally substituted with 1, 2, or 3 substituents independently selected from the group consisting of

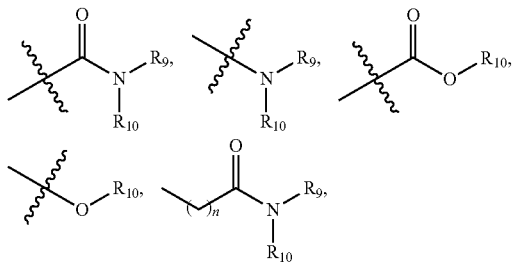

wherein n is 0, 1, or 2;

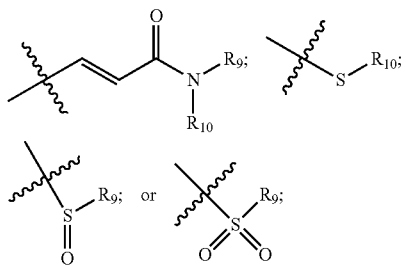

and

R9 and R10 are as defined in connection with structural formula (A). In other embodiments, such compounds are specifically excluded from structural formulae (A) and/or (A-6b).

Some embodiments specifically include and some embodiments only include (1) compounds of structural formula (A-6b1) and (2) compounds of any of structural formulae (A-6b2), (A-6b3), (A-6b4), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b1) and (2) compounds of up to 12 (e.g., 1, 2, 3, 4, 5, 6, 7, 8, 9, 10, 11, or 12) of structural formulae (A-6b2), (A-6b3), (A-6b4), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b2) and (2) compounds of any of structural formulae (A-6b1), (A-6b3), (A-6b4), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b2) and (2) compounds of up to 12 (e.g., 1, 2, 3, 4, 5, 6, 7, 8, 9, 10, 11, or 12) of structural formulae (A-6b1), (A-6b3), (A-6b4), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b3) and (2) compounds of any of structural formulae (A-6b1), (A-6b2), (A-6b4), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b3) and (2) compounds of up to 12 (e.g., 1, 2, 3, 4, 5, 6, 7, 8, 9, 10, 11 or 12) of structural formulae (A-6b1), (A-6b2), (A-6b4), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b4) and (2) compounds of any of structural formulae (A-6b1), (A-6b2), (A-6b3), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b4) and (2) compounds of up to 12 (e.g., 1, 2, 3, 4, 5, 6, 7, 8, 9, 10, 11, or 12) of structural formulae (A-6b1), (A-6b2), (A-6b3), (A-6b5), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b5) and (2) compounds of any of structural formulae (A-6b1), (A-6b2), (A-6b3), (A-6b4), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b5) and (2) compounds of up to 12 (e.g., 1, 2, 3, 4, 5, 6, 7, 8, 9, 10, 11 or 12) of structural formulae (A-6b1), (A-6b2), (A-6b3), (A-6b4), (A-6b6), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b6) and (2) compounds of any of structural formulae (A-6b1), (A-6b2), (A-6b3), (A-6b4), (A-6b5), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b6) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b7), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b7) and (2) compounds of any of structural formulae (A-6b1), (A-6b2), (A-6b3), (A-6b4), (A-6b5), (A-6b6), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b7) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b8), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b8) and (2) compounds of any of structural formulae (A-6b1), (A-6b2), (A-6b3), (A-6b4), (A-6b5), (A-6b6), (A-6b7), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b8) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b7), (A-6b9), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b9) and (2) compounds of any of structural formulae (A-6b1), (A-6b2), (A-6b3), (A-6b4), (A-6b5), (A-6b6), (A-6b7), (A-6b8), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b9) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b7), (A-6b8), (A-6b10), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b10) and (2) compounds of any of structural formulae (A-6b1), (A-6b2), (A-6b3), (A-6b4), (A-6b5), (A-6b6), (A-6b7), (A-6b8), (A-6b9), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b10) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b7), (A-6b8), (A-6b9), (A-6b11), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b11) and (2) compounds of any of structural formulae (A-6b1), (A-6b2), (A-6b3), (A-6b4), (A-6b5), (A-6b6), (A-6b7), (A-6b8), (A-6b9), (A-6b10), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b11) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b7), (A-6b8), (A-6b9), (A-6b10), (A-6b12), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b12) and (2) compounds of any of structural formulae (A-6b1), (A-6b2), (A-6b3), (A-6b4), (A-6b5), (A-6b6), (A-6b7), (A-6b8), (A-6b9), (A-6b10), (A-6b11), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b12) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b7), (A-6b8), (A-6b9), (A-6b10), (A-6b11), and (A-6b13). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b13) and (2) compounds of any of structural formulae (A-6b1), (A-6b2), (A-6b3), (A-6b4), (A-6b5), (A-6b6), (A-6b7), (A-6b8), (A-6b9), (A-6b10), (A-6b11), and (A-6b12). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b13) and (2) compounds of up to 12 (e.g., 1, 2, 3, 4, 5, 6, 7, 8, 9, 10, 11, or 12) of structural formulae (A-6b1), (A-6b2), (A-6b3), (A-6b4), (A-6b5), (A-6b6), (A-6b7), (A-6b8), (A-6b9), (A-6b10), (A-6b11), and (A-6b12). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b13) and (2) compounds of any of structural formulae (A-6b1), (A-6b2), (A-6b3), (A-6b4), (A-6b5), (A-6b6), (A-6b7), (A-6b8), (A-6b9), (A-6b10), (A-6b11), or (A-6b12). In other embodiments, such compounds are specifically excluded from structural formulae (A) and/or (A-6b). Each possible combination is specifically contemplated as if set forth explicitly herein.

Some embodiments specifically include and some embodiments only include (1) compounds of structural formula (A-6b13) and (2) compounds of up to 12 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of structural formulae (A-6b1), (A-6b2), (A-6b3), (A-6b4), (A-6b5), (A-6b6), (A-6b7), (A-6b8), (A-6b9), (A-6b10), (A-6b11), or (A-6b12). In other embodiments, such compounds are specifically excluded from structural formulae (A) and/or (A-6b). Each possible combination is specifically contemplated as if set forth explicitly herein.

Some embodiments specifically include and some embodiments only include compounds which have structural formula (A-7a), which can exist as a mixture of two tautomers:

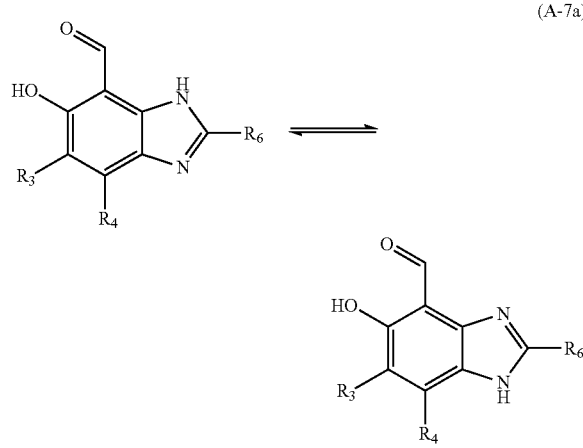

wherein $R_3$, $R_4$, and $R_6$ are as defined in structural formula (A). In other embodiments, such compounds are specifically excluded from structural formula (A).

Structural formula (A-7a1). Some embodiments specifically include and some embodiments only include compounds of structural formula (A-7a) in which $R_3$ is hydrogen. In other embodiments, such compounds are specifically excluded from structural formulae (A) and/or (A-7a).

Structural formula (A-7a2). Some embodiments specifically include and some embodiments only include compounds of structural formula (A-7a) in which $R_4$ is hydrogen. In other embodiments, such compounds are specifically excluded from structural formulae (A) and/or (A-7a).

Structural formula (A-7a3). Some embodiments specifically include and some embodiments only include compounds of structural formula (A-7a) in which $R_3$ and $R_4$ are hydrogen. In other embodiments, such compounds are specifically excluded from structural formulae (A) and/or (A-7a).

Structural formula (A-7a4). Some embodiments include only those compounds of formula (A-7a) in which $R_3$ and $R_4$ are hydrogen. In other embodiments, such compounds are specifically excluded from structural formulae (A) and/or (A-7a).

Structural formula (A-7a5). Some embodiments specifically include and some embodiments only include compounds of structural formula (A-7a) in which $R_6$ is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-7a).

Structural formula (A-7a6). Some embodiments specifically include and some embodiments only include compounds of structural formula (A-7a) in which $R_6$ is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-7a).

Structural formula (A-7a7). Some embodiments specifically include and some embodiments only include compounds of structural formula (A-7a) in which $R_6$ is alkenyl, alkyne, phenyl, or a 5- or 6-membered heteroaryl, each optionally substituted with 1, 2, or 3 substituents independently selected from the group consisting of

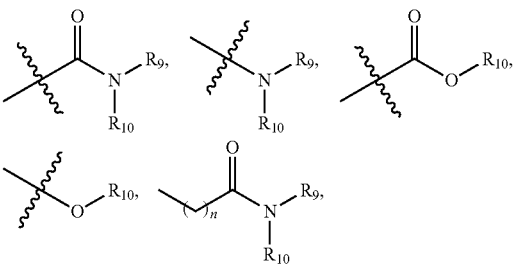

wherein n is 0, 1, or 2;

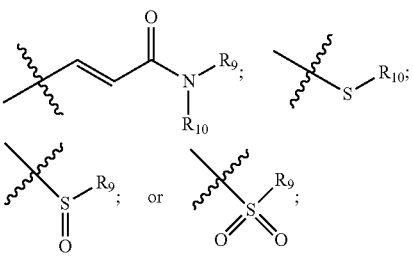

and $R_9$ and $R_{10}$ are as defined in connection with structural formula (A).

In other embodiments, such compounds are specifically excluded from structural formulae (A) and/or (A-7a).

Some embodiments specifically include and some embodiments only include (1) compounds of structural formula (A-7a1) and (2) compounds of any of structural formulae (A-7a2), (A-7a3), (A-7a4), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a1) and (2) compounds of up to 6 (e.g., 1, 2, 3, 4, 5, or 6) of structural formulae (A-7a2), (A-7a3), (A-7a4), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a2) and (2) compounds of any of structural formulae (A-7a1), (A-7a3), (A-7a4), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a2) and (2) compounds of up to 6 (e.g., 1, 2, 3, 4, 5, or 6) of structural formulae (A-7a1), (A-7a3), (A-7a4), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a3) and (2) compounds of any of structural formulae (A-7a1), (A-7a2), (A-7a4), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a3) and (2) compounds of up to 6 (e.g., 1, 2, 3, 4, 5, or 6) of structural formulae (A-7a1), (A-7a2), (A-7a4), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a4) and (2) compounds of any of structural formulae (A-7a1), (A-7a2), (A-7a3), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a4) and (2) compounds of up to 6 (e.g., 1, 2, 3, 4, 5, or 6) of structural formulae (A-7a1), (A-7a2), (A-7a3), (A-7a5), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a5) and (2) compounds of any of structural formulae (A-7a1), (A-7a2), (A-7a3), (A-7a4), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a5) and (2) compounds of up to 6 (e.g., 1, 2, 3, 4, 5, or 6) of structural formulae (A-7a1), (A-7a2), (A-7a3), (A-7a4), (A-7a6), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a6) and (2) compounds of any of structural formulae (A-7a1), (A-7a2), (A-7a3), (A-7a4), (A-7a5), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a6) and (2) compounds of up to 6 (e.g., 1, 2, 3, 4, 5, or 6) of structural formulae (A-7a1), (A-7a2), (A-7a3), (A-7a4), (A-7a5), and (A-7a7). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a7) and (2) compounds of any of structural formulae (A-7a1), (A-7a2), (A-7a3), (A-7a4), (A-7a5), and (A-7a6). In other embodiments, such compounds are specifically excluded from structural formulae (A) and/or (A-7a). Each possible combination is specifically contemplated as if set forth explicitly herein.

Some embodiments specifically include and some embodiments only include (1) compounds of structural formula (A-7a7) and (2) compounds of up to 6 (e.g., 1, 2, 3, 4, 5, or 6) of structural formulae (A-7a1), (A-7a2), (A-7a3), (A-7a4), (A-7a5), and (A-7a6). In other embodiments, such compounds are specifically excluded from structural formulae (A) and/or (A-7a). Each possible combination is specifically contemplated as if set forth explicitly herein.

Some embodiments specifically include and some embodiments only include compounds which have structural formula (A-7b):

(A-7b)

wherein $R_3$, $R_4$, and $R_6$ are as defined in structural formula (A) and $R_7$ is hydrogen or C1-C3 alkyl. In other embodiments, such compounds are specifically excluded from structural formula (A).

Structural formula (A-7b1). Some embodiments specifically include and some embodiments only include compounds of structural formula (A-7b) in which R3 is hydrogen. In other embodiments, such compounds are specifically excluded from structural formulae (A) and/or (A-7b).

Structural formula (A-7b2). Some embodiments specifically include and some embodiments only include compounds of structural formula (A-7b) in which R4 is hydrogen. In other embodiments, such compounds are specifically excluded from structural formulae (A) and/or (A-7b).

Structural formula (A-7b3). Some embodiments specifically include and some embodiments only include compounds of structural formula (A-7b) in which R3 and R4 are hydrogen. In other embodiments, such compounds are specifically excluded from structural formulae (A) and/or (A-7b).

Structural formula (A-7b4). Some embodiments specifically include and some embodiments only include compounds of structural formula (A-7b) in which R7 is C1-C3 alkyl. In other embodiments, such compounds are specifically excluded from structural formulae (A) and/or (A-7b).

Structural formula (A-7b5). Some embodiments specifically include and some embodiments only include compounds of structural formula (A-7b) in which R7 is methyl. In other embodiments, such compounds are specifically excluded from structural formulae (A) and/or (A-7b).

Structural formula (A-7b6). Some embodiments specifically include and some embodiments only include compounds of structural formula (A-7b) in which R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-7b).

Structural formula (A-7b7). Some embodiments specifically include and some embodiments only include compounds of structural formula (A-7b) in which R6 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-7b).

Structural formula (A-7b8). Some embodiments specifically include and some embodiments only include compounds of structural formula (A-7b) in which R6 is alkenyl, alkyne, phenyl, or a 5- or 6-membered heteroaryl, each optionally substituted with 1, 2, or 3 substituents independently selected from the group consisting of

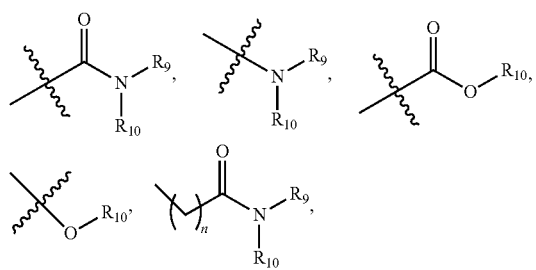

wherein n is 0, 1, or 2;

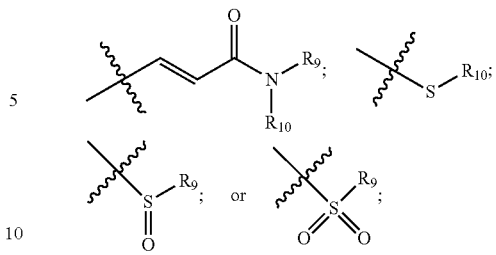

and
R9 and R10 are as defined in connection with structural formula (A). In other embodiments, such compounds are specifically excluded from structural formulae (A) and/or (A-7b).

Structural formula (A-7b9). Some embodiments specifically include and some embodiments only include compounds of structural formula (A-7b) in which R6 is

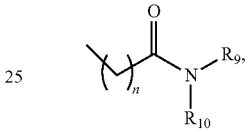

wherein n is 0, 1, or 2; or,

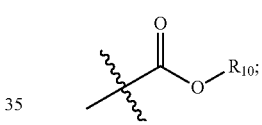

and R9 and R10 are as defined in connection with structural formula (A). In other embodiments, such compounds are specifically excluded from structural formulae (A) and/or (A-7b).

Structural formula (A-7b10). Some embodiments specifically include and some embodiments only include compounds of structural formula (A-7b) in which
a. R3 is hydrogen; and
b. R6 is

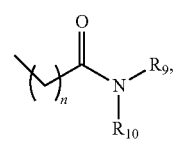

wherein n is 0, 1, or 2; or,

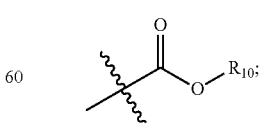

and R9 and R10 are as defined in connection with structural formula (A).

In other embodiments, such compounds are specifically excluded from structural formulae (A) and/or (A-7b).

Structural formula (A-7b11). Some embodiments specifically include and some embodiments only include compounds of structural formula (A-7b) in which
  a. R3 is hydrogen; and
  b. R6 is

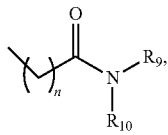

wherein n is 0, 1, or 2; or,

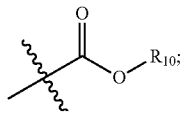

and R9 and R10 are as defined in connection with structural formula (A); and
  c. R7 is C1-C3 alkyl.

In other embodiments, such compounds are specifically excluded from structural formulae (A) and/or (A-7b).

Structural formula (A-7b12). Some embodiments specifically include and some embodiments only include compounds of structural formula (A-7b) in which
  a. R3 is hydrogen; and
  b. R6 is

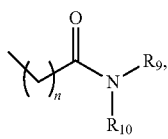

wherein n is 0, 1, or 2; or,

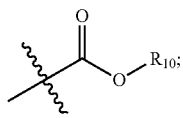

and R9 and R10 are as defined in connection with structural formula (A); and
  c. R7 is methyl.

In other embodiments, such compounds are specifically excluded from structural formulae (A) and/or (A-7b).

Structural formula (A-7b13). Some embodiments specifically include and some embodiments only include compounds of structural formula (A-7b) in which
  a. R4 is hydrogen; and
  b. R6 is

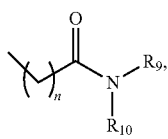

wherein n is 0, 1, or 2; or,

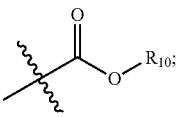

and R9 and R10 are as defined in connection with structural formula (A).

In other embodiments, such compounds are specifically excluded from structural formulae (A) and/or (A-7b).

Structural formula (A-7b14). Some embodiments specifically include and some embodiments only include compounds of structural formula (A-7b) in which
  a. R4 is hydrogen; and
  b. R6 is

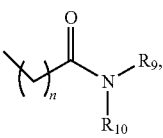

wherein n is 0, 1, or 2; or,

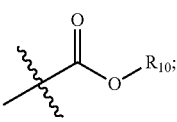

and R9 and R10 are as defined in connection with structural formula (A); and
  c. R7 is C1-C3 alkyl.

In other embodiments, such compounds are specifically excluded from structural formulae (A) and/or (A-7b).

Structural formula (A-7b15). Some embodiments specifically include and some embodiments only include compounds of structural formula (A-7b) in which
  a. R4 is hydrogen; and
  b. R6 is

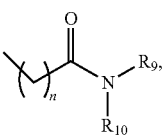

wherein n is 0, 1, or 2; or

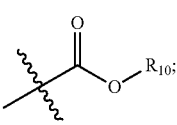

and R9 and R10 are as defined in connection with structural formula (A); and
  c. R7 is methyl.

In other embodiments, such compounds are specifically excluded from structural formulae (A) and/or (A-7b).

Structural formula (A-7b16). Some embodiments specifically include and some embodiments only include compounds of structural formula (A-7b) in which a. R3 and R4 are hydrogen; and
b. R6 is

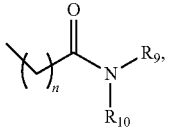

wherein n is 0, 1, or 2; or,

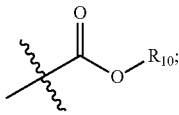

and R9 and R10 are as defined in connection with structural formula (A).

In other embodiments, such compounds are specifically excluded from structural formulae (A) and/or (A-7b).

Structural formula (A-7b17). Some embodiments specifically include and some embodiments only include compounds of structural formula (A-7b) in which
a. R3 and R4 are hydrogen; and
b. R6 is

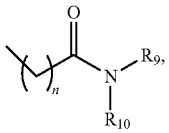

wherein n is 0, 1, or 2; or,

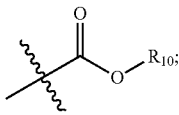

and R9 and R10 are as defined in connection with structural formula (A); and
c. R7 is C1-C3 alkyl.

In other embodiments, such compounds are specifically excluded from structural formulae (A) and/or (A-7b).

Structural formula (A-7b18). Some embodiments specifically include and some embodiments only include compounds of structural formula (A-7b) in which
a. R3 and R4 are hydrogen; and
b. R6 is

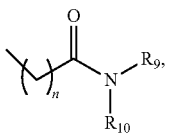

wherein n is 0, 1, or 2; or,

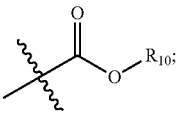

and R9 and R10 are as defined in connection with structural formula (A); and
c. R7 is methyl.

In other embodiments, such compounds are specifically excluded from structural formulae (A) and/or (A-7b).

Some embodiments specifically include and some embodiments only include (1) compounds of structural formula (A-7b1) and (2) compounds of any of structural formulae (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b).

Some embodiments specifically include and some embodiments only include (1) compounds of structural formula (A-7b1) and (2) compounds of up to 17 (e.g., 1, 2, 3, 4, 5, 6, 7, 8, 9, 10, 11, 12, 13, 14, 15, 16, or 17) of structural formulae (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b).

Some embodiments specifically include and some embodiments only include (1) compounds of structural formula (A-7b2) and (2) compounds of any of structural formulae (A-7b1), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b2) and (2) compounds of up to 17 (e.g., 1, 2, 3, 4, 5, 6, 7, 8, 9, 10, 11, 12, 13, 14, 15, 16, or 17) of structural formulae (A-7b1), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b3) and (2) compounds of any of structural formulae (A-7b1), (A-7b2), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b3) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b4) and (2) compounds of any of structural formulae (A-7b1), (A-7b2), (A-7b3), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b4) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b5), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b5) and (2) compounds of any of structural formulae (A-7b1), (A-7b2), (A-7b3), (A-7b4), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b5) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b6), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b6) and (2) compounds of any of structural formulae (A-7b1), (A-7b2), (A-7b3), (A-7b4), (A-7b5), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b6) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b7), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b7) and (2) compounds of any of structural formulae (A-7b1), (A-7b2), (A-7b3), (A-7b4), (A-7b5), (A-7b6), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b7) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b8), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b8) and (2) compounds of any of structural formulae (A-7b1), (A-7b2), (A-7b3), (A-7b4), (A-7b5), (A-7b6), (A-7b7), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b8) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b9), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b9) and (2) compounds of any of structural formulae (A-7b1), (A-7b2), (A-7b3), (A-7b4), (A-7b5), (A-7b6), (A-7b7), (A-7b8), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b9) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b10), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b10) and (2) compounds of any of structural formulae (A-7b1), (A-7b2), (A-7b3), (A-7b4), (A-7b5), (A-7b6), (A-7b7), (A-7b8), (A-7b9), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b10) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b11), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b11) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b11) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b12), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b12) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b12) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b13), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b13) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b13) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b14), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b14) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b14) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b15), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b15) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b15) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b16), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b16) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b16) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b17), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b17) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b17) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7a16), and (A-7b18). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b18) and (2) compounds of any of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), and (A-7b17). In other embodiments, such compounds are specifically excluded from structural formulae (A) and/or (A-7b). Each possible combination is specifically contemplated as if set forth explicitly herein.

Some embodiments specifically include and some embodiments only include (1) compounds of structural formula (A-7b18) and (2) compounds of up to 17 (e.g., 1, 2, 3, 4, 5, 6, 7, 8, 9, 10, 11, 12, 13, 14, 15, 16, or 17) of structural formulae (A-7b1), (A-7b2), (A-7b3), (A-7b4), (A-7b5), (A-7b6), (A-7b7), (A-7b8), (A-7b9), (A-7b10), (A-7b11), (A-7b12), (A-7b13), (A-7b14), (A-7b15), (A-7b16), and (A-7b17). In other embodiments, such compounds are specifically excluded from structural formulae (A) and/or (A-7b). Each possible combination is specifically contemplated as if set forth explicitly herein.

Some embodiments specifically include and some embodiments only include compounds which have structural formula (A-7c):

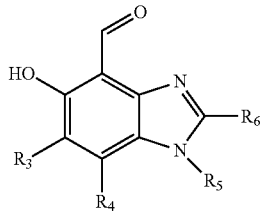

(A-7c)

wherein R3, R4, and R6 are as defined in structural formula (A) and R5 is hydrogen or C1-C3 alkyl. In other embodiments, such compounds are specifically excluded from structural formula (A).

Structural formula (A-7c1). Some embodiments specifically include and some embodiments only include compounds of structural formula (A-7c) in which R3 is hydrogen. In other embodiments, such compounds are specifically excluded from structural formulae (A) and/or (A-7c).

Structural formula (A-7c2). Some embodiments specifically include and some embodiments only include compounds of structural formula (A-7c) in which R4 is hydrogen. In other embodiments, such compounds are specifically excluded from structural formulae (A) and/or (A-7c).

Structural formula (A-7c3). Some embodiments specifically include and some embodiments only include compounds of structural formula (A-7c) in which R3 and R4 are hydrogen. In other embodiments, such compounds are specifically excluded from structural formulae (A) and/or (A-7c).

Structural formula (A-7c4). Some embodiments specifically include and some embodiments only include compounds of structural formula (A-7c) in which R5 is C1-C3 alkyl. In other embodiments, such compounds are specifically excluded from structural formulae (A) and/or (A-7c).

Structural formula (A-7c5). Some embodiments specifically include and some embodiments only include compounds of structural formula (A-7c) in which R5 is methyl. In other embodiments, such compounds are specifically excluded from structural formulae (A) and/or (A-7c).

Structural formula (A-7c6). Some embodiments specifically include and some embodiments only include compounds of structural formula (A-7c) in which R6 is hydrogen; halogen; —CN; optionally substituted alkyl; or optionally substituted alkoxyl. Optional substituents for the alkyl and for the alkoxyl are (1) a C1-C6 hydrocarbon chain containing a nitrogen or oxygen atom and optionally substituted with a C1-C3 perfluoroalkyl, and (2) a cycloalkyl which may contain 1 or 2 heteroatoms selected from N, O, and S, and which is optionally substituted with a C1-C3 perfluoroalkyl. In other embodiments, such compounds are specifically excluded from structural formulae (A) and/or (A-7c).

Structural formula (A-7c7). Some embodiments specifically include and some embodiments only include compounds of structural formula (A-7c) in which R6 is a side chain selected from the group consisting of alkyl, perfluoroalkyl, alkoxyl, hydroxylalkyl, alkoxylalkyl, and perfluoroalkoxyl, each optionally substituted with 1-3 substituents selected from halogen, —CN, alkyl, perfluoroalkyl, alkoxy, hydroxylalkyl, alkoxylalkyl, and perfluoroalkoxyl. In other embodiments, such compounds are specifically excluded from structural formulae (A) and/or (A-7c).

Structural formula (A-7c8). Some embodiments specifically include and some embodiments only include compounds of structural formula (A-7c) in which R6 is alkenyl, alkyne, phenyl, or a 5- or 6-membered heteroaryl, each optionally substituted with 1, 2, or 3 substituents independently selected from the group consisting of

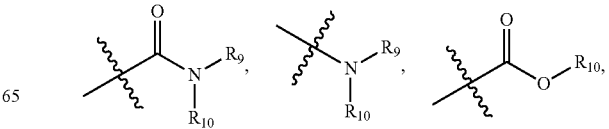

-continued

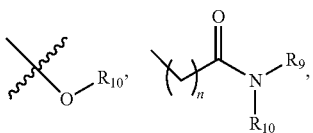

wherein n is 0, 1, or 2;

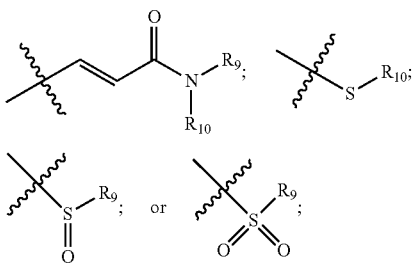

and

R9 and R10 are as defined in connection with structural formula (A). In other embodiments, such compounds are specifically excluded from structural formulae (A) and/or (A-7c).

Structural formula (A-7c9). Some embodiments specifically include and some embodiments only include compounds of structural formula (A-7c) in which R6 is

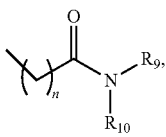

wherein n is 0, 1, or 2; or,

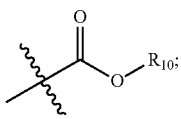

and R9 and R10 are as defined in connection with structural formula (A). In other embodiments, such compounds are specifically excluded from structural formulae (A) and/or (A-7c).

Structural formula (A-7c10). Some embodiments specifically include and some embodiments only include compounds of structural formula (A-7c) in which
a. R3 is hydrogen; and
b. R6 is,

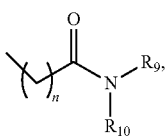

wherein n is 0, 1, or 2; or,

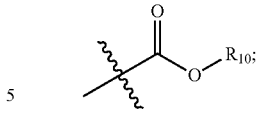

and R9 and R10 are as defined in connection with structural formula (A).

In other embodiments, such compounds are specifically excluded from structural formulae (A) and/or (A-7c).

Structural formula (A-7c11). Some embodiments specifically include and some embodiments only include compounds of structural formula (A-7c) in which
a. R3 is hydrogen; and
b. R6 is

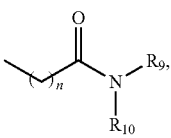

wherein n is 0, 1, or 2; or,

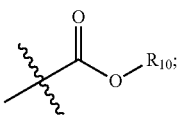

and R9 and R10 are as defined in connection with structural formula (A); and
c. R5 is C1-C3 alkyl.

In other embodiments, such compounds are specifically excluded from structural formulae (A) and/or (A-7c).

Structural formula (A-7c12). Some embodiments specifically include and some embodiments only include compounds of structural formula (A-7c) in which
a. R3 is hydrogen; and
b. R6 is

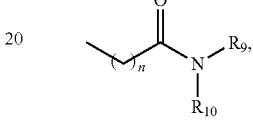

wherein n is 0, 1, or 2; or,

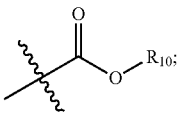

and R9 and R10 are as defined in connection with structural formula (A); and
c. R5 is methyl.

In other embodiments, such compounds are specifically excluded from structural formulae (A) and/or (A-7c).

Structural formula (A-7c13). Some embodiments specifically include and some embodiments only include compounds of structural formula (A-7c) in which a. R4 is hydrogen; and
b. R6 is

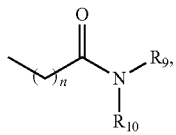

wherein n is 0, 1, or 2; or

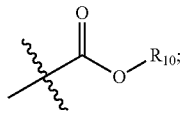

and R9 and R10 are as defined in connection with structural formula (A).

In other embodiments, such compounds are specifically excluded from structural formulae (A) and/or (A-7c).

Structural formula (A-7c14). Some embodiments specifically include and some embodiments only include compounds of structural formula (A-7c) in which
a. R4 is hydrogen; and
b. R6 is

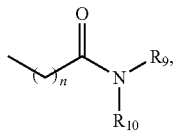

wherein n is 0, 1, or 2; or,

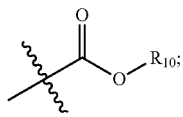

and R9 and R10 are as defined in connection with structural formula (A); and
c. R5 is C1-C3 alkyl.

In other embodiments, such compounds are specifically excluded from structural formulae (A) and/or (A-7c).

Structural formula (A-7c15). Some embodiments specifically include and some embodiments only include compounds of structural formula (A-7c) in which
a. R4 is hydrogen; and
b. R6 is

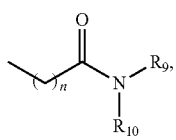

wherein n is 0, 1, or 2; or,

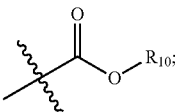

and R9 and R10 are as defined in connection with structural formula (A); and
c. R5 is methyl.

In other embodiments, such compounds are specifically excluded from structural formulae (A) and/or (A-7c).

Structural formula (A-7c16). Some embodiments specifically include and some embodiments only include compounds of structural formula (A-7c) in which
a. R3 and R4 are hydrogen; and
b. R6 is

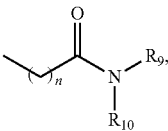

wherein n is 0, 1, or 2; or

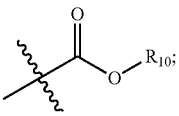

and R9 and R10 are as defined in connection with structural formula (A).

In other embodiments, such compounds are specifically excluded from structural formulae (A) and/or (A-7c).

Structural formula (A-7c17). Some embodiments specifically include and some embodiments only include compounds of structural formula (A-7c) in which
a. R3 and R4 are hydrogen; and
b. R6 is

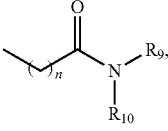

wherein n is 0, 1, or 2; or

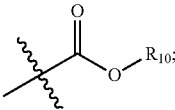

and R9 and R10 are as defined in connection with structural formula (A); and
c. R5 is C1-C3 alkyl.

In other embodiments, such compounds are specifically excluded from structural formulae (A) and/or (A-7c).

Structural formula (A-7c18). Some embodiments specifically include and some embodiments only include compounds of structural formula (A-7c) in which a. R3 and R4 are hydrogen; and
b. R6 is $$\text{structure: } (CH_2)_n\text{-C(=O)-N(R_9)(R_{10})},$$

wherein n is 0, 1, or 2; or, $$\text{structure: -C(=O)-O-R_{10};}$$

and R9 and R10 are as defined in connection with structural formula (A); and c. R5 is methyl.

In other embodiments, such compounds are specifically excluded from structural formulae (A) and/or (A-7c).

Some embodiments specifically include and some embodiments only include (1) compounds of structural formula (A-7c1) and (2) compounds of any of structural formulae (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c).

Some embodiments specifically include and some embodiments only include (1) compounds of structural formula (A-7c1) and (2) compounds of up to 17 (e.g., 1, 2, 3, 4, 5, 6, 7, 8, 9, 10, 11, 12, 13, 14, 15, 16, or 17) of structural formulae (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c).

Some embodiments specifically include and some embodiments only include (1) compounds of structural formula (A-7c2) and (2) compounds of any of structural formulae (A-7c1), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c2) and (2) compounds of up to 17 (e.g., 1, 2, 3, 4, 5, 6, 7, 8, 9, 10, 11, 12, 13, 14, 15, 16, or 17) of structural formulae (A-7c1), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c3) and (2) compounds of any of structural formulae (A-7c1), (A-7c2), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c3) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c4) and (2) compounds of any of structural formulae (A-7c1), (A-7c2), (A-7c3), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c4) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c5), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c5) and (2) compounds of any of structural formulae (A-7c1), (A-7c2), (A-7c3), (A-7c4), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c5) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c6), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c6) and (2) compounds of any of structural formulae (A-7c1), (A-7c2), (A-7c3), (A-7c4), (A-7c5), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c6) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c7), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c7) and (2) compounds of any of structural formulae (A-7c1), (A-7c2), (A-7c3), (A-7c4), (A-7c5), (A-7c6), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c7) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c8), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c8) and (2) compounds of any of structural formulae (A-7c1), (A-7c2), (A-7c3), (A-7c4), (A-7c5), (A-7c6), (A-7c7), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c8) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c9), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c9) and (2) compounds of any of structural formulae (A-7c1), (A-7c2), (A-7c3), (A-7c4), (A-7c5), (A-7c6), (A-7c7), (A-7c8), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c9) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c10), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c10) and (2) compounds of any of structural formulae (A-7c1), (A-7c2), (A-7c3), (A-7c4), (A-7c5), (A-7c6), (A-7c7), (A-7c8), (A-7c9), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c10) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c11), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c11) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c11) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c12), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c12) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c12) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c13), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c13) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c13) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c14), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c14) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c14) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c15), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c15) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c15) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c16), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c16) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c16) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c17), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c17) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c17) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7a16), and (A-7c18). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c18) and (2) compounds of any of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), and (A-7c17). In other embodiments, such compounds are specifically excluded from structural formulae (A) and/or (A-7c). Each possible combination is specifically contemplated as if set forth explicitly herein.

Some embodiments specifically include and some embodiments only include (1) compounds of structural formula (A-7c18) and (2) compounds of up to 17 (e.g., 1, 2, 3, 4, 5, 6, 7, 8, 9, 10, 11, 12, 13, 14, 15, 16, or 17) of structural formulae (A-7c1), (A-7c2), (A-7c3), (A-7c4), (A-7c5), (A-7c6), (A-7c7), (A-7c8), (A-7c9), (A-7c10), (A-7c11), (A-7c12), (A-7c13), (A-7c14), (A-7c15), (A-7c16), and (A-7c17). In other embodiments, such compounds are specifically excluded from structural formulae (A) and/or (A-7c). Each possible combination is specifically contemplated as if set forth explicitly herein.

Some embodiments specifically include and some embodiments only include compounds which have structural formula (A-8a):

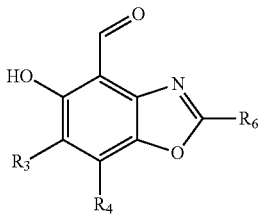

(A-8a)

wherein:

R3, R4, and R6 are as defined in structural formula (A). In other embodiments, such compounds are specifically excluded from structural formula (A).

Structural formula (A-8a1). Some embodiments specifically include and some embodiments only include compounds of structural formula (A-8a) in which R3 is hydrogen. In other embodiments, such compounds are specifically excluded from structural formulae (A) and/or (A-8a).

Structural formula (A-8a2). Some embodiments specifically include and some embodiments only include compounds of structural formula (A-8a) in which R4 is hydrogen. In other embodiments, such compounds are specifically excluded from structural formulae (A) and/or (A-8a).

Structural formula (A-8a3). Some embodiments specifically include and some embodiments only include compounds of structural formula (A-8a) in which R3 and R4 are hydrogen. In other embodiments, such compounds are specifically excluded from structural formulae (A) and/or (A-8a).

Structural formula (A-8a4). Some embodiments specifically include and some embodiments only include compounds of structural formula (A-8a) in which
a. R3 and R4 are hydrogen and
b. R6 is hydrogen, alkyl,

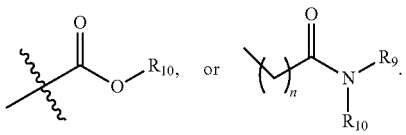

In other embodiments, such compounds are specifically excluded from structural formulae (A) and/or (A-8a).

Structural formula (A-8a5). Some embodiments specifically include and some embodiments only include compounds of structural formula (A-8a) in which
a. R3 and R4 are hydrogen and
b. R6 is alkyl.

In other embodiments, such compounds are specifically excluded from structural formulae (A) and/or (A-8a).

Structural formula (A-8a6). Some embodiments specifically include and some embodiments only include compounds of structural formula (A-8a) in which
a. R3 and R4 are hydrogen and
b. R6 is

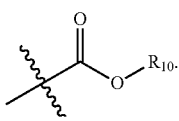

In other embodiments, such compounds are specifically excluded from structural formulae (A) and/or (A-8a).

Structural formula (A-8a7). Some embodiments specifically include and some embodiments only include compounds of structural formula (A-8a) in which
a. R3 and R4 are hydrogen,
b. R6 is

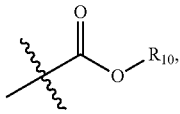

and
c. R10 is alkyl.

In other embodiments, such compounds are specifically excluded from structural formulae (A) and/or (A-8a).

Structural formula (A-8a8). Some embodiments specifically include and some embodiments only include compounds of structural formula (A-8a) in which
a. R3 and R4 are hydrogen and
b. R6 is

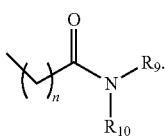

In other embodiments, such compounds are specifically excluded from structural formulae (A) and/or (A-8a).

Structural formula (A-8a9). Some embodiments specifically include and some embodiments only include compounds of structural formula (A-8a) in which
a. R3 and R4 are hydrogen and
b. R6 is

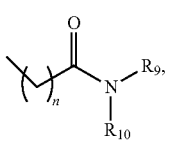

and n is 2.

In other embodiments, such compounds are specifically excluded from structural formulae (A) and/or (A-8a).

Structural formula (A-8a10). Some embodiments specifically include and some embodiments only include compounds of structural formula (A-8a) in which
a. R3 and R4 are hydrogen and
b. R6 is

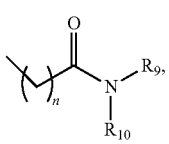

and
c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-8a).

Structural formula (A-8a11). Some embodiments specifically include and some embodiments only include compounds of structural formula (A-8a) in which
 a. R3 and R4 are hydrogen and
 b. R6 is $$\underset{R_{10}}{\overset{O}{\underset{|}{\text{\Large{$\wedge\wedge$}}\!\!\!\!-\!\!(CH_2)_n\!-\!\!C\!-\!N\!-\!R_9,}}}$$

c. R9 is alkyl or alkoxylalkyl, and
 d. R10 is hydrogen.

In other embodiments, such compounds are specifically excluded from structural formulae (A) and/or (A-8a).

Some embodiments specifically include and some embodiments only include (1) compounds of structural formula (A-8a1) and (2) compounds of any of structural formulae (A-8a2), (A-8a3), (A-8a4), (A-8a5), (A-8a6), (A-8a7), (A-8a8), (A-8a9), (A-8a10), and (A-8a11). In other embodiments, such compounds are specifically excluded from structural formulae (A) and/or (A-8a).

Some embodiments specifically include and some embodiments only include (1) compounds of structural formula (A-8a1) and (2) compounds of up to 10 (e.g., 1, 2, 3, 4, 5, 6, 7, 8, 9, or 10) of structural formulae (A-8a2), (A-8a3), (A-8a4), (A-8a5), (A-8a6), (A-8a7), (A-8a8), (A-8a9), (A-8a10), and (A-8a11). In other embodiments, such compounds are specifically excluded from structural formulae (A) and/or (A-8a).

Some embodiments specifically include and some embodiments only include (1) compounds of structural formula (A-8a2) and (2) compounds of any of structural formulae (A-8a1), (A-8a3), (A-8a4), (A-8a5), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a2) and (2) compounds of up to 10 (e.g., 1, 2, 3, 4, 5, 6, 7, 8, 9, or 10) of structural formulae (A-8a1), (A-8a3), (A-8a4), (A-8a5), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a3) and (2) compounds of any of structural formulae (A-8a1), (A-8a2), (A-8a4), (A-8a5), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a3) and (2) compounds of up to 10 (e.g., 1, 2, 3, 4, 5, 6, 7, 8, 9, or 10) of structural formulae (A-8a1), (A-8a2), (A-8a4), (A-8a5), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a4) and (2) compounds of any of structural formulae (A-8a1), (A-8a2), (A-8a3), (A-8a5), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a4) and (2) compounds of up to 10 (e.g., 1, 2, 3, 4, 5, 6, 7, 8, 9, or 10) of structural formulae (A-8a1), (A-8a2), (A-8a3), (A-8a5), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a5) and (2) compounds of any of structural formulae (A-8a1), (A-8a2), (A-8a3), (A-8a4), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a5) and (2) compounds of up to 10 (e.g., 1, 2, 3, 4, 5, 6, 7, 8, 9, or 10) of structural formulae (A-8a1), (A-8a2), (A-8a3), (A-8a4), (A-8a6), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a6) and (2) compounds of any of structural formulae (A-8a1), (A-8a2), (A-8a3), (A-8a4), (A-8a5), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a6) and (2) compounds of up to 10 (e.g., 1, 2, 3, 4, 5, 6, 7, 8, 9, or 10) of structural formulae (A-8a1), (A-8a2), (A-8a3), (A-8a4), (A-8a5), (A-8a7), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a7) and (2) compounds of any of structural formulae (A-8a1), (A-8a2), (A-8a3), (A-8a4), (A-8a5), (A-8a6), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a7) and (2) compounds of up to 10 (e.g., 1, 2, 3, 4, 5, 6, 7, 8, 9, or 10) of structural formulae (A-8a1), (A-8a2), (A-8a3), (A-8a4), (A-8a5), (A-8a6), (A-8a8), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a8) and (2) compounds of any of structural formulae (A-8a1), (A-8a2), (A-8a3), (A-8a4), (A-8a5), (A-8a6), (A-8a7), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a8) and (2) compounds of up to 10 (e.g., 1, 2, 3, 4, 5, 6, 7, 8, 9, or 10) of structural formulae (A-8a1), (A-8a2), (A-8a3), (A-8a4), (A-8a5), (A-8a6), (A-8a7), (A-8a9), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a9) and (2) compounds of any of structural formulae (A-8a1), (A-8a2), (A-8a3), (A-8a4), (A-8a5), (A-8a6), (A-8a7), (A-8a8), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a9) and (2) compounds of up to 10 (e.g., 1, 2, 3, 4, 5, 6, 7, 8, 9, or 10) of structural formulae (A-8a1), (A-8a2), (A-8a3), (A-8a4), (A-8a5), (A-8a6), (A-8a7), (A-8a8), (A-8a10), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a10) and (2) compounds of any of structural formulae (A-8a1), (A-8a2), (A-8a3), (A-8a4), (A-8a5), (A-8a6), (A-8a7), (A-8a8), (A-8a9), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a10) and (2) compounds of up to 10 (e.g., 1, 2, 3, 4, 5, 6, 7, 8, 9, or 10) of structural formulae (A-8a1), (A-8a2), (A-8a3), (A-8a4), (A-8a5), (A-8a6), (A-8a7), (A-8a8), (A-8a9), and (A-8a11). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a11) and (2) compounds of any of structural formulae (A-8a1), (A-8a2), (A-8a3), (A-8a4), (A-8a5), (A-8a6), (A-8a7), (A-8a8), (A-8a9), and (A-8a10). In other embodiments, such compounds are specifically excluded from structural formulae (A) and/or (A-8a). Each possible combination is specifically contemplated as if set forth explicitly herein.

Some embodiments specifically include and some embodiments only include (1) compounds of structural formula (A-8a11) and (2) compounds of up to 10 (e.g., 1, 2, 3, 4, 5, 6, 7, 8, 9, or 10) of structural formulae (A-8a1), (A-8a2), (A-8a3), (A-8a4), (A-8a5), (A-8a6), (A-8a7), (A-8a8), (A-8a9), and (A-8a10). In other embodiments, such compounds are specifically excluded from structural formulae (A) and/or (A-8a). Each possible combination is specifically contemplated as if set forth explicitly herein.

Some embodiments specifically include and some embodiments only include compounds which have structural formula (A-8b):

(A-8b)

wherein:
R3, R4, and R6 are as defined in structural formula (A). In other embodiments, such compounds are specifically excluded from structural formula (A).

Structural formula (A-8b1). Some embodiments specifically include and some embodiments only include compounds of structural formula (A-8b) in which R3 is hydrogen. In other embodiments, such compounds are specifically excluded from structural formulae (A) and/or (A-8b).

Structural formula (A-8b2). Some embodiments specifically include and some embodiments only include compounds of structural formula (A-8b) in which R4 is hydrogen. In other embodiments, such compounds are specifically excluded from structural formulae (A) and/or (A-8b).

Structural formula (A-8b3). Some embodiments specifically include and some embodiments only include compounds of structural formula (A-8b) in which R3 and R4 are hydrogen. In other embodiments, such compounds are specifically excluded from structural formulae (A) and/or (A-8b).

Structural formula (A-8b4). Some embodiments specifically include and some embodiments only include compounds of structural formula (A-8b) in which
  a. R3 and R4 are hydrogen and
  b. R6 is hydrogen, alkyl, In other embodiments, such compounds are specifically excluded from structural formulae (A) and/or (A-8b).

Structural formula (A-8b5). Some embodiments specifically include and some embodiments only include compounds of structural formula (A-8b) in which
  a. R3 and R4 are hydrogen and
  b. R6 is alkyl.

In other embodiments, such compounds are specifically excluded from structural formulae (A) and/or (A-8b).

Structural formula (A-8b6). Some embodiments specifically include and some embodiments only include compounds of structural formula (A-8b) in which
a. R3 and R4 are hydrogen and
b. R6 is

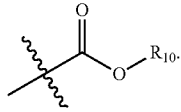

In other embodiments, such compounds are specifically excluded from structural formulae (A) and/or (A-8b).

Structural formula (A-8b7). Some embodiments specifically include and some embodiments only include compounds of structural formula (A-8b) in which
a. R3 and R4 are hydrogen,
b. R6 is

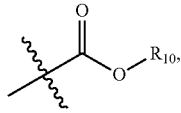

and
c. R10 is alkyl.

In other embodiments, such compounds are specifically excluded from structural formulae (A) and/or (A-8b).

Structural formula (A-8b8). Some embodiments specifically include and some embodiments only include compounds of structural formula (A-8b) in which
a. R3 and R4 are hydrogen and
b. R6 is

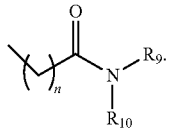

In other embodiments, such compounds are specifically excluded from structural formulae (A) and/or (A-8b).

Structural formula (A-8b9). Some embodiments specifically include and some embodiments only include compounds of structural formula (A-8b) in which
a. R3 and R4 are hydrogen and
b. R6 is

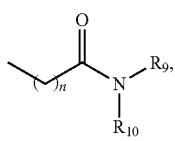

and n is 2.

In other embodiments, such compounds are specifically excluded from structural formulae (A) and/or (A-8b).

Structural formula (A-8b10). Some embodiments specifically include and some embodiments only include compounds of structural formula (A-8b) in which
a. R3 and R4 are hydrogen and
b. R6 is

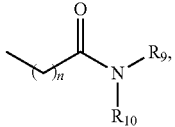

and
c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-8b).

Structural formula (A-8b11). Some embodiments specifically include and some embodiments only include compounds of structural formula (A-8b) in which
a. R3 and R4 are hydrogen and
b. R6 is

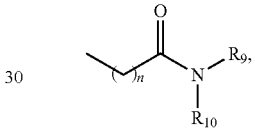

c. R9 is alkyl or alkoxylalkyl, and
d. R10 is hydrogen.

In other embodiments, such compounds are specifically excluded from structural formulae (A) and/or (A-8b).

Some embodiments specifically include and some embodiments only include (1) compounds of structural formula (A-8b1) and (2) compounds of any of structural formulae (A-8b2), (A-8b3), (A-8b4), (A-8b5), (A-8b6), (A-8b7), (A-8b8), (A-8b9), (A-8b10), and (A-8b11). In other embodiments, such compounds are specifically excluded from structural formulae (A) and/or (A-8b).

Some embodiments specifically include and some embodiments only include (1) compounds of structural formula (A-8b1) and (2) compounds of up to 10 (e.g., 1, 2, 3, 4, 5, 6, 7, 8, 9, or 10) of structural formulae (A-8b2), (A-8b3), (A-8b4), (A-8b5), (A-8b6), (A-8b7), (A-8b8), (A-8b9), (A-8b10), and (A-8b11). In other embodiments, such compounds are specifically excluded from structural formulae (A) and/or (A-8b).

Some embodiments specifically include and some embodiments only include (1) compounds of structural formula (A-8b2) and (2) compounds of any of structural formulae (A-8b1), (A-8b3), (A-8b4), (A-8b5), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b2) and (2) compounds of up to 10 (e.g., 1, 2, 3, 4, 5, 6, 7, 8, 9, or 10) of structural formulae (A-8b1), (A-8b3), (A-8b4), (A-8b5), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b3) and (2) compounds of any of structural formulae (A-8b1), (A-8b2), (A-8b4), (A-8b5), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b3) and (2) compounds of up to 10 (e.g., 1, 2, 3, 4, 5, 6, 7, 8, 9, or 10) of structural formulae (A-8b1), (A-8b2), (A-8b4), (A-8b5), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b4) and (2) compounds of any of structural formulae (A-8b1), (A-8b2), (A-8b3), (A-8b5), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b4) and (2) compounds of up to 10 (e.g., 1, 2, 3, 4, 5, 6, 7, 8, 9, or 10) of structural formulae (A-8b1), (A-8b2), (A-8b3), (A-8b5), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b5) and (2) compounds of any of structural formulae (A-8b1), (A-8b2), (A-8b3), (A-8b4), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b5) and (2) compounds of up to 10 (e.g., 1, 2, 3, 4, 5, 6, 7, 8, 9, or 10) of structural formulae (A-8b1), (A-8b2), (A-8b3), (A-8b4), (A-8b6), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b6) and (2) compounds of any of structural formulae (A-8b1), (A-8b2), (A-8b3), (A-8b4), (A-8b5), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b6) and (2) compounds of up to 10 (e.g., 1, 2, 3, 4, 5, 6, 7, 8, 9, or 10) of structural formulae (A-8b1), (A-8b2), (A-8b3), (A-8b4), (A-8b5), (A-8b7), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b7) and (2) compounds of any of structural formulae (A-8b1), (A-8b2), (A-8b3), (A-8b4), (A-8b5), (A-8b6), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b7) and (2) compounds of up to 10 (e.g., 1, 2, 3, 4, 5, 6, 7, 8, 9, or 10) of structural formulae (A-8b1), (A-8b2), (A-8b3), (A-8b4), (A-8b5), (A-8b6), (A-8b8), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b8) and (2) compounds of any of structural formulae (A-8b1), (A-8b2), (A-8b3), (A-8b4), (A-8b5), (A-8b6), (A-8b7), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b8) and (2) compounds of up to 10 (e.g., 1, 2, 3, 4, 5, 6, 7, 8, 9, or 10) of structural formulae (A-8b1), (A-8b2), (A-8b3), (A-8b4), (A-8b5), (A-8b6), (A-8b7), (A-8b9), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b9) and (2) compounds of any of structural formulae (A-8b1), (A-8b2), (A-8b3), (A-8b4), (A-8b5), (A-8b6), (A-8b7), (A-8b8), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b9) and (2) compounds of up to 10 (e.g., 1, 2, 3, 4, 5, 6, 7, 8, 9, or 10) of structural formulae (A-8b1), (A-8b2), (A-8b3), (A-8b4), (A-8b5), (A-8b6), (A-8b7), (A-8b8), (A-8b10), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b10) and (2) compounds of any of structural formulae (A-8b1), (A-8b2), (A-8b3), (A-8b4), (A-8b5), (A-8b6), (A-8b7), (A-8b8), (A-8b9), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b10) and (2) compounds of up to 10 (e.g., 1, 2, 3, 4, 5, 6, 7, 8, 9, or 10) of structural formulae (A-8b1), (A-8b2), (A-8b3), (A-8b4), (A-8b5), (A-8b6), (A-8b7), (A-8b8), (A-8b9), and (A-8b11). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b11) and (2) compounds of any of structural formulae (A-8b1), (A-8b2), (A-8b3), (A-8b4), (A-8b5), (A-8b6), (A-8b7), (A-8b8), (A-8b9), and (A-8b10). In other embodiments, such compounds are specifically excluded from structural formulae (A) and/or (A-8b). Each possible combination is specifically contemplated as if set forth explicitly herein.

Some embodiments specifically include and some embodiments only include (1) compounds of structural formula (A-8b11) and (2) compounds of up to 10 (e.g., 1, 2, 3, 4, 5, 6, 7, 8, 9, or 10) of structural formulae (A-8b1), (A-8b2), (A-8b3), (A-8b4), (A-8b5), (A-8b6), (A-8b7), (A-8b8), (A-8b9), and (A-8b10). In other embodiments, such compounds are specifically excluded from structural formulae (A) and/or (A-8b). Each possible combination is specifically contemplated as if set forth explicitly herein.

Some embodiments specifically include and some embodiments only include compounds which have structural formula (A-9a):

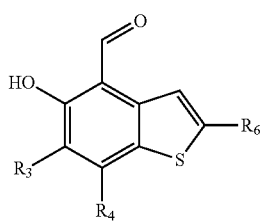

(A-9a)

wherein:
R3, R4, and R6 are as defined in structural formula (A). In other embodiments, such compounds are specifically excluded from structural formula (A).

Structural formula (A-9a1). Some embodiments specifically include and some embodiments only include compounds of structural formula (A-9a) in which R3 is hydrogen. In other embodiments, such compounds are specifically excluded from structural formulae (A) and/or (A-9a).

Structural formula (A-9a2). Some embodiments specifically include and some embodiments only include compounds of structural formula (A-9a) in which R4 is hydrogen. In other embodiments, such compounds are specifically excluded from structural formulae (A) and/or (A-9a).

Structural formula (A-9a3). Some embodiments specifically include and some embodiments only include compounds of structural formula (A-9a) in which R3 and R4 are hydrogen. In other embodiments, such compounds are specifically excluded from structural formulae (A) and/or (A-9a).

Structural formula (A-9a4). Some embodiments specifically include and some embodiments only include compounds of structural formula (A-9a) in which
a. R3 and R4 are hydrogen and
b. R6 is hydrogen, alkyl,

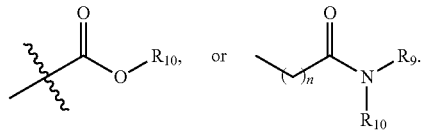

In other embodiments, such compounds are specifically excluded from structural formulae (A) and/or (A-9a).

Structural formula (A-9a5). Some embodiments specifically include and some embodiments only include compounds of structural formula (A-9a) in which
a. R3 and R4 are hydrogen and
b. R6 is alkyl.

In other embodiments, such compounds are specifically excluded from structural formulae (A) and/or (A-9a).

Structural formula (A-9a6). Some embodiments specifically include and some embodiments only include compounds of structural formula (A-9a) in which
a. R3 and R4 are hydrogen and
b. R6 is

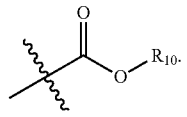

In other embodiments, such compounds are specifically excluded from structural formulae (A) and/or (A-9a).

Structural formula (A-9a7). Some embodiments specifically include and some embodiments only include compounds of structural formula (A-9a) in which
a. R3 and R4 are hydrogen,
b. R6 is

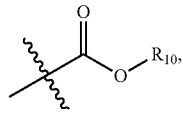

and
c. R10 is alkyl.

In other embodiments, such compounds are specifically excluded from structural formulae (A) and/or (A-9a).

Structural formula (A-9a8). Some embodiments specifically include and some embodiments only include compounds of structural formula (A-9a) in which
a. R3 and R4 are hydrogen and
b. R6 is

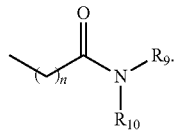

In other embodiments, such compounds are specifically excluded from structural formulae (A) and/or (A-9a).

Structural formula (A-9a9). Some embodiments specifically include and some embodiments only include compounds of structural formula (A-9a) in which
   a. R3 and R4 are hydrogen and
   b. R6 is

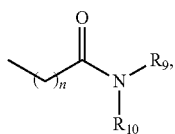

and n is 2.

In other embodiments, such compounds are specifically excluded from structural formulae (A) and/or (A-9a).

Structural formula (A-9a10). Some embodiments specifically include and some embodiments only include compounds of structural formula (A-9a) in which
   a. R3 and R4 are hydrogen and
   b. R6 is

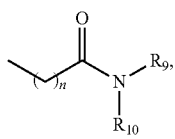

and
   c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-9a).

Structural formula (A-9a11). Some embodiments include only those compounds of structural formula (A-9a) in which
   a. R3 and R4 are hydrogen and
   b. R6 is

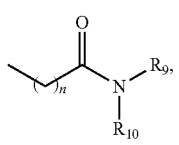

c. R9 is alkyl or alkoxylalkyl, and
   d. R10 is hydrogen.

In other embodiments, such compounds are specifically excluded from structural formulae (A) and/or (A-9a).

Some embodiments specifically include and some embodiments only include (1) compounds of structural formula (A-9a1) and (2) compounds of any of structural formulae (A-9a2), (A-9a3), (A-9a4), (A-9a5), (A-9a6), (A-9a7), (A-9a8), (A-9a9), (A-9a10), and (A-9a11). In other embodiments, such compounds are specifically excluded from structural formulae (A) and/or (A-9a).

Some embodiments specifically include and some embodiments only include (1) compounds of structural formula (A-9a1) and (2) compounds of up to 10 (e.g., 1, 2, 3, 4, 5, 6, 7, 8, 9, or 10) of structural formulae (A-9a2), (A-9a3), (A-9a4), (A-9a5), (A-9a6), (A-9a7), (A-9a8), (A-9a9), (A-9a10), and (A-9a11). In other embodiments, such compounds are specifically excluded from structural formulae (A) and/or (A-9a).

Some embodiments specifically include and some embodiments only include (1) compounds of structural formula (A-9a2) and (2) compounds of any of structural formulae (A-9a1), (A-9a3), (A-9a4), (A-9a5), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a2) and (2) compounds of up to 10 (e.g., 1, 2, 3, 4, 5, 6, 7, 8, 9, or 10) of structural formulae (A-9a1), (A-9a3), (A-9a4), (A-9a5), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a3) and (2) compounds of any of structural formulae (A-9a1), (A-9a2), (A-9a4), (A-9a5), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a3) and (2) compounds of up to 10 (e.g., 1, 2, 3, 4, 5, 6, 7, 8, 9, or 10) of structural formulae (A-9a1), (A-9a2), (A-9a4), (A-9a5), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a4) and (2) compounds of any of structural formulae (A-9a1), (A-9a2), (A-9a3), (A-9a5), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a4) and (2) compounds of up to 10 (e.g., 1, 2, 3, 4, 5, 6, 7, 8, 9, or 10) of structural formulae (A-9a1), (A-9a2), (A-9a3), (A-9a5), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a5) and (2) compounds of any of structural formulae (A-9a1), (A-9a2), (A-9a3), (A-9a4), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a5) and (2) compounds of up to 10 (e.g., 1, 2, 3, 4, 5, 6, 7, 8, 9, or 10) of structural formulae (A-9a1), (A-9a2), (A-9a3), (A-9a4), (A-9a6), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a6) and (2) compounds of any of structural formulae (A-9a1), (A-9a2), (A-9a3), (A-9a4), (A-9a5), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a6) and (2) compounds of up to 10 (e.g., 1, 2, 3, 4, 5, 6, 7, 8, 9, or 10) of structural formulae (A-9a1), (A-9a2), (A-9a3), (A-9a4), (A-9a5), (A-9a7), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a7) and (2) compounds of any of structural formulae (A-9a1), (A-9a2), (A-9a3), (A-9a4), (A-9a5), (A-9a6), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a7) and (2) compounds of up to 10 (e.g., 1, 2, 3, 4, 5, 6, 7, 8, 9, or 10) of structural formulae (A-9a1), (A-9a2), (A-9a3), (A-9a4), (A-9a5), (A-9a6), (A-9a8), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a8) and (2) compounds of any of structural formulae (A-9a1), (A-9a2), (A-9a3), (A-9a4), (A-9a5), (A-9a6), (A-9a7), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a8) and (2) compounds of up to 10 (e.g., 1, 2, 3, 4, 5, 6, 7, 8, 9, or 10) of structural formulae (A-9a1), (A-9a2), (A-9a3), (A-9a4), (A-9a5), (A-9a6), (A-9a7), (A-9a9), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a9) and (2) compounds of any of structural formulae (A-9a1), (A-9a2), (A-9a3), (A-9a4), (A-9a5), (A-9a6), (A-9a7), (A-9a8), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a9) and (2) compounds of up to 10 (e.g., 1, 2, 3, 4, 5, 6, 7, 8, 9, or 10) of structural formulae (A-9a1), (A-9a2), (A-9a3), (A-9a4), (A-9a5), (A-9a6), (A-9a7), (A-9a8), (A-9a10), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a10) and (2) compounds of any of structural formulae (A-9a1), (A-9a2), (A-9a3), (A-9a4), (A-9a5), (A-9a6), (A-9a7), (A-9a8), (A-9a9), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a10) and (2) compounds of up to 10 (e.g., 1, 2, 3, 4, 5, 6, 7, 8, 9, or 10) of structural formulae (A-9a1), (A-9a2), (A-9a3), (A-9a4), (A-9a5), (A-9a6), (A-9a7), (A-9a8), (A-9a9), and (A-9a11). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a11) and (2) compounds of any of structural formulae (A-9a1), (A-9a2), (A-9a3), (A-9a4), (A-9a5), (A-9a6), (A-9a7), (A-9a8), (A-9a9), and (A-9a10). In other embodiments, such compounds are specifically excluded from structural formulae (A) and/or (A-9a). Each possible combination is specifically contemplated as if set forth explicitly herein.

Some embodiments specifically include and some embodiments only include (1) compounds of structural formula (A-9a11) and (2) compounds of up to 10 (e.g., 1, 2, 3, 4, 5, 6, 7, 8, 9, or 10) of structural formulae (A-9a1), (A-9a2), (A-9a3), (A-9a4), (A-9a5), (A-9a6), (A-9a7), (A-9a8), (A-9a9), and (A-9a10). In other embodiments, such compounds are specifically excluded from structural formulae (A) and/or (A-9a). Each possible combination is specifically contemplated as if set forth explicitly herein.

Some embodiments specifically include and some embodiments only include compounds which have structural formula (A-9b):

wherein:
R3, R4, and R6 are as defined in structural formula (A). In other embodiments, such compounds are specifically excluded from structural formula (A).

Structural formula (A-9b1). Some embodiments specifically include and some embodiments only include compounds of structural formula (A-9b) in which R3 is hydrogen. In other embodiments, such compounds are specifically excluded from structural formulae (A) and/or (A-9b).

Structural formula (A-9b2). Some embodiments specifically include and some embodiments only include compounds of structural formula (A-9b) in which R4 is hydrogen. In other embodiments, such compounds are specifically excluded from structural formulae (A) and/or (A-9b).

Structural formula (A-9b3). Some embodiments specifically include and some embodiments only include compounds of structural formula (A-9b) in which R3 and R4 are hydrogen. In other embodiments, such compounds are specifically excluded from structural formulae (A) and/or (A-9b).

Structural formula (A-9b4). Some embodiments specifically include and some embodiments only include compounds of structural formula (A-9b) in which
a. R3 and R4 are hydrogen and
b. R6 is hydrogen, alkyl,

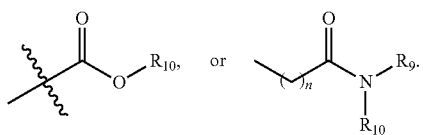

In other embodiments, such compounds are specifically excluded from structural formulae (A) and/or (A-9b).

Structural formula (A-9b5). Some embodiments specifically include and some embodiments only include compounds of structural formula (A-9b) in which
a. R3 and R4 are hydrogen and
b. R6 is alkyl.

In other embodiments, such compounds are specifically excluded from structural formulae (A) and/or (A-9b).

Structural formula (A-9b6). Some embodiments specifically include and some embodiments only include compounds of structural formula (A-9b) in which
a. R3 and R4 are hydrogen and
b. R6 is

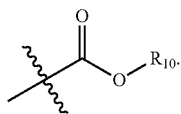

In other embodiments, such compounds are specifically excluded from structural formulae (A) and/or (A-9b).

Structural formula (A-967). Some embodiments specifically include and some embodiments only include compounds of structural formula (A-9b) in which
a. R3 and R4 are hydrogen,
b. R6 is

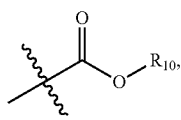

and
c. R10 is alkyl.

In other embodiments, such compounds are specifically excluded from structural formulae (A) and/or (A-9b).

Structural formula (A-968). Some embodiments specifically include and some embodiments only include compounds of structural formula (A-9b) in which
a. R3 and R4 are hydrogen and
b. R6 is

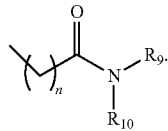

In other embodiments, such compounds are specifically excluded from structural formulae (A) and/or (A-9b).

Structural formula (A-9b9). Some embodiments specifically include and some embodiments only include compounds of structural formula (A-9b) in which
a. R3 and R4 are hydrogen and
b. R6 is

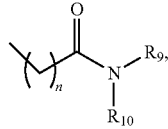

and n is 2.

In other embodiments, such compounds are specifically excluded from structural formulae (A) and/or (A-9b).

Structural formula (A-9b10). Some embodiments specifically include and some embodiments only include compounds of structural formula (A-9b) in which
a. R3 and R4 are hydrogen and
b. R6 is

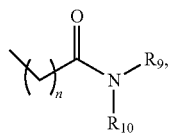

and
c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-9b).

Structural formula (A-9b11). Some embodiments specifically include and some embodiments only include compounds of structural formula (A-9b) in which
a. R3 and R4 are hydrogen and R6 is

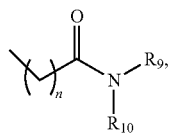

b. R9 is alkyl or alkoxylalkyl, and
c. R10 is hydrogen.

In other embodiments, such compounds are specifically excluded from structural formulae (A) and/or (A-9b).

Some embodiments specifically include and some embodiments only include (1) compounds of structural formula (A-9b1) and (2) compounds of any of structural formulae (A-9b2), (A-9b3), (A-9b4), (A-9b5), (A-9b6), (A-967), (A-968), (A-9b9), (A-9b10), and (A-9b11). In other embodiments, such compounds are specifically excluded from structural formulae (A) and/or (A-9b).

Some embodiments specifically include and some embodiments only include (1) compounds of structural formula (A-9b1) and (2) compounds of up to 10 (e.g., 1, 2, 3, 4, 5, 6, 7, 8, 9, or 10) of structural formulae (A-9b2), (A-9b3), (A-9b4), (A-9b5), (A-9b6), (A-967), (A-968), (A-9b9), (A-9b10), and (A-9b11). In other embodiments, such compounds are specifically excluded from structural formulae (A) and/or (A-9b).

Some embodiments specifically include and some embodiments only include (1) compounds of structural formula (A-9b2) and (2) compounds of any of structural formulae (A-9b1), (A-9b3), (A-9b4), (A-9b5), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b2) and (2) compounds of up to 10 (e.g., 1, 2, 3, 4, 5, 6, 7, 8, 9, or 10) of structural formulae (A-9b1), (A-9b3), (A-9b4), (A-9b5), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b3) and (2) compounds of any of structural formulae (A-9b1), (A-9b2), (A-9b4), (A-9b5), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b3) and (2) compounds of up to 10 (e.g., 1, 2, 3, 4, 5, 6, 7, 8, 9, or 10) of structural formulae (A-9b1), (A-9b2), (A-9b4), (A-9b5), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b4) and (2) compounds of any of structural formulae (A-9b1), (A-9b2), (A-9b3), (A-9b5), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b4) and (2) compounds of up to 10 (e.g., 1, 2, 3, 4, 5, 6, 7, 8, 9, or 10) of structural formulae (A-9b1), (A-9b2), (A-9b3), (A-9b5), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b5) and (2) compounds of any of structural formulae (A-9b1), (A-9b2), (A-9b3), (A-9b4), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b5) and (2) compounds of up to 10 (e.g., 1, 2, 3, 4, 5, 6, 7, 8, 9, or 10) of structural formulae (A-9b1), (A-9b2), (A-9b3), (A-9b4), (A-9b6), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b6) and (2) compounds of any of structural formulae (A-9b1), (A-9b2), (A-9b3), (A-9b4), (A-9b5), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b6) and (2) compounds of up to 10 (e.g., 1, 2, 3, 4, 5, 6, 7, 8, 9, or 10) of structural formulae (A-9b1), (A-9b2), (A-9b3), (A-9b4), (A-9b5), (A-967), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-967) and (2) compounds of any of structural formulae (A-9b1), (A-9b2), (A-9b3), (A-9b4), (A-9b5), (A-9b6), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-967) and (2) compounds of up to 10 (e.g., 1, 2, 3, 4, 5, 6, 7, 8, 9, or 10) of structural formulae (A-9b1), (A-9b2), (A-9b3), (A-9b4), (A-9b5), (A-9b6), (A-968), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-968) and (2) compounds of any of structural formulae (A-9b1), (A-9b2), (A-9b3), (A-9b4), (A-9b5), (A-9b6), (A-967), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-968) and (2) compounds of up to 10 (e.g., 1, 2, 3, 4, 5, 6, 7, 8, 9, or 10) of structural formulae (A-9b1), (A-9b2), (A-9b3), (A-9b4), (A-9b5), (A-9b6), (A-967), (A-9b9), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b9) and (2) compounds of any of structural formulae (A-9b1), (A-9b2), (A-9b3), (A-9b4), (A-9b5), (A-9b6), (A-967), (A-968), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b9) and (2) compounds of up to 10 (e.g., 1, 2, 3, 4, 5, 6, 7, 8, 9, or 10) of structural formulae (A-9b1), (A-9b2), (A-9b3), (A-9b4), (A-9b5), (A-9b6), (A-967), (A-968), (A-9b10), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b10) and (2) compounds of any of structural formulae (A-9b1), (A-9b2), (A-9b3), (A-9b4), (A-9b5), (A-9b6), (A-967), (A-968), (A-9b9), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b10) and (2) compounds of up to 10 (e.g., 1, 2, 3, 4, 5, 6, 7, 8, 9, or 10) of structural formulae (A-9b1), (A-9b2), (A-9b3), (A-9b4), (A-9b5), (A-9b6), (A-967), (A-968), (A-9b9), and (A-9b11). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b11) and (2) compounds of any of structural formulae (A-9b1), (A-9b2), (A-9b3), (A-9b4), (A-9b5), (A-9b6), (A-967), (A-968), (A-9b9), and (A-9b10). In other embodiments, such compounds are specifically excluded from structural formulae (A) and/or (A-9b). Each possible combination is specifically contemplated as if set forth explicitly herein.

Some embodiments specifically include and some embodiments only include (1) compounds of structural formula (A-9b11) and (2) compounds of up to 10 (e.g., 1, 2, 3, 4, 5, 6, 7, 8, 9, or 10) of structural formulae (A-9b1), (A-9b2), (A-9b3), (A-9b4), (A-9b5), (A-9b6), (A-967), (A-968), (A-9b9), and (A-9b10). In other embodiments, such compounds are specifically excluded from structural formulae (A) and/or (A-9b). Each possible combination is specifically contemplated as if set forth explicitly herein.

Some embodiments specifically include and some embodiments only include compounds which have structural formula (A-10a):

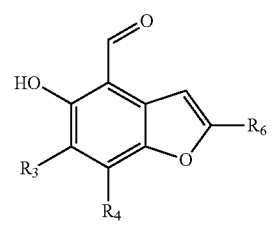

(A-10a)

wherein:
R3, R4, and R6 are as defined in structural formula (A). In other embodiments, such compounds are specifically excluded from structural formula (A).

Structural formula (A-10a1). Some embodiments specifically include and some embodiments only include compounds of structural formula (A-10a) in which R3 is hydrogen. In other embodiments, such compounds are specifically excluded from structural formulae (A) and/or (A-10a).

Structural formula (A-10a2). Some embodiments specifically include and some embodiments only include compounds of structural formula (A-10a) in which R4 is hydrogen. In other embodiments, such compounds are specifically excluded from structural formulae (A) and/or (A-10a).

Structural formula (A-10a3). Some embodiments specifically include and some embodiments only include compounds of structural formula (A-10a) in which R3 and R4 are hydrogen. In other embodiments, such compounds are specifically excluded from structural formulae (A) and/or (A-10a).

Structural formula (A-10a4). Some embodiments specifically include and some embodiments only include compounds of structural formula (A-10a) in which
 a. R3 and R4 are hydrogen and
 b. R6 is hydrogen, alkyl,

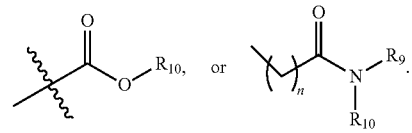

In other embodiments, such compounds are specifically excluded from structural formulae (A) and/or (A-10a).

Structural formula (A-10a5). Some embodiments specifically include and some embodiments only include compounds of structural formula (A-10a) in which
 a. R3 and R4 are hydrogen and
 b. R6 is alkyl.
In other embodiments, such compounds are specifically excluded from structural formulae (A) and/or (A-10a).

Structural formula (A-10a6). Some embodiments specifically include and some embodiments only include compounds of structural formula (A-10a) in which
 a. R3 and R4 are hydrogen and
 b. R6 is

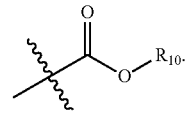

In other embodiments, such compounds are specifically excluded from structural formulae (A) and/or (A-10a).

Structural formula (A-10a7). Some embodiments specifically include and some embodiments only include compounds of structural formula (A-10a) in which
   a. R3 and R4 are hydrogen,
   b. R6 is

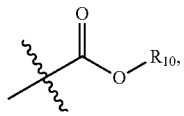

and
   c. R10 is alkyl.

In other embodiments, such compounds are specifically excluded from structural formulae (A) and/or (A-10a).

Structural formula (A-10a8). Some embodiments specifically include and some embodiments only include compounds of structural formula (A-10a) in which
   a. R3 and R4 are hydrogen and
   b. R6 is

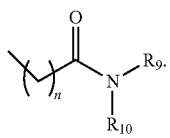

In other embodiments, such compounds are specifically excluded from structural formulae (A) and/or (A-10a).

Structural formula (A-10a9). Some embodiments specifically include and some embodiments only include compounds of structural formula (A-10a) in which
   a. R3 and R4 are hydrogen and
   b. R6 is

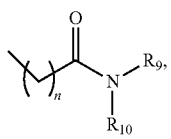

and n is 2.

In other embodiments, such compounds are specifically excluded from structural formulae (A) and/or (A-10a).

Structural formula (A-10a10). Some embodiments specifically include and some embodiments only include compounds of structural formula (A-10a) in which
   a. R3 and R4 are hydrogen and
   b. R6 is

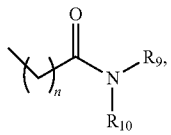

and
   c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-10a).

Structural formula (A-10a11). Some embodiments specifically include and some embodiments only include compounds of structural formula (A-10a) in which
   a. R3 and R4 are hydrogen and
   b. R6 is

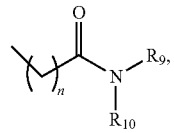

c. R9 is alkyl or alkoxylalkyl, and
   d. R10 is hydrogen.

In other embodiments, such compounds are specifically excluded from structural formulae (A) and/or (A-10a).

Some embodiments specifically include and some embodiments only include (1) compounds of structural formula (A-10a1) and (2) compounds of any of structural formulae (A-10a2), (A-10a3), (A-10a4), (A-10a5), (A-10a6), (A-10a7), (A-10a8), (A-10a9), (A-10a10), and (A-10a11). In other embodiments, such compounds are specifically excluded from structural formulae (A) and/or (A-10a).

Some embodiments specifically include and some embodiments only include (1) compounds of structural formula (A-10a1) and (2) compounds of up to 10 (e.g., 1, 2, 3, 4, 5, 6, 7, 8, 9, or 10) of structural formulae (A-10a2), (A-10a3), (A-10a4), (A-10a5), (A-10a6), (A-10a7), (A-10a8), (A-10a9), (A-10a10), and (A-10a11). In other embodiments, such compounds are specifically excluded from structural formulae (A) and/or (A-10a).

Some embodiments specifically include and some embodiments only include (1) compounds of structural formula (A-10a2) and (2) compounds of any of structural formulae (A-10a1), (A-10a3), (A-10a4), (A-10a5), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a2) and (2) compounds of up to 10 (e.g., 1, 2, 3, 4, 5, 6, 7, 8, 9, or 10) of structural formulae (A-10a1), (A-10a3), (A-10a4), (A-10a5), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a3) and (2) compounds of any of structural formulae (A-10a1), (A-10a2), (A-10a4), (A-10a5), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a3) and (2) compounds of up to 10 (e.g., 1, 2, 3, 4, 5, 6, 7, 8, 9, or 10) of structural formulae (A-10a1), (A-10a2), (A-10a4), (A-10a5), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a4) and (2) compounds of any of structural formulae (A-10a1), (A-10a2), (A-10a3), (A-10a5), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a4) and (2) compounds of up to 10 (e.g., 1, 2, 3, 4, 5, 6, 7, 8, 9, or 10) of structural formulae (A-10a1), (A-10a2), (A-10a3), (A-10a5), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a5) and (2) compounds of any of structural formulae (A-10a1), (A-10a2), (A-10a3), (A-10a4), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a5) and (2) compounds of up to 10 (e.g., 1, 2, 3, 4, 5, 6, 7, 8, 9, or 10) of structural formulae (A-10a1), (A-10a2), (A-10a3), (A-10a4), (A-10a6), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a6) and (2) compounds of any of structural formulae (A-10a1), (A-10a2), (A-10a3), (A-10a4), (A-10a5), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a6) and (2) compounds of up to 10 (e.g., 1, 2, 3, 4, 5, 6, 7, 8, 9, or 10) of structural formulae (A-10a1), (A-10a2), (A-10a3), (A-10a4), (A-10a5), (A-10a7), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a7) and (2) compounds of any of structural formulae (A-10a1), (A-10a2), (A-10a3), (A-10a4), (A-10a5), (A-10a6), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a7) and (2) compounds of up to 10 (e.g., 1, 2, 3, 4, 5, 6, 7, 8, 9, or 10) of structural formulae (A-10a1), (A-10a2), (A-10a3), (A-10a4), (A-10a5), (A-10a6), (A-10a8), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a8) and (2) compounds of any of structural formulae (A-10a1), (A-10a2), (A-10a3), (A-10a4), (A-10a5), (A-10a6), (A-10a7), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a8) and (2) compounds of up to 10 (e.g., 1, 2, 3, 4, 5, 6, 7, 8, 9, or 10) of structural formulae (A-10a1), (A-10a2), (A-10a3), (A-10a4), (A-10a5), (A-10a6), (A-10a7), (A-10a9), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a9) and (2) compounds of any of structural formulae (A-10a1), (A-10a2), (A-10a3), (A-10a4), (A-10a5), (A-10a6), (A-10a7), (A-10a8), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a9) and (2) compounds of up to 10 (e.g., 1, 2, 3, 4, 5, 6, 7, 8, 9, or 10) of structural formulae (A-10a1), (A-10a2), (A-10a3), (A-10a4), (A-10a5), (A-10a6), (A-10a7), (A-10a8), (A-10a10), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a10) and (2) compounds of any of structural formulae (A-10a1), (A-10a2), (A-10a3), (A-10a4), (A-10a5), (A-10a6), (A-10a7), (A-10a8), (A-10a9), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a10) and (2) compounds of up to 10 (e.g., 1, 2, 3, 4, 5, 6, 7, 8, 9, or 10) of structural formulae (A-10a1), (A-10a2), (A-10a3), (A-10a4), (A-10a5), (A-10a6), (A-10a7), (A-10a8), (A-10a9), and (A-10a11). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a11) and (2) compounds of any of structural formulae (A-10a1), (A-10a2), (A-10a3), (A-10a4), (A-10a5), (A-10a6), (A-10a7), (A-10a8), (A-10a9), and (A-10a10). In other embodiments, such compounds are specifically excluded from structural formulae (A) and/or (A-10a). Each possible combination is specifically contemplated as if set forth explicitly herein.

Some embodiments specifically include and some embodiments only include (1) compounds of structural formula (A-10a11) and (2) compounds of up to 10 (e.g., 1, 2, 3, 4, 5, 6, 7, 8, 9, or 10) of structural formulae (A-10a1), (A-10a2), (A-10a3), (A-10a4), (A-10a5), (A-10a6), (A-10a7), (A-10a8), (A-10a9), and (A-10a10). In other embodiments, such compounds are specifically excluded from structural formulae (A) and/or (A-10a). Each possible combination is specifically contemplated as if set forth explicitly herein.

Some embodiments specifically include and some embodiments only include compounds which have structural formula (A-10b):

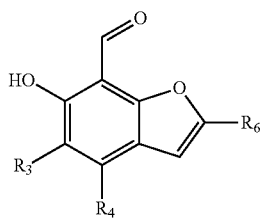

(A-10b)

wherein:
R3, R4, and R6 are as defined in structural formula (A). In other embodiments, such compounds are specifically excluded from structural formula (A).

Structural formula (A-10b1). Some embodiments specifically include and some embodiments only include compounds of structural formula (A-10b) in which R3 is hydrogen. In other embodiments, such compounds are specifically excluded from structural formulae (A) and/or (A-10b).

Structural formula (A-10b2). Some embodiments specifically include and some embodiments only include compounds of structural formula (A-10b) in which R4 is hydrogen. In other embodiments, such compounds are specifically excluded from structural formulae (A) and/or (A-10b).

Structural formula (A-10b3). Some embodiments specifically include and some embodiments only include compounds of structural formula (A-10b) in which R3 and R4 are hydrogen. In other embodiments, such compounds are specifically excluded from structural formulae (A) and/or (A-10b).

Structural formula (A-10b4). Some embodiments specifically include and some embodiments only include compounds of structural formula (A-10b) in which a. R3 and R4 are hydrogen and
b. R6 is hydrogen, alkyl,

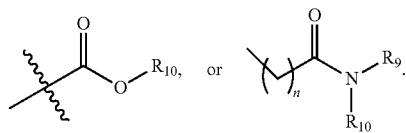

In other embodiments, such compounds are specifically excluded from structural formulae (A) and/or (A-10b).

Structural formula (A-10b5). Some embodiments specifically include and some embodiments only include compounds of structural formula (A-10b) in which
a. R3 and R4 are hydrogen and
b. R6 is alkyl.

In other embodiments, such compounds are specifically excluded from structural formulae (A) and/or (A-10b).

Structural formula (A-10b6). Some embodiments specifically include and some embodiments only include compounds of structural formula (A-10b) in which
a. R3 and R4 are hydrogen and
b. R6 is

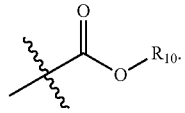

In other embodiments, such compounds are specifically excluded from structural formulae (A) and/or (A-10b).

Structural formula (A-10b7). Some embodiments specifically include and some embodiments only include compounds of structural formula (A-10b) in which
a. R3 and R4 are hydrogen,
b. R6 is

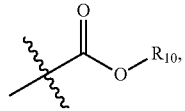

and
c. R10 is alkyl.

In other embodiments, such compounds are specifically excluded from structural formulae (A) and/or (A-10b).

Structural formula (A-10b8). Some embodiments specifically include and some embodiments only include compounds of structural formula (A-10b) in which
a. R3 and R4 are hydrogen and
b. R6 is

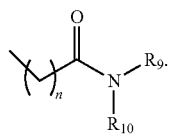

In other embodiments, such compounds are specifically excluded from structural formulae (A) and/or (A-10b).

Structural formula (A-10b9). Some embodiments specifically include and some embodiments only include compounds of structural formula (A-10b) in which
a. R3 and R4 are hydrogen and
b. R6 is

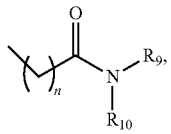

and n is 2.

In other embodiments, such compounds are specifically excluded from structural formulae (A) and/or (A-10b).

Structural formula (A-10b10). Some embodiments specifically include and some embodiments only include compounds of structural formula (A-10b) in which
a. R3 and R4 are hydrogen and
b. R6 is

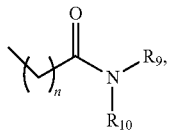

and
c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-10b).

Structural formula (A-1011). Some embodiments specifically include and some embodiments only include compounds of structural formula (A-10b) in which
a. R3 and R4 are hydrogen and R6 is

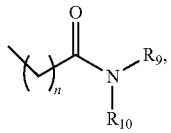

b. R9 is alkyl or alkoxylalkyl, and
c. R10 is hydrogen.

In other embodiments, such compounds are specifically excluded from structural formulae (A) and/or (A-10b).

Some embodiments specifically include and some embodiments only include (1) compounds of structural formula (A-10b1) and (2) compounds of any of structural formulae (A-10b2), (A-10b3), (A-10b4), (A-10b5), (A-10b6), (A-10b7), (A-10b8), (A-10b9), (A-10b10), and (A-10b11). In other embodiments, such compounds are specifically excluded from structural formulae (A) and/or (A-10b).

Some embodiments specifically include and some embodiments only include (1) compounds of structural formula (A-10b1) and (2) compounds of up to 10 (e.g., 1, 2, 3, 4, 5, 6, 7, 8, 9, or 10) of structural formulae (A-10b2), (A-10b3), (A-10b4), (A-10b5), (A-10b6), (A-10b7), (A-10b8), (A-10b9), (A-10b10), and (A-10b11). In other embodiments, such compounds are specifically excluded from structural formulae (A) and/or (A-10b).

Some embodiments specifically include and some embodiments only include (1) compounds of structural formula (A-10b2) and (2) compounds of any of structural formulae (A-10b1), (A-10b3), (A-10b4), (A-10b5), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b2) and (2) compounds of up to 10 (e.g., 1, 2, 3, 4, 5, 6, 7, 8, 9, or 10) of structural formulae (A-10b1), (A-10b3), (A-10b4), (A-10b5), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b3) and (2) compounds of any of structural formulae (A-10b1), (A-10b2), (A-10b4), (A-10b5), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b3) and (2) compounds of up to 10 (e.g., 1, 2, 3, 4, 5, 6, 7, 8, 9, or 10) of structural formulae (A-10b1), (A-10b2), (A-10b4), (A-10b5), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b4) and (2) compounds of any of structural formulae (A-10b1), (A-10b2), (A-10b3), (A-10b5), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b4) and (2) compounds of up to 10 (e.g., 1, 2, 3, 4, 5, 6, 7, 8, 9, or 10) of structural formulae (A-10b1), (A-10b2), (A-10b3), (A-10b5), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b5) and (2) compounds of any of structural formulae (A-10b1), (A-10b2), (A-10b3), (A-10b4), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b5) and (2) compounds of up to 10 (e.g., 1, 2, 3, 4, 5, 6, 7, 8, 9, or 10) of structural formulae (A-10b1), (A-10b2), (A-10b3), (A-10b4), (A-10b6), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b6) and (2) compounds of any of structural formulae (A-10b1), (A-10b2), (A-10b3), (A-10b4), (A-10b5), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b6) and (2) compounds of up to 10 (e.g., 1, 2, 3, 4, 5, 6, 7, 8, 9, or 10) of structural formulae (A-10b1), (A-10b2), (A-10b3), (A-10b4), (A-10b5), (A-10b7), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b7) and (2) compounds of any of structural formulae (A-10b1), (A-10b2), (A-10b3), (A-10b4), (A-10b5), (A-10b6), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b7) and (2) compounds of up to 10 (e.g., 1, 2, 3, 4, 5, 6, 7, 8, 9, or 10) of structural formulae (A-10b1), (A-10b2), (A-10b3), (A-10b4), (A-10b5), (A-10b6), (A-10b8), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b8) and (2) compounds of any of structural formulae (A-10b1), (A-10b2), (A-10b3), (A-10b4), (A-10b5), (A-10b6), (A-10b7), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b8) and (2) compounds of up to 10 (e.g., 1, 2, 3, 4, 5, 6, 7, 8, 9, or 10) of structural formulae (A-10b1), (A-10b2), (A-10b3), (A-10b4), (A-10b5), (A-10b6), (A-10b7), (A-10b9), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b9) and (2) compounds of any of structural formulae (A-10b1), (A-10b2), (A-10b3), (A-10b4), (A-10b5), (A-10b6), (A-10b7), (A-10b8), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b9) and (2) compounds of up to 10 (e.g., 1, 2, 3, 4, 5, 6, 7, 8, 9, or 10) of structural formulae (A-10b1), (A-10b2), (A-10b3), (A-10b4), (A-10b5), (A-10b6), (A-10b7), (A-10b8), (A-10b10), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b10) and (2) compounds of any of structural formulae (A-10b1), (A-10b2), (A-10b3), (A-10b4), (A-10b5), (A-10b6), (A-10b7), (A-10b8), (A-10b9), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b10) and (2) compounds of up to 10 (e.g., 1, 2, 3, 4, 5, 6, 7, 8, 9, or 10) of structural formulae (A-10b1), (A-10b2), (A-10b3), (A-10b4), (A-10b5), (A-10b6), (A-10b7), (A-10b8), (A-10b9), and (A-10b11). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b11) and (2) compounds of any of structural formulae (A-10b1), (A-10b2), (A-10b3), (A-10b4), (A-10b5), (A-10b6), (A-10b7), (A-10b8), (A-10b9), and (A-10b10). In other embodiments, such compounds are specifically excluded from structural formulae (A) and/or (A-10b). Each possible combination is specifically contemplated as if set forth explicitly herein.

Some embodiments specifically include and some embodiments only include (1) compounds of structural formula (A-10b11) and (2) compounds of up to 10 (e.g., 1, 2, 3, 4, 5, 6, 7, 8, 9, or 10) of structural formulae (A-10b1), (A-10b2), (A-10b3), (A-10b4), (A-10b5), (A-10b6), (A-10b7), (A-10b8), (A-10b9), and (A-10b10). In other embodiments, such compounds are specifically excluded from structural formulae (A) and/or (A-10b). Each possible combination is specifically contemplated as if set forth explicitly herein.

Some embodiments specifically include and some embodiments only include compounds which have structural formula (A-11a):

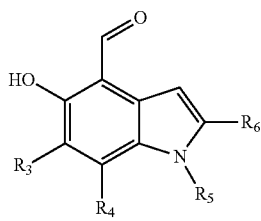

(A-11a)

wherein:

R3, R4, and R6 are as defined in structural formula (A); and R5 is hydrogen or C1-C3 alkyl. In other embodiments, such compounds are specifically excluded from structural formula (A).

Structural formula (A-11a1). Some embodiments specifically include and some embodiments only include compounds of structural formula (A-11a) in which R3 is hydrogen. In other embodiments, such compounds are specifically excluded from structural formulae (A) and/or (A-11a).

Structural formula (A-11a2). Some embodiments specifically include and some embodiments only include compounds of structural formula (A-11a) in which R4 is hydrogen. In other embodiments, such compounds are specifically excluded from structural formulae (A) and/or (A-11a).

Structural formula (A-11a3). Some embodiments specifically include and some embodiments only include compounds of structural formula (A-11a) in which R3 and R4 are hydrogen. In other embodiments, such compounds are specifically excluded from structural formulae (A) and/or (A-11a).

Structural formula (A-11a4). Some embodiments specifically include and some embodiments only include compounds of structural formula (A-11a) in which
  a. R3 and R4 are hydrogen and
  b. R6 is hydrogen, alkyl,

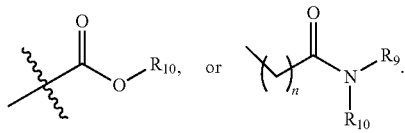

In other embodiments, such compounds are specifically excluded from structural formulae (A) and/or (A-11a).

Structural formula (A-11a5). Some embodiments specifically include and some embodiments only include compounds of structural formula (A-11a) in which
  a. R3 and R4 are hydrogen and
  b. R6 is alkyl.

In other embodiments, such compounds are specifically excluded from structural formulae (A) and/or (A-11a).

Structural formula (A-11a6). Some embodiments specifically include and some embodiments only include compounds of structural formula (A-11a) in which
  a. R3 and R4 are hydrogen and
  b. R6 is

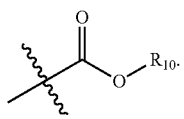

In other embodiments, such compounds are specifically excluded from structural formulae (A) and/or (A-11a).

Structural formula (A-11a7). Some embodiments specifically include and some embodiments only include compounds of structural formula (A-11a) in which
  a. R3 and R4 are hydrogen,
  b. R6 is

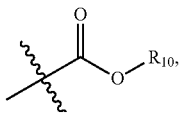

and
  c. R10 is alkyl.

In other embodiments, such compounds are specifically excluded from structural formulae (A) and/or (A-11a).

Structural formula (A-11a8). Some embodiments specifically include and some embodiments only include compounds of structural formula (A-11a) in which
  a. R3 and R4 are hydrogen and
  b. R6 is

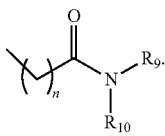

In other embodiments, such compounds are specifically excluded from structural formulae (A) and/or (A-11a).

Structural formula (A-11a9). Some embodiments specifically include and some embodiments only include compounds of structural formula (A-11a) in which
  a. R3 and R4 are hydrogen and
  b. R6 is

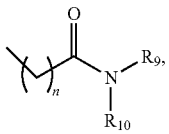

and n is 2.

In other embodiments, such compounds are specifically excluded from structural formulae (A) and/or (A-11a).

Structural formula (A-11a10). Some embodiments specifically include and some embodiments only include compounds of structural formula (A-11a) in which
  a. R3 and R4 are hydrogen and
  b. R6 is

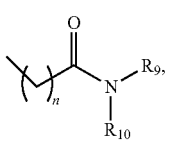

and
  c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-11a).

Structural formula (A-11a11). Some embodiments specifically include and some embodiments only include compounds of structural formula (A-11a) in which
  a. R3 and R4 are hydrogen and
  b. R6 is $$\underset{R_{10}}{\overset{O}{\underset{|}{\overset{\|}{\underset{N}{\text{---}}}}}}$$

c. R9 is alkyl or alkoxylalkyl, and
  d. R10 is hydrogen.

In other embodiments, such compounds are specifically excluded from structural formulae (A) and/or (A-11a).

Some embodiments specifically include and some embodiments only include (1) compounds of structural formula (A-11a1) and (2) compounds of any of structural formulae (A-11a2), (A-11a3), (A-11a4), (A-11a5), (A-11a6), (A-11a7), (A-11a8), (A-11a9), (A-11a10), and (A-11a11). In other embodiments, such compounds are specifically excluded from structural formulae (A) and/or (A-11a).

Some embodiments specifically include and some embodiments only include (1) compounds of structural formula (A-11a1) and (2) compounds of up to 10 (e.g., 1, 2, 3, 4, 5, 6, 7, 8, 9, or 10) of structural formulae (A-11a2), (A-11a3), (A-11a4), (A-11a5), (A-11a6), (A-11a7), (A-11a8), (A-11a9), (A-11a10), and (A-11a11). In other embodiments, such compounds are specifically excluded from structural formulae (A) and/or (A-11a).

Some embodiments specifically include and some embodiments only include (1) compounds of structural formula (A-11a2) and (2) compounds of any of structural formulae (A-11a1), (A-11a3), (A-11a4), (A-11a5), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a2) and (2) compounds of up to 10 (e.g., 1, 2, 3, 4, 5, 6, 7, 8, 9, or 10) of structural formulae (A-11a1), (A-11a3), (A-11a4), (A-11a5), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a3) and (2) compounds of any of structural formulae (A-11a1), (A-11a2), (A-11a4), (A-11a5), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a3) and (2) compounds of up to 10 (e.g., 1, 2, 3, 4, 5, 6, 7, 8, 9, or 10) of structural formulae (A-11a1), (A-11a2), (A-11a4), (A-11a5), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a4) and (2) compounds of any of structural formulae (A-11a1), (A-11a2), (A-11a3), (A-11a5), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a4) and (2) compounds of up to 10 (e.g., 1, 2, 3, 4, 5, 6, 7, 8, 9, or 10) of structural formulae (A-11a1), (A-11a2), (A-11a3), (A-11a5), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a5) and (2) compounds of any of structural formulae (A-11a1), (A-11a2), (A-11a3), (A-11a4), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a5) and (2) compounds of up to 10 (e.g., 1, 2, 3, 4, 5, 6, 7, 8, 9, or 10) of structural formulae (A-11a1), (A-11a2), (A-11a3), (A-11a4), (A-11a6), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a6) and (2) compounds of any of structural formulae (A-11a1), (A-11a2), (A-11a3), (A-11a4), (A-11a5), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a6) and (2) compounds of up to 10 (e.g., 1, 2, 3, 4, 5, 6, 7, 8, 9, or 10) of structural formulae (A-11a1), (A-11a2), (A-11a3), (A-11a4), (A-11a5), (A-11a7), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a7) and (2) compounds of any of structural formulae (A-11a1), (A-11a2), (A-11a3), (A-11a4), (A-11a5), (A-11a6), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a7) and (2) compounds of up to 10 (e.g., 1, 2, 3, 4, 5, 6, 7, 8, 9, or 10) of structural formulae (A-11a1), (A-11a2), (A-11a3), (A-11a4), (A-11a5), (A-11a6), (A-11a8), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a8) and (2) compounds of any of structural formulae (A-11a1), (A-11a2), (A-11a3), (A-11a4), (A-11a5), (A-11a6), (A-11a7), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a8) and (2) compounds of up to 10 (e.g., 1, 2, 3, 4, 5, 6, 7, 8, 9, or 10) of structural formulae (A-11a1), (A-11a2), (A-11a3), (A-11a4), (A-11a5), (A-11a6), (A-11a7), (A-11a9), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a9) and (2) compounds of any of structural formulae (A-11a1), (A-11a2), (A-11a3), (A-11a4), (A-11a5), (A-11a6), (A-11a7), (A-11a8), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a9) and (2) compounds of up to 10 (e.g., 1, 2, 3, 4, 5, 6, 7, 8, 9, or 10) of structural formulae (A-11a1), (A-11a2), (A-11a3), (A-11a4), (A-11a5), (A-11a6), (A-11a7), (A-11a8), (A-11a10), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a10) and (2) compounds of any of structural formulae (A-11a1), (A-11a2), (A-11a3), (A-11a4), (A-11a5), (A-11a6), (A-11a7), (A-11a8), (A-11a9), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a10) and (2) compounds of up to 10 (e.g., 1, 2, 3, 4, 5, 6, 7, 8, 9, or 10) of structural formulae (A-11a1), (A-11a2), (A-11a3), (A-11a4), (A-11a5), (A-11a6), (A-11a7), (A-11a8), (A-11a9), and (A-11a11). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a11) and (2) compounds of any of structural formulae (A-11a1), (A-11a2), (A-11a3), (A-11a4), (A-11a5), (A-11a6), (A-11a7), (A-11a8), (A-11a9), and (A-11a10). In other embodiments, such compounds are specifically excluded from structural formulae (A) and/or (A-11a). Each possible combination is specifically contemplated as if set forth explicitly herein.

Some embodiments specifically include and some embodiments only include (1) compounds of structural formula (A-11a11) and (2) compounds of up to 10 (e.g., 1, 2, 3, 4, 5, 6, 7, 8, 9, or 10) of structural formulae (A-11a1), (A-11a2), (A-11a3), (A-11a4), (A-11a5), (A-11a6), (A-11a7), (A-11a8), (A-11a9), and (A-11a10). In other embodiments, such compounds are specifically excluded from structural formulae (A) and/or (A-11a). Each possible combination is specifically contemplated as if set forth explicitly herein.

Some embodiments specifically include and some embodiments only include compounds which have structural formula (A-11b):

(A-11b)

wherein:

$R_3$, $R_4$, and $R_6$ are as defined in structural formula (A) and $R_7$ is hydrogen or C1-C3 alkyl. In other embodiments, such compounds are specifically excluded from structural formula (A).

Structural formula (A-11b1). Some embodiments specifically include and some embodiments only include compounds of structural formula (A-11b) in which $R_3$ is hydrogen. In other embodiments, such compounds are specifically excluded from structural formulae (A) and/or (A-11b).

Structural formula (A-11b2). Some embodiments specifically include and some embodiments only include compounds of structural formula (A-11b) in which $R_4$ is hydrogen. In other embodiments, such compounds are specifically excluded from structural formulae (A) and/or (A-11b).

Structural formula (A-11b3). Some embodiments specifically include and some embodiments only include compounds of structural formula (A-11b) in which $R_3$ and $R_4$ are hydrogen. In other embodiments, such compounds are specifically excluded from structural formulae (A) and/or (A-11b).

Structural formula (A-11b4). Some embodiments specifically include and some embodiments only include compounds of structural formula (A-11b) in which a. $R_3$ and $R_4$ are hydrogen and b. $R_6$ is hydrogen, alkyl,

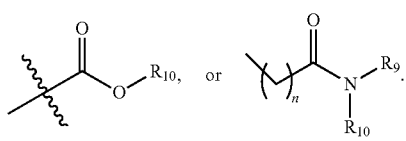

In other embodiments, such compounds are specifically excluded from structural formulae (A) and/or (A-11b).

Structural formula (A-11b5). Some embodiments specifically include and some embodiments only include compounds of structural formula (A-11b) in which
  a. R3 and R4 are hydrogen and
  b. R6 is alkyl.

In other embodiments, such compounds are specifically excluded from structural formulae (A) and/or (A-11b).

Structural formula (A-11b6). Some embodiments specifically include and some embodiments only include compounds of structural formula (A-11b) in which
  a. R3 and R4 are hydrogen and
  b. R6 is

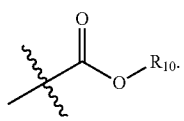

In other embodiments, such compounds are specifically excluded from structural formulae (A) and/or (A-11b).

Structural formula (A-11b7). Some embodiments specifically include and some embodiments only include compounds of structural formula (A-11b) in which
  a. R3 and R4 are hydrogen,
  b. R6 is

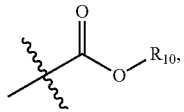

and
  c. R10 is alkyl.

In other embodiments, such compounds are specifically excluded from structural formulae (A) and/or (A-11b).

Structural formula (A-11b8). Some embodiments specifically include and some embodiments only include compounds of structural formula (A-11b) in which
  a. R3 and R4 are hydrogen and
  b. R6 is

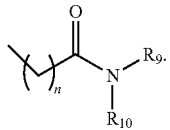

In other embodiments, such compounds are specifically excluded from structural formulae (A) and/or (A-11b).

Structural formula (A-11b9). Some embodiments specifically include and some embodiments only include compounds of structural formula (A-11b) in which
  a. R3 and R4 are hydrogen and
  b. R6 is

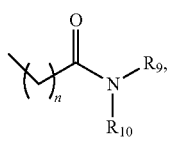

and n is 2.

In other embodiments, such compounds are specifically excluded from structural formulae (A) and/or (A-11b).

Structural formula (A-11b10). Some embodiments specifically include and some embodiments only include compounds of structural formula (A-11b) in which
  a. R3 and R4 are hydrogen and
  b. R6 is

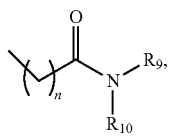

and
  c. R9 and R10, together with the nitrogen atom to which they are attached, form a heterocycle containing 1, 2, 3, or 4 heteroatoms selected from N, O, and S, optionally substituted with 1, 2, or 3 substituents selected independently from R11, wherein R11 is as defined in structural formula (A).

In other embodiments, such compounds are specifically excluded from structural formulae (A) and/or (A-11b).

Structural formula (A-11b11). Some embodiments specifically include and some embodiments only include compounds of structural formula (A-11b) in which
  a. R3 and R4 are hydrogen and
  b. R6 is

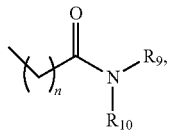

c. R9 is alkyl or alkoxylalkyl, and
  d. R10 is hydrogen.

In other embodiments, such compounds are specifically excluded from structural formulae (A) and/or (A-11b).

Some embodiments specifically include and some embodiments only include (1) compounds of structural formula (A-11b1) and (2) compounds of any of structural formulae (A-11b2), (A-11b3), (A-11b4), (A-11b5), (A-11b6), (A-11b7), (A-11b8), (A-11b9), (A-11b10), and (A-11b11). In other embodiments, such compounds are specifically excluded from structural formulae (A) and/or (A-11b).

Some embodiments specifically include and some embodiments only include (1) compounds of structural formula (A-11b1) and (2) compounds of up to 10 (e.g., 1, 2, 3, 4, 5, 6, 7, 8, 9, or 10) of structural formulae (A-11b2), (A-11b3), (A-11b4), (A-11b5), (A-11b6), (A-11b7), (A-11b8), (A-11b9), (A-11b10), and (A-11b11). In other embodiments, such compounds are specifically excluded from structural formulae (A) and/or (A-11b).

Some embodiments specifically include and some embodiments only include (1) compounds of structural formula (A-11b2) and (2) compounds of any of structural formulae (A-11b1), (A-11b3), (A-11b4), (A-11b5), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b2) and (2) compounds of up to 10 (e.g., 1, 2, 3, 4, 5, 6, 7, 8, 9, or 10) of structural formulae (A-11b1), (A-11b3), (A-11b4), (A-11b5), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b3) and (2) compounds of any of structural formulae (A-11b1), (A-11b2), (A-11b4), (A-11b5), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b3) and (2) compounds of up to 10 (e.g., 1, 2, 3, 4, 5, 6, 7, 8, 9, or 10) of structural formulae (A-11b1), (A-11b2), (A-11b4), (A-11b5), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b4) and (2) compounds of any of structural formulae (A-11b1), (A-11b2), (A-11b3), (A-11b5), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b4) and (2) compounds of up to 10 (e.g., 1, 2, 3, 4, 5, 6, 7, 8, 9, or 10) of structural formulae (A-11b1), (A-11b2), (A-11b3), (A-11b5), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b5) and (2) compounds of any of structural formulae (A-11b1), (A-11b2), (A-11b3), (A-11b4), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b5) and (2) compounds of up to 10 (e.g., 1, 2, 3, 4, 5, 6, 7, 8, 9, or 10) of structural formulae (A-11b1), (A-11b2), (A-11b3), (A-11b4), (A-11b6), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b6) and (2) compounds of any of structural formulae (A-11b1), (A-11b2), (A-11b3), (A-11b4), (A-11b5), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b6) and (2) compounds of up to 10 (e.g., 1, 2, 3, 4, 5, 6, 7, 8, 9, or 10) of structural formulae (A-11b1), (A-11b2), (A-11b3), (A-11b4), (A-11b5), (A-11b7), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b7) and (2) compounds of any of structural formulae (A-11b1), (A-11b2), (A-11b3), (A-11b4), (A-11b5), (A-11b6), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b7) and (2) compounds of up to 10 (e.g., 1, 2, 3, 4, 5, 6, 7, 8, 9, or 10) of structural formulae (A-11b1), (A-11b2), (A-11b3), (A-11b4), (A-11b5), (A-11b6), (A-11b8), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b8) and (2) compounds of any of structural formulae (A-11b1), (A-11b2), (A-11b3), (A-11b4), (A-11b5), (A-11b6), (A-11b7), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b8) and (2) compounds of up to 10 (e.g., 1, 2, 3, 4, 5, 6, 7, 8, 9, or 10) of structural formulae (A-11b1), (A-11b2), (A-11b3), (A-11b4), (A-11b5), (A-11b6), (A-11b7), (A-11b9), (A-11b10), and (A-11b11). In other embodiments, such compounds are specifically excluded from structural formulae (A) and/or (A-11b). Each possible combination is specifically contemplated as if set forth explicitly herein.

Some embodiments include and some embodiments only include (1) compounds of structural formula (A-11b9) and (2) compounds of any of structural formulae (A-11b1), (A-11b2), (A-11b3), (A-11b4), (A-11b5), (A-11b6), (A-11b7), (A-11b8), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b9) and (2) compounds of up to 10 (e.g., 1, 2, 3, 4, 5, 6, 7, 8, 9, or 10) of structural formulae (A-11b1), (A-11b2), (A-11b3), (A-11b4), (A-11b5), (A-11b6), (A-11b7), (A-11b8), (A-11b10), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b10) and (2) compounds of any of structural formulae (A-11b1), (A-11b2), (A-11b3), (A-11b4), (A-11b5), (A-11b6), (A-11b7), (A-11b8), (A-11b9), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b10) and (2) compounds of up to 10 (e.g., 1, 2, 3, 4, 5, 6, 7, 8, 9, or 10) of structural formulae (A-11b1), (A-11b2), (A-11b3), (A-11b4), (A-11b5), (A-11b6), (A-11b7), (A-11b8), (A-11b9), and (A-11b11). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b11) and (2) compounds of any of structural formulae (A-11b1), (A-11b2), (A-11b3), (A-11b4), (A-11b5), (A-11b6), (A-11b7), (A-11b8), (A-11b9), and (A-11b10). In other embodiments, such compounds are specifically excluded from structural formulae (A) and/or (A-11b). Each possible combination is specifically contemplated as if set forth explicitly herein.

Some embodiments specifically include and some embodiments only include (1) compounds of structural formula (A-11b11) and (2) compounds of up to 10 (e.g., 1, 2, 3, 4, 5, 6, 7, 8, 9, or 10) of structural formulae (A-11b1), (A-11b2), (A-11b3), (A-11b4), (A-11b5), (A-11b6), (A-11b7), (A-11b8), (A-11b9), and (A-11b10). In other embodiments, such compounds are specifically excluded from structural formulae (A) and/or (A-11b). Each possible combination is specifically contemplated as if set forth explicitly herein.

Table 1 provides examples of compounds encompassed by one or more of the structural formulae described above. The average $IC_{50}$ and $EC_{50}$ were determined as described in the Examples below. These and other compounds within the scope of the formulae described above can be synthesized according to general methods known in the art and as described in the specific Examples, below.

TABLE 1

| Compound | Structure | IC50_av (µM) | EC50_av (µM) |
|---|---|---|---|
| 1 | 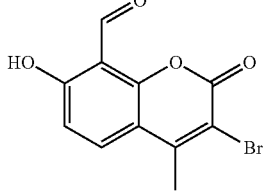 | <0.1 | <10 |
| 2 | 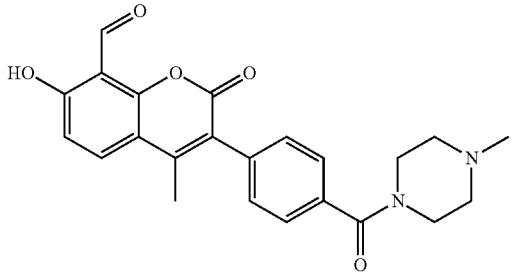 [SMILES: Cc1c(-c2ccc(C(=O)N3CCN(C)CC3)cc2)c(=O)oc2c(C=O)c(O)ccc12] | <0.1 | <10 |
| 3 | 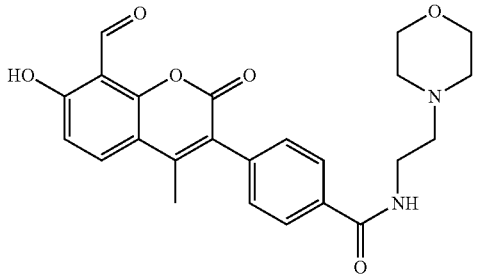 [SMILES: Cc1c(-c2ccc(C(=O)NCCN3CCOCC3)cc2)c(=O)oc2c(C=O)c(O)ccc12] | <0.1 | <10 |

TABLE 1-continued

| Compound Structure | IC50_av (μM) | EC50_av (μM) |
|---|---|---|
| 4 (7-hydroxy-4-methyl-3-(2-(diethylamino)ethyl)-8-formyl coumarin) | <0.1 | >10 |
| 5 (7-hydroxy-4-isopropyl-8-formyl coumarin) | <0.1 | <10 |
| 6 (7-hydroxy-6-methoxy-4-methyl-3-bromo-8-formyl coumarin) | <0.1 | <10 |
| 7 (7-hydroxy-3-(4-bromophenyl)-8-formyl coumarin) | <0.1 | >10 |
| 8 (7-hydroxy-8-formyl coumarin-3-carboxylic acid) | >10 | >10 |
| 9 (7-hydroxy-6-fluoro-4-methyl-3-bromo-8-formyl coumarin) | <1 | <10 |

TABLE 1-continued
| Compound | Structure | IC50_av (μM) | EC50_av (μM) |
|---|---|---|---|
| 10 | 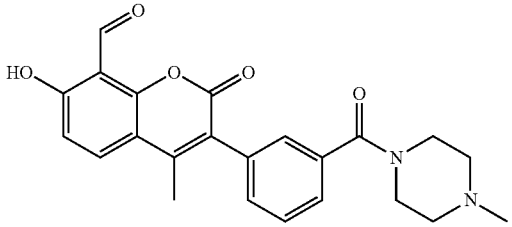 [SMILES: Cc1c(-c2cccc(C(=O)N3CCN(C)CC3)c2)c(=O)oc2c(C=O)c(O)ccc12] | <0.1 | <10 |
| 11 | 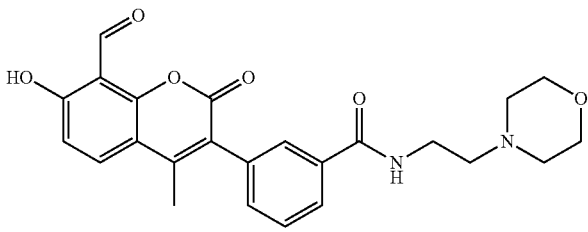 [SMILES: Cc1c(-c2cccc(C(=O)NCCN3CCOCC3)c2)c(=O)oc2c(C=O)c(O)ccc12] | <0.1 | <10 |
| 12 | 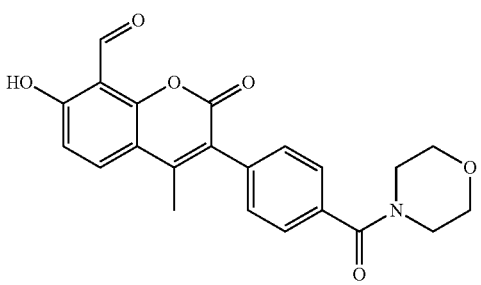 [SMILES: Cc1c(-c2ccc(C(=O)N3CCOCC3)cc2)c(=O)oc2c(C=O)c(O)ccc12] | <0.1 | <10 |
| 13 | 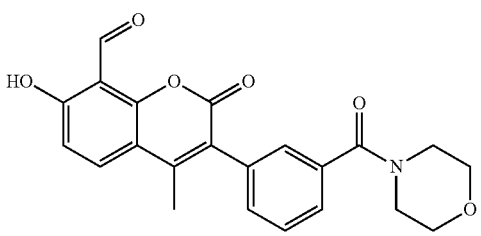 [SMILES: Cc1c(-c2cccc(C(=O)N3CCOCC3)c2)c(=O)oc2c(C=O)c(O)ccc12] | <0.1 | <10 |
| 14 | 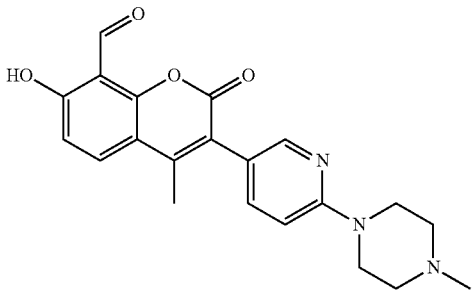 [SMILES: Cc1c(-c2ccc(N3CCN(C)CC3)nc2)c(=O)oc2c(C=O)c(O)ccc12] | <0.1 | <10 |
| 15 | 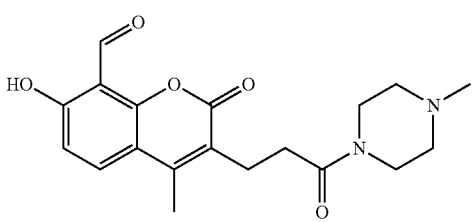 [SMILES: Cc1c(CCC(=O)N2CCN(C)CC2)c(=O)oc2c(C=O)c(O)ccc12] | nd | <10 |

TABLE 1-continued

| Compound Structure | IC50_av (μM) | EC50_av (μM) |
|---|---|---|
| 16 | <0.1 | >10 |
| 17 | <0.1 | <10 |
| 18 | <1 | <10 |
| 19 | >1 | <10 |
| 20 | <1 | >10 |

TABLE 1-continued
| Compound Structure | IC50_av (μM) | EC50_av (μM) |
|---|---|---|
| 21 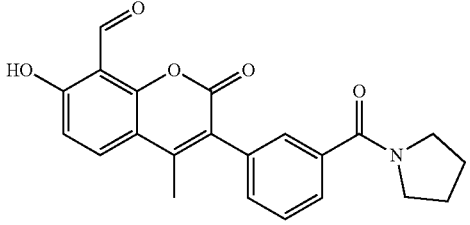 [SMILES: Cc1c(-c2cccc(C(=O)N3CCCC3)c2)c(=O)oc2c(C=O)c(O)ccc12] | <0.1 | >10 |
| 22 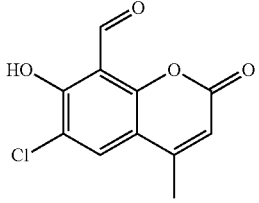 | <0.1 | <10 |
| 23 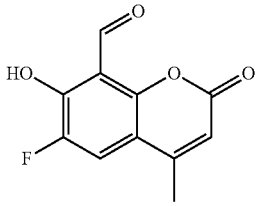 | <1 | <10 |
| 24 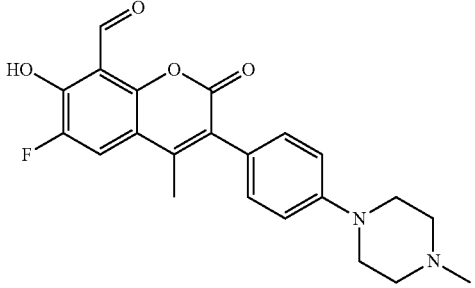 [SMILES: Cc1c(-c2ccc(N3CCN(C)CC3)cc2)c(=O)oc2c(C=O)c(O)c(F)cc12] | <0.1 | <10 |
| 25 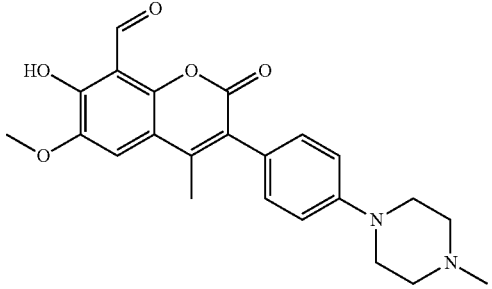 | <0.1 | <10 |
| 26 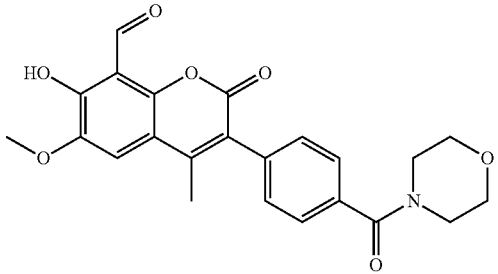 [SMILES: COc1cc2c(C)c(-c3ccc(C(=O)N4CCOCC4)cc3)c(=O)oc2c(C=O)c1O] | <1 | <10 |

TABLE 1-continued

| Compound Structure | IC50_av (μM) | EC50_av (μM) |
|---|---|---|
| 27 | <0.1 | <10 |
| 28 | <10 | >10 |
| 29 | >10 | nd |
| 30 | >10 | nd |
| 31 | >10 | nd |
| 32 | <10 | nd |

145 146
TABLE 1-continued
| Compound Structure | IC50_av (μM) | EC50_av (μM) |
|---|---|---|
| 33 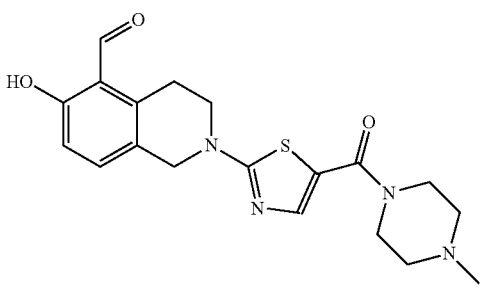 [SMILES: CN1CCN(C(=O)c2cnc(N3CCc4c(ccc(O)c4C=O)C3)s2)CC1] | <10 | >10 |
| 34 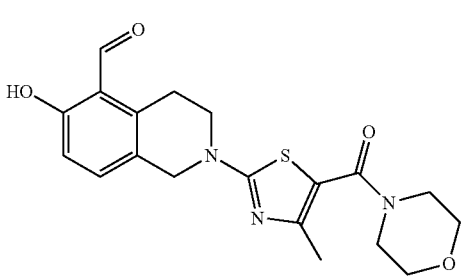 [SMILES: Cc1nc(N2CCc3c(ccc(O)c3C=O)C2)sc1C(=O)N1CCOCC1] | <10 | >10 |
| 35 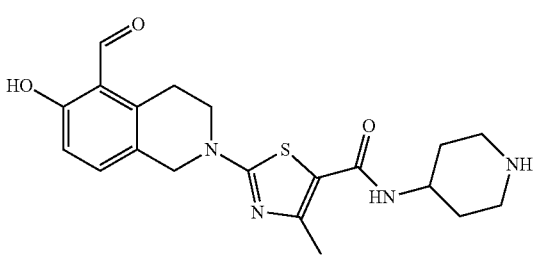 [SMILES: Cc1nc(N2CCc3c(ccc(O)c3C=O)C2)sc1C(=O)NC1CCNCC1] | <0.1 | >10 |
| 36 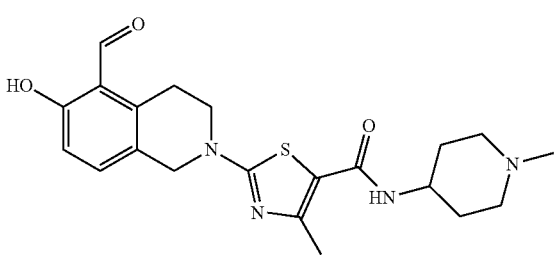 [SMILES: Cc1nc(N2CCc3c(ccc(O)c3C=O)C2)sc1C(=O)NC1CCN(C)CC1] | <1 | >10 |
| 37 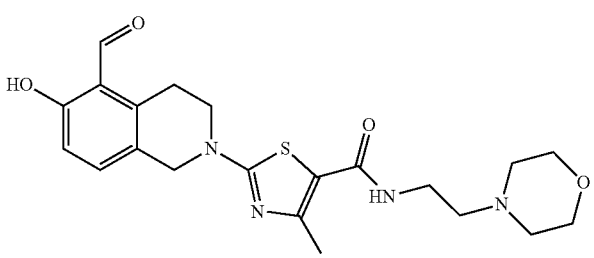 [SMILES: Cc1nc(N2CCc3c(ccc(O)c3C=O)C2)sc1C(=O)NCCN1CCOCC1] | <0.1 | >10 |
| 38 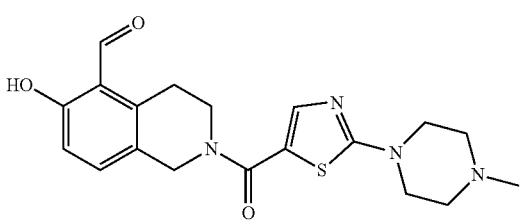 [SMILES: CN1CCN(c2ncc(C(=O)N3CCc4c(ccc(O)c4C=O)C3)s2)CC1] | <0.1 | >10 |

TABLE 1-continued

| Compound Structure | IC50_av (μM) | EC50_av (μM) |
|---|---|---|
| 39 | <0.1 | >10 |
| 40 | <1 | >10 |
| 41 | <1 | <10 |
| 42 | <1 | <10 |
| 43 | <1 | <10 |
| 44 | <1 | <10 |

TABLE 1-continued
| Compound Structure | IC50_av (µM) | EC50_av (µM) |
|---|---|---|
| 45 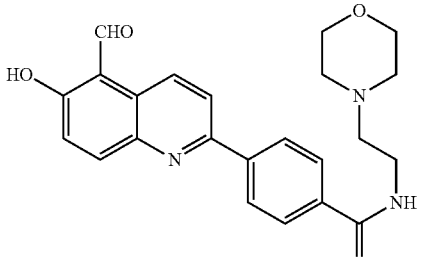 | <1 | <10 |
| 46 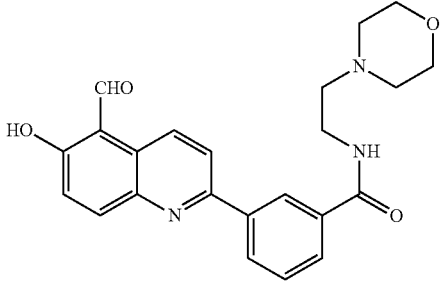 [SMILES: O=Cc1c(O)ccc2nc(-c3cccc(C(=O)NCCN4CCOCC4)c3)ccc12] | <0.1 | <10 |
| 47 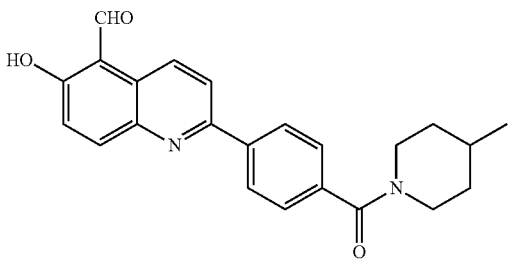 [SMILES: CC1CCN(C(=O)c2ccc(-c3ccc4c(C=O)c(O)ccc4n3)cc2)CC1] | <0.1 | >10 |
| 48 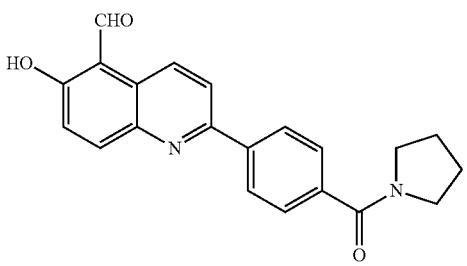 [SMILES: O=Cc1c(O)ccc2nc(-c3ccc(C(=O)N4CCCC4)cc3)ccc12] | <0.1 | <10 |
| 49 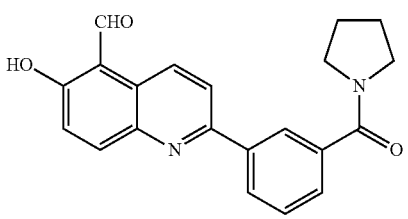 [SMILES: O=Cc1c(O)ccc2nc(-c3cccc(C(=O)N4CCCC4)c3)ccc12] | <0.1 | >10 |
| 50 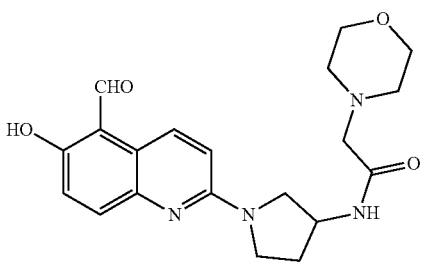 [SMILES: O=Cc1c(O)ccc2nc(N3CCC(NC(=O)CN4CCOCC4)C3)ccc12] | <0.1 | <10 |

TABLE 1-continued
| Compound Structure | IC50_av (μM) | EC50_av (μM) |
|---|---|---|
| 51 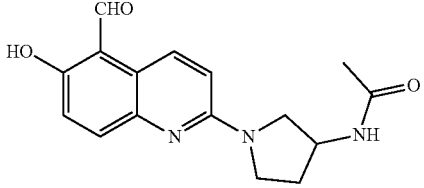 [SMILES: CC(=O)NC1CCN(c2ccc3c(C=O)c(O)ccc3n2)C1] | <0.1 | <10 |
| 52 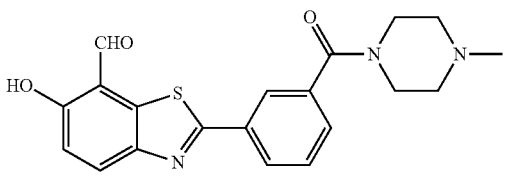 [SMILES: CN1CCN(C(=O)c2cccc(-c3nc4ccc(O)c(C=O)c4s3)c2)CC1] | <0.1 | >10 |
| 53 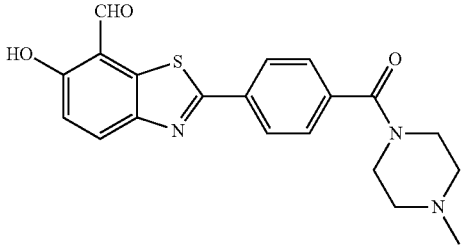 [SMILES: CN1CCN(C(=O)c2ccc(-c3nc4ccc(O)c(C=O)c4s3)cc2)CC1] | <0.1 | >10 |
| 54 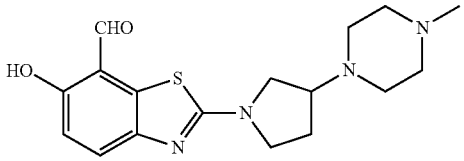 [SMILES: CN1CCN(C2CCN(c3nc4ccc(O)c(C=O)c4s3)C2)CC1] | <0.1 | >10 |
| 55 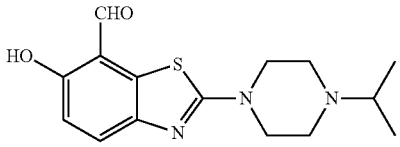 [SMILES: CC(C)N1CCN(c2nc3ccc(O)c(C=O)c3s2)CC1] | <0.1 | >10 |
| 56 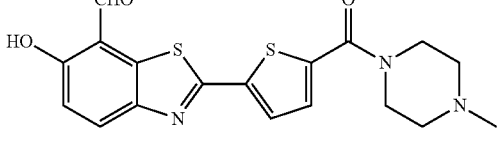 | <0.1 | >10 |
| 57 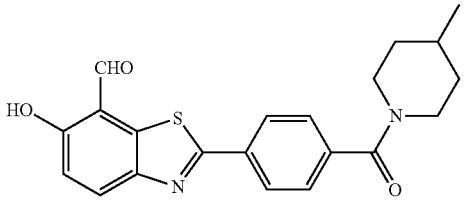 [SMILES: CC1CCN(C(=O)c2ccc(-c3nc4ccc(O)c(C=O)c4s3)cc2)CC1] | <0.1 | >10 |
| 58 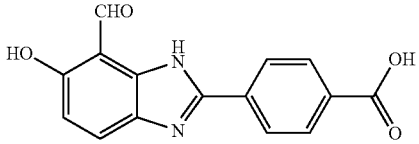 [SMILES: O=Cc1c(O)ccc2nc(-c3ccc(C(=O)O)cc3)[nH]c12] | <1 | >10 |

TABLE 1-continued

| | Compound Structure | IC50_av (μM) | EC50_av (μM) |
|---|---|---|---|
| 59 | (5-hydroxy-benzimidazole with CHO, 2-aryl-COOMe) | <1 | >10 |
| 60 | (5-hydroxy-benzimidazole with CHO, 2-aryl-CONH-CH2CH2-morpholine) | <0.1 | >10 |
| 61 | (5-hydroxy-benzimidazole with CHO, 2-aryl-CO-morpholine) | <0.1 | >10 |
| 62 | (5-hydroxy-benzimidazole with CHO, 2-aryl-CO-N-methylpiperazine) | <0.1 | >10 |
| 63 | (5-hydroxy-benzimidazole with CHO, 2-S-CH2-COOH) | <0.1 | >10 |
| 64 | (5-hydroxy-benzimidazole with CHO, 2-(3-carboxyphenyl)) | <0.1 | >10 |
| 65 | (5-hydroxy-benzimidazole with CHO, 2-(3-COOMe-phenyl)) | <0.1 | <10 |
| 66 | (7-hydroxy-8-formyl-coumarin-3-yl thiazole-5-carboxylic acid ethyl ester) | | |

TABLE 1-continued
| Compound Structure | IC50_av (μM) | EC50_av (μM) |
|---|---|---|
| 67 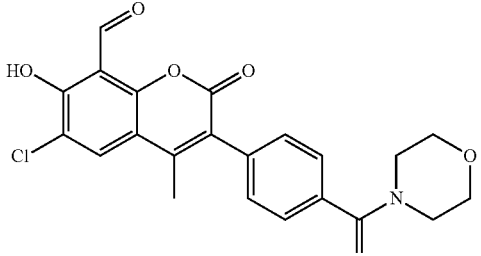 | <1 | >10 |
| 68 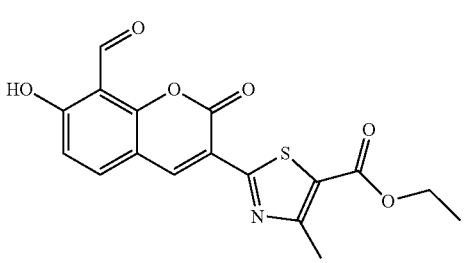 [SMILES: CCOC(=O)c1sc(-c2cc3ccc(O)c(C=O)c3oc2=O)nc1C] | <0.1 | <10 |
| 69 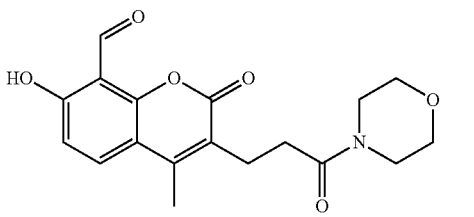 [SMILES: Cc1c(CCC(=O)N2CCOCC2)c(=O)oc2c(C=O)c(O)ccc12] | <0.1 | <10 |
| 70 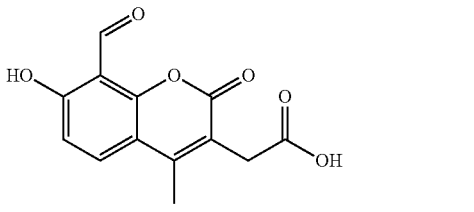 [SMILES: Cc1c(CC(=O)O)c(=O)oc2c(C=O)c(O)ccc12] | <0.1 | >10 |
| 71 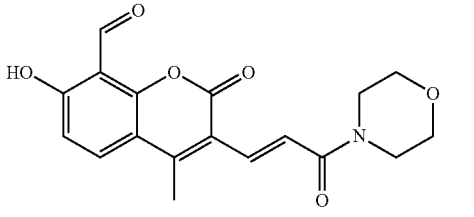 [SMILES: Cc1c(/C=C/C(=O)N2CCOCC2)c(=O)oc2c(C=O)c(O)ccc12] | | |
| 72 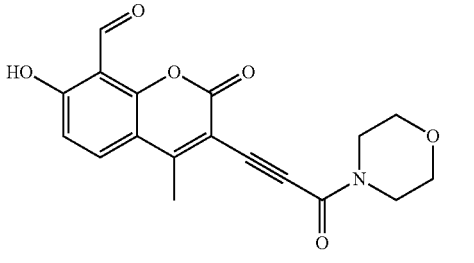 [SMILES: Cc1c(C#CC(=O)N2CCOCC2)c(=O)oc2c(C=O)c(O)ccc12] | | |

TABLE 1-continued
| Compound Structure | IC50_av (μM) | EC50_av (μM) |
|---|---|---|
| 73 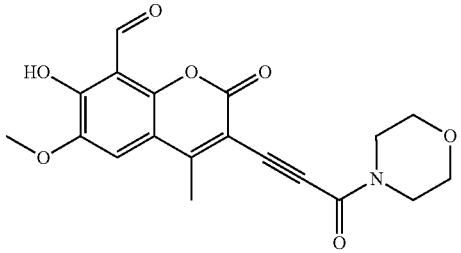 [SMILES: COc1cc2c(C)c(C#CC(=O)N3CCOCC3)c(=O)oc2c(C=O)c1O] | | |
| 74 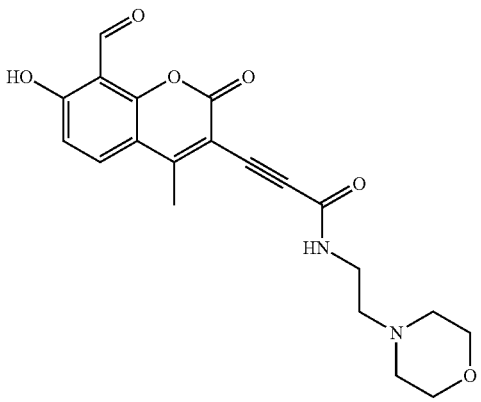 [SMILES: Cc1c(C#CC(=O)NCCN2CCOCC2)c(=O)oc2c(C=O)c(O)ccc12] | | |
| 75 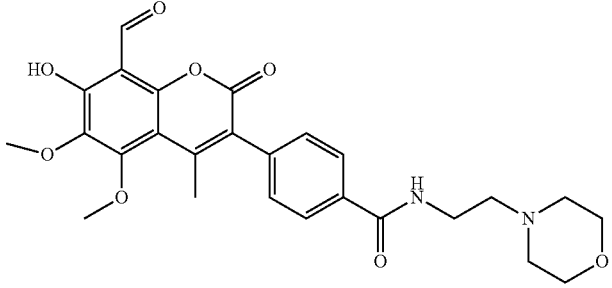 [SMILES: COc1c(O)c(C=O)c2oc(=O)c(-c3ccc(C(=O)NCCN4CCOCC4)cc3)c(C)c2c1OC] | | |
| 76 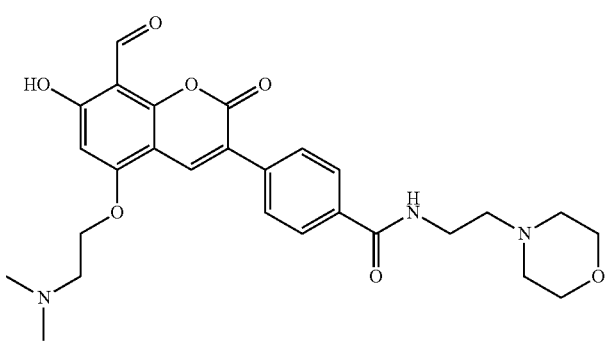 [SMILES: CN(C)CCOc1cc(O)c(C=O)c2oc(=O)c(-c3ccc(C(=O)NCCN4CCOCC4)cc3)cc12] | | |
| 77 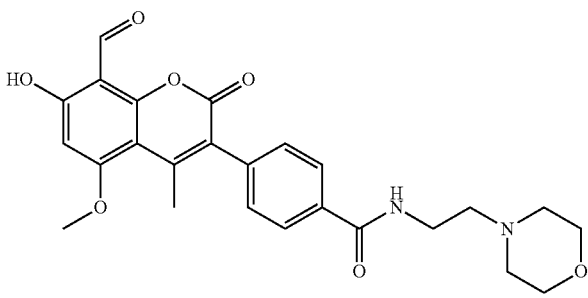 [SMILES: COc1cc(O)c(C=O)c2oc(=O)c(-c3ccc(C(=O)NCCN4CCOCC4)cc3)c(C)c12] | | |

TABLE 1-continued

| Compound Structure | IC50_av (μM) | EC50_av (μM) |
|---|---|---|

78

79

80

81

82

83

TABLE 1-continued
| Compound Structure | IC50_av (μM) | EC50_av (μM) |
|---|---|---|
84 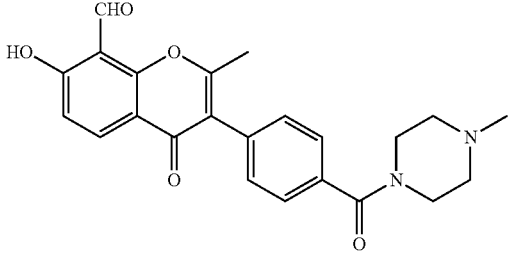 [SMILES: Cc1oc2c(C=O)c(O)ccc2c(=O)c1-c1ccc(C(=O)N2CCN(C)CC2)cc1]
85 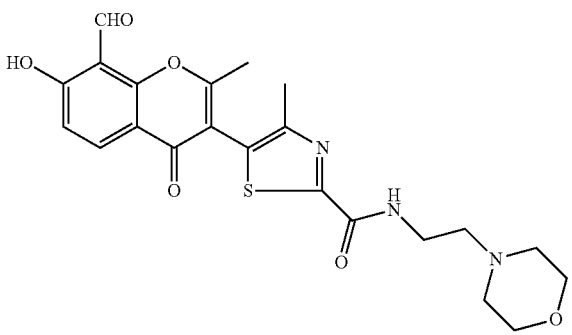 [SMILES: Cc1nc(C(=O)NCCN2CCOCC2)sc1-c1c(C)oc2c(C=O)c(O)ccc2c1=O]
86 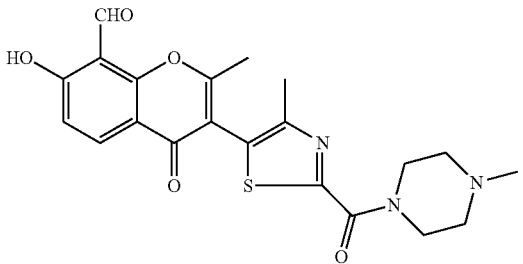 [SMILES: Cc1nc(C(=O)N2CCN(C)CC2)sc1-c1c(C)oc2c(C=O)c(O)ccc2c1=O]
87 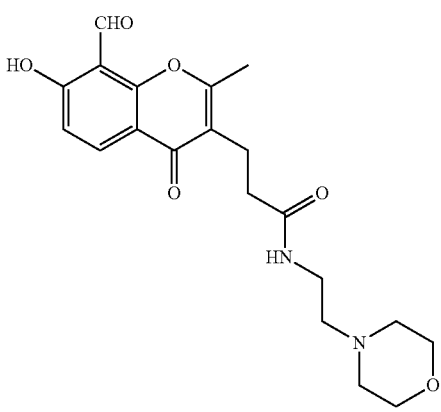 [SMILES: Cc1oc2c(C=O)c(O)ccc2c(=O)c1CCC(=O)NCCN1CCOCC1]

TABLE 1-continued

| Compound Structure | IC50_av (μM) | EC50_av (μM) |
|---|---|---|
| 88 | | >10 |
| 89 | | |
| 90 | | |
| 91 | | |
| 92 | | |

TABLE 1-continued

| Compound Structure | IC50_av (μM) | EC50_av (μM) |
|---|---|---|
| 93 | | >10 |
| 94 | | >10 |
| 95 | | |
| 96 | | |

TABLE 1-continued

| Compound Structure | IC50_av (μM) | EC50_av (μM) |
|---|---|---|

97

98

99

100

101

102

103

US 10,357,475 B2
169                                                                 170
TABLE 1-continued
| Compound Structure | IC50_av (μM) | EC50_av (μM) |
|---|---|---|
| 104 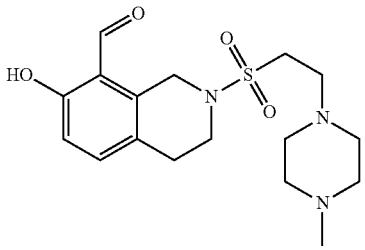 [SMILES: CN1CCN(CCS(=O)(=O)N2CCc3ccc(O)c(C=O)c3C2)CC1] | | |
| 105 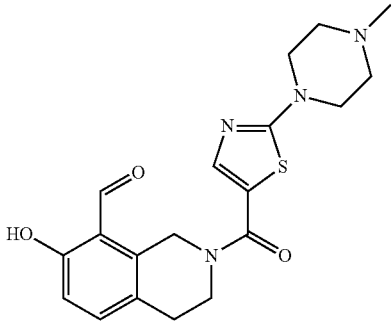 [SMILES: CN1CCN(c2ncc(C(=O)N3CCc4ccc(O)c(C=O)c4C3)s2)CC1] | | |
| 106 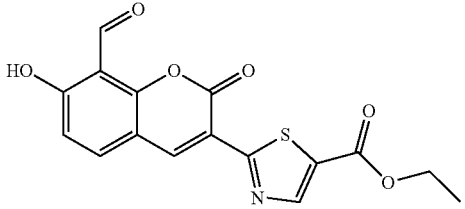 [SMILES: CCOC(=O)c1cnc(-c2cc3ccc(O)c(C=O)c3oc2=O)s1] | <0.1 | <10 |
| 107 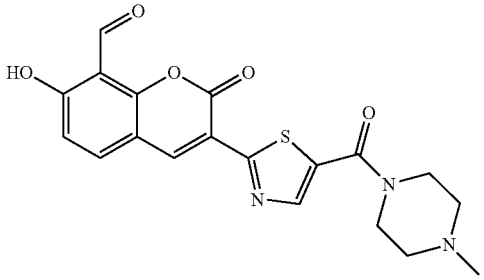 [SMILES: CN1CCN(C(=O)c2cnc(-c3cc4ccc(O)c(C=O)c4oc3=O)s2)CC1] | <0.1 | <10 |
| 108 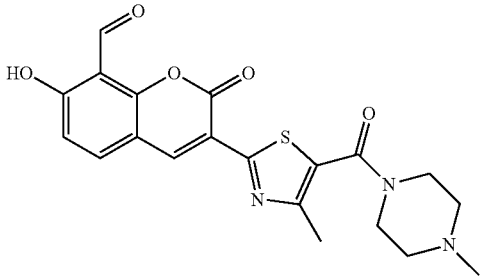 [SMILES: Cc1nc(-c2cc3ccc(O)c(C=O)c3oc2=O)sc1C(=O)N1CCN(C)CC1] | <0.1 | <10 |

TABLE 1-continued
| Compound Structure | IC50_av (μM) | EC50_av (μM) |
|---|---|---|
| 109 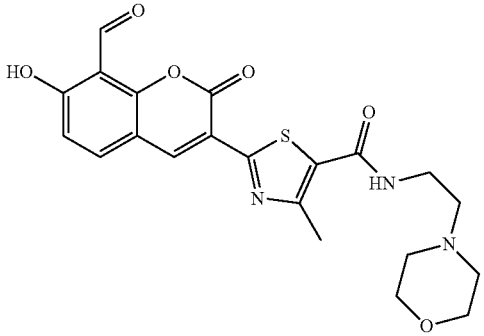 [SMILES: Cc1nc(-c2cc3ccc(O)c(C=O)c3oc2=O)sc1C(=O)NCCN1CCOCC1] | <0.1 | <10 |
| 110 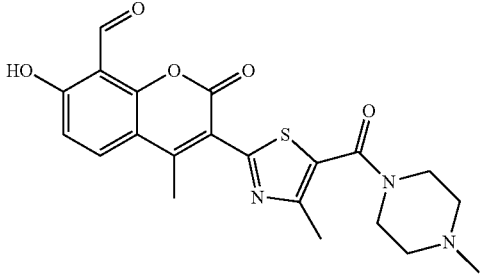 | <1 | <10 |
| 111 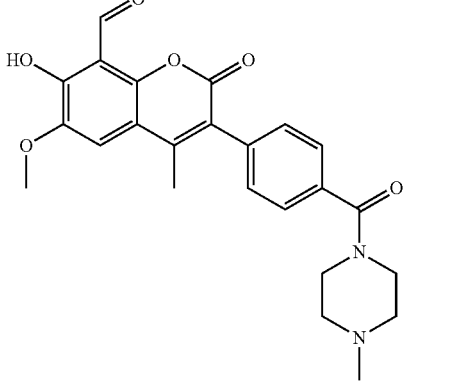 | <0.1 | <10 |
| 112 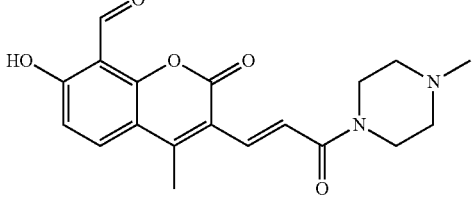 | <0.1 | <10 |
| 113 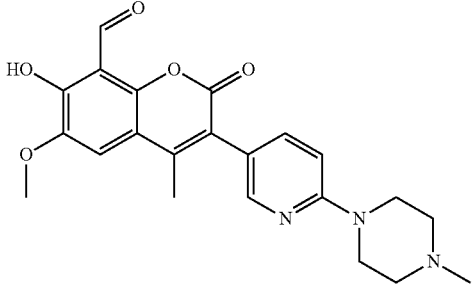 [SMILES: COc1cc2c(C)c(-c3ccc(N4CCN(C)CC4)nc3)c(=O)oc2c(C=O)c1O] | <0.1 | <10 |

TABLE 1-continued

| Compound Structure | IC50_av (μM) | EC50_av (μM) |
|---|---|---|
| 114 | <1 | <10 |
| 115 | <1 | <10 |
| 116 | <0.1 | <10 |
| 117 | <1 | <10 |
| 118 | <0.1 | <10 |

TABLE 1-continued
| Compound Structure | IC50_av (μM) | EC50_av (μM) |
|---|---|---|
| 119 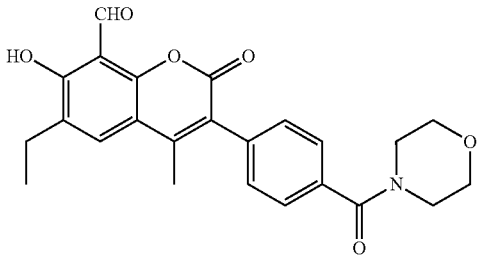 [SMILES: CCc1cc2c(C)c(-c3ccc(C(=O)N4CCOCC4)cc3)c(=O)oc2c(C=O)c1O] | <1 | >10 |
| 120 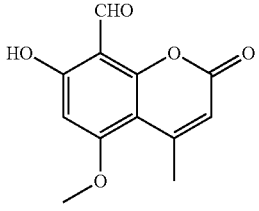 | <1 | <10 |
| 121 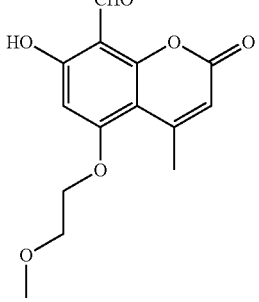 | <0.1 | <10 |
| 122 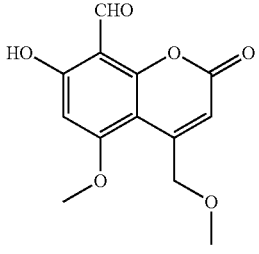 [SMILES: COCc1cc(=O)oc2c(C=O)c(O)cc(OC)c12] | ND | <10 |
| 123 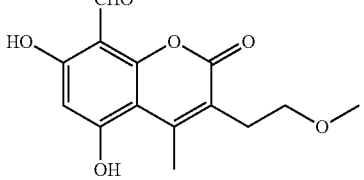 | ND | <10 |
| 124 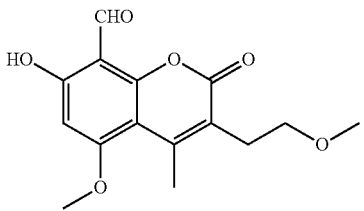 [SMILES: COCCc1c(C)c2c(OC)cc(O)c(C=O)c2oc1=O] | ND | <10 |

TABLE 1-continued

| Compound Structure | IC50_av (μM) | EC50_av (μM) |
|---|---|---|
| 125 | ND | <10 |
| 126 | ND | <10 |
| 127 | <0.1 | <10 |
| 128 | <1 | >10 |
| 129 | <0.1 | <10 |
| 130 | <0.1 | <10 |
| 131 | <0.1 | <10 |

TABLE 1-continued

| Compound Structure | IC50_av (μM) | EC50_av (μM) |
|---|---|---|
| 132 | <0.1 | <10 |
| 133 | <0.1 | <10 |
| 134 | ND | <10 |
| 135 | ND | <10 |
| 136 | <1 | <10 |
| 137 | <0.1 | <10 |

TABLE 1-continued
| Compound Structure | IC50_av (μM) | EC50_av (μM) |
|---|---|---|
| 138 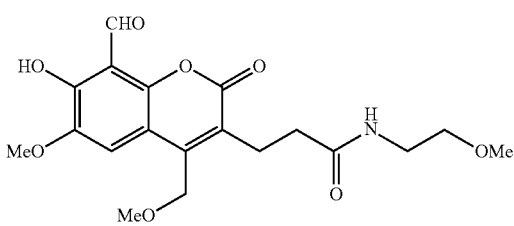 [SMILES: COCCNC(=O)CCc1c(COC)c2cc(OC)c(O)c(C=O)c2oc1=O] | <1 | >10 |
| 139 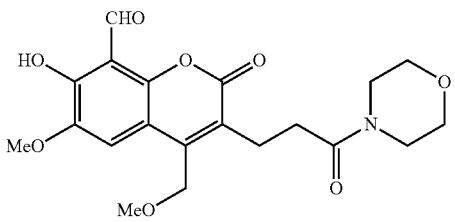 [SMILES: COCc1c(CCC(=O)N2CCOCC2)c(=O)oc2c(C=O)c(O)c(OC)cc12] | <0.1 | <10 |
| 140 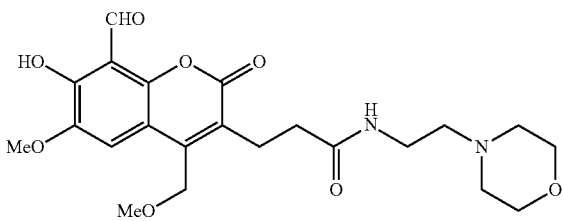 [SMILES: COCc1c(CCC(=O)NCCN2CCOCC2)c(=O)oc2c(C=O)c(O)c(OC)cc12] | <1 | >10 |
| 141 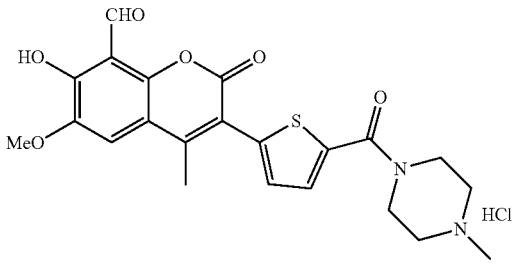 [SMILES: COc1cc2c(C)c(-c3ccc(C(=O)N4CCN(C)CC4)s3)c(=O)oc2c(C=O)c1O ; Cl] | <0.1 | <10 |
| 142 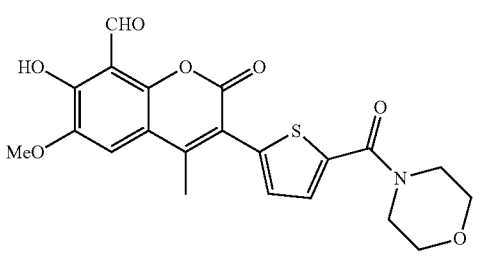 [SMILES: COc1cc2c(C)c(-c3ccc(C(=O)N4CCOCC4)s3)c(=O)oc2c(C=O)c1O] | <0.1 | <10 |
| 143 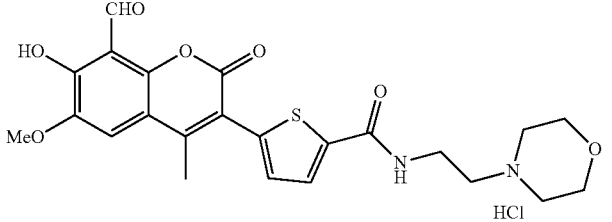 [SMILES: COc1cc2c(C)c(-c3ccc(C(=O)NCCN4CCOCC4)s3)c(=O)oc2c(C=O)c1O ; Cl] | <1 | <10 |

TABLE 1-continued

| Compound | Structure | IC50_av (μM) | EC50_av (μM) |
|---|---|---|---|
| 144 | (coumarin with 8-CHO, 7-OH, 6-N(Me)(Ac), 4-Me, 3-CH2CH2C(O)OEt) | ND | >10 |
| 145 | (coumarin with 8-CHO, 7-OH, 5-OMe, 4-Me, 3-CH2CH2OCH2CH2OMe) | ND | <10 |
| 146 | (coumarin with 8-CHO, 7-OH, 6-OMe, 4-iPr) | <0.1 | <10 |
| 147 | (coumarin with 8-CHO, 7-OH, 6-OMe, 4-Me, 3-CH2CH2C(O)NHCH2CH2OH) | <0.1 | >10 |
| 148 | (coumarin with 8-CHO, 7-OH, 6-OMe, 4-Me, 3-CH2C(O)NHCH2CH2OH) | <0.1 | >10 |
| 149 | (coumarin with 8-CHO, 7-OH, 6-OMe, 4-Me, 3-CH2C(O)NHCH2CH2OCH2OMe) | <1 | <10 |
| 150 | (coumarin with 8-CHO, 7-OH, 6-Cl, 4-Me, 3-(4-(C(O)NHCH2CH2OMe)phenyl)) | <1 | >10 |

TABLE 1-continued

| Compound Structure | IC50_av (μM) | EC50_av (μM) |
|---|---|---|
| 151 | <1 | >10 |
| 152 | <1 | <10 |
| 153 | <0.1 | <10 |
| 154 | <0.1 | <10 |
| 155 | <1 | <10 |
| 156 | <1 | >10 |

TABLE 1-continued

| Compound Structure | IC50_av (μM) | EC50_av (μM) |
|---|---|---|
| 157 | <1 | >10 |
| 158 | ND | <10 |
| 159 | ND | <10 |
| 160 | ND | <10 |
| 161 | ND | <10 |
| 162 | ND | <10 |
| 163 | ND | <10 |

TABLE 1-continued

| Compound | Structure | IC50_av (μM) | EC50_av (μM) |
|---|---|---|---|
| 164 | | ND | >10 |
| 165 | | ND | <10 |
| 166 | | <1 | <10 |
| 167 | | <0.1 | <10 |
| 168 | | <0.1 | <10 |
| 169 | | <0.1 | <10 |
| 170 | | <1 | <10 |

TABLE 1-continued

| Compound Structure | IC50_av (μM) | EC50_av (μM) |
|---|---|---|
| 171 [8-CHO-7-OH-6-OMe-4-Me-coumarin-3-yl CH2CH2C(O)NH-CH2CH2-OMe] | <0.1 | <10 |
| 172 [8-CHO-7-OH-6-OMe-4-Me-coumarin-3-yl CH2CH2C(O)-morpholine] | <0.1 | <10 |
| 173 [8-CHO-7-OH-6-OMe-4-Me-coumarin-3-yl CH2CH2C(O)-N-methylpiperazine] | <0.1 | <10 |
| 174 [8-CHO-7-OH-6-OMe-4-Me-coumarin-3-yl CH2CH2C(O)NH-Et] | <0.1 | <10 |
| 175 [8-CHO-7-OH-6-OMe-4-Me-coumarin-3-yl CH2CH2C(O)NH-CH2CH2-NMe2] | <1 | >10 |
| 176 [8-CHO-7-OH-5-OMe-4-Me-coumarin-3-yl CH2C(O)NH-CH2CH2-OMe] | <0.1 | <10 |
| 177 [8-CHO-7-OH-5-OMe-4-Me-coumarin-3-yl CH2C(O)-morpholine] | <0.1 | <10 |

TABLE 1-continued
| Compound | Structure | IC50_av (μM) | EC50_av (μM) |
|---|---|---|---|
| 178 | 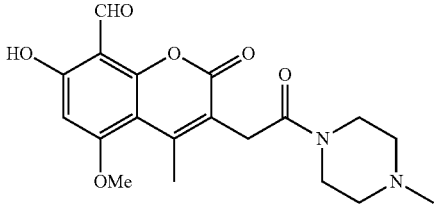 [SMILES: COc1cc(O)c(C=O)c2oc(=O)c(CC(=O)N3CCN(C)CC3)c(C)c12] | ND | <10 |
| 179 | 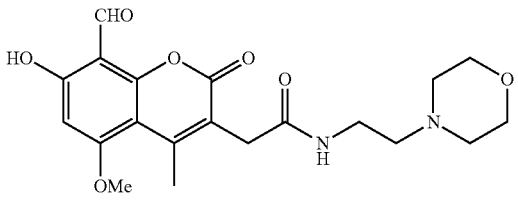 [SMILES: COc1cc(O)c(C=O)c2oc(=O)c(CC(=O)NCCN3CCOCC3)c(C)c12] | <1 | <10 |
| 180 | 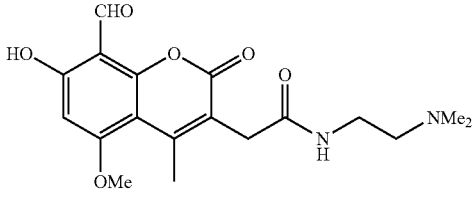 [SMILES: COc1cc(O)c(C=O)c2oc(=O)c(CC(=O)NCCN(C)C)c(C)c12] | <0.1 | <10 |
| 181 | 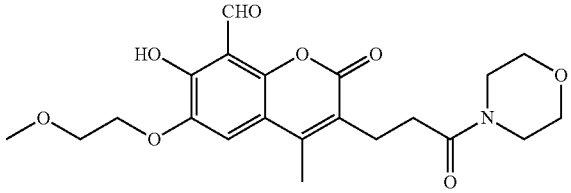 [SMILES: COCCOc1cc2c(C)c(CCC(=O)N3CCOCC3)c(=O)oc2c(C=O)c1O] | <0.1 | <10 |
| 182 | 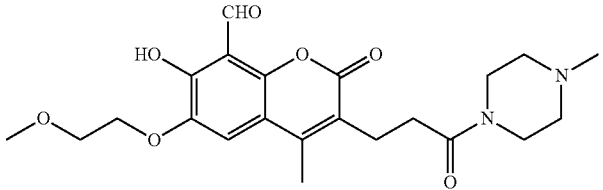 | <0.1 | <10 |
| 183 | 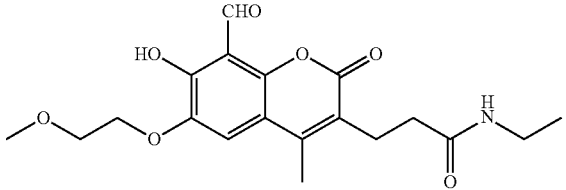 [SMILES: CCNC(=O)CCc1c(C)c2cc(OCCOC)c(O)c(C=O)c2oc1=O] | ND | <10 |
| 184 | 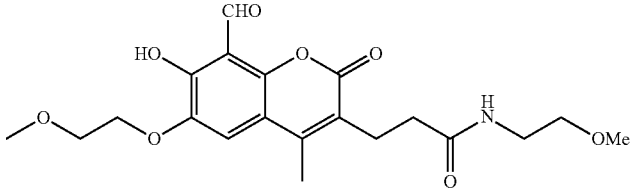 [SMILES: COCCNC(=O)CCc1c(C)c2cc(OCCOC)c(O)c(C=O)c2oc1=O] | <0.1 | <10 |

TABLE 1-continued
| Compound Structure | IC50_av (μM) | EC50_av (μM) |
|---|---|---|
| 185 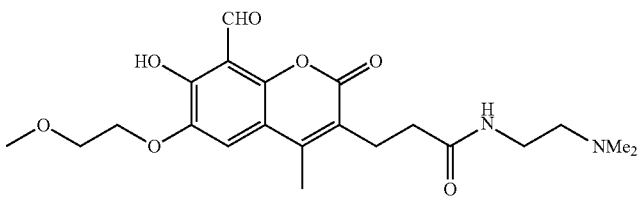 [SMILES: COCCOc1cc2c(C)c(CCC(=O)NCCN(C)C)c(=O)oc2c(C=O)c1O] | <0.1 | >10 |
| 186 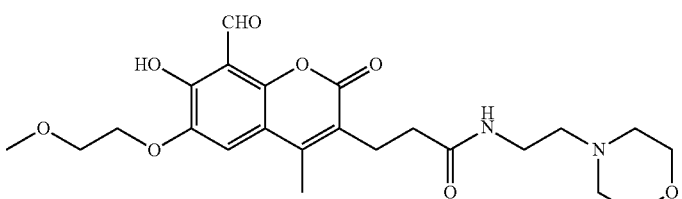 | <1 | >10 |
| 187 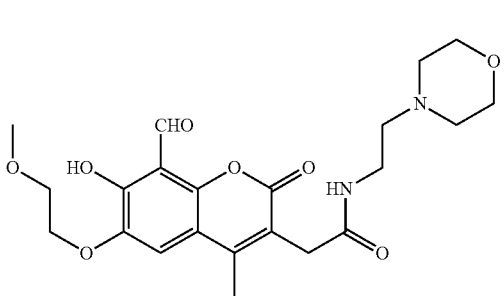 [SMILES: COCCOc1cc2c(C)c(CC(=O)NCCN3CCOCC3)c(=O)oc2c(C=O)c1O] | ND | <10 |
| 188 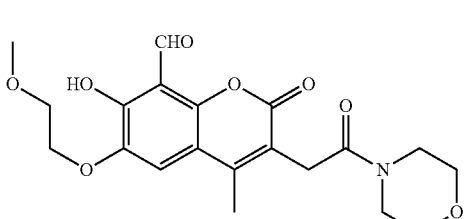 | ND | <10 |
| 189 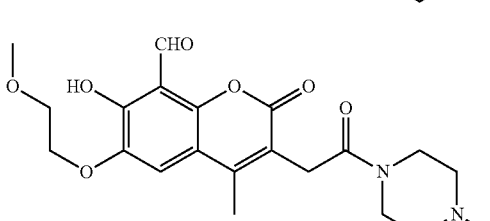 | ND | <10 |
| 190 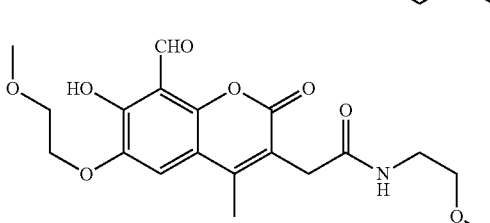 | ND | <10 |
| 191 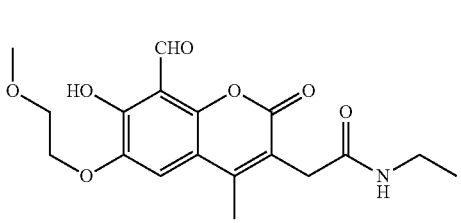 [SMILES: CCNC(=O)Cc1c(C)c2cc(OCCOC)c(O)c(C=O)c2oc1=O] | ND | <10 |

TABLE 1-continued

| Compound Structure | IC50_av (μM) | EC50_av (μM) |
|---|---|---|
| 192 | <1 | <10 |
| 193 | <0.1 | <10 |
| 194 | <0.1 | <10 |
| 195 | ND | <10 |
| 196 | <0.1 | <10 |
| 197 | <1 | <10 |
| 198 | >1 | <10 |

TABLE 1-continued

| Compound Structure | IC50_av (μM) | EC50_av (μM) |
|---|---|---|
| 199 (coumarin with CHO, HO, MeO, Me, Me substituents) | <0.1 | >10 |
| 200 (coumarin with CHO, HO, MeO, Me, iPr substituents) | <0.1 | >10 |
| 201 (coumarin with CHO, HO, Me, propanamide-ethyl-morpholine) | <0.1 | <10 |
| 202 (coumarin with CHO, HO, morpholinoethoxy, Me, propanamide-methoxyethyl) | ND | >10 |
| 203 (coumarin with CHO, HO, morpholinoethoxy, Me, Me) | ND | <10 |
| 204 (coumarin with CHO, HO, morpholinoethoxy, Me, propanamide-ethyl) | ND | >10 |
| 205 (coumarin with CHO, HO, morpholinoethoxy, Me, acetamide-methoxyethyl) | ND | 10 |

TABLE 1-continued

| Compound Structure | IC50_av (μM) | EC50_av (μM) |
|---|---|---|
| 206 | ND | 10 |
| 207 | | >10 |
| 208 | | >10 |
| 209 | | <10 |
| 210 | | >10 |
| 211 | | >10 |
| 212 | | >10 |

TABLE 1-continued

| Compound Structure | IC50_av (μM) | EC50_av (μM) |
|---|---|---|
| 213 — 8-CHO, 7-OH, 6-OMe, 2-methyl-chromone-3-yl-CH₂CH₂C(O)NH-Et | | >10 |
| 214 — 8-CHO, 7-OH, 6-OMe, 2-methyl-chromone-3-yl-CH₂CH₂C(O)NH-CH₂CH₂N(Me)₂·HCl | | >10 |
| 215 — 8-CHO, 7-OH, 2-methyl-chromone-3-yl-CH₂CH₂C(O)NH-CH₂CH₂OMe | | <10 |
| 216 — 8-CHO, 7-OH, 2-methyl-chromone-3-yl-CH₂CH₂C(O)-morpholine | | <10 |
| 217 — 8-CHO, 7-OH, 2-methyl-chromone-3-yl-CH₂CH₂C(O)NH-Et | | <10 |
| 218 — 8-CHO, 7-OH, 2-methyl-chromone-3-yl-CH₂CH₂C(O)NH-CH₂CH₂-NMe₂ | | >10 |
| 219 — 8-CHO, 7-OH, 2-methyl-chromone-3-yl-CH₂CH₂C(O)NH-CH₂CH₂-morpholine | | >10 |

TABLE 1-continued
| Compound Structure | IC50_av (μM) | EC50_av (μM) |
|---|---|---|
| 220 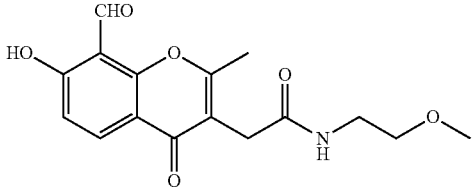 [SMILES: COCCNC(=O)Cc1c(C)oc2c(C=O)c(O)ccc2c1=O] | | <10 |
| 221 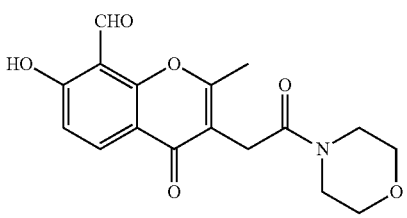 [SMILES: Cc1oc2c(C=O)c(O)ccc2c(=O)c1CC(=O)N1CCOCC1] | | >10 |
| 222 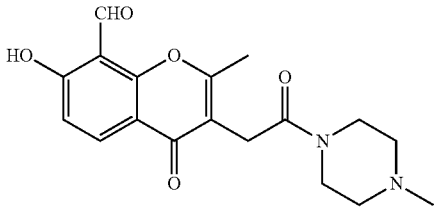 [SMILES: Cc1oc2c(C=O)c(O)ccc2c(=O)c1CC(=O)N1CCN(C)CC1] | | <10 |
| 223 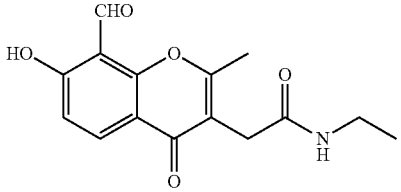 [SMILES: CCNC(=O)Cc1c(C)oc2c(C=O)c(O)ccc2c1=O] | | <10 |
| 224 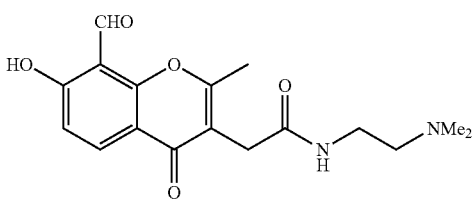 [SMILES: Cc1oc2c(C=O)c(O)ccc2c(=O)c1CC(=O)NCCN(C)C] | | >10 |
| 225 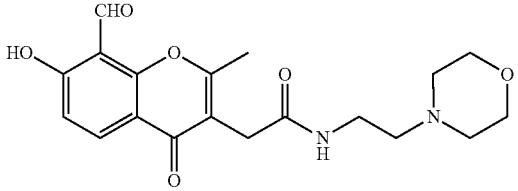 [SMILES: Cc1oc2c(C=O)c(O)ccc2c(=O)c1CC(=O)NCCN1CCOCC1] | | >10 |
| 226 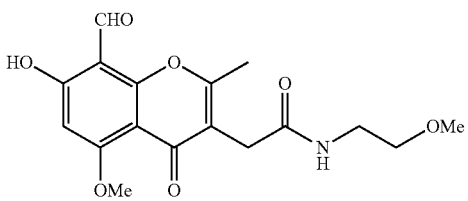 [SMILES: COCCNC(=O)Cc1c(C)oc2c(C=O)c(O)cc(OC)c2c1=O] | | <10 |

TABLE 1-continued
| Compound Structure | IC50_av (μM) | EC50_av (μM) |
|---|---|---|
| 227 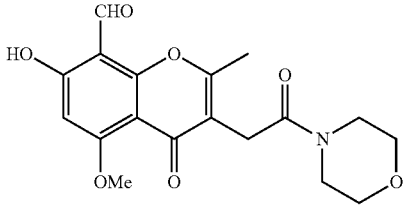 | | <10 |
| 228 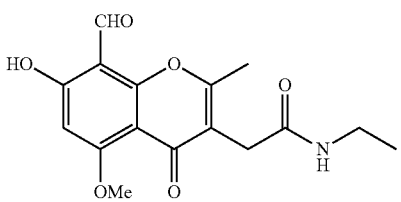 [SMILES: CCNC(=O)Cc1c(C)oc2c(C=O)c(O)cc(OC)c2c1=O] | | <10 |
| 229 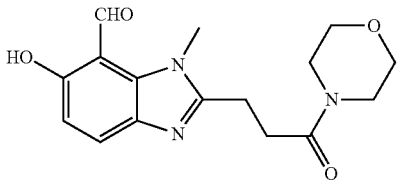 [SMILES: Cn1c(CCC(=O)N2CCOCC2)nc2ccc(O)c(C=O)c21] | | >10 |
| 230 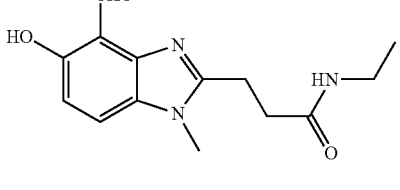 | | >10 |
| 231 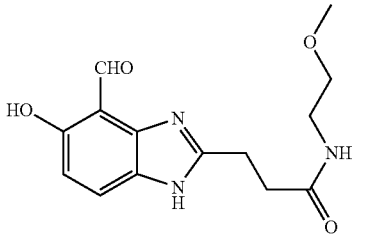 [SMILES: COCCNC(=O)CCc1nc2c(C=O)c(O)ccc2[nH]1] | | >10 |
| 232 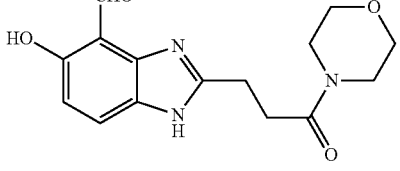 | | >10 |
| 233 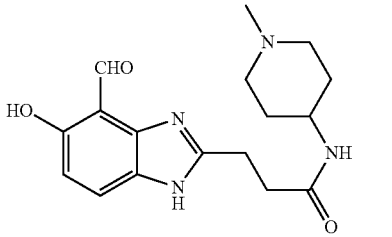 [SMILES: CN1CCC(NC(=O)CCc2nc3c(C=O)c(O)ccc3[nH]2)CC1] | | <10 |

TABLE 1-continued
| Compound Structure | IC50_av (μM) | EC50_av (μM) |
|---|---|---|
| 234 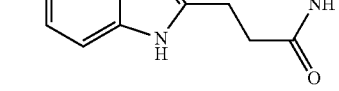 | | >10 |
| 235  | | >10 |
| 236 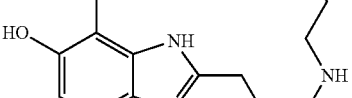 | | >10 |
| 237  | | >10 |
| 238 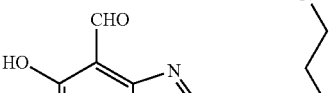 | | >10 |
| 239 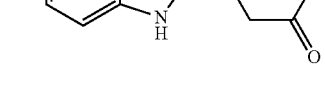 | | >10 |
| 240 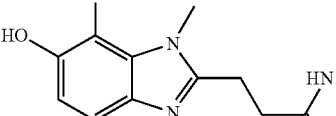 | | >10 |

TABLE 1-continued
| Compound | Structure | IC50_av (μM) | EC50_av (μM) |
|---|---|---|---|
| 241 | 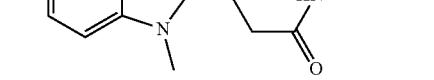 | | >10 |
| 242 |  | | >10 |
| 243 | 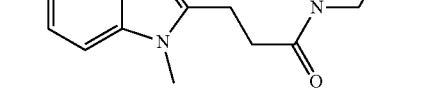 | | >10 |
| 244 |  | | >10 |
| 245 | 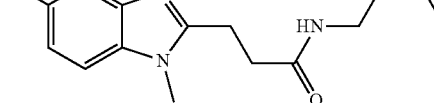 | | <10 |
| 246 |  | | >10 |
| 247 | 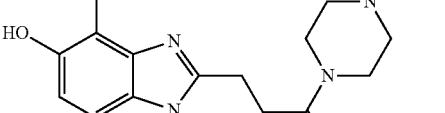 | | >10 |
| 248 |  | | >10 |

TABLE 1-continued
| Compound Structure | IC50_av (μM) | EC50_av (μM) |
|---|---|---|
| 249 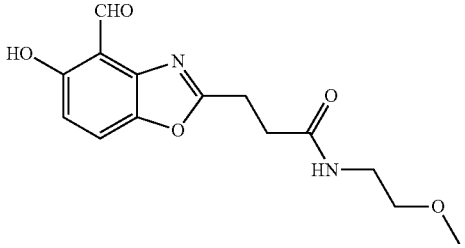 [SMILES: COCCNC(=O)CCc1nc2c(C=O)c(O)ccc2o1] | | >10 |
| 250 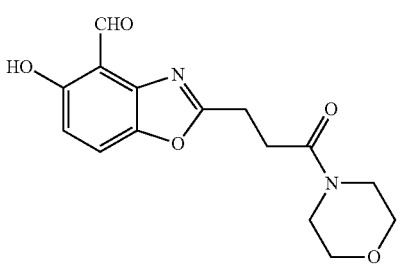 [SMILES: O=Cc1c(O)ccc2oc(CCC(=O)N3CCOCC3)nc12] | | >10 |
| 251 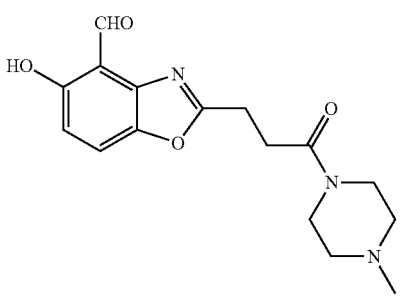 [SMILES: CN1CCN(C(=O)CCc2nc3c(C=O)c(O)ccc3o2)CC1] | | >10 |
| 252 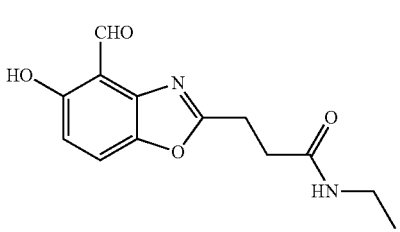 [SMILES: CCNC(=O)CCc1nc2c(C=O)c(O)ccc2o1] | | >10 |
| 253 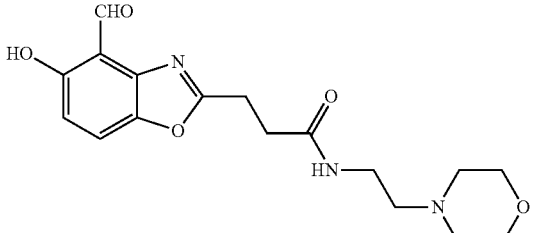 | | <10 |
| 254 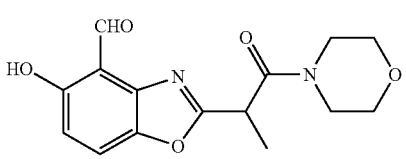 [SMILES: CC(C(=O)N1CCOCC1)c1nc2c(C=O)c(O)ccc2o1] | | >10 |

TABLE 1-continued
| Compound Structure | IC50_av (μM) | EC50_av (μM) |
|---|---|---|
| 255 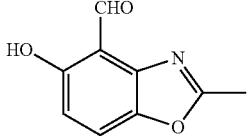 | | <10 |
| 256 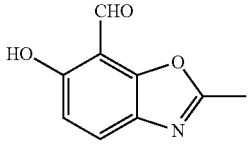 | | >10 |
| 257 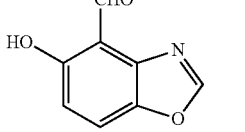 | | >10 |
| 258 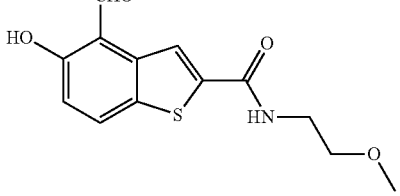 | | >10 |
| 259 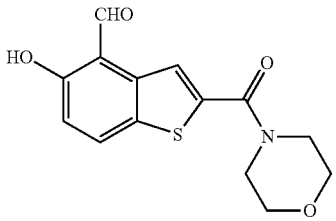 [SMILES: O=Cc1c(O)ccc2sc(C(=O)N3CCOCC3)cc12] | | >10 |
| 260 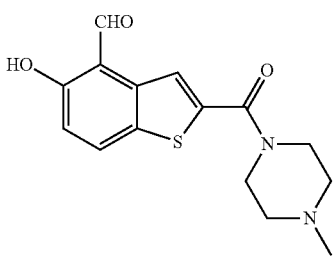 [SMILES: CN1CCN(C(=O)c2cc3c(C=O)c(O)ccc3s2)CC1] | | >10 |
| 261 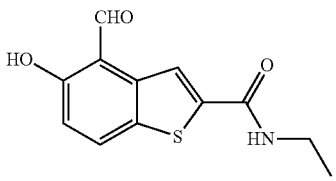 [SMILES: CCNC(=O)c1cc2c(C=O)c(O)ccc2s1] | | <10 |
| 262 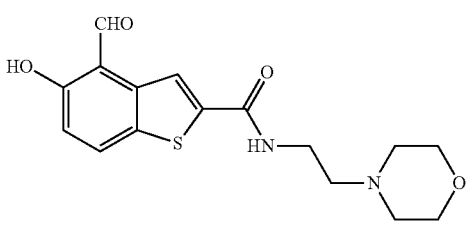 | | <10 |

TABLE 1-continued
| Compound Structure | IC50_av (μM) | EC50_av (μM) |
|---|---|---|
| 263 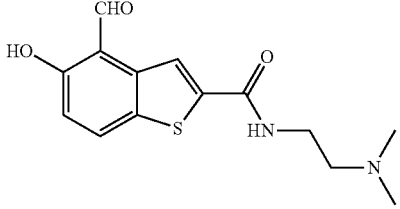 [SMILES: CN(C)CCNC(=O)c1cc2c(C=O)c(O)ccc2s1] | | >10 |
| 264 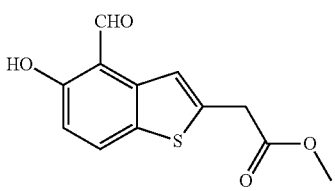 [SMILES: COC(=O)Cc1cc2c(C=O)c(O)ccc2s1] | | >10 |
| 265 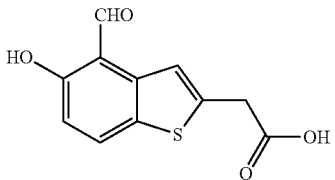 [SMILES: O=Cc1c(O)ccc2sc(CC(=O)O)cc12] | | >10 |
| 266 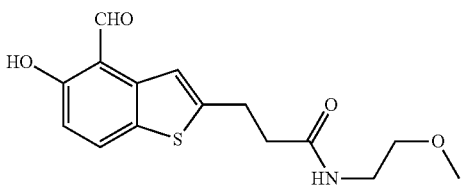 [SMILES: COCCNC(=O)CCc1cc2c(C=O)c(O)ccc2s1] | | <10 |
| 267 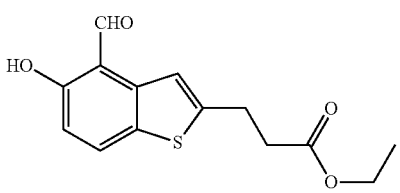 [SMILES: CCOC(=O)CCc1cc2c(C=O)c(O)ccc2s1] | | >10 |
| 268 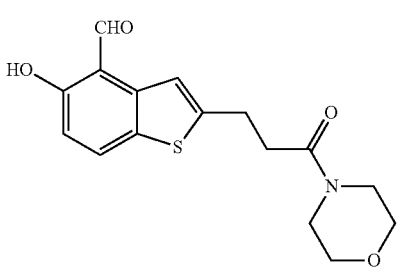 [SMILES: O=Cc1c(O)ccc2sc(CCC(=O)N3CCOCC3)cc12] | | >10 |
| 269 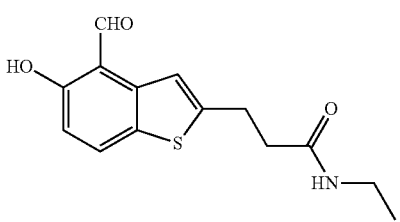 [SMILES: CCNC(=O)CCc1cc2c(C=O)c(O)ccc2s1] | | >10 |

TABLE 1-continued
| Compound Structure | IC50_av (μM) | EC50_av (μM) |
|---|---|---|
| 270 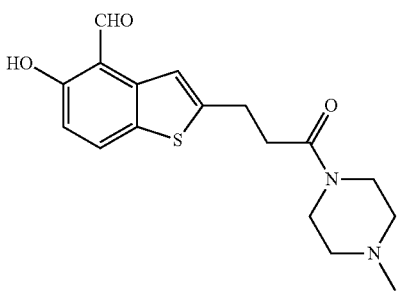 [SMILES: CN1CCN(C(=O)CCc2cc3c(C=O)c(O)ccc3s2)CC1] | | ND |
| 271 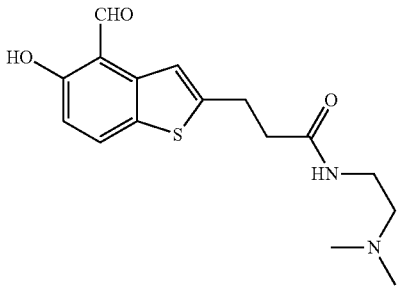 [SMILES: CN(C)CCNC(=O)CCc1cc2c(C=O)c(O)ccc2s1] | | <10 |
| 272 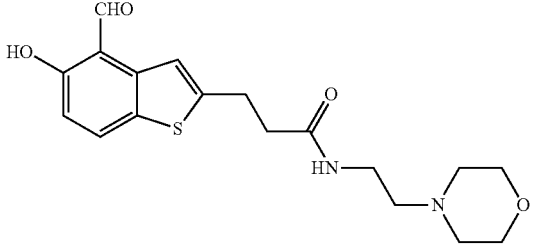 [SMILES: O=Cc1c(O)ccc2sc(CCC(=O)NCCN3CCOCC3)cc12] | | ND |
| 273 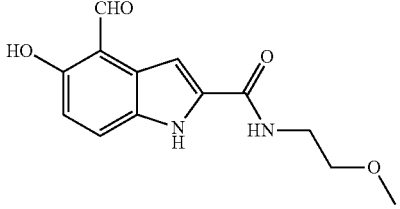 [SMILES: COCCNC(=O)c1cc2c(C=O)c(O)ccc2[nH]1] | | >10 |
| 274 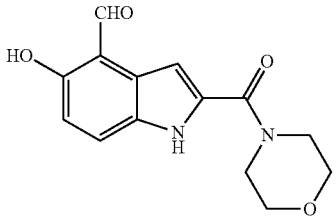 [SMILES: O=Cc1c(O)ccc2[nH]c(C(=O)N3CCOCC3)cc12] | | >10 |
| 275 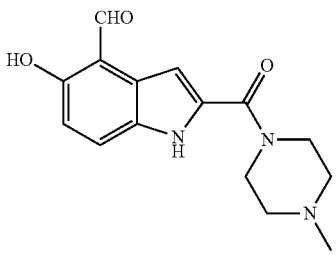 | | >10 |

TABLE 1-continued

| Compound Structure | | IC50_av (μM) | EC50_av (μM) |
|---|---|---|---|
| 276 | 4-CHO, 5-OH-1H-indole-2-carboxamide, N-ethyl | | >10 |
| 277 | 4-CHO, 5-OH-1H-indole-2-carboxamide, N-(2-morpholinoethyl) | | >10 |
| 278 | 4-CHO, 5-OH-1H-indole-2-carboxamide, N-(2-(dimethylamino)ethyl) | | >10 |
| 279 | 4-CHO, 5-OH-1H-indole-2-carboxylic acid ethyl ester | | >10 |
| 280 | 4-CHO, 5-OH-benzofuran-2-carboxylic acid ethyl ester | | >10 |
| 281 | 4-CHO, 5-OH-benzofuran-2-carboxylic acid | | >10 |
| 282 | 4-CHO, 5-OH-benzofuran-2-carboxamide, N-(2-methoxyethyl) | | >10 |
| 283 | 4-CHO, 5-OH-benzofuran-2-yl morpholinomethanone | | >10 |

TABLE 1-continued
| Compound Structure | IC50_av (µM) | EC50_av (µM) |
|---|---|---|
| 284 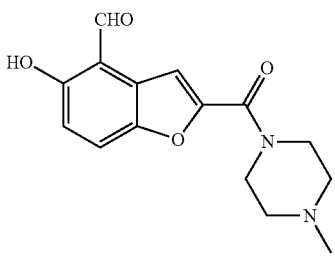 [SMILES: CN1CCN(C(=O)c2cc3c(C=O)c(O)ccc3o2)CC1] | | >10 |
| 285 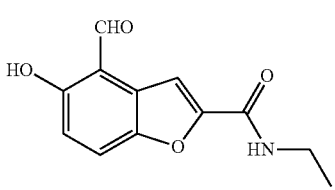 [SMILES: CCNC(=O)c1cc2c(C=O)c(O)ccc2o1] | | <10 |
| 286 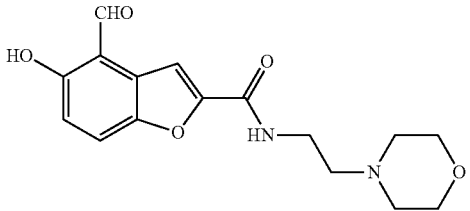 [SMILES: O=Cc1c(O)ccc2oc(C(=O)NCCN3CCOCC3)cc12] | | <10 |
| 287 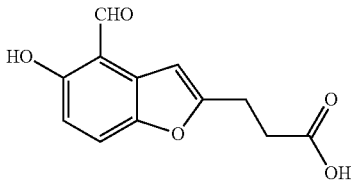 [SMILES: O=Cc1c(O)ccc2oc(CCC(=O)O)cc12] | | ND |
| 288 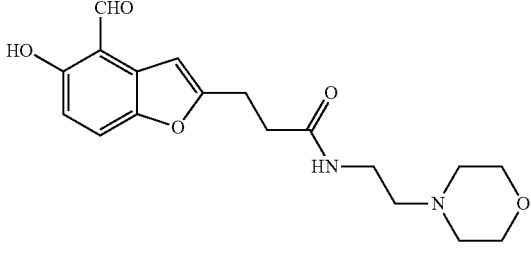 [SMILES: O=Cc1c(O)ccc2oc(CCC(=O)NCCN3CCOCC3)cc12] | | ND |
| 289 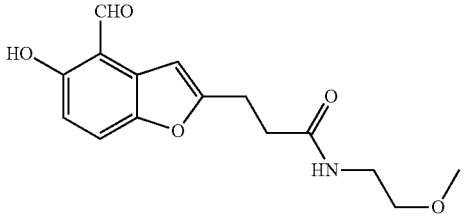 [SMILES: COCCNC(=O)CCc1cc2c(C=O)c(O)ccc2o1] | | ND |

TABLE 1-continued
| Compound Structure | IC50_av (μM) | EC50_av (μM) |
|---|---|---|
| 290 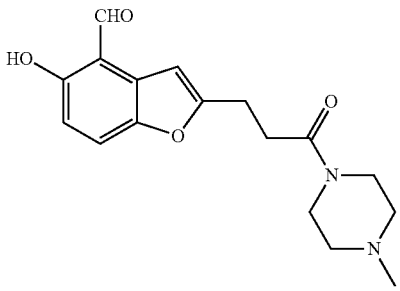 [SMILES: CN1CCN(C(=O)CCc2cc3c(C=O)c(O)ccc3o2)CC1] | | ND |
| 291 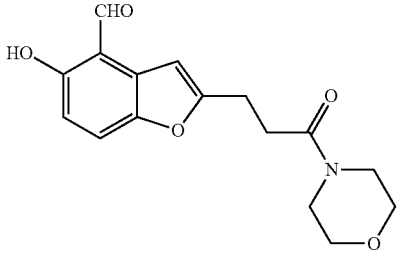 [SMILES: O=Cc1c(O)ccc2oc(CCC(=O)N3CCOCC3)cc12] | | ND |
| 292 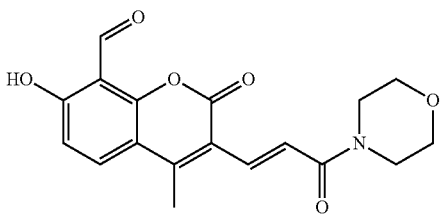 [SMILES: Cc1c(/C=C/C(=O)N2CCOCC2)c(=O)oc2c(C=O)c(O)ccc12] | | |
| 293 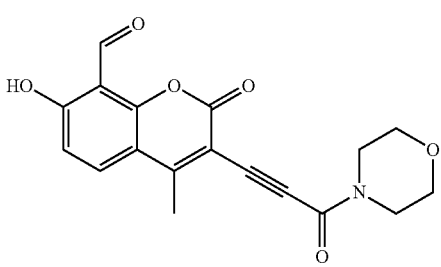 [SMILES: Cc1c(C#CC(=O)N2CCOCC2)c(=O)oc2c(C=O)c(O)ccc12] | | |
| 294 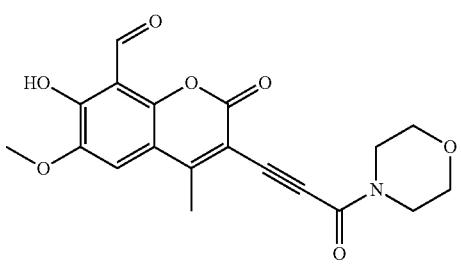 [SMILES: COc1cc2c(C)c(C#CC(=O)N3CCOCC3)c(=O)oc2c(C=O)c1O] | | |

TABLE 1-continued

| Compound Structure | IC50_av (μM) | EC50_av (μM) |
|---|---|---|
| 295 | | |
| 296 | | |
| 297 | | |
| 298 | | |

TABLE 1-continued
| Compound Structure | IC50_av (μM) | EC50_av (μM) |
|---|---|---|
| 299 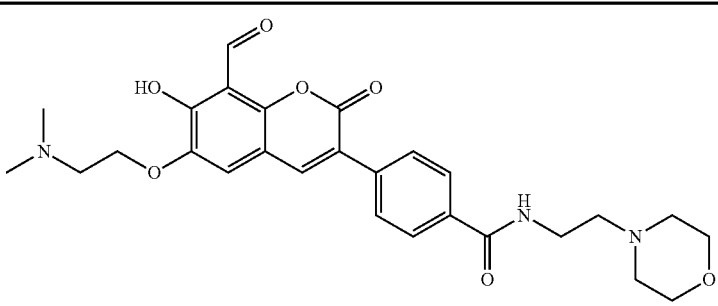 | | |
| 300 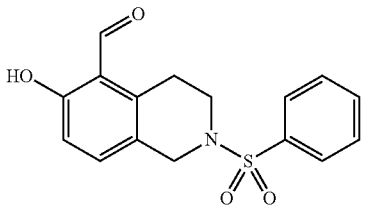 [SMILES: O=Cc1c(O)ccc2c1CCN(S(=O)(=O)c1ccccc1)C2] | | |
| 301 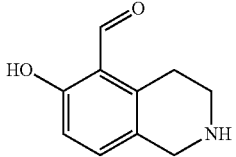 [SMILES: O=Cc1c(O)ccc2c1CCNC2] | | |
| 302 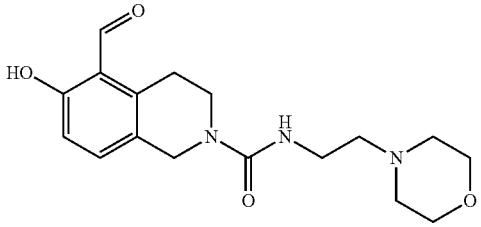 [SMILES: O=Cc1c(O)ccc2c1CCN(C(=O)NCCN1CCOCC1)C2] | | |
| 303 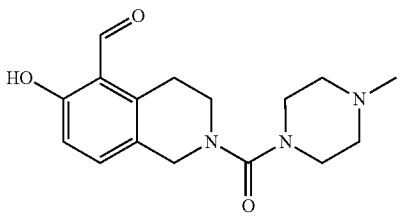 | | |
| 304 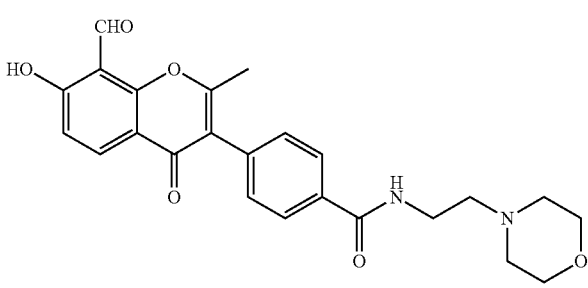 [SMILES: Cc1oc2c(C=O)c(O)ccc2c(=O)c1-c1ccc(C(=O)NCCN2CCOCC2)cc1] | | |

TABLE 1-continued

| Compound Structure | IC50_av (μM) | EC50_av (μM) |
|---|---|---|
| 305 | | |
| 306 | | |
| 307 | | |
| 308 | | |
| 309 | | |

TABLE 1-continued

| Compound Structure | IC50_av (μM) | EC50_av (μM) |
|---|---|---|

310

311

312

313

TABLE 1-continued

| Compound Structure | IC50_av (µM) | EC50_av (µM) |
|---|---|---|
| 314 | | |
| 315 | | |
| 316 | | |
| 317 | | |
| 318 | | |
| 319 | | |

TABLE 1-continued

| Compound Structure | IC50_av (µM) | EC50_av (µM) |
|---|---|---|
| 320 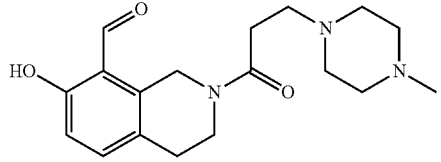 [SMILES: CN1CCN(CCC(=O)N2CCc3ccc(O)c(C=O)c3C2)CC1] | | |
| 321 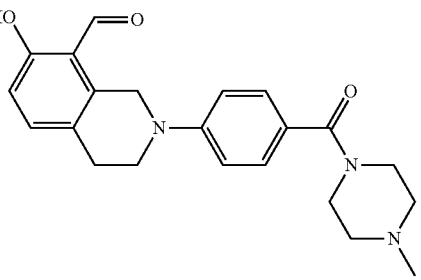 | | |
| 322 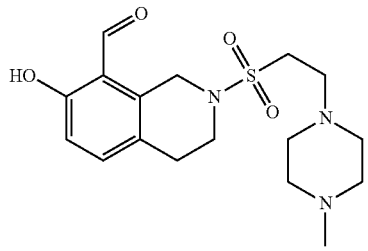 [SMILES: CN1CCN(CCS(=O)(=O)N2CCc3ccc(O)c(C=O)c3C2)CC1] | | |
| 323 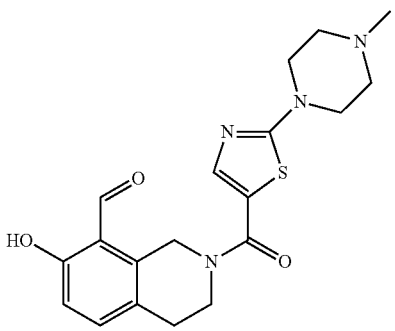 [SMILES: CN1CCN(c2ncc(C(=O)N3CCc4ccc(O)c(C=O)c4C3)s2)CC1] | | |

IRE-1α inhibitor compounds include both the free forms and pharmaceutically acceptable salts of pharmaceutically usable stereoisomers, E/Z isomers, enantiomers, racemates, diastereomers, hydrates, and solvates. Some of the specific IRE-1α inhibitor compounds described herein are the protonated salts of amine compounds. The term "free form" refers to the amine compounds in non-salt form. The encompassed pharmaceutically acceptable salts not only include the salts described for the specific compounds disclosed herein, but also all the typical pharmaceutically acceptable salts of the free form of IRE-1α inhibitor compounds and prodrugs thereof.

The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms.

Pharmaceutically acceptable salts of the disclosed IRE-1α inhibitor compounds can be synthesized which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Pharmaceutically acceptable salts of IRE-1α inhibitor compounds include the conventional non-toxic salts of the compounds as formed by reacting a basic compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, benzenesulfonic, methanesulfonic, ethane disulfonic, oxalic, isethionic, trifluoroacetic and the like.

When an IRE-1α inhibitor compound is acidic, suitable pharmaceutically acceptable salts include salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular salts are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. The preparation of the pharmaceutically acceptable salts described above and other typical pharmaceutically acceptable salts is more fully described by Berg et al., "Pharmaceutical Salts," *J. Pharm. Sci.*, 1977: 66:1-19.

Some IRE-1α compounds or prodrugs are potentially internal salts or zwitterions, because under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

IRE-1α inhibitor compounds or prodrugs thereof may have asymmetric centers, chiral axes, and chiral planes (as described in: E. L. Eliel and S. H. Wilen, Stereochemistry of Carbon Compounds, John Wiley & Sons, New York, 1994, pages 1119-1190), and may occur as racemates, racemic mixtures, and as individual diastereomers, with all possible isomers and mixtures thereof, including optical isomers, being included.

An IRE-1α inhibitor compound or prodrug thereof may be of such a nature that its constituent atoms are capable of being arranged spatially in two or more ways, despite having identical bonds. As a consequence, this compound exists in the form of stereoisomers. Cis/trans isomerism is only one type of stereoisomerism. If the stereoisomers are image and mirror image which cannot be superimposed, they are enantiomers which have chirality or handedness since one or more asymmetric carbon atoms are present in the structure forming them. Enantiomers are optically active and therefore distinguishable since they rotate the plane of polarized light to an equal extent, but in opposite directions.

"Solvates" are adductions of inert solvent molecules onto the compounds which form owing to their mutual attractive force. Solvates are, for example, monohydrates, dihydrates or alcoholates.

If two or more asymmetric carbon atoms are present in an IRE-1α compound, two possible configurations exist at each of these carbon atoms. If two asymmetric carbon atoms are present, four possible stereoisomers exist, for example.

Furthermore, these four possible stereoisomers can be divided into six possible pairs of stereoisomers that differ from each other. In order for a pair of molecules with more than one asymmetric carbon to be enantiomers, they must have different configurations at each asymmetric carbon. Those pairs that do not behave as enantiomers have a different stereochemical relationship, which is known as a diastereomeric relationship. Stereoisomers that are not enantiomers are known as diastereoisomers, or, more frequently, diastereomers.

IRE-1α inhibitor compounds thus include stereoisomers, and, if these are enantiomers, the individual enantiomers, racemic mixtures of these enantiomers, and artificial, i.e. synthetic, mixtures comprising proportions of these enantiomers which are different from the proportions of these enantiomers observed in a racemic mixture. If an IRE-1α inhibitor compound has stereoisomers that are diastereomers, this compound includes the individual diastereomers as well as mixtures of any two or more of these diastereomers in any desired proportions.

The specific biological effects and/or physical and chemical properties of a pair or set of enantiomers of an IRE-1α inhibitor compound—if present—may make it desirable to use these enantiomers in certain ratios, for example to form a final therapeutic product. The following is intended to serve for illustration: if a pair of enantiomers exists, the enantiomers can be used in ratios such as 90% (R)-10% (S), 80% (R)-20% (S), 70% (R)-30% (S), 60% (R)-40% (S), 50% (R)-50% (S), 40% (R)-60% (S), 30% (R)-70% (S), 20% (R)-80% (S), and 10% (R)-90% (S). After evaluation of the properties of the various enantiomers of an IRE-1α inhibitor compound—if they exist—the corresponding amount of one or more of these enantiomers having certain desired properties which form the final therapeutic product can be determined in a simple manner.

For IRE-1α inhibitor compounds disclosed herein which may exist as tautomers, both tautomeric forms are encompassed by a depicted structural formula, even though only one tautomeric structure is depicted. For example, a compound such as that below drawn as the keto tautomer includes the enol tautomer, and vice versa, as well as mixtures thereof.

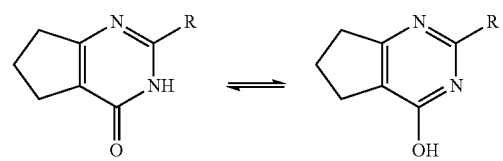

Prodrugs

A "prodrug" as used herein is a compound that can be metabolized to active IRE-1α inhibitor compound after administration. For example, IRE-1α inhibitor compounds disclosed herein can be modified, e.g., with alkyl or acyl groups, sugars, or oligopeptides and which are rapidly cleaved in vivo to release the active IRE-1α inhibitor compounds.

Derivatives of the corresponding aromatic alcohols can serve as prodrugs for aromatic aldehydes because alcohols and aldehydes are metabolically interconvertible, according to the following general scheme:

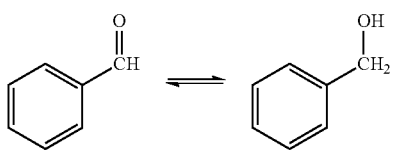 [SMILES: O=Cc1ccccc1 ; OCc1ccccc1]

Scheline, 1972, *Xenobiotica*, 2, 227-36.

Examples of prodrugs of aldehydes, ketones, alcohols and other functional groups are described in Wermuth et al., 1996, *Designing Prodrugs and Bioprecursors I: Carrier Prodrugs. In The Practice of Medicinal Chemistry*, pp. 672-696; and in Wermuth, 1996, "Preparation of Water-Soluble Compounds by Covalent Attachment of Solubilizing Moieties," in Wermuth, ed., *The Practice of Medicinal Chemistry*, pp. 756-776. Other general aldehyde derivatives and alcohol derivatives that can perform prodrug functions as well as methods for their preparation are described in Cheronis et al., 1965, *Semimicro Qualitative Organic Analysis*, New York: Interscience, pp. 465-518.

Methods of Preparing IRE-1α Inhibitor Compounds and Prodrugs

IRE-1α inhibitor compounds and starting materials for their synthesis can be prepared by appropriate modification of methods known in the art as described in the literature, for example in standard works such as Houben-Weyl, Methoden der organischen Chemie, Georg-Thieme-Verlag, Stuttgart. Methods may also be found by computer search in The MDL® CrossFire Beilstein database, in which the reaction domain details the preparation of substances. See also the specific Examples, below.

Pharmaceutical Preparations

Any of the IRE-1α inhibitor compounds and prodrugs disclosed herein can be formulated as pharmaceuticals using methods well known in the art. Pharmaceutical formulations typically comprise at least one IRE-1α inhibitor compound or prodrug thereof mixed with a carrier, diluted with a diluent, and/or enclosed or encapsulated by an ingestible carrier in the form of a capsule, sachet, cachet, paper, or other container, or by a disposable container such as an ampoule.

A carrier or diluent can be a solid, semi-solid, or liquid material. Some examples of diluents or carriers which can be employed in the pharmaceutical compositions are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, methyl cellulose, polyoxyethylene sorbitan monolaurate, ethyl lactate, propylhydroxybenzoate, sorbitan trioleate, sorbitan sesquioleate, and oleyl alcohol.

Pharmaceutical compositions can be manufactured by methods well known in the art, including conventional mixing, dissolving, granulating, dragee-making, levigating, emulsifying, encapsulating, entrapping, or lyophilizing processes.

For injection, the IRE-1α inhibitor compounds can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. If desired, any of the IRE-1α inhibitor compounds or prodrugs thereof disclosed herein can be provided in a pyrogen-free pharmaceutically acceptable vehicle.

For oral administration, an IRE-1α inhibitor compound or prodrug thereof can be combined with pharmaceutically acceptable carriers or vehicles which enable the IRE-1α inhibitor compound or prodrug thereof to be formulated as tablets, pills, dragees, capsules, liquids, gels, syrups, slurries, suspensions and the like. Fillers can be used, such as gelatin, sugars (e.g., lactose, sucrose, mannitol, or sorbitol), cellulose preparations (e.g., maize starch, wheat starch, rice starch, potato starch, gum tragacanth, methyl cellulose, hydroxypropylmethyl-cellulose, sodium carboxymethylcellulose), and/or polyvinylpyrrolidone (PVP). If desired, disintegrating agents can be added, such as the cross-linked polyvinyl pyrrolidone, agar, or alginic acid or a salt thereof, such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, an IRE-1α inhibitor compound or prodrug thereof can be dissolved or suspended in a suitable liquid, such as fatty oils, liquid paraffin, or liquid polyethylene glycols. In addition, stabilizers can be added. All formulations for oral administration preferably are in dosages suitable for such administration.

For buccal administration, the compositions can take the form of tablets or lozenges formulated in conventional manners.

For administration by inhalation, pharmaceutical preparations can be delivered in the form of an aerosol sprays from a pressurized pack or a nebulizer, with the use of a suitable propellant, e.g., dichlorodifluoromethane, trichlorofluoromethane, dichlorotetrafluoroethane, carbon dioxide, or other suitable gas. If desired, a valve can be used to deliver a metered amount. Capsules and cartridges of, e.g., gelatin for use in an inhaler or insufflator, can be formulated containing a powder mix of an IRE-1α inhibitor compound or prodrug thereof and a suitable powder base, such as lactose or starch.

IRE-1α inhibitor compounds or prodrugs thereof can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of an IRE-1α inhibitor compound or prodrug thereof. Additionally, a suspension of an IRE-1α inhibitor compound or prodrug thereof can be prepared as an appropriate oily injection suspension. Suitable lipophilic solvents or vehicles include fatty oils such as sesame oil, synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of an IRE-1α inhibitor compound or prodrug thereof to allow for the preparation of highly concentrated solutions.

Alternatively, an IRE-1α inhibitor compound or prodrug thereof can be in powder form for constitution with a suitable vehicle, e.g., sterile pyrogen-free water, before use.

IRE-1α inhibitor compounds or prodrugs thereof can also be formulated in rectal compositions such as suppositories or retention enemas, e.g., containing conventional suppository bases such as cocoa butter or other glycerides.

In addition to the formulations described previously, an IRE-1α inhibitor compound or prodrug thereof can also be formulated as a depot preparation. Such long-acting formulations can be administered by implantation (for example, subcutaneously or intramuscularly) or by intramuscular injection. Thus, for example, an IRE-1α inhibitor compound or prodrug thereof can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

In addition to the common dosage forms set out above, an IRE-1α inhibitor compound or prodrug thereof can be administered by a controlled release means and/or delivery device, including ALZET® osmotic pumps (Alza Corporation). Suitable delivery devices are described in U.S. Pat. Nos. 3,845,770; 3,916,899; 3,536,809; 3,598,123; 3,944,064; and 4,008,719.

Methods

IRE-1α inhibitor compounds or prodrugs thereof can be used to inhibit IRE-1α activity (e.g., cleavage of RNA or mRNA, RNA or mRNA splicing). In some embodiments IRE-1α activity (e.g., cleavage of RNA or mRNA, RNA or mRNA splicing) is inhibited in vitro. In other embodiments IRE-1α activity (e.g., cleavage of RNA or mRNA, RNA or mRNA splicing) is inhibited in vivo.

IRE-1α inhibitor compounds or prodrugs thereof can be used to prepare formulations or medicaments for inhibiting tumor cell growth and for treating the disorders disclosed below. IRE-1α inhibitor compounds or prodrugs thereof can be administered to a patient, preferably a human patient, in pharmaceutical preparations as disclosed above, preferably with a pyrogen-free pharmaceutically acceptable vehicle, at doses effective to treat or ameliorate a symptom of a disorder associated with the unfolded protein response. IRE-1α inhibitor compounds and prodrugs thereof can be used to treat patient populations which are not entirely coincident with those most commonly receiving treatment for disorders associated with the unfolded protein response (e.g., cancer therapies or therapies for autoimmune disorders). For example, IRE-1α inhibitor compounds and prodrugs thereof can be administered to patients at the earliest stages of these conditions, even those to whom traditional therapies are commonly not offered.

Disorders Associated with UPR

A fine balance exists between a cell's life and death depending on how protein folding stress is managed by the cell (proteostasis). Imbalances in proteostasis lead to many metabolic, oncological, neurodegenerative, inflammatory, cardiovascular disorders and infectious disease (Balch et al., Science 319, 916, 2008). The UPR relates specifically to the proteostasis of the endoplasmic reticulum where all secreted and membrane proteins are translated, folded and processed for delivery to their individual site of action. Therefore, activation of the UPR enhances protein folding in the ER allowing the cell to survive. If protein folding stress is not managed in the ER, the cells will initiate apoptosis.

Protein folding stress may be a natural hallmark of the type of cell for example insulin secreting β-islet cells or antibody secreting plasma cells. In both cases, the cell has fine tuned the machinery to deal with the stress by activating the UPR. Depending on the disease type, it may be therapeutically beneficial to induce or inhibit the UPR. For example, in type II diabetes or Alzheimer's disease, it may be therapeutically beneficial to activate the UPR in such a way where β-islet cells survive the stress of over producing insulin or neurons survive the apoptotic effects due to unfolded aggregates of β-amyloid protein. Diseases such as cancer, inflammation, and viral infection may be therapeutically modulated by inhibition of the UPR. In these types of conditions, cellular survival due to corruption of the UPR may be impacted. Protein folding in the ER is negatively impacted by such conditions in the tumor microenvironment as hypoxia, glucose starvation, amino acid deprivation, acidosis and mutant malfolded and oncogenic proteins. Additionally chemo-, bio-, and radiotherapy can lead to protein folding stress. It may be possible to induce apoptosis in these conditions by inhibiting the anti-apoptotic effects of the UPR. Myeloma derived from neoplastic antibody secreting plasma cells provides an example of a condition in which this approach can be applied.

Lastly, enveloped viruses must use and corrupt this system to ensure production of progeny from infected cells. Viruses often produce vast quantities of viral membrane glycoproteins which are folded and modified in the ER. Therefore, activation of the UPR by the virus for this purpose as a survival mechanism is entirely conceivable. It is therefore logical that inhibition of the UPR during viral infection can impact the outcome of the disease in a beneficial way.

Only specialized secretory cells and diseased cells activate the UPR for their own benefit. Most cells are not under such protein folding stress and therefore would not be impacted by a UPR inhibitor. Thus, "disorders associated with the UPR" as used herein means conditions for which pathogenesis can be advantageously impacted by inhibition of the UPR. In various embodiments such inhibition of the UPR is accomplished through inhibition of IRE-1α.

In some embodiments the IRE-1α inhibitor compounds or prodrugs thereof are useful to treat or ameliorate a symptom of a B cell autoimmune disease, certain cancers, and infections of enveloped viruses that use the endoplasmic reticulum as a viral factory for expressing viral surface and spike proteins for budding and infection. IRE-1α inhibitors and prodrugs thereof can be used as single agents or in combination therapies, as described below.

B cell autoimmune diseases which can be treated include, but are not limited to, Addison's disease, antiphospholipid syndrome, aplastic anemia, autoimmune hemolytic anemias, autoimmune hepatitis, autoimmune hypophysitis, autoimmune lymphoproliferative disorders, autoimmune myocarditis, Churg-Strauss syndrome, epidermolysis bullosa acquisita, giant cell arteritis, Goodpasture's syndrome, Graves' disease, Guillain-Barré syndrome, Hashimoto's thyroiditis, idiopathic thrombocytopenic purpura, IgA nephropathy, myasthenia gravis, pemphigus foliaceous, pemphigus vulgaris, polyarteritis nodosa, polymyositis/dermatomyositis, rheumatoid arthritis, scleroderma, Sjögren's syndrome, systemic lupus erythematosus, Takayasu's arteritis, and Wegener's granulomatosis.

Cancers which can be treated include solid tumors, such as tumors of the breast, bone, prostate, lung, adrenal gland (e.g., adrenocortical tumors), bile duct, bladder, bronchus, nervous tissue (including neuronal and glial tumors), gall bladder, stomach, salivary gland, esophagus, small intestine, cervix, colon, rectum, liver, ovary, pancreas, pituitary adenomas, and secretory adenomas. Methods are particularly useful for treating drug- or radiation-resistant solid tumors.

Cancers of the blood (e.g., lymphomas and leukemias) also can be treated including, but not limited to, multiple myeloma, Hodgkin's lymphoma, non-Hodgkin's lymphomas (e.g., cutaneous T cell lymphomas such as Sezary syndrome and Mycosis fungoides, diffuse large cell lymphoma, HTLV-1 associated T cell lymphoma, nodal peripheral T cell lymphoma, extranodal peripheral T cell lymphoma, central nervous system lymphoma, and AIDS-related lymphoma). Leukemias include acute and chronic types of both lymphocytic and myelogenous leukemia (e.g, acute lymphocytic or lymphoblastic leukemia, acute myelogenous leukemia, acute myeloid leukemia, chronic myelogenous leukemia, chronic lymphocytic leukemia, T cell prolymphocytic leukemia, adult T cell leukemia, and hairy cell leukemia). Monoclonal gammopathy of undetermined significance (MGUS), the precursor of myeloma, also can be treated.

Viral infections which can be treated include infections of enveloped viruses which use the unfolded protein response pathway when they replicate and form infectious progeny (e.g., measles, pox viruses, Ebola, etc.). Infections also include those of Epstein Barr virus (EBV), cytomegalovirus (CMV), Flaviviruses (e.g., Japanese Encephalitis Virus and West Nile Virus), and Hepatitis C virus (HCV).

Combination Therapies

Various types of physiological stress induce the unfolded protein response including, but not limited to, hypoxia, nutrient starvation, acidosis, and genetic damage resulting in mutant or over-expressed misfolded proteins (oncogenic stress). One or more of these conditions are manifest in cancer cells, which may in part be mediated by the microenviroment of the tumor. It is likely the cytoprotective arm of the unfolded protein response (UPR) plays an anti-apoptotic role in tumor survival. In addition, bio- and chemotherapeutic drugs and thermal and radiation treatments may further impact the protein folding and degradation cycle in the ER thereby inducing the UPR as a protective resistance mechanism. Patients succumb to cancer because either the tumor is resistant to conventional therapies, or returns in a resistant form after an initial response to treatment and, therefore, new treatments and treatment combinations are needed.

Angiogenesis inhibitors block tumor growth by inhibiting new blood vessel formation, a process that would enhance the stress effects of the tumor microenvironment. A promising approach to further reduce tumor burden would be to administer anti-angiogenesis agents in combination with IRE-1α/XBP-1 inhibitors to obtain a similar effect as that demonstrated by RNAi knockdown of GRP78, the major chaperone of the ER and target of XBP-1s (Dong et al., Cancer Res. 2007 Jul. 15; 67(2):6700-7). In addition, IRE-1α itself regulates angiogensis by influencing the expression of VEGF.

In some embodiments an IRE-1α inhibitor compound or prodrug thereof is administered in combination with a therapeutic agent that induces or up-regulates IRE-1α expression (e.g., Hsp90 and or HDAC inhibitors, both of which induce IRE-1α activation and XBP-1 splicing) or a therapeutic agent which is less effective when IRE-1α is expressed (e.g., 17-AAG (TANESPIMYCIN®) and suberoylanilide hydroxamic acid (SAHA)).

In some embodiments an IRE-1α inhibitor compound or prodrug thereof is administered in combination with one or more cancer therapies. These therapies include treatments such as radiation therapy or thermal treatment (heat shock) as well as administration of therapeutic agents, such as chemotherapeutic agents and biotherapeutic agents, as described below. Such therapies can be administered separately or together with the IRE-1α inhibitor compound or prodrug, e.g., the one or more treatments can independently be administered at essentially the same time as the IRE-1α inhibitor compound or prodrug or can be administered either before or after the IRE-1α inhibitor compound.

Cancer therapeutic agents which can be used according to various embodiments include, but are not limited to, agents in the following categories (which may overlap):

a. proteasome inhibitors, such as bortezomib ([(1R)-3-methyl-1-[[(2S)-1-oxo-3-phenyl-2-[(pyrazinylcarbonyl) amino]propyl]amino]butyl] boronic acid; MG-341; VELCADE®), MG-132 (N-[(phenylmethoxy)carbonyl]-L-leucyl-N-[(1S)-1-formyl-3-methylbutyl]-L-leucinamide);

b. cytotoxic anticancer therapeutics, such as:
   i. pyrimidine analogs (e.g., 5-fluorouracil, floxuridine, capecitabine, gemcitabine and cytarabine); and purine analogs,
   ii. alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes—dacarbazinine (DTIC);
   iii. microtubule disruptors such as taxane (paclitaxel, docetaxel), vincristin, vinblastin, nocodazole, epothilones and navelbine, and epidipodophyllotoxins (e.g., teniposide); natural products such as vinca alkaloids (e.g., vinblastine, vincristine, and vinorelbine);
   iv. DNA damaging agents, such as actinomycin, amsacrine, anthracyclines, bleomycin, busulfan, camptothecin, carboplatin, chlorambucil, cisplatin, cyclophosphamide, Cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP 16); and platinum coordination complexes (e.g., cisplatin, carboplatin), procarbazine, hydroxyurea, mitotane, aminoglutethimide;

c. antibiotics, such as dactinomycin (actinomycin D), daunorubicin, doxorubicin (adriamycin), idarubicin, anthracyclines, mitoxantrone, bleomycins, plicamycin (mithramycin) and mitomycin;

d. folate antagonists and related inhibitors (e.g., mercaptopurine, thioguanine, pentostatin and 2-chlorodeoxyadenosine [cladribine]); folic acid analogs (e.g., methotrexate)

e. hormones, hormone analogs (e.g., estrogen, tamoxifen, goserelin, bicalutamide, nilutamide);
f. aromatase inhibitors (e.g., letrozole, anastrozole);
g. fibrinolytic agents (such as tissue plasminogen activator, streptokinase and urokinase), aspirin, COX-2 inhibitors, dipyridamole, ticlopidine, clopidogrel, abciximab;
h. antimigratory agents;
i. antisecretory agents (e.g., breveldin); immunosuppressives (e.g., cyclosporine, tacrolimus (FK-506), sirolimus (rapamycin), azathioprine, mycophenolate mofetil);
j. anti-angiogenic compounds (e.g., TNP-470, genistein, Sutent, Vatalinib) and growth factor inhibitors (e.g., vascular endothelial growth factor (VEGF) inhibitors, fibroblast growth factor (FGF) inhibitors, epidermal growth factor (EGF) inhibitors); and multi-kinase inhibitors (e.g., lestaurtinib);
k. antibodies (e.g., trastuzumab (HERCEPTIN®), AVASTIN®, ERBITUX®);
l. cell cycle inhibitors and differentiation inducers (e.g., tretinoin);
m. mTOR (mammalian target of rapamycin) inhibitors (e.g., everolimus, sirolimus);
n. topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan);
o. corticosteroids (e.g., cortisone, dexamethasone, hydrocortisone, methylpednisolone, prednisone, and prenisolone);
p. HSP90 inhibitors (e.g., 17-AAG)
q. mitochondrial dysfunction inducers (e.g., 2-deoxyglucose, dichloroacetic acid);
r. caspase activators; and
s. chromatin disruptors.

In some embodiments the cancer therapeutic agent is selected from the group consisting of alemtuzumab, aminoglutethimide, amsacrine, anastrozole, asparaginase, beg, bevacizumab, bicalutamide, bleomycin, bortezomib, buserelin, busulfan, campothecin, capecitabine, carboplatin, carmustine, CeaVac, cetuximab, chlorambucil, cisplatin, cladribine, clodronate, colchicine, cyclophosphamide, cyproterone, cytarabine, dacarbazine, daclizumab, dactinomycin, daunorubicin, dienestrol, diethylstilbestrol, docetaxel, doxorubicin, edrecolomab, epirubicin, epratuzumab, erlotinib, estradiol, estramustine, etoposide, exemestane, filgrastim, fludarabine, fludrocortisone, fluorouracil, fluoxymesterone, flutamide, gemcitabine, gemtuzumab, genistein, goserelin, huJ591, hydroxyurea, ibritumomab, idarubicin, ifosfamide, IGN-101, imatinib, interferon, irinotecan, ironotecan, letrozole, leucovorin, leuprolide, levamisole, lintuzumab, lomustine, MDX-210, mechlorethamine, medroxyprogesterone, megestrol, melphalan, mercaptopurine, mesna, methotrexate, mitomycin, mitotane, mitoxantrone, mitumomab, nilutamide, nocodazole, octreotide, oxaliplatin, paclitaxel, pamidronate, pentostatin, pertuzumab, plicamycin, porfimer, procarbazine, raltitrexed, rituximab, streptozocin, sunitinib, suramin, tamoxifen, temozolomide, teniposide, testosterone, thalidomide, thioguanine, thiotepa, titanocene dichloride, topotecan, tositumomab, trastuzumab, tretinoin, vatalanib, vinblastine, vincristine, vindesine, and vinorelbine.

Inhibition of IRE-1α Dependent Decay of Membrane Associated mRNAs (RIDD) Pathway Using IRE-1α Inhibitors Inositol requiring enzyme-1 (IRE-1α) is the most highly conserved signaling node of the unfolded protein response (UPR) and represents a potential therapeutic target for a number of diseases associated with endoplasmic reticulum (ER) stress. IRE-1α activates the XBP-1 transcription factor by site specific cleavage of two hairpin loops within its mRNA promoting its nonconventional splicing and alternative translation. In addition, the endoribonuclease of IRE-1α is required for the cleavage and degradation of certain mRNAs coding for primarily secreted and transmembrane proteins targeted to the ER called IRE-1α dependent mRNA decay (RIDD). However, it had not been known whether this is a direct activity or the subsequent activation of a second endoribonuclease. Using IRE-1α specific endoribonuclease inhibitors, Examples 43-46 below demonstrate that this activity is likely direct from the IRE-1α endoribonuclease and that inhibitors selectivity block down-regulation of known targets of the RIDD pathway including but not limited to CD59 and Blos1. IRE-1α inhibitors therefore be useful to treat or ameliorate a symptom of a neurological disorder, or disorders that involve overproduction of insulin or inflammation.

Protein folding perturbations resulting in endoplasmic reticulum (ER) stress are thought to play a role in the pathogenesis of diseases as diverse as neurodegeneration, diabetes and cancer. The unfolded protein response (UPR) coordinates the ability of a cell to respond to ER stress by altering protein translation, folding, and post translational modification of all secreted and membrane proteins. Terminally unfolded proteins are retro-transported to the cytosol by the ER associated degradation (ERAD) machinery for proteolysis by the proteasome. The ER is also the site of lipid biosynthesis and membrane expansion. These activities are linked physiologically to specialized secretory cells; however, depending on stress levels, the UPR can control cellular survival or death via autophagy and apoptosis (Ron & Walter, *Nat Rev Mol Cell Biol.* 8(7), 519-29, 2007). Secretion and membrane composition are balanced by the high caloric demand of these activities against the energy homeostasis of the cell (Ron & Walter, 2007).

Inositol requiring enzyme 1 (IRE-1α) is the most highly conserved signaling node of the unfolded protein response (Ron & Walter, 2007). A unique ER resident transmembrane kinase with a novel C-terminal endoribonuclease domain, IRE-1α is activated in part by the disassociation of BiP/GRP78 in the presence of unfolded protein in the ER lumen (Ron & Walter, 2007). The signal is transduced to the cytosol by the sequential dimerization/multimerization, trans-autophosphorylation and activation of its endoribonuclease (Tirasophon et al., *Genes Dev.* 14 (21) 2725-36, 2000). The specific activity of the endoribonuclease is responsible for the unconventional cytosolic splicing of HAC1 in yeast and excision of the 26 nucleotide intron of the X-box binding protein (XBP-1) transcription factor in metazoan organisms (Ron & Walter, 2007). In mammalian cells IRE-1α acts in concert with companion UPR signaling molecules PKR-like ER resident kinase (PERK) and ATF6 (Ron & Walter, 2007).

XBP-1 mRNA, a major substrate of the IRE-1α endoribonuclease, is cleaved specifically at two conserved stem-loop sites. Each site is located 3' to a mirrored guanosine residue in the 7 base loop (Ron & Walter, 2007). The resulting internal fragment, a 26-nt intron, is removed and the two exon ends are ligated by and unknown mechanism in mammalian cells and by tRNA ligase in yeast (Ron & Walter, 2007). The rejoined mRNA shifts the Open Reading Frame (ORF) and extends the C-terminal domain of XBP-1 from amino acid 164 with an alternative 212 amino acid reading frame producing the active "spliced" transcription factor, XBP-1s, which regulates a broad range of ER resident chaperones, ER translocon channels, ERAD components and lipid metabolic enzymes (Ron & Walter, 2007). An emerging and important activity of IRE-1α is regulated Ire1-dependent decay (RIDD) of mRNAs encoding ER targeted membrane and secreted proteins during stress analogous to the less discriminate but targeted activities of IRE-1α's evolutionary homologue, RNase L (Hollien & Weissman, *Science* 313(5783) 104-07, 2006). This activity in combination with XBP-1s expression has the potential to alter the surface composition of stressed cells and the extracellular proteome. In addition, it appears to selectively target different mRNAs in different types of cells. Substrates include but are not limited to insulin (Han et al., *Cell* 138(3) 562-75, 2009), CD59 (Oikawa et al., *Biochem Biophys Res Commun.* 360(1) 122-127, 2007), Blos1 (Hollien et al., *J Cell Biol.* 186(3) 323-31, 2009), DGAT2 (Thorpe & Schwarze, *Cell Stress Chaperones.* 15(5) 497-508, 2010) and IRE-1α's own mRNA (Tirasophon et al., 2000). IRE-1α endoribonuclease inhibitors selectively block mRNA degradation by IRE-1α including Blos1, DGAT2 and CD59 and IRE-1α itself.

Example 43 below demonstrates that selective and potent IRE-1α endoribonuclease inhibitors disclosed herein can block the RIDD of mRNA targets in both unstressed and ER stressed RPMI 8226 myeloma cells. Diseases linked to ER stress include neurodegenerative diseases, diabetes, inflammation and cancer. This has important implications for disease management.

For example, CD59 is a GPI linked cell surface glycoprotein which as member of the complement regulatory factor family which includes CD46 and CD55. Compliment regulatory factors inhibit complement mediated lysis of cells by preventing membrane attack complex formation. Down modulation of CD59 may play a role in many diseases with an immune component, such as Barraquer-Simons Syndrome, asthma, lupus erythematous, glomerulonephritis, various forms of arthritis, autoimmune heart disease, multiple sclerosis, inflammatory bowel disease, and ischemia-reperfusion injuries, autoimmune hemocytopenias and rejection of transplanted organs (Song, *Autoimmunity* 39(5) 403-10, 2006; Ruiz-Argüelles & Llorente, *Autoimmun Rev.* 6(3):155-61, 2007; Arumugam et al., *Shock* 21(5) 401-06, 2004; Asgari et al., *Curr Opin Organ Transplant* 15(4):486-91, 2010).

Blos1 is a component of endosome-localized Biogenesis of Lysosome-related Organelles Complex-1 (BLOC-1). Alteration of components of this complex are associated with schizophrenia. It is conceivable that down modulation of Blos1 (BLOC1S1) due to IRE-1α activation by ER stress may impact normal synaptic transmission (Ryder & Faundez, *Sci Signal.* 2(93): 66, 2009).

IRE-1α inhibitors disclosed herein (or prodrugs or pharmaceutically acceptable salts of IRE-1α inhibitors) can be used to block degradation of Blos1 mRNA, DGAT2 mRNA, CD59 mRNA, and IRE-1α mRNA. In some embodiments, a cell comprising an mRNA selected from the group consisting of Blos1 mRNA, DGAT2 mRNA, CD59 mRNA, and IRE-1α mRNA is contacted with an IRE-1α inhibitor or a prodrug or pharmaceutically acceptable salt of an IRE-1α inhibitor. In some embodiments, the cell is in vitro. In other embodiments, the cell is in vivo.

In some embodiments, an IRE-1α inhibitor or a prodrug or pharmaceutically acceptable salt of an IRE-1α inhibitor is administered to treat Barraquer-Simons Syndrome, asthma, lupus erythematous, glomerulonephritis, various forms of arthritis, autoimmune heart disease, multiple sclerosis, inflammatory bowel disease, and ischemia-reperfusion injuries, autoimmune hemocytopenias and rejection of transplanted organs.

In some embodiments, an IRE-1α inhibitor or a prodrug or pharmaceutically acceptable salt of an IRE-1α inhibitor is administered to treat schizophrenia.

Routes of Administration

Pharmaceutical preparations constituting embodiments can be administered locally or systemically. Suitable routes of administration include oral, pulmonary, rectal, transmucosal, intestinal, parenteral (including intramuscular, subcutaneous, intramedullary routes), intranodal, intrathecal, direct intraventricular, intravenous, intraperitoneal, intranasal, intraocular, transdermal, topical, and vaginal routes. As described in more detail above, dosage forms include, but are not limited to, tablets, troches, dispersions, suspensions, suppositories, solutions, capsules, creams, patches, minipumps and the like. Targeted delivery systems also can be used (for example, a liposome coated with target-specific antibody).

Dosage

A pharmaceutical composition embodiment comprises at least one active ingredient (an IRE-1α inhibitor compound or prodrug thereof) in a therapeutically effective dose. A "therapeutically effective dose" is the amount of an IRE-1α inhibitor compound or prodrug thereof which, when administered to a patient over a treatment period, results in a measurable improvement in survival time and/or quality of life. Such improvements include, for example, a delay or halt in the progression of a cancer, partial or complete regression, reduced severity of one or more existing symptoms, delay or prevention of the development of one or more symptoms, and one or more improved laboratory values (including, but not limited to, a biological marker e.g., XBP-1 splicing and down stream targets such as EDEM, VEGF-A, ERdj4). Various methods and assays can be used to assess whether and to what extent an improvement occurs.

Determination of therapeutically effective doses is well within the capability of those skilled in the art. A therapeutically effective dose initially can be estimated from in vitro enzyme assays, cell culture assays, and/or animal models. For example, a dose can be formulated in an animal model to achieve a circulating concentration range at least as concentrated as the $IC_{50}$ as determined in an in vitro enzyme assay or in a cell culture (i.e., the concentration of the test compound which achieves a half-maximal inhibition of IRE-1α activity). Such information can be used to more accurately determine useful doses in humans. See the FDA guidance document "Guidance for Industry and Reviewers Estimating the Safe Starting Dose in Clinical Trials for Therapeutics in Adult Healthy Volunteers" (HFA-305), which provides an equation for use in calculating a human equivalent dose (HED) based on in vivo animal studies.

Appropriate animal models for the relevant diseases are known in the art. See, e.g., Lupus. 1996 October; 5(5b): 451-5 (antiphospholipid syndrome); Blood. 1974 July; 44(1):49-56 (aplastic anemia); Autoimmunity. 2001; 33(5): 265-74 (autoimmune hypophysitis); Methods. 2007 January; 41(1):118-22 (autoimmune myocarditis); Clin Exp Rheumatol. 2003 November-December; 21(6 Suppl 32): S55-63 (Churg-Strauss syndrome, Wegener's granulomatosis); J Clin Invest. 2005 April; 115(5):870-8 (epidermolysis bullosa acquisita); Circulation. 2005 Jun. 14; 111(23):3135-40. Epub 2005 Jun. 6 (giant cell arteritis; Takayusu's arteritis); Int J Immunopathol Pharmacol. 2005 October-December; 18(5):701-8 (IgA nephropathy); Vet Rec. 1984 May 12; 114(19):479 (pemphigus foliaceous); *J. Neuroimmunol.* 98, 130-35, 1999 (polymyositis); *Am. J. Pathol.* 120, 323-25, 1985 (dermatomyositis); *Cell. Mol. Immunol.* 2, 461-65, 2005 (myasthenia gravis); *Arthritis Rheum.* 50, 3250-59, 2004 (lupus erythymatosus); *Clin. Exp. Immunol.* 99, 294-302, 1995 (Grave's disease); *J. Clin. Invest.* 116, 961-973, 2006 (rheumatoid arthritis); *Exp Mol Pathol.* 77, 161-67, 2004 (Hashimoto's thyroiditis); *Rheumatol.* 32, 1071-75, 2005 (Sjögren's syndrome); *Brain Pathol.* 12, 420-29, 2002 (Guillain-Barré syndrome); *Vet. Pathol.* 32, 337-45, 1995 (polyarteritis nodosa); *Immunol. Invest.* 3.47-61, 2006 (pemphigus vulgaris); *Arch. Dermatol. Res.* 297, 333-44, 2006 (scleroderma); *J. Exp. Med.* 191, 899-906, 2000 (Goodpasture's syndrome); *Clin. Exp. Immunol.* 99, 294-302, 1995 (Grave's disease); *J. Clin. Invest.* 91, 1507-15, 1993 (membranous nephropathy); *J. Immunol.* 169, 4889-96, 2002 (autoimmune hepatitis); *Surgery* 128, 999-1006, 2000 (Addison's disease); *Eur. J. Immunol.* 32, 1147-56, 2002 (autoimmune hemolytic anemia); and *Haematologica* 88, 679-87, 2003 (autoimmune thrombocytopenic purpura).

$LD_{50}$ (the dose lethal to 50% of the population) and the $ED_{50}$ (the dose therapeutically effective in 50% of the population) can be determined by standard pharmaceutical procedures in cell cultures and/or experimental animals. Data obtained from cell culture assays or animal studies can be used to determine initial human doses. As is known in the art, the dosage may vary depending upon the dosage form and route of administration used.

Usual dosages for systemic administration to a human patient range from 1 μg/kg to 100 mg/kg (e.g., 1-10 μg/kg, 20-80 μg/kg, 5-50 μg/kg, 75-150 μg/kg, 100-500 μg/kg, 250-750 μg/kg, 500-1000 μg/kg, 1-10 mg/kg, 5-50 mg/kg, 25-75 mg/kg, 50-100 mg/kg, 5 mg/kg, 20 mg/kg, or 50 mg/kg). In some embodiments, the treatment schedule can require that a plasma concentration of an IRE-1α inhibitor compound be maintained for a period of time (e.g., several days or a week) and then allowed to decay by ceasing administration for a period of time (e.g., 1, 2, 3, or 4 weeks). The amount of composition administered will, of course, be dependent on the subject being treated, on the subject's weight, the severity of the disorder, the manner of administration and the judgment of the prescribing physician.

The following specific examples are provided for purposes of illustration only and are not intended to limit the scope of the subject matter described above.

EXAMPLES

The analytical LC/MS method used in Examples 1-20 employed an Agilent 1200 with Variable Wavelength detector extracted at 220 nm and Agilent 6140 Single quadrupole mass spectrometer. The HPLC column was a Zorbax SB-C18, 3.5 μm, 2.1 mm×30 mm, maintained at 40° C. The HPLC Gradient was 0.4 mL/min, 95:5:0.1 water:acetonitrile:formic acid for 0.1 min then to 5:95:0.1 water:acetonitrile:formic acid in 3.9 min, maintaining for 0.5 min.

Example 1

7-Hydroxy-1,2,3,4-tetrahydro-isoquinoline-6-carbaldehyde hydrobromide

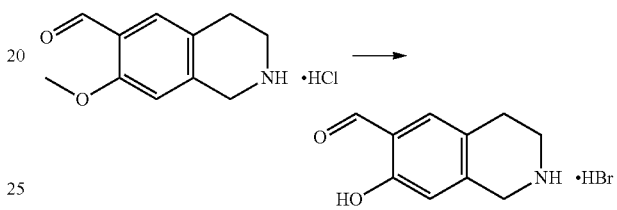

To a stirred suspension of 7-methoxy-1,2,3,4-tetrahydroisoquinoline-6-carbaldehyde hydrochloride (91 mg, 0.40 mmol) in anhydrous $CH_2Cl_2$ (5 mL) boron tribromide (0.42 g, 1.68 mmol) was added under argon at −78° C. The reaction was stirred for 1 h, allowed to warm to room temperature and stirred for 2 h. After addition of isopropanol and diethyl ether the precipitated product was collected and washed with ether. In this manner the title compound (79 mg, 0.31 mmol, 77.5%) was obtained as a pink powder. LCMS/BB_LCMS01(+)/: M+1=178, Rt: 1.331 min.

$^1$H NMR (400 MHz, DMSO-$d_6$) δ ppm 10.65 (s, 1H), 10.23 (s, 1H), 9.07 (br. s., 2H), 7.52 (s, 1H), 6.84 (s, 1H), 4.30 (s, 2H), 3.34-3.40 (m, 2H), 2.95 (t, J=6.3 Hz, 2H).

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 1-1 | 5-3 | 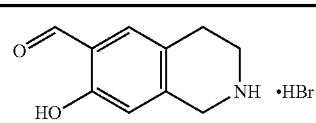 | BB_LCMS01(+) | 178 | 1.331 | 99 | 98 |
| 1-2 | 5-1 | 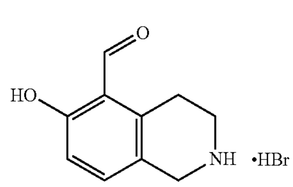 [SMILES: O=Cc1c(O)ccc2c1CCNC2 ; Br] | BB_LCMS01(+) | 178 | 0.389 | 100 | 95 |
| 1-3 | 5-2 | 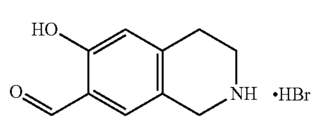 [SMILES: O=Cc1cc2c(cc1O)CCNC2 ; Br] | BB_LCMS02(+) | 178 | 1.228 | 96 | 96 |

Example 2

6-Hydroxy-2-(pyridine-3-carbonyl)-1,2,3,4-tetrahydro-isoquinoline-5-carbaldehyde

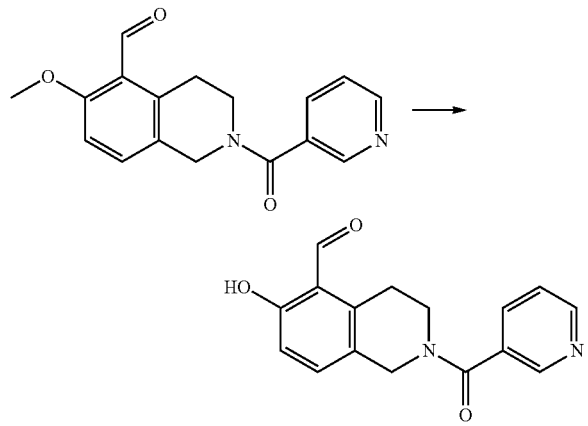

To a solution of 6-methoxy-2-(pyridine-3-carbonyl)-1,2,3,4-tetrahydro-isoquinoline-5-carbaldehyde (62 mg, 0.21 mmol) in dichloromethane (5 mL) stirred under argon at −78° C. was added boron tribromide (0.12 mL, 0.31 g, 1.25 mmol). The reaction was stirred for 1 h, allowed to warm to room temperature and stirred for 2 h. The reaction was quenched by addition of methanol (2 mL) at −78° C. and the mixture was stirred for 1 h. After warming to room temperature, ethyl acetate (3 mL) and diethyl ether (30 mL) were added, upon scratching the product started to precipitate. The mixture was allowed to stand refrigerated overnight, the product was collected, washed with ethyl acetate and dried over $P_2O_5$ to give the title compound (48 mg, 0.13 mmol, 61.9%) as a beige powder.

LCMS/BB_LCMS01(+)/: M+1=283, Rt: 2.668 min.

$^1$H NMR (400 MHz, DMSO-$d_6$) δ ppm 11.16 (br. s., 1H), 10.42 (s, 1H), 8.97 (s, 1H), 8.91 (dd, J=5.4, 1.1 Hz, 1H), 8.42 (br. s., 1H), 7.94 (dd, J=7.9, 5.6 Hz, 1H), 7.33 (br. s., 1H), 6.87 (br. s., 1H), 4.63 (br. s., 2H), 3.55 (br. s., 2H), 3.21 (br. s., 2H).

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 2-1 | 6-1 | 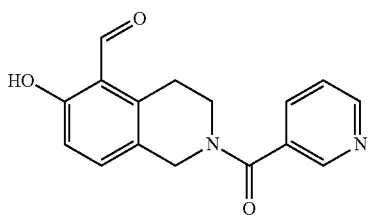 [SMILES: O=Cc1c(O)ccc2c1CCN(C(=O)c1cccnc1)C2] | BB_LCMS01(+) | 283 | 2.668 | 94 | 92 |
| 2-2 | 6-2 | 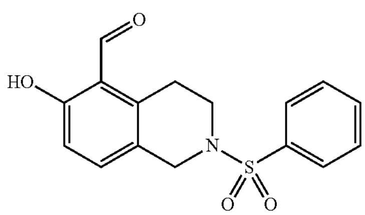 [SMILES: O=Cc1c(O)ccc2c1CCN(S(=O)(=O)c1ccccc1)C2] | BB_LCMS01(+) | 318 | 3.624 | 99 | 98 |
| 2-3 | 6-3 | 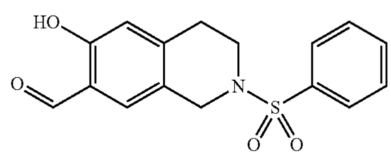 [SMILES: O=Cc1cc2c(cc1O)CCN(S(=O)(=O)c1ccccc1)C2] | BB_LCMS01(+) | 318 | 3.572 | 89 + 9 = 98 | 98 |
| 2-4 | 6-4 | 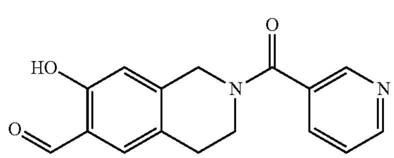 [SMILES: O=Cc1cc2c(cc1O)CN(C(=O)c1cccnc1)CC2] | BB_LCMS01(+) | 283 | 2.613 | 94 | 95 |
| 2-5 | 6-5 | 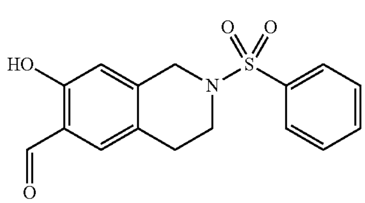 [SMILES: O=Cc1cc2c(cc1O)CN(S(=O)(=O)c1ccccc1)CC2] | BB_LCMS01(+) | 318.1 | 3.595 | 100 | 98 |

| EX-AMPLE | Made From | Structure | LCMS method | LCMS Ion | LCMS Rt (min) | LCMS purity (%) | NMR purity (%) |
|---|---|---|---|---|---|---|---|
| 2-6 | 6-6 | 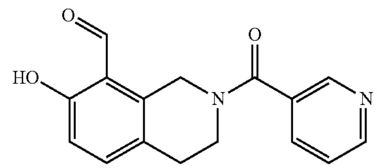 [SMILES: O=Cc1c(O)ccc2c1CN(C(=O)c1cccnc1)CC2] | BB_LCMS01(+) | 283.1 | 2.643 | 96 | 96 |
| 2-7 | 7-1 | 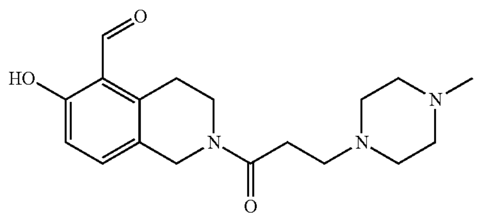 [SMILES: CN1CCN(CCC(=O)N2CCc3c(ccc(O)c3C=O)C2)CC1] | BB_LCMS01(+) | 332 | 1.189 | 99 | 98 |
| 2-8 | 7-2 | 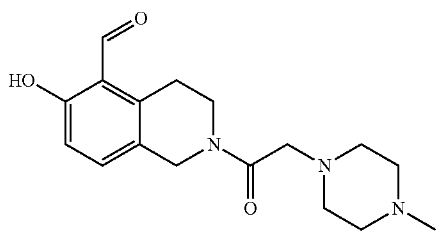 [SMILES: CN1CCN(CC(=O)N2CCc3c(ccc(O)c3C=O)C2)CC1] | BB_LCMS01(+) | 318 | 1.967 | 95 | 95 |
| 2-9 | 7-3 | 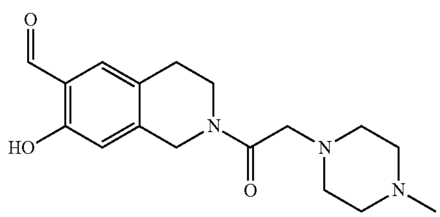 [SMILES: CN1CCN(CC(=O)N2CCc3cc(C=O)c(O)cc3C2)CC1] | BB_LCMS01(+) | 318.1 | 1.917 | 97 | 98 |
| 2-10 | 7-4 | 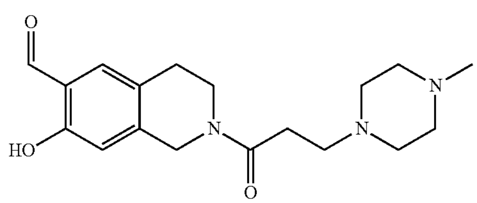 [SMILES: CN1CCN(CCC(=O)N2CCc3cc(C=O)c(O)cc3C2)CC1] | BB_LCMS01(+) | 332.2 | 1.176 | 96 | 98 |
| 2-11 | 8-1 | 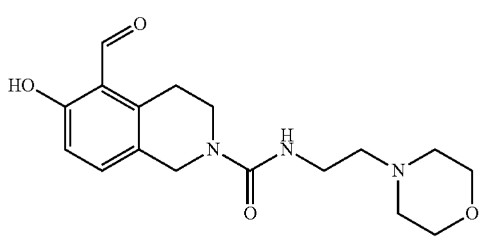 [SMILES: O=Cc1c(O)ccc2c1CCN(C(=O)NCCN1CCOCC1)C2] | BB_LCMS01(+) | 334 | 2.185 | 96 | 93 |
| 2-12 | 8-2 | 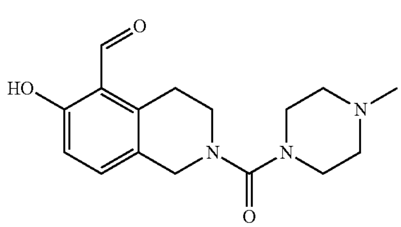 [SMILES: CN1CCN(C(=O)N2CCc3c(ccc(O)c3C=O)C2)CC1] | BB_LCMS01(+) | 304 | 2.202 | 94 | 93 |

-continued

| EX-AMPLE | Made From | Structure | LCMS method | LCMS Ion | LCMS Rt (min) | LCMS purity (%) | NMR purity (%) |
|---|---|---|---|---|---|---|---|
| 2-13 | 8-3 | 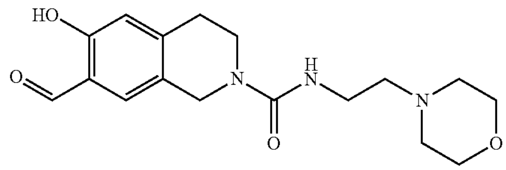 [SMILES: O=Cc1cc2c(cc1O)CCN(C(=O)NCCN1CCOCC1)C2] | BB_LCMS01(+) | 334 | 2.188 | 99 | 98 |
| 2-14 | 8-4 | 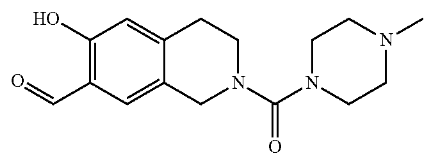 [SMILES: CN1CCN(C(=O)N2CCc3cc(O)c(C=O)cc3C2)CC1] | BB_LCMS01(+) | 304 | 2.117 | 96 | 92 |
| 2-15 | 9-1 | 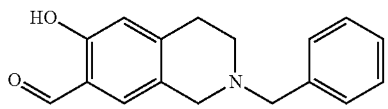 [SMILES: O=Cc1cc2c(cc1O)CCN(Cc1ccccc1)C2] | BB_LCMS01(+) | 268 | 2.326 | 100 | 98 |
| 2-16 | 9-2 | 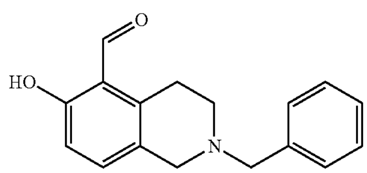 [SMILES: O=Cc1c(O)ccc2c1CCN(Cc1ccccc1)C2] | BB_LCMS01(+) | 268 | 2.333 | 93 | 90 |
| 2-17 | 9-3 | 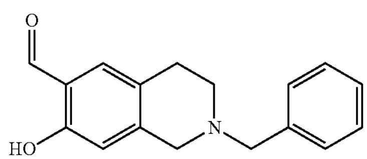 [SMILES: O=Cc1cc2c(cc1O)CN(Cc1ccccc1)CC2] | BB_LCMS01(+) | 268.1 | 2.317 | 96 | 98 |
| 2-18 | 10-1 | 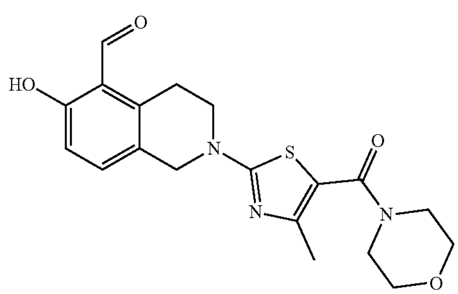 [SMILES: Cc1nc(N2CCc3c(ccc(O)c3C=O)C2)sc1C(=O)N1CCOCC1] | BB_LCMS01(+) | 388 | 3.033 | 94 | 98 |
| 2-19 | 10-2 | 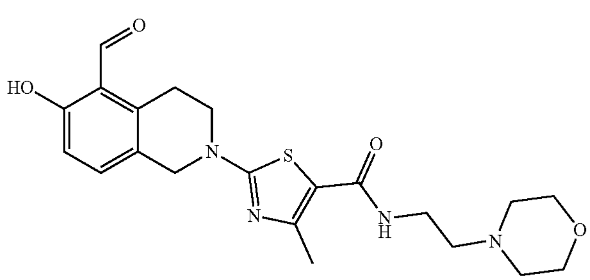 [SMILES: Cc1nc(N2CCc3c(ccc(O)c3C=O)C2)sc1C(=O)NCCN1CCOCC1] | BB_LCMS01(+) | 431 | 2.527 | 95 | 98 |

| EX-AMPLE | Made From | Structure | LCMS method | LCMS Ion | LCMS Rt (min) | LCMS purity (%) | NMR purity (%) |
|---|---|---|---|---|---|---|---|
| 2-20 | 10-3 | 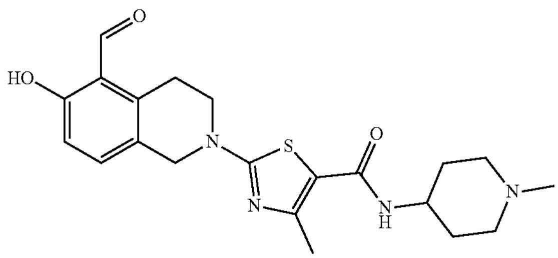 [SMILES: Cc1nc(N2CCc3c(ccc(O)c3C=O)C2)sc1C(=O)NC1CCN(C)CC1] | BB_LCMS01(+) | 415 | 2.536 | 92 | 92 |
| 2-21* | 10-4 | 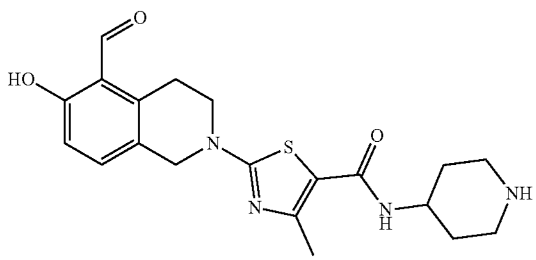 [SMILES: Cc1nc(N2CCc3c(ccc(O)c3C=O)C2)sc1C(=O)NC1CCNCC1] | BB_LCMS01(+) | 401 | 2.514 | 91 | 95 |
| 2-22 | 10-5 | 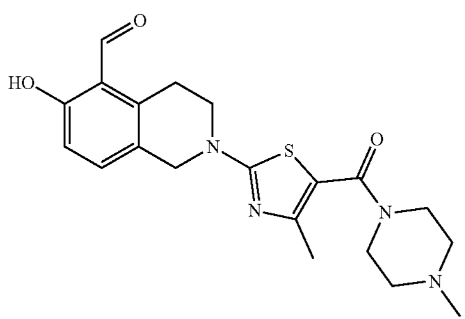 [SMILES: Cc1nc(N2CCc3c(ccc(O)c3C=O)C2)sc1C(=O)N1CCN(C)CC1] | BB_LCMS01(+) | 401 | 2.465 | 92 | 95 |
| 2-23 | 10-6 | 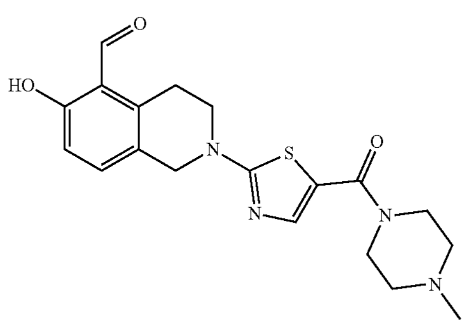 [SMILES: CN1CCN(C(=O)c2cnc(N3CCc4c(ccc(O)c4C=O)C3)s2)CC1] | BB_LCMS01(+) | 387 | 2.516 | 94 | 95 |
| 2-24 | 10-7 | 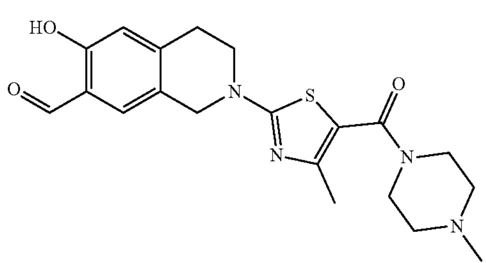 [SMILES: Cc1nc(N2CCc3cc(O)c(C=O)cc3C2)sc1C(=O)N1CCN(C)CC1] | BB_LCMS01(+) | 401 | 2.440 | 94 | 95 |

| EXAMPLE | Made From | Structure | LCMS method | LCMS Ion | LCMS Rt (min) | LCMS purity (%) | NMR purity (%) |
|---|---|---|---|---|---|---|---|
| 2-25 | 10-8 | 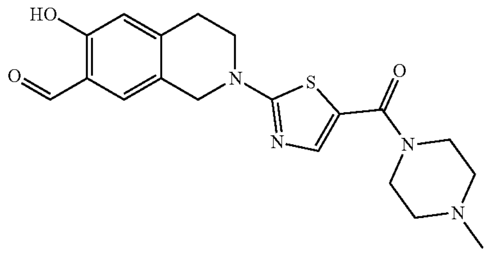 [SMILES: CN1CCN(C(=O)c2cnc(N3CCc4cc(O)c(C=O)cc4C3)s2)CC1] | BB_LCMS01(+) | 387 | 2.476 | 91 | 92 |
| 2-26 | 11-1 | 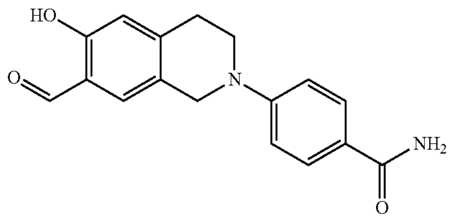 [SMILES: NC(=O)c1ccc(N2CCc3cc(O)c(C=O)cc3C2)cc1] | BB_LCMS01(+) | 297 | 3.075 | 99 | 95 |
| 2-27 | 12-1 | 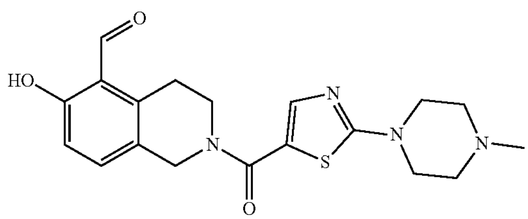 [SMILES: CN1CCN(c2ncc(C(=O)N3CCc4c(ccc(O)c4C=O)C3)s2)CC1] | BB_LCMS01(+) | 387 | 2.441 | 91 | 90 |

*During O-demethylation the N-Boc protecting group of the precursor was also removed.

Example 3

6-Hydroxy-2-(pyridine-3-carbonyl)-1,2,3,4-tetrahydro-isoquinoline-7-carbaldehyde

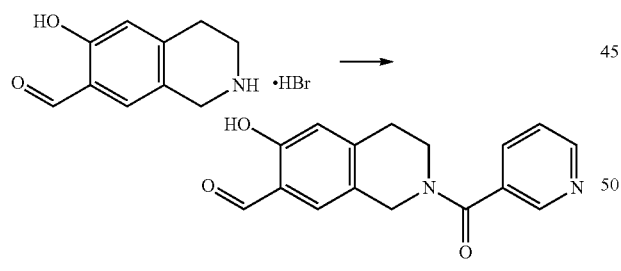

To a stirred suspension of 6-hydroxy-1,2,3,4-tetrahydro-isoquinoline-7-carbaldehyde hydrobromide (129 mg, 0.5 mmol) and nicotinoyl chloride hydrochloride (107 mg, 0.6 mmol) in 1,2-dichloroethane (6 mL), ethyldiisopropylamine (259 μL, 194 mg, 1.5 mmol) was added and the mixture was stirred at room temperature for 3 h. After dilution with 1,2-dichloroethane (30 mL) the mixture was washed with water (3×5 mL). After drying over MgSO$_4$ and concentration the title compound (99 mg, 0.35 mmol, 70%) was obtained.

LCMS/BB_LCMS01(−)/: M+1=281, Rt: 2.592 min.

$^1$H NMR (400 MHz, DMSO-d$_6$) δ salt, 2 sets of signals A and B in ratio of 55:45 ppm 10.58 (br. s., 1H, A+B), 10.20 (br. s., 0.55H, A), 10.12 (br. s., 0.45H, B), 8.67 (br. s., 2H, A+B), 7.88 (br. s., 1H, A+B), 7.57 (br. s., 0.55H, A), 7.49 (dd, J=7.8, 4.8 Hz, 1H, A+B), 7.36 (br. s., 0.45H, B), 6.81 (s, 1H, A+B), 4.73 (br. s., 1.1H, A), 4.54 (br. s., 0.9H, B), 3.82 (br. s., 0.9H, B), 3.53 (br. s., 1.1H, A), 2.89 (br. s., 2H, A+B).

| EXAMPLE | Made From | Structure | LCMS method | LCMS Ion | LCMS Rt (min) | LCMS purity (%) | NMR purity (%) |
|---|---|---|---|---|---|---|---|
| 3-1 | 1-2 | 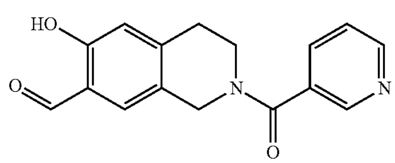 [SMILES: O=Cc1cc2c(cc1O)CCN(C(=O)c1cccnc1)C2] | BB_LCMS01(−) | 281 | 2.592 | 100 | 98 |

Example 4

6-Hydroxy-2-[3-(4-methyl-piperazin-1-yl)-propionyl]-1,2,3,4-tetrahydro-isoquinoline-7-carbaldehyde

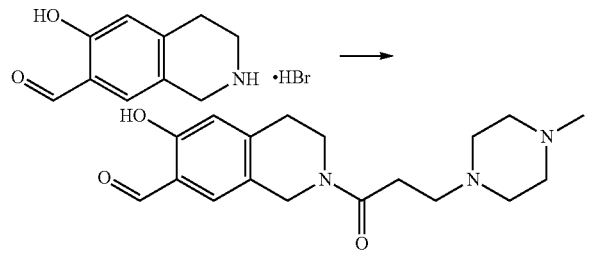

To a stirred mixture of 6-hydroxy-1,2,3,4-tetrahydro-isoquinoline-7-carbaldehyde hydrobromide (82 mg, 0.46 mmol) and triethylamine (322 μL, 234 mg, 2.3 mmol) in anhydrous tetrahydrofuran (2 mL), 3-(4-methyl-piperazin-1-yl)-propionic acid (80 mg, 0.46 mmol), (3-dimethyl-amino-propyl)-ethyl-carbodiimide hydrochloride (98 mg, 0.51 mmol) and 1-hydroxybenzotriazole (69 mg, 0.51 mmol) were added in the above order and the mixture was stirred at room temperature for 7 h. After evaporation, the residue was taken up in chloroform (10 mL) and washed with sat $NaHCO_3$ (2×5 mL) and brine (5 mL). The organic phase was dried over $MgSO_4$ and evaporated. The obtained crude product (94 mg) was purified by column chromatography on silica gel, eluting with $CHCl_3$/MeOH 94/6 mixture. In this manner the title compound (33 mg, 0.10 mmol, 21%) was obtained.

LCMS/BB_LCMS02(+)/: M+1=332, Rt: 1.86 min.

$^1$H NMR (400 MHz, DMSO-$d_6$) δ ppm 10.47 (br. s., 1H), 10.18 (s, 1H), 7.51 (s, 1H), 6.85 (s, 1H), 4.59 (s, 2H), 3.67 (t, J=6.0 Hz, 2H), 3.49 (s, 2H), 2.87 (br. s., 10H), 2.71 (s, 3H).

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 4-1 | 1-2 | HO, O, N, N-N- | BB_LCMS02(+) | 332 | 1.860 | 97 | 98 |
| 4-2* | 1-2 | HO, O, N, N-N- × 2 HCl | BB_LCMS01(+) | 318 | 1.912 | 100 | 98 |

*isolated from EtOAc with HCl/EtOAc

Example 5

6-Methoxy-1,2,3,4-tetrahydro-isoquinoline-5- and 7-carbaldehydes

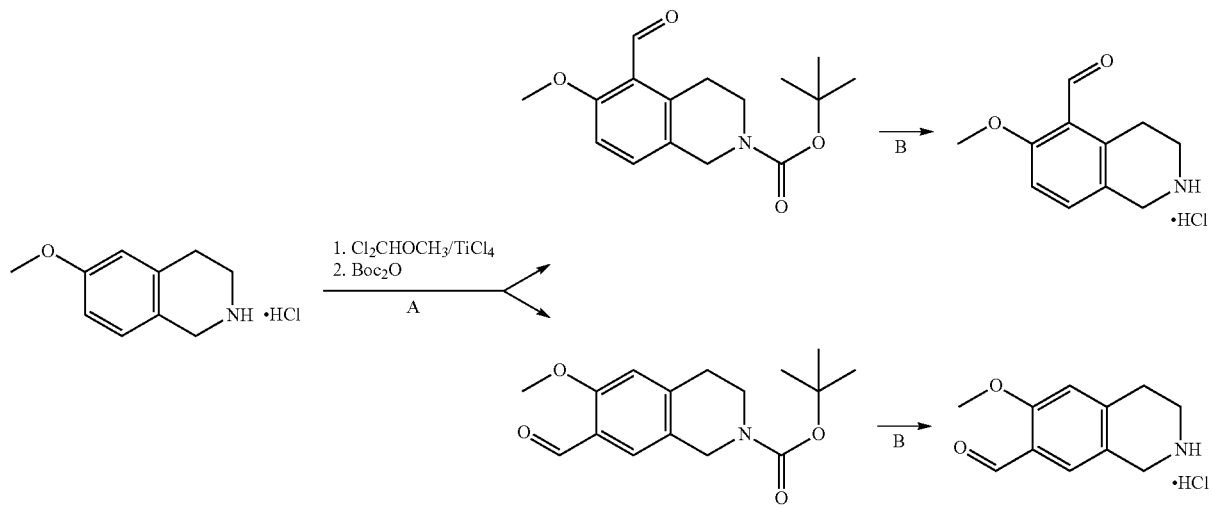

Step A

5-Formyl-6-methoxy-3,4-dihydro-1H-isoquinoline-2-carboxylic acid tert-butyl ester and 7-formyl-6-methoxy-3,4-dihydro-1H-isoquinoline-2-carboxylic acid tert-butyl ester (HI-227d and HI-2271)

To dichloromethane (80 mL) at 0° C., titanium tetrachloride (8.8 mL, 15.2 g, 80 mmol) and then dichloromethyl methyl ether (7.2 mL, 9.2 g, 80 mmol) were added dropwise followed by the addition of 6-methoxy-1,2,3,4-tetrahydroisoquinoline hydrochloride (4.0 g, 20 mmol) in small portions and the mixture was stirred at 0° C. for 3 h. The reaction was quenched by slow addition of 2 N HCl (50 mL) and the layers were separated. The organic layer was extracted with 1 N HCl (2×10 mL) and the combined acidic aqueous layers were washed with dichloromethane (1×20 mL). Dichloromethane (100 mL) was added to the aqueous layers and the pH of the two-phase mixture was adjusted to 10 with 10 N NaOH (70 mL) under ice cooling. After addition of di-tert-butyl dicarbonate (4.8 g, 22 mmol) the mixture was stirred overnight. The reaction was diluted with dichloromethane (120 mL) and water (200 mL), the aqueous layer was separated and extracted with dichloromethane (2×100 mL). The combined organic layers were washed with water (3×150 mL), dried over MgSO₄ and concentrated. The residual oil was chromatographed on silica (200 g), eluting first with a 8:1 mixture of n-hexane and ethyl acetate, followed by a 4:1 mixture and finally with a 2:1 mixture of the same solvents. By combining the appropriate fractions, concentration and trituration of the residues with n-hexane first 5-formyl-6-methoxy-3,4-dihydro-1H-isoquinoline-2-carboxylic acid tert-butyl ester (1.72 g, 5.9 mmol, 29.5%) and then 7-formyl-6-methoxy-3,4-dihydro-1H-isoquinoline-2-carboxylic acid tert-butyl ester (2.88 g, 9.9 mmol, 49.5%) were obtained as colorless solids.

5a-1: LCMS/BB_LCMS01(+)/: M+1=236, Rt: 3.955 min,
5a-2: LCMS/BB_LCMS01(+)/: M+1=236, Rt: 3.811 min, The following compounds (includes title compound) were made by the above procedure:

| EXAMPLE | Made From | Structure | LCMS method | LCMS Ion | LCMS Rt (min) | LCMS purity (%) |
|---|---|---|---|---|---|---|
| — | | 5-formyl-6-methoxy-N-Boc-tetrahydroisoquinoline | BB_LCMS01(+) | 236 | 3.955 | 100 | n/a |
| — | | 7-formyl-6-methoxy-N-Boc-tetrahydroisoquinoline | BB_LCMS01(+) | 236 | 3.811 | 99.5 | n/a |
| — | | 6-formyl-7-methoxy-N-Boc-tetrahydroisoquinoline + 7-methoxy-8-formyl-N-Boc-tetrahydroisoquinoline (inseparable mixture) | BB_LCMS01(+) | 236 | 3.855 and 3.926 | 68.2 and 28.8 | n/a |

*Inseparable mixture

Step B

6-Hydroxy-1,2,3,4-tetrahydro-isoquinoline-5-carbaldehyde hydrochloride

To 5-formyl-6-methoxy-3,4-dihydro-1H-isoquinoline-2-carboxylic acid tert-butyl ester (1.41 g, 4.84 mmol) in ethyl acetate (10 mL), a 3.3 M solution of anhydrous HCl in ethyl acetate was added and the mixture was stirred at room temperature for 2 h. The precipitated product was collected, washed with ethyl acetate and dried in air. In this manner the title compound (1.03 g, 4.52 mmol, 93.4%) was obtained as a white powder.

LCMS/BB_LCMS01(+)/: M+1=192, Rt: 0.654 min,

The following compounds (includes title compound) were made by the above procedure:

| EXAMPLE | Made From | Structure | LCMS method | LCMS Ion | LCMS Rt (min) | LCMS purity (%) | |
|---|---|---|---|---|---|---|---|
| 5-1 | 5a-1 | 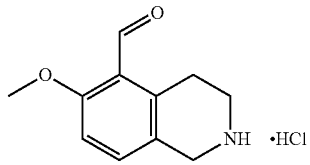 | BB_LCMS01(+) | 192 | 0.654 | 100 | n/a |
| 5-2 | 5a-2 | 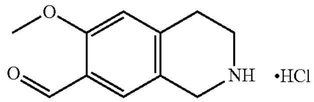 | BB_LCMS01(+) | 192 | 0.562 | 96.4 | n/a |
| 5-3 | 5a-3 | 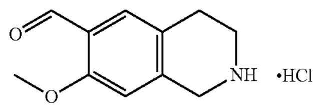 | BB_LCMS01(+) | 192 | 0.542 | 98.9 | n/a |
| 5-4 | 5a-3 | 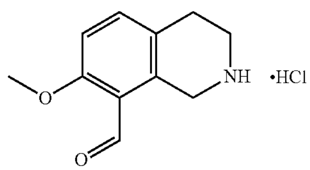 | BB_LCMS01(+) | 192 | 0.745 | 87.7 | n/a |

Example 6

6-Methoxy-2-(pyridine-3-carbonyl)-1,2,3,4-tetrahydro-isoquinoline-5-carbaldehyde

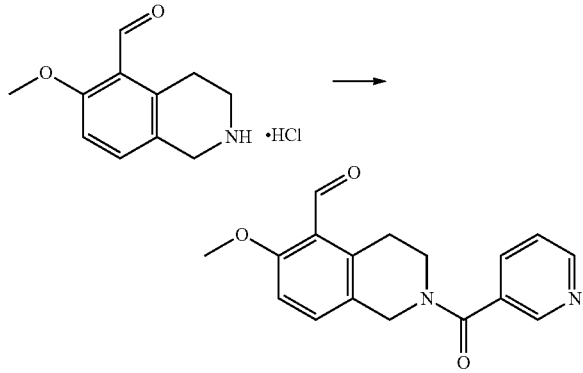

To a stirred suspension of 6-methoxy-1,2,3,4-tetrahydro-isoquinoline-5-carbaldehyde hydrochloride (91 mg, 0.4 mmol) and nicotinoyl chloride hydrochloride (89 mg, 0.5 mmol) in 1,2-dichloroethane (6 mL) diisopropylethylamine (261 µL, 194 mg, 1.5 mmol) was added and the mixture was stirred at room temperature for 3 h. After dilution with 1,2-dichloroethane (30 mL) the mixture was washed sequentially with water (5 mL), 1 N aqueous NaOH (5 mL) and again with water (3×5 mL). After drying over MgSO₄ and concentration, the title compound (110 mg, 0.38 mmol, 95%) was obtained as a beige solid.

LCMS/BB_LCMS01(+)/: M+1=297, Rt: 2.792 min.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 6-1 | 5-1 | 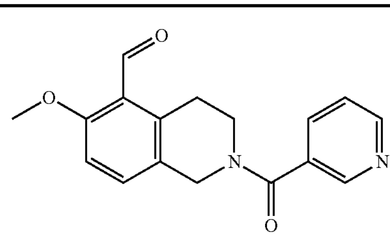 | BB_LCMS01(+) | 297 | 2.792 | 98.1 | n/a |

| EXAMPLE | Made From | Structure | LCMS method | LCMS Ion | LCMS Rt (min) | LCMS purity (%) | NMR purity (%) |
|---|---|---|---|---|---|---|---|
| 6-2 | 5-1 | 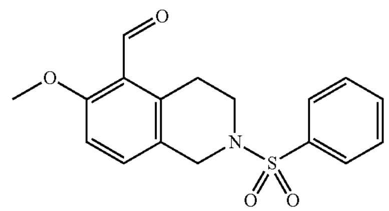 [SMILES: COc1ccc2c(c1C=O)CCN(S(=O)(=O)c1ccccc1)C2] | BB_LCMS01(+) | 332 | 3.732 | 100 | n/a |
| 6-3 | 5-2 | 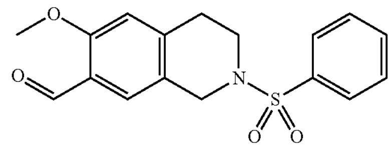 [SMILES: COc1cc2c(cc1C=O)CN(S(=O)(=O)c1ccccc1)CC2] | BB_LCMS01(+) | 332 | 3.651 | 97.4 | n/a |
| 6-4 | 5-3 | 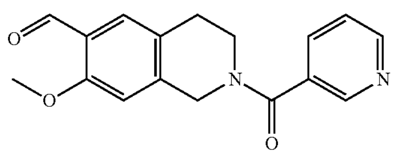 [SMILES: COc1cc2c(cc1C=O)CCN(C(=O)c1cccnc1)C2] | BB_LCMS01(+) | 297 | 2.738 | 93 | n/a |
| 6-5 | 5-3 | 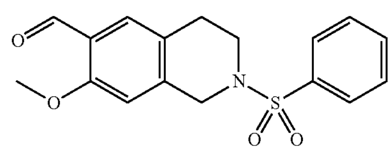 [SMILES: COc1cc2c(cc1C=O)CCN(S(=O)(=O)c1ccccc1)C2] | BB_LCMS01(+) | 332 | 3.667 | 98.5 | n/a |
| 6-6 | 5-4 | 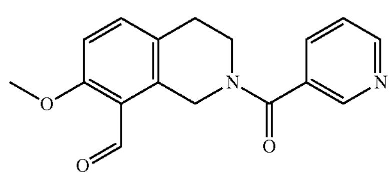 [SMILES: COc1ccc2c(c1C=O)CN(C(=O)c1cccnc1)CC2] | BB_LCMS01(+) | 297 | 2.807 | 98.2 | n/a |

Example 7

6-Methoxy-2-[3-(4-methyl-piperazin-1-yl)-propionyl]-1,2,3,4-tetrahydro-isoquinoline-5-carbaldehyde

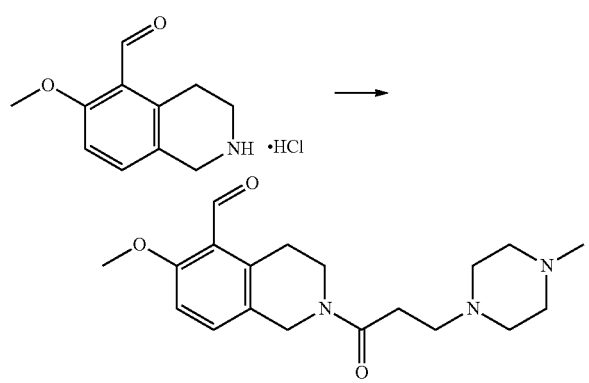

To a stirred mixture of 6-methoxy-1,2,3,4-tetrahydro-isoquinoline-5-carbaldehyde hydrochloride (153 mg, 0.67 mmol) and triethylamine (447 µL, 324 mg, 3.2 mmol) in anhydrous tetrahydrofuran (8 mL) 3-(4-methyl-piperazin-1-yl)-propionic acid (172 mg, 1.0 mmol), (3-dimethylaminopropyl)-ethyl-carbodiimide hydrochloride (192 mg, 1.0 mmol) and 1-hydroxy-benzotriazole (135 mg, 1.0 mmol) were added in the above order and the mixture was stirred at room temperature for 3 h. After dilution with ethyl acetate (20 mL) the mixture was washed with 1 N aqueous NaOH (3×5 mL) and water (3×5 mL) and then the product was extracted into 1 N HCl (3×5 mL). The aqueous acidic layer was rendered alkaline (pH=10) with 10% aqueous NaOH and extracted with chloroform (3×10 mL). The combined chloroform layers were washed with water (3×5 mL), dried over MgSO$_4$ and concentrated. In this manner the title compound (206 mg, 0.60 mmol, 89.6%) was obtained as a yellow oil.

LCMS/BB_LCMS01(+)/: M+1=346, Rt: 2.085 min.

The following compounds (includes title compound) were made by the above procedure:

| EXAMPLE | Made From | Structure | LCMS method | LCMS on | LCMS Rt (min) | LCMS purity (%) | NMR purity (%) |
|---|---|---|---|---|---|---|---|
| 7-1 | 5-1 | ![structure] | BB_LCMS01(+) | 346 | 2.085 | 96.4 | n/a |
| 7-2 | 5-1 | ![structure] | BB_LCMS01(+) | 332 | 2.293 | 97 | n/a |
| 7-3 | 5-3 | ![structure] | BB_LCMS01(+) | 332 | 2.165 | 98.6 | n/a |
| 7-4 | 5-3 | ![structure] | BB_LCMS01(+) | 346 | 1.996 | 96.7 | n/a |

Example 8

5-Formyl-6-methoxy-3,4-dihydro-1H-isoquinoline-2-carboxylic acid (2-morpholin-4-yl-ethyl)-amide

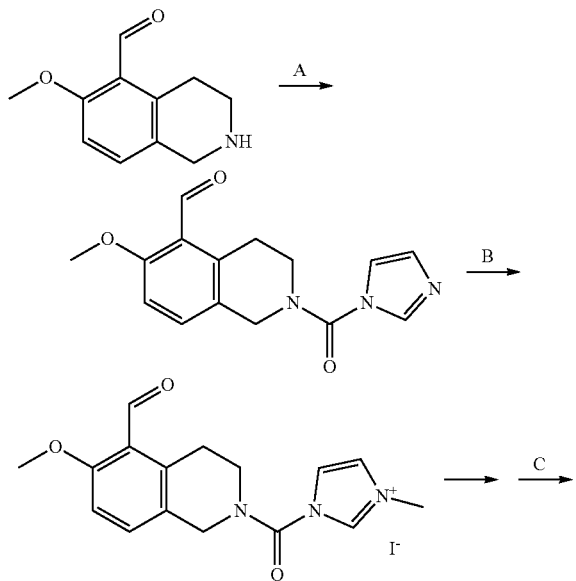

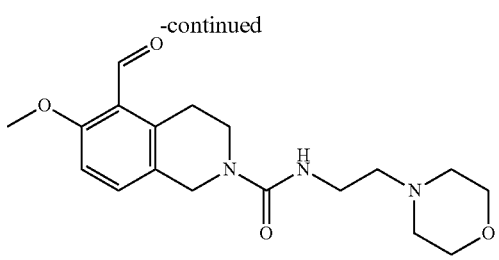

Step A

2-(Imidazole-1-carbonyl)-6-methoxy-1,2,3,4-tetrahydro-isoquinoline-5-carbaldehyde To a solution of freshly dried di-imidazol-1-yl-methanone (276 mg, 1.7 mmol) in anhydrous tetrahydrofuran (20 mL) the solution of 6-methoxy-1,2,3,4-tetrahydro-isoquinoline-5-carbaldehyde (325 mg, 1.7 mmol) in anhydrous tetrahydrofuran (10 mL) was added and the mixture was stirred at 80° C. oil bath for 14 h. The solution was concentrated and the residue was dissolved in dichloromethane, washed with water (2×10 mL), dried over $MgSO_4$ and concentrated. In this manner the title compound (426 mg, 1.50 mmol, 88.2%) was obtained as a brownish yellow foam.

LCMS/BB_LCMS01(+)/: M+1=286, Rt: 2.524 min.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 8a-1 | 5-1 | 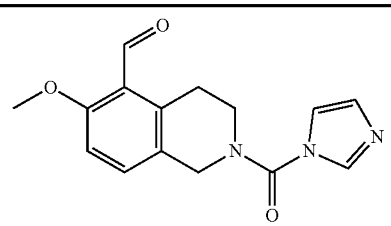 | BB_LCMS01(+) | 286 | 2.524 | 93.5 | n/a |
| 8a-2 | 5-2 | 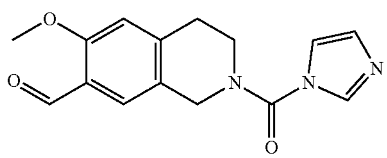 [SMILES: COc1cc2c(cc1C=O)CN(C(=O)n1ccnc1)CC2] | BB_LCMS01(+) | 286 | 2.390 | 92.9 | n/a |

Step B

3-(5-Formyl-6-methoxy-3,4-dihydro-1H-isoquinoline-2-carbonyl)-1-methyl-3H-imidazol-1-ium iodide A mixture of 2-(imidazole-1-carbonyl)-6-methoxy-1,2,3,4-tetrahydro-isoquinoline-5-carbaldehyde (426 mg, 1.50 mmol) and methyl iodide (475 µL, 1.05 g, 7.6 mmol) in anhydrous acetonitrile (10 mL) was stirred at room temperature for 24 h. After evaporation of the solvent the title compound (640 mg, 1.50 mmol, 100%) was obtained as a brownish foam.

LCMS/BB_LCMS01(+)/: M+1=300, Rt: 2.251 min.

The following compounds (includes title compound) were made by the above procedure:

Step C

5-Formyl-6-methoxy-3,4-dihydro-1H-isoquinoline-2-carboxylic acid (2-morpholin-4-yl-ethyl)-amide A mixture of 3-(5-formyl-6-methoxy-3,4-dihydro-1H-isoquinoline-2-carbonyl)-1-methyl-3H-imidazol-1-ium iodide (321 mg, 0.75 mmol), 2-(morpholin-4-yl)-ethylamine (99.5 µL, 99.5 mg, 0.75 mmol) and triethylamine (106 µL, 76 mg, 0.75 mmol) in anhydrous dichloromethane (10 mL) was stirred at room temperature for 24 h. After dilution with dichloromethane (10 mL), the solution was washed with brine (2×5 mL), dried over MgSO$_4$ and concentrated. The residue was purified by column chromatography over silica, eluting with a 9:1 mixture of chloroform and methanol. In this manner the title compound (154 mg, 0.44 mmol, 58.7%) was obtained.

LCMS/BB_LCMS01(+)/: M+1=348, Rt: 2.343 min.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 8b-1 | 8a-1 | 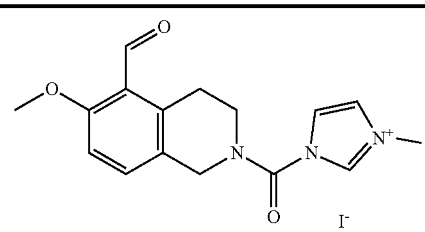 | BB_LCMS01(+) | 300 | 2.251 | 92.2 | n/a |
| 8b-2 | 8a-2 | 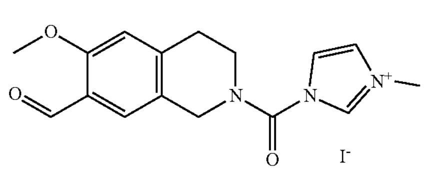 | BB_LCMS01(+) | 300 | 2.103 | 82.4 | n/a |

| EX-AMPLE | Made From | Structure | LCMS method | LCMS Ion | LCMS Rt (min) | LCMS purity (%) | NMR purity (%) |
|---|---|---|---|---|---|---|---|
| 8-1 | 8b-1 | 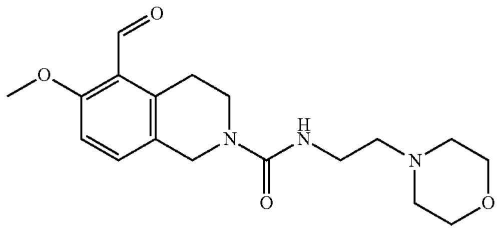 [SMILES: COc1ccc2c(c1C=O)CCN(C(=O)NCCN1CCOCC1)C2] | BB_LCMS01(+) | 348 | 2.343 | 98.7 | n/a |
| 8-2 | 8b-1 | 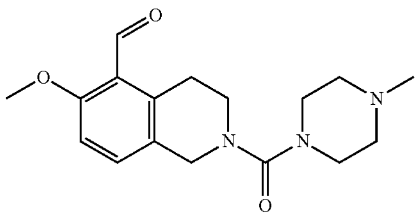 | BB_LCMS01(+) | 318 | 2.403 | 100 | n/a |
| 8-3 | 8b-2 | 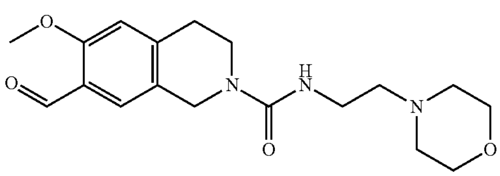 [SMILES: COc1cc2c(cc1C=O)CN(C(=O)NCCN1CCOCC1)CC2] | BB_LCMS01(+) | 348 | 2.336 | 96.1 | n/a |
| 8-4 | 8b-2 | 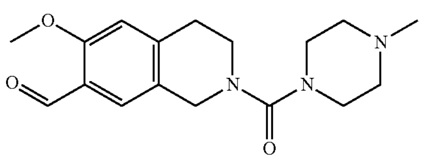 | BB_LCMS01(+) | 318 | 2.258 | 96 | n/a |

Example 9

2-Benzyl-6-methoxy-1,2,3,4-tetrahydro-isoquinoline-7-carbaldehyde

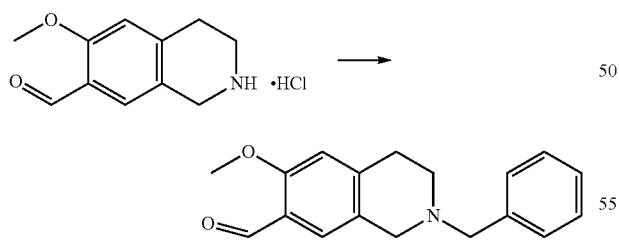

To a mixture of 6-methoxy-1,2,3,4-tetrahydro-isoquinoline-7-carbaldehyde hydrochloride (114 mg, 0.5 mmol) and freshly dried $K_2CO_3$ (173 mg, 1.25 mmol) in anhydrous dimethylformamide (5 mL), benzyl chloride (69 µL, 76 mg, 0.6 mmol) was added and the mixture was stirred at room temperature for 24 h. The mixture was poured into water (25 mL) and extracted with diethyl ether (3×10 mL). The combined organic layers were washed with brine (3×5 mL), dried over $MgSO_4$ and concentrated. The title compound (112 mg, 0.40 mmol, 80%) was obtained as a yellow oil.

LCMS/BB_LCMS01(+)/: M+1=282, Rt: 2.415 min.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 9-1 | 5-2 | 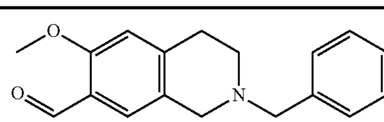 | BB_LCMS01(+) | 282 | 2.430 | 95 | n/a |

| EXAMPLE | Made From | Structure | LCMS method | LCMS Ion | LCMS Rt (min) | LCMS purity (%) | NMR purity (%) |
|---|---|---|---|---|---|---|---|
| 9-2 | 5-1 | 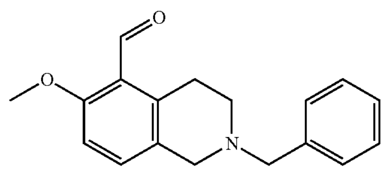 [SMILES: COc1ccc2c(c1C=O)CCN(Cc1ccccc1)C2] | BB_LCMS01(+) | 282 | 2.538 | 67.3 | n/a |
| 9-3 | 5-3 | 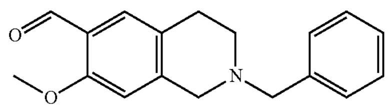 [SMILES: COc1cc2c(cc1C=O)CCN(Cc1ccccc1)C2] | BB_LCMS01(+) | 282 | 2.436 | 82.9 | n/a |

Example 10

6-Methoxy-2-[4-methyl-5-(morpholine-4-carbonyl)-thiazol-2-yl]-1,2,3,4-tetrahydro-isoquinoline-5-carbaldehyde

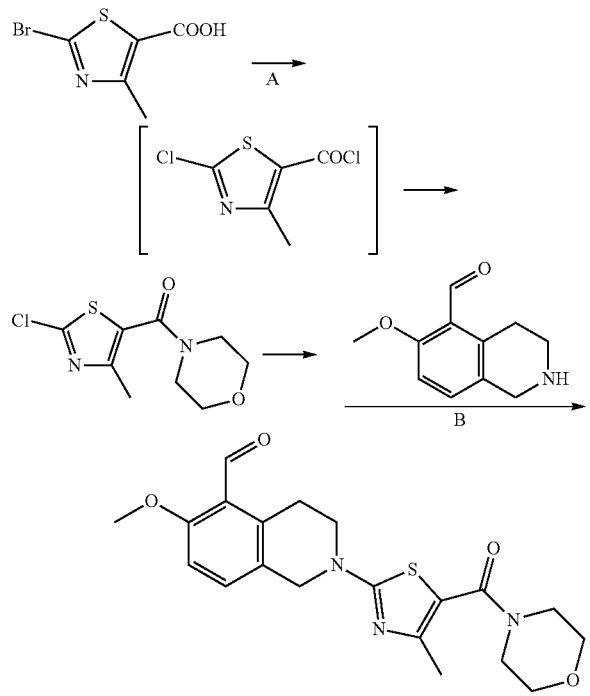

Step A

(2-Chloro-4-methyl-thiazol-5-yl)-morpholin-4-yl-methanone

A mixture of 2-bromo-4-methyl-thiazole-5-carboxylic acid (1.11 g, 5.0 mmol) and thionyl chloride (11 mL, 18.2 g, 0.153 mol) was heated under reflux for 30 min. After cooling, the volatiles were evaporated, followed by addition and evaporation of three 10 mL portions of toluene. A sample of the residue was treated with methanol and the obtained methyl ester was shown to be the 2-chlorothiazole compound [LCMS/BB_LCMS01(+)/: M+1=192, Rt: 3.424 min] indicating that the product (0.91 g, 4.7 mmol, 95%) was 2-chloro-4-methyl-thiazole-5-carbonyl chloride.

To a solution of the above acid chloride (200 mg, 1.02 mmol) in dichloromethane (5 mL) at 0° C., a mixture of morpholine (88 µL, 89 mg, 1.02 mmol) and diisopropylethylamine (148 µL, 124 mg, 1.03 mmol) in dichloromethane (3 mL) was added dropwise and the reaction mixture was stirred at room temperature for 1 h. After dilution with dichloromethane (20 mL) the solution was washed with water (2×5 mL), dried over MgSO$_4$ and evaporated to yield the title compound (208 mg, 0.84 mmol, yield: 82% calculated from the starting acid chloride) as a yellow oil.

LCMS/BB_LCMS01(+)/: M+1=247, Rt: 2.534 min.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 10a-1 | — | 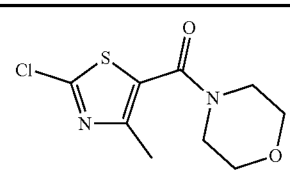 | BB_LCMS01(+) | 247 | 2.534 | 1011 | n/a |

| EXAMPLE | Made From | Structure | LCMS method | LCMS Ion | LCMS Rt (min) | LCMS purity (%) | NMR purity (%) |
|---|---|---|---|---|---|---|---|
| 10a-2 | — | (2-chloro-4-methylthiazol-5-yl)-(morpholin-4-yl)methanone with ethyl linker amide | BB_LCMS01(+) | 290 | 0.777 | 100 | n/a |

Step A'

2-Bromo-4-methyl-thiazole-5-carboxylic acid (1-methyl-piperidin-4-yl)-amide

To a stirred mixture of 1-methyl-4-aminopiperidine (125 μL, 114 mg, 1 mmol) and triethylamine (570 μL, 414 mg, 4.1 mmol) in anhydrous tetrahydrofuran (10 mL), 2-bromo-4-methyl-thiazole-5-carboxylic acid (266 mg, 1.2 mmol), (3-dimethylaminopropyl)-ethyl-carbodiimide hydrochloride (232 mg, 1.2 mmol) and 1-hydroxy-benzotriazole (164 mg, 1.2 mmol) were sequentially and the mixture was stirred at room temperature for 22 h. After dilution with dichloromethane (20 mL), the mixture was washed with water (3×10 mL), dried over MgSO₄ and concentrated. In this manner the title compound (277 mg, 0.87 mmol, 87%) was obtained as a yellow solid.

LCMS/BB_LCMS01(+)/: M+1=318, Rt: 1.102 min.

The following compounds (includes title compound) were made by the above procedure:

Step B

6-Methoxy-2-[4-methyl-5-(morpholine-4-carbonyl)-thiazol-2-yl]-1,2,3,4-tetrahydro-isoquinoline-5-carbaldehyde A mixture of 6-methoxy-1,2,3,4-tetrahydro-isoquinoline-5-carbaldehyde hydrochloride (82 mg, 0.36 mmol), anhydrous dimethylformamide (5 mL), (2-chloro-4-methyl-thiazol-5-yl)-morpholin-4-yl-methanone (89 mg, 0.36 mmol) and freshly dried potassium carbonate (149 mg, 1.08 mmol) was stirred under argon at 120° C. for 3.5 h and then at 150° C. for 1 h. Water (20 mL) was added and the separated solid product was filtered off. The filtrate was extracted with diethyl ether (5×10 mL) and the combined extracts were washed with water (2×10 mL), dried and concentrated. The residue and the above solid product were combined and triturated repeatedly with diisopropyl ether. In this manner the title compound (37 mg, 0.092 mmol, 26%) was obtained as a beige powder.

LCMS/BB_LCMS01(+)/: M+1=402, Rt: 3.129 min.

| EXAMPLE | Made From | Structure | LCMS method | LCMS Ion | LCMS Rt (min) | LCMS purity (%) | NMR purity (%) |
|---|---|---|---|---|---|---|---|
| 10a-3 | — | 2-bromo-4-methylthiazole-5-carboxamide N-(1-methylpiperidin-4-yl) | BB_LCMS01(+) | 318 | 1.102 | 96.8 | n/a |
| 10a-4 | — | 2-bromo-4-methylthiazole-5-carboxamide N-(1-Boc-piperidin-4-yl) | BB_LCMS01(+) | 348 | 3.620 | 93.8 | n/a |
| 10a-5 | — | (2-bromo-4-methylthiazol-5-yl)-(4-methylpiperazin-1-yl)methanone | BB_LCMS01(+) | 304 | 0.555 | 99.1 | n/a |
| 10a-6 | — | (2-bromothiazol-5-yl)-(4-methylpiperazin-1-yl)methanone | BB_LCMS01(+) | 290 | 0.492 | 100 | n/a |

The following compounds (includes title compound) were made by the above procedure:

| EX-AMPLE | Made From | Structure | LCMS method | LCMS Ion | LCMS Rt (min) | LCMS purity (%) | NMR purity (%) |
|---|---|---|---|---|---|---|---|
| 10-1 | 10a-1 | 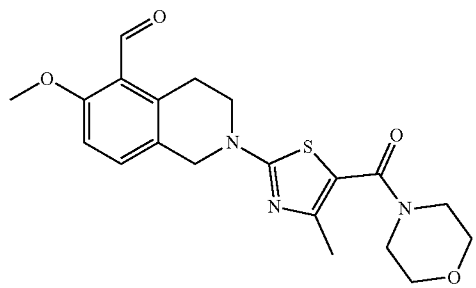 [SMILES: COc1ccc2c(c1C=O)CCN(c1nc(C)c(C(=O)N3CCOCC3)s1)C2] | BB_LCMS01(+) | 402 | 3.129 | 88.9 | n/a |
| 10-2 | 10a-2 | 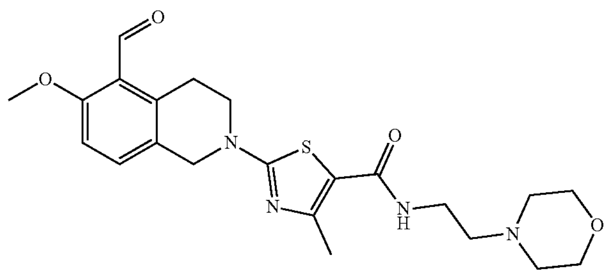 [SMILES: COc1ccc2c(c1C=O)CCN(c1nc(C)c(C(=O)NCCN3CCOCC3)s1)C2] | BB_LCMS01(+) | 445 | 2.655 | 96.1 | n/a |
| 10-3 | 10a-3 | 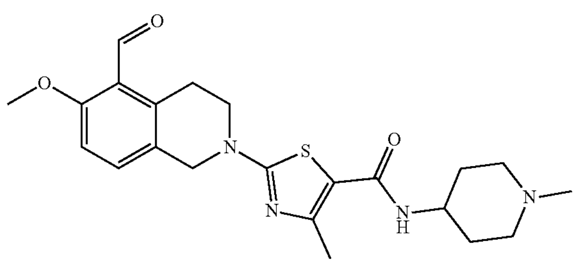 | BB_LCMS01(+) | 429 | 2.624 | 91.3 | n/a |
| 10-4 | 10a-4 | 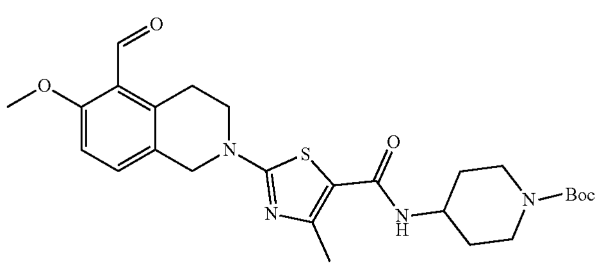 [SMILES: COc1ccc2c(c1C=O)CCN(c1nc(C)c(C(=O)NC3CCN(C(=O)OC(C)(C)C)CC3)s1)C2] | BB_LCMS01(+) | 515 | 3.849 | 90.7 | n/a |
| 10-5 | 10a-5 | 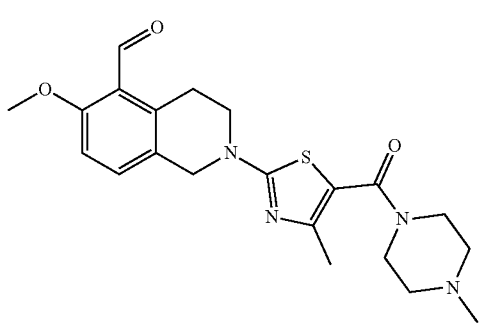 | | | | | n/a |

| EX-AMPLE | Made From | Structure | LCMS method | LCMS Ion | LCMS Rt (min) | LCMS purity (%) | NMR purity (%) |
|---|---|---|---|---|---|---|---|
| 10-6 | 10a-6 | 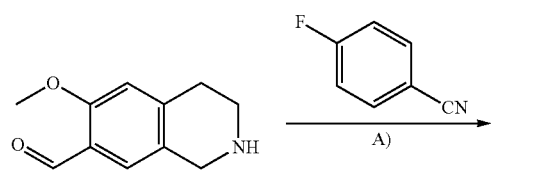 | | | | | n/a |
| 10-7 | 10a-5 | 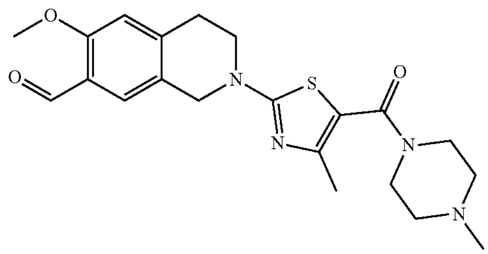 | BB_LCMS01(+) | 415 | 2.470 | 96 | n/a |
| 10-8 | 10a-6 | 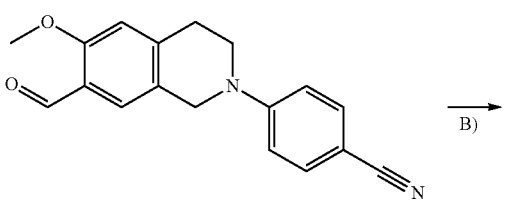 | | | | | n/a |

Example 11

4-(7-Formyl-6-methoxy-3,4-dihydro-1H-isoquinolin-2-yl)-benzamide

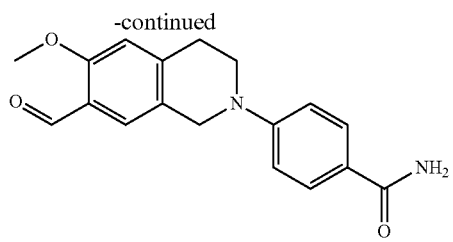

Step A 4-(7-Formyl-6-methoxy-3,4-dihydro-1H-isoquinolin-2-yl)-benzonitrile

A mixture of 6-methoxy-1,2,3,4-tetrahydro-isoquinoline-7-carbaldehyde hydrochloride (1.0 g, 4.39 mmol), 1-fluoro-4-methyl-benzene (2.42 g, 20.0 mmol) and freshly dried $K_2CO_3$ (3.0 g, 21.7 mmol) in anhydrous dimethylformamide (11 mL) was stirred under nitrogen at 130° C. for 6 h. The mixture was poured into water (50 mL) and extracted with ethyl acetate (3×50 mL). The organic extracts were dried over $MgSO_4$ and evaporated. The residue was purified by column chromatography over silica by eluting with a 2:1 mixture of n-hexane and ethyl acetate. In this manner the title compound (0.45 g, 1.54 mmol, 35.1%) was obtained.

| EXAMPLE | Made From | Structure | LCMS method | LCMS Ion | LCMS Rt (min) | LCMS purity (%) | NMR purity (%) |
|---|---|---|---|---|---|---|---|
| 11a | — | ![structure] | BB_LCMS01(+) | 293 | 3.828 | 100 | n/a |

Step B

4-(5-Formyl-6-methoxy-3,4-dihydro-1H-isoquinolin-2-yl)-benzamide

A mixture of 4-(7-formyl-6-methoxy-3,4-dihydro-1H-isoquinolin-2-yl)-benzonitrile (200 mg, 0.68 mmol) and 96% (w/w) sulfuric acid (3 mL) was stirred at room temperature overnight. The next day poured onto ice-water (10 mL), the pH was adjusted with $K_2CO_3$ to 9 and the mixture was extracted with ethyl acetate. The residue was purified by column chromatography over silica, eluting with a 95:5 mixture of chloroform and methanol. In this manner the title compound (85 mg, 0.27 mmol, 39.7%) was obtained as a solid.

| EXAMPLE | Made From | Structure | LCMS method | LCMS Ion | LCMS Rt (min) | LCMS purity (%) | NMR purity (%) |
|---|---|---|---|---|---|---|---|
| 11-1 | 11a | ![structure] | BB_LCMS01(+) | 311 | 3.121 | 100 | n/a |

Example 12

6-Methoxy-2-[2-(4-methyl-piperazin-1-yl)-thiazole-5-carbonyl]-1,2,3,4-tetrahydro-isoquinoline-5-carbaldehyde

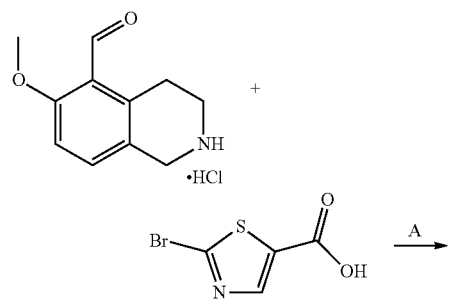

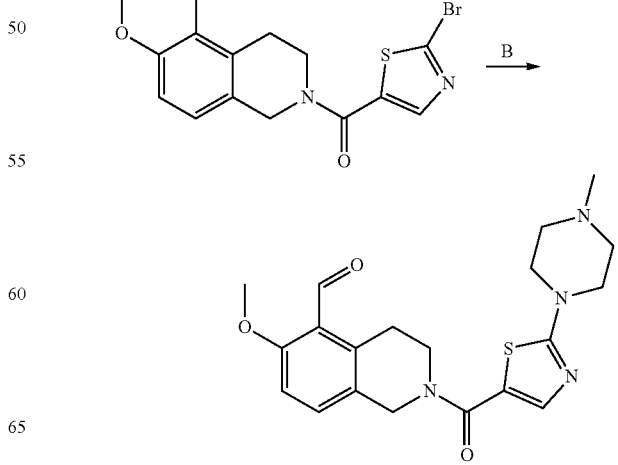

-continued

Step A

2-(2-Bromo-thiazole-5-carbonyl)-6-methoxy-1,2,3,4-tetrahydro-isoquinoline-5-carbaldehyde

To a mixture of dry tetrahydrofuran (20 mL) 6-Methoxy-1,2,3,4-tetrahydro-isoquinoline-5-carbaldehyde hydrochloride (683 mg, 3.00 mmol), and triethylamine (2.1 mL, 1.52 g, 15 mmol), 2-bromothiazole-5-carboxylic acid (655 mg, 3.15 mmol), 1-hydroxybenzotriazole (446 mg, 3.30 mmol) and 1-ethyl-(3-dimethylaminopropyl)-carbodiimide hydrochloride (634 mg, 3.30 mmol) were added sequentially. The mixture was stirred at room temperature for 2 h and the resulted yellow suspension was evaporated and partitioned between chloroform (30 mL) and 0.1N HCl (15 mL). The organic layer was separated and washed with saturated sodium bicarbonate (15 mL) and brine (15 mL). The organic phase was dried, evaporated and purified by column chromatography (Kieselgel 60), with chloroform as the eluent. The title compound (600 mg, 1.57 mmol, 53%) was isolated as a solid.

| EXAMPLE | Made From | Structure | LCMS method | LCMS Ion | LCMS Rt (min) | LCMS purity (%) | NMR purity (%) |
|---|---|---|---|---|---|---|---|
| 12a | — | 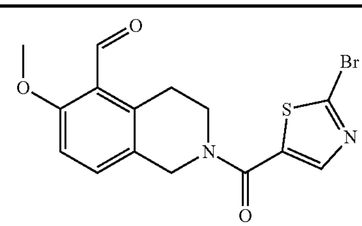 | BB_LCMS01(+) | 382 | 3.470 | 100 | n/a |

Step B

6-Methoxy-2-[2-(4-methyl-piperazin-1-yl)-thiazole-5-carbonyl]-1,2,3,4-tetrahydro-isoquinoline-5-carbaldehyde

To a solution of 2-(2-Bromo-thiazole-5-carbonyl)-6-methoxy-1,2,3,4-tetrahydro-isoquinoline-5-carbaldehyde (229 mg, 0.60 mg) in abs. N,N-dimethylformamide (4 mL), N-methyl piperazine (133 μL, 120 mg, 1.20 mmol) and dry potassium carbonate (248 mg, 1.80 mmol) was added. The resultant mixture was stirred under nitrogen at 100° C. for 2 h in a closed vial. The reaction was cooled, water (10 mL) was added, and the resultant solution was extracted with ethyl acetate (3×15 mL) The combined organic layers were dried (MgSO$_4$) and evaporated to afford title compound (92 mg, 0.23 mmol, 38%) as a pale yellow crystalline solid.

| EXAMPLE | Made From | Structure | LCMS method | LCMS Ion | LCMS Rt (min) | LCMS purity (%) | NMR purity (%) |
|---|---|---|---|---|---|---|---|
| 12-1 | 12a | 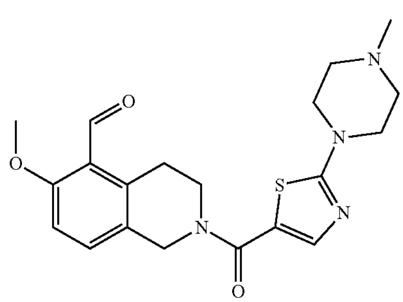 [SMILES: COc1ccc2c(c1C=O)CCN(C(=O)c1cnc(N3CCN(C)CC3)s1)C2] | BB_LCMS01(+) | 401 | 2.550 | 93 | n/a |

Example 13

7-Hydroxy-3-[4-methyl-5-(4-methyl-piperazine-1-carbonyl)-thiazol-2-yl]-2-oxo-2H-chromene-8-carbaldehyde

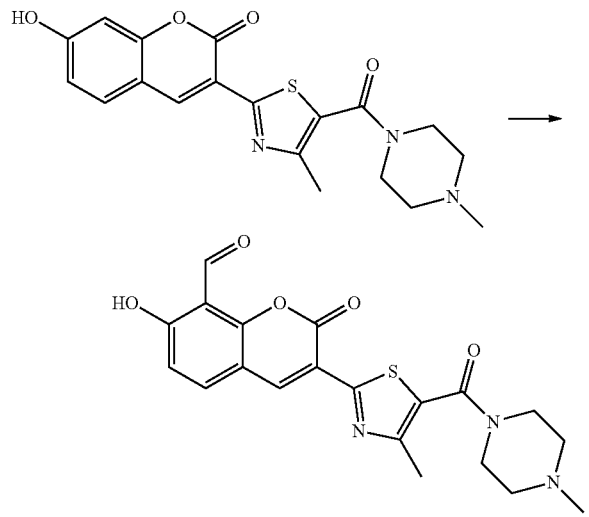

A mixture of 7-hydroxy-3-[4-methyl-5-(4-methyl-piperazine-1-carbonyl)-thiazol-2-yl]-chromen-2-one (156 mg, 0.40 mmol) and hexamethylenetetramine (224 mg, 1.6 mmol) in trifluoroacetic acid (4 mL) was stirred in a closed vial under argon at 110° C. for 40 min. After cooling water (15 mL) was added and the mixture was extracted with dichloromethane (3×5 mL). The combined organic extracts were washed with water (3×5 mL), dried over $MgSO_4$ and concentrated. The obtained crude product (83 mg) was purified by column chromatography over silica, eluting with a 9:1 mixture of chloroform and methanol. In this manner the title compound (30.5 mg, 0.074 mmol, 18.5%) was obtained as a yellow solid.

LCMS/BB_LCMS01(+)/: M+1=414, Rt: 3.085 min.

$^1$H NMR (400 MHz, DMSO-$d_6$) δ ppm 10.41 (s, 1H), 8.86 (s, 1H), 7.97 (d, J=9.0 Hz, 1H), 6.83 (d, J=9.0 Hz, 1H), 3.59 (br. s., 4H), 2.55-2.64 (m, 4H), 2.41 (s, 3H), 2.38 (s, 3H).

The following compounds (includes title compound) were made by the above procedure:

| Ex | Made From | Structure | LCMS method | LCMS Ion | LCMS Rt (min) | LCMS purity (%) | NMR purity (%) |
|---|---|---|---|---|---|---|---|
| 13-1 | 20-1 | 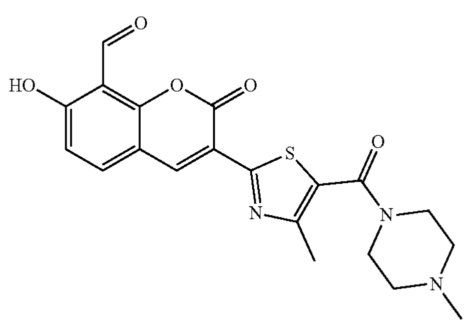 [SMILES: Cc1nc(-c2cc3ccc(O)c(C=O)c3oc2=O)sc1C(=O)N1CCN(C)CC1] | BB_LCMS01(+) | 414 | 3.085 | 100 | 98 |
| 13-2 | 6093-68-1 | 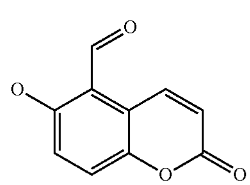 [SMILES: O=Cc1c(O)ccc2oc(=O)ccc12] | BB_LCMS01(−) | 189 | 2.621 | 100 | 98 |
| 13-3 | 23251-28-7 | 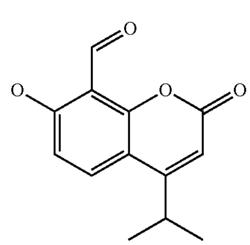 [SMILES: CC(C)c1cc(=O)oc2c(C=O)c(O)ccc12] | BB_LCMS01(−) | 231 | 3.505 | 98 | 95 |

-continued

| Ex | Made From | Structure | LCMS method | LCMS Ion | LCMS Rt (min) | LCMS purity (%) | NMR purity (%) |
|---|---|---|---|---|---|---|---|
| 13-4 | 20052-60-2 | 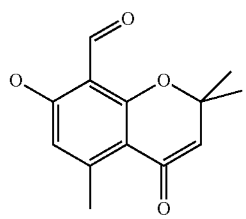 | BB_LCMS01(+) | 235 | 3.709 | 96 | 97 |
| 13-5 | 56437-16-2 | 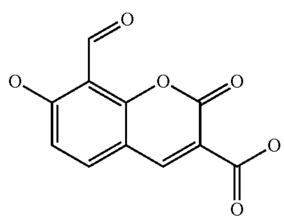 [SMILES: O=Cc1c(O)ccc2cc(C(=O)O)c(=O)oc12] | BB_LCMS01(−) | 233 | 2.496 | 95 | 98 |
| 13-6 | Indofine 19-244 | 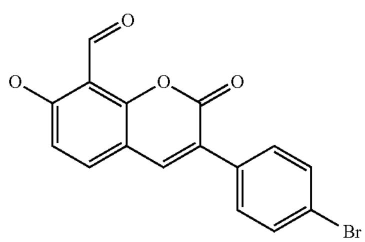 [SMILES: O=Cc1c(O)ccc2cc(-c3ccc(Br)cc3)c(=O)oc12] | BB_LCMS01(−) | 345 | 4.068 | 100 | 98 |
| 13-7 | Princeton PBMR-019293 | 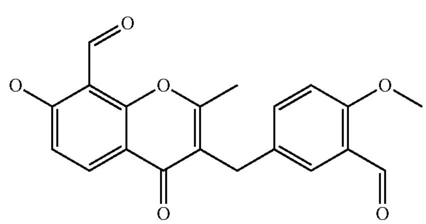 [SMILES: COc1ccc(Cc2c(C)oc3c(C=O)c(O)ccc3c2=O)cc1C=O] | BB_LCMS01(+) | 355 | 3.495 | 100 | 98 |
| 13-8 | Princeton PBMR 015251 | 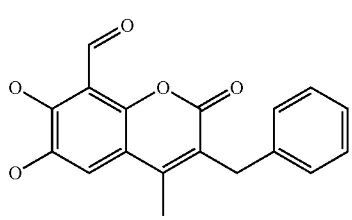 [SMILES: Cc1c(Cc2ccccc2)c(=O)oc2c(C=O)c(O)c(O)cc12] | BB_LCMS01(+) | 311 | 3.467 | 94 | 95 |
| 13-9 | Princeton PBMR-001612 | 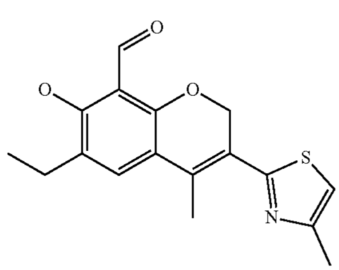 [SMILES: CCc1cc2c(c(C=O)c1O)OCC(c1nc(C)cs1)=C2C] | BB_LCMS01(+) | 316 | 4.081 | 97 | 98 |

-continued

| Ex | Made From | Structure | LCMS method | LCMS Ion | LCMS Rt (min) | LCMS purity (%) | NMR purity (%) |
|---|---|---|---|---|---|---|---|
| 13-10 | 61034-11-5 | 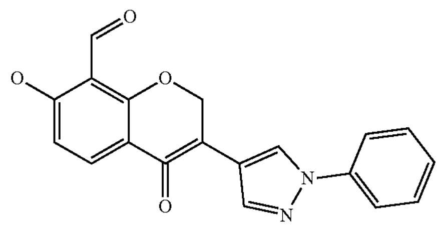 | BB_LCMS01(+) | 333 | 3.785 | 100 | 98 |
| 13-11 | 19492-02-5 | 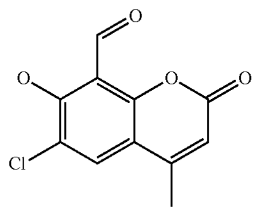 [SMILES: Cc1cc(=O)oc2c(C=O)c(O)c(Cl)cc12] | BB_LCMS01(−) | 237 | 3.453 | 98 | 98 |
| 13-12 | 219965-92-1 | 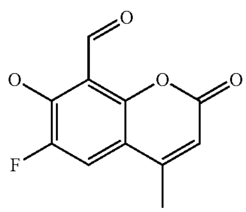 [SMILES: Cc1cc(=O)oc2c(C=O)c(O)c(F)cc12] | BB_LCMS01(−) | 221 | 3.177 | 93 | 98 |
| 13-13 | 5852-03-9 | 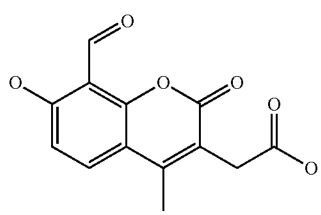 [SMILES: Cc1c(CC(=O)O)c(=O)oc2c(C=O)c(O)ccc12] | BB_LCMS01(−) | 261 | 3.224 | 88 | 90 |
| 13-14 | 90-33-5 | 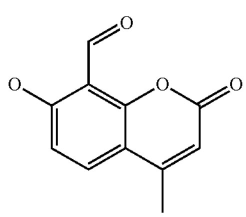 | BB_LCMS01(+) | 205 | 3.278 | 100 | 98 |
| 13-15 | 6100-60-3 | 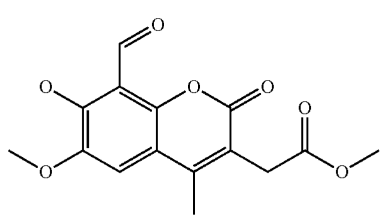 | BB_LCMS07(+) | 321 | 1.401 | 98 | 98 |
| 13-16 | 55977-10-1 | 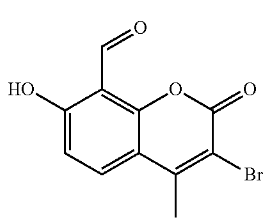 [SMILES: Cc1c(Br)c(=O)oc2c(C=O)c(O)ccc12] | BB_LCMS01(−) | 281 | 3.453 | 95 | n/a |

-continued
| Ex | Made From | Structure | LCMS method | LCMS Ion | LCMS Rt (min) | LCMS purity (%) | NMR purity (%) |
|---|---|---|---|---|---|---|---|
| 13-17 | 19a-1 | 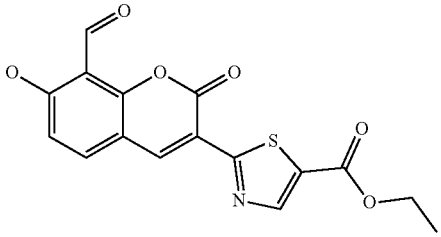 [SMILES: CCOC(=O)c1cnc(-c2cc3ccc(O)c(C=O)c3oc2=O)s1] | BB_LCMS01(−) | 344 | 3.844 | 90 | 95 |
| 13-18 | 19a-2 | 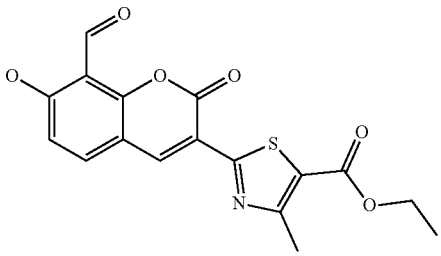 [SMILES: CCOC(=O)c1sc(-c2cc3ccc(O)c(C=O)c3oc2=O)nc1C] | BB_LCMS01(−) | 358 | 3.948 | 97 | 96 |
| 13-19 | 20-2 | 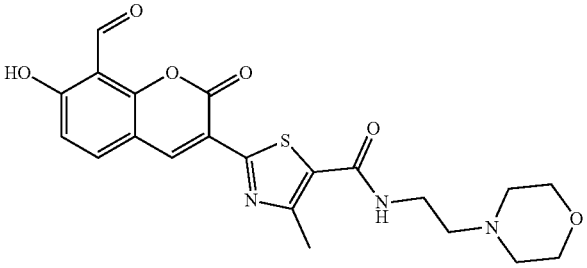 [SMILES: Cc1nc(-c2cc3ccc(O)c(C=O)c3oc2=O)sc1C(=O)NCCN1CCOCC1] | BB_LCMS01(+) | 444 | 3.124 | 100 | 98 |
| 13-20 | 20-3 | 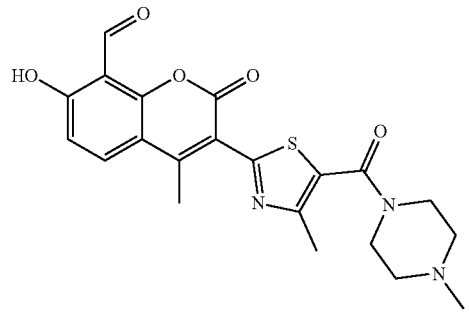 | BB_LCMS01(+) | 428 | 3.033 | 100 | 94 |
| 13-21 | 20-5 | 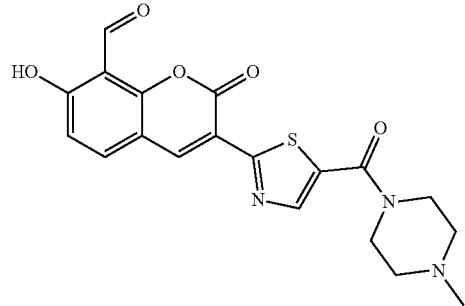 | BB_LCMS07(+) | 400 | 1.276 | 99 | 98 |

-continued
| Ex | Made From | Structure | LCMS method | LCMS Ion | LCMS Rt (min) | LCMS purity (%) | NMR purity (%) |
|---|---|---|---|---|---|---|---|
| 13-22 | 21-1 | 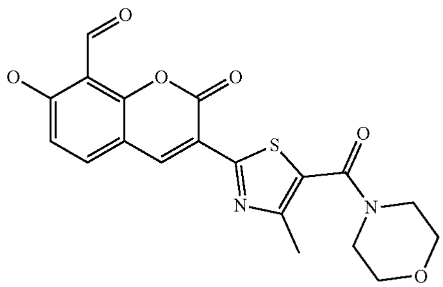 [SMILES: Cc1nc(-c2cc3ccc(O)c(C=O)c3oc2=O)sc1C(=O)N1CCOCC1] | BB_LCMS01(+) | 401 | 3.359 | 96 | 95 |
| 13-23 | 22-1 | 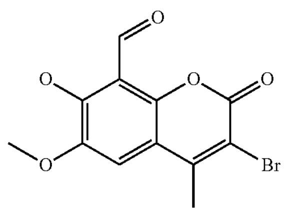 [SMILES: COc1cc2c(C)c(Br)c(=O)oc2c(C=O)c1O] | BB_LCMS01(−) | 311 | 3.290 | 100 | 98 |
| 13-24 | 22-2 | 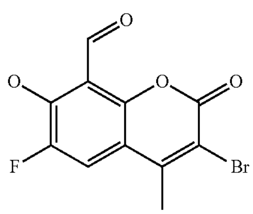 [SMILES: Cc1c(Br)c(=O)oc2c(C=O)c(O)c(F)cc12] | BB_LCMS01(−) | 299 | 3.419 | 99 | 98 |
| 13-25 | 22-3 | 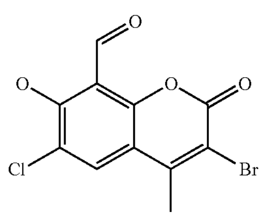 [SMILES: Cc1c(Br)c(=O)oc2c(C=O)c(O)c(Cl)cc12] | BB_LCMS01(−) | 315 | 3.229 | 79 | n/a |
Example 14
[4-(6-Hydroxy-benzothiazol-2-yl)-phenyl]-(4-methyl-piperidin-1-yl)-methanone
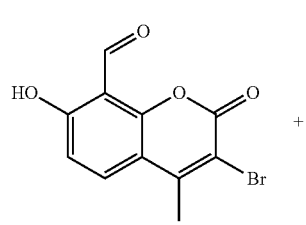
+
-continued
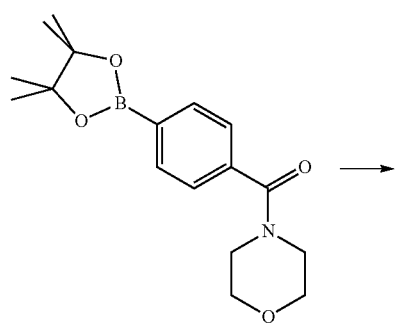

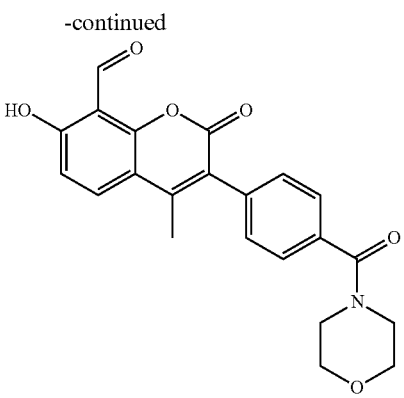

3-Bromo-7-hydroxy-4-methyl-2-oxo-2H-chromene-8-carbaldehyde (142 mg, 0.50 mmol), 4-(4-morpholine-4-carbonyl)phenylboronic acid pinacol ester (175 mg, 0.55 mmol), potassium phosphate (424 mg, 2.00 mmol) and tetrakis(triphenylphosphine)palladium (17 mg, 0.015 mmol) were dissolved in a degassed mixture of 4.5 mL 2-ethoxyethanol and 0.5 mL water. The mixture was stirred at 115° C. under argon for 2 h. The reaction mixture was allowed to reach room temperature, then activated-carbon (40 mg) was added and was stirred for 20 min. The solid was filtered off, washed with ethanol and the combined filtrates were evaporated. The residue was suspended in saturated sodium bicarbonate (20 mL) and extracted with dichloromethane (3×20 mL). The combined organic layers were dried ($Na_2SO_4$) and evaporated. The solid residue was purified by column chromatography (Kieselgel 60) with chloroform-methanol 98:2 as the eluent. The crude product was triturated with $Et_2O$, filtered off and air dried, affording the title compound (31 mg, 0.08 mmol, 16%) as a white powder.

The following compounds (includes title compound) were made by the above procedure:

| Ex | Made From | Structure | LCMS method | LCMS Ion | LCMS Rt (min) | LCMS purity (%) | NMR purity (%) |
|---|---|---|---|---|---|---|---|
| 14-1 | 55977-10-1 | 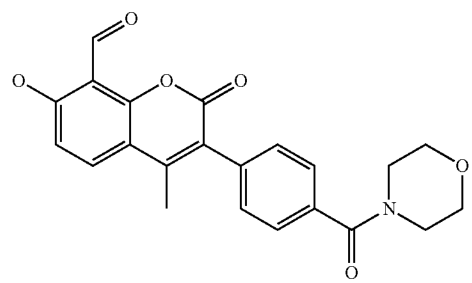 [SMILES: Cc1c(-c2ccc(C(=O)N3CCOCC3)cc2)c(=O)oc2c(C=O)c(O)ccc12] | BB_LCMS01(+) | 394 | 3.175 | 100 | 98 |
| 14-2 | 55977-10-1 | 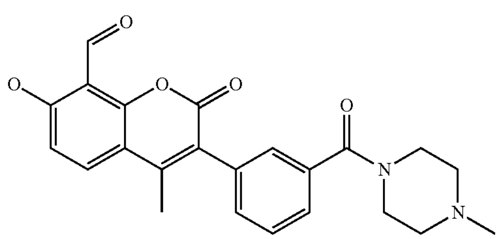 [SMILES: Cc1c(-c2cccc(C(=O)N3CCN(C)CC3)c2)c(=O)oc2c(C=O)c(O)ccc12] | BB_LCMS01(+) | 407 | 2.596 | 99 | 98 |
| 14-3 | 55977-10-1 | 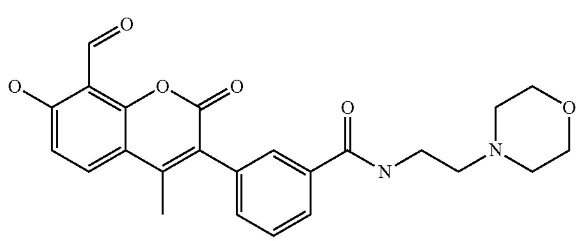 [SMILES: Cc1c(-c2cccc(C(=O)NCCN3CCOCC3)c2)c(=O)oc2c(C=O)c(O)ccc12] | BB_LCMS01(+) | 437 | 2.714 | 100 | 98 |
| 14-4 | 55977-10-1 | 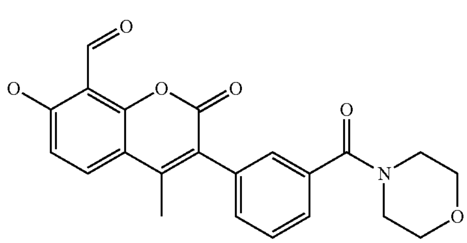 [SMILES: Cc1c(-c2cccc(C(=O)N3CCOCC3)c2)c(=O)oc2c(C=O)c(O)ccc12] | BB_LCMS01(+) | 394 | 3.199 | 99 | 98 |

-continued

| Ex | Made From | Structure | LCMS method | LCMS Ion | LCMS Rt (min) | LCMS purity (%) | NMR purity (%) |
|---|---|---|---|---|---|---|---|
| 14-5 | 55977-10-1 | 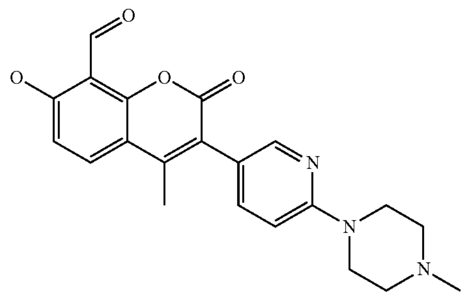 [SMILES: Cc1c(-c2ccc(N3CCN(C)CC3)nc2)c(=O)oc2c(C=O)c(O)ccc12] | BB_LCMS01(+) | 380 | 2.574 | 97 | 98 |
| 14-6 | 55977-10-1 | 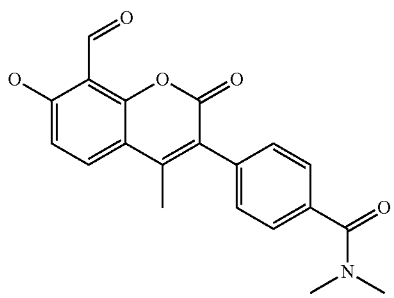 [SMILES: Cc1c(-c2ccc(C(=O)N(C)C)cc2)c(=O)oc2c(C=O)c(O)ccc12] | BB_LCMS01(+) | 352 | 3.233 | 96 | 98 |
| 14-7 | 55977-10-1 | 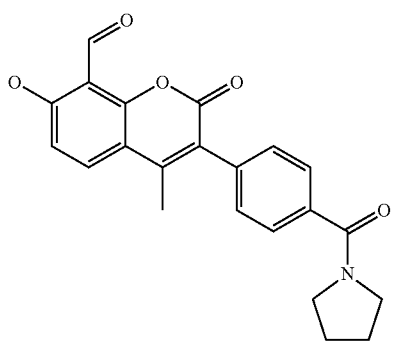 [SMILES: Cc1c(-c2ccc(C(=O)N3CCCC3)cc2)c(=O)oc2c(C=O)c(O)ccc12] | BB_LCMS01(+) | 378 | 3.416 | 99 | 98 |
| 14-8 | 55977-10-1 | 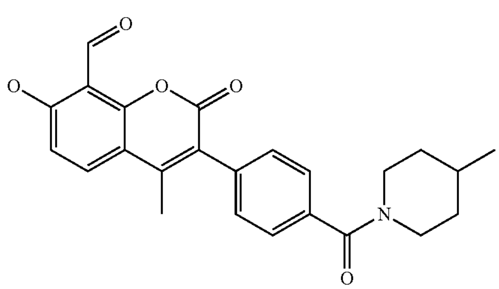 [SMILES: Cc1c(-c2ccc(C(=O)N3CCC(C)CC3)cc2)c(=O)oc2c(C=O)c(O)ccc12] | BB_LCMS01(+) | 406 | 3.815 | 94 | 98 |
| 14-9 | 55977-10-1 | 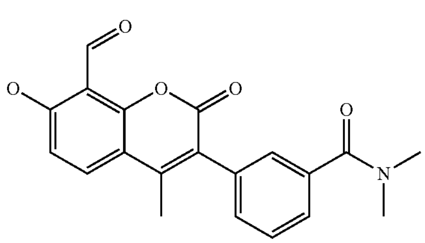 [SMILES: Cc1c(-c2cccc(C(=O)N(C)C)c2)c(=O)oc2c(C=O)c(O)ccc12] | BB_LCMS01(+) | 352 | 3.292 | 98 | 98 |

-continued

| Ex | Made From | Structure | LCMS method | LCMS Ion | LCMS Rt (min) | LCMS purity (%) | NMR purity (%) |
|---|---|---|---|---|---|---|---|
| 14-10 | 55977-10-1 | 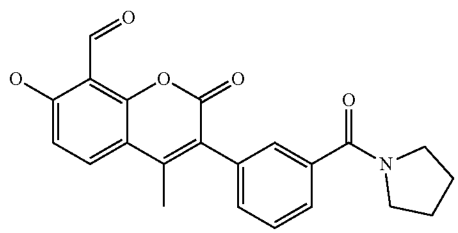 [SMILES: Cc1c(-c2cccc(C(=O)N3CCCC3)c2)c(=O)oc2c(C=O)c(O)ccc12] | BB_LCMS01(+) | 378 | 3.439 | 95 | 98 |
| 14-11 | 13-23 | 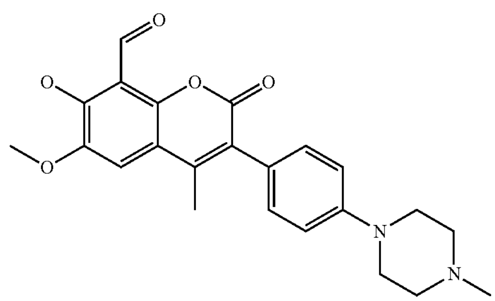 | BB_LCMS01(+) | 409 | 2.929 | 100 | 95 |
| 14-12 | 13-23 | 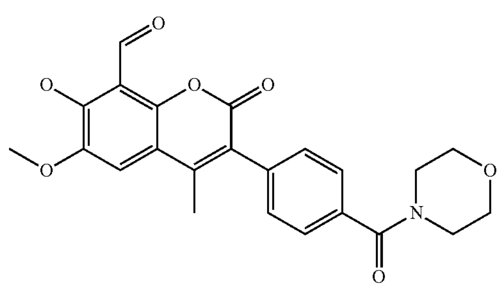 [SMILES: COc1cc2c(C)c(-c3ccc(C(=O)N4CCOCC4)cc3)c(=O)oc2c(C=O)c1O] | BB_LCMS01(+) | 424 | 3.196 | 96 | 95 |
| 14-13 | 13-23 | 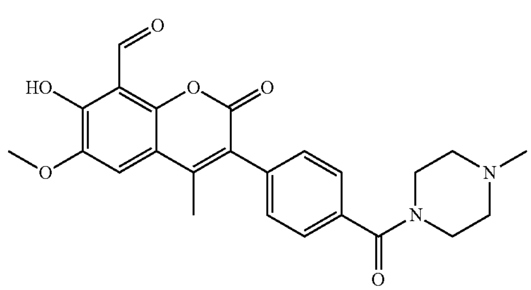 | BB_LCMS01(+) | 437 | 3.020 | 100 | 98 |
| 14-14 | 13-24 | 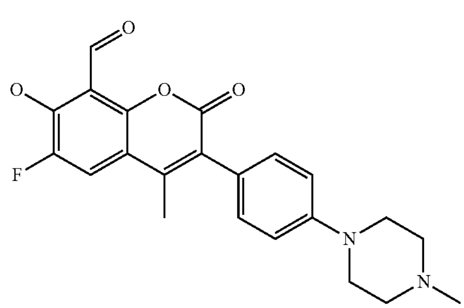 [SMILES: Cc1c(-c2ccc(N3CCN(C)CC3)cc2)c(=O)oc2c(C=O)c(O)c(F)cc12] | BB_LCMS01(+) | 397 | 3.017 | 92 | 95 |

| Ex | Made From | Structure | LCMS method | LCMS Ion | LCMS Rt (min) | LCMS purity (%) | NMR purity (%) |
|---|---|---|---|---|---|---|---|
| 14-15 | 13-25 | 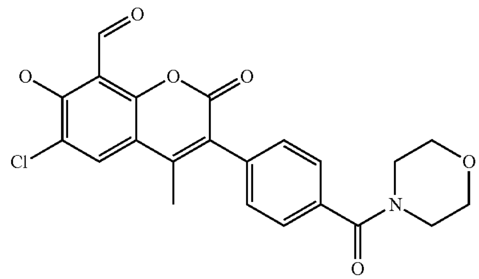 [SMILES: Cc1c(-c2ccc(C(=O)N3CCOCC3)cc2)c(=O)oc2c(C=O)c(O)c(Cl)cc12] | BB_LCMS01(+) | 428 | 3.550 | 94 | 98 |

Example 15

7-hydroxy-4-methyl-3-(3-morpholin-4-yl-3-oxo-propyl)-2-oxo-2H-chromene-8-carbaldehyde

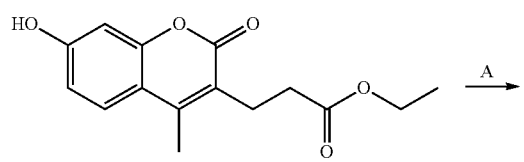

A ⟶

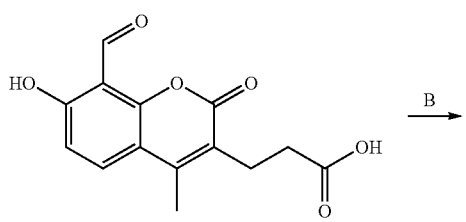

B ⟶

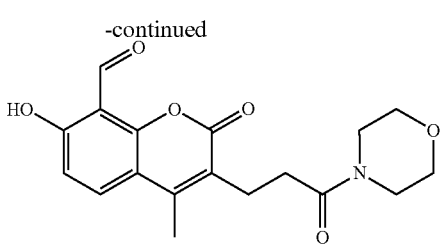

Step A

3-(8-Formyl-7-hydroxy-4-methyl-2-oxo-2H-chromen-3-yl)-propionic acid

A mixture of 3-(7-hydroxy-4-methyl-2-oxo-2H-chromen-3-yl)-propionic acid ethyl ester (100 mg, 0.36 mmol) and hexamethylenetetramine (203 mg, 1.44 mmol) in trifluoroacetic acid (3.6 mL) was stirred in a closed vial under argon at 110° C. for 2 h. The reaction was poured onto crushed ice (15 mL), warmed to room temperature, and the solid precipitate was filtered off. This mixture of formylated ester and corresponding carboxylic acid was dissolved in dioxane –1N NaOH (1:1) and was stirred at room temperature. After 2 h, 15 mL of dichloromethane was added. The aqueous layer was separated and acidified by portionwise addition of 1N HCl. The precipitate was collected, washed with water, and dried to afford title compound (15 mg, 0.043 mmol, 13%) as a light brown powder.

| Ex | Made From | Structure | LCMS method | LCMS Ion | LCMS Rt (min) | LCMS purity (%) | NMR purity (%) |
|---|---|---|---|---|---|---|---|
| 15a-1 | 5969-19-7 | 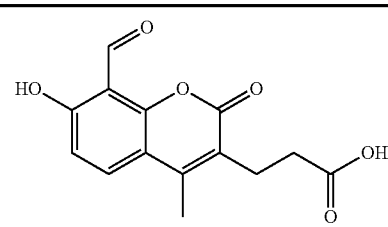 | BB_LCMS01(+) | 277 | 3.268 | 90 | n/a |
| 15a-2 | 6100-60-3 | 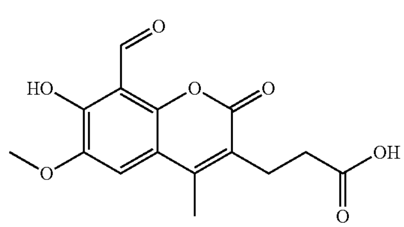 [SMILES: COc1cc2c(C)c(CCC(=O)O)c(=O)oc2c(C=O)c1O] | BB_LCMS07(+) | 307 | 1.386 | 79 | n/a |

Step B

7-Hydroxy-4-methyl-3-(3-morpholin-4-yl-3-oxo-propyl)-2-oxo-2H-chromene-8-carbaldehyde To a mixture of dry tetrahydrofuran (8.5 mL) and N,N-dimethylformamide (2 mL), morpholine (93 μL, 94 mg, 1.08 mmol), triethylamine (340 μl, 247 mg, 2.45 mmol) 3-(8-formyl-7-hydroxy-4-methyl-2-oxo-2H-chromen-3-yl)-propionic acid (148 mg, 0.49 mmol), 1-hydroxybenzotriazole (146 mg, 1.08 mmol) and 1-ethyl-(3-dimethylaminopropyl)-carbodiimide hydrochloride (205 mg, 1.08 mmol) were added in order. The mixture was stirred at room temperature overnight, then 5 mL of 2N HCl was added and the stirring was continued for 2 h. The resultant solution was extracted with dichloromethane (2×10 mL), the combined organic layers were washed with saturated sodium bicarbonate (10 mL) and brine (10 mL), the organic phase was dried ($Na_2SO_4$) and evaporated. The title compound (399 mg, 1.070 mmol, 57%) was isolated by column chromatography (Kieselgel 60), with chloroform-methanol 20:1 as eluent, as a white powder.

$^1$H NMR (400 MHz, DMSO-$d_6$) δ ppm 11.74 (br. s., 1H), 10.45 (s, 1H), 7.98 (d, J=9.0 Hz, 1H), 6.96 (d, J=9.0 Hz, 1H), 3.49-3.60 (m, 4H), 3.39-3.45 (m, 4H), 2.75-2.81 (m, 2H), 2.47-2.53 (m, 2H), 2.41 (s, 3H).

The following compounds (includes title compound) were made by the above procedure:

| Ex | Made From | Structure | LCMS method | LCMS Ion | LCMS Rt (min) | LCMS purity (%) | NMR purity (%) |
|---|---|---|---|---|---|---|---|
| 15-1 | 15a-1 | 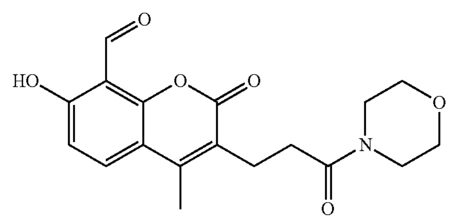 [SMILES: Cc1c(CCC(=O)N2CCOCC2)c(=O)oc2c(C=O)c(O)ccc12] | BB_LCMS01(+) | 346 | 3.286 | 99 | 98 |
| 15-2 | 15a-1 | 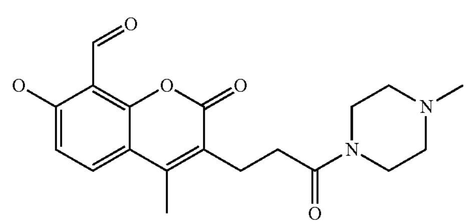 [SMILES: Cc1c(CCC(=O)N2CCN(C)CC2)c(=O)oc2c(C=O)c(O)ccc12] | BB_LCMS01(+) | 359 | 2.945 | 100 | 98 |
| 15-3 | 15a-1 | 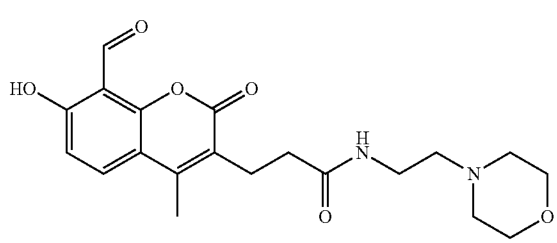 [SMILES: Cc1c(CCC(=O)NCCN2CCOCC2)c(=O)oc2c(C=O)c(O)ccc12] | BB_LCMS01(+) | 389 | 2.928 | 98 | 97 |
| 15-4 | 15a-2 | 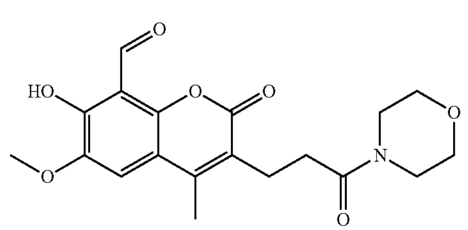 [SMILES: COc1cc2c(C)c(CCC(=O)N3CCOCC3)c(=O)oc2c(C=O)c1O] | BB_LCMS07(+) | 376 | 1.199 | 100 | 98 |

| Ex | Made From | Structure | LCMS method | LCMS Ion | LCMS Rt (min) | LCMS purity (%) | NMR purity (%) |
|---|---|---|---|---|---|---|---|
| 15-5 | 5852-10-8 | 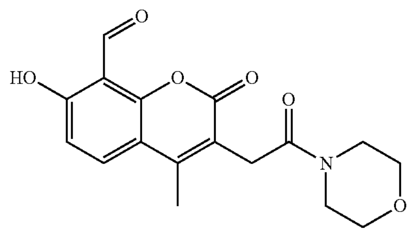 [SMILES: Cc1c(CC(=O)N2CCOCC2)c(=O)oc2c(C=O)c(O)ccc12] | BB_LCMS07(+) | 332 | 1.404 | 100 | 98 |
| 15-6 | 5852-10-8 | 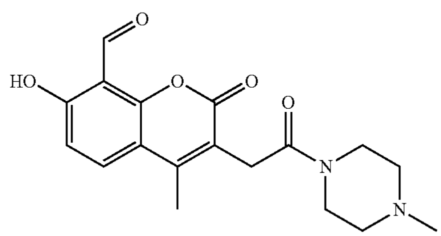 [SMILES: Cc1c(CC(=O)N2CCN(C)CC2)c(=O)oc2c(C=O)c(O)ccc12] | BB_LCMS07(+) | 345 | 1.307 | 99 | 98 |

Example 16

7-Hydroxy-4-methyl-3-[3-(4-methyl-piperazin-1-yl)-3-oxo-propenyl]-2-oxo-2H-chromene-8-carbaldehyde

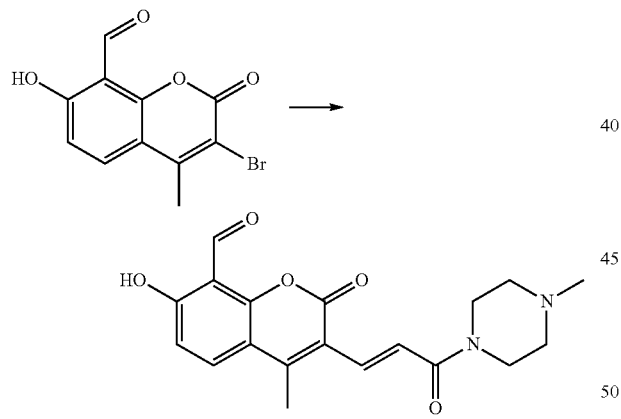

3-Bromo-7-hydroxy-4-methyl-2-oxo-2H-chromene-8-carbaldehyde (142 mg, 0.50 mmol), 1-(4-methyl-piperazin-1-yl)-propenone (93 mg, 0.60 mmol), palladium acetate (4 mg, 15 µmol), tri-o-tolyl-phosphane (9 mg, 30 µmol) and silver acetate (167 mg, 1.0 mmol) were dissolved in abs. N,N-dimethylformamide (4 mL). The mixture was irradiated in a microwave reactor for 1 h at 120° C. under inert atmosphere. The reaction mixture was poured into water (10 mL) and extracted with chloroform (3×15 mL). The combined organic layers were dried ($Na_2SO_4$) and evaporated. The title compound (15 mg, 0.042 mmol, 8%) was isolated by column chromatography (Kieselgel 60), with chloroform as eluent, as a yellow powder.

$^1$H NMR (400 MHz, DMSO-$d_6$) δ ppm 10.43 (s, 1H), 8.05 (d, J=9.0 Hz, 1H), 7.59 (d, J=15.1 Hz, 1H), 7.50 (d, J=15.1 Hz, 1H), 6.92 (d, J=9.0 Hz, 1H), 3.56-3.66 (m, 4H), 2.55 (s, 3H), 2.38 (br. s., 4H), 2.27 (s, 3H).

| Ex | Made From | Structure | LCMS method | LCMS Ion | LCMS Rt (min) | LCMS purity (%) | NMR purity (%) |
|---|---|---|---|---|---|---|---|
| 16-1 | 55977-10-1 | 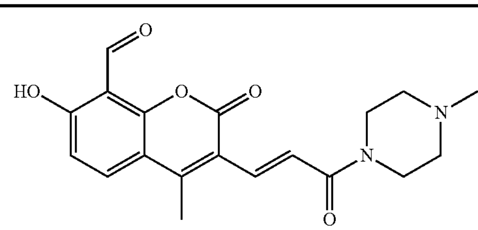 | BB_LCMS01(+) | 357 | 3.011 | 99 | 94 |

Example 17

7-Hydroxy-4-methyl-2-oxo-2H-chromene-3-carbothioic acid amide

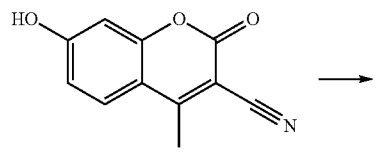

To a solution of 7-Hydroxy-4-methyl-2-oxo-2H-chromene-3-carbonitrile (7.50 g, 37.31 mmol) in N,N-dimethylformamide (150 mL), ammonium sulfide (40-48 wt % solution in water; 38 mL, 560 mmol) was added, and the resulted mixture was stirred at room temperature for a week. An additional portion of ammonium sulfide (38 mL) was added on every second day. The solution was evaporated and the solid residue was triturated with water, filtered and dried. The obtained crude product was purified by column chromatography (Kieselgel 60), with chloroform-methanol (1:1) as eluent. The title compound (3.20 g, 13.6 mmol, 36%) was isolated as a yellow powder.

| Ex | Made From | Structure | LCMS method | LCMS Ion | LCMS Rt (min) | LCMS purity (%) | NMR purity (%) |
|---|---|---|---|---|---|---|---|
| 17-1 | 2829-46-1 | 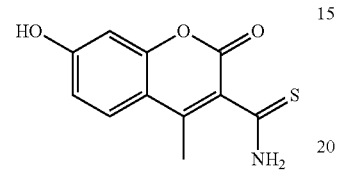 | BB_LCMS01(+) | 236 | 2.554 | 99 | n/a |

Example 18

7-methoxy-3-[4-methyl-5-(4-methyl-piperazine-1-carbonyl)-thiazol-2-yl]-chromen-2-one

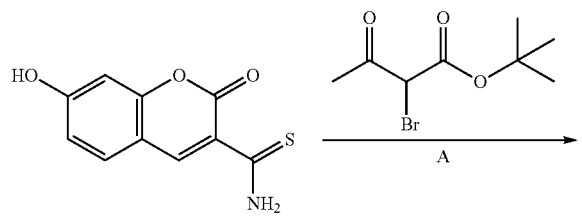

Step A

2-(7-Hydroxy-2-oxo-2H-chromen-3-yl)-4-methyl-thiazole-5-carboxylic acid tert-butyl ester

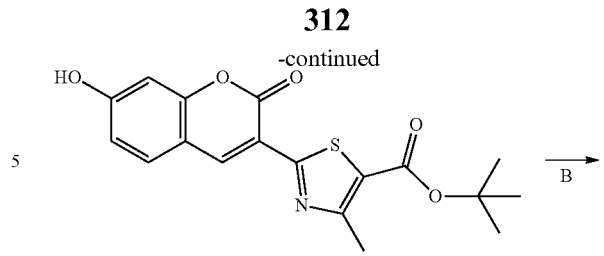

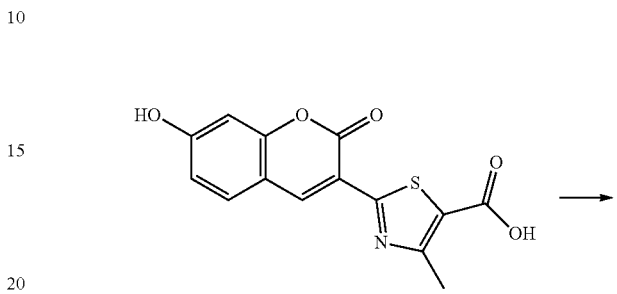

To a suspension of 7-hydroxy-2-oxo-2H-chromene-3-carbothioic acid amide (221 mg, 1.0 mmol) in anhydrous N,N-dimethylformamide (5 mL) stirred at 0° C., sodium hydride (60% in oil, 44 mg, 1.1 mmol) was added portionwise. During addition a clear solution was formed with moderate effervescence. After 10 min, a solution of 2-bromo-3-oxo-butyric acid tert-butyl ester (474 mg, 2.0 mmol) in anhydrous N,N-dimethylformamide (2 mL) was added dropwise and the mixture was stirred at room temperature for 16 h. The reaction was poured into water (20 mL) and extracted with chloroform (3×10 mL). The combined organic extracts were washed with water (3×5 mL), dried over MgSO₄ and concentrated. The residue was triturated with diethyl ether, the solid product was collected and washed with diethyl ether. The title compound (224 mg, 0.623 mmol, 62.3%) was obtained as a yellow solid.

The following compounds (includes title compound) were made by the above procedure:

| Ex | Made From | Structure | LCMS method | LCMS Ion | LCMS Rt (min) | LCMS purity (%) | NMR purity (%) |
|---|---|---|---|---|---|---|---|
| 18a-1 | 69015-66-3 | 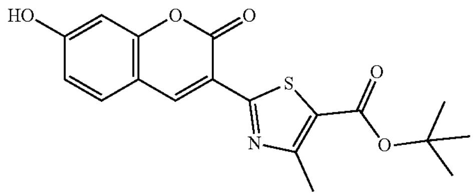 [SMILES: Cc1nc(-c2cc3ccc(O)cc3oc2=O)sc1C(=O)OC(C)(C)C] | BB_LCMS07(+) | 360 | 3.928 | 97.1 | n/a |
| 18a-2 | 17-1 | 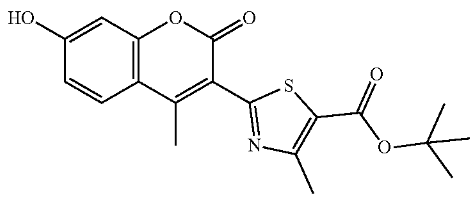 [SMILES: Cc1nc(-c2c(C)c3ccc(O)cc3oc2=O)sc1C(=O)OC(C)(C)C] | BB_LCMS07(+) | 374 | 3.913 | 96.3 | n/a |

Step B

2-(7-Hydroxy-2-oxo-2H-chromen-3-yl)-4-methyl-thiazole-5-carboxylic acid

To a suspension of 2-(7-hydroxy-2-oxo-2H-chromen-3-yl)-4-methyl-thiazole-5-carboxylic acid tert-butyl ester (387 mg, 1.08 mmol) and anisole (117 µL, 117 mg, 1.08 mmol) in anhydrous dichloromethane (5 mL) was added trifluoroacetic acid (5 mL) and the obtained solution was stirred at room temperature for 6 h. Diethyl ether (30 mL) was added, the precipitate was collected, washed with diethyl ether and dried in air. In this manner the title compound (285 mg, 0.94 mmol, 87%) was obtained as a light brown solid.

LCMS/BB_LCMS01(+)/: M+1=304, Rt: 3.297 min.

The following compounds (includes title compound) were made by the above procedure:

Example 19

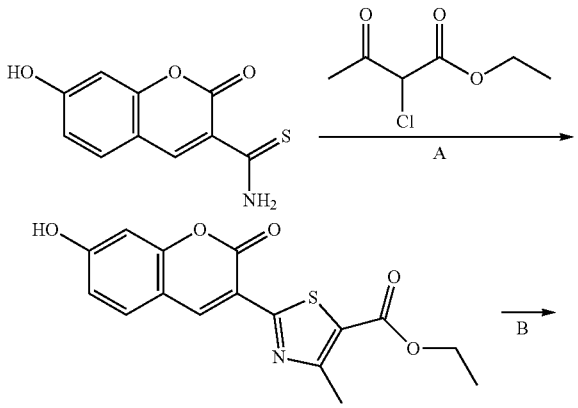

| Ex | Made From | Structure | LCMS method | LCMS Ion | LCMS Rt (min) | LCMS purity (%) | NMR purity (%) |
|---|---|---|---|---|---|---|---|
| 18-1 | 18a-1 | 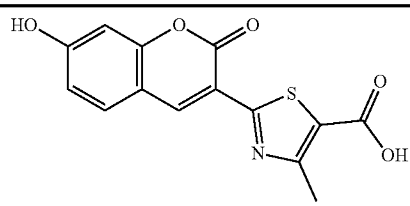 | BB_LCMS07(+) | BB_LCMS07(+) | 304 | 3.297 | 99.3 |
| 18-2 | 18a-2 | 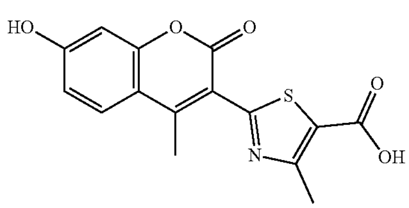 [SMILES: Cc1nc(-c2c(C)c3ccc(O)cc3oc2=O)sc1C(=O)O] | BB_LCMS07(+) | BB_LCMS07(+) | 318 | 3.293 | 99.7 |

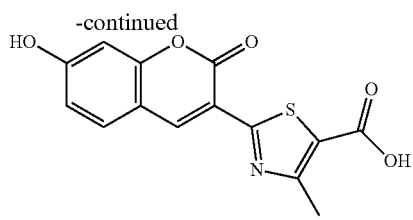

Step A

2-(7-Hydroxy-2-oxo-2H-chromen-3-yl)-4-methyl-thiazole-5-carboxylic acid ethyl ester To a solution of 7-hydroxy-2-oxo-2H-chromene-3-carbothioic acid amide (66 mg, 0.3 mmol) in anhydrous N,N-dimethylformamide (5 mL), freshly dried $K_2CO_3$ (263 mg, 1.9 mmol) was added followed by 2-chloro-3-oxo-butyric acid ethyl ester (79 µL, 94 mg, 0.54 mmol) and the mixture was stirred at room temperature for 19 h. The mixture was poured into water (25 mL) and extracted first with chloroform (3×10 mL) and, after saturation with NaCl, with tetrahydrofuran (3×10 mL). The combined organic extracts were dried over $MgSO_4$ and concentrated. The residue was dissolved in chloroform (8 mL), pyridinium p-toluenesulfonate (7.5 mg, 0.03 mmol) was added and the mixture was stirred at 60° C. for 4.5 h. After cooling, the solution was washed with brine (3×5 mL), dried over $MgSO_4$ and concentrated. The residue was purified by column chromatography on silica, eluting with a 9:1:0.1 mixture of chloroform, methanol and cc. $NH_4OH$. The title compound (14.5 mg, 0.044 mmol, 14.7%) was obtained as a yellow solid.

LCMS/BB_LCMS01(+)/: M+1=332, Rt: 3.748 min.

The following compounds (includes title compound) were made by the above procedure:

| Ex | Made From | Structure | LCMS method | LCMS Ion | LCMS Rt (min) | LCMS purity (%) | NMR purity (%) |
|---|---|---|---|---|---|---|---|
| 19a-1 | 69015-66-3 | ![structure] | BB_LCMS07(+) | 318 | 3.643 | 98.9 | n/a |
| 19a-2 | 69015-66-3 | ![structure] | BB_LCMS07(+) | 332 | 3.748 | 90.4 | n/a |

Step B

2-(7-Hydroxy-2-oxo-2H-chromen-3-yl)-thiazole-5-carboxylic acid)

A suspension of 2-(7-hydroxy-2-oxo-2H-chromen-3-yl)-thiazole-5-carboxylic acid ethyl ester (50 mg, 0.16 mmol) in 70% (w/w) sulfuric acid (3 mL) was stirred at 100° C. for 1 h. During heating the solids dissolved and a solid precipitated after 1 h. The precipitate was collected, washed with water and dried in air. In this manner the title compound (30.5 mg, 0.10 mmol, 62.5%) was obtained as a pale brown solid.

| Ex | Made From | Structure | LCMS method | LCMS Ion | LCMS Rt (min) | LCMS purity (%) | NMR purity (%) |
|---|---|---|---|---|---|---|---|
| 19-1 | 19a-1 | ![structure] | BB_LCMS07(+) | 290 | 3.181 | 98 | n/a |

Example 20

7-Hydroxy-4-methyl-3-[4-methyl-5-(4-methyl-piperazine-1-carbonyl)-thiazol-2-yl]-chromen-2-one

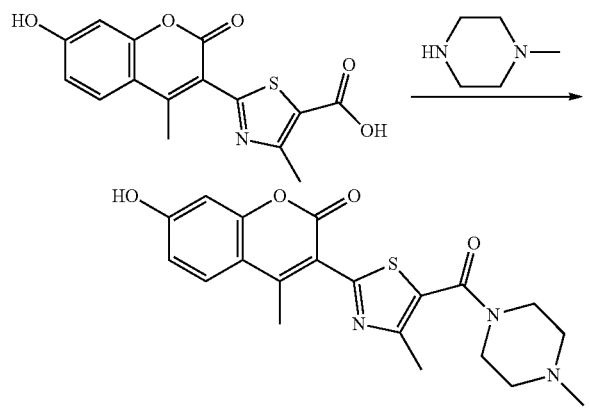

To dry tetrahydrofuran (12 mL) at 0° C., 1-methylpiperazine (61 μL, 55 mg, 0.55 mmol), triethylamine (210 μL, 152 mg, 1.5 mmol), 2-(7-hydroxy-2-oxo-2H-chromen-3-yl)-4-methyl-thiazole-5-carboxylic acid (156 mg, 0.49 mmol), (3-dimethylamino-propyl)-ethyl-carbodiimid hydrochloride (105 mg, 0.55 mmol) and 1-hydroxybenzotriazole monohydrate (84 mg, 0.55 mmol) were added sequentially, and the mixture was stirred at room temperature for 16 h. After addition of water (30 mL) the pH was adjusted to 8 by addition of a 5% aqueous solution of NaHCO$_3$ and the mixture was extracted with tetrahydrofuran (3×15 mL). After drying (MgSO$_4$) and evaporation, the residue was purified by column chromatography over silica (Kieselgel 60) using chloroform-methanol 9:1 as eluent. The title compound (156 mg, 0.41 mmol, 81%) was obtained as a yellow solid.

The following compounds (includes title compound) were made by the above procedure:

| Ex | Made From | Structure | LCMS method | LCMS Ion | LCMS Rt (min) | LCMS purity (%) | NMR purity (%) |
|---|---|---|---|---|---|---|---|
| 20-1 | 18-1 | 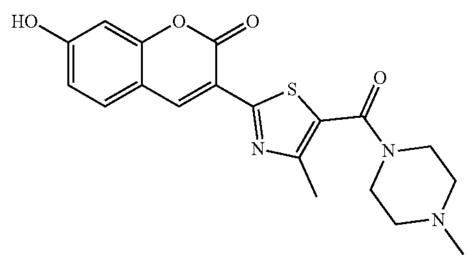 [SMILES: Cc1nc(-c2cc3ccc(O)cc3oc2=O)sc1C(=O)N1CCN(C)CC1] | BB_LCMS07(+) | 386 | 2.955 | 100 | n/a |
| 20-2 | 18-1 | 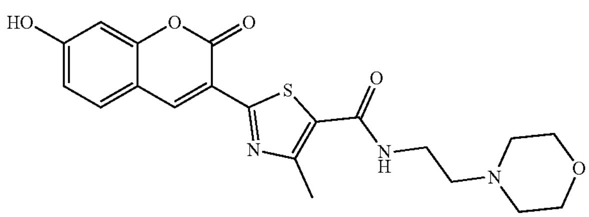 [SMILES: Cc1nc(-c2cc3ccc(O)cc3oc2=O)sc1C(=O)NCCN1CCOCC1] | BB_LCMS07(+) | 416 | 2.966 | 100 | n/a |
| 20-3 | 18-2 | 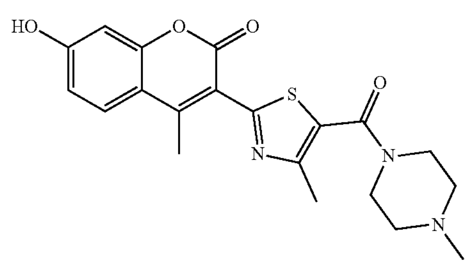 [SMILES: Cc1nc(-c2c(C)c3ccc(O)cc3oc2=O)sc1C(=O)N1CCN(C)CC1] | BB_LCMS07(+) | 400 | 2.949 | 100 | n/a |
| 20-4 | 18-2 | 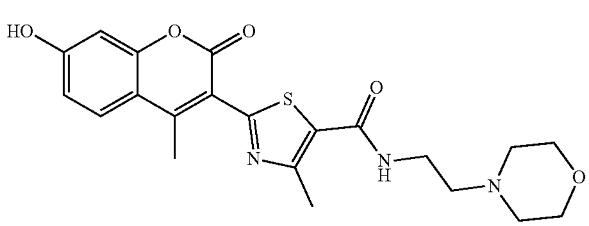 [SMILES: Cc1nc(-c2c(C)c3ccc(O)cc3oc2=O)sc1C(=O)NCCN1CCOCC1] | BB_LCMS07(+) | 430 | 3.001 | 100 | n/a |

| Ex | Made From | Structure | LCMS method | LCMS Ion | LCMS Rt (min) | LCMS purity (%) | NMR purity (%) |
|---|---|---|---|---|---|---|---|
| 20-5 | 19-1 | HO-chromen-2-one-thiazole-C(O)-N-piperazine-N-methyl | BB_LCMS07(+) | 372 | 1.215 | 95.8 | n/a |

Example 21

7-Hydroxy-3-[4-methyl-5-(morpholine-4-carbonyl)-thiazol-2-yl]-chromen-2-one

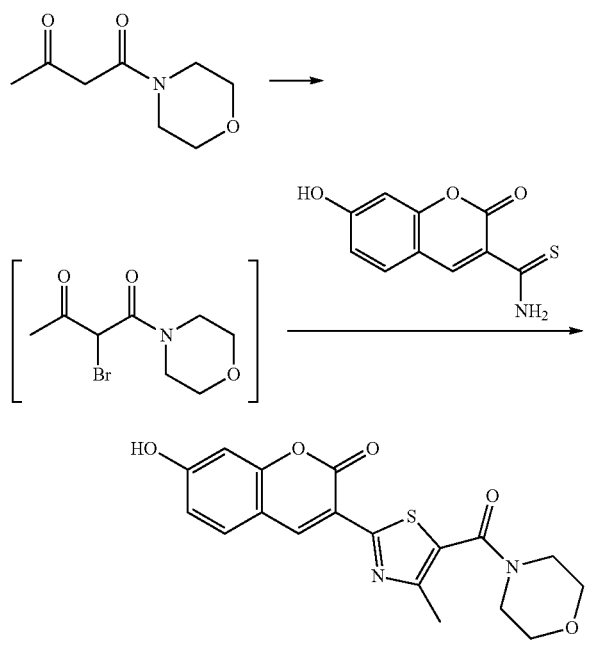

To a solution of 1-morpholin-4-yl-butane-1,3-dione (0.53 g, 3.1 mmol) in 1,2-dichloroethane (30 mL) stirred at 0° C., N-bromosuccinimide (0.55 mg, 3.1 mmol) was added in small portions and the mixture was stirred for 1 h. The solution was washed with brine (3×5 mL), dried over MgSO₄ and concentrated below 30° C. 2-Bromo-1-morpholin-4-yl-butane-1,3-dione 0.76 g, 3.04 mmol, 98.1%, LCMS/BB_LCMS01(+)/: M+1=250, 252, Rt: 1.831 min] was obtained as a yellowish oil.

To a stirred suspension of 7-hydroxy-2-oxo-2H-chromene-3-carbothioic acid amide (354 mg, 1.6 mmol) in anhydrous N,N-dimethylformamide (7 mL), 1,8-diazabicyclo-[5.4.0]undec-7-ene (480 µL, 490 mg, 3.2 mmol) was added followed by a solution of 2-bromo-1-morpholin-4-yl-butane-1,3-dione (750 mg, 3.0 mmol) in anhydrous N,N-dimethylformamide (15 mL) and the mixture was stirred at room temperature for 15 h. The reaction mixture was poured into water (100 mL) and extracted first with chloroform (3×30 mL) then after saturation with NaCl, with tetrahydrofuran (3×50 mL). The combined organic extracts were dried over MgSO₄ and concentrated. The residue was dissolved in chloroform (16 mL), pyridinium p-toluenesulfonate (40.2 mg, 0.16 mmol) was added and the mixture was stirred at 60° C. for 4.5 h. The reaction mixture was washed with a mixture of brine (10 mL) and 5% NaHCO₃ solution (5 mL) and then with brine (2×15 mL), dried over MgSO₄ and concentrated. The residue was purified by column chromatography on silica, eluting with a 9:1:0.1 mixture of chloroform, methanol and cc. NH₄OH. The title compound (34.6 mg, 0.093 mmol, 5.8%) was obtained as a yellow solid.

| Ex | Made From | Structure | LCMS method | LCMS Ion | LCMS Rt (min) | LCMS purity (%) | NMR purity (%) |
|---|---|---|---|---|---|---|---|
| 21-1 | 69015-66-3 | HO-chromen-2-one-thiazole(4-Me)-C(O)-morpholine | BB_LCMS01(+) | 373 | 3.040 | 100 | n/a |

Example 22

3-Bromo-7-hydroxy-6-methoxy-4-methyl-chromen-2-one

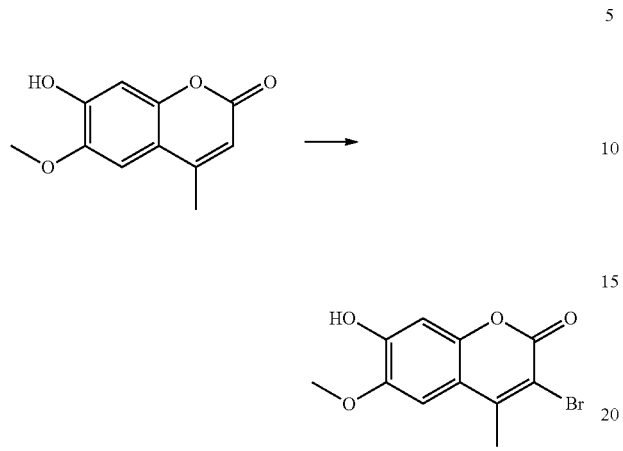

A bromine (2.55 g, 15.96 mmol) solution in acetic acid (8 mL) was added dropwise to a stirred suspension of 7-hydroxy-6-methoxy-4-methyl-chromen-2-one (3.20 g, 15.5 mmol) in glacial acetic acid (31 mL) at room temperature. The mixture was stirred for 10 min, then poured onto crushed ice (400 mL). To the resultant light yellow suspension, 1 mL of saturated sodium bisulphite solution was added and the mixture was allowed to reach room temperature. The precipitated solids were filtered off, washed with water, dried and recrystallized from glacial acetic acid. The obtained white powder (3.39 g, 11.88 mmol, 76%) was used without further purification.

The following compounds (includes title compound) were made by the above procedure:

Example 23

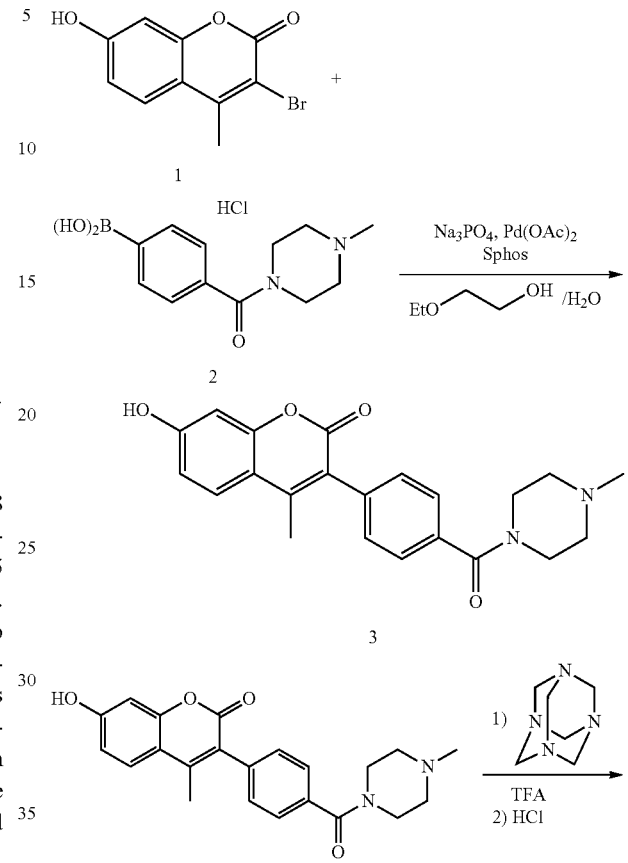

| Ex | Made From | Structure | LCMS method | LCMS Ion | LCMS Rt (min) | LCMS purity (%) | NMR purity (%) |
|---|---|---|---|---|---|---|---|
| 22-1 | 3374-03-6 | 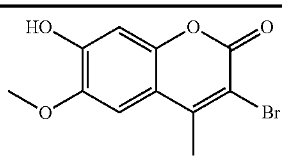 | BB_LCMS01(+) | 286 | 3.316 | 78 | n/a |
| 22-2 | 219965-92-1 | 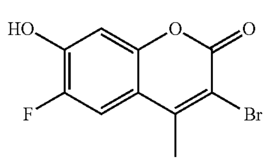 | BB_LCMS01(+) | 274 | 3.390 | 92 | n/a |
| 22-3 | 19492-02-5 | 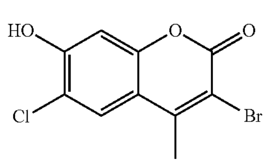 | BB_LCMS01(+) | 289 | 3.589 | 92 | n/a |

323

-continued

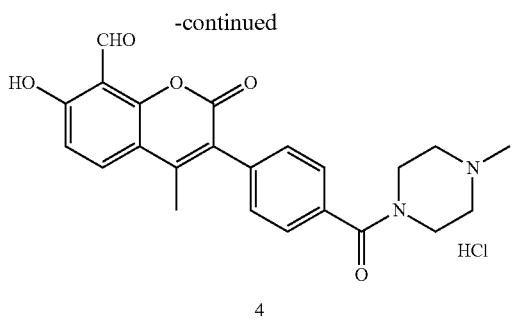

4

Step A 7-hydroxy-4-methyl-3-(4-(4-methylpiperazine-1-carbonyl)phenyl)-2H-chromen-2-one (3)

A mixture of 3-bromo-7-hydroxy-4-methyl-2H-chromen-2-one (1) (7.66 g, 30 mmol), 4-(4-methylpiperazine-1-carbonyl)phenylboronic acid hydrochloride (2) (10.24 g, 36 mmol), $Na_3PO_4$ (22.14 g, 135 mmol), ethoxyethanol (140 g) and water (14 g) was purged with Argon for five minutes in a 250 mL pressure vessel. Ligand Sphos (obtained from Aldrich, Cat No. 638072) (739 mg, 1.8 mmol) and Pd(OAc)$_2$ (202 mg, 0.90 mmol) were added under an Argon atmosphere then the vessel was sealed and heated for 60 min in a 150° C. oil bath with strong stirring. This process was repeated once. Upon cooling, the reaction mixtures were filtered through a silica plug using $CH_2Cl_2$ and MeOH wash. The unified solutions were evaporated to 100 mL slowly diluted with water (100 mL) and crystallized at 0° C. The product was filtered, washed with 50% MeOH (2×30 mL) and dried to afford 18.52 g (81%) of the title compound. MS (ESI): 379 (M+H)$^+$. $^1$H NMR (δ, DMSO (2.5 ppm)): 10.57 (s, br, 1H), 7.69 (d, 1H), 7.44 (d, 2H), 7.36 (d, 2H), 6.84 (dd, 1H), 6.76 (d, 1H), 3.65-3.30 (m, 8H), 2.23 (s, 3H), 2.20 (s, 3H).

Step B 7-hydroxy-4-methyl-3-(4-(4-methylpiperazine-1-carbonyl)phenyl)-2-oxo-2H-chromene-8-carbaldehyde hydrochloride (4)

A mixture of 7-hydroxy-4-methyl-3-(4-(4-methylpiperazine-1-carbonyl)phenyl)-2H-chromen-2-one (3) (9.11 g, 24.0 mmol) and hexamethylenetetramine (13.46 g, 96.0 mmol) in TFA (283 g) was heated in a pressure flask in a 120° C. oil bath for 40 minutes. This process was repeated once. Upon cooling, the unified solutions were evaporated to 182 g weight and, after addition of $CH_2Cl_2$ (500 mL) and water (100 mL) it was cooled to 0° C. The mixture was neutralized with NaOH (2N, 400 mL) and then close to the end point with $NaHCO_3$ (10%) with cooling and stirring. The product was extracted with $CH_2Cl_2$ (5×100 mL), washed with water (backextracted), dried on $MgSO_4$ and evaporated to afford 23.5 g crude product. The crude product was loaded on 33 g silica and purified by medium pressure chromatography (4×100 g columns+4×100 g reruns) using 2-3% MeOH in $CH_2Cl_2$ by collecting the front fractions to afford 7.00 g of free base This product was dissolved in EtOH (130 mL) and HCl (8 mL, 6N) with heating. Upon cooling to 20° C. the salt crystallized. It was filtered and

324 washed with abs EtOH (2×20 mL), dried on air then at 50° C. under 5 Hgmm vacuum to afford 6.65 g (34%) of the title compound.

MS (ESI): 407 (M+H)$^+$.

$^1$H NMR (δ, DMSO (2.5 ppm)): 11.93 (s, br, 1H), 10.90 (s, br, 1H), 10.50 (s, 1H), 8.04 (d, 1H), 7.55 (d, 2H), 7.43 (d, 2H), 7.04 (d, 1H), 4.4-3.3 (m, br, 8H), 2.79 (s, 3H), 2.28 (s, 3H).

Elemental analysis of a previous air dried sample corresponds well to 2 crystal water:

| % | Measured | | Calculated | | |
|---|---|---|---|---|---|
| | Air dried[a] | Deep dried[b] | 4 | 4 + H$_2$O | 4 + 2H$_2$O |
| C | 57.66 | 60.91 | 62.37 | 59.94 | 57.68 |
| H | 5.61 | 5.75 | 5.23 | 5.47 | 5.68 |
| N | 5.78 | 6.11 | 6.33 | 6.08 | 5.85 |
| Cl | 7.47 | 7.75 | 8.00 | 7.69 | 7.40 |
| Pd | <10 ppm | <10 ppm | | | |

[a]Air dried: equilibrated at 22° C.
[b]Deep dried: equilibrated at 50° C. under 1 Hgmm for 24 hours.

Example 24

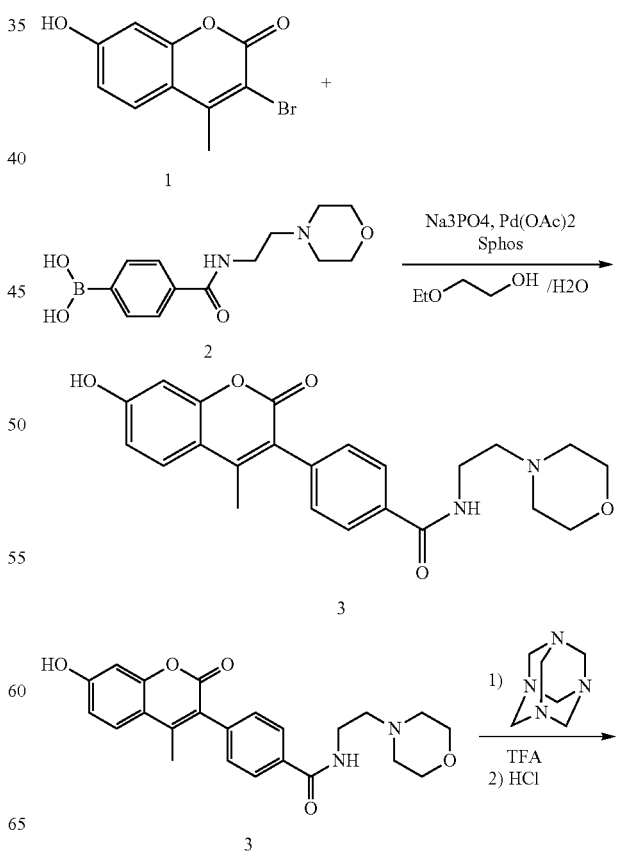

-continued

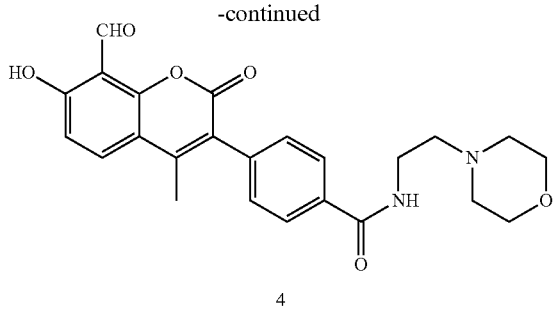

4

Step A

4-(7-Hydroxy-4-methyl-2-oxo-2H-chromen-3-yl)-N-(2-morpholinoethyl)benzamide (6)

A mixture of 3-bromo-7-hydroxy-4-methyl-2H-chromen-2-one (1) (7.66 g, 30 mmol), 4-(2-morpholinoethylcarbamoyl)phenylboronic acid (2) (10.02 g, 36 mmol), Na3PO₄ (17.21 g, 105 mmol) in a mixture of ethoxyethanol (140 g) and water (14 g) was purged with Argon for five minutes in a 250 mL pressure vessel. Ligand Sphos (738 mg, 1.8 mmol) and Pd(OAc)₂ (206 mg, 0.90 mmol) were added under an Argon atmosphere then the vessel was sealed and heated for 60 min in a 150° C. oil bath with strong stirring. This process was repeated once. Upon cooling, the reaction mixtures were filtered through a silica plug using CH₂Cl₂ and MeOH wash. The unified solutions were evaporated to 100 mL slowly diluted with water (100 mL) and crystallized at 0° C. The product was filtered, washed with 50% MeOH (2×50 mL) and dried to afford 22.33 g (91%) of the title compound. MS (ESI): 409 (M+H)+. 1H NMR (δ, DMSO (2.5 ppm)): 10.57 (s, br, 1H), 8.46 (t, 1H), 7.88 (d, 2H), 7.69 (d, 1H), 7.39 (d, 2H), 6.84 (dd, 1H), 6.76 (d, 1H), 3.57 (m, 4H), 3.40 and 2.48 (2q, 2×2H), 2.43 (m, 4H), 2.22 (s, 3H).

Step B

4-(8-Formyl-7-hydroxy-4-methyl-2-oxo-2H-chromen-3-yl)-N-(2-morpholinoethyl) benzamide (4)

A mixture of 4-(7-hydroxy-4-methyl-2-oxo-2H-chromen-3-yl)-N-(2-morpholinoethyl) benzamide (3) (8.17 g, 20.0 mmol) and hexamethylenetetramine (11.22 g, 80.0 mmol) in TFA (200 mL) was heated in a pressure flask in a 115° C. oil bath for 40 minutes. This process was repeated once. Upon cooling, the unified solutions were evaporated to 158 g weight and, after addition of CH₂Cl₂ (500 mL) and water (100 mL) it was cooled to 0° C. The mixture was neutralized with NaOH (2N, 350 mL) and then close to the end point with NaHCO₃ (10%) with cooling and stirring. The product was extracted with CH₂Cl₂ (5×100 mL), washed with water (backextracted), dried on MgSO₄ and evaporated to afford 17.2 g crude product. The crude product was loaded on 40 g silica and purified by medium pressure chromatography (4×100 g columns) using 1-3% MeOH in CH₂Cl₂ by collecting the front fractions to afford 6.2 g (31%) of the title compound. This product can be turned into its HCl salt by dissolving it in EtOH (100 mL) and adding 6N HCl (10 mL). The salt was filtered and washed with 70% EtOH (2×20 mL), dried on air then at 50° C. under 5 Hgmm vacuum to afford 6.0 g HCl salt of the title compound.

MS (ESI): 437 (M+H)+.
¹H NMR (δ, DMSO (2.5 ppm)): 10.50 (s, 1H), 8.48 (t, 1H), 8.02 (d, 1H), 7.89 (d, 2H), 7.42 (d, 2H), 7.00 (d, 1H), 3.58 (t, 4H), 3.41 and 2.50 (2q, 2×2H), 2.48 (m, 4H), 2.25 (s, 3H). HCl-salt: 11.93 (s, br, 1H), 10.62 (s, br, 1H), 10.50 (s, 1H), 8.96 (t, 1H), 8.04 (d, 1H), 8.00 (d, 2H), 7.45 (d, 2H), 7.04 (d, 1H), 3.98, 3.79, 3.71, 3.55, 3.34, 3.14 (6m, 6×2H), 2.26 (s, 3H).

Elemental analysis of a previous air dried sample corresponds well to one crystal water which is lost on further drying:

| % | Measured | | Calculated | | |
| --- | --- | --- | --- | --- | --- |
|  | Air dried[a] | Deep dried[b] | 7 | 7 + H₂O | 7 + 2H₂O |
| C | 60.46 | 58.64 | 60.95 | 58.72 | 56.64 |
| H | 5.56 | 5.64 | 5.33 | 5.54 | 5.74 |
| N | 5.82 | 5.61 | 5.92 | 5.71 | 5.50 |
| Cl | 7.46 | 7.28 | 7.50 | 7.22 | 6.97 |
| Pd | <10 ppm | <10 ppm | | | |

[a]Air dried: equilibrated at 22° C.
[b]Deep dried: equilibrated at 50° C. under 1 Hgmm for 24 hours.

Example 25

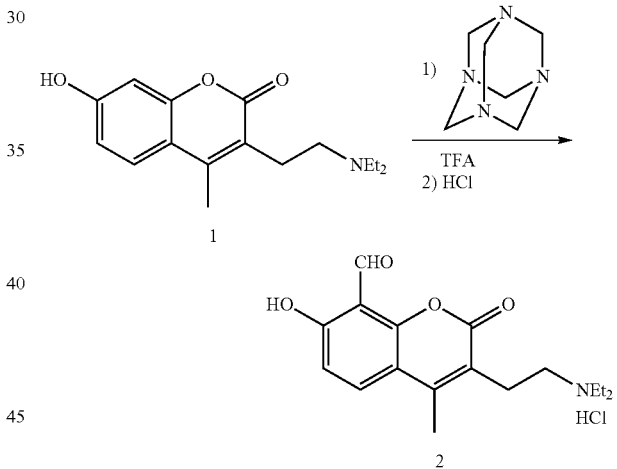

3-(2-(Diethylamino)ethyl)-7-hydroxy-4-methyl-2-oxo-2H-chromene-8-carbaldehyde hydrochloride (2)

A mixture of 3-(2-(diethylamino)ethyl)-7-hydroxy-4-methyl-2H-chromen-2-one (1 (312 mg, 1.0 mmol) and hexamethylenetetramine (280 mg, 2.0 mmol) in trifluoroacetic acid (5 mL) was microwave irradiated for 20 min at 110° C. Upon cooling, the reaction mixture was evaporated. The residue was diluted with water (10 mL) and CH₂Cl₂ (30 mL), cooled to 0° C., neutralized with NaHCO₃ solution and extracted with CH₂Cl₂. The organic phase was dried and HCl (1 mL, 2M in ether) was added to it. Evaporation and crystallization from a CH₂Cl₂/hexane mixture afforded the title product. MS (ESI): 304 (M+H)+. ¹H NMR (δ, DMSO (2.5 ppm)): 10.45 (s, 1H), 8.02 (d, 1H), 7.00 (d, 1H), 3.22 (q, 4H), 3.11 (m, 2H), 2.94 (m, 2H), 2.46 (s, 3H), 1.24 (t, 6H).

Example 26

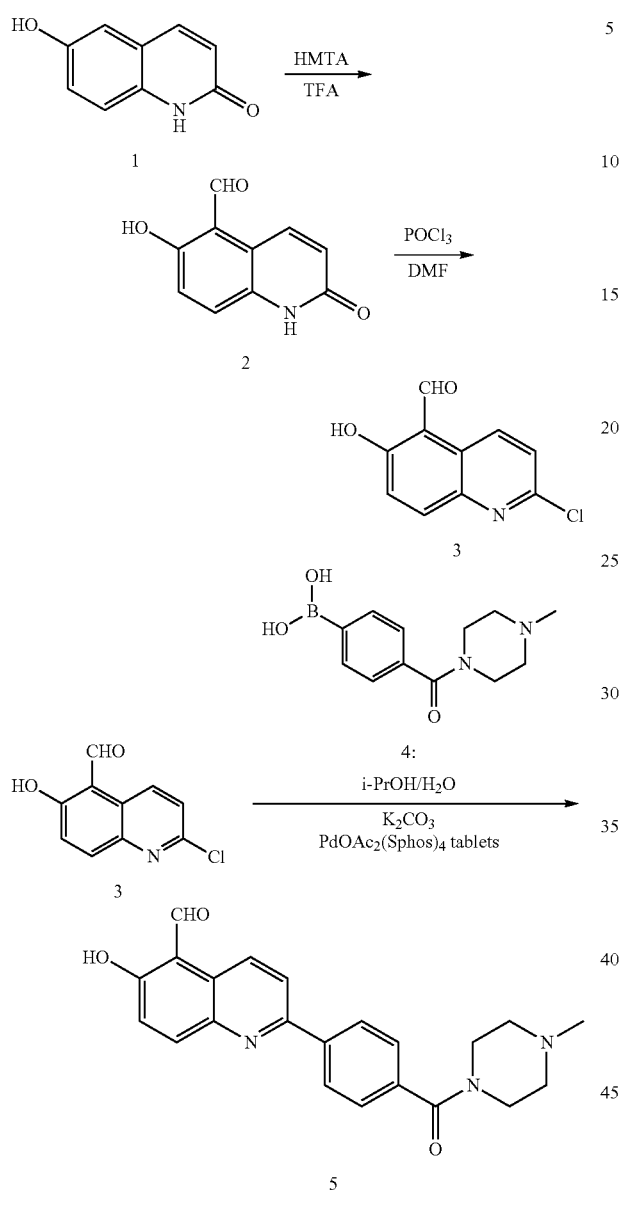

Step A

6-Hydroxy-2-oxo-1,2-dihydroquinoline-5-carbaldehyde (2)

A mixture of 6-hydroxyquinolin-2(1H)-one (1) (TCI: 2,6-dihydroxyquinoline) (806 mg, 5.0 mmol) and hexamethylenetetramine (1.40 g, 10.0 mmol) in trifluoroacetic acid (6 mL) was microwave irradiated for 20 min at 100° C. The reaction was run twice with two parallels on a 5 mmol scale. Upon cooling, the two reaction mixtures were washed into a 100 mL flask with MeOH (40 mL). The mixture was evaporated to ~10 mL and diluted with water (70 mL) with vigorous stirring. The precipitated product was filtered, washed with water and dried on air to afford 1.85 g (97%) title compound. MS (ESI): 190 (M+H)$^+$. $^1$H NMR ($\delta$, DMSO (2.5 ppm)): 11.84 (s, 1H, OH), 11.07 (s, 1H, NH), 10.61 (s, 1H, CHO), 8.86, 7.51, 7.24 and 6.63 (4d, 4×1H).

Step B

2-Chloro-6-hydroxyquinoline-5-carbaldehyde (3)

POCl$_3$ (973 μL, 10.4 mmol) was added dropwise to a DMF (5 mL) solution of 6-hydroxy-2-oxo-1,2-dihydroquinoline-5-carbaldehyde (658 mg, 3.48 mmol) at 0° C. The mixture was stirred for 20 hours at 20° C. then cooled to 0° C. Upon addition of ice water the product precipitated. It was filtered, washed with water and dried on air to afford 580 mg (88%) of the title compound. MS (ESI): 208 (M+H)$^+$. $^1$H NMR ($\delta$, DMSO (2.5 ppm)): 11.95 (s, 1H, OH), 10.70 (s, 1H, CHO), 9.38, 8.10, 7.67 and 7.55 (4d, 4×1H).

Step C

6-Hydroxy-2-(4-(4-methylpiperazine-1-carbonyl)phenyl)quinoline-5-carbaldehyde (5)

A mixture of 2-chloro-6-hydroxyquinolin-5-carbaldehyde (3) (104 mg, 0.5 mmol), 4-(4-methylpiperazine-1-carbonyl)phenylboronic acid (4) (198 mg, 0.7 mmol) and K$_2$CO$_3$ (174 mg, 1.25 mmol) in a mixture of i-PrOH and water (6 mL 10:1) was purged with Argon for five minutes in a microwave vessel. A tablet of PdOAc$_2$(Sphos)$_4$ (Aldrich, Cat. No. 694088) was added under an Argon atmosphere then the vessel was sealed and irradiated for 45 min at 165° C. Upon cooling, the reaction mixture was filtered through a silica plug using MeOH. The solution was evaporated and purified by Flash chromatography using 0-5% MeOH in CH$_2$Cl$_2$. The product was recrystallized from CH$_2$Cl$_2$/hexanes to afford the title compound. MS (ESI): 376 (M+H)$^+$. $^1$H NMR ($\delta$, DMSO (2.5 ppm)): 10.74 (s, 1H), 9.44 8.25, 7.21 and 7.49 (4d, 4×1H), 8.29 and 7.54 (2d, 2×2H), 3.64, 3.38, 2.41 and 2.33 (4 broad s, 4×2H), 2.23 (s, 3H).

Example 27

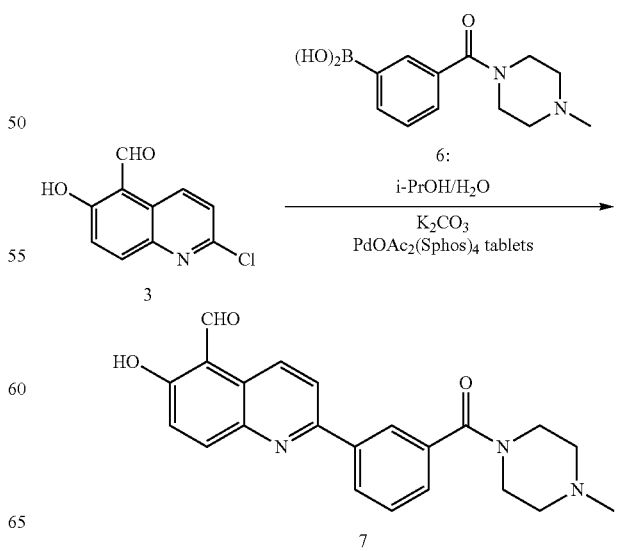

6-hydroxy-2-(3-(4-methylpiperazine-1-carbonyl)phenyl)quinoline-5-carbaldehyde (7)

A mixture of 2-chloro-6-hydroxyquinolin-5-carbaldehyde (3) (104 mg, 0.5 mmol), 3-(4-methylpiperazine-1-carbonyl) phenylboronic acid (6) (198 mg, 0.7 mmol) and $K_2CO_3$ (174 mg, 1.25 mmol) in a mixture of i-PrOH and water (6 mL 10:1) was purged with Argon for five minutes in a microwave vessel. A tablet of $PdOAc_2(Sphos)_4$ (Aldrich, Cat. No. 694088) was added under an Argon atmosphere then the vessel was sealed and irradiated for 45 min at 165° C. Upon cooling, the reaction mixture was filtered through a silica plug using MeOH. The solution was evaporated and purified by Flash chromatography using 0-5% MeOH in $CH_2Cl_2$. The product was recrystallized from $CH_2Cl_2$/hexanes to afford the title compound. MS (ESI): 376 (M+H)$^+$. $^1$H NMR (δ, DMSO (2.5 ppm)): 10.74 (s, 1H), 9.44 (d, 1H), 8.30 (dd, 1H), 8.27 (d, 1H), 8.24 (s, 1H), 8.23 (d, 1H), 7.61 (t, 1H), 7.49 (d, 1H), 7.47 (dd, 1H), 3.60, 3.40, 2.40 and 2.30 (4 broad s, 4×2H), 2.23 (s, 3H).

Example 28

6-Hydroxy-2-[4-(4-methyl-piperidine-1-carbonyl)-phenyl]-benzothiazole-7-carbaldehyde

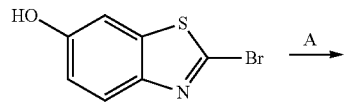

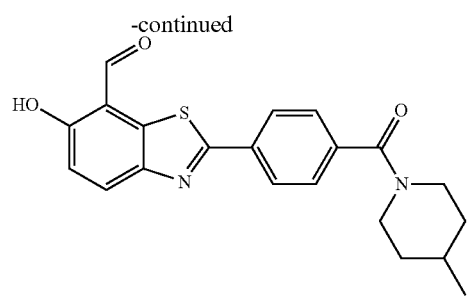

Step A

[4-(6-Hydroxy-benzothiazol-2-yl)-phenyl]-(4-methyl-piperidin-1-yl)-methanone

2-Bromo-6-hydroxybenzothiazole (400 mg, 1.74 mmol), 4-(4-methylpiperidine-1-carbonyl)phenylboronic acid (472 mg, 1.91 mmol), potassium phosphate (848 mg, 6.96 mmol) and tetrakis(triphenylphosphine)palladium (60 mg, 0.05 mmol) were dissolved in a mixture of 13.5 mL 2-ethoxy-ethanol and 1.5 mL water. The mixture was stirred at 115° C. under argon for 2 h. The reaction mixture was let to reach room temperature then activated-carbon was added and stirred for 20 min. The mixture was filtered, the solid was washed with ethanol and the combined filtrates were evaporated. The residue was purified by column chromatography (Kieselgel 60) with chloroform as the eluent. The crude product was triturated with $Et_2O$, collected and air dried, affording the title compound (122 mg, 0.35 mmol, 20%).

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 28a-1 | — | ![structure] | BB_LCMS01(+) | 353 | 3.598 | 100 | n/a |
| 28a-2 | — | ![structure] | BB_LCMS01(+) | 354 | 2.375 | 99 | n/a |

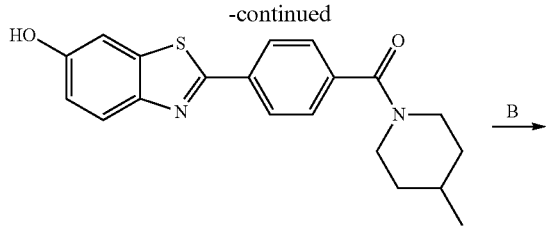

Step B

6-Hydroxy-2-[4-(4-methyl-piperidine-1-carbonyl)-phenyl]-benzothiazole-7-carbaldehyde A mixture of [4-(6-Hydroxy-benzothiazol-2-yl)-phenyl]-(4-methyl-piperidin-1-yl)-methanone (120 mg, 0.34 mmol), hexamethylenetetramine (190 mg, 1.36 mmol) and trifluoroacetic acid (2 mL) was stirred in a closed vessel under argon atmosphere at 120° C. for 1 h. The reaction was cooled to room temperature and 10 mL of water was added. The pH of the mixture was adjusted to 8 by dropwise addition of saturated NaHCO$_3$ solution, and extracted with dichloromethane (3×15 mL). The combined organic layers were dried (MgSO$_4$), filtered and evaporated. The residue was purified by column chromatography on silica (Kieselgel 60), eluting with chloroform-methanol 99:1. The title compound (34 mg, 0.089 mmol, 26%) was obtained as pale yellow crystals.

$^1$H NMR (400 MHz, CDCl$_3$) δ ppm 11.20 (s, 1H), 10.35 (s, 1H), 8.13 (d, J=9.3 Hz, 1H), 8.08 (d, J=8.3 Hz, 2H), 7.52 (d, J=8.3 Hz, 2H), 7.13 (d, J=9.3 Hz, 1H), 4.66 (br. s., 1H), 3.76 (br. s., 1H), 3.03 (br. s., 1H), 2.80 (br. s., 1H), 1.81 (br. s., 1H), 1.57-1.72 (m, 2H), 1.07-1.35 (m, 2H), 1.00 (d, J=6.5 Hz, 3H).

The following compounds (includes title compound) were made by the above procedure:

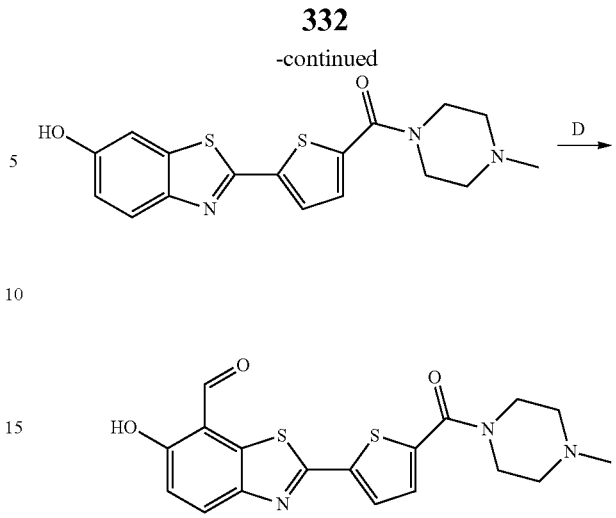

| EX-AM-PLE | Made From | Structure | LCMS method | LCMS Ion | LCMS Rt (min) | LCMS purity (%) | NMR purity (%) |
|---|---|---|---|---|---|---|---|
| 28-1 | 28a-1 | 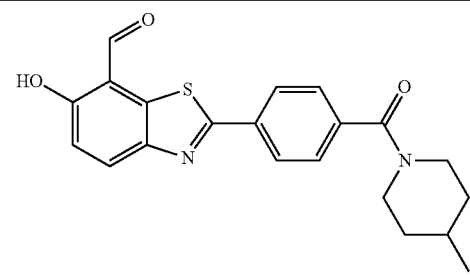 | BB_LCMS01(−) | 381 | 3.645 | 100 | 98 |
| 28-2 | 28a-2 | 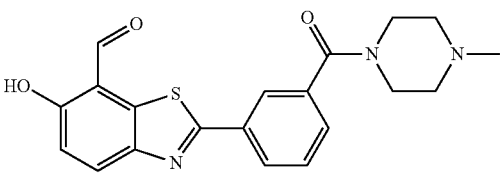 [SMILES: CN1CCN(C(=O)c2cccc(-c3nc4ccc(O)c(C=O)c4s3)c2)CC1] | BB_LCMS01(+) | 382 | 2.479 | 97 | 95 |

Example 29

6-Hydroxy-2-[5-(4-methyl-piperazine-1-carbonyl)-thiophen-2-yl]-benzothiazole-7-carbaldehyde

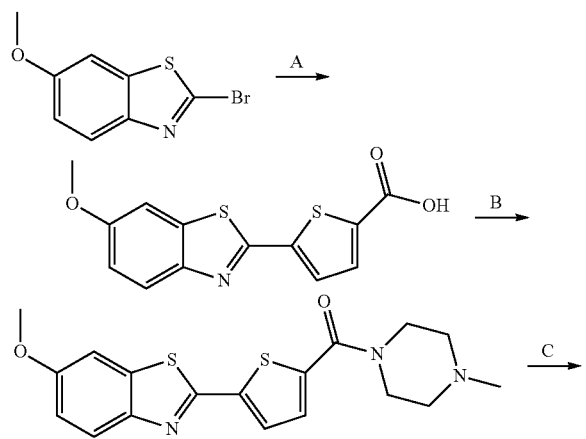

Step A 5-(6-Methoxy-benzothiazol-2-yl)-thiophene-2-carboxylic acid

2-Bromo-6-methoxy-benzothiazole (1.22 g, 5.00 mmol), 2-carboxythiophene-5-boronic acid (860 mg, 5.00 mmol), sodium carbonate (2.65 g, 25.00 mmol) and tetrakis(triphenylphosphine)palladium (300 mg, 0.25 mmol) were dissolved in a mixture of 80 mL N,N-dimethylformamide and 80 mL water. The mixture was stirred at 120° C. under argon for 2 h. The reaction mixture was evaporated and the residue was partitioned between 100 mL of water and 100 mL of dichloromethane. A considerable amount of white solid precipitated between the layers and was filtered off and triturated with diethyl ether, affording the title compound (550 mg, 1.89 mmol, 38%) as a white powder.

| EXAMPLE | Made From | Structure | LCMS method | LCMS Ion | LCMS Rt (min) | LCMS purity (%) | NMR purity (%) |
|---|---|---|---|---|---|---|---|
| 29a | — | (6-methoxy-benzothiazol-2-yl)-thiophene-2-carboxylic acid | BB_LCMS01(+) | 292 | 3.490 | 94 | n/a |

Step B

5-(6-Hydroxy-benzothiazol-2-yl)-thiophene-2-carboxylic acid

To dry tetrahydrofuran (30 mL), 1-methylpiperazine (834 μL, 756 mg, 7.56 mmol), triethylamine (1.05 mL, 762 mg, 7.56 mmol) 5-(6-Methoxy-benzothiazol-2-yl)-thiophene-2-carboxylic acid (550 mg, 1.89 mmol), 1-hydroxybenzotriazole (510 mg, 3.78 mmol) and 1-ethyl-3-(dimethylaminopropyl)-carbodiimid hydrochloride (726 mg, 3.78) were added sequentially. The mixture was stirred at room temperature overnight then was evaporated. The residue was suspended in saturated sodium bicarbonate (20 mL) and extracted with dichloromethane (3×20 mL). The combined organic layers were dried (Na₂SO₄), evaporated and recrystallized from toluene. The title compound (399 mg, 1.070 mmol, 57%) was isolated as a white powder.

| EXAMPLE | Made From | Structure | LCMS method | LCMS Ion | LCMS Rt (min) | LCMS purity (%) | NMR purity (%) |
|---|---|---|---|---|---|---|---|
| 29b | 29a | 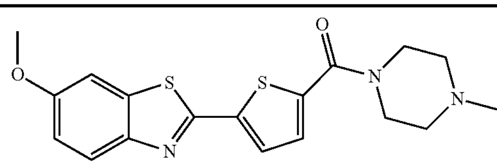 | BB_LCMS01(+) | 374 | 2.708 | 94 | n/a |

Step C

[5-(6-Hydroxy-benzothiazol-2-yl)-thiophen-2-yl]-(4-methyl-piperazin-1-yl)-methanone To a solution of 5-(6-Hydroxy-benzothiazol-2-yl)-thiophene-2-carboxylic acid (375 mg, 1.00 mmol) in abs. dichloromethane (3 mL) stirred under argon at −78° C., boron tribromide (769 μl, 2.00 g, 8.00 mmol) was added via syringe and the mixture was stirred for 1 h and then allowed to warm to room temperature and stirred for 12 h. The reaction was quenched at −78° C. by addition of methanol (0.50 mL) and the mixture was for 1 h and allowed to warm to room temperature and stirred for 1 h. The volatiles were removed and the solid residue was recrystallized with ethanol, filtered, washed with diethyl-ether and dried to give the title compound (295 mg, 0.82 mmol, 82%) as a gray solid.

| EXAMPLE | Made From | Structure | LCMS method | LCMS Ion | LCMS Rt (min) | LCMS purity (%) | NMR purity (%) |
|---|---|---|---|---|---|---|---|
| 29c | 29b | 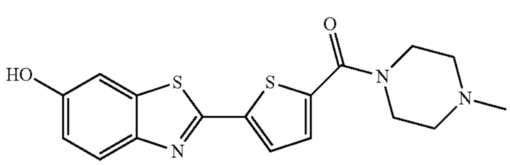 [SMILES: CN1CCN(C(=O)c2ccc(-c3nc4ccc(O)cc4s3)s2)CC1] | BB_LCMS01(+) | 360 | 2.346 | 95 | n/a |

Step D

6-Hydroxy-2-[5-(4-methyl-piperazine-1-carbonyl)-thiophen-2-yl]-benzothiazole-7-carbaldehyde A mixture of [5-(6-Hydroxy-benzothiazol-2-yl)-thiophen-2-yl]-(4-methyl-piperazin-1-yl)-methanone (290 mg, 0.81 mmol), hexamethylenetetramine (453 mg, 3.23 mmol) and trifluoroacetic acid (3 mL) was stirred in a closed vessel under argon atmosphere at 120° C. for 1 h. The mixture was cooled to room temperature and 10 mL of water was added. The pH of the mixture was adjusted to 8 by slow addition of a saturated NaHCO$_3$ solution, then extracted with dichloromethane (3×20 mL). After drying (MgSO$_4$), filtration and evaporation of the solvent, the residue was purified by column chromatography by ISCO on silica (Kieselgel 60) using a chloroform-methanol gradient followed by trituration with diethyl ether. The title compound (23 mg, 0.059 mmol, 10%) was obtained as an orange solid.

$^1$H NMR (400 MHz, DMSO-d$_6$) δ ppm 10.50 (s, 1H), 8.16 (d, J=9.0 Hz, 1H), 7.81 (d, J=3.8 Hz, 1H), 7.46 (d, J=3.8 Hz, 1H), 7.21 (d, J=9.0 Hz, 1H), 3.63-3.70 (m, 4H), 2.34-2.43 (m, 4H), 2.23 (s, 3H).

| EXAMPLE | Made From | Structure | LCMS method | LCMS Ion | LCMS Rt (min) | LCMS purity (%) | NMR purity (%) |
|---|---|---|---|---|---|---|---|
| 29-1 | 29c | 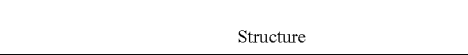 | BB_LCMS01(+) | 388 | 2.465 | 97 | 98 |

Example 30

6-Hydroxy-2-(4-isopropyl-piperazin-1-yl)-benzothiazole-7-carbaldehyde

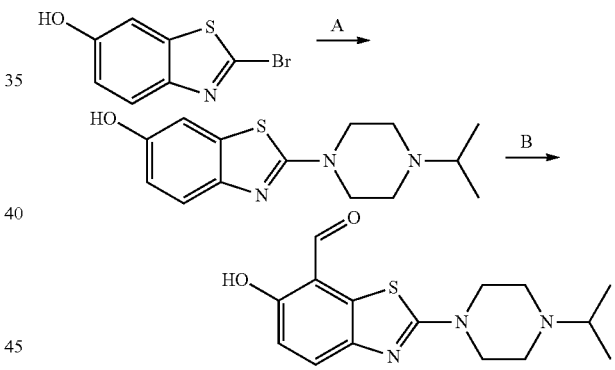

Step A 2-(4-Isopropyl-piperazin-1-yl)-benzothiazol-6-ol

2-Bromo-6-hydroxybenzothiazole (345 mg, 1.5 mmol), 1-isopropyl-piperazine hydrochloride (271 mg, 1.65 mmol) and dry potassium carbonate (828 mg, 6.00 mmol), were dissolved in 6 mL of dry N,N-dimethylformamide. The resulted pale brown solution was stirred at 100° C. for 18 h in a closed vial. The reaction mixture was evaporated, suspended in 20 mL of water and extracted with dichloromethane (3×15 mL). The combined organic layers were washed with saturated sodium bicarbonate and brine, then dried over MgSO$_4$. After evaporation the residue was purified by column chromatography (Kieselgel 60) using chloroform-methanol 49:1 as the eluent. The title compound (76 mg, 0.27 mmol, 18%) was obtained as a white solid.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 30a-1 | — | (structure) | BB_LCMS01(+) | 278 | 1.345 | 87 | n/a |
| 30a-2 | — | (structure) | BB_LCMS01(+) | 278 | 1.141 | 87 | n/a |
| 30a-3 | — | (structure) | BB_LCMS01(+) | 318 | 0.452 | 93 | n/a |

Step B

6-Hydroxy-2-(4-isopropyl-piperazin-1-yl)-benzothiazole-7-carbaldehyde

A mixture of 2-(4-Isopropyl-piperazin-1-yl)-benzothiazol-6-ol (76 mg, 0.027 mmol), hexamethylenetetramine (153 mg, 1.10 mmol) and trifluoroacetic acid (2 mL) was stirred in a closed vessel under argon atmosphere at 120° C. for 1 h. The mixture was cooled to room temperature then 10 mL of water was added. The pH of the mixture was adjusted to 8 by portionwise addition of saturated NaHCO₃ solution, and extracted with dichloromethane (3×15 mL). After drying (MgSO₄), filtration and evaporation of the solvent, the residue was purified by column chromatography (Kieselgel 60) using chloroform-methanol 49:1 as eluent followed by trituration with diethyl ether and n-hexane. The title compound (14 mg, 0.040 mmol, 14%) was obtained as a yellow solid.

$^1$H NMR (400 MHz, DMSO-d$_6$) δ ppm 10.66 (br. s., 1H), 10.44 (s, 1H), 7.62 (d, J=8.5 Hz, 1H), 6.97 (d, J=8.5 Hz, 1H), 3.48-3.55 (m, 4H), 2.66-2.79 (m, 1H), 2.53-2.59 (m, 4H), 0.99 (d, J=6.5 Hz, 6H).

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 30-1 | 30a-1 | (structure) | BB_LCMS01(+) | 306 | 2.228 | 90 | 90 |
| 30-2 | 30a-2 | (structure) | BB_LCMS01(+) | 306 | 2.629 | 95 | 95 |
| 30-3 | 30a-3 | (structure) | BB_LCMS01(+) | 347 | 1.969 | 95 | 93 |

Example 31

4-(7-Formyl-6-hydroxy-1H-benzoimidazol-2-yl)-benzoic acid methyl ester

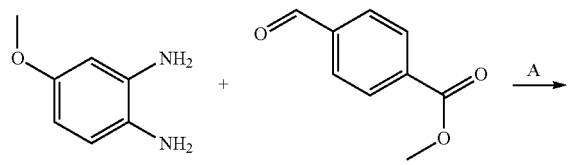

Step A 4-(6-Methoxy-1H-benzoimidazol-2-yl)-benzoic acid methyl ester

4-Methoxybenzene-1,2-diamine (1.96 g, 14.2 mmol), 4-formylbenzoic acid methyl ester (2.33 g, 14.2 mmol) and sodium bisulphite (1.55 g, 14.9 mmol) were refluxed in methanol (50 mL) for 3 h, then evaporated to dryness. The solid residue was partitioned between dichloromethane and water. The organic layer was dried, evaporated and purified by column chromatography, eluting with. The title compound (2.65 g, 9.40 mmol, 66%) was obtained as a dark solid.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 31a-1 | — | 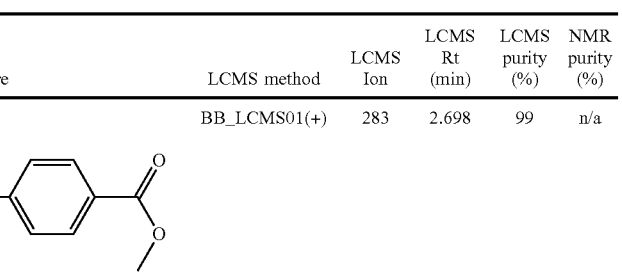 | BB_LCMS01(+) | 283 | 2.698 | 99 | n/a |
| 31a-2 | — | 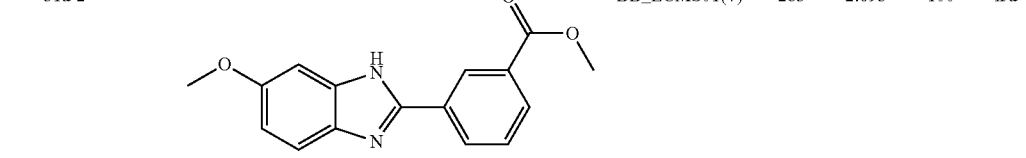 | BB_LCMS01(+) | 283 | 2.693 | 100 | n/a |

-continued

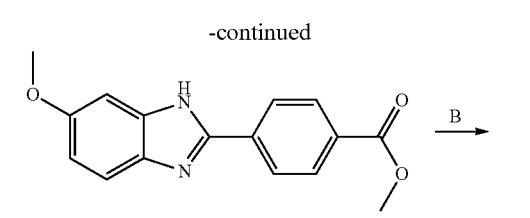

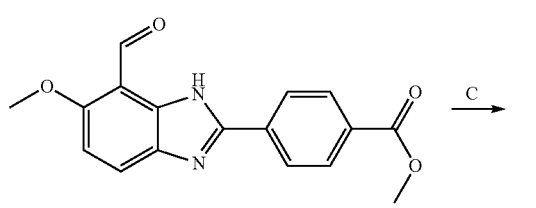

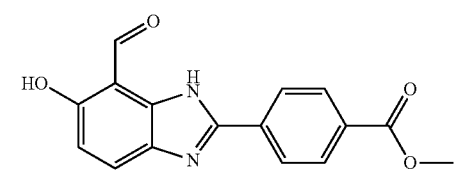

Step B 4-(7-Formyl-6-methoxy-1H-benzoimidazol-2-yl)-benzoic acid methyl ester A mixture of 4-(6-Methoxy-1H-benzoimidazol-2-yl)-benzoic acid methyl ester (1.50 g, 5.3 mmol), hexamethylenetetramine (1.50 mg, 10.60 mmol) and trifluoroacetic acid (12 mL) was stirred in a closed vessel under an argon atmosphere at 130° C. for 3 h. The resultant brown solution was poured onto 250 mL of crushed ice. The mixture was extracted with chloroform-ethanol 95:5 (2×100 mL). The combined organic layers were dried ($Na_2SO_4$), and evaporated. The solid residue was purified by column chromatography over silica (Kieselgel 60) using chloroform as the eluent to give title compound (350 mg, 1.13 mmol, 21%) yellow crystals.

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 31b-1 | 31a-1 | 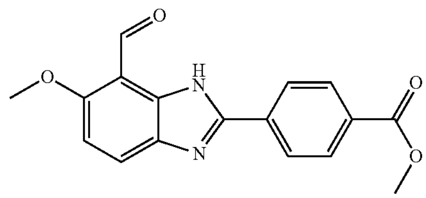 [SMILES: COC(=O)c1ccc(-c2nc3ccc(OC)c(C=O)c3[nH]2)cc1] | BB_LCMS01(+) | 311 | 3.287 | 100 | n/a |
| 31b-2 | 31a-2 | 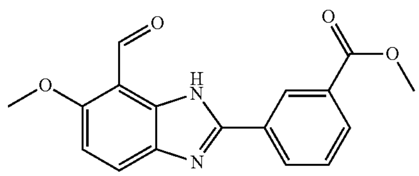 | BB_LCMS01(+) | 311 | 3.218 | 60 | n/a |

Step C 4-(7-Formyl-6-hydroxy-1H-benzoimidazol-2-yl)-benzoic acid methyl ester

To a solution of 4-(7-Formyl-6-methoxy-1H-benzoimidazol-2-yl)-benzoic acid methyl ester (650 mg, 2.1 mmol) in abs. dichloromethane (30 mL) at −78° C., boron tribromide (1.20 mL, 3.20 g, 12.60 mmol) was added dropwise and the mixture was stirred for 1 h, then overnight at room temperature. The yellow suspension was cooled to −78° C. and quenched with methanol (30 mL) followed by evaporation. The residue was partitioned between saturated sodium bicarbonate (30 mL) and chloroform (30 mL). The organic phase was dried (Na$_2$SO$_4$) and evaporated. The title compound (360 mg, 1.22 mmol, 58%) was isolated as a light green solid.

$^1$H NMR (400 MHz, DMSO-d$_6$) δ ppm 12.69 (br. s., 1H), 10.54 (s, 1H), 8.38 (d, J=8.5 Hz, 2H), 8.09 (d, J=8.5 Hz, 2H), 7.84 (d, J=8.8 Hz, 1H), 6.87 (d, J=8.8 Hz, 1H), 3.89 (s, 3H).

The following compounds (includes title compound) were made by the above procedure:

Example 32

4-(7-Formyl-6-hydroxy-1H-benzoimidazol-2-yl)-benzoic acid

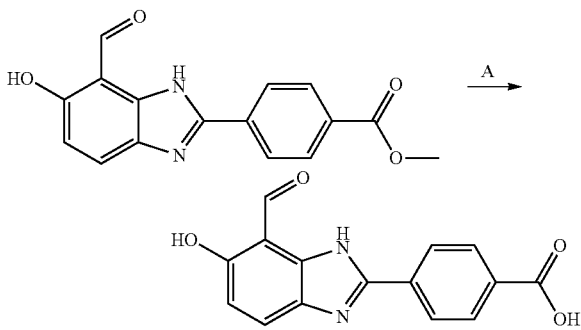

4-(7-Formyl-6-hydroxy-1H-benzoimidazol-2-yl)-benzoic acid methyl ester (360 mg, 1.22 mmol) was dissolved in a mixture of dioxane (6 mL) and 1N NaOH (6 mL) and was

| EXAMPLE | Made From | Structure | LCMS method | LCMS Ion | LCMS Rt (min) | LCMS purity (%) | NMR purity (%) |
|---|---|---|---|---|---|---|---|
| 31-1 | 31b-1 | 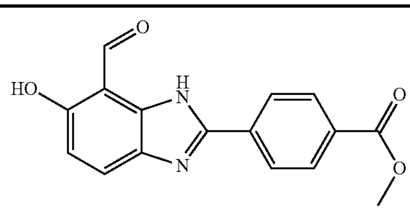 | BB_LCMS01(−) | 295 | 3.100 | 98 | 98 |
| 31-2 | 31b-2 | | BB_LCMS01(−) | 295 | 3.054 | 100 | 98 | stirred at 50° C. for 1 h. The mixture was evaporated to half volume and acidified with glacial acetic acid. The precipitate was collected, washed with acetone and dried. The title compound (305 mg, 1.08 mmol, 89%) was isolated as a brown solid.

$^1$H NMR (400 MHz, DMSO-d$_6$) δ ppm 12.75 (br. s., 1H), 10.57 (s, 1H), 8.33 (d, J=8.5 Hz, 2H), 8.07 (d, J=8.5 Hz, 2H), 7.85 (d, J=8.8 Hz, 1H), 6.90 (d, J=8.8 Hz, 1H).

The following compounds (includes title compound) were made by the above procedure:

| EXAMPLE | Made From | Structure | LCMS method | LCMS Ion | LCMS Rt (min) | LCMS purity (%) | NMR purity (%) |
|---|---|---|---|---|---|---|---|
| 32-1 | 31-1 | 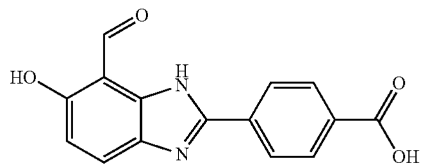 [SMILES: O=Cc1c(O)ccc2nc(-c3ccc(C(=O)O)cc3)[nH]c12] | BB_LCMS01(+) | 283 | 2.636 | 100 | 98 |
| 32-2 | 31-2 | 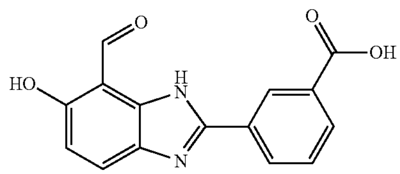 [SMILES: O=Cc1c(O)ccc2nc(-c3cccc(C(=O)O)c3)[nH]c12] | BB_LCMS01(+) | 283 | 2.609 | 100 | 95 |

Example 33

5-Hydroxy-2-[4-(4-methyl-piperazine-1-carbonyl)-phenyl]-3H-benzoimidazole-4-carbaldehyde

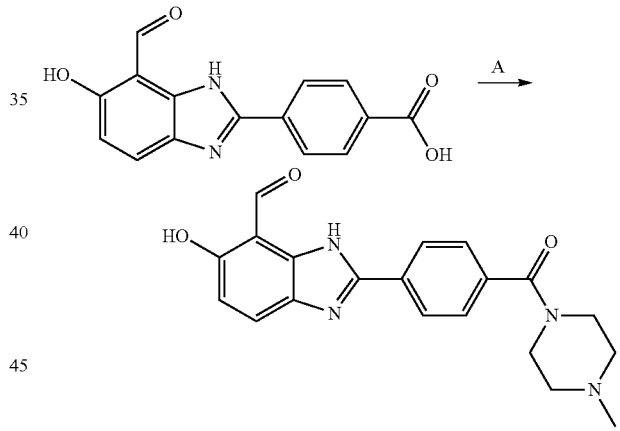

To dry tetrahydrofuran (5 mL), 1-methylpiperazine (69 μL, 63 mg, 0.62 mmol), triethylamine (196 μL, 142 mg, 1.40 mmol), 4-(7-Formyl-6-hydroxy-1H-benzoimidazol-2-yl)-benzoic acid (80 mg, 0.28 mmol), 1-hydroxybenzotriazole (84 mg, 0.62 mmol) and 1-ethyl-3-(dimethylaminopropyl)-carbodiimide hydrochloride (120 mg, 0.62) were added in the above order. The mixture was stirred at room temperature overnight. The resulted brown solution was suspended in saturated sodium bicarbonate (60 mL) and extracted with dichloromethane (3×20 mL). The combined organic layers were dried (Na$_2$SO$_4$), evaporated and purified by column chromatography (Kieselgel 60), eluting with chloroform-methanol 9:1. The title compound (35 mg, 0.096 mmol, 34%) was isolated as a white powder.

$^1$H NMR (400 MHz, DMSO-d$_6$) δ ppm 12.71 (br. s., 1H), 10.51 (br. s., 1H), 8.28 (br. s., 2H), 7.83 (br. s., 1H), 7.53 (br. s., 2H), 6.87 (d, J=8.8 Hz, 1H), 3.50 (br. s., 4H), 2.33 (br. s., 4H), 2.21 (s, 3H).

The following compounds (includes title compound) were made by the above procedure:

| EXAM-PLE | Made From | Structure | LCMS method | LCMS Ion | LCMS Rt (min) | LCMS purity (%) | NMR purity (%) |
|---|---|---|---|---|---|---|---|
| 33-1 | 32-1 | 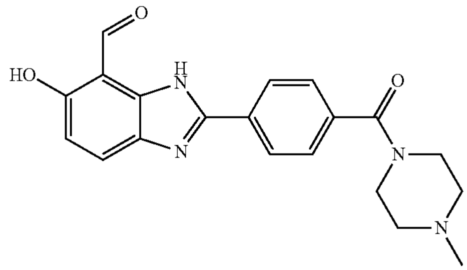 [SMILES: CN1CCN(C(=O)c2ccc(-c3nc4ccc(O)c(C=O)c4[nH]3)cc2)CC1] | BB_LCMS01(+) | 365 | 2.057 | 100 | 90 |
| 33-2 | 32-1 | 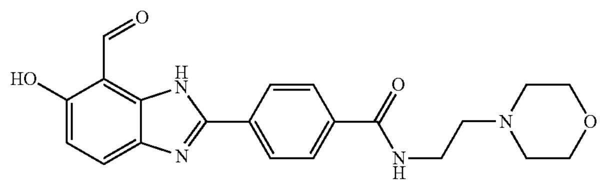 [SMILES: O=Cc1c(O)ccc2nc(-c3ccc(C(=O)NCCN4CCOCC4)cc3)[nH]c12] | BB_LCMS01(+) | 395 | 2.261 | 100 | 80 |
| 33-3 | 32-1 | 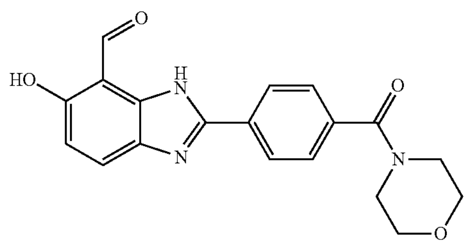 [SMILES: O=Cc1c(O)ccc2nc(-c3ccc(C(=O)N4CCOCC4)cc3)[nH]c12] | BB_LCMS01(+) | 352 | 2.587 | 100 | 95 |

Example 34

(7-Formyl-6-hydroxy-1H-benzoimidazol-2-ylsulfanyl)-acetic acid

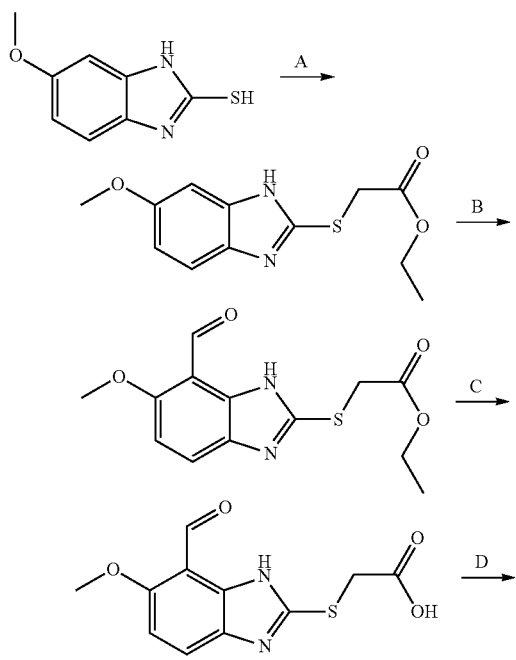

-continued

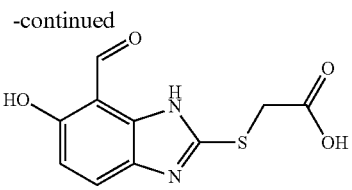

Step A (6-Methoxy-1H-benzoimidazol-2-ylsulfanyl)-acetic acid ethyl ester

6-Methoxy-1H-benzoimidazole-2-thiol (10.00 g, 55.56 mmol) was dissolved in DMF (300 mL). NaH (2.44 g, 60 w/w % in mineral oil, 61.11 mmol) was added in small portions at room temperature. The resulted mixture was stirred for one h then bromo-acetic acid ethyl ester (10.21 g, 61.11 mmol) was added. After 12 h the mixture was evaporated and the resulted slurry was diluted with HCl (340 mL, 2N) and was stirred for a 0.5 h at room temperature then was filtered, washed with water and n-hexane respectively. The title compound (14.70 g, 99%) was isolated as a pale yellow powder.

LCMS/BB_LCMS01(+)/: M+1=267, Rt: 2.586 min, pur: 99%

| EXAMPLE | Made From | Structure | LCMS method | LCMS Ion | LCMS Rt (min) | LCMS purity (%) | NMR purity (%) |
|---|---|---|---|---|---|---|---|
| 34a | — | 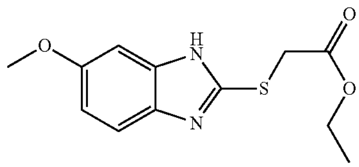 [SMILES: CCOC(=O)CSc1nc2ccc(OC)cc2[nH]1] | BB_LCMS01(+) | 267 | 2.586 | 99 | n/a |

Step B (7-Formyl-6-methoxy-1H-benzoimidazol-2-ylsulfanyl)-acetic acid ethyl ester A mixture of (6-methoxy-1H-benzoimidazol-2-ylsulfanyl)-acetic acid ethyl ester (14.70 g, 55.26 mmol), hexamethylenetetramine (15.47 g, 100.53 mmol) and trifluoroacetic acid (61 mL) was stirred under argon atmosphere at 120° C. for 1 h. The solution was cooled to room temperature and water (950 mL) was added. This aqueous mixture was extracted with EtOAc (3×200 mL). The combined organic layers were dried over $Na_2SO_4$ and evaporated. The title compound (1.432 g, 4.87 mmol, 9%) was obtained by column chromatography in 2 consecutive steps followed by trituration with diethyl ether.

LCMS/BB_LCMS01(+)/: M+1=295, Rt: 3.084 min, pur: 97%

| EXAMPLE | Made From | Structure | LCMS method | LCMS Ion | LCMS Rt (min) | LCMS purity (%) | NMR purity (%) |
|---|---|---|---|---|---|---|---|
| 34b | 34a | 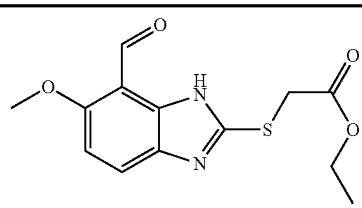 | BB_LCMS01(+) | 295 | 3.084 | 97 | n/a |

Step C (7-Formyl-6-methoxy-1H-benzoimidazol-2-ylsulfanyl)-acetic acid (7-Formyl-6-methoxy-1H-benzoimidazol-2-ylsulfanyl)-acetic acid ethyl ester (1.432 g, 4.87 mmol) was dissolved in a mixture of 19.5 mL of 1N sodium hydroxide and 15 mL of dioxane. The solution was stirred at 50° C. for 2 h, cooled to 0° C., and the pH was adjusted to 3.5 by dropwise addition of 6N HCl, keeping the temperature at 0° C. The precipitated yellow solid was filtered, washed with ice cold water and dried. The title compound (1.10 g, 4.15 mmol, 85%) was isolated as a yellow powder.

LCMS/BB_LCMS01(−)/: M+1=265, Rt: 2.390 min, pur: 100%

| EXAMPLE | Made From | Structure | LCMS method | LCMS Ion | LCMS Rt (min) | LCMS purity (%) | NMR purity (%) |
|---|---|---|---|---|---|---|---|
| 34c | 34b | 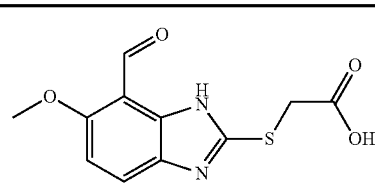 | BB_LCMS01(+) | 267 | 2.384 | 100 | n/a |

Step D (7-Formyl-6-hydroxy-1H-benzoimidazol-2-ylsulfanyl)-acetic acid

To a solution of (7-Formyl-6-methoxy-1H-benzoimidazol-2-ylsulfanyl)-acetic acid ethyl ester (500 mg, 1.88 mmol) in abs. dichloromethane (40 mL) stirred under argon at −78° C., boron tribromide (723 μL, 1.88 g, 7.52 mmol) was added dropwise and the mixture was warmed to room temperature and stirred for 2 h. An additional portion of boron tribromide (723 μl, 1.88 g, 7.52 mmol) was added at −78° C. and stirred for 2 h at room temperature. The mixture was quenched by slow addition of 120 mL of water. The mixture was evaporated to dryness, suspended in boiling ethyl acetate, and the solid was filtered off. The filtrate was evaporated and triturated with diethyl ether. The title compound (220 mg, 0.87 mmol, 46%) was obtained as a light orange powder.

$^1$H NMR (400 MHz, DMSO-$d_6$) δ ppm 10.64 (br. s., 1H), 10.41 (s, 1H), 7.64 (d, J=8.5 Hz, 1H), 6.78 (d, J=8.5 Hz, 1H), 4.10 (s, 2H).

| EXAMPLE | Made From | Structure | LCMS method | LCMS Ion | LCMS Rt (min) | LCMS purity (%) | NMR purity (%) |
|---|---|---|---|---|---|---|---|
| 34-1 | 34c | 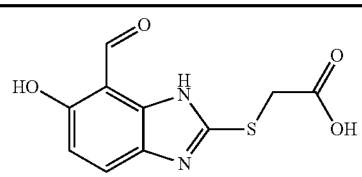 | BB_LCMS01(+) | 253 | 1.977 | 92 | 95 |

Example 35

IRE-1α Assay

A fusion protein comprising glutathione S transferase (GST) and human IRE-1α (GST-IRE-1α) obtained from a 500 ml baculovirus-infected insect cell culture can be used to measure IRE-1α activity in vitro.

Five μl of a reaction mixture comprising 1× reaction buffer (5× reaction buffer is 100 mM Hepes pH 7.5, 250 mM KOAc, 2.5 mM $MgCl_2$), 3 mM DTT, and 0.4% polyethylene glycol water is added to each well of 384 well plates. Twenty-five nanoliters of a 1 mM test compound solution are added to test wells. Three μl of a 128 ng/ml IRE-1α preparation are added to each test well and to positive control wells (final concentration 5.82 ng/well). Negative control wells contain only reaction mixture and test compound.

After spinning the plates at 1200 rpm for 30 seconds, 3 μl of an IRE-1α human mini-XBP-1 mRNA stem-loop substrate 5′-CAGUCCGCAGCACUG-3′ (SEQ ID NO:1), labeled with the fluorescent dye Cy5 at the 5′ end and Black Hole Quencher 2 (BH2) at the 3′ end, are added to each well of a control plate. The plates are again spun at 1200 rpm for 30 seconds. Final concentrations for the assay are: 63 nM IRE-1α substrate, 5.82 ng IRE-1α protein, and 2.5 μM test compound.

The plates are covered with lids and incubated for one hour at 30° C. The plates are then transferred to an ACQUEST™ microplate reader. Data is analyzed using data analysis software, and the percent activity of IRE-1α is calculated.

Example 36

Determination of $IC_{50}$ for Inhibition of IRE-1α

$IC_{50}$ for inhibition of IRE-1α of compounds identified in Table 1 was measured as described in EXAMPLE 35.

Example 37

Kinase Selectivity Assays

Compounds are assayed for their ability to inhibit 86 different kinases at a concentration of 10 μM. The results of the assays demonstrate that these compounds are selective for IRE-1α.

Example 38

Cell-Based Assays

Human myeloma MM.1s cells are incubated with a compound for 1.25 hours before stressing the cells with 2 mM dithiothreitol (DTT). After an additional 45 minutes (2 hours total) with compound and DTT, the cells are harvested with TRIZOL™ (a mono-phasic solution of phenol and guanidine isothiocyanate), and total RNA is prepared as directed by the manufacturer (Invitrogen). Human XBP-1 is amplified by RT-PCR with the following primers, which flank the 26 base unconventional intron excised by IRE-1α:

```
(forward)
                               (SEQ ID NO: 2)
CCTGGTTGCTGAAGAGGAGG
and (reverse)
                               (SEQ ID NO: 3)
CCATGGGAGATGTTCTGGAG.
```

In unstressed cells, IRE-1α is inactive and hence, the 26 base intron is left in the XBP-1 mRNA. RT-PCR of unstressed (U) cells then generates the upper band. When cells are stressed (S) with the endoplasmic reticulum (ER) stressing agent DTT, IRE-1α is activated due to accumulating unfolded protein and the resulting RT-PCR product is 26 base pairs shorter. Increasing amounts of the compound block IRE-1α-mediated XBP-1 splicing as demonstrated by a shift from a lower band to an upper band. Compound potency reflects SAR in the in vitro enzyme assay.

Determination of Cellular $EC_{50}$ for IRE-1α Inhibitors

Compounds which pass specificity assays are assayed for cellular $EC_{50}$ using endogenous XBP-1 splicing in myeloma cells. XBP-1 is regulated through the excision of a 26 nucleotide intron from the XBP-1 mRNA by the highly specific endoribonuclease activity of IRE-1α. This splicing event induces a frame shift in the ORF of the C-terminus of XBP-1 leading to the translation of the larger 54 kD active transcription factor rather than the inactive 33 kD form. This splicing event is used to measure IRE-1α activity on XBP-1 mRNA in cells and tissues.

Briefly, compounds are incubated in the presence or absence of an ER stress agent (e.g., DTT), and the ratio of XBP-1u (unspliced) to XBP-1s (spliced) is quantified by RT-PCR. The $ED_{50}$ is determined as the 50% XBP-1s to total XPB-1 levels. Compounds which have $EC_{50}$s equal to or below 10 µM are used in standard apoptosis assays, including Annexin V staining and CASPASE-GLO®.

Proliferation assays using myeloma cell lines (U266, RPMI8226 and MM.1s) are used to determine $ED_{50}$. Compounds are used as single agents and in combination with other chemotherapeutic drugs. IRE-1α inhibitor compounds inhibit the proliferation of RPMI8226 myeloma cells, which have endogenous activation of the pathway and are further induced by the addition of bortezomib. When an IRE-1α inhibitor compound is used in combination with MG-132, increased apoptosis is observed with U266 myeloma cells.

Example 39

Animal Model/Preclinical Validation Studies

The preclinical validation strategy employs a set of animal models representing normal tissues under chemical stress and multiple myeloma xenografts. The normal animal model is employed as a surrogate model where dose-related on-target activity of compounds can be confirmed in tissues sensitive to standard UPR inducing agents such as tunicamycin (Wu et al., Dev Cell. 2007 September; 13(1d): 351-64). Normal mouse tissues are not under ER stress, and therefore the XBP-1 mRNA remains as the inactive, unspliced form. Upon induction with tunicamycin, tissues induce active XBP-1 mRNA splicing, and this activity is suppressed by IRE-1α inhibitors. This on-target ER stress animal model is a useful screening and early pharmacokinetic tool.

Antibody production is evaluated in a second surrogate model. However, in cell-based models, IRE-1α inhibitors have been shown to potently inhibit antibody production.

Final efficacy studies are performed in myeloma xenograft models, as described below.

Example 40

RPMI8226 Xenograft Efficacy Model

SCID mice are evaluated for their ability to support implantation of desired tumor cells in support of model development and characterization. Mice are injected intravenously (5) or implanted either subcutaneously (SC) or intraperitoneally (IP). To generate a relevant animal model mimicking human disease, it is desirable that all three approaches are evaluated for improved implantation rates and relevant disease progression, as is well known in the art. SC injections provide an easy way to measure tumor growth and efficacy, and IV and IP injections represent a more physiologically relevant model of human tumor spread. SC injections are given primarily in the flank, while IV injections are administered in the tail vein. Mice are manually restrained for SC and IP injections, and a Broome mouse restrainer is used for IV injections.

Example 41

Evaluation of IRE-1α Inhibitor Compounds in a Xenograft Efficacy Model

SCID mice are implanted with tumor cells (human RPMI8226 myeloma cells) via IP, IV or SC routes based on the results from the xenograft model development studies (above). Mice are treated with compound or mock treated (vehicle) for a period of up to 4-5 weeks. Compound administration can be via IV, IP, PO or SC routes. In some cases, tunicamycin is administered via IP injection in order to stimulate stress in the animal. This stress mimics the stress an animal may undergo during times of tumor growth. The tunicaymycin injection mimics tumor growth during times of stress and permits evaluation of biomarkers which indicate the effectiveness of a compound (such as XBP-1 splicing) by RT-PCR, immunohistochemistry, or Western blots.

Mice are monitored for tumor growth, regression and general health. Tumors are collected and characterized by immunohistochemistry and/or FACS analysis. Tumor growth is measured by calipers, ultrasound, or by abdominal lavage. Biomarkers in the blood or tumor can evaluated (primarily XBP-1 splicing).

In some experiments, blood samples are collected at various time points during the dosing (i.e., day 1 or week 4 etc.) to evaluate the pharmacokinetic profile. The time points of blood collection vary depending on the pharmacokinetic properties of the drug being tested. The volume of blood sample is 100 microliters/per time point, and mice are bled twice after drug administration within a 24 hour period via retro-orbital sinus. If the same mouse is used, blood samples are collected once from each eye during 24 hours.

Tumor cells are cultured and injected IP, IV (tail vein) or SC (flank) in the mouse using a 21G needle in a volume of approx 100 µL. Mice are treated with compounds or vehicle alone as a control by IV, IP, SC or PO routes 5 days per week for up to 4-5 weeks. Blood is collected via retroorbital bleed (100 µl) at 2 time points (different eyes). The endpoint of the study depends on the overall health of the mice: while mice are euthanized at the end of 4-5 weeks in most studies, mice are maintained until day 40 in a few studies if their general health will allow. The reason for maintaining studies for 40 days is to determine if the tested compounds have a long term effect on inhibiting tumor growth. Euthanization of mice in which tumor regression is observed will depend on the experimental design. In screening mode, the experiment will end with tumors in the control/untreated group reach 1.5 cm, are ulcerated or when loss of motility is observed in that group. In follow up experiments, mice in which tumor regression is observed may be maintained longer, until they show signs of tumor growth or ill health.

Therapeutic dosing with bortezomib 0.75 mg/kg IV twice weekly of SCID mice bearing human myeloma RPMI8226 tumor xenografts resulted in suppression of tumor growth. However, after cessation of bortezomib therapy, tumors often recurred and grew into large masses. Therefore, mice will be treated in combination as with both bortezomib (as indicated) and twice daily with 10-60 mg/kg IRE-1α/XBP-1 inhibitors such as compound 17-1 by oral, IP or IV administration. Compounds which reduce the incidence of tumor recurrence are identified.

Example 42

Combination Therapies

The spliced form of XBP-1, as a homodimer and heterodimer with ATF-6, transcriptionally regulates genes involved in adapting to ER stress (Wu et al., Dev Cell. 2007 September; 13(1d):351-64). Many of these downstream targets are major chaperones, co-chaperones and ERAD components of the ER. Chaperones such as GRP78 and GRP94 are stable and long lived proteins with half lives on the order of days (Wu et al., Dev Cell. 2007 September;

13(1d):351-64). Therefore, treatment of cancer with an IRE-1α/XBP-1 inhibitor may require up to 5 to 6 days of treatment in each cycle.

In some embodiments, combination therapy given in cycles such as with proteasome inhibitors involves giving the patient 2 days of pretreatment with IRE-1α/XBP-1 inhibitor and then simultaneously with the chemotherapeutic agent until a pharmacodynamic effect is achieved (typically 24 hours post bortezomib infusion). Bortezomib is typically administered on three week cycles, every 1, 4, 8 and 11 days (of 21). Dosing is 1.3 mg/m² by IV administration. IRE-1α/XBP-1 inhibitors can be administered 2 day prior and 24 hours post infusion of bortezomib at 10 to 100 mg/kg by the IV or oral route once, twice or three times daily depending on the PK/PD relationship.

A similar protocol can be employed with Hsp90 and or HDAC inhibitors. Alternatively, both agents are administered simultaneously for the duration of each cycle depending on the PK/PD relation of the inhibitor. IRE-1α/XBP-1 inhibitors can be given to breast cancer patients in combination with Tamoxifen (Gomez et al., FASEB J. 2007 December; 21(2):4013-27) or in combination with Sorafinib to various other cancers including kidney carcinoma and hepatocellular carcinoma (Rahmani et al., Mol Cell Biol. 2007 August; 27(15):5499-513).

In general, because many kinase inhibitors often are not selective on their targeted kinase and often affect many additional kinases; they may cause non-specific cellular stress which may activate the UPR. Therefore, combination approaches may be useful using IRE-1α/XBP-1 inhibitors as sensitizing agents.

Example 43

Inhibition of RIDD-Targeted Degradation a. Experimental Procedures

Cell culture. RPMI 8226 cells were grown in monolayer culture using Dulbecco's Modified Eagle Medium (DMEM) supplemented with 10% fetal calf serum (FCS) at 37° C. and 5% $CO_2$. Compounds were kept as 10 mM stock in DMSO at −20° C. and diluted in medium to 10 μM. Thapsigargin (Tg) was resuspended in DMSO and diluted in medium.

RT-qPCR. Procedures for measuring XBP-1s and XBP-1u mRNAs have been described previously (Volkmann et al., *J. Biol. Chem.* 286, 12743-55, 2011). Briefly, total RNA was harvested from cells or tissue using TRIZOL® (Invitrogen) according to the manufacture's procedures. After ethanol precipitation and resuspension of the RNA, RIBOGREEN® (Invitrogen) was used to quantify the yield-and normalize the RNA concentration in the source tube containing isolated RNA. RT-PCR was performed by oligo dT priming, SUPERSCRIPT® II (Invitrogen) and reverse transcription using the AMPLITAQ GOLD® Kit (Applied Biosystems) according to the manufacturer's protocols. Primers for human XBP-1 were

```
(forward, SEQ ID NO: 2)
5'-CCTGGTTGCTGAAGAGGAGG-3'
and (reverse, SEQ ID NO: 3)
5'-CCATGGGGAGATGTTCTGGAG-3'.
```

All DNA oligos were purchased from IDT DNA Technologies. PCR reactions were run on a Bio-Rad PTC-100® 96-well thermocycler; heating at 94° C. for 30 seconds, annealing at 58° C. for 30 seconds polymerizing at 72° C. for 30 seconds for 35 cycles.

The same RNA preparations were used to evaluate levels of CD59 and Blos1 by RT-qPCR. CD59 primers were and the probe and primer sequences were

```
CD59 224s:
                                        (SEQ ID NO: 4)
    CCAGTTGGTGTAGGAGTTGAGACC;

CD59 354a:
                                        (SEQ ID NO: 5)
    AGGCTATGACCTGAATGGCAGA;
and CD59ap:
                                        (SEQ ID NO: 6)
    CAGCCAGGACGAGCAGCAGCCCG.
```

Blos1 probes were commercially available from Applied Biosciences (Hs00155241_m1).

b. Results

Figure 2A:
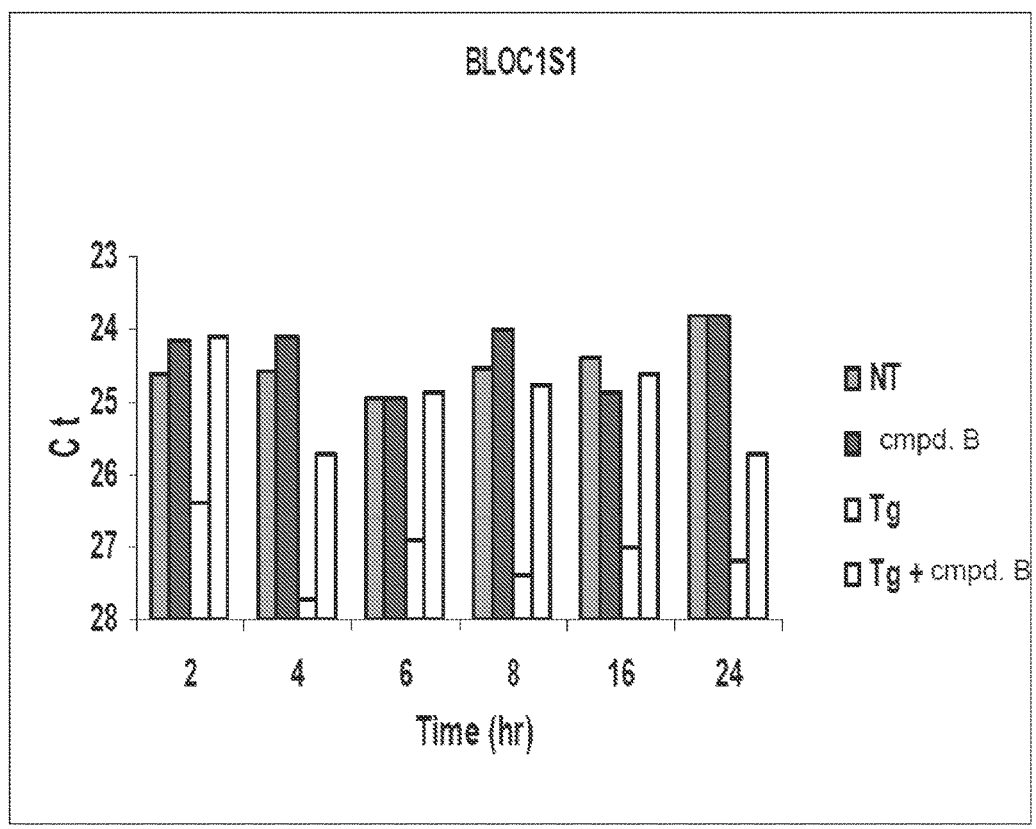
FIG. 2A shows inhibition of regulated IRE1-dependent decay (RIDD) of Blos1 in human RPMI 8226 cells using a selective IRE-1α endoribonuclease inhibitor.
Figure 2B:
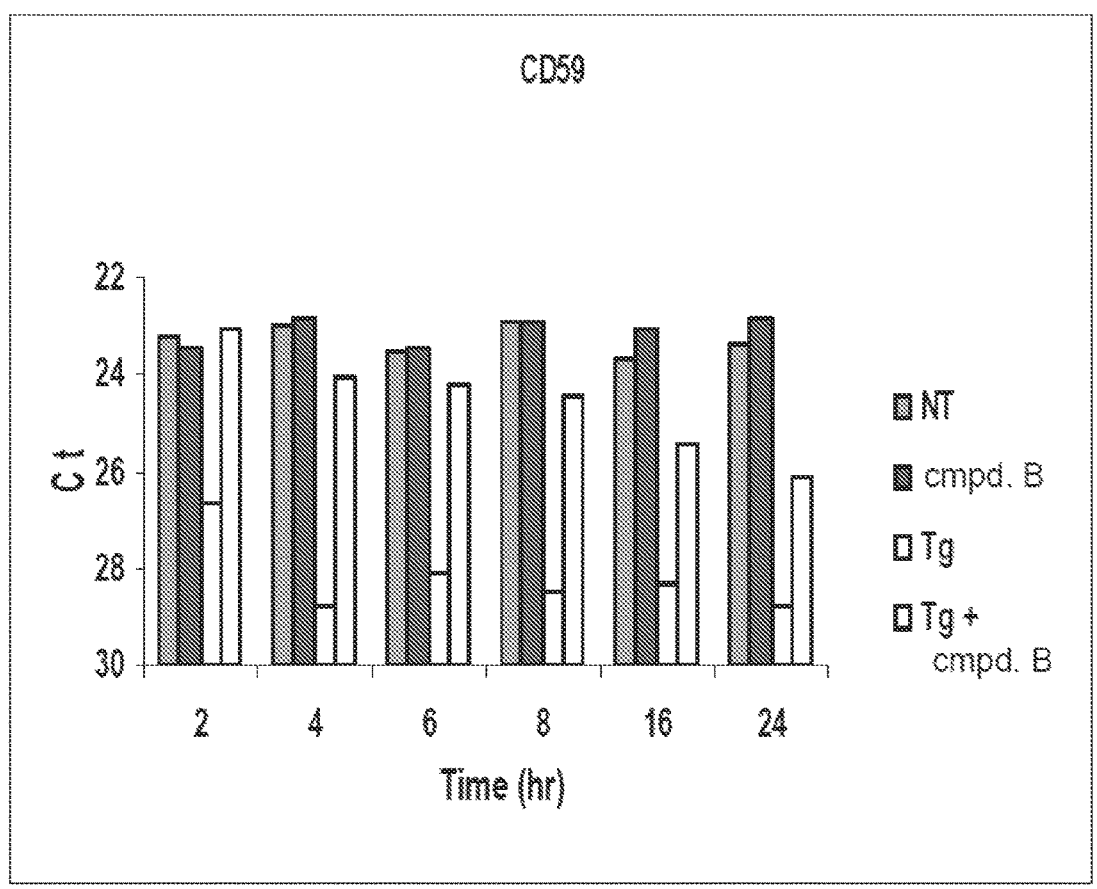
FIG. 2B shows inhibition of regulated IRE1-dependent decay (RIDD) of CD59 in human RPMI 8226 cells using a selective IRE-1α endoribonuclease inhibitor.
Figure 2C:
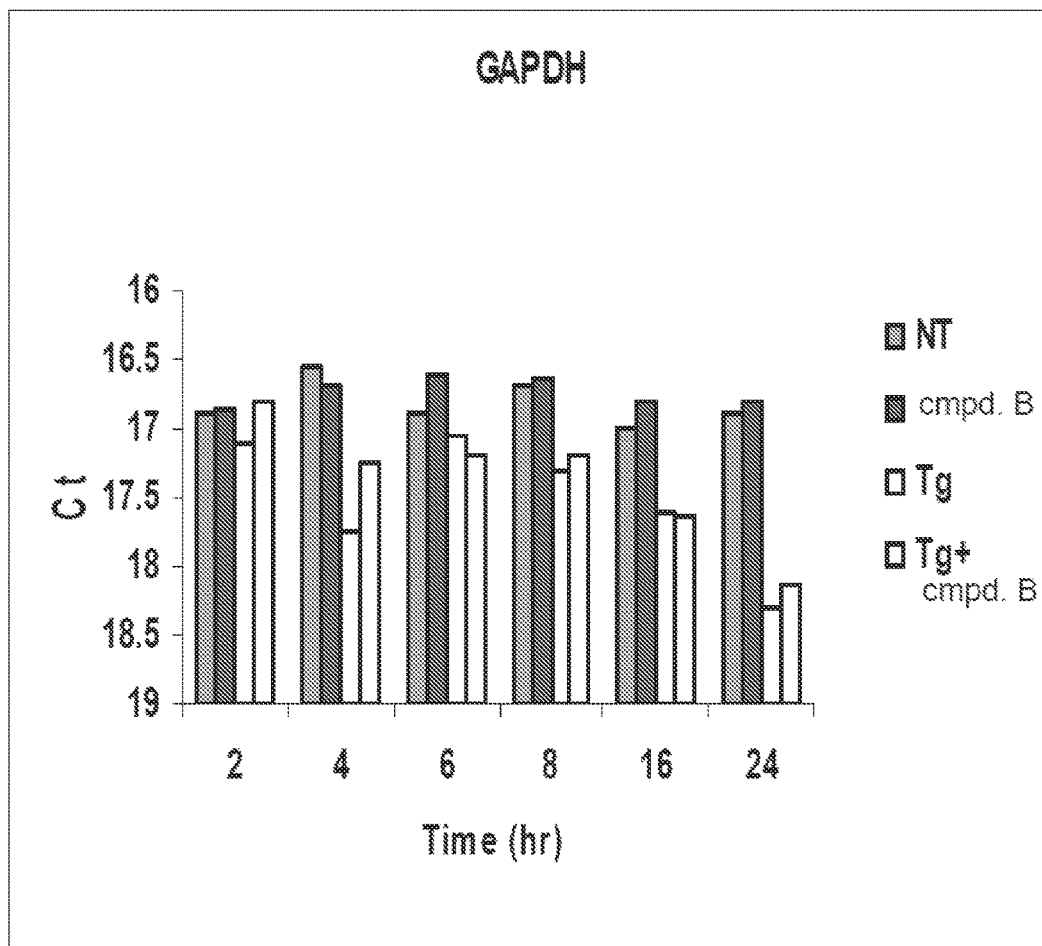
FIG. 2C shows GAPDH as a control. Cells were left untreated or treated with 10 μM IRE-1α inhibitor or 300 nM thapsigargin (Tg) or both or for 2, 4, 6, 8, 16 or 24 hours. Total RNA was harvested and RT-qPCR was performed using specific primers for each of the individual mRNAs. The expression levels are shown as Ct values where one PCR cycle correlates to a 2-fold change.

Low levels of IRE-1α activation where observed in unstressed human RPMI 8226 plasmacytoma cells as demonstrated small amounts of XBP-1s relative to XBP-1u (FIG. 1). Treatment of RPMI cells for 2 hours with 300 nM Thapsigargin (Tg) induced near complete conversion of XBP-1u to XBP-1s and 10 uM compound inhibited this completely (FIG. 1). When compound B was added in combination with Tg for the 2, 4, 6, 8, 16 and 24 hours, complete inhibition of XBP-1s with repopulation of XBP-1u was observed. RNA samples from this experiment were subjected RT-qPCR using specific primers for CD59 and Blos1. Inhibition of RIDD targeted degradation of Blos1 (Hollien, 2009) and CD59 (Oikawa, 2007) was observed by RT-qPCR. (FIG. 2).

Example 44

Figures 3A, 3B:
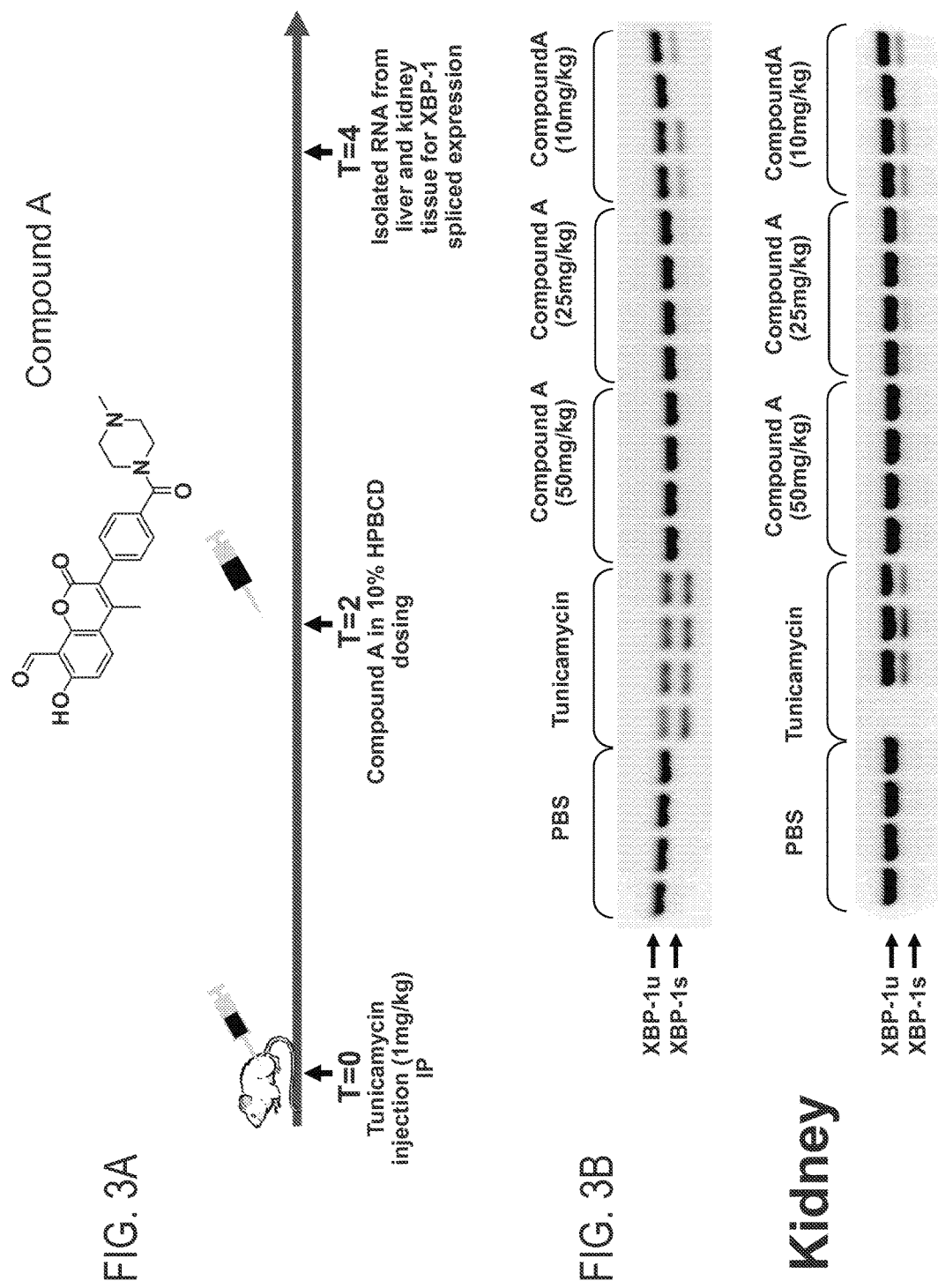
FIG. 3A shows a time course of experiment described in Example 44.
FIG. 3B shows results of RT-PCR analysis performed using murine-specific XBP-1 primers from total RNA harvested from specified organs after intraperitoneal treatment with an IRE-1α inhibitor (Example 44).

Measurement of XBP-1 Slicing Inhibition in the Livers and Kidneys of CB17 SCID Mice in Response to Tunicamycin and Subsequent Treatment with an IRE-1α Inhibitor CB17 SCID mice were treated with 1 mg/kg tunicamycin by intraperitoneal (IP) injection at time 0 (T=0). Two hours later, compound A formulated in 10% hydroxy beta propyl cyclo dextran HBPCD was administered by IP injection. Doses were 50 mg/kg, 25 mg/kg and 10 mg/kg (4 mice in each group). Mice were sacrificed two hours later (4 hours from T=0), and the designated organs were harvested (FIG. 3A).

RT-PCR analysis was performed using murine-specific XBP-1 primers from total RNA harvested from specified organs. The results are shown in FIG. 4B. Tunicamycin alone induces XBP-1 spliced (XBP-1s) relative to PBS treated mice. Dose response for target inhibition (XBP-1s) can be observed with increasing doses of compound A administered IP in both the liver and kidney. Each lane represents an individual mouse where RNA was harvested and RT-PCR was performed. Method of RNA extraction and RT-PCR analysis is described in Volkmann et al., *J. Biol. Chem.* 286, 12743-55, 2011.

The experiment was repeated using intravenous (IV) administration of compound A (50 mg/kg, 25 mg/kg and 10 mg/kg) and oral administration of compound A (100 mg/kg, 50 mg/kg or 25 mg/kg). The results are shown in FIGS. 4A and 4B, respectively.

Example 45

Inhibition of XBP-1 Splicing in the Tumors of RPMI 8226 Human Myeloma Cells in Tumor Bearing SCID Mice by Intraperitoneal Administration of an IRE-1α Inhibitor Mice were implanted subcutaneously with $10^7$ RPMI8226 cells on day 0. After 32 days of tumor growth, mice were treated with 100 mg/kg compound B by IP administration. After 3, 6 and 24 hours of exposure, tumors were harvested and RNA was prepared (FIG. 5A). RT-PCR amplification of XBP-1 was performed using human specific primers (Volkmann et al., *J. Biol. Chem.* 286, 12743-55, 2011) and splicing was analyzed by agarose gel electrophoresis. Three tumors for each of the time points were analyzed against untreated, 3 tumors, and 2 vehicle treated tumors (FIG. 5B). Target inhibition was observed for all 3 time points up to 24 hours when compared to endogenous splicing levels in control groups.

Example 46

Inhibition of XBP-1 Splicing in the Tumors of RPMI 8226 Human Myeloma Cells in Tumor-Bearing SCID Mice by Oral Dosing with an IRE-1α Inhibitor Mice were implanted with $10^7$ RPMI8226 cells subcutaneously on day 0. After 28 days of tumor growth, mice were treated with 200 mg/kg, 100 mg/kg, 50 mg/kg and 25 mg/kg compound Y by oral dosing. After 4 hours of exposure, tumors were harvested and RNA was prepared (FIG. 6A). RT-PCR amplification of XBP-1 was performed using human specific primers (Volkmann et al., *J. Biol. Chem.* 286, 12743-55, 2011) and splicing was analyzed by agarose gel electrophoresis. Four tumors for each dose group were analyzed against 4 untreated control tumors (FIG. 6B). Target inhibition was observed for the 3 higher dose groups: 200, 100 and 50 mg/kg while the lowest dose group, 25 mg/kg was comparable to endogenous splicing levels in the control group.

Example 47

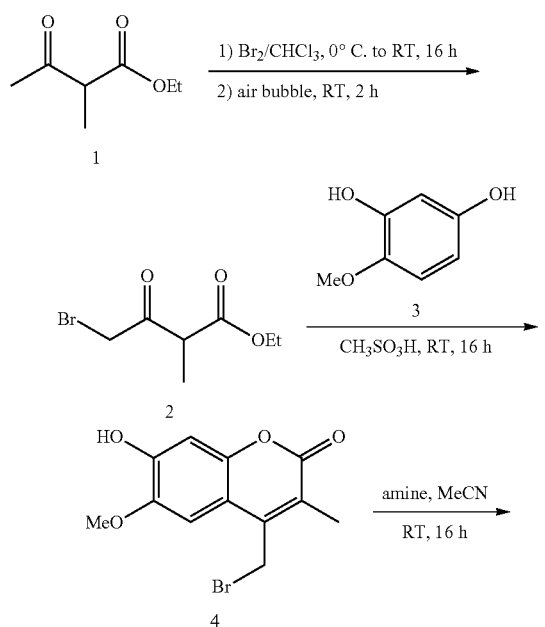

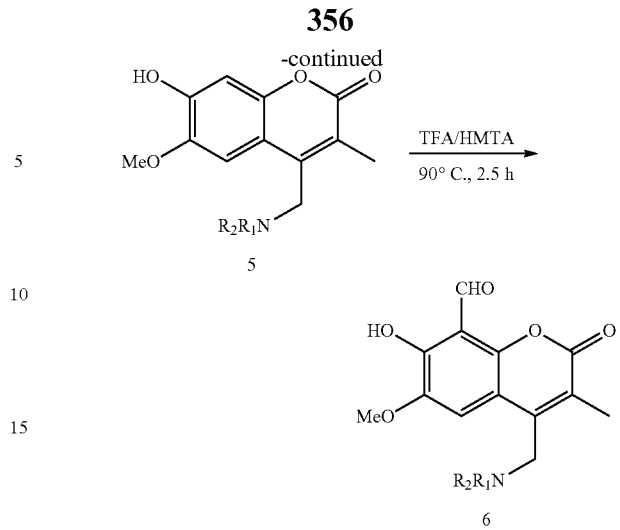

Synthesis of ethyl 4-bromo-2-methyl-3-oxobutanoate

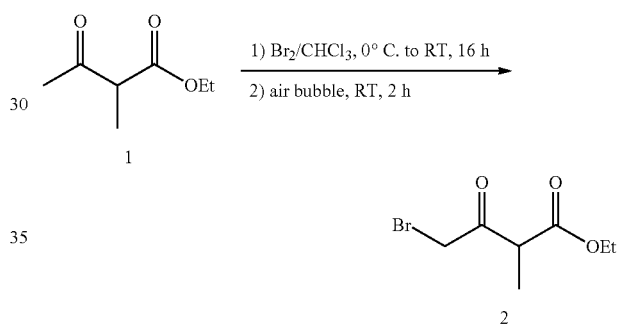

The solution of $Br_2$ (58.0 g, 364.5 mmol) in $CHCl_3$ (50 mL) was added dropwise to the solution of compound 1 (50.0 g, 347.2 mmol) in $CHCl_3$ (320 mL) at 0° C. Then the reaction mixture was allowed to warm slowly to RT and stirred for 16 h. Air was bubbled to the reaction mixture at RT for 2 h. The reaction mixture was diluted with DCM (300 mL), washed with sat. $Na_2SO_3$ (150 mL) and brine (100 mL×2). The organic layer was dried over $Na_2SO_4$, filtered, concentrated, afforded crude compound 2 (50 g) as light yellow oil without further purification. The crude product was stored in frige below 0° C.

Synthesis of 4-(bromomethyl)-7-hydroxy-6-methoxy-3-methyl-2H-chromen-2-one

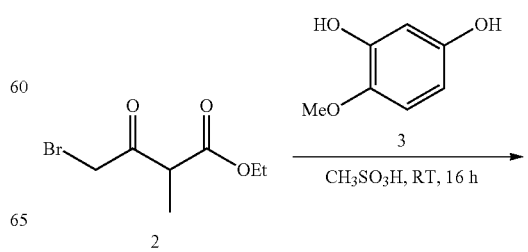

-continued

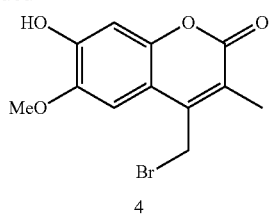

4

Compound 2 (19.0 g, 85.71 mmol) and compound 3 (10.0 g, 71.42 mmol) were added to CH₃SO₃H (80 mL) at RT. The reaction mixture was stirred at RT for 16 h, then poured into ice-water (300 mL), extracted with EA (100 mL×3). The combined EA was washed with brine, dried over Na₂SO₄, filtered, concentrated, purified by silica gel column (PE: EA=2:1), afforded 5.6 g of the crude compound 4. Then the crude product was triturated with EA, afforded compound 4 (2.5 g, 9.7%) as white solid.

Synthesis of Compound 5

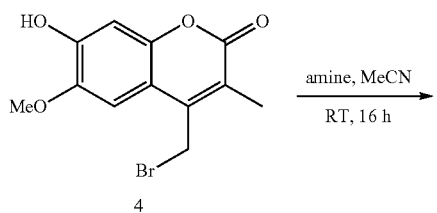

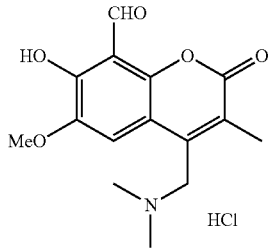

5

Compound 4 (1 eq) was added to MeCN. The solution of amine (2.5 eq) in MeCN was added dropwise at RT and stirred for 16 h. The reaction mixture was concentrated. The residue was diluted with H₂O, extracted with DCM. The combined DCM was dried over Na₂SO₄, filtered, concentrated, afforded crude compound 5 without further purification.

Synthesis of Compound 6

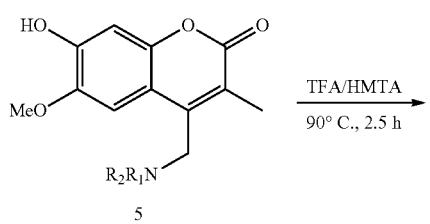

5

-continued

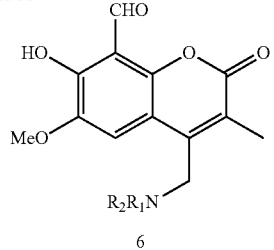

6

Compound 5 (1 eq) and HMTA (4 eq) were added to TFA. The mixture was heated to 90° C. for 2.5 h. After cooled to RT, the reaction mixture was concentrated, purified by prep-HPLC afforded compound 6.

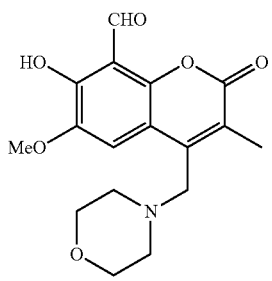 [SMILES: COc1cc2c(CN3CCOCC3)c(C)c(=O)oc2c(C=O)c1O]

7-Hydroxy-6-methoxy-3-methyl-4-(morpholinomethyl)-2-oxo-2H-chromene-8-carbaldehyde was obtained by the above procedure at 45.7% yield. ¹HNMR (CDCl₃, 400 MHz): δ 12.43 (s, 1H, OH), 10.59 (s, 1H, CHO), 7.75 (s, 1H, ArH), 3.93 (s, 3H, ArOCH₃), 3.68-3.66 (m, 6H), 2.56-2.53 (m, 4H), 2.26 (s, 3H, CH₃). MS [ESI, MH⁺]: 334.1

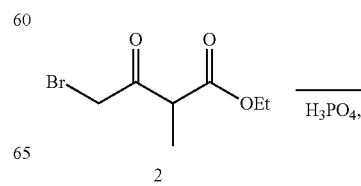

4-((Dimethylamino)methyl)-7-hydroxy-6-methoxy-3-methyl-2-oxo-2H-chromene-8-carbaldehyde hydrochloride was obtained by the above procedure at 22% yield.

¹HNMR (DMSO-d6, 400 MHz): δ 10.45 (s, 1H, CHO), 7.58 (s, 1H, ArH), 4.68 (s, 2H, NCH₂), 4.00 (s, 3H, OCH₃), 2.86 (s, 6H, 2CH₃), 2.25 (s, 3H, CH₃). MS [ESI, MH⁺]: 292.1

Example 48

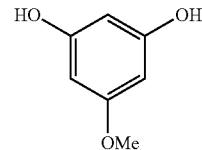

7

2

-continued

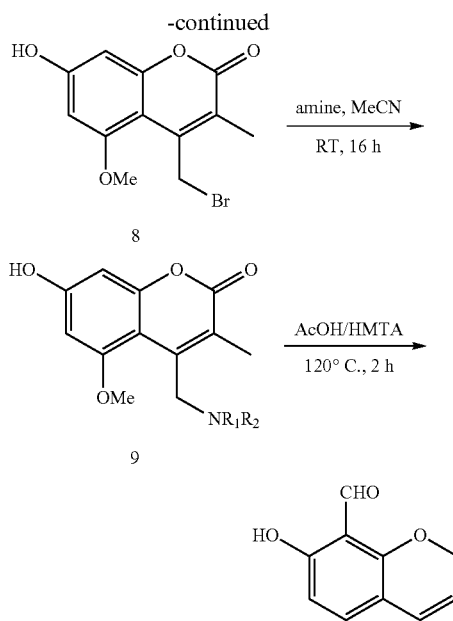

Synthesis of 4-(bromomethyl)-7-hydroxy-5-methoxy-3-methyl-2H-chromen-2-one

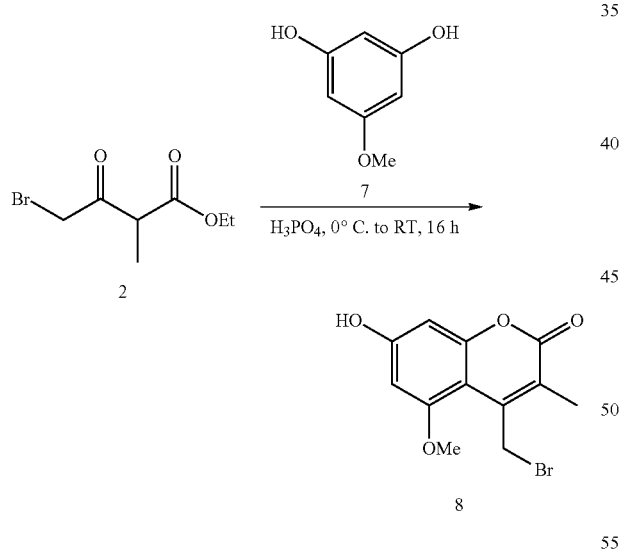

Compound 2 (38.0 g, 171.1 mmol) was added dropwise to the solution of compound 7 (20.0 g, 142.8 mmol) in $H_3PO_4$ (200 mL) at 0° C. The reaction mixture was warmed slowly to RT and stirred for 16 h, then poured into ice-water (500 mL), extracted with EA (200 mL×3). The combined EA was washed with sat. $NaHCO_3$, dried over $Na_2SO_4$, filtered, concentrated. The crude product was purified by silica gel column (PE:EA=3:1), then washed with DCM, afforded crude 4-(bromomethyl)-7-hydroxy-5-methoxy-3-methyl-2H-chromen-2-one (8 g, 55% purity) without further purification.

Synthesis of Compound 9

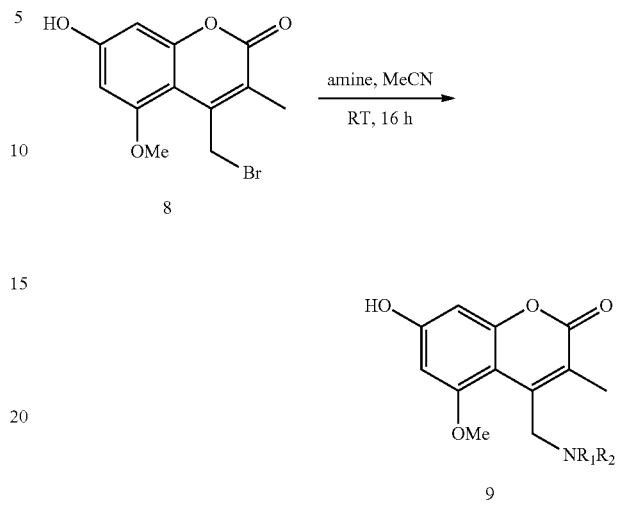

Compound 8 (1 eq) was added to MeCN. The solution of amine (2.5 eq) in MeCN was added dropwise at RT and stirred for 16 h. The reaction mixture was concentrated. 1N HCl was added to the residue, stirred for 15 min. The undissolved material was removed by filtration. The filter was washed with DCM, then basified by saturated $NaHCO_3$, extracted with DCM. The combined DCM was dried over $Na_2SO_4$, filtered, concentrated, afforded compound 9 as light green solid.

Synthesis of Compound 10

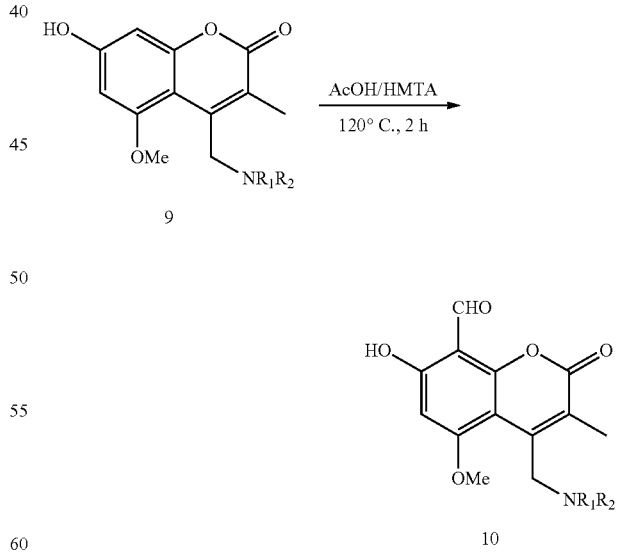

Compound 9 (1 eq) and HMTA (4 eq) were added to AcOH. The mixture was heated to 120° C. for 2 h. After cooled to RT, the reaction mixture was concentrated, purified by prep-HPLC and prep-TLC, afforded compound 10 as yellow solid.

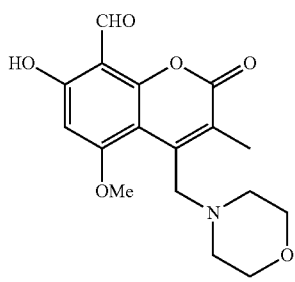 [SMILES: COc1cc(O)c(C=O)c2oc(=O)c(C)c(CN3CCOCC3)c12]

7-Hydroxy-5-methoxy-3-methyl-4-(morpholinomethyl)-2-oxo-2H-chromene-8-carbaldehyde was obtained by the above procedure at 19.6% yield. $^1$HNMR (CDCl$_3$, 400 MHz): δ 12.57 (s, 1H, OH), 10.41 (s, 1H, CHO), 6.30 (s, 1H, ArH), 3.94 (s, 3H, ArOCH$_3$), 3.83 (s, 2H, CH$_2$), 3.61 (br, 4H, 2CH$_2$), 2.48 (br, 4H, 2CH$_2$), 2.24 (s, 3H, CH$_3$). MS [ESI, MH$^+$]: 334.1.

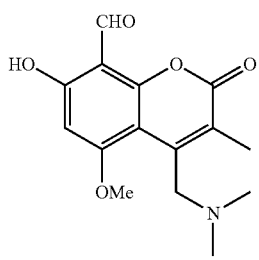 [SMILES: COc1cc(O)c(C=O)c2oc(=O)c(C)c(CN(C)C)c12]

4-((Dimethylamino)methyl)-7-hydroxy-5-methoxy-3-methyl-2-oxo-2H-chromene-8-carbaldehyde was obtained by the above procedure at 20% yield. $^1$HNMR (CDCl$_3$, 400 MHz): δ 12.54 (br, 1H, OH), 10.40 (s, 1H, CHO), 6.30 (s, 1H, ArH), 3.99 (s, 3H, ArOCH$_3$), 3.78 (s, 2H, CH$_2$), 2.29 (s, 6H, 2CH$_3$), 2.24 (s, 3H, CH$_3$). MS [ESI, MH$^+$]: 292.1.

Example 49

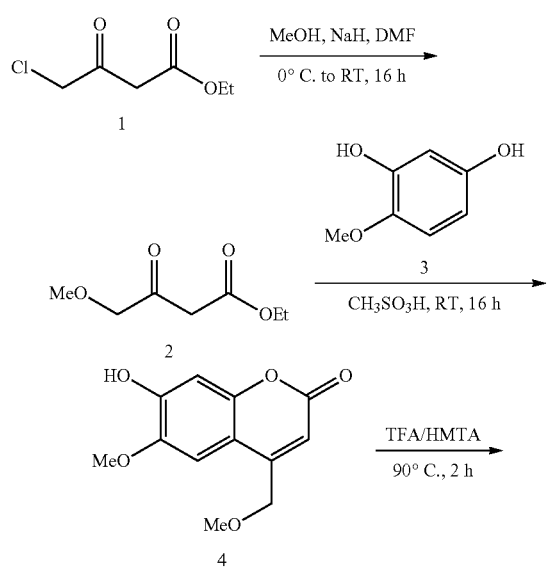

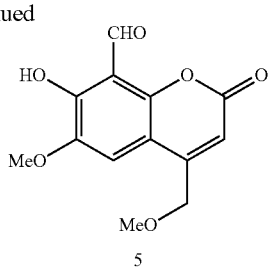

Synthesis of ethyl 4-methoxy-3-oxobutanoate

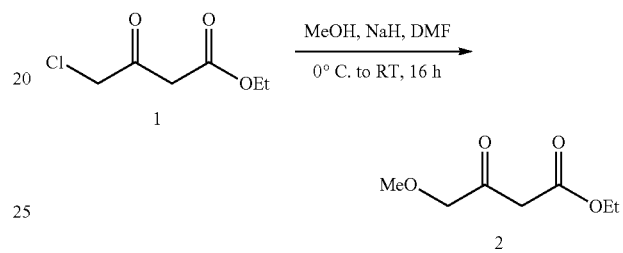

NaH (7.71 g, 192.7 mmol) was suspended in DMF (110 mL). The solution of MeOH (2.64 g, 82.5 mmol) in DMF (55 mL) was added dropwise at 0° C. After that, the mixture was stirred at 0° C. for 30 min. The solution of compound 1 (9.54 g, 57.9 mmol) in DMF (55 mL) was added dropwise at 0° C., then the reaction mixture was allowed to warm slowly to RT and stirred for 16 h. The reaction mixture was diluted with 1N HCl (400 mL), extracted with MTBE (250 mL×3). The combined organic layer was washed with H$_2$O (200 mL×5), dried over Na$_2$SO$_4$, filtered, concentrated, purified by silica gel column (PE:EA=10:1) afforded ethyl 4-methoxy-3-oxobutanoate (1.4 g, 15.1%) as light yellow oil.

Synthesis of 7-hydroxy-6-methoxy-4-(methoxymethyl)-2H-chromen-2-one

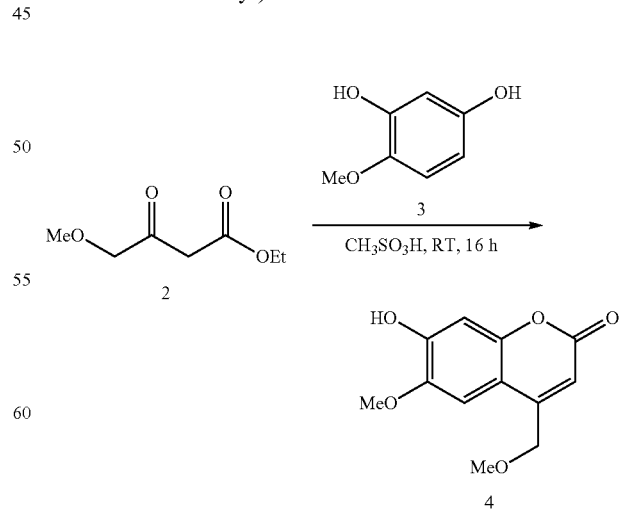

Compound 2 (1.50 g, 3.61 mmol) and compound 3 (1.24 g, 8.85 mmol) were added to CH$_3$SO$_3$H (15 mL) at RT. The reaction mixture was stirred at RT for 16 h, then poured into ice-water (100 mL), extracted with EA (30 mL×3). The combined EA was washed with sat. NaHCO₃, dried over Na₂SO₄, filtered, concentrated, purified by silica gel column (PE:EA=3:1) 7-hydroxy-6-methoxy-4-(methoxymethyl)-2H-chromen-2-one (620 mg, 27.9%) as white solid.

Synthesis of 7-hydroxy-6-methoxy-4-(methoxymethyl)-2-oxo-2H-chromene-8-carbaldehyde

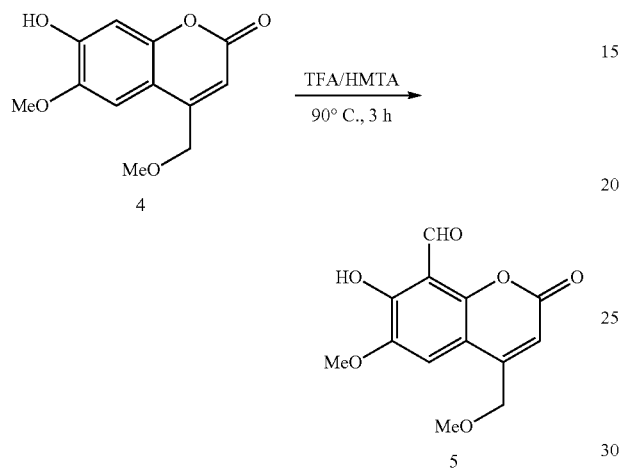

Compound 4 (520 mg, 2.21 mmol) and HMTA (1230 mg, 8.78 mmol) were added to TFA (30 mL). The mixture was heated to reflux for 3 h. After cooled to RT, the reaction mixture was concentrated, purified by pre-HPLC, afforded 7-hydroxy-6-methoxy-4-(methoxymethyl)-2-oxo-2H-chromene-8-carbaldehyde (200 mg, 34.2%) as yellow solid. ¹HNMR (CDCl₃, 400 MHz): δ 12.55 (s, 1H, OH), 10.61 (s, 1H, CHO), 7.20 (s, 1H, ArH), 6.43 (s, 1H, =CH), 4.57 (s, 2H, OCH₂), 3.95 (s, 3H, ArOCH₃), 3.50 (s, 3H, OCH₃). MS [ESI, MH⁺]: 265.2.

Example 50

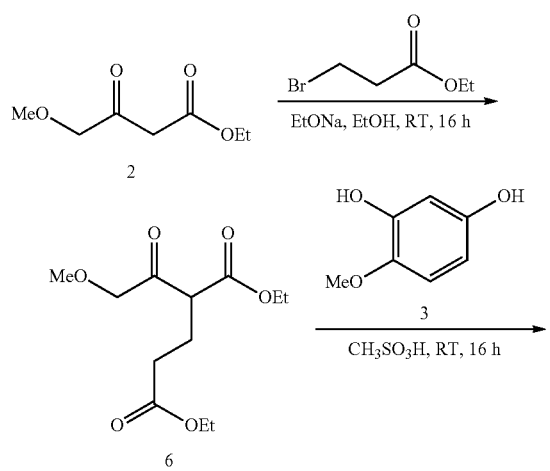

Synthesis of Compound 6

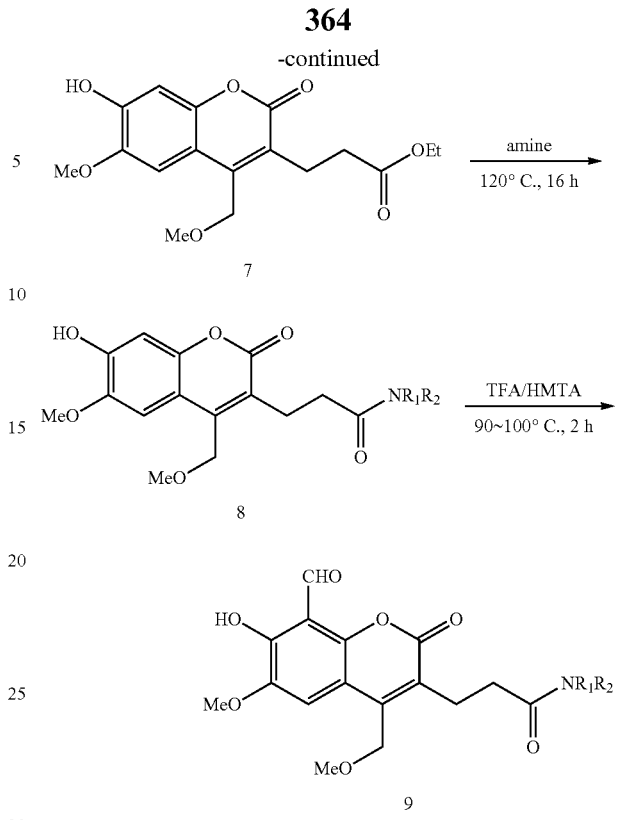

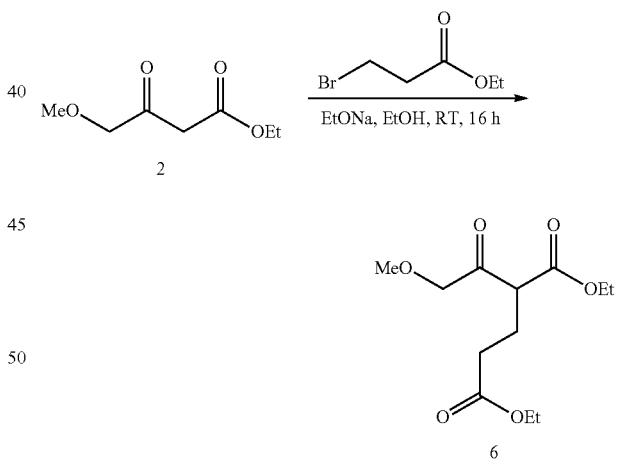

EtONa (1.48 g, 21.87 mmol) was suspended in EtOH (35 mL). The solution of compound 2 (3.50 g, 21.87 mmol) in EtOH (15 mL) was added dropwise at RT and stirred for 30 min. The solution of Br(CH₂)₂COOEt (3.93 g, 21.87 mmol) in EtOH (15 mL) was added dropwise and stirred at RT for 16 h. The reaction was quenched with 2 N HCl (10 mL), concentrated. The residue was diluted with H₂O (50 mL), extracted with DCM (25 mL×3). The combined DCM was dried over Na₂SO₄, filtered, concentrated, afforded crude compound 6. (5.4 g) as yellow oil, without further purification.

Synthesis of Compound 7

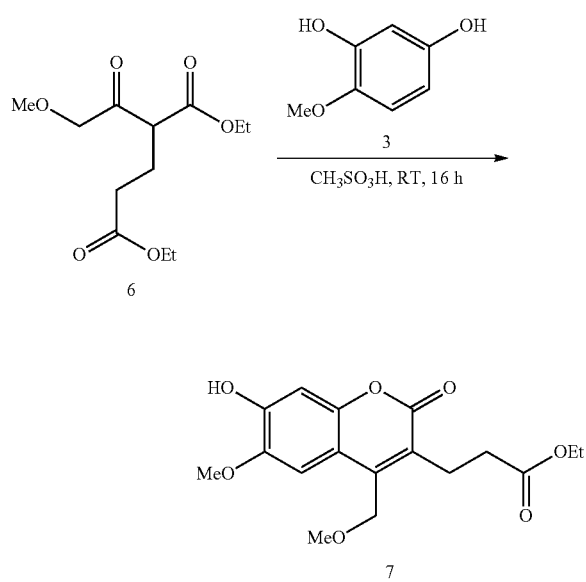

Compound 6 (5.4 g, 20.76 mmol) and compound 3 (2.32 g, 8.85 mmol) were added to CH$_3$SO$_3$H (55 mL) at RT. The reaction mixture was stirred at RT for 16 h, then poured into ice-water (300 mL), extracted with EA (100 mL×3). The combined EA was washed with sat. NaHCO$_3$, dried over Na$_2$SO$_4$, filtered, concentrated, purified by silica gel column (PE:EA=3:1), afforded compound 7 (3.0 g, 42.9%) as white solid.

Synthesis of Compound 8

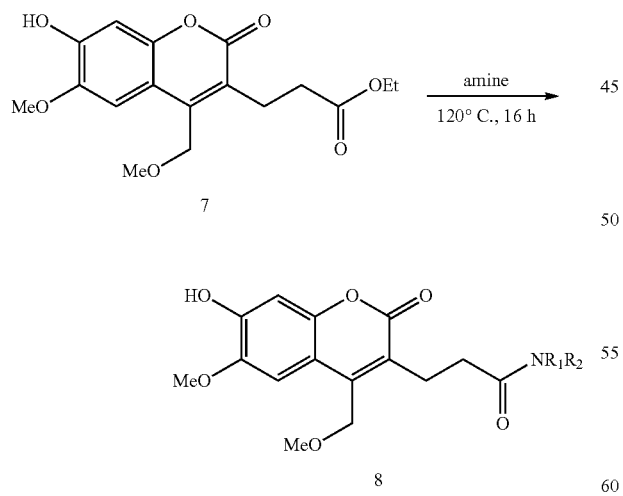

Compound 7 was added to amine and the reaction mixture was stirred at 120° C. for 16 h. LC-MS showed that the starting material was almost consumed completely. The solvent was removed under vacuum. The residue was purified by silica gel column, afforded compound 8.

Synthesis of Compound 9

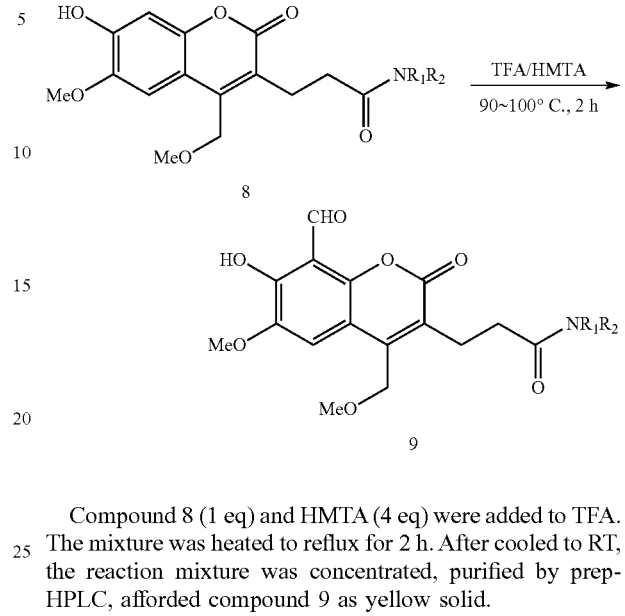

Compound 8 (1 eq) and HMTA (4 eq) were added to TFA. The mixture was heated to reflux for 2 h. After cooled to RT, the reaction mixture was concentrated, purified by prep-HPLC, afforded compound 9 as yellow solid.

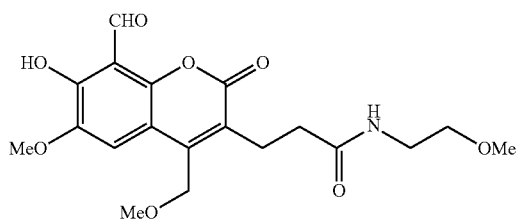 [SMILES: COCCNC(=O)CCc1c(COC)c2cc(OC)c(O)c(C=O)c2oc1=O]

3-(8-formyl-7-hydroxy-6-methoxy-4-(methoxymethyl)-2-oxo-2H-chromen-3-yl)-N-(2-methoxyethyl)propanamide was obtained by the above procedure from amine A1. 26.7% yield. $^1$HNMR (CDCl$_3$, 400 MHz): δ2.47 (s, 1H, OH), 10.58 (s, 1H, CHO), 7.44 (s, 1H, ArH), 5.84 (br, 1H, NH), 4.72 (s, 2H, OCH$_2$), 3.94 (s, 3H, ArOCH$_3$), 3.46 (s, 3H, OCH$_3$), 3.40-3.39 (m, 4H, 2CH$_2$), 3.29 (s, 3H, OCH$_3$), 3.03 (t, J=7.2 Hz, 2H), 2.51 (t, J=7.2 Hz, 2H). MS [ESI, MH$^+$]: 394.2.

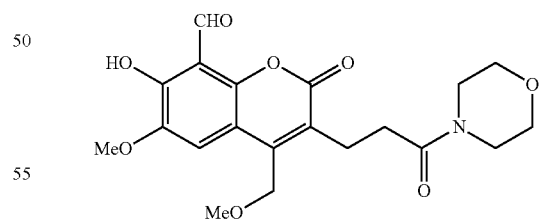

7-Hydroxy-6-methoxy-4-(methoxymethyl)-3-(3-morpholino-3-oxopropyl)-2-oxo-2H-chromene-8-carbaldehyde was obtained by the above procedure from amine A2. 12.7% yield. $^1$HNMR (CDCl$_3$, 400 MHz): δ 12.44 (s, 1H, OH), 10.58 (s, 1H, CHO), 7.44 (s, 1H, ArH), 4.76 (s, 2H, OCH$_2$), 3.94 (s, 3H, ArOCH$_3$), 3.66-3.63 (m, 4H, 2CH$_2$), 3.59-3.58 (m, 2H, CH$_2$), 3.50-3.49 (m, 2H, CH$_2$), 3.49 (s, 3H, OCH$_3$), 3.02 (t, 2H, J=7.2 Hz, CH$_2$), 2.65 (t, 2H, J=7.2 Hz, CH$_2$). MS [ESI, MH$^+$]: 406.2

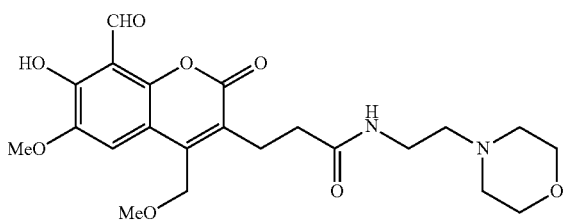 [SMILES: COCc1c(CCC(=O)NCCN2CCOCC2)c(=O)oc2c(C=O)c(O)c(OC)cc12]

3-(8-Formyl-7-hydroxy-6-methoxy-4-(methoxymethyl)-2-oxo-2H-chromen-3-yl)-N-(2-morpholinoethyl)propanamide as obtained by the above procedure from amine A5. 37.9% yield. $^1$HNMR (CDCl$_3$, 400 MHz): δ10.58 (s, 1H, CHO), 7.44 (s, 1H, ArH), 4.72 (s, 2H, CH$_2$), 3.94 (s, 3H, ArOCH$_3$), 3.73 (br, 4H, 2CH$_2$), 3.46 (s, 3H, OCH$_3$), 3.35 (br, 2H, CH$_2$), 3.04 (t, J=7.2 Hz, 2H, CH$_2$), 2.53-2.50 (m, 8H); MS [ESI, MH$^+$]: 449.2

Example 51

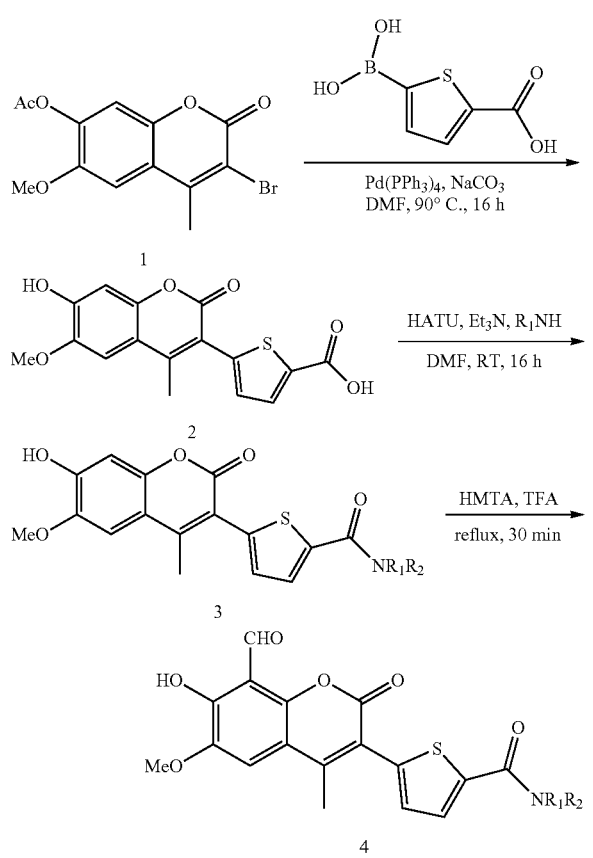

Synthesis of 5-(7-hydroxy-6-methoxy-4-methyl-2-oxo-2H-chromen-3-yl) thiophene-2-carboxylic acid

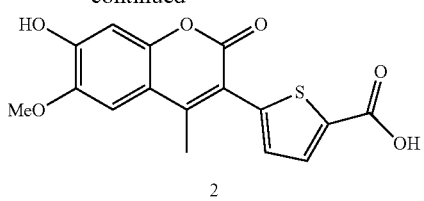

Compound 1 (15 g, 46 mmol), the boric acid (8.7 g, 50.6 mmol), Pd(PPh$_3$)$_4$ (1.88 g, 2.3 mmol), Na$_2$CO$_3$ (12.1 g, 115 mmol) were added to DMF (250 mL). The reaction mixture was degassed with N$_2$ for three times, and then heated to 90° C. for 16 h. After cooled to RT, the solvent was concentrated, the residue was dissolved in sat Na$_2$CO$_3$ (150 mL). The aqueous was washed with DCM (100 mL×4), and then acidified by con.HCl to pH to ~4. The result precipitate was collected by filtration, triturated with hot EA (50 mL), afforded compound 2 (6.5 g, 42%) as yellow solid. $^1$HNMR (DMSO-d6, 400 MHz): δ 10.55 (s, 1H), 7.71 (d, J=4.0 Hz, 1H), 7.24 (s, 1H), 7.19 (d, J=4.0 Hz, 1H), 6.86 (s, 1H), 3.88 (s, 3H), 2.45 (s, 3H).

Synthesis of Compound 3

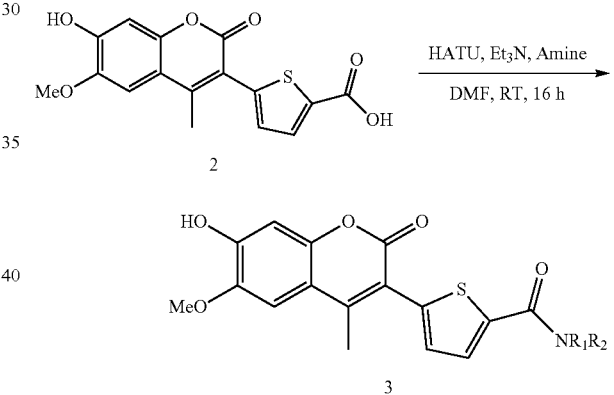

Compound 2 (1 eq), HATU (1.5 eq) and Et$_3$N (2.5 eq) were added to dry DMF. The mixture was stirred at RT for 30 min, then amine (1.5 eq) was added. The reaction mixture was stirred at RT overnight. 2N HCl was added, later extracted with DCM. The combined DCM was washed with saturated NaHCO$_3$, dried over Na$_2$SO$_4$, filtered, concentrated, purified by silica gel column, afforded compound 3.

Synthesis of Compound 4

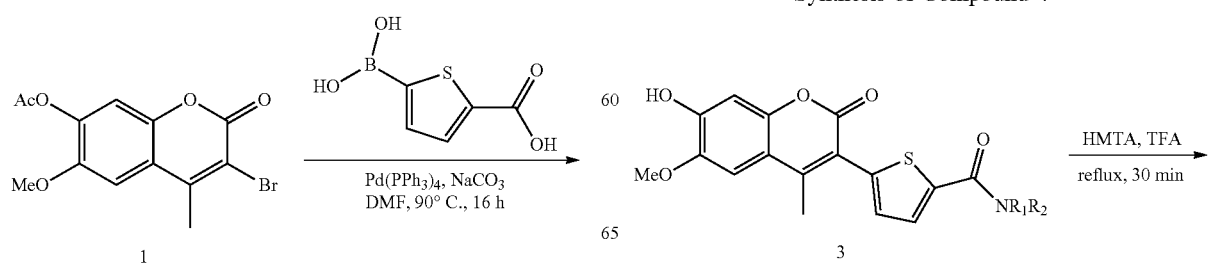

-continued

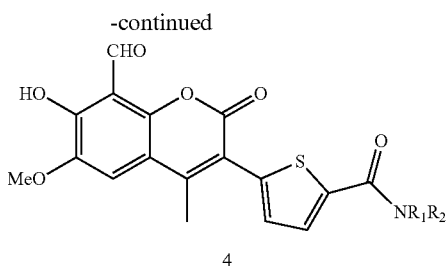

4

Compound 3 (1 eq) and HMTA (4 eq) were added to TFA. The mixture was heated to reflux for 30 min. After cooled to RT, the reaction mixture was concentrated, purified by prep-HPLC, afforded compound 4.

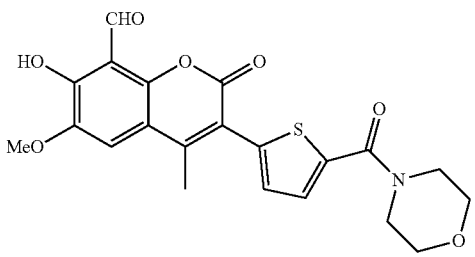 [SMILES: COc1cc2c(C)c(-c3ccc(C(=O)N4CCOCC4)s3)c(=O)oc2c(C=O)c1O]

7-Hydroxy-6-methoxy-4-methyl-3-(5-(morpholine-4-carbonyl)thiophen-2-yl)-2-oxo-2H-chromene-8-carbaldehyde was obtained by the above procedure from amine A2. 31% yield. $^1$HNMR (DMSO-d6, 400 MHz): δ 10.46 (s, 1H), 10.38 (s, 1H), 7.53 (s, 1H), 7.44 (d, J=3.6 Hz, 1H), 7.17 (d, J=3.6 Hz, 1H), 3.94 (s, 3H), 3.67-3.64 (m, 8H), 2.48 (s, 3H). $^1$HNMR (CDCl$_3$, 400 MHz): δ2.57 (s, 1H), 10.63 (s, 1H), 7.31 (d, J=3.6 Hz, 1H), 7.23 (s, 1H), 7.06 (d, J=3.6 Hz, 1H), 3.98 (s, 3H), 3.81-3.74 (m, 8H), 2.48 (s, 3H). MS [ESI, MH$^+$]: 430.1.

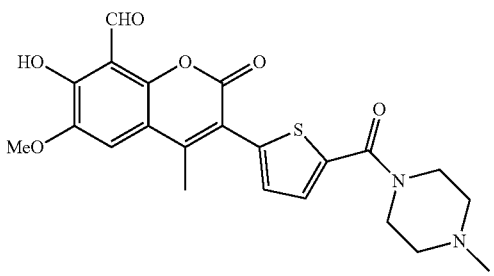 [SMILES: COc1cc2c(C)c(-c3ccc(C(=O)N4CCN(C)CC4)s3)c(=O)oc2c(C=O)c1O]

7-Hydroxy-6-methoxy-4-methyl-3-(5-(4-methylpiperazine-1-carbonyl)thiophen-2-yl)-2-oxo-2H-chromene-8-carbaldehyde hydrochloride was obtained by the above procedure from amine A3. 34% yield. $^1$HNMR (MeOD, 400 MHz): δ 7.48 (d, J=4.0 Hz, 1H), 7.23 (s, 1H), 7.13 (d, J=4.0 Hz, 1H), 6.02 (s, 1H), 4.66-4.62 (m, 2H), 3.94 (s, 3H), 3.61-3.52 (m, 4H), 3.25-3.19 (m, 2H), 2.97 (s, 3H), 2.50 (s, 3H).

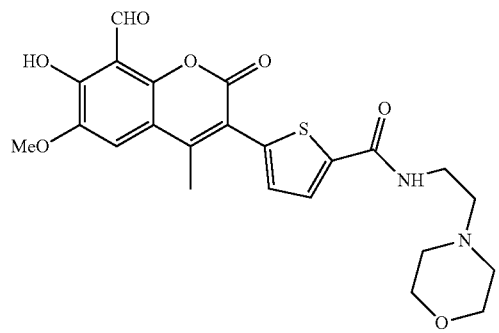 [SMILES: COc1cc2c(C)c(-c3ccc(C(=O)NCCN4CCOCC4)s3)c(=O)oc2c(C=O)c1O]

5-(8-Formyl-7-hydroxy-6-methoxy-4-methyl-2-oxo-2H-chromen-3-yl)-N-(2-morpholinoethyl)thiophene-2-carboxamide hydrochloride was obtained by the above procedure from amine A5. 22% yield. $^1$HNMR (MeOD, 400 MHz): δ7.73 (d, J=4 Hz, 1H), 7.27 (s, 1H), 7.14 (d, 4 Hz, 1H), 6.03 (s, 1H), 4.11-4.07 (m, 2H), 3.95 (s, 3H), 3.82-3.76 (m, 4H), 3.70-3.67 (m, 2H), 3.43-3.40 (m, 2H), 3.25-3.21 (m, 2H), 2.50 (s, 3H).
$^1$HNMR (DMSO, 400 MHz, T=273+80K): δ10.49 (s, 1H), 8.88 (t, J=6.0 Hz, 1H), 7.90 (d, J=4 Hz, 1H), 7.55 (s, 1H), 7.18 (d, J=4 Hz, 1H), 3.95 (s, 3H), 3.94-3.92 (m, 4H), 3.74-3.69 (m, 2H), 3.34-3.31 (m, 4H), 3.31-3.10 (m, 2H), 2.48 (s, 3H). MS [ESI, MH$^+$]: 473.2.

Example 52

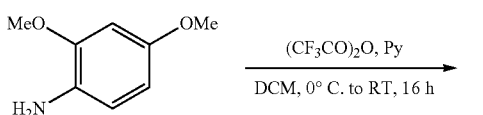

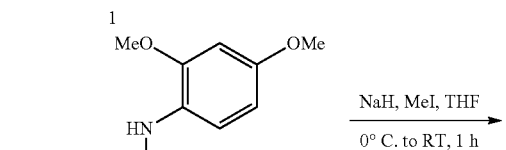

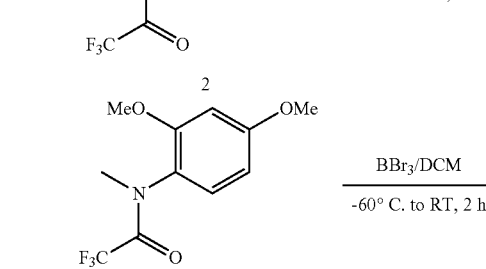

-continued

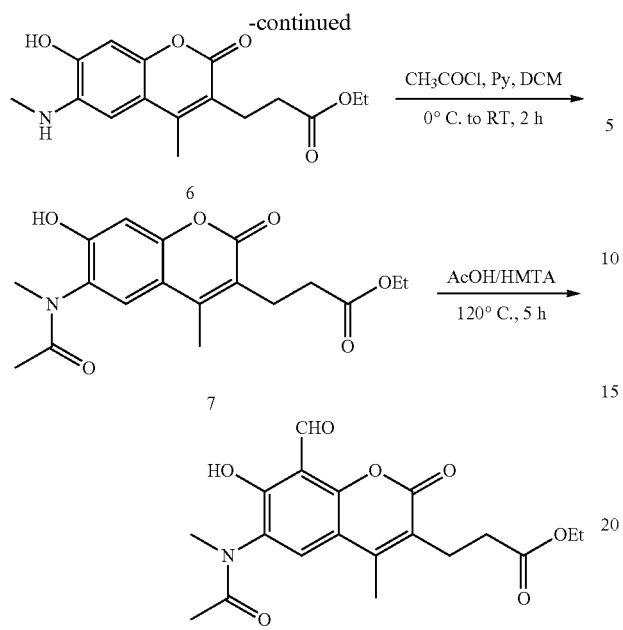

Synthesis of N-(2,4-dimethoxyphenyl)-2,2,2-trifluoroacetamide

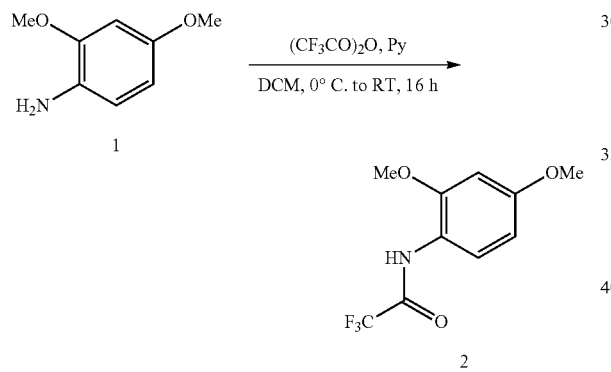

Compound 1 (38 g, 249.6 mmol) and pyridine (21.7 g, 275.0 mmol) were dissolved in DCM (750 mL). (CF₃CO)₂O (57.7 g, 275.0 mmol) was added dropwise at 0° C. After that the reaction mixture was stirred at RT for 16 h. The reaction mixture was diluted with DCM (500 mL), washed with 1N HCl, concentrated. The residue was purified by silica gel column (PE:EA=10:1), afforded compound 2 (45 g, 72%) as white solid.

Synthesis of N-(2,4-dimethoxyphenyl)-2,2,2-trifluoro-N-methylacetamide

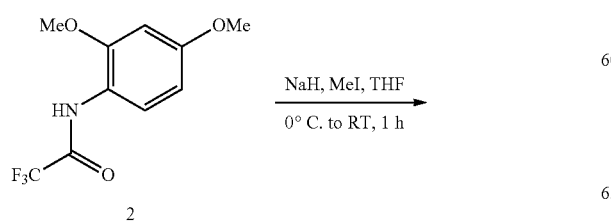

-continued

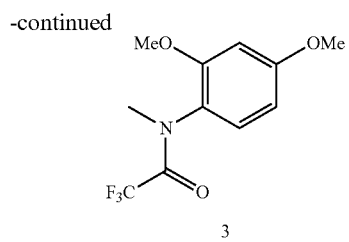

NaH (2.2 g, 90.3 mmol) was suspended in DMF (25 mL), cooled to −20° C. The solution of compound 2 (15 g, 60.2 mmol) in DMF (50 mL) was added dropwise and stirred 0° C. for 1 h. MeI (17.1 g, 120.4 mmol) was added dropwise at −20° C., then stirred at RT for another 1 h. The reaction mixture was quenched with H₂O, extracted with EA, dried over Na₂SO₄, filtered, concentrated. The residue was purified by silica gel column (PE:EA=3:1), afforded compound 3 (14 g, 88%) as white solid.

Synthesis of N-(2,4-dihydroxyphenyl)-2,2,2-trifluoro-N-methylacetamide

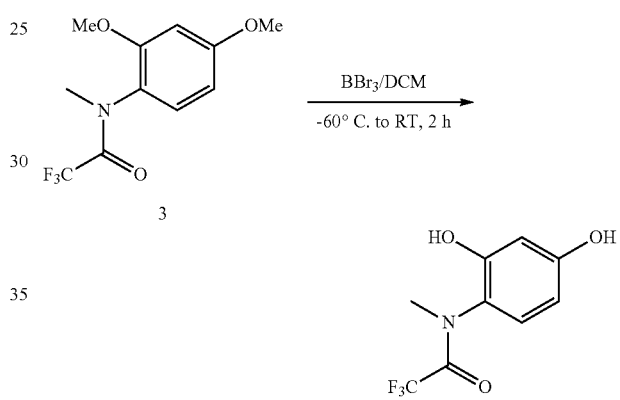

Compound 3 (8 g, 30.4 mmol) was dissolved in DCM (80 mL), cooled to −60° C. The solution of BBr₃ (30.4 g, 121.6 mmol) in DCM (40 mL) was added at −60° C. After that, the reaction mixture was stirred at RT for 1 h. Then the reaction was quenched with H₂O, extracted with DCM. The combined DCM was dried over Na₂SO₄, filtered, concentrated. The residue was purified by silica gel column (PE:EA=1:1), afforded compound 4 (6.1 g, 85.9%) as white solid.

Synthesis of ethyl 3-(7-hydroxy-4-methyl-6-(methylamino)-2-oxo-2H-chromen-3-yl)propanoate

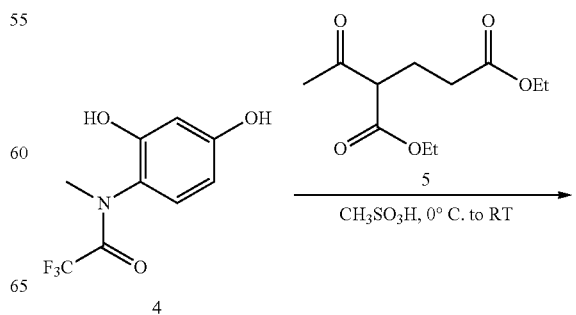

373

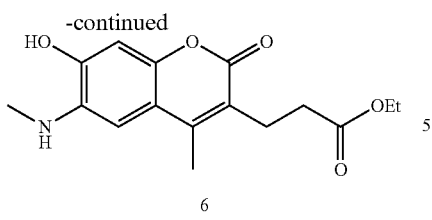

6

374

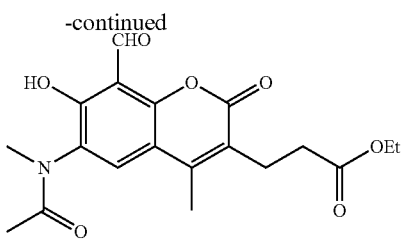

Compound 4 (5 g, 21.2 mmol) and compound 5 (5.6 g, 24.3 mmol) were stirred at 0° C. CH₃SO₃H (50 mL) was added dropwise. Then the mixture was stirred at RT for 16 h. The reaction mixture was poured into crush ice, extracted by DCM. The DCM layer was washed with sat.Na₂HPO₄, dried over Na₂SO₄, filtered, concentrated. The residue was purified by silica gel column (DCM:EtOH=50:1), afforded compound 6 (1.2 g, 18%) as light yellow solid.

Synthesis of ethyl 3-(7-hydroxy-4-methyl-6-(N-methylacetamido)-2-oxo-2H-chromen-3-yl) propanoate

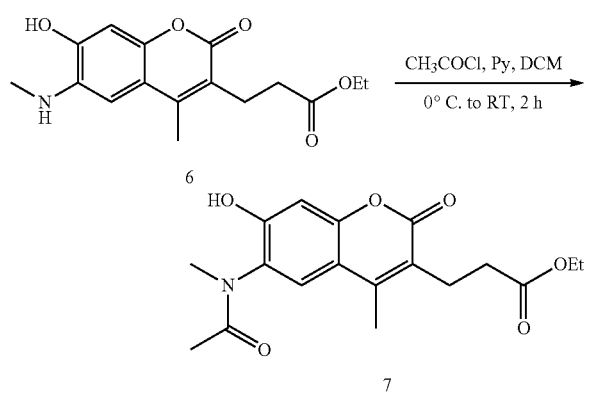

Compound 6 (0.7 g, 2.2 mmol) and pyridine (0.18 g, 2.3 mmol) were dissolved in DCM (10 mL). CH₃COCl (0.2 g, 2.5 mmol) was added dropwise at 0° C. After that the reaction mixture was stirred at RT for 2 h. The reaction mixture was diluted with DCM (10 mL), washed with 1N HCl, concentrated. The residue was purified by silica gel column (DCM:EtOH=100:1), afforded compound 7 (0.56 g, 70%) as light yellow solid. ¹HNMR (CDCl₃, 400 MHz): δ 7.38 (s, 1H, ArH), 7.00 (s, 1H, ArH), 4.13 (q, J=7.2 Hz, 2H, CH₂), 3.46 (s, 3H, NCH₃), 2.96 (t, J=7.2 Hz, 2H, CH₂), 2.61 (t, J=7.2 Hz, 2H, CH₂), 2.43 (s, 3H, CH₃), 1.90 (s, 3H, CH₃), 1.24 (t, J=7.2 Hz, 3H, CH₃).

Synthesis of ethyl 3-(8-formyl-7-hydroxy-4-methyl-6-(N-methylacetamido)-2-oxo-2H-chromen-3-yl) propanoate

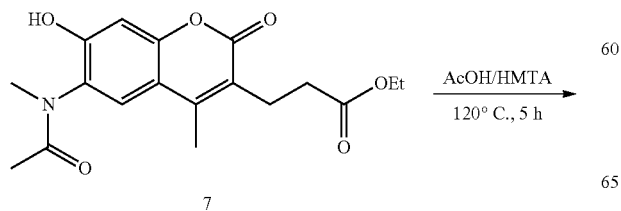

Compound 7 (516 mg, 1.48 mmol) and HMTA (832.8 mg, 5.94 mmol) were added to AcOH (13 mL). The reaction mixture was heated to 120° C. for 5 h. The reaction mixture was concentrated. The residue was purified by prep-HPLC and prep-TLC successively, afforded Synthesis of ethyl 3-(8-formyl-7-hydroxy-4-methyl-6-(N-methylacetamido)-2-oxo-2H-chromen-3-yl)propanoate (65 mg, 11.7%) as yellow solid. MS [ESI, MH⁺]: 376.1. ¹HNMR (CDCl₃, 400 MHz): δ 12.42 (s, 1H, OH), 10.63 (s, 1H, CHO), 7.67 (s, 1H, ArH), 4.13 (q, J=7.2 Hz, 2H, CH₂), 3.21 (s, 3H, NCH₃), 2.98 (t, J=7.2 Hz, 2H, CH₂), 2.63 (t, J=7.2 Hz, 2H, CH₂), 2.46 (s, 3H, CH₃), 1.86 (s, 3H, CH₃), 1.24 (t, J=7.2 Hz, 3H, CH₃).

Example 53

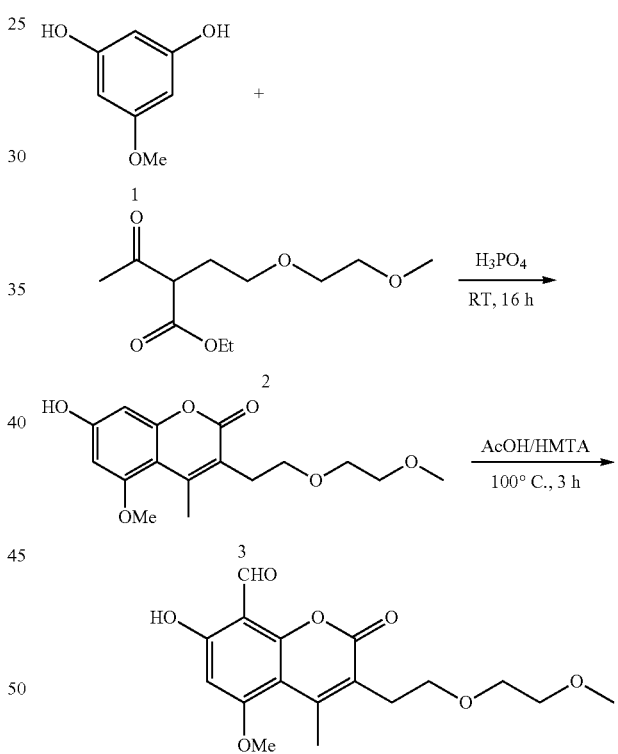

Synthesis of 7-hydroxy-5-methoxy-3-(2-(2-methoxyethoxy)ethyl)-4-methyl-2H-chromen-2-one

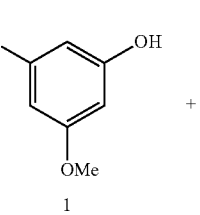

1

Example 54

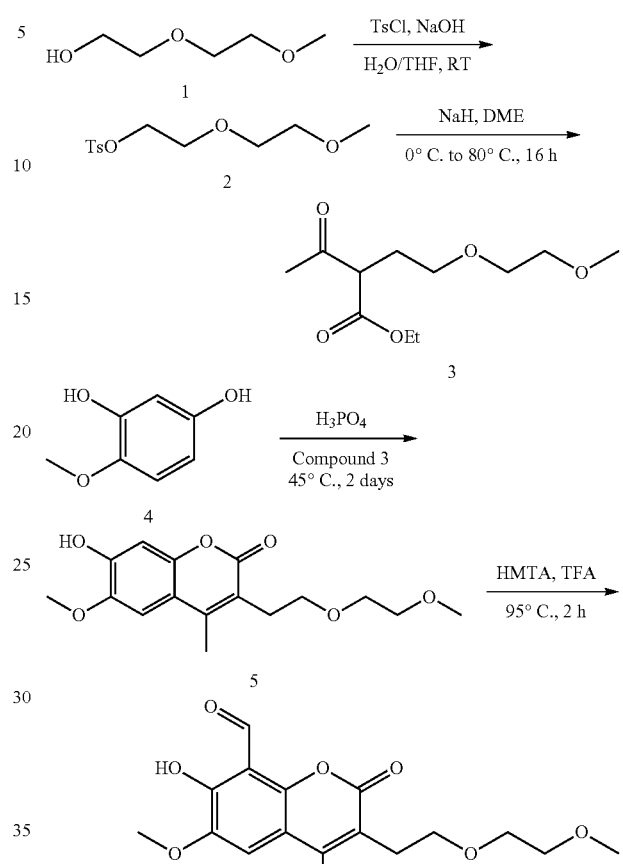

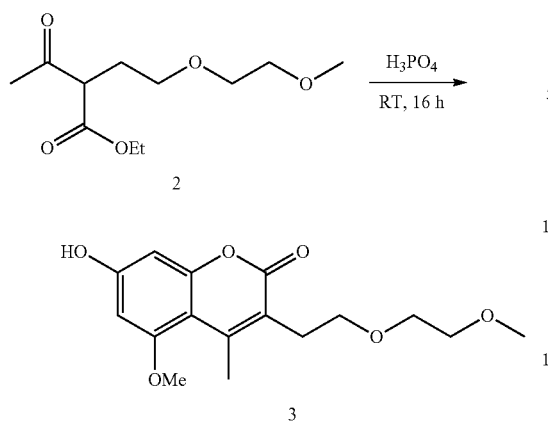

Compound 1 (0.67 g, 4.8 mmol) and compound 2 (1.13 g, 4.8 mmol) were stirred at 0° C. H₃PO₄ (15 mL) was added dropwise. Then the mixture was stirred at RT for 16 h. The reaction mixture was poured into crush ice, extracted by EA. The EA layer was concentrated; DCM (15 mL) was added, stirred for 15 min. The undissolved material was removed by filtration. The filter was concentrated. The residue was purified by prep-TLC, afforded crude compound 3 (687 mg, 60% purity) without further purification.

Synthesis of 7-hydroxy-5-methoxy-3-(2-(2-methoxyethoxy)ethyl)-4-methyl-2-oxo-2H-chromene-8-carbaldehyde

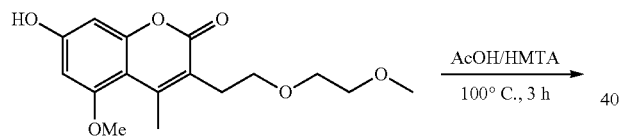

7-hydroxy-5-methoxy-3-(2-(2-methoxyethoxy)ethyl)-4-methyl-2-oxo-2H-chromene-8-carbaldehyde Compound 3 (0.58 g, 1.88 mmol) and HMTA (1.05 g, 7.5 mmol) were added to AcOH (25 mL). The reaction mixture was heated to 100° C. under N₂ for 3 h. The solvent was removed under vacuum, diluted with H₂O, extracted by EA, concentrated. The residue was purified by prep-TLC, afforded 7-hydroxy-5-methoxy-3-(2-(2-methoxyethoxy)ethyl)-4-methyl-2-oxo-2H-chromene-8-carbaldehyde (60 mg, 15.8%) as yellow solid. ¹HNMR (CDCl₃, 400 MHz): δ 12.58 (s, 1H, OH), 10.38 (s, 1H, CHO), 6.26 (s, 1H, ArH), 3.93 (s, 3H, ArOCH₃) 3.63-3.60 (m, 4H), 3.53-3.50 (m, 2H), 3.36 (s, 3H, CH₃), 2.95 (t, J=7.2 Hz, 2H), 2.56 (s, 3H, CH₃). MS [ESI, MH⁺]: 337.0

Synthesis of compound 2

The solution of NaOH (2.38 g, 0.0595 mol) in H₂O (125 mL) was mixed together with the solution of compound 1 (5 g, 0.042 mol) in THF (200 mL). Then the mixture was cooled to 0° C., a solution of TsCl (7.38 g, 0.0388 mol) in THF (200 mL) was added dropwise while keeping the inner temperature below 5° C. After that, the reaction mixture was stirred at 0° C.~5° C. while monitoring the reaction progress with TLC. After the reaction was completed (~2 h), the mixture was poured into ice-water (500 mL), extracted with DCM (150 mL×3). The combined DCM was washed with water and brine, dried over Na₂SO₄, concentrated to afford compound 2 (9.50 g, yield: 89%) as light yellow needle solid without further purification. ¹H NMR (400 MHz, CDCl₃): δ 7.79 (d, J=8.4 Hz, 2H, ArH), 7.33 (d, J=8.4 Hz, 2H, ArH), 4.16 (t, J=4.8 Hz, 2H, CH$_2$), 3.68 (t, J=4.8 Hz, 2H, CH$_2$), 3.58-3.56 (m, 2H, CH$_2$), 3.48-3.47 (m, 2H, CH$_2$), 3.34 (s, 3H, OCH$_3$), 2.44 (s, 3H, ArCH$_3$).

Synthesis of compound 3

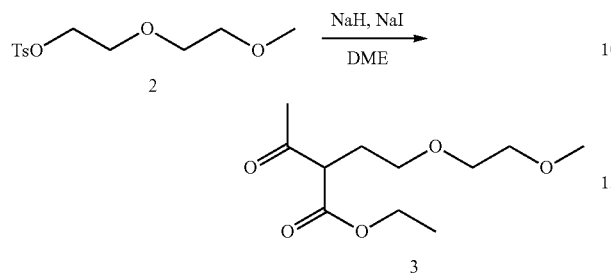

To the suspension of NaH (0.992 g, 0.0248 mol) in DME (25 mL) was added dropwise the solution of CH$_3$COCH$_2$COOEt (3.07 g, 0.0236 mol) in DME (550 mL) at 0° C. After that, the mixture was stirred at RT for 30 min. The solution of compound 2 (6.79 g, 0.0247 mmol) in DME (100 mL) and NaI (3.72 g, 0.0248 mol) were added to the reaction mixture successively at RT. The result mixture was stirred at RT for 2 h until some precipitate was formed. Then the mixture was heated to 80° C. overnight under N$_2$. Progress of this reaction was monitored by LCMS. After the reaction was completed (~16 h), the undisclosed material was removed by filtration. The filtrate was concentrated, diluted by H$_2$O, acidified by 2N HCl to pH=~3, extracted by DCM (100 mL×3). The combined DCM was concentrated, purified by silica gel column (PE:EA=6:1) to afford compound 3 as light yellow oil (1.8 g, 32% yield). HNMR indicated few EA entrained that didn't make influence on the next step.

$^1$H NMR (400 MHz, CDCl$_3$): δ 4.19-4.16 (m, 2H, CH$_2$), 4.12-4.10 (m, 1H, CH), 3.66 (m, 1H, CH), 3.52-3.48 (m, 6H, 3CH$_2$), 3.36 (s, 3H, OCH$_3$), 2.25 (s, 3H, COCH$_3$), 2.17-2.11 (m, 2H, CH$_2$), 1.49 (t, J=7.2 Hz, 3H, CH$_3$).

Synthesis of compound 5

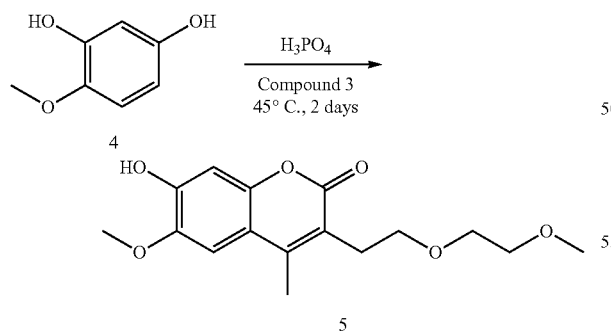

Compound 3 (2.25 g, 0.0097 mol) and 2-hydroxyl-3-methoxyl-phenol (1.30 g, 0.0093 mol) were added to H$_3$PO$_4$ (200 mL). The reaction mixture was stirred at 45° C. for 2 days. Progress of this reaction was monitored by LCMS. After the reaction was completed (~48 h), the mixture was diluted with EA (100 mL), poured into ice-water (1 L) and stirred for 15 min. Then the solid was collected by filtration, washed with cold sat NaHCO$_3$, brine and H$_2$O successively. The solid was dried by azeotropy with toluene to afford compound 4 as light yellow solid (1.25 g, 41% yield). $^1$H NMR (400 MHz, DMSO-d6): δ 7.14 (s, 1H, ArH), 6.74 (s, 1H, ArH), 3.85 (s, 3H, CH$_3$), 3.49-3.47 (m, 4H, 2CH$_2$), 3.41-3.33 (m, 2H, CH$_2$), 3.20 (s, 3H, CH$_3$), 2.78 (t, J=7.2 Hz, 2H, CH$_2$), 2.40 (s, 3H, CH$_3$).

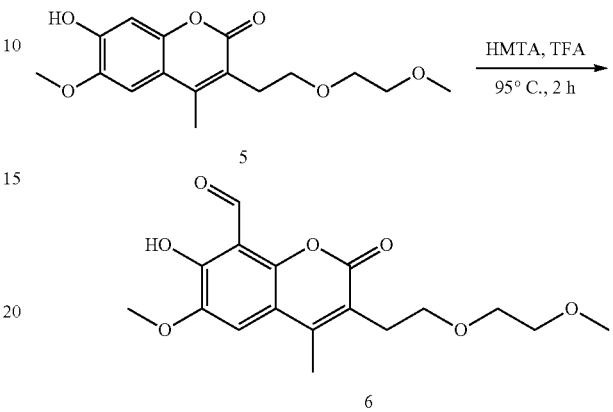

7-Hydroxy-6-methoxy-3-(2-(2-methoxyethoxy)ethyl)-4-methyl-2-oxo-2H-chromene-8-carbaldehyde: Compound 5 (2.0 g, 0.0064 mol) and HMTA (3.65 g, 0.026 mol) were added to TFA (85 mL). The reaction mixture was heated to 95° C. for 2 h. Progress of this reaction was monitored by LCMS. After the reaction was completed, the reaction mixture was concentrated. The residue was diluted with H$_2$O, extracted by DCM (100 mL×3), the combined DCM was washed with cold sat.NaHCO$_3$, brine, dried over Na$_2$SO$_4$, concentrated. The crude product was purified by silica gel column (DCM:MeOH=100:1) to afforded 1.3 g of desired product (94.7% purity on 220 nm). The product was further purification by recrystallization from EA to afford 7-hydroxy-6-methoxy-3-(2-(2-methoxyethoxy)ethyl)-4-methyl-2-oxo-2H-chromene-8-carbaldehyde (0.8 g, 37% yield) as yellow solid. $^1$H NMR (400 MHz, CDCl$_3$): δ 12.46 (s, 1H, OH), 10.66 (s, 1H, CHO), 7.30 (s, 1H, ArH), 4.01 (s, 3H, ArOCH$_3$), 3.72 (t, J=6.8 Hz, 2H, CH$_2$), 3.65-3.64 (m, 2H, CH$_2$), 3.56-3.55 (m, 2H, CH$_2$), 3.40 (s, 3H, OCH$_3$), 3.02 (t, J=6.8 Hz, 2H, CH$_2$), 2.49 (s, 3H, CH$_3$); LCMS [M+H]$^+$=337.2.

Example 55

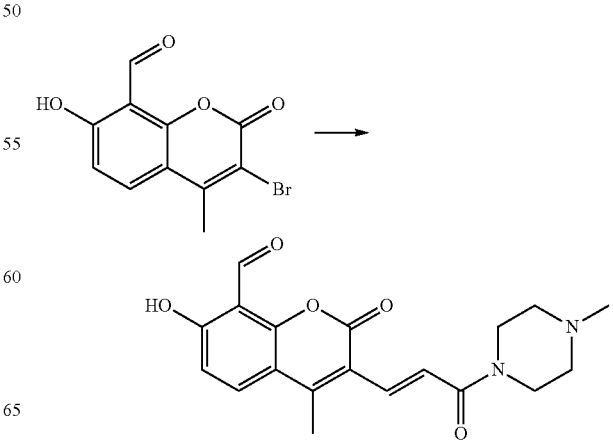

7-Hydroxy-4-methyl-3-[3-(4-methyl-piperazin-1-yl)-3-oxo-propenyl]-2-oxo-2H-chromene-8-carbaldehyde:

3-Bromo-7-hydroxy-4-methyl-2-oxo-2H-chromene-8-carbaldehyde (142 mg, 0.50 mmol), 1-(4-methyl-piperazin-1-yl)-propenone (93 mg, 0.60 mmol), palladium acetate (4 mg, 15 µmol), tri-o-tolyl-phosphane (9 mg, 30 µmol) and silver acetate (167 mg, 1.0 mmol) were dissolved in abs. N,N-dimethylformamide (4 mL). The mixture was irradiated in a microwave reactor for 1 h at 120° C. under inert atmosphere. The reaction mixture was poured into water (10 mL) and extracted with chloroform (3×15 mL). The combined organic layers were dried (Na2SO4) and evaporated. The title compound (15 mg, 0.042 mmol, 8%) was isolated by column chromatography (Kieselgel 60), with chloroform as eluent, as a yellow powder. $^1$HNMR (400 MHz, DMSO-d6) δ ppm 10.43 (s, 1H), 8.05 (d, J=9.0 Hz, 1H), 7.59 (d, J=15.1 Hz, 1H), 7.50 (d, J=15.1 Hz, 1H), 6.92 (d, J=9.0 Hz, 1H), 3.56-3.66 (m, 4H), 2.55 (s, 3H), 2.38 (br. s., 4H), 2.27 (s, 3H).

Example 56

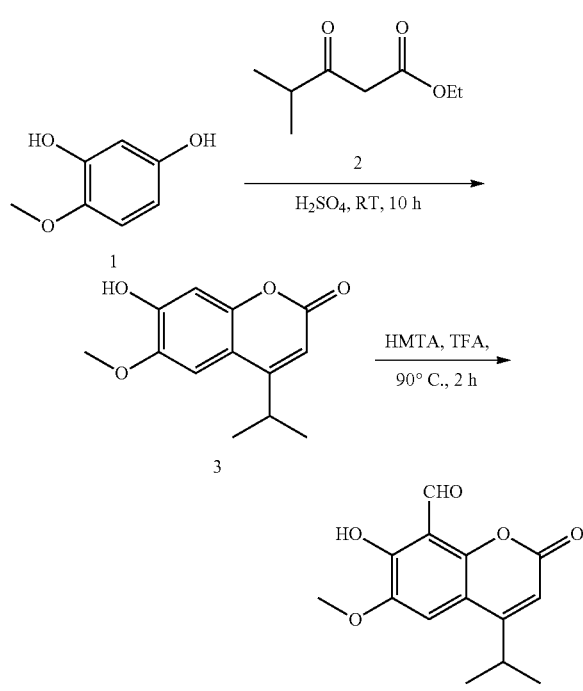

Synthesis of Compound 2

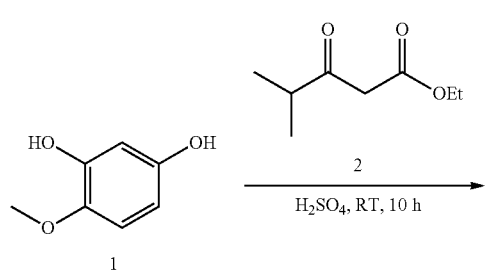

-continued

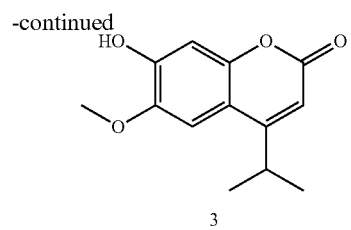

To the mixture of compound 1 (3.0 g, 21.0 mmol) and compound 2 (4.0 g, 25.0 mmol), $H_2SO_4$ (9 mL) was added slowly at 0° C. The mixture was stirred at RT overnight. The reaction mixture was poured into $H_2O$ (10 mL) and stirred for 30 mins, the formed precipitate was filtered and washed with water, dried to give compound 3 (2.0 g, 41% yield) as light yellow solid.

Synthesis of Compound 7-hydroxy-4-isopropyl-6-methoxy-2-oxo-2H-chromene-8-carbaldehyde

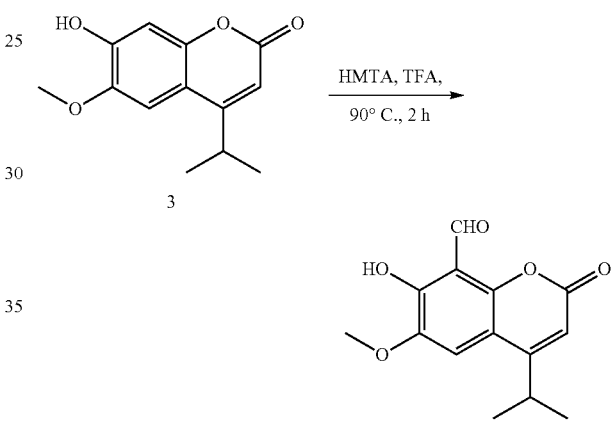

A mixture of compound 3 (500 mg, 2.1 mmol) and HMTA (1.1 g, 9.4 mmol) in TFA (50 mL) was heated to 90° C. under $N_2$ for 2 h. LC-MS indicated that the reaction was completed. After cooling to RT, the solvent was removed under vacuum. The residue was purified by prep-HPLC, afforded 7-hydroxy-4-isopropyl-6-methoxy-2-oxo-2H-chromene-8-carbaldehyde (150 mg, 26%). $^1$HNMR (DMSO, 400 MHz): δ 11.91 (s, 1H, OH), 10.42 (s, 1H, CHO), 7.50 (s, 1H, ArH), 6.23 (s, 1H, ArH), 3.90 (s, 3H, $CH_3$), 3.29 (s, 1H, CH), 1.24 (d, 6H, J=6.8 Hz, $2CH_3$). MS [ESI, MH$^+$]: 263.1.

Example 57

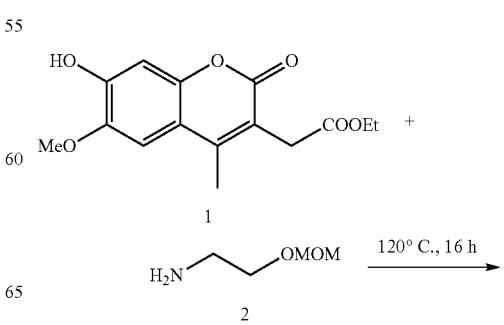

Synthesis of Compound 3

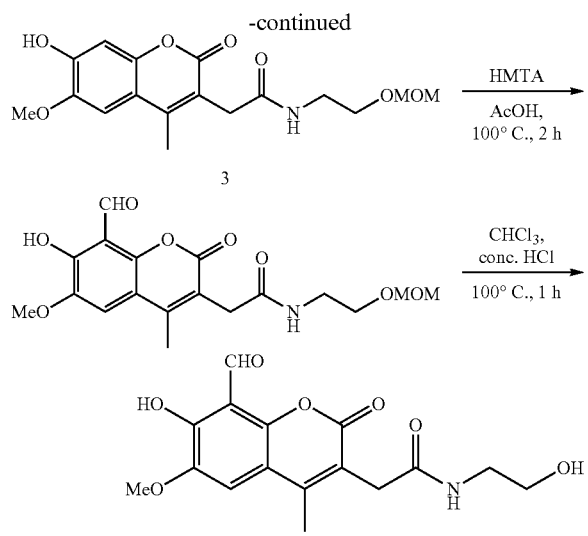

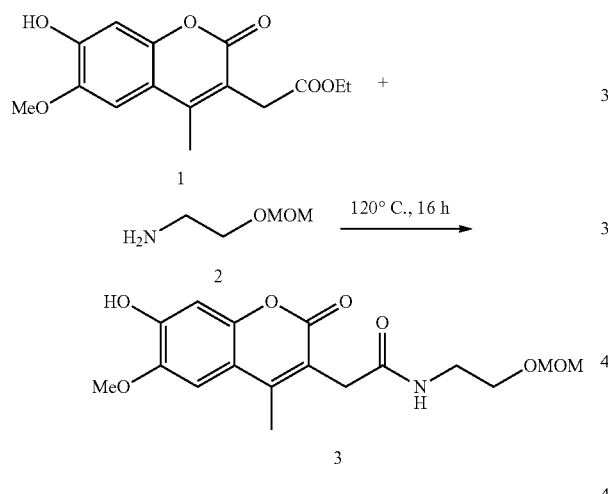

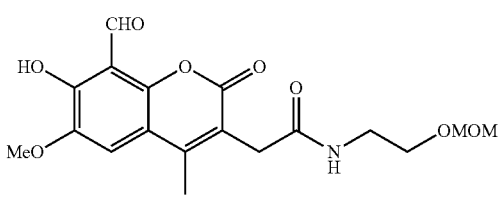

A suspension of compound 2 (11 g, 105 mmol) and compound 1 (2 g, 6.8 mmol) was heated to 120° C. for 16 h. The reaction mixture was diluted with DCM (300 mL), washed with 1 N aq.HCl (20 mL×3), sat. NaHCO$_3$ (50 mL), brine (50 mL), dried over MgSO$_4$ and concentrated to give the residue, then recrystallized in MeOH to give compound 6 (1.5 g, 63.0%) as white solid.

2-(8-Formyl-7-hydroxy-6-methoxy-4-methyl-2-oxo-2H-chromen-3-yl)-N-(2-(methoxymethoxy)ethyl)acetamide: A solution of compound 3 (750 mg, 1.98 mmol) and HMTA (1.11 g, 7.92 mmol) in AcOH (50 mL) was heated to 100° C. for 2 h. After cooling to RT, the reaction mixture was concentrated to give the residue, and then diluted with DCM (200 mL), washed with water (20 mL), brine (20 mL), dried over Na$_2$SO$_4$ concentrated to give 2-(8-Formyl-7-hydroxy-6-methoxy-4-methyl-2-oxo-2H-chromen-3-yl)-N-(2-(methoxymethoxy)ethyl)acetamide (200 mg, 26.7%). $^1$HNMR: (DMSO, 400 MHz) δ 11.78 (s, 1H, OH), 10.41 (s, 1H, CHO), 7.88 (s, 1H, ArH), 7.45 (br, 1H, NH), 3.90 (s, 3H, OCH$_3$), 3.46 (s, 2H, CH$_2$), 3.37-3.33 (m, 2H, CH$_2$), 3.08 (d, J=6.0, 2H, CH$_2$), 2.36 (s, 3H, CH$_3$); MS [ESI, MH$^+$]: 336.2.

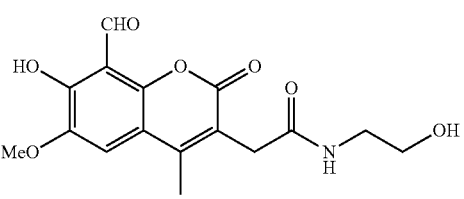 [SMILES: COc1cc2c(C)c(CC(=O)NCCO)c(=O)oc2c(C=O)c1O]

2-(8-Formyl-7-hydroxy-6-methoxy-4-methyl-2-oxo-2H-chromen-3-yl)-N-(2-hydroxyethyl)acetamide: A solution of 2-(8-Formyl-7-hydroxy-6-methoxy-4-methyl-2-oxo-2H-chromen-3-yl)-N-(2-(methoxymethoxy)ethyl)acetamide (400 mg, 1.06 mmol) in CHCl$_3$ (40 mL) and conc.HCl (20 mL) was heated to reflux for 1 h, and then concentrated to give the residue and purified by prep.HPLC to give 2-(8-Formyl-7-hydroxy-6-methoxy-4-methyl-2-oxo-2H-chromen-3-yl)-N-(2-hydroxyethyl)acetamide (40 mg, 11.3%) as yellow solid. $^1$H NMR: (CDCl$_3$, 400 MHz) δ 12.47 (d, J=0.4 Hz, 1H, OH), 10.02 (s, 1H, CHO), 7.22 (s, 1H, ArH), 6.60 (br, 1H, NH), 4.63 (s, 2H, CH$_2$), 3.97 (s, 3H, OCH$_3$), 3.60 (t, J=5.4 Hz, 4H, CH$_2$), 3.45 (m, 2H, CH$_2$), 3.36 (d, J=0.4 Hz, 2H, CH$_2$), 2.57 (s, 3H, CH$_3$); MS [ESI, MH$^+$]: 380.2.

Example 58

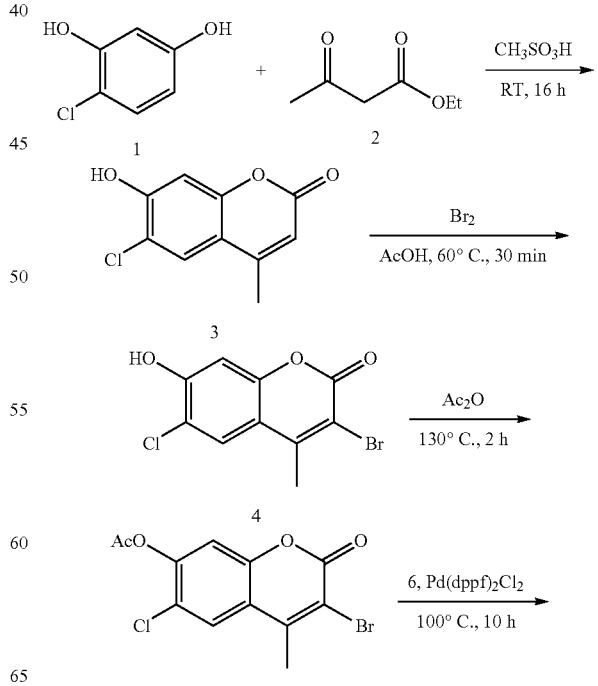

383
-continued

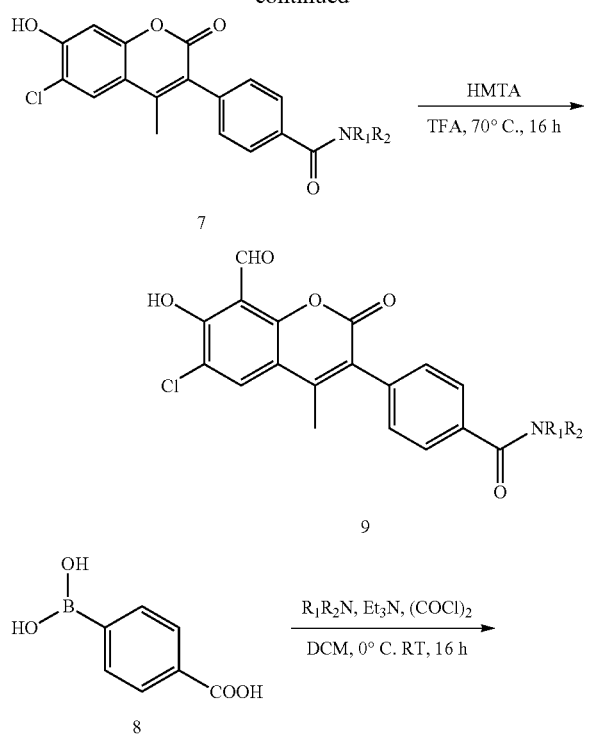

Synthesis of Compound 3

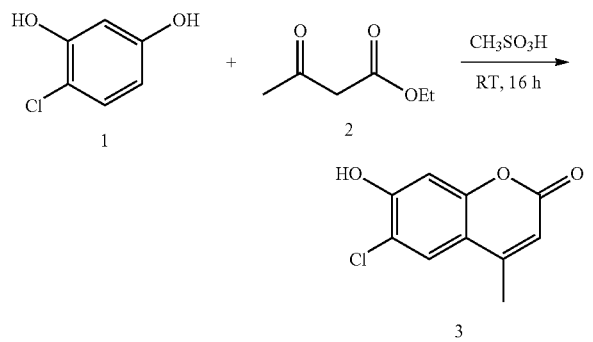

To a suspension of compound 1 (30 g, 0.209 mol) and compound 2 (41 g, 0.313 mol) was added CH$_3$SO$_3$H (200 mL) while keeping inner temperature below 25° C. The reaction mixture was stirred at RT for 16 h and then poured in to ice water, filtered and the filter cake was washed with water (50 mL×3), dried in vacuum to give compound 3 (30 g, 68%) as white solid.

384

Synthesis of Compound 4

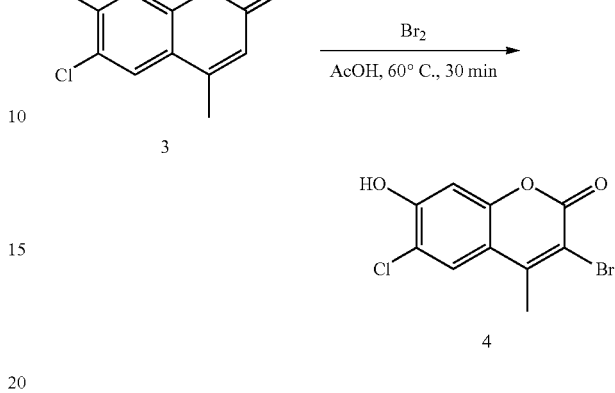

To a suspension of compound 3 (30 g, 0.143 mol) in AcOH (300 mL) was added Br$_2$ (22.7 g, 0.143 mol) dropwise at 60° C. for 30 min. After cooling to RT, the reaction mixture was filtered and the filter cake was washed with water (50 mL×4), dried in vacuum to give compound 4 (30 g, 73%) as white solid.

Synthesis of Compound 5

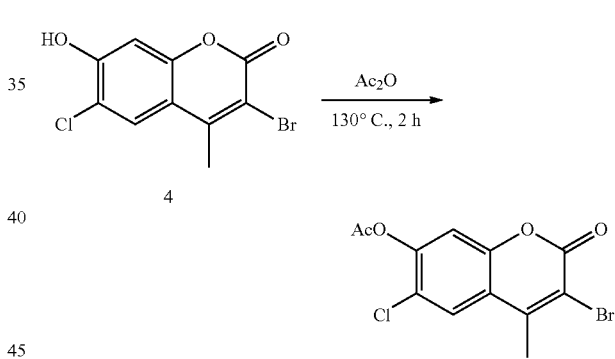

A suspension of compound 4 (30 g, 0.104 mol) in Ac$_2$O (200 mL) was heated to 130° C. for 2 h. After cooling to room temperature, the reaction mixture was filtered and the filter cake was washed with water (50 mL×3), dried in vacuum to give compound 5 as white solid (28 g, 81.1%).

Synthesis of Compound 7

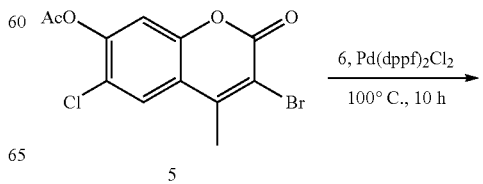

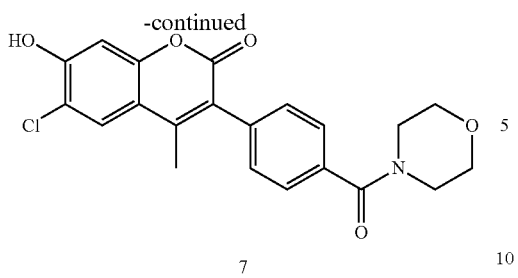

A suspension of compound 5 (1 g, 3.0 mmol), compound 6 (1.41 g, 6.0 mmol), Pd (dppf)$_2$ Cl$_2$ (110 mg, 0.15 mmol) and Na$_2$CO$_3$(0.636 g, 6.0 mmol) in DMF (50 mL) and water (5 mL) was heated to 100° C. for 10 h. The solvent was removed under reduced pressure and then purified by column chromatography on silica gel to give compound 7 (600 mg, 50%) as yellow solid.

Synthesis of Compound 9

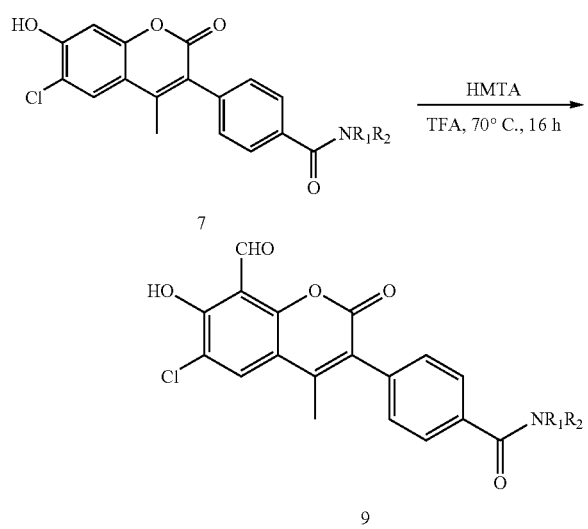

A solution of compound 7 (1 eq) and HMTA (4 eq) in TFA was heated to 70° C. for 16 h. After cooling to room temperature, the reaction mixture was concentrated to give the residue, and then purified by prep.HPLC to give compound 9.

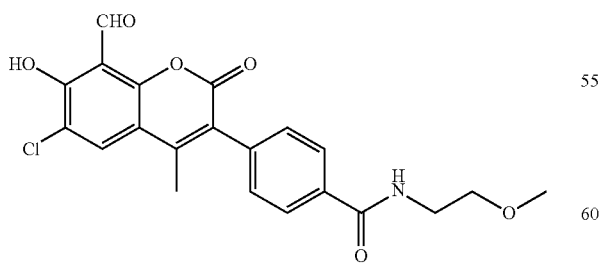

4-(6-Chloro-8-formyl-7-hydroxy-4-methyl-2-oxo-2H-chromen-3-yl)-N-(2-methoxyethyl)benzamide was obtained by the above procedure from amine A1 7.0% yield $^1$H NMR (CDCl$_3$ 400 MHz): δ 12.74 (s, 1H, OH), 10.65 (s, 1H, CHO), 7.89 (d, J=8 Hz, 3H, ArH), 7.38 (d, J=8.8 Hz, 2H, ArH), 6.55 (br, 1H, NH), 3.68 (t, J=7.2 Hz, 2H, CH$_2$), 3.58 (t, J=7.2 Hz, 2H, CH$_2$), 3.40 (s, 3H, OCH$_3$), 2.30 (s, 3H, CH$_3$); MS [ESI, MH$^+$]: 416.2.

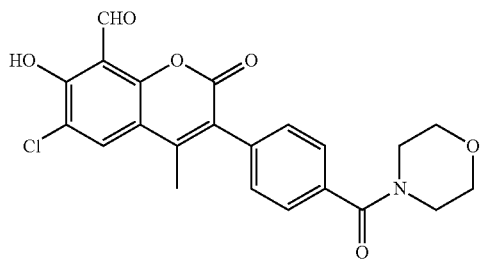 [SMILES: Cc1c(-c2ccc(C(=O)N3CCOCC3)cc2)c(=O)oc2c(C=O)c(O)c(Cl)cc12]

6-Chloro-7-hydroxy-4-methyl-3-(4-(morpholine-4-carbonyl)phenyl)-2-oxo-2H-chromene-8-carbaldehyde was obtained by the above procedure from amine A2. 9.4% yield $^1$H NMR: (CDCl$_3$ 400 MHz) δ 12.7 (s, 1H, OH), 10.66 (s, 1H, CHO), 7.90 (s, 1H, ArH), 7.53 (t, J=8 Hz, 2H, ArH), 7.37 (t, J=12 Hz, 2H, ArH) 3.77-3.55 (m, 8H), 2.30 (s, 3H, CH$_3$); MS [ESI, MH$^+$]: 428.2

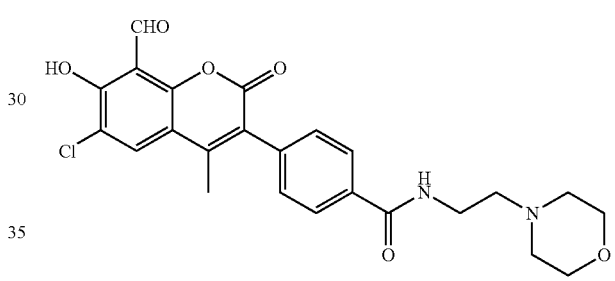

4-(6-Chloro-8-formyl-7-hydroxy-4-methyl-2-oxo-2H-chromen-3-yl)-N-(2-morpholinoethyl)benzamide was obtained by the above procedure from amine A5 9.5% yield $^1$H NMR (DMSO 400 MHz) δ 10.46 (s, 1H, CHO), 8.78 (br, 1H. NH), 8.23 (s, 1H, ArH), 7.94 (d, J=8.4 Hz, 2H, ArH), 7.45 (d, J=8.4 Hz 2H, ArH) 3.82 (s, 4H, 2CH$_2$), 3.65 (d, J=4.0 Hz, 2H, CH$_2$), 2.53 (d, J=4.0 Hz 2H, CH$_2$), 2.26 (s, 3H, CH$_3$). MS [ESI, MH$^+$]: 471.3.

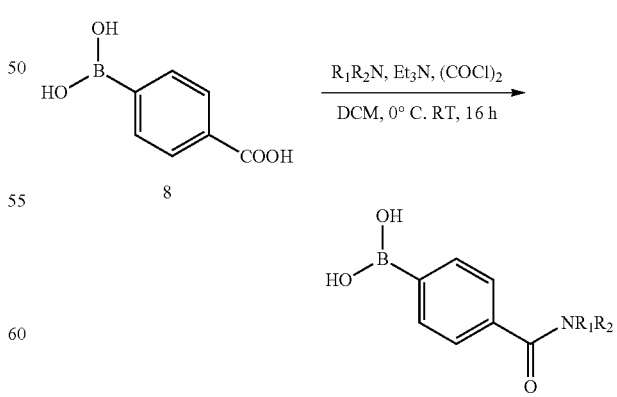

To a suspension of compound 8 1.0 eq) and DMF (5 mL) in DCM (1 L) was added (COCl)$_2$ (2 eq) dropwise at 0° C.

in 1 h. The reaction mixture was stirred at room temperature overnight and then removed the solvent to give the chloride acid. To a solution of the chloride acid in DCM (1 L) was added morpholine (1.0 eq) and TEA (2.0 eq) dropwise at 0° C. After 2 h, the solvent was removed to give compound 6.

Example 59

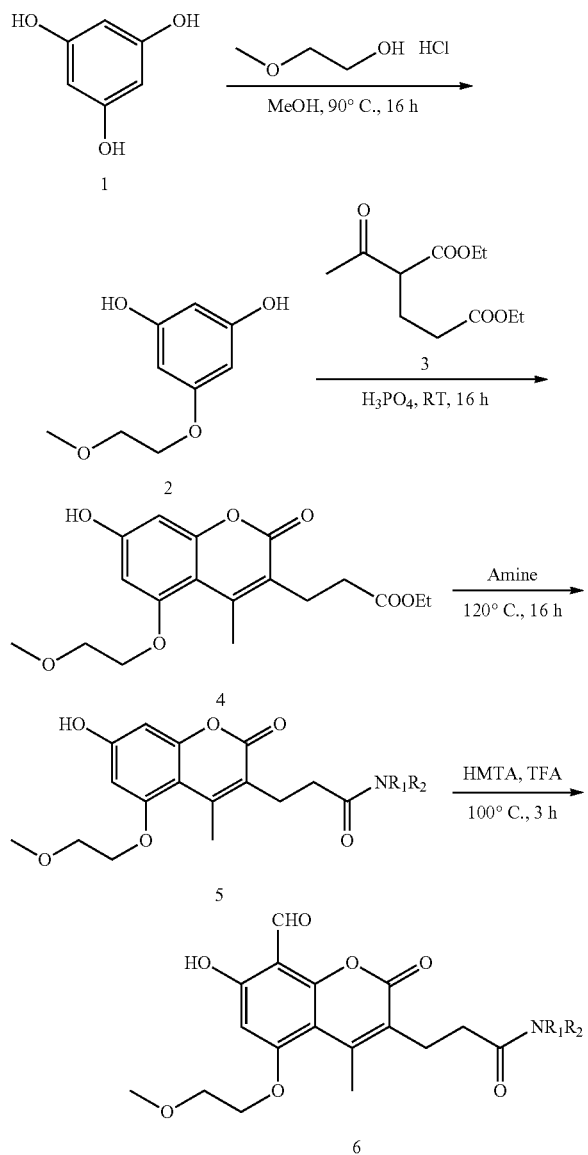

Synthesis of Compound 2

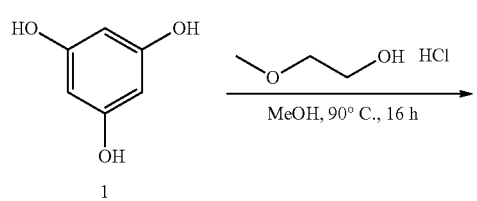

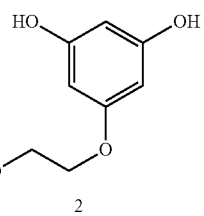

To a solution of compound 1 (50 g, 0.4 mol) and 2-Methoxy-ethanol (200 mL) in dioxane (800 mL) and MeOH (200 mL) was bubbled HCl gas at 0° C. over 20 min, and then heated to 90° C. for 16 h. The reaction mixture was concentrated under reduced pressure to removed dioxane, and then the residue was purified by column chromatography on silica gel to give compound 2 (30 g, 40.8%) as waxy solid.

MS [ESI, MH$^+$]: 185.2

Synthesis of Compound 4

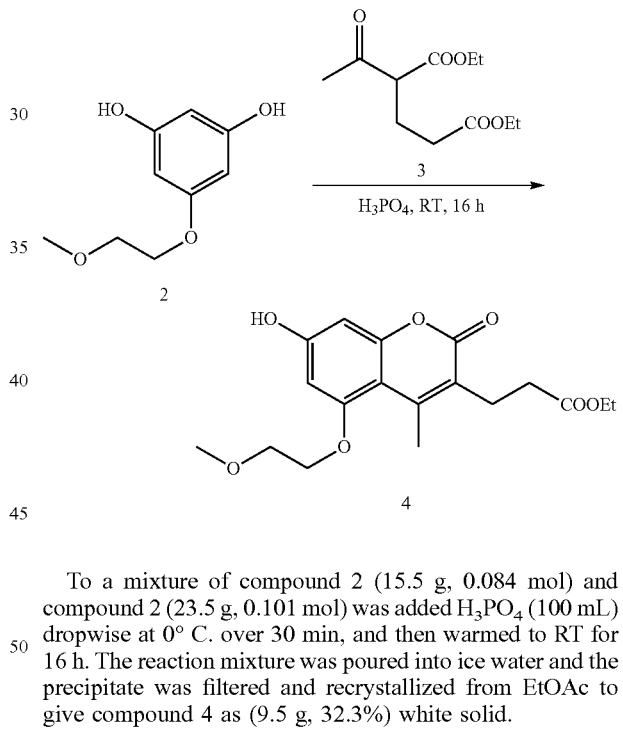

To a mixture of compound 2 (15.5 g, 0.084 mol) and compound 2 (23.5 g, 0.101 mol) was added H$_3$PO$_4$ (100 mL) dropwise at 0° C. over 30 min, and then warmed to RT for 16 h. The reaction mixture was poured into ice water and the precipitate was filtered and recrystallized from EtOAc to give compound 4 as (9.5 g, 32.3%) white solid.

Synthesis of Compound 5

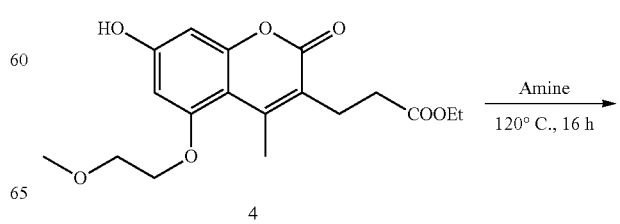

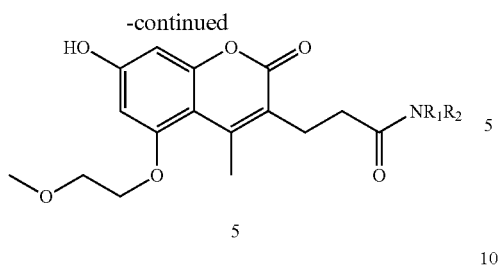

5

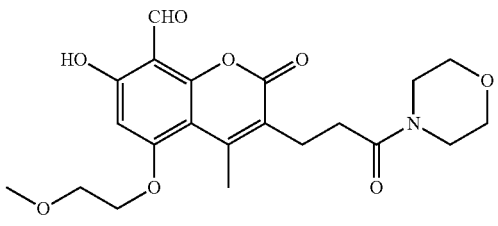 [SMILES: COCCOc1cc(O)c(C=O)c2oc(=O)c(CCC(=O)N3CCOCC3)c(C)c12]

A mixture of compound 4 1 eq) and amine was heated to 120° C. for 16 h. The reaction mixture was concentrated to give the residue, and then purified by column chromatography on silica gel to give the crude product, and then recrystallized from MeOH to give compound 5

Synthesis of Compound 6

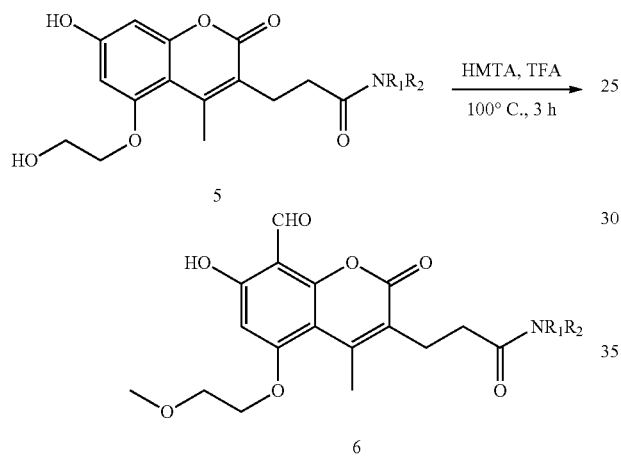

A solution of compound 5 (1 eq) and HMTA (4.0 eq) in TFA was heated to 100° C. for 3 h. After cooling to room temperature, the reaction mixture was concentrated to give the residue, and then purified by Prep-HPLC to give compound 6

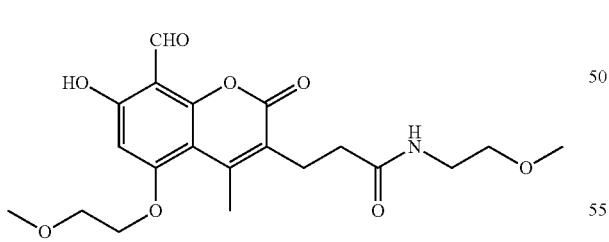

3-(8-Formyl-7-hydroxy-5-(2-methoxyethoxy)-4-methyl-2-oxo-2H-chromen-3-yl)-N-(2-methoxyethyl)propanamide was obtained by the above procedure from amine A1. 15% yield. $^1$HNMR (CDCl$_3$, 400 MHz): δ 12.58 (s, 1H, OH), 10.40 (d, J=2.8 Hz, CHO), 6.25 (d, J=2.4, 1H, ArH), 6.04 (br, 1H, NH), 4.21 (d, J=2.4 Hz, ArOCH$_2$), 3.79 (d, J=2.8 Hz, OCH$_2$), 3.44 (s, 7H), 3.33 (s, 3H, OCH$_3$), 2.97 (s, 2H, CH$_2$), 2.64 (s, 3H, CH$_3$), 2.44 (s, 2H, CH$_2$); MS [ESI, MH$^+$]: 408.3.

7-Hydroxy-5-(2-methoxyethoxy)-4-methyl-3-(3-morpholino-3-oxopropyl)-2-oxo-2H-chromene-8-carbaldehyde was obtained by the above procedure from amine A2. 52.2% yield $^1$H NMR (CDCl$_3$ 400 MHz): δ 12.55 (d, J=3.2 Hz, OH), 10.37 (d, J=3.2 Hz, 1H, CHO), 6.23 (d, J=3.2 Hz, 1H, ArH), 4.20 (t, J=3.0 Hz, 2H, ArOCH$_2$), 3.81-3.79 (m, 2H, OCH$_2$), 3.66 (s, 4H, 2CH$_2$), 3.62 (s, 2H, CH$_2$), 3.54 (s, 2H, CH$_2$), 3.43 (d, J=3.6 Hz, 3H, OCH$_3$), 2.96-2.92 (m, 2H, CH$_2$), 2.63 (d, J=3.2 Hz, 3H, CH$_3$), 2.56-2.51 (m, 2H, CH$_2$). MS [ESI, MH$^+$]: 420.2.

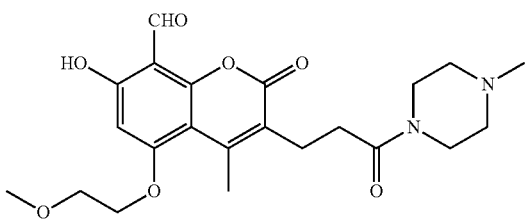

7-Hydroxy-5-(2-methoxyethoxy)-4-methyl-3-(3-(4-methylpiperazin-1-yl)-3-oxopropyl)-2-oxo-2H-chromene-8-carbaldehyde was obtained by the above procedure from amine A3. 28% yield. $^1$H NMR (D$_2$O, 400 MHz): δ 9.69 (s, 1H, CHO), 6.01 (s, 1H, ArH), 4.42 (s, 1H, CH$_2$), 4.12 (s, 1H, CH$_2$), 3.98 (s, 1H, ArOCH$_2$), 3.72 (s, 2H, OCH$_2$), 3.50-3.32 (m, 3H, CH$_2$), 3.31 (s, 3H, OCH$_3$), 3.07-2.93 (m, 3H, CH$_2$), 2.81 (s, 3H, NCH$_3$), 2.57 (d, J=7.6 Hz, 2H, CH$_2$), 2.45 (t, J=7.4 Hz, 2H, CH$_2$), 2.23 (s, 3H, CH$_3$); MS [ESI, MH$^+$]: 433.2.

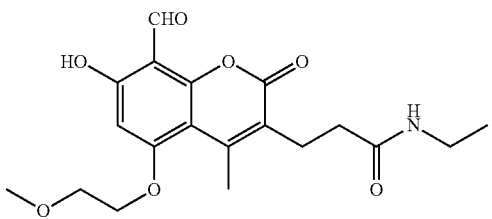 [SMILES: CCNC(=O)CCc1c(C)c2c(OCCOC)cc(O)c(C=O)c2oc1=O]

N-Ethyl-3-(8-formyl-7-hydroxy-5-(2-methoxyethoxy)-4-methyl-2-oxo-2H-chromen-3-yl)propanamide was obtained by the above procedure from amine A4. 9.3% yield. $^1$H NMR (CDCl$_3$ 400 MHz): δ 12.59 (s, 1H, OH), 10.40 (s, 1H, CHO), 6.26 (s, 1H, ArH), 5.71 (s, 1H, CONH), 4.23-4.21 (m, 2H, ArOCH$_2$), 3.82-3.79 (m, 2H, OCH$_2$), 3.45 (d, J=2.4 Hz, 3H, OCH$_3$), 3.29 (t, J=5.6 Hz, 2H, CH$_2$), 2.98 (t, J=7.4 Hz, 2H, CH$_2$), 2.65 (s, 3H, CH$_3$), 2.41 (t, J=7.6 Hz, 2H, CH$_2$), 1.15-1.12 (m, 3H, CH$_3$). MS [ESI, MH$^+$]: 378.1

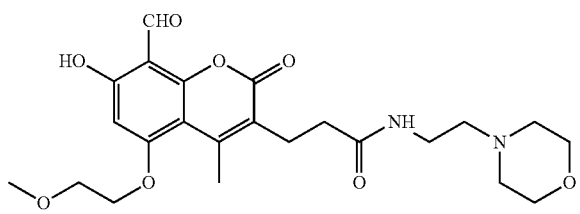 [SMILES: COCCOc1cc(O)c(C=O)c2oc(=O)c(CCC(=O)NCCN3CCOCC3)c(C)c12]

3-(8-Formyl-7-hydroxy-5-(2-methoxyethoxy)-4-methyl-2-oxo-2H-chromen-3-yl)-N-(2-morpholinoethyl)propanamide was obtained by the above procedure from amine A5. 23% (D$_2$O, 400 MHz): δ 9.74 (s, 1H, CHO), 6.06 (s, 1H, ArH), 4.01 (s, 2H, ArOCH$_2$), 3.97 (s, 2H, OCH$_2$), 3.75-3.69 (m, 4H, CH$_2$), 3.49 (s, 4H, CH$_2$), 3.32 (s, 3H, OCH$_3$), 3.19 (t, J=6.0 Hz, CH$_2$), 3.12-3.08 (m, 2H, CH$_2$), 2.63 (d, J=8.4 Hz, 2H, CH$_2$), 2.26 (s, 3H, CH$_3$); MS [ESI, MH$^+$]: 463.2.

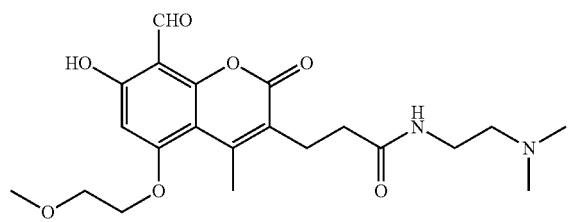

N-(2-(Dimethylamino)ethyl)-3-(8-formyl-7-hydroxy-5-(2-methoxyethoxy)-4-methyl-2-oxo-2H-chromen-3-yl)propanamide was obtained by the above procedure from amine A6. 9.5% yield $^1$H NMR (D$_2$O 400 MHz): δ 9.95 (s, 1H, CHO), 6.25 (s, 1H, ArH), 4.20 (s, 2H, ArOCH$_2$), 3.91 (s, 2H, OCH$_2$), 3.59 (t, J=6.0 Hz, 2H, CH$_2$), 3.48 (s, 3H, OCH$_3$), 3.32 (t, J=6.0 Hz, 2H, CH$_2$), 2.95 (s, 6H, 2NCH$_3$), 2.81 (t, J=7.8 Hz, 2H), 2.45 (s, 5H); MS [ESI, MH$^+$]: 421.2

Example 60

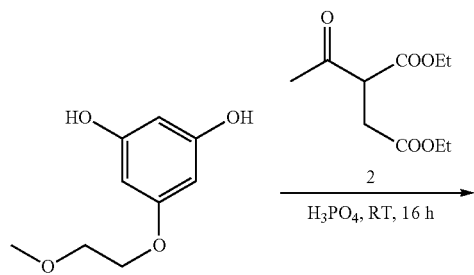

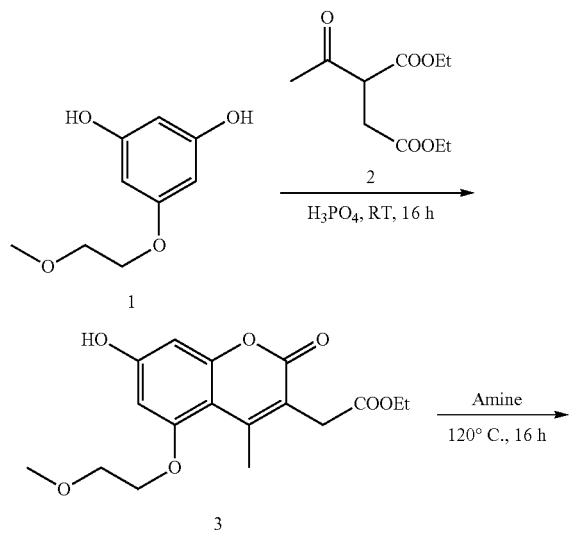

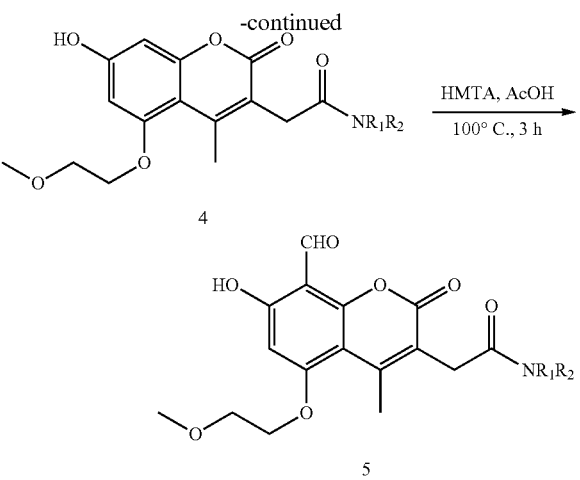

Synthesis of Compound 3

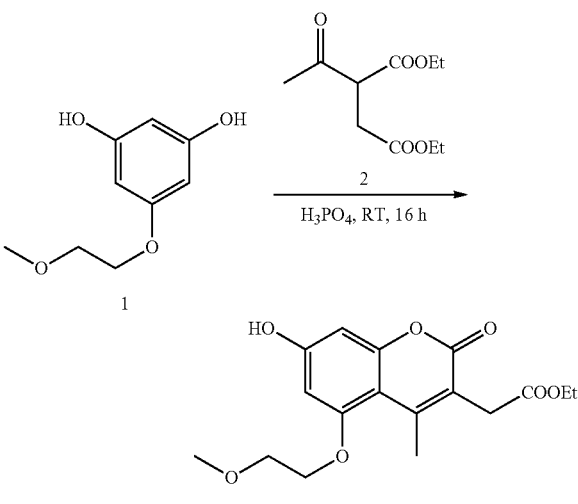

To a mixture of compound 1 (15.5 g, 0.084 mol) and compound 2 (21.8 g, 0.101 mol) was added H$_3$PO$_4$ (100 mL) dropwise at 0° C. over 30 min, and then warmed to RT for 16 h. The reaction mixture was poured into ice water and the precipitate was filtered and recrystallized from EtOAc to give compound 3 (5.5 g, 19.5%) as white solid.

MS [ESI, MH$^+$]: 337.1

Synthesis of Compound 4

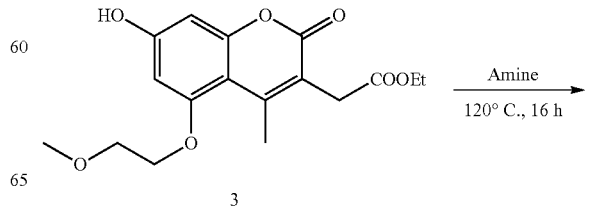

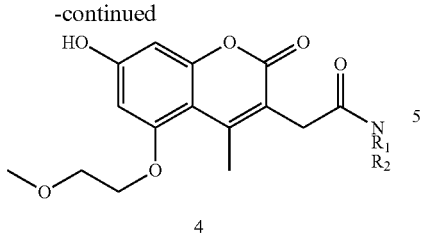

A mixture of compound 4 (2.0 g, 6.0 mmol) and amine (20 mL) was heated to 120° C. for 16 h. The reaction mixture was concentrated to give the residue, and then purified by column chromatography on silica gel to give the crude product, and then recrystallized in MeCN to give compound 5 (0.4 g, 18.4%) as white solid.

Synthesis of Compound 5

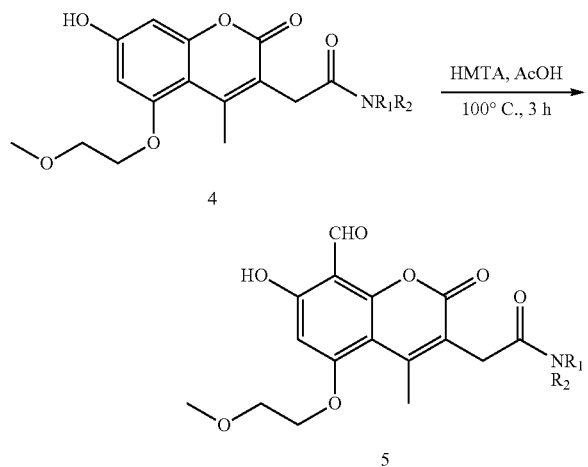

A solution of compound 4 (1 eq) and HMTA (4.0 eq) in AcOH was heated to 100° C. for 3 h. After cooling to room temperature, the reaction mixture was concentrated to give the residue, and then purified by Prep-HPLC to give compound 5

2-(8-Formyl-7-hydroxy-5-(2-methoxyethoxy)-4-methyl-2-oxo-2H-chromen-3-yl)-N-(2-methoxyethyl)acetamide was obtained by the above procedure from amine A1. 3.5% yield. $^1$HNMR (CDCl$_3$, 400 MHz): δ 12.61 (s, 1H, OH), 10.40 (s, 1H, CHO), 6.43 (br, 1H, NH), 6.27 (s, 1H, ArH), 4.22 (t, J=4.4 Hz, 2H, ArOCH$_2$), 3.79 (t, J=4.4 Hz, 2H, OCH$_2$), 3.58 (s, 3H, CH$_2$), 3.43 (m, 7H), 3.35 (d, J=4.0 Hz, 3H, OCH$_3$), 2.72 (s, 3H, CH$_3$). MS [ESI, MH$^+$]: 394.1

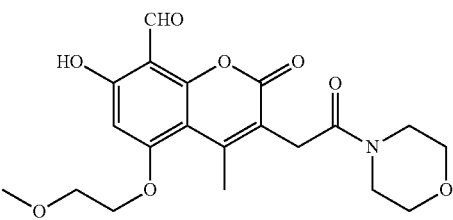 [SMILES: COCCOc1cc(O)c(C=O)c2oc(=O)c(CC(=O)N3CCOCC3)c(C)c12]

7-Hydroxy-5-(2-methoxyethoxy)-4-methyl-3-(2-morpholino-2-oxoethyl)-2-oxo-2H-chromene-8-carbaldehyde was obtained by the above procedure from amine A2. 14% yield. $^1$H NMR (CDCl$_3$, 400 MHz): δ 12.62 (s, 1H, OH), 10.41 (s, 1H, CHO), 6.27 (s, 1H, ArH), 4.22 (t, J=4.4 Hz, 2H, ArOCH$_2$), 3.81-3.76 (m, 4H, OCH$_2$ and CH$_2$), 3.70 (d, J=3.6 Hz, 6H, CH$_2$), 3.65 (d, J=4.8 Hz, 2H, CH$_2$), 3.43 (s, 3H, OCH$_3$), 2.61 (s, 3H, CH$_3$) MS [ESI, MH$^+$]: 406.1

7-Hydroxy-5-(2-methoxyethoxy)-4-methyl-3-(2-(4-methylpiperazin-1-yl)-2-oxoethyl)-2-oxo-2H-chromene-8-carbaldehyde was obtained by the above procedure from amine A3. 3.9% yield. $^1$H NMR (D$_2$O, 400 MHz): δ 9.89 (s, 1H, CHO), 6.18 (s, 1H, ArH), 4.60 (d, J=12.4 Hz, 1H), 4.41 (d, J=14.8 Hz, 1H), 4.14 (s, 2H, ArOCH$_2$), 3.88-3.62 (m, 8H), 3.45 (s, 3H, OCH$_3$), 3.33 (d, J=2.8 Hz, 1H), 3.19 (d, J=12.8 Hz, 2H, CH$_2$), 3.01 (s, 3H, NCH$_3$), 2.37 (s, 3H, CH$_3$); MS [ESI, MH$^+$]: 419.3.

N-Ethyl-2-(8-formyl-7-hydroxy-5-(2-methoxyethoxy)-4-methyl-2-oxo-2H-chromen-3-yl)acetamide was obtained by the above procedure from amine A4. 9.6% yield. $^1$HNMR (MeOD, 400 MHz): δ 10.35 (s, 1H, CHO), 6.46 (s, 1H, ArH), 4.30-4.28 (m, 2H, ArOCH$_2$), 3.82-3.80 (m, 2H, OCH$_2$), 3.59 (s, 2H, CH$_2$), 3.41 (s, 3H, OCH$_3$), 3.22-3.20 (m, 2H, CH$_2$), 2.59 (s, 3H, CH$_3$), 1.12 (t, J=4.0 Hz, 3H, CH$_3$). MS [ESI, MH$^+$]: 364.1

2-(8-Formyl-7-hydroxy-5-(2-methoxyethoxy)-4-methyl-2-oxo-2H-chromen-3-yl)-N-(2-morpholinoethyl)acetamide was obtained by the above procedure from amine A5. 5.0% yield. $^1$H NMR (CDCl$_3$, 400 MHz): δ 10.40 (s, 1H, CHO), 6.83 (br, 1H, NH), 6.27 (s, 1H, ArH), 4.22 (t, J=4.4 Hz, 2H, ArOCH$_2$), 3.79 (t, J=4.4 Hz, 2H, OCH$_2$), 3.74 (s, 4H, CH$_2$), 3.63 (s, 2H, CH$_2$), 3.43 (s, 3H, OCH$_3$), 3.38 (d, J=5.2 Hz, 2H, CH$_2$), 2.71 (s, 3H, CH$_3$), 2.56 (s, 6H, CH$_2$). MS [ESI, MH$^+$]: 449.1

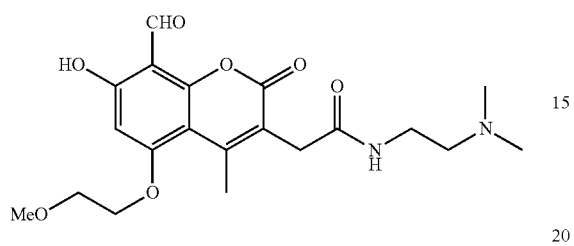

N-(2-(Dimethylamino)ethyl)-2-(8-formyl-7-hydroxy-5-(2-methoxyethoxy)-4-methyl-2-oxo-2H-chromen-3-yl)acetamide was obtained by the above procedure from amine A6. 10% yield. $^1$HNMR (D$_2$O, 400 MHz): δ 10.12 (s, 1H, CHO), 6.40 (s, 1H, ArH), 4.29 (d, J=4.0 Hz, 2H, ArOCH$_2$), 3.96 (t, J=2.0 Hz, 2H, OCH$_2$), 3.70-3.65 (m, 4H, 2CH$_2$), 3.50 (s, 3H, OCH$_3$), 3.36 (t, J=6.2 Hz, 2H, CH$_2$) 2.97 (s, 6H, 2NCH$_3$), 2.54 (s, 3H, CH$_3$). MS [ESI, MH$^+$]: 407.1

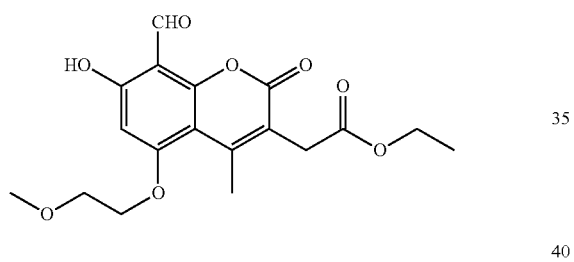

Ethyl 2-(8-formyl-7-hydroxy-5-(2-methoxyethoxy)-4-methyl-2-oxo-2H-chromen-3-yl) acetate: $^1$HNMR (CDCl$_3$, 400 MHz): δ 12.62 (s, 1H, OH), 10.41 (s, 1H, CHO), 6.27 (s, 1H, ArH), 4.23-4.18 (m, 4H), 3.80 (t, J=4.6 Hz, 2H, OCH$_2$), 3.72 (s, 2H, CH$_2$), 3.44 (s, 3H, OCH$_3$), 2.56 (s, 3H, CH$_3$), 1.27 (t, J=4.0 Hz, 3H, CH$_3$); MS [ESI, MH$^+$]: 365.2.

Example 61

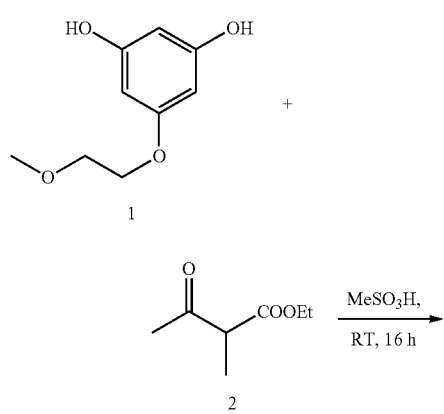

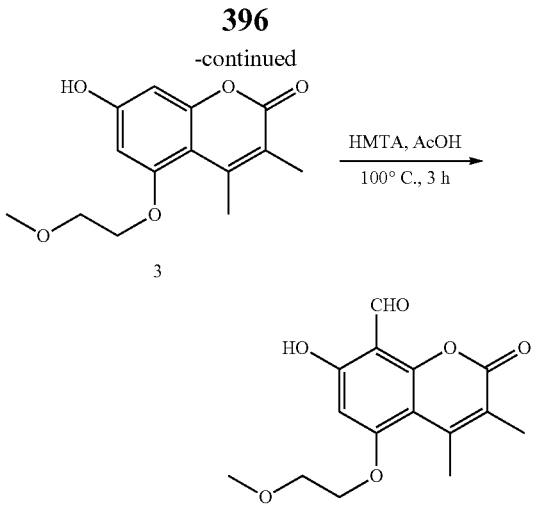

Synthesis of Compound 3

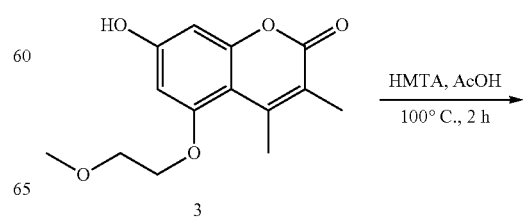

To a mixture of compound 1 (1.0 g, 5.43 mmol) and compound 2 (0.94 g, 6.52 mmol) was added MeSO$_3$H (20 mL) dropwise at 0° C. over 30 min, and then warmed to RT for 16 h. The reaction mixture was poured into ice water and the precipitate was filtered and recrystallized from EtOAc to give compound 3 (830 mg, 55.8%) as white solid.

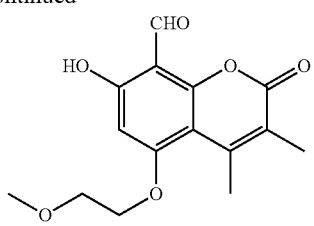

7-Hydroxy-5-(2-methoxyethoxy)-3,4-dimethyl-2-oxo-2H-chromene-8-carbaldehyde: A solution of compound 3 (800 mg, 3.14 mmol) and HMTA (1.76 g, 12.6 mmol) in AcOH (50 mL) was heated to 100° C. for 2 h. After cooling to room temperature, the reaction mixture was concentrated to give the residue, and then purified by Prep-HPLC to give the target compound (32 mg, 3.5%). $^1$H NMR (CDCl$_3$, 400 MHz): δ 12.57 (s, 1H, OH), 10.41 (s, 1H, CHO), 6.24 (s, 1H, ArH), 4.23-4.21 (m, 2H, Ar OCH$_2$), 3.82-3.80 (m, 2H, OCH$_2$), 3.44 (s, 3H, OCH$_3$), 2.57 (d, J=0.8 Hz, 3H, CH$_3$), 2.17 (d, J=0.8 Hz 3H, CH$_3$). LC-MS MS [ESI, MH$^+$]: 293.0.

Example 62

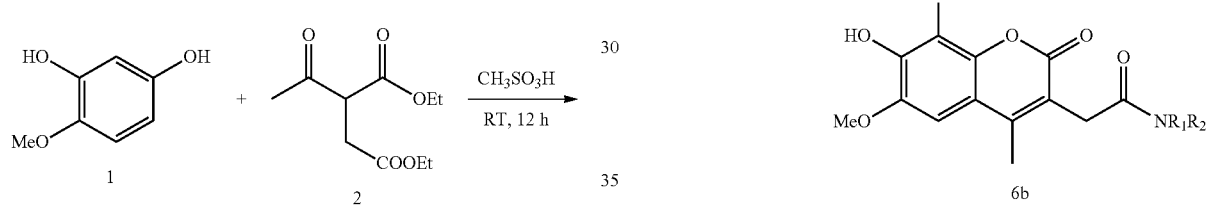

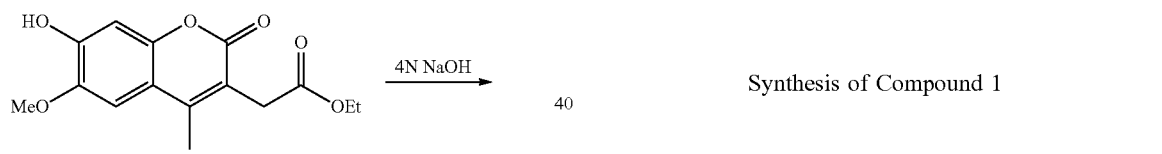

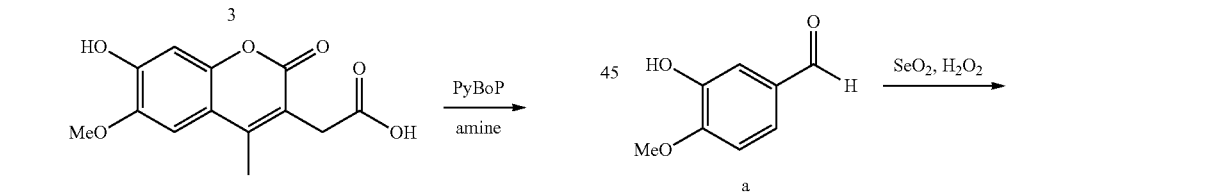

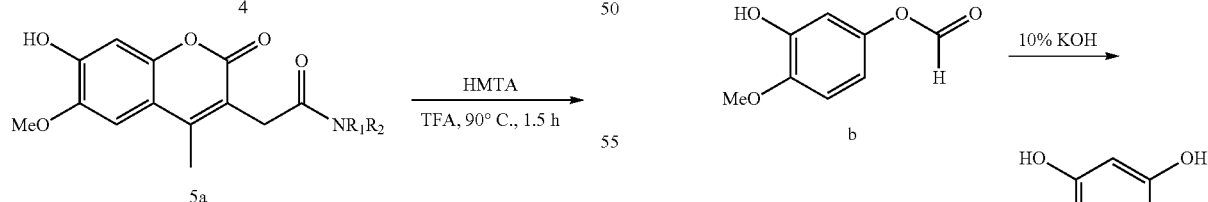

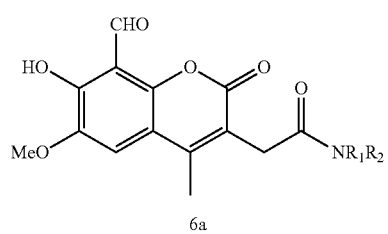

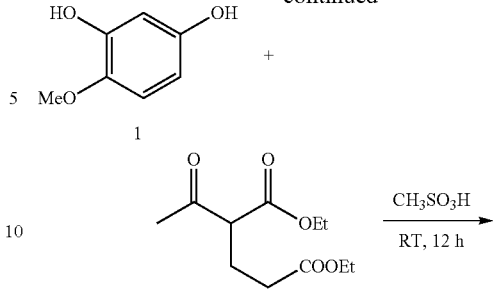

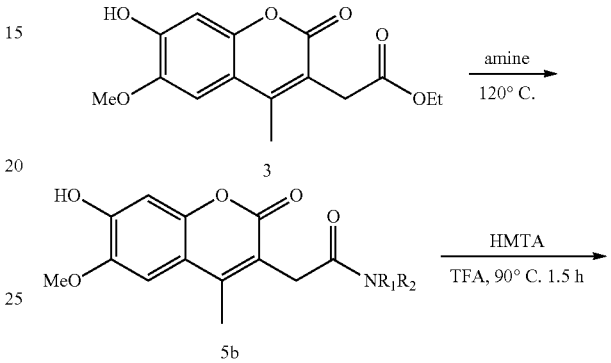

Synthesis of Compound 1

To a solution of compound a (300 g, 1.98 mol) and SeO$_2$ (17.4 g, 0.156 mol) in DCM (4 L) was added H$_2$O$_2$ (512 mL) dropwise at ice-bath. The mixture solution was stirred at RT for 16 h. The reaction mixture turned to dark-brown in the period. The reaction was monitored by TLC (PE:EA=1:1).

After the material was consumed completely (~12 h), the organic phase was separated and washed with 10% NaHSO₃ (1 L), followed by Na₂CO₃ (1 L) and brine (1 L), then dried on NaSO4, the solvent was removed to get the crude compound 2 and use at the next step directly.

The crude compound b was hydrolyzed in a mixture of MeOH (3 L) and 10% KOH (2 L) at RT over night. After MeOH was removed, the mixture was acidified by 6M HCl to PH=3 and extracted with DCM (2 L×8). The combined organic phase was washed with brine and dried on NaSO₄. After the solvent was removed, the residue was purified by chromatography (EA:PE=6:1 to EA:PE=4:1) to give compound 3 (140 g, 50.5%) as light-yellow solid. ¹HNMR (MeOD, 400 MHz): δ 6.70 (d, J=8.8 Hz, 1H, ArH), 6.29 (d, J=3.2 Hz, 1H, ArH), 6.18 (dd, J=8.8, 2.8 Hz, 1H, ArH), 3.73 (s, 3H, CH₃).

Synthesis of Compound 3

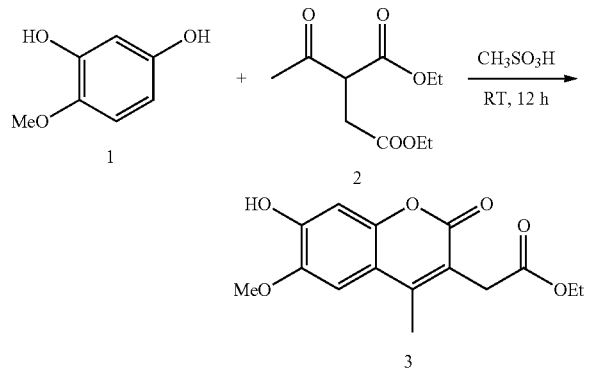

To a suspension of compound 1 (120 g, 0.86 mol) in diethyl acetylsuccinate (220 g, 1.03 mol), CH₃SO₃H (1200 mL) was added in one portion. The mixture was stirred at RT overnight. LC-MS showed that starting material was consumed completely. The reaction mixture was poured into ice-water (1000 ml) and stirred for 30 min. The formed precipitate was filtered and washed with water and EA, dried to afford the crude product (150 g, 60%) as white solid. ¹HNMR (MeOD, 400 MHz): δ 7.15 (s, 1H, ArH), 6.75 (s, 1H, ArH), 4.18-4.12 (q, 2H, CH2), 3.93 (s, 3H, CH₃), 2.41 (s, 3H, CH₃), 1.25 (t, 3H, CH₃).

Synthesis of Compound 4

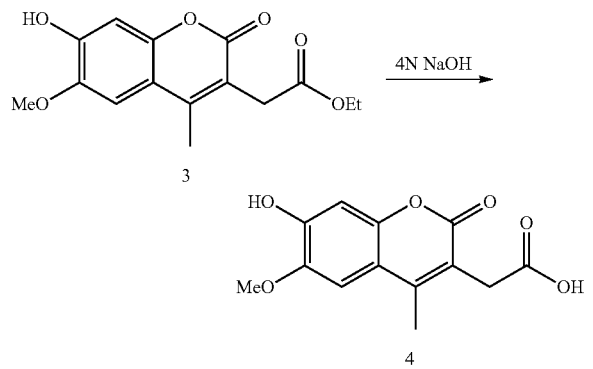

Compound 3 (180 g, 0.6 mol) was added into 4M NaOH (500 mL) in one portion and stirred at RT overnight. TLC (EA/MeOH=10/1) indicated that the reaction was complete. The reaction mixture was acidified with 5M HCl to PH=3. The formed precipitate was filtered, which was washed with EA and dried in vacuo to give compound 4 as white solid (140 g, 67%)

Synthesis of Compound 5a

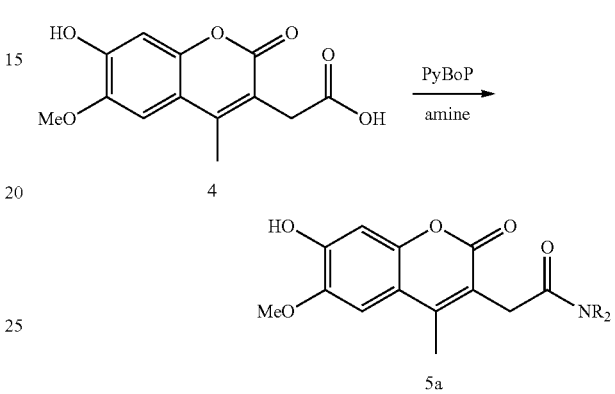

To a suspension of compound 4(1 eq) in DMF, amine and PyBOP (1.2 eq) was added sequentially. The mixture was cooled to 0° C., DIPEA (1.2 eq) was then added dropwise while controlling the temperature below 10° C. The reaction mixture was stirred at RT overnight. LCMS showed that starting material was consumed completed, the precipitate was filtered and washed with water and EA, dried in vacuo to give compound 5a as a white solid. 5A2, 5A3 used the method Synthesis of Compound 5b

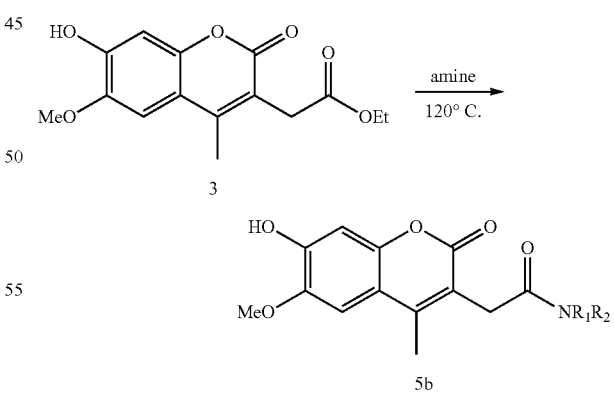

Compound 3 (1.0 eq) was added to amine. The reaction mixture was stirred at 120° C. for 48 h. LC-MS showed that the starting material was almost consumed completely. The solvent was removed under vacuum. The residue was washed with DCM (3×5 mL) and concentrated under vacuum, afforded compound 5b, 5A1, 5A4, 5A5 used the method

Synthesis of Compound 6

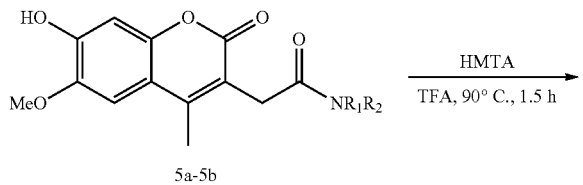

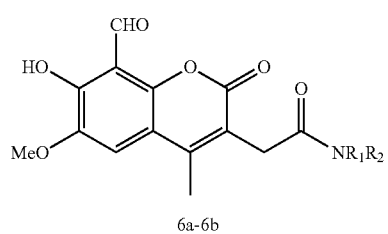

A mixture of compound 5 (1 eq) and HMTA (4 eq) in HOAc was heated at 120° C. under nitrogen for 1.5 h. The reaction mixture turned to dark-yellow in the period. LCMS indicated that the reaction was completed. After cooled to RT, the solvent was removed under reduced pressure, the product was purified by Prep-HPLC to give compound 6.

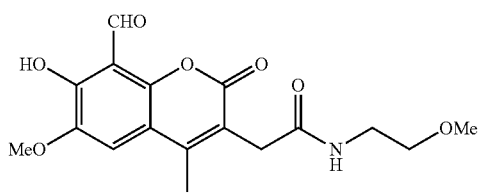 [SMILES: COCCNC(=O)Cc1c(C)c2cc(OC)c(O)c(C=O)c2oc1=O]

2-(8-Formyl-7-hydroxy-6-methoxy-4-methyl-2-oxo-2H-chromen-3-yl)-N-(2-methoxyethyl)acetamide was obtained by the above procedure from amine A1.18% yield $^{1}$HNMR (CDCl$_{3}$, 400 MHz): δ 12.48 (s, 1H, OH), 10.61 (s, 1H, CHO), 7.22 (s, 1H, ArH), 6.61 (br, 1H, NH), 3.97 (s, 3H, OCH$_{3}$), 3.61 (s, 2H, CH$_{2}$), 3.46-341 (m, 4H, 2CH$_{2}$), 3.36 (s, 3H, CH$_{3}$), 2.55 (s, 3H, CH$_{3}$), MS [ESI, MH$^{+}$]: 350.1

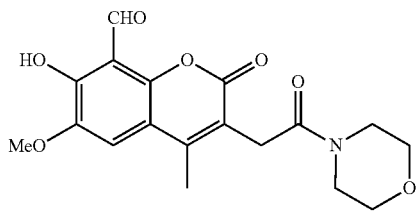 [SMILES: COc1cc2c(C)c(CC(=O)N3CCOCC3)c(=O)oc2c(C=O)c1O]

7-Hydroxy-6-methoxy-4-methyl-3-(2-morpholino-2-oxo-ethyl)-2-oxo-2H-chromene-8-carbaldehyde was obtained by the above procedure from amine A2.46% yield $^{1}$H NMR (CDCl$_{3}$, 400 MHz): δ 12.45 (s, 1H, OH), 10.59 (s, 1H, CHO), 7.24 (s, 1H, ArH), 3.95 (s, 3H, OCH$_{3}$), 3.78-3.62 (m, 10H) 2.46 (s, 3H, CH$_{3}$). MS [ESI, MH$^{+}$]: 362.2.

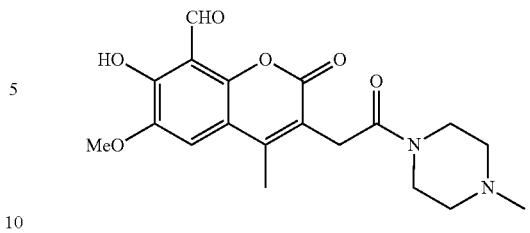

7-Hydroxy-6-methoxy-4-methyl-3-(2-(4-methylpiperazin-1-yl)-2-oxoethyl)-2-oxo-2H-chromene-8-carbaldehyde was obtained by the above procedure from amine A3. 7.7% yield. $^{1}$HNMR (D$_{2}$O, 400 MHz) δ 10.10 (s, 1H, CHO), 7.11 (s, 1H, ArH), 4.44 (d, 1H, J=12.0 HZ, CH), 4.29 (d, 1H, J=14.4 HZ, CH), 3.74-2.98 (m, 11H), 2.85 (s, 3H$_{2}$OCH$_{3}$), 2.19 (s, 3H, CH$_{3}$); MS [ESI, MH$^{+}$]: 375.1.

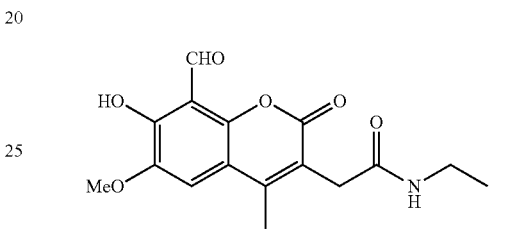

N-Ethyl-2-(8-formyl-7-hydroxy-6-methoxy-4-methyl-2-oxo-2H-chromen-3-yl)acetamide was obtained by the above procedure from amine A4.18% yield. $^{1}$HNMR (CDCl3, 400 MHz) δ 12.49 (s, 1H$_{2}$OH), 10.61 (s, 1H, CHO), 7.22 (s, 1H, ArH), 6.48 (br, 1H, NH), 3.97 (s, 3H$_{2}$OCH$_{3}$), 3.60 (s, 2H, CH$_{2}$), 3.28-3.23 (m, 2H, CH$_{2}$), 2.57 (s, 3H, CH$_{3}$), 1.13 (t, 3H, J=7.2 HZ, CH3); MS [ESI, MH$^{+}$]: 320.2.

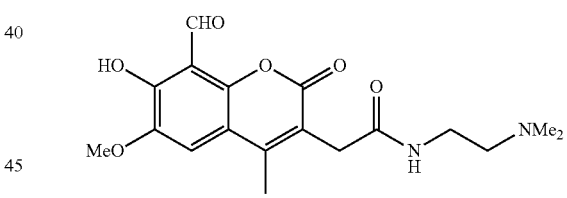

N-(2-(dimethylamino)ethyl)-2-(8-formyl-7-hydroxy-6-methoxy-4-methyl-2-oxo-2H-chromen-3-yl)acetamide was obtained by the above procedure from amine A6.9.2% yield. $^{1}$HNMR (D2O, 400 MHz): 10.61 (s, 1H, CHO), 7.26 (s, 1H, ArH), 3.90 (s, 3H, OCH$_{3}$), 3.69-3.64 (m, 4H, 2CH$_{2}$), 3.56 (t, 2H, J=6.0 HZ, CH$_{2}$), 2.95 (s, 6H, 2NCH$_{3}$), 2.39 (s, 3H, CH$_{3}$); MS [ESI, MH$^{+}$]: 363.3.

Example 63

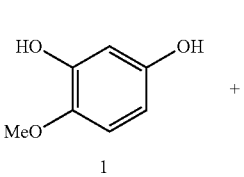

Synthesis of Compound 4

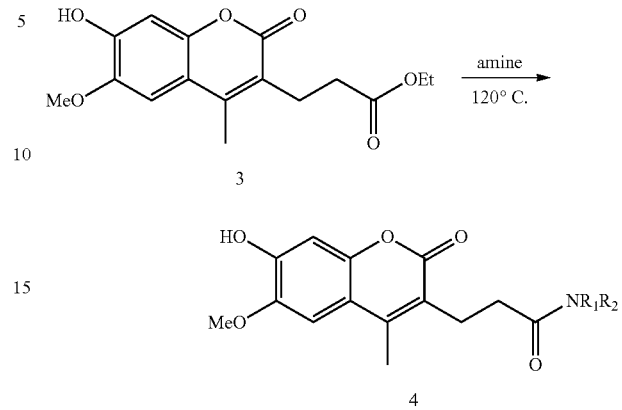

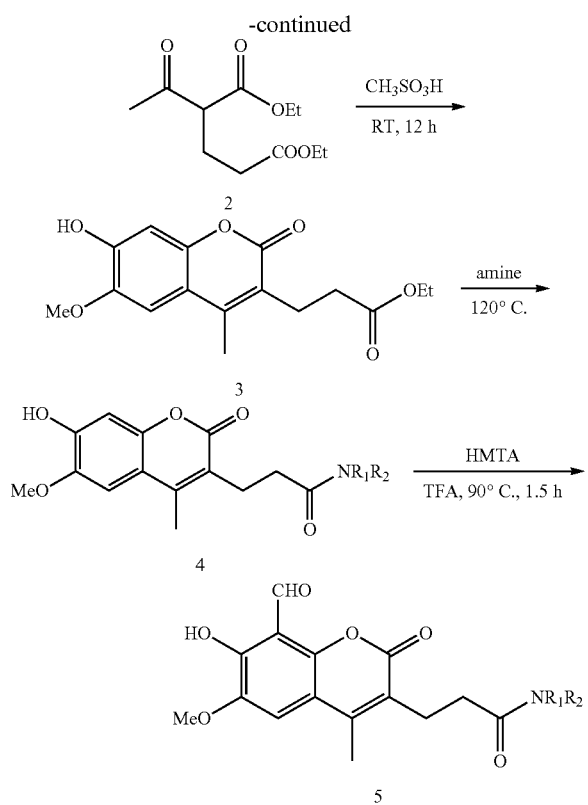

Compound 3 (1.0 eq) was added to amine, The reaction mixture was stirred at 120° C. for 48 h. LC-MS showed that the starting material was almost consumed completely. The solvent was removed under vacuum. The residue was washed with DCM and concentrated under vacuum to afforded compound 4.

Synthesis of Compound 5

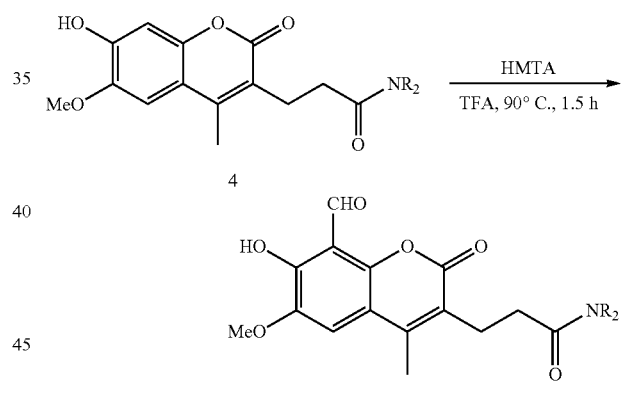

A mixture of compound 4 (1.0 eq) and HMTA (4.0 eq) in TFA was heated to 90° C. under nitrogen for 2 h. LC-MS indicated that the reaction was completed. After cooled to RT, the solvent was removed under vacuum. The residue was purified by Prep-HPLC, afforded compound 5.

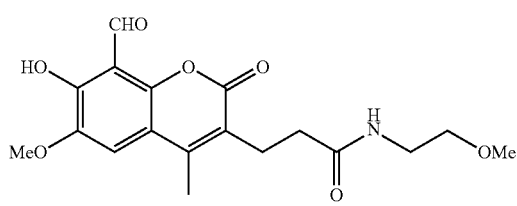 [SMILES: COCCNC(=O)CCc1c(C)c2cc(OC)c(O)c(C=O)c2oc1=O]

3-(8-Formyl-7-hydroxy-6-methoxy-4-methyl-2-oxo-2H-chromen-3-yl)-N-(2-methoxyethyl)propanamide was

Synthesis of Compound 3

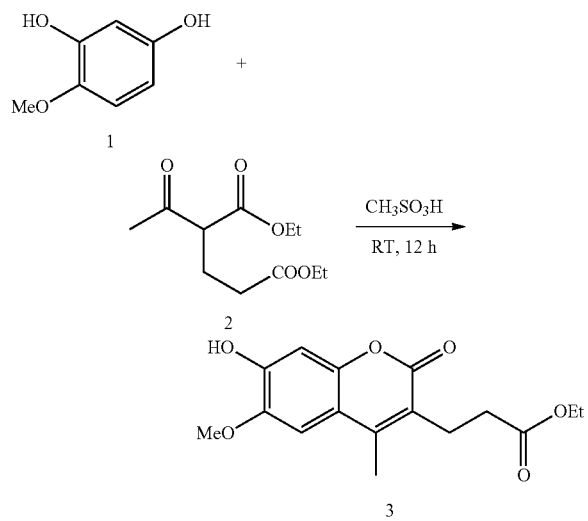

To a suspension of compound 1 (8.8 g, 0.063 mol) in compound 2 (18 g, 0.078 mol), $CH_3SO_3H$ (144 mL) was added in one portion. The mixture was stirred at RT for 12 h. LC-MS showed that starting material was consumed completely. The reaction mixture was poured into ice-water (300 mL) and stirred for 30 min. The formed precipitate was filtered and washed with water and EA, dried to afford the crude Compound 3 (11.2 g, 59%) as white solid; MS [ESI, $MH^+$]: 306.9.

obtained by the above procedure from amine A1.23.5% yield. ¹HNMR (CDCl₃, 400 MHz): δ 12.42 (s, 1H₂OH), 10.61 (s, 1H, CHO), 7.20 (s, 1H, ArH), 3.41 (m, 4H, 2CH₂), 3.30 (s, 3H, CH₃), 2.99 (t, 2H, J=7.2 Hz, CH₂), 2.52-2.48 (m, 5H); MS [ESI, MH⁺]: 364.2.

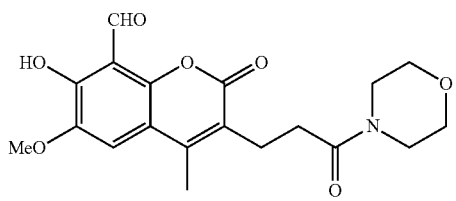 [SMILES: COc1cc2c(C)c(CCC(=O)N3CCOCC3)c(=O)oc2c(C=O)c1O]

7-Hydroxy-6-methoxy-4-methyl-3-(3-morpholino-3-oxopropyl)-2-oxo-2H-chromene-8-carbaldehyde was obtained by the above procedure from amine A2.39.6% yield ¹HNMR (MeOD, 400 MHz): δ 7.20 (s, 1H, CHO), 6.01 (s, 1H, ArH), 3.93 (s, 3H, OCH₃), 3.63-3.60 (m, 4H, 2CH₂), 3.58-3.55 (m, 4H, 2CH₂), 2.92 (t, 2H, J=7.6 Hz, CH₂), 2.61 (t, 2H, J=7.6 Hz, CH₂), 2.48 (s, 3H, CH₃); MS [ESI, MH⁺]: 376.2.

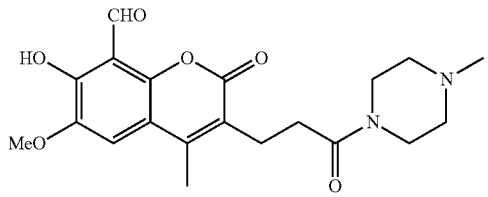 [SMILES: COc1cc2c(C)c(CCC(=O)N3CCN(C)CC3)c(=O)oc2c(C=O)c1O]

7-Hydroxy-6-methoxy-4-methyl-3-(3-(4-methylpiperazin-1-yl)-3-oxopropyl)-2-oxo-2H-chromene-8-carbaldehyde was obtained by the above procedure from amine A3.4.6% yield. ¹HNMR (CDCl₃, 400 MHz): δ 10.61 (s, 1H, CHO), 7.21 (s, 1H, ArH), 3.96 (s, 3H, CH₃), 3.60-3.59 (m, 3H, OCH₃), 2.97 (t, 2H, J=7.6. Hz, CH₂), 2.64 (t, 2H, J=7.6 Hz, 2H, CH₂), 2.50-2.34 (m, 11H); MS [ESI, MH⁺]: 389.2.

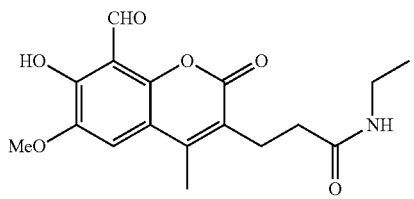 [SMILES: CCNC(=O)CCc1c(C)c2cc(OC)c(O)c(C=O)c2oc1=O]

N-Ethyl-3-(8-formyl-7-hydroxy-6-methoxy-4-methyl-2-oxo-2H-chromen-3-yl)propanamide was obtained by the above procedure from amine A4. 1.2% yield. ¹HNMR (CDCl₃, 400 MHz): δ 12.39 (s, 1H, OH), 10.58 (s, 1H, CHO), 7.20 (s, 1H, ArH), 5.71 (s, 1H, NH), 3.95 (s, 3H, OCH₃), 3.25 (t, 2H, J=5.6 Hz, CH₂), 2.98 (t, 2H, J=6.8 Hz, CH₂), 2.47 (s, 5H,), 1.11-1.07 (m, 3H, CH₃); MS [ESI, MH⁺]: 334.1

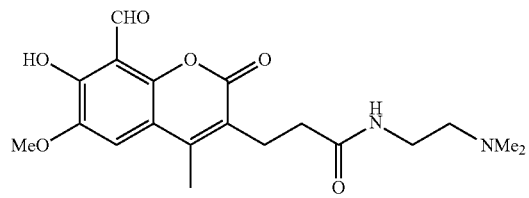 [SMILES: COc1cc2c(C)c(CCC(=O)NCCN(C)C)c(=O)oc2c(C=O)c1O]

N-(2-(Dimethylamino)ethyl)-3-(8-formyl-7-hydroxy-6-methoxy-4-methyl-2-oxo-2H-chromen-3-yl)propanamide was obtained by the above procedure from amine A6. 16% yield. ¹HNMR (DMSO-d6, 400 MHz): 10.44 (s, 1H, CHO), 8.24 (s, 1H, OH), 7.46 (s, 1H, ArH), 3.92 (s, 3H, CH₃), 3.41-3.36 (m, 2H, CH₂), 2.83-2.79 (m, 2H, CH₂), 2.76-2.74 (m, 6H), 2.49 (s, 3H, CH₃), 2.45-2.30 (m, 2H, CH₂); ¹HNMR (MeOD, 400 MHz): 7.20 (d, 1H, J=12.8 Hz, ArH), 5.99 (s, 1H, CHO), 3.93 (s, 3H, CH₃), 3.53-3.50 (m, 2H, CH₂), 3.26-3.23 (m, 2H, CH₂), 2.99-2.96 (m, 8H), 2.47 (s, 3H, CH₃), 2.45-2.43 (m, 2H, CH₂).

Example 64

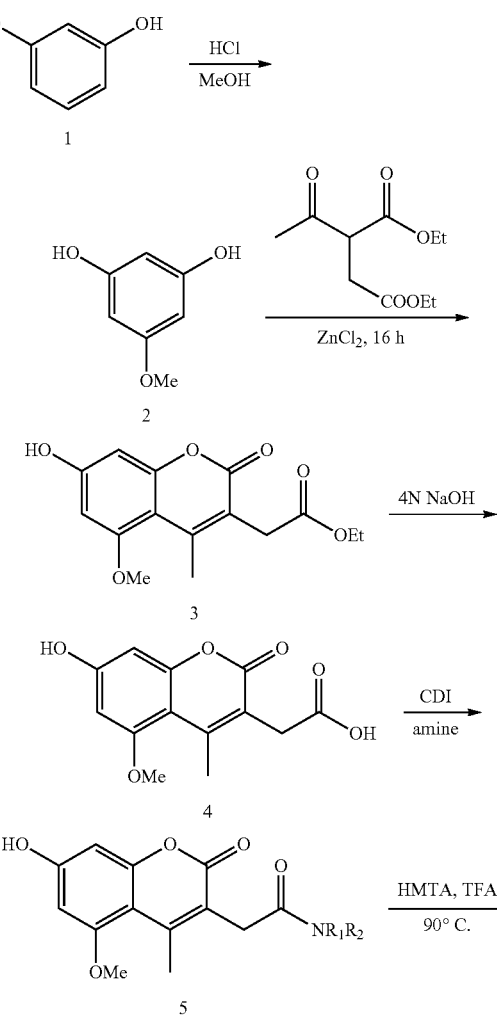

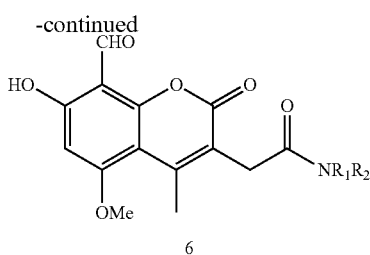

Synthesis of Compound 3

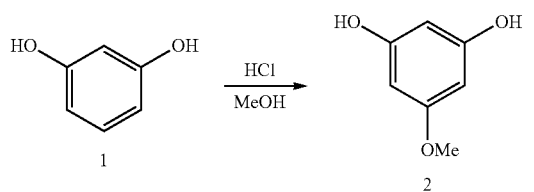 [SMILES: "MeOH" ; Oc1cccc(O)c1 ; Cl ; COc1cc(O)cc(O)c1]

To a solution of compound 1 (1000 g, 7.93 mol) in 1,4-Dixone (2 L) was added HCl/MeOH (8 L, saturated with dry HCl at 0° C.) in one portion with stirring at RT. The result solution was stirred at 80° C. overnight. The reaction was monitored by TLC (PE:EA=1:1) and HPLC. After ~16 h (Note 1), the solvent was removed and the residue was purified by chromatography on silica gel (PE:EA=12:1-8:1) to give compound 2 (514 g, 46%) as white solid.

Note 1: HPLC indicated that the material was not consumed. However, the disubstituted by-product would increase if the reaction was prolonged.

Synthesis of Compound 3

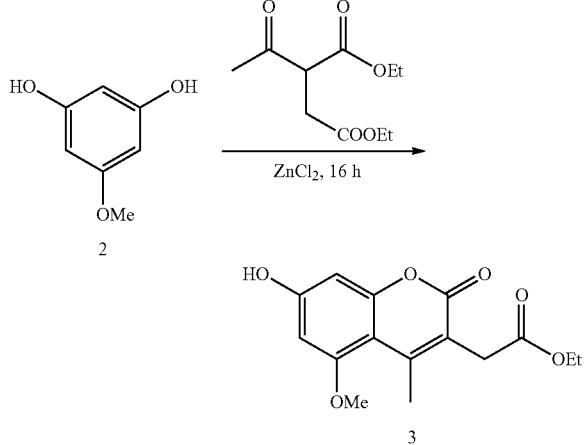

To a suspension of compound 2 (112 g, 0.8 mol) in diethyl acetylsuccinate (208 g, 0.96 mol) was added ZnCl$_2$ (112 g, 0.82 mol) in one portion with stirring at RT. The mixture solution stirred at 100° C. overnight. LC-MS showed that starting material was consumed completely. Then ice-water (400 ml) was added followed by MeOH (1000 ml) and the result mixture was stirred for 30 mins. The precipitate was filtered and washed with EA and MeOH (1:1, 800 mL) to afford the desired product (35 g, 15%, containing ~10% isomer) as white solid. MS [ESI, MH$^+$]: 293

Synthesis of Compound 4

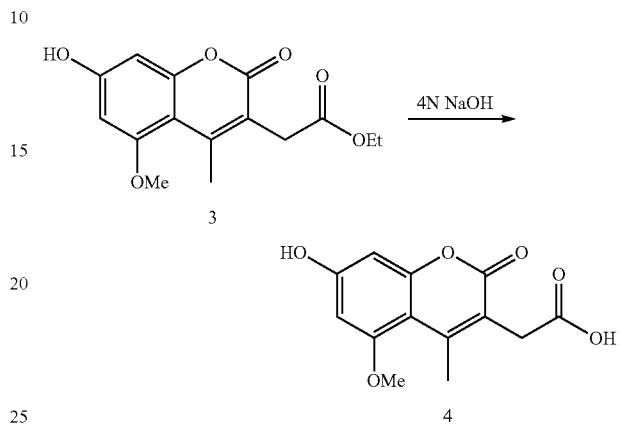

The compound 3 (100 g, 0.34 mol) was added into 4 N NaOH (256 mL, 1.03 mol) in portions with stirring at RT overnight. TLC showed that starting material was consumed completely 5N HCl was added until PH=2. The precipitate was filtered and washed with EA, dried in vacuo to give compound 4 as white solid (60 g, 67%)

Synthesis of Compound 5

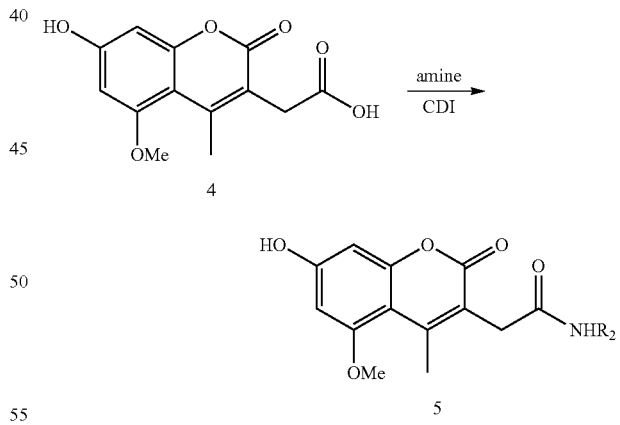

To a solution of compound 4 (1 eq) in DMF was added CDI (1.4 eq) in one portion. The solution was stirred at RT for 3 h. TLC showed that starting material was consumed completely. amine (1.4 eq) was added into the solution in one portion. The mixture solution was stirred at RT overnight. The solvent was removed under reduced pressure and the residue was treated with EA and DCM to give a suspension. The precipitate was filtered to give the product as solid.

Synthesis of Compound 6

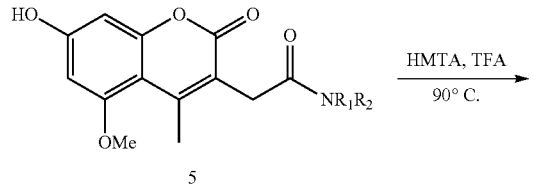

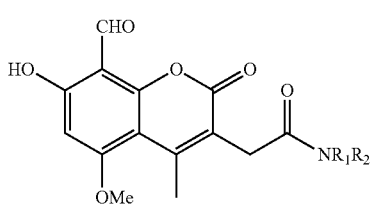

A mixture of compound 5 (1 eq) and HMTA (4 eq) in TFA was heated at 90° C. under nitrogen for 1.5 h. The reaction mixture turned to dark-yellow in the period. LCMS indicated that the reaction was completed. After cooled to RT, the solvent was removed under reduced pressure, the product was purified by Prep-HPLC to give compound 6.

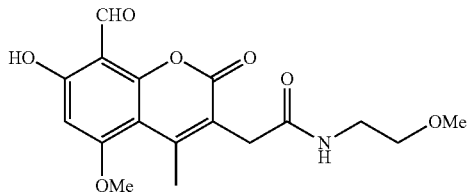 [SMILES: COCCNC(=O)Cc1c(C)c2c(OC)cc(O)c(C=O)c2oc1=O]

2-(8-Formyl-7-hydroxy-5-methoxy-4-methyl-2-oxo-2H-chromen-3-yl)-N-(2-methoxyethyl)acetamide was obtained by the above procedure from amine A1. 12% yield. $^1$HNMR (CDCl$_3$, 400 MHz): δ 12.56 (s, 1H, OH), 10.34 (s, 1H, CHO), 6.23 (s, 1H, ArH), 3.88 (s, 3H, CH$_3$), 3.51 (s, 2H, CH$_2$), 3.37-3.33 (m, 4H, CH$_2$), 3.28 (s, 3H, CH$_3$), 2.61 (s, 3H, CH$_3$); MS [ESI, MH$^+$]: 350.1

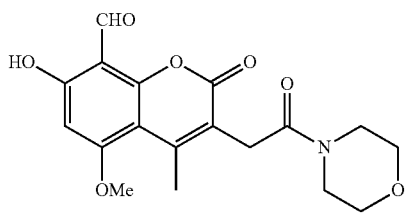 [SMILES: COc1cc(O)c(C=O)c2oc(=O)c(CC(=O)N3CCOCC3)c(C)c12]

7-Hydroxy-5-methoxy-4-methyl-3-(2-morpholino-2-oxo-ethyl)-2-oxo-2H-chromene-8-carbaldehyde was obtained by the above procedure from amine A2. 46% yield.

$^1$H NMR (CDCl$_3$, 400 MHz): δ 12.60 (s, 1H, OH), 10.38 (s, 1H, CHO), 6.27 (s, 1H, ArH), 3.92 (s, 3H, CH$_3$), 3.75-3.62 (m, 10H), 2.53 (s, 3H, CH$_3$). MS [ESI, MH$^+$]: 362.2

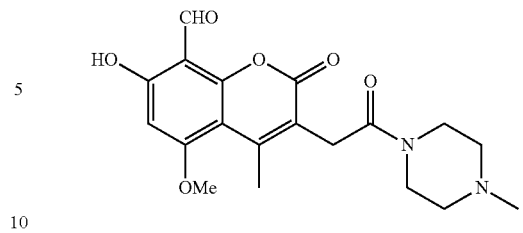

7-Hydroxy-5-methoxy-4-methyl-3-(2-(4-methylpiperazin-1-yl)-2-oxoethyl)-2-oxo-2H-chromene-8-carbaldehyde was obtained by the above procedure from amine A3. 9.2% yield. $^1$HNMR (D$_2$O, 400 MHz): δ 9.65 (s, 1H, CHO), 5.99 (s, 1H, ArH), 4.41 (d, 1H, J=12.4 Hz CH$_2$), 4.22 (d, 1H, J=14.4 Hz, CH$_2$), 3.65 (s, 3H, CH$_3$), 3.59-3.15 (m, 8H), 2.83 (s, 3H, CH$_3$), 2.15 (s, 3H, CH$_3$); MS [ESI, MH$^+$]: 375.1.

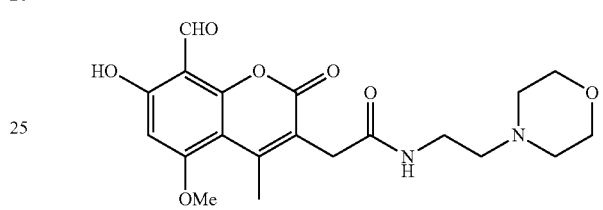

2-(8-Formyl-7-hydroxy-5-methoxy-4-methyl-2-oxo-2H-chromen-3-yl)-N-(2-morpholinoethyl)acetamide was obtained by the above procedure from amine A6. 9.3% yield. $^1$HNMR (D$_2$O, 400 MHz): δ 9.89 (s, 1H, CHO), 6.23 (s, 1H, ArH), 4.16-3.23 (m, 17H), 2.41 (s, 3H, CH$_3$); MS [ESI, MH$^+$]: 405.3

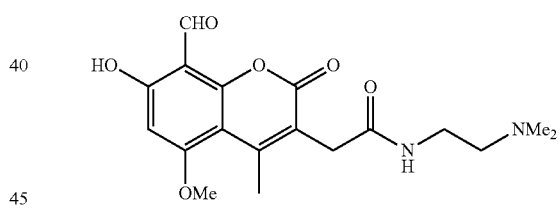

N-(2-(Dimethylamino)ethyl)-2-(8-formyl-7-hydroxy-5-methoxy-4-methyl-2-oxo-2H-chromen-3-yl)acetamide was obtained by the above procedure from amine A5. 11% yield. $^1$HNMR (CDCl$_3$, 400 MHz): δ 10.42 (s, 1H, CHO), 6.75 (br, 1H, NH), 6.31 (s, 1H, ArH), 3.97 (s, 3H, CH$_3$), 3.61 (s, 2H, CH$_2$), 3.37 (t, 2H, J=3.2 HZ, CH$_2$), 3.28 (s, 3H, CH$_3$), 2.52 (t, 2H, J=3.2 HZ, CH$_2$) 2.33 (s, 6H, 2NCH$_3$); MS [ESI, MH$^+$]: 363.2.

Example 65

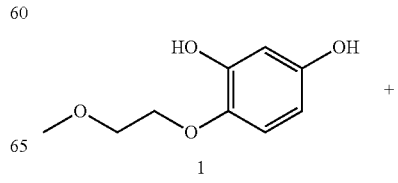

-continued

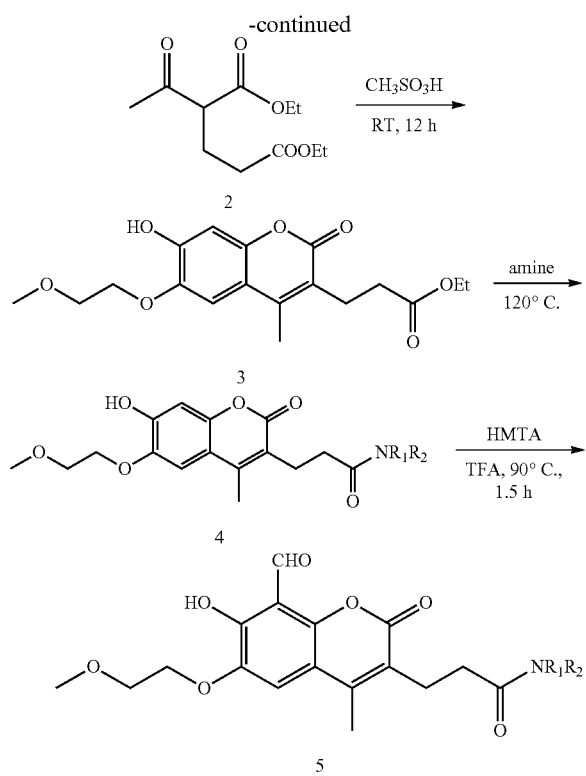

Synthesis of Compound 1

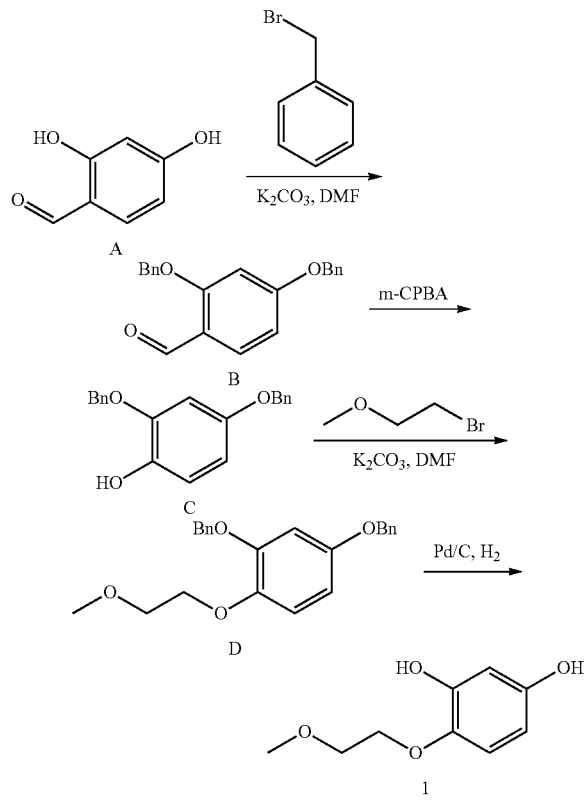

A mixture of compound A (200 g, 1.44 mol), BnBr (345 mL, 2.88 mol) and $K_2CO_3$ (300 g, 2.16 mol) in acetone was refluxed over night. The reaction mixture was filtered and the filtrate was concentrated to give compound B (421 g, 91.5%). 85% meta-perchlorobenzoic acid (348 g, 1.72 mol) was added, with stirring, at ambient temperature to a solution of compound B (421 g, 1.32 mol) in 4000 mL anhydrous methylene chloride. After stirring for 30 minutes, the mixture was filtered and the filtrate was washed with a solution of sodium bicarbonate, then with a solution of $NaHSO_3$ and finally with water. After drying on sodium sulphate, the solvent was evaporated, the residue were taken up in methanol (2000 mL) and water (2000 mL), NaOH (263.8 g, 6.60 mol) was added and stirring was carried out for 30 minutes after which the mixture was acidified with concentrated HCl. One extracts with methylene chloride and then washed with water until neutral. After drying on sodium sulphate, the solvent was evaporated, compound C (300 g, 74%) was obtained. A mixture of compound C (22 g, 71.89 mmol), 1-bromo-2-methoxyethane (13.4 mL, 14.38 mmol) and $K_2CO_3$(30 g, 21.57 mmol) in DMF was stirred at 80° C. over night. The reaction mixture was filtered and filtrate was concentrated to give compound D (20 g, 84%). A slurry of compound D (20 g, 54.94 mmol) and Pd/C (4.0 g) in methanol (500 mL) was stirred at ambient temperature for 4 hours under 2 atm $H_2$ (30 PSI). The mixture was filtered and filtrate was concentrated, the residue was purified by column chromatogram to give compound 1(9.7 g, 95%).

Synthesis of Compound 3

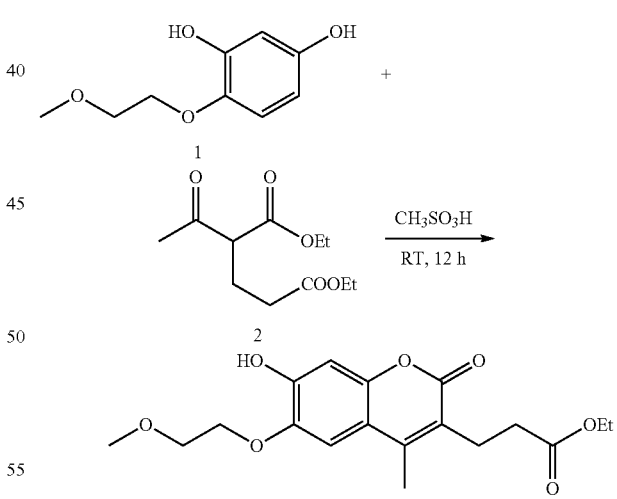

Compound 1 (9.7 g, 52.7 mmol) and compound 2 (12.1 g, 52.7 mmol) were added to $CH_3SO_3H$ (500 mL) at RT. The mixture was stirred at RT for 12 h. LC-MS showed that starting material was consumed completely. The reaction mixture was poured into ice-water (300 mL) and stirred for 30 min. The formed precipitate was filtered and washed with water and EA, dried, afforded the crude compound 3 (19.5 g, 100%) as white solid.

Synthesis of Compound 4

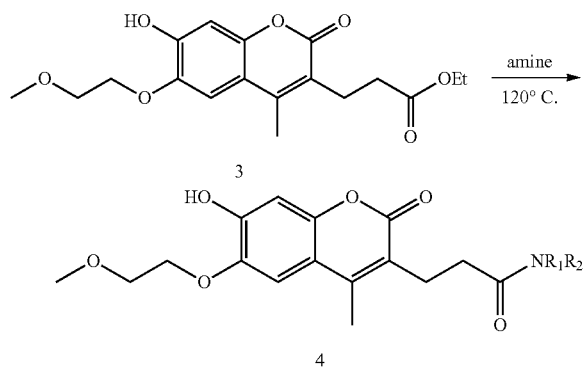

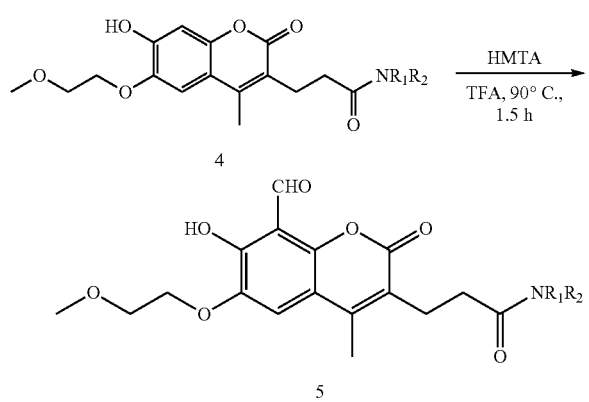

Compound 3 (1.0 eq) was added to amine The reaction mixture was stirred at 120° C. for 48 h. LC-MS showed that the starting material was almost consumed completely. The solvent was removed under vacuum. The residue was washed with DCM and concentrated under vacuum, afforded compound 4.

Synthesis of Compound 5

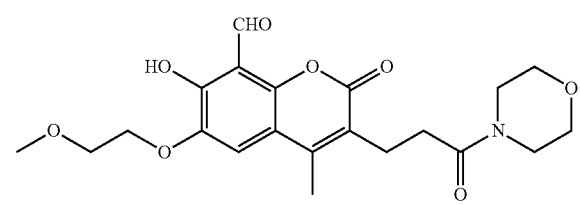 [SMILES: COCCOc1cc2c(C)c(CCC(=O)N3CCOCC3)c(=O)oc2c(C=O)c1O]

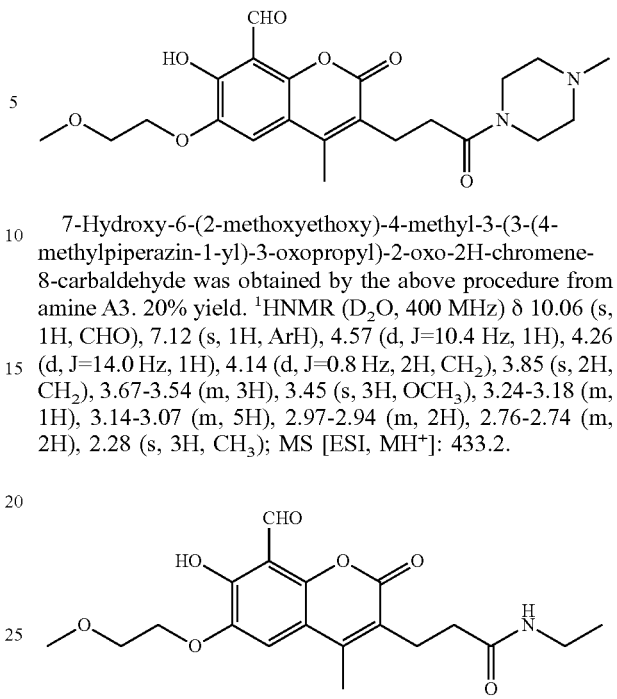

A mixture of compound 4 (1.0 eq) and HMTA (4.0 eq) in TFA (100 mL) was heated to 90° C. under nitrogen for 2 h. LC-MS indicated that the reaction was completed. After cooled to RT, the solvent was removed under vacuum. The residue was purified by Prep-HPLC, afforded compound 5.

7-Hydroxy-6-(2-methoxyethoxy)-4-methyl-3-(3-morpholino-3-oxopropyl)-2-oxo-2H-chromene-8-carbaldehyde was obtained by the above procedure from amine A2. 40% yield. $^1$HNMR (CDCl$_3$, 400 MHz) δ 10.56 (s, 1H, CHO), 7.36 (s, 1H, ArH), 4.24-4.21 (m, 2H, CH$_2$), 3.83 (t, J=5.4 Hz, 2H, CH$_2$), 3.76-3.66 (m, 8H), 3.47 (s, 3H, CH$_3$), 2.95-2.91 (m, 2H, CH$_2$), 2.69-2.65 (m, 2H, CH$_2$), 2.43 (s, 3H, CH$_3$); MS [ESI, MH$^+$]: 420.1.

7-Hydroxy-6-(2-methoxyethoxy)-4-methyl-3-(3-(4-methylpiperazin-1-yl)-3-oxopropyl)-2-oxo-2H-chromene-8-carbaldehyde was obtained by the above procedure from amine A3. 20% yield. $^1$HNMR (D$_2$O, 400 MHz) δ 10.06 (s, 1H, CHO), 7.12 (s, 1H, ArH), 4.57 (d, J=10.4 Hz, 1H), 4.26 (d, J=14.0 Hz, 1H), 4.14 (d, J=0.8 Hz, 2H, CH$_2$), 3.85 (s, 2H, CH$_2$), 3.67-3.54 (m, 3H), 3.45 (s, 3H, OCH$_3$), 3.24-3.18 (m, 1H), 3.14-3.07 (m, 5H), 2.97-2.94 (m, 2H), 2.76-2.74 (m, 2H), 2.28 (s, 3H, CH$_3$); MS [ESI, MH$^+$]: 433.2.

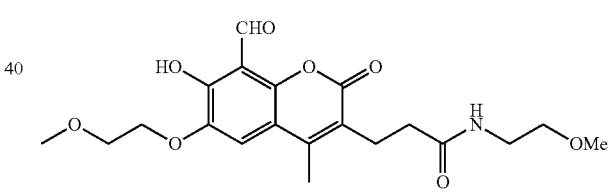

N-Ethyl-3-(8-formyl-7-hydroxy-6-(2-methoxyethoxy)-4-methyl-2-oxo-2H-chromen-3-yl)propanamide was obtained by the above procedure from amine A4. 12% yield.
$^1$HNMR (CDCl$_3$, 400 MHz) δ 12.36 (s, 1H, OH), 10.58 (s, 1H, CHO) 7.38 (s, 1H, ArH), 4.25-4.22 (m, 2H, CH$_2$), 3.79-3.77 (m, 2H, CH$_2$), 3.44 (s, 3H, OCH$_3$), 3.26-3.23 (m, 2H, CH$_2$), 2.96 (t, J=7.6 Hz, 2H, CH$_2$), 2.48-2.42 (m, 5H), 1.08 (t, J=7.2 Hz, 3H, CH$_3$); MS [ESI, MH$^+$]: 378.1.

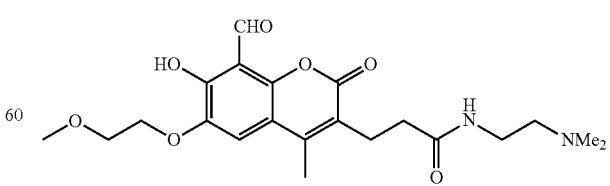

3-(8-Formyl-7-hydroxy-6-(2-methoxyethoxy)-4-methyl-2-oxo-2H-chromen-3-yl)-N-(2-methoxyethyl)propanamide was obtained by the above procedure from amine A1. 12% yield. $^1$HNMR (CDCl$_3$, 400 MHz) δ 12.41 (d, J=16.8 Hz, 1H, OH), 10.59 (s, 1H, CHO) 7.38 (s, 1H, ArH), 4.24 (t, J=4.6 Hz 2H, CH$_2$), 3.79 (t, J=4.6 Hz, 2H, CH$_2$), 3.45 (s, 3H, OCH$_3$), 3.41 (d, J=2.4 Hz, 4H, 2CH$_2$), 3.30 (s, 3H, OCH$_3$), 2.97 (t, J=7.6 Hz, 2H, CH$_2$), 2.43 (t, J=7.6 Hz, 2H, CH$_2$), 2.26 (s, 3H, CH$_3$); MS [ESI, MH$^+$]: 408.1.

N-(2-(Dimethylamino)ethyl)-3-(8-formyl-7-hydroxy-6-(2-methoxyethoxy)-4-methyl-2-oxo-2H-chromen-3-yl)propanamide was obtained by the above procedure from amine A6. 9% yield. $^1$HNMR (D$_2$O, 400 MHz) δ 9.66 (s, 1H, CHO), 6.76 (s, 1H, ArH), 3.89 (s, 2H, CH$_2$), 3.70 (s, 2H, CH$_2$), 3.50 (d, J=5.6 Hz, 2H, CH$_2$), 3.35 (s, 3H, OCH$_3$), 3.24 (d, J=5.6 Hz, 2H, CH$_2$), 2.86 (s, 6H, 2NCH$_3$), 2.58 (d, J=7.2 Hz, 1H), 2.32 (d, J=7.2 Hz, 1H), 2.05 (s, 3H, CH$_3$); MS [ESI, MH$^+$]: 421.2.

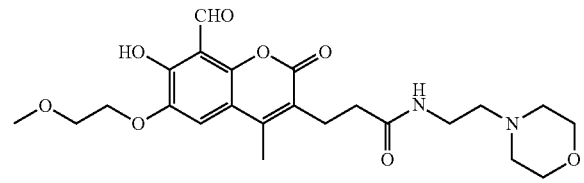 [SMILES: COCCOc1cc2c(C)c(CCC(=O)NCCN3CCOCC3)c(=O)oc2c(C=O)c1O]

3-(8-Formyl-7-hydroxy-6-(2-methoxyethoxy)-4-methyl-2-oxo-2H-chromen-3-yl)-N-(2-morpholinoethyl)propanamide was obtained by the above procedure from amine A2. 13% yield. $^1$HNMR (D$_2$O, 400 MHz) δ 9.64 (s, 1H, CHO), 6.75 (s, 1H, ArH), 4.09 (d, J=12.8 Hz, 2H, CH$_2$), 3.88 (s, 2H, CH$_2$), 3.83 (d, J=13.6 Hz, 2H, CH$_2$), 3.77 (s, 4H, CH$_2$), 3.70 (s, 2H, CH$_2$), 3.36 (d, J=2.0 Hz, 3H, OCH$_3$), 3.30 (d, J=5.6 Hz, 2H, CH$_2$), 3.15 (t, J=11.6 Hz, 2H, CH$_2$), 2.58 (s, 2H, CH$_2$), 2.32 (s, 2H, CH$_2$), 2.05 (s, 3H, CH$_3$); MS [ESI, MH$^+$]: 463.2.

Example 66

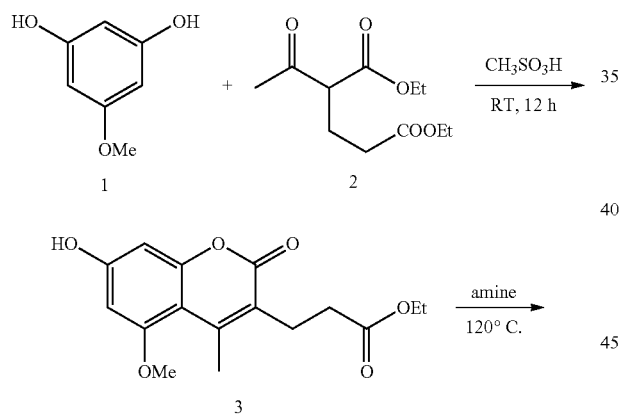

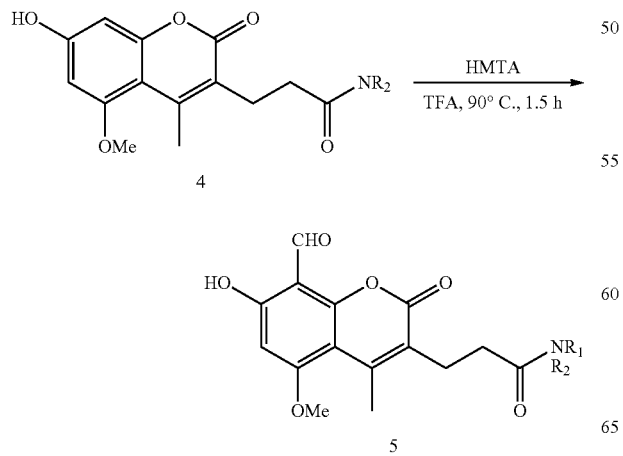

Synthesis of Compound 1

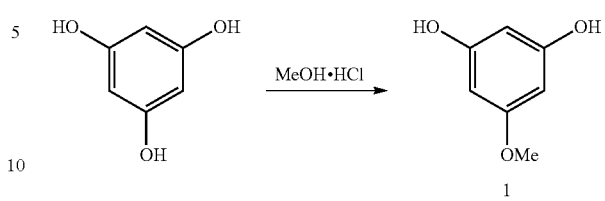

The solution of compound (50 g, 396.82 mmol) in solvent (methanol:1,2-dioxane=4:1, 1000 mL) was stirred at 0° C. under HCl (gas) for 1 hour, then the mixture was refluxed for 24 hours. The mixture was concentrated and purified by column chromatogram to give Compound 1 (33 g, 58.9%).

Synthesis of Compound 3

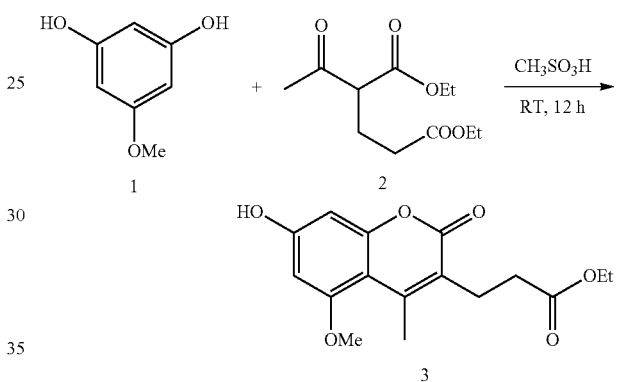

Compound 1 (25 g, 0.178 mol) and compound 2 (40.7 g, 0.178 mol) were added to CH$_3$SO$_3$H (500 mL) at RT. The mixture was stirred at RT for 12 h. LC-MS showed that starting material was consumed completely. The reaction mixture was poured into ice-water (300 mL) and stirred for 30 min. The formed precipitate was filtered and washed with water and EA, dried, afforded the crude compound 3 (10.2 g, 18.6%) as white solid.

Synthesis of Compound 4

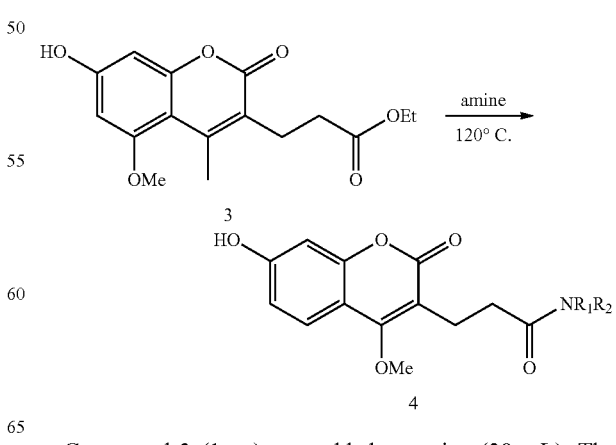

Compound 3 (1 eq) was added to amine (20 mL). The reaction mixture was stirred at 120° C. for 48 h. LC-MS showed that the starting material was almost consumed completely. The solvent was removed under vacuum. The residue was washed with DCM and concentrated under vacuum, afforded compound 4.

Synthesis of Compound 5

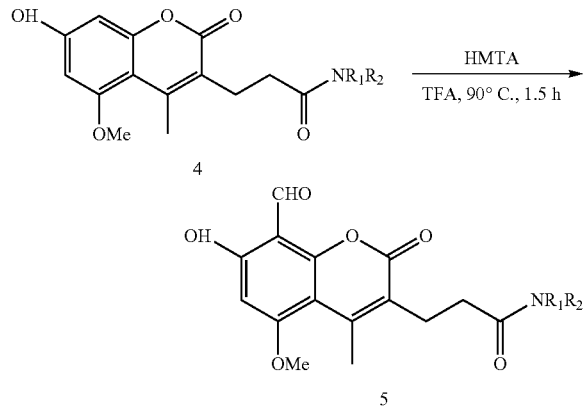

A mixture of compound 4 (1.0 eq) and HMTA (4.0 eq) in TFA (100 mL) was heated to 90° C. under nitrogen for 2 h. LC-MS indicated that the reaction was completed. After cooled to RT, the solvent was removed under vacuum. The residue was purified by Prep-HPLC, afforded compound 5.

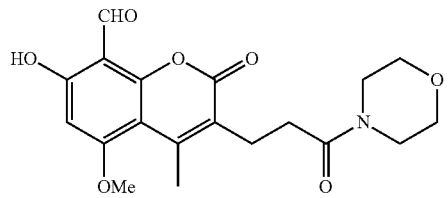 [SMILES: COc1cc(O)c(C=O)c2oc(=O)c(CCC(=O)N3CCOCC3)c(C)c12]

7-Hydroxy-5-methoxy-4-methyl-3-(3-morpholino-3-oxo-propyl)-2-oxo-2H-chromene-8-carbaldehyde was obtained by the above procedure from amine A2. 15% yield.

$^1$HNMR (CDCl$_3$, 400 MHz): δ 10.38 (s, 1H, CHO), 6.27 (s, 1H, ArH), 3.93 (s, 3H, ArOCH$_3$), 3.70-3.56 (m, 8H, CH$_2$), 2.94-2.90 (m, 2H, CH$_2$), 2.58 (s, 3H, CH$_3$), 2.58-2.53 (m, 2H, CH$_2$); MS [ESI, MH$^+$]: 376.2.

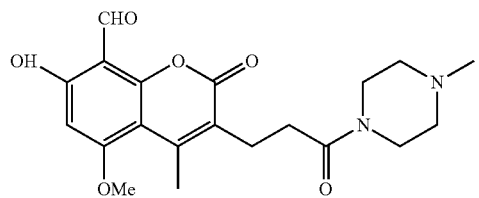 [SMILES: COc1cc(O)c(C=O)c2oc(=O)c(CCC(=O)N3CCN(C)CC3)c(C)c12]

7-Hydroxy-5-methoxy-4-methyl-3-(3-(4-methylpiper-azin-1-yl)-3-oxopropyl)-2-oxo-2H-chromene-8-carbalde-hyde was obtained by the above procedure from amine A3. 9.2% yield. $^1$HNMR (MeOD, 400 MHz): δ 10.30 (s, 1H, CHO), 6.44 (s, 1H, ArH), 3.97 (s, 3H, ArOCH$_3$), 3.29-3.27 (m, 5H, CH$_2$), 2.93 (s, 3H, CH$_3$), 2.92-2.87 (m, 4H, CH$_2$), 2.596-2.593 (m, 6H, CH$_2$); MS [ESI, MH$^+$]: 389.2.

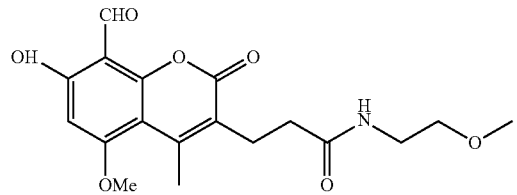 [SMILES: COCCNC(=O)CCc1c(C)c2c(OC)cc(O)c(C=O)c2oc1=O]

3-(8-Formyl-7-hydroxy-5-methoxy-4-methyl-2-oxo-2H-chromen-3-yl)-N-(2-methoxyethyl)propanamide was obtained by the above procedure from amine A1. 13% yield. $^1$HNMR (CDCl3, 400 MHz): δ10.36 (s, 1H, CHO), 6.30 (s, 1H, —NH), 6.26 (s, 1H, ArH), 3.93 (s, 3H, ArOCH$_3$), 3.44-3.43 (m, 4H, 2CH$_2$), 3.31 (s, 3H, OCH$_3$), 2.95 (t, 2H, J=8 Hz, CH$_2$), 2.56 (s, 3H, CH$_3$), 2.47 (t, 2H, J=8.0 Hz, CH$_2$). MS [ESI, MH$^+$]: 364.1.

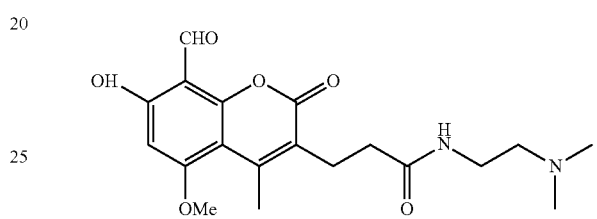

N-(2-(Dimethylamino)ethyl)-3-(8-formyl-7-hydroxy-5-methoxy-4-methyl-2-oxo-2H-chromen-3-yl)propanamide was obtained by the above procedure from amine A1. 10% yield. $^1$HNMR (D$_2$O, 400 MHz): δ9.72 (s, 1H, CHO), 6.10 (s, 1H, ArH), 6.26 (s, 1H, ArH), 3.81 (s, 3H, ArOCH$_3$), 3.59 (t, 2H, J=6.0 Hz CH$_2$), 3.32 (t, 2H, J=6.0 Hz CH$_2$), 2.95 (s, 6H, 2CH$_3$), 2.72 (t, 2H, J=7.6 Hz, CH$_2$). 2.39 (t, 2H, J=7.6 Hz, CH$_2$), 2.37 (s, 3H, CH$_3$); MS [ESI, MH$^+$]: 377.1.

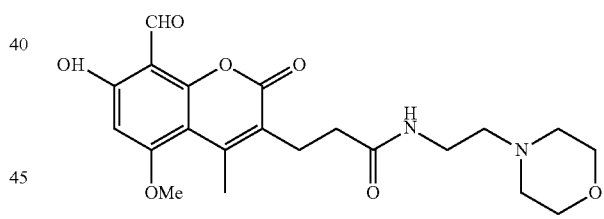

3-(8-Formyl-7-hydroxy-5-methoxy-4-methyl-2-oxo-2H-chromen-3-yl)-N-(2-morpholinoethyl)propanamide was obtained by the above procedure from amine A5. 7.8% yield. $^1$HNMR (MeOD, 400 MHz): δ 10.26 (s, 1H, CHO), 6.42 (s, 1H, —NH), 5.89 (s, 1H, ArH), 4.05 (s, 2H, CH$_2$), 3.96 (s, 3H, ArOCH$_3$), 3.87-3.51 (m, 8H, CH$_2$), 3.14 (s, 2H, CH$_2$), 2.93 (t, 2H, J=7.6 Hz, CH$_2$), 2.56 (s, 3H, CH$_3$), 2.43-2.36 (m, 2H, CH$_2$). MS [ESI, MH$^+$]: 419.2.

Example 67

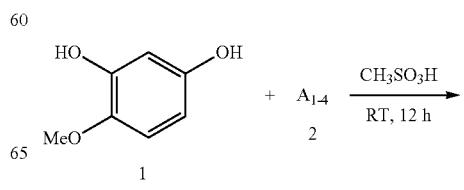

-continued

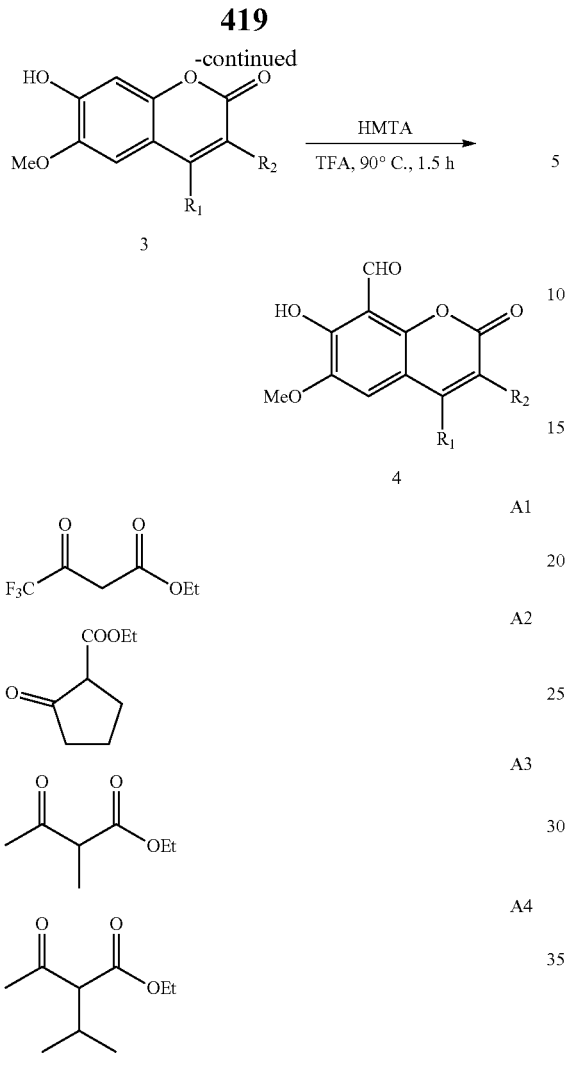

Synthesis of Compound 3

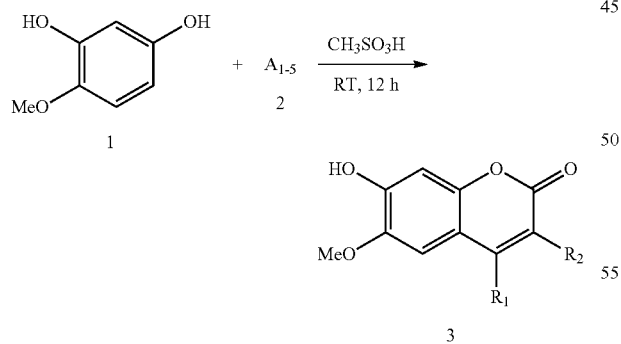

To a suspension of compound 1 (1 eq), compound 2 (1.2 eq), CH$_3$SO$_3$H was added in one portion. The mixture was stirred at RT 12 h. LC-MS showed that starting material was consumed completely. The reaction mixture was poured into ice-water (100 mL) and stirred for 30 min. The formed precipitate was filtered and washed with water and EA, dried to afford the crude compound 3 and use at the next step directly.

Synthesis of Compound 4

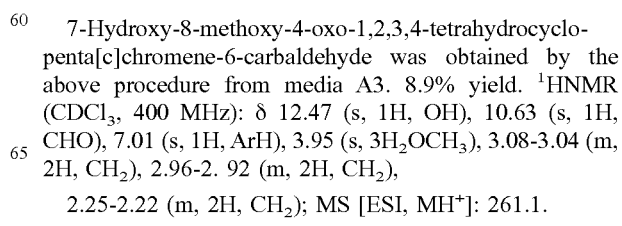

A mixture of compound 3 (1 eq) and HMTA (4 eq) in TFA was heated at 100° C. under nitrogen for 1.5 h. The reaction mixture turned to dark-yellow in the period. LCMS indicated that the reaction was completed. After cooled to RT, the solvent was removed under reduced pressure, the product was purified by Prep-HPLC to give compound 4.

7-Hydroxy-6-methoxy-2-oxo-4-(trifluoromethyl)-2H-chromene-8-carbaldehyde was obtained by the above procedure from media A1. 39.6% yield. $^1$HNMR (CDCl$_3$, 400 MHz): δ 12.69 (s, 1H, OH), 10.59 (s, 1H, CHO), 7.23 (s, 1H, ArH), 6.72 (s, 1H, CH), 3.96 (s, 3H, OCH$_3$); MS [ESI, MH$^+$]: 289.0.

7-Hydroxy-8-methoxy-4-oxo-1,2,3,4-tetrahydrocyclopenta[c]chromene-6-carbaldehyde was obtained by the above procedure from media A3. 8.9% yield. $^1$HNMR (CDCl$_3$, 400 MHz): δ 12.47 (s, 1H, OH), 10.63 (s, 1H, CHO), 7.01 (s, 1H, ArH), 3.95 (s, 3H$_2$OCH$_3$), 3.08-3.04 (m, 2H, CH$_2$), 2.96-2.92 (m, 2H, CH$_2$), 2.25-2.22 (m, 2H, CH$_2$); MS [ESI, MH$^+$]: 261.1.

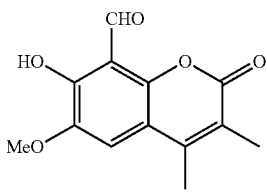

7-Hydroxy-6-methoxy-3,4-dimethyl-2-oxo-2H-chromene-8-carbaldehyde was obtained by the above procedure from media A3.1.2% yield. $^1$HNMR (CDCl$_3$, 400 MHz): δ 12.38 (s, 1H, OH), 10.61 (s, 1H, CHO), 7.18 (s, 1H, ArH), 3.95 (s, 3H, OCH$_3$), 2.38 (d, 3H, J=8.0 HZ CH$_3$), 2.20 (d, 3H, J=8.0 HZ CH$_2$); MS [ESI, MH$^+$]: 249.1.

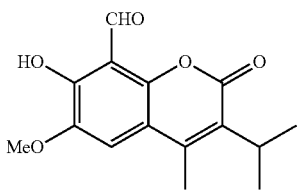 [SMILES: COc1cc2c(C)c(C(C)C)c(=O)oc2c(C=O)c1O]

7-Hydroxy-3-isopropyl-6-methoxy-4-methyl-2-oxo-2H-chromene-8-carbaldehyde was obtained by the above procedure from media A4.5% yield. $^1$HNMR (CDCl$_3$, 400 MHz): δ 12.38 (s, 1H, OH), 10.61 (s, 1H, CHO), 7.24 (d, 1H, J=14.8 HZ, ArH), 3.96 (s, 3H, OCH$_3$), 2.38 (m, 1H, CH), 2.41 (s, 3H, CH$_3$), 1.37-1.35 (m, 6H).

Example 68

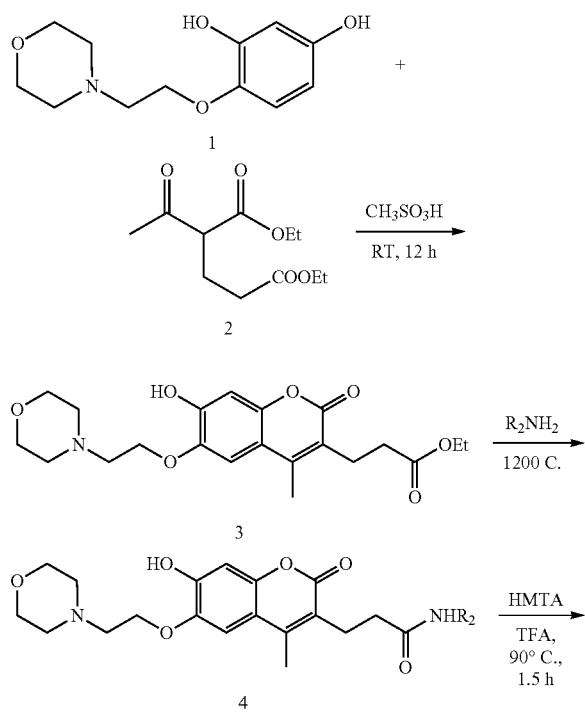

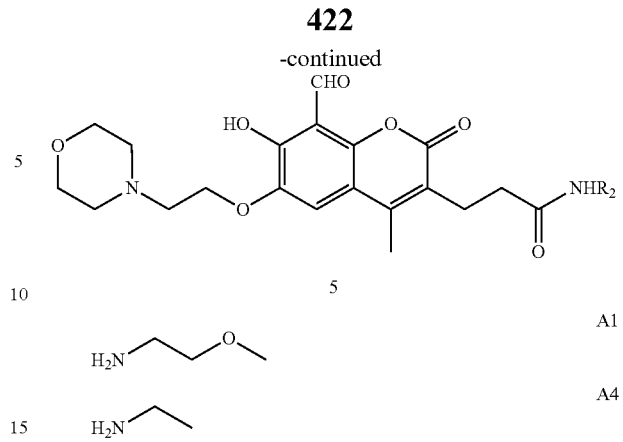

Synthesis of Compound 1

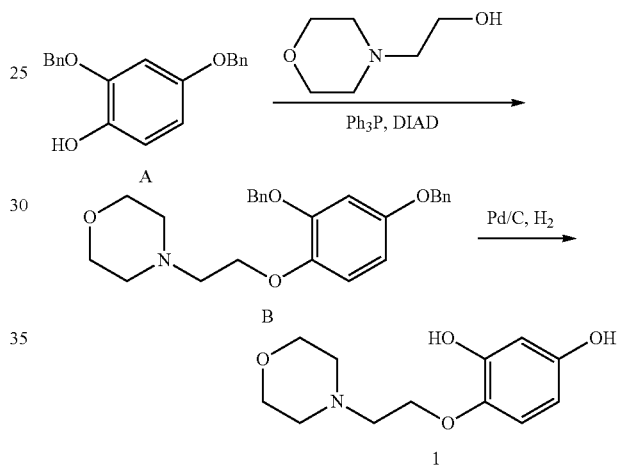

To a solution of compound A (55 g, 179.74 mmol), 2-morpholinoethanol (23.5 g, 179.74 mmol) and triphenylphosphine (56.5 g, 215.69 mmol) in THF, DIAD (43.5 g, 215.69 mmol) was added in portions. The solution was stirred at ambient temperature over night. The reaction mixture was concentrated and purified by column chromatogram to give compound B (52.6 g, 69.8%). A slurry of compound B (52.6 g, 125.54 mmol), CH$_3$COOH (100 mL) and Pd/C (14.0 g) in methanol (800 mL) was stirred at ambient temperature for 4 hours under 2 atm H$_2$ (30 PSI). The mixture was filtered and filtrate was concentrated, the residue was purified by column chromatogram y to give compound 1(30 g, 98%).

Synthesis of Compound 3

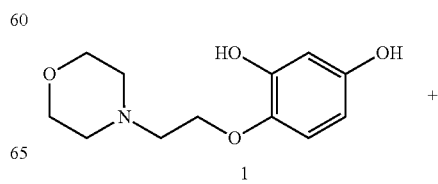

423
-continued

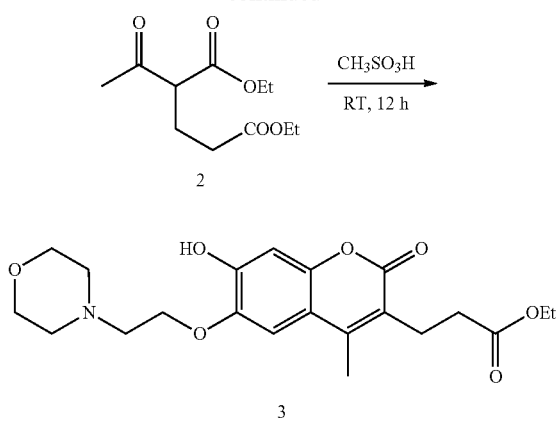

A mixture of compound 1(6.7 g, 28.0 mmol) and compound 2(7.06 g, 28.0 mmol) in methane sulfonic acid was stirred at ambient temperature over night. The reaction mixture was poured into ice-water and stirred for 30 minutes. The formed precipitate was filtered and washed with water and EA, dried to afford the compound 3(5.0 g, 44%).

Synthesis of Compound 4

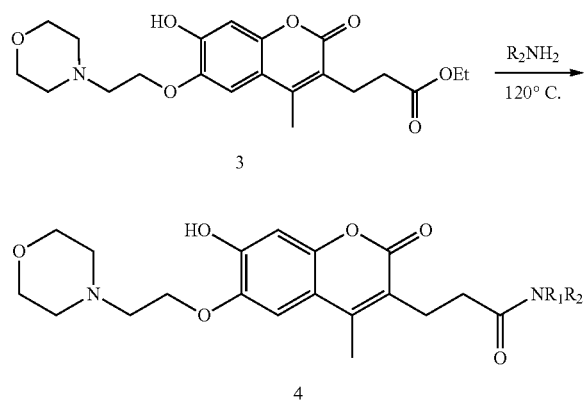

Compound 3 (1.0 eq) was added to Amine (20 mL). The reaction mixture was stirred at 120° C. for 48 h. LC-MS showed that the starting material was almost consumed completely. The solvent was removed under vacuum. The residue was washed with DCM (3×5 mL) and concentrated under vacuum, afforded compound 4.

Synthesis of Compound 5

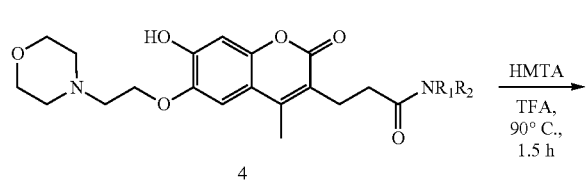

424
-continued

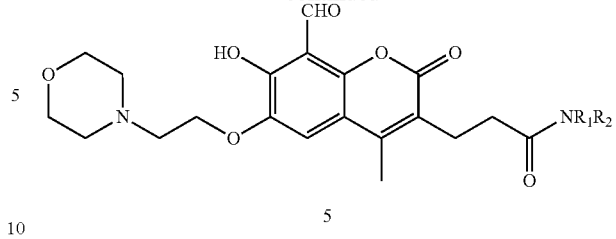

A mixture of compound 4 (1.0 eq) and HMTA (4.0 eq) in TFA (100 mL) was heated to 90° C. under nitrogen for 2 h. LC-MS indicated that the reaction was completed. After cooled to RT, the solvent was removed under vacuum. The residue was purified by Prep-HPLC, afforded Compound 5.

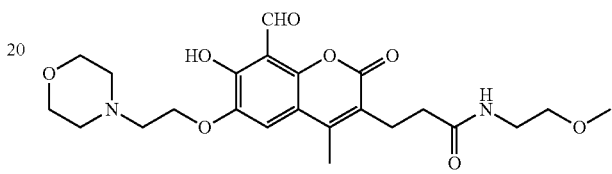

3-(8-Formyl-7-hydroxy-4-methyl-6-(2-morpholinoethoxy)-2-oxo-2H-chromen-3-yl)-N-(2-methoxyethyl)propanamide was obtained by the above procedure from amine A1. 10% yield. $^1$HNMR (D$_2$O, 400 MHz): δ10.11 (s, 1H, CHO), 7.31 (s, 1H, ArH), 4.39 (t, J=4.4 Hz, 2H, CH$_2$), 4.06 (d, J=12.4 Hz, 2H, CH$_2$), 3.79 (t, J=12.4 Hz, 2H, CH$_2$), 3.64-3.58 (m, 4H, CH$_2$), 3.32-3.25 (m, 4H, CH$_2$), 3.16 (t, J=5.6 Hz, 2H, CH$_2$), 3.07 (s, 3H, OCH$_3$), 2.73 (t, J=7.6 Hz, 2H, CH$_2$), 2.32 (t, J=6.8 Hz, 2H, CH$_2$), 2.24 (s, 3H, CH$_3$); MS [ESI, MH$^+$]: 462.23.

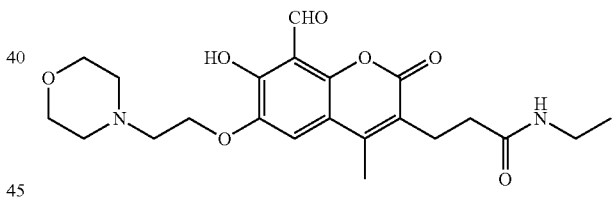

N-Ethyl-3-(8-formyl-7-hydroxy-4-methyl-6-(2-morpholinoethoxy)-2-oxo-2H-chromen-3-yl)propanamide was obtained by the above procedure from amine A4. 7.4% yield. $^1$HNMR (D$_2$O, 400 MHz): δ9.97 (s, 1H, CHO), 7.25 (s, 1H, ArH), 4.35 (t, J=4.4 Hz, 2H, CH$_2$), 4.03 (d, J=12.8 Hz, 2H, CH$_2$), 3.79 (t, J=12.8 Hz, 2H, CH$_2$), 3.61-3.55 (m, 4H, CH$_2$), 3.26-3.23 (m, 2H, CH$_2$), 2.95-2.64 (m, 4H), 2.21-2.18 (m, 5H), 0.82 (t, J=7.2 Hz, CH$_3$; MS [ESI, MH$^+$]: 433.2.

Example 69

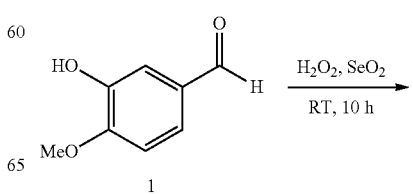

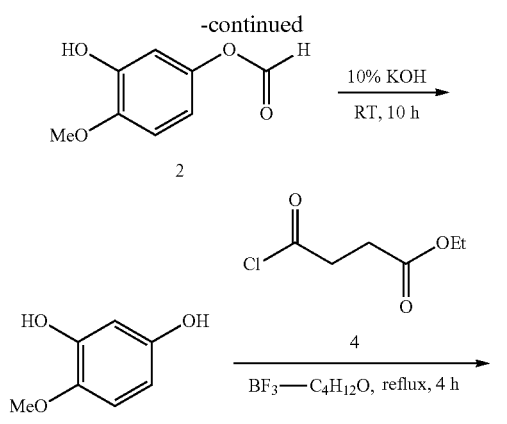
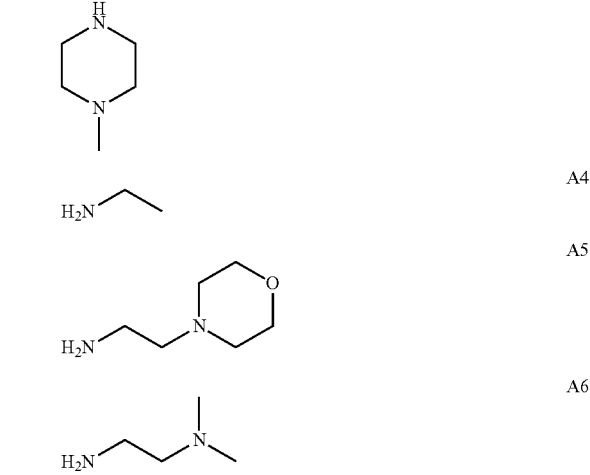
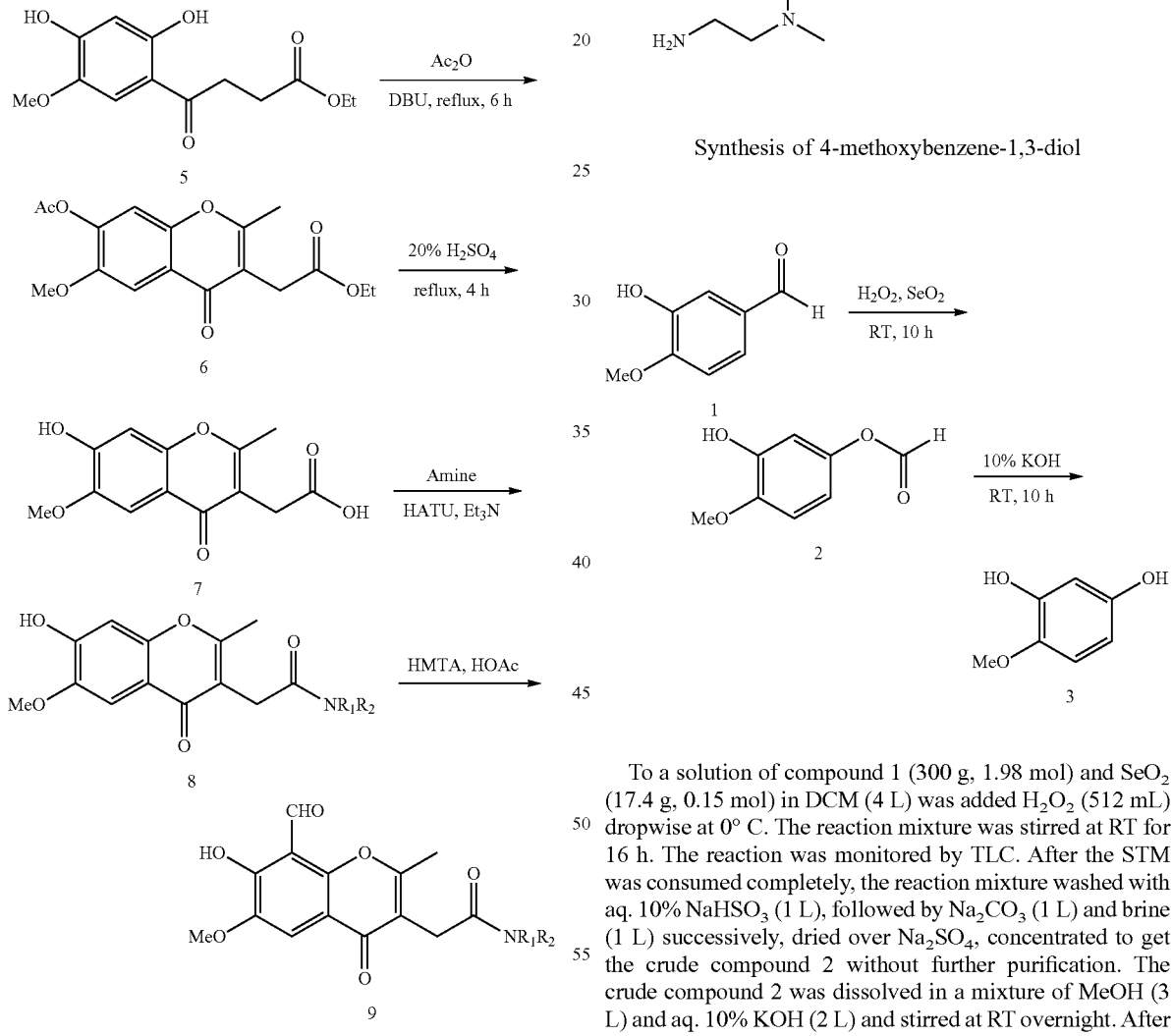

Synthesis of 4-methoxybenzene-1,3-diol

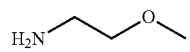
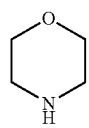

To a solution of compound 1 (300 g, 1.98 mol) and SeO$_2$ (17.4 g, 0.15 mol) in DCM (4 L) was added H$_2$O$_2$ (512 mL) dropwise at 0° C. The reaction mixture was stirred at RT for 16 h. The reaction was monitored by TLC. After the STM was consumed completely, the reaction mixture washed with aq. 10% NaHSO$_3$ (1 L), followed by Na$_2$CO$_3$ (1 L) and brine (1 L) successively, dried over Na$_2$SO$_4$, concentrated to get the crude compound 2 without further purification. The crude compound 2 was dissolved in a mixture of MeOH (3 L) and aq. 10% KOH (2 L) and stirred at RT overnight. After MeOH was removed, the mixture was acidified by 6M HCl to pH=3 and extracted with DCM (2 L×8). The combined DCM phase was washed with brine and dried over NaSO$_4$, concentrated. The residue was purified by silica gel column (EA:PE=6:1 to EA:PE=4:1) to give 4-methoxybenzene-1,3-diol (140 g, 50.5% yield) as light-yellow solid. $^1$HNMR (MeOD, 400 MHz): δ 6.70 (d, J=8.8 Hz, 1H, ArH), 6.29 (d, J=3.2 Hz, 1H, ArH), 6.18 (dd, J=8.8, 2.8 Hz, 1H, ArH), 3.73 (s, 3H, CH$_3$).

Synthesis of ethyl 4-(2,4-dihydroxy-5-methoxyphenyl)-4-oxobutanoate

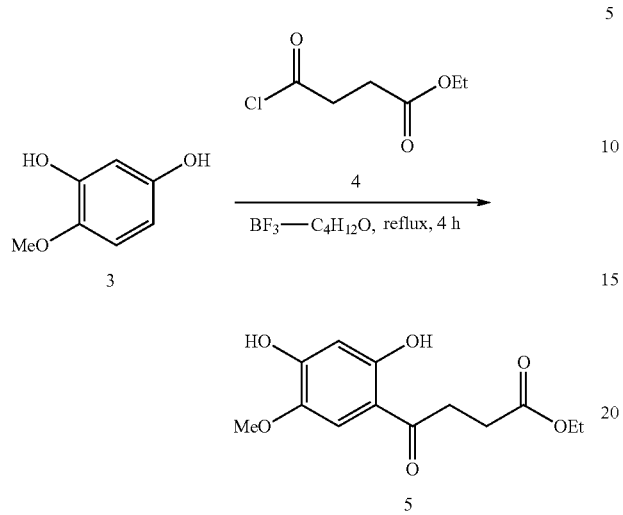

To a suspension of compound 3 (15 g, 0.11 mol) and compound 4 (21 g, 0.13 mol) in Dichloroethane (300 mL) was added $BF_3 \cdot C_2H_6O$ (15 g, 0.11 mol) in one portion. The mixture was stirred at RT for 4 h. After standing overnight, the reaction mixture was heated to reflux for 4 h, then cooled to RT. The formed precipitate was filtered and washed with water and EA, dried to afford the crude ethyl 4-(2,4-dihydroxy-5-methoxyphenyl)-4-oxobutanoate (20 g, 69% yield) as yellow oil. MS [ESI, $MH^+$]: 268.1.

Synthesis of ethyl 2-(7-acetoxy-6-methoxy-2-methyl-4-oxo-4H-chromen-3-yl) acetate

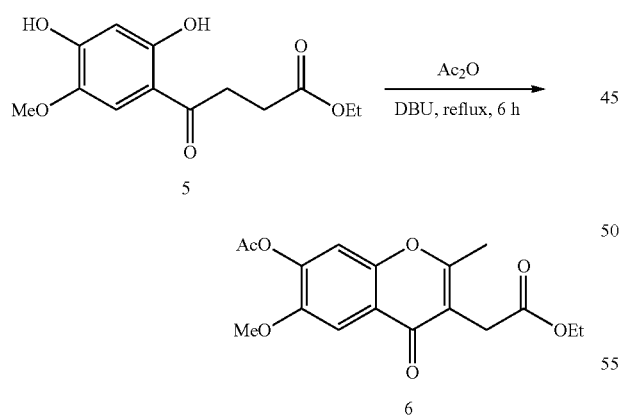

The mixture of compound 5 (20 g, 0.07 mol), $Ac_2O$ (31 g, 0.29 mol) and DBU (9 g, 0.55 mol) was heated to reflux for 6 h. After cooling to RT, the reaction mixture was dissolved in DCM (400 mL), then the solution was washed with water, dried over $Na_2SO_4$ and concentrated to give the ethyl 2-(7-acetoxy-6-methoxy-2-methyl-4-oxo-4H-chromen-3-yl)acetate (12 g, 48% yield). MS [ESI, $MNa^+$]: 356.9.

Synthesis of 2-(7-hydroxy-6-methoxy-2-methyl-4-oxo-4H-chromen-3-yl) acetic acid

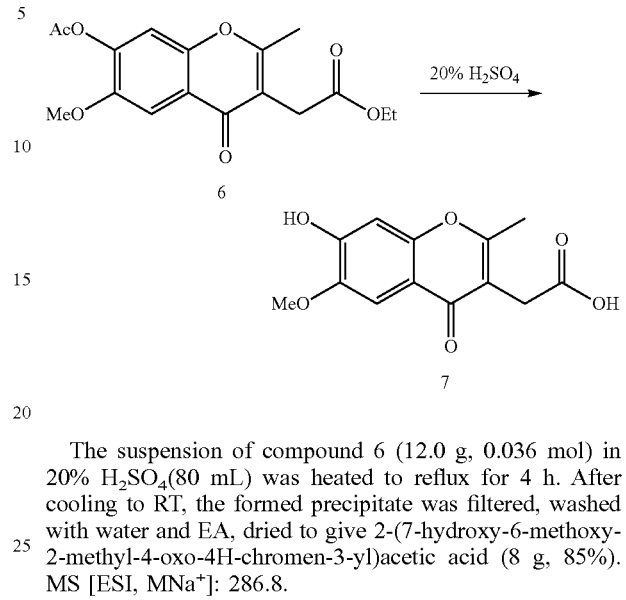

The suspension of compound 6 (12.0 g, 0.036 mol) in 20% $H_2SO_4$ (80 mL) was heated to reflux for 4 h. After cooling to RT, the formed precipitate was filtered, washed with water and EA, dried to give 2-(7-hydroxy-6-methoxy-2-methyl-4-oxo-4H-chromen-3-yl)acetic acid (8 g, 85%). MS [ESI, $MNa^+$]: 286.8.

Synthesis of Compound 8

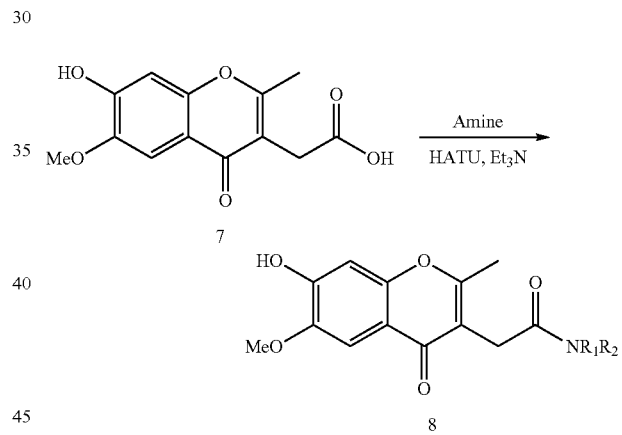

To the suspension of compound 7 (1 eq) and HATU (1 eq) in DMF was added $Et_3N$ (2 eq) dropwise at RT. The mixture was stirred at RT for 1 h. Then amine (1.5 eq) was added. The reaction mixture was stirred at RT for another 10 h. DMF was removed under vacuum, the residue was diluted with MeOH, the formed precipitate was filtered and washed with EA, dried to give compound 8.

Synthesis of Compound 9

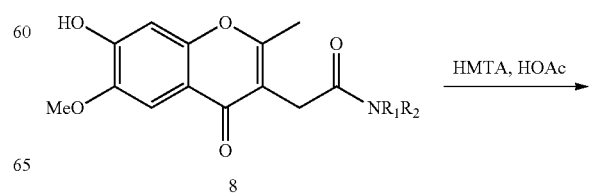

-continued

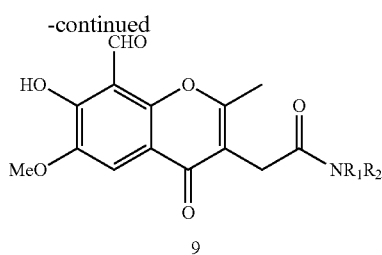

9

A mixture of compound 8 (1 eq) and HMTA (4 eq) in HOAc was heated to 90° C. under $N_2$ for 1.5 h. The reaction was monitored by LCMS. After cooled to RT, the solvent was removed under vacuum; the residue was purified by prep-HPLC to give compound 9.

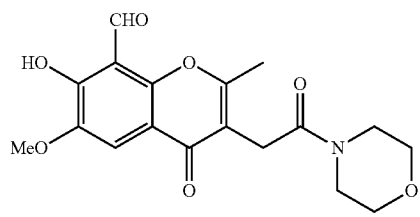 [SMILES: COc1cc2c(=O)c(CC(=O)N3CCOCC3)c(C)oc2c(C=O)c1O]

7-Hydroxy-6-methoxy-2-methyl-3-(2-morpholino-2-oxoethyl)-4-oxo-4H-chromene-8-carbaldehyde was obtained by the above procedure from amine A2. 12% yield.

$^1$HNMR (CDCl$_3$, 400 MHz): δ 12.80 (s, 1H, OH), 10.53 (d, 1H, J=1.2 Hz, CHO), 7.68 (s, 1H, ArH), 3.97 (s, 3H, ArOCH$_3$), 3.77-3.61 (m, 10H), 2.53 (s, 3H, CH$_3$). MS [ESI, MH$^+$]: 362.0.

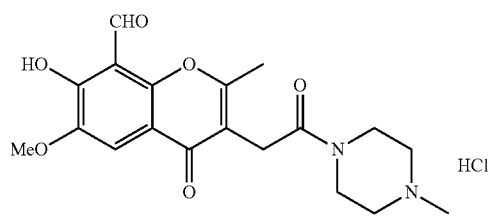 [SMILES: COc1cc2c(=O)c(CC(=O)N3CCN(C)CC3)c(C)oc2c(C=O)c1O ; Cl]

7-Hydroxy-6-methoxy-2-methyl-3-(2-(4-methylpiperazin-1-yl)-2-oxoethyl)-4-oxo-4H-chromene-8-carbaldehyde hydrochloride was obtained by the above procedure from amine A3. 8% yield. $^1$HNMR (MeOD, 400 MHz): δ 7.47 (s, 1H, ArH), 6.02 (s, 1H, CHO), 3.93 (s, 3H, CH$_3$), 3.58-3.54 (m, 10H), 2.95 (s, 3H, CH$_3$), 2.45 (s, 3H, CH$_3$). MS [ESI, MH$^+$]: 375.1.

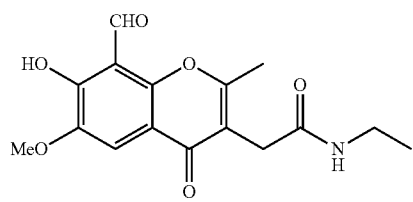 [SMILES: CCNC(=O)Cc1c(C)oc2c(C=O)c(O)c(OC)cc2c1=O]

N-Ethyl-2-(8-formyl-7-hydroxy-6-methoxy-2-methyl-4-oxo-4H-chromen-3-yl)acetamide was obtained by the above procedure from amine A4. 9% yield. $^1$HNMR (CDCl$_3$, 400 MHz): δ 10.53 (d, 1H, J=0.8 Hz, CHO), 7.69 (s, 1H, ArH), 6.50 (br, 1H, NH), 3.99 (s, 3H, ArOCH$_3$), 3.42 (s, 2H, CH$_2$), 3.22-3.18 (m, 2H, CH$_2$), 2.62 (s, 3H, CH$_3$), 1.09 (t, 3H, J=0.8 Hz, CH$_3$). MS [ESI, MH$^+$]: 320.1.

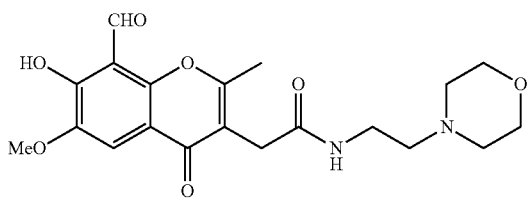 [SMILES: COc1cc2c(=O)c(CC(=O)NCCN3CCOCC3)c(C)oc2c(C=O)c1O]

2-(8-Formyl-7-hydroxy-6-methoxy-2-methyl-4-oxo-4H-chromen-3-yl)-N-(2-morpholinoethyl)acetamide was obtained by the above procedure from amine A5. 9% yield. $^1$HNMR (D$_2$O, 400 MHz): δ 10.21 (s, 1H, CHO), 7.26 (s, 1H, ArH), 4.14 (d, 2H, J=12.4 Hz, CH$_2$), 3.88-3.82 (m, 6H, 3CH$_2$), 3.67 (t, 4H, J=6.0 Hz, 2CH$_2$), 3.53 (s, 2H, CH$_2$), 3.40 (d, 2H, J=6.0 Hz, CH$_2$), 3.29-3.22 (m, 1H), 2.47 (s, 3H, CH$_3$). MS [ESI, MH$^+$]: 405.1.

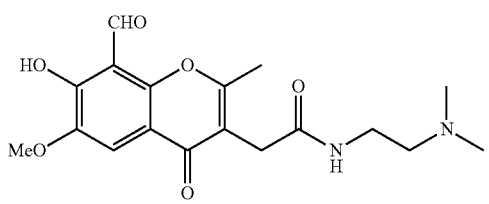 [SMILES: COc1cc2c(=O)c(CC(=O)NCCN(C)C)c(C)oc2c(C=O)c1O]

N-(2-(dimethylamino)ethyl)-2-(8-formyl-7-hydroxy-6-methoxy-2-methyl-4-oxo-4H-chromen-3-yl)acetamide was obtained by the above procedure from amine A6. 8% yield. $^1$HNMR (D$_2$O, 400 MHz): δ 10.26 (s, 1H, CHO), 7.32 (s, 1H, ArH), 3.88 (s, 3H, CH$_3$), 3.66 (t, 2H, J=5.6 Hz, CH$_2$), 3.56 (s, 2H, CH$_2$), 3.37 (t, 2H, J=5.6 Hz, CH$_2$), 2.97 (s, 6H, 2CH$_3$), 2.50 (s, 3H, CH$_3$). MS [ESI, MH$^+$]: 363.1.

Example 70

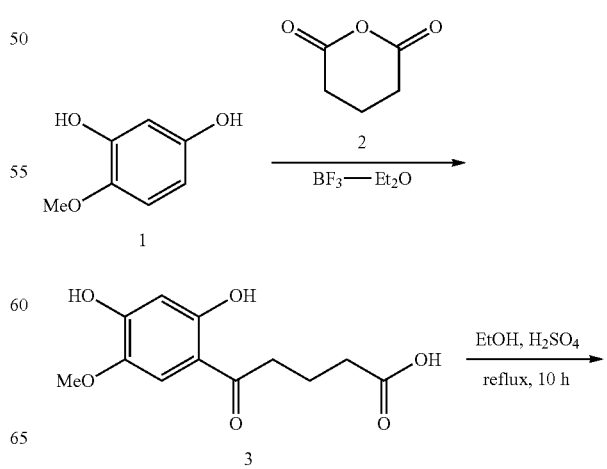

431
-continued

432
Synthesis of Compound 3

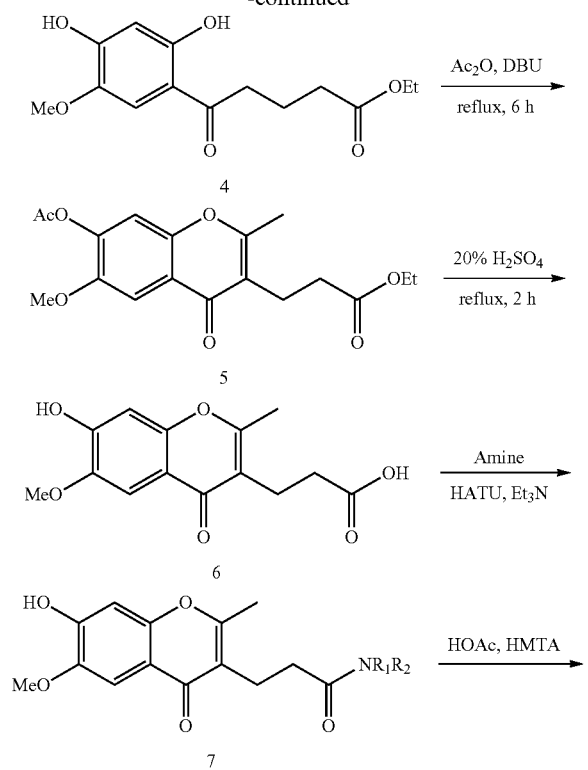

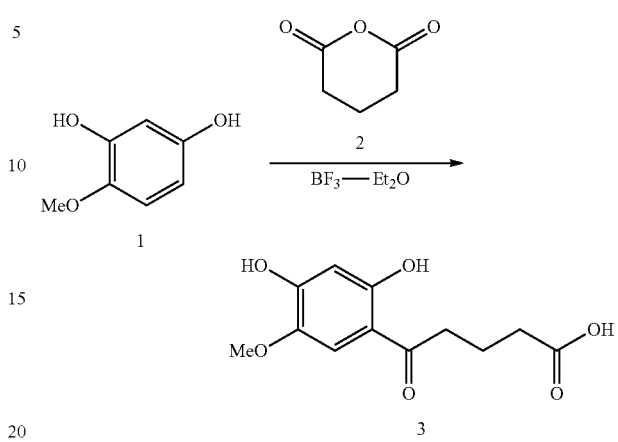

To a suspension of compound 1 (15 g, 0.11 mol) and compound 2 (21 g, 0.13 mol) in Dichloroethane (300 ml), BF$_3$·C$_2$H$_6$O (15 g, 0.11 mol) was added in one portion. The mixture was first stirred at RT for 4 h, then heated to reflux for 4 h. After cooling to RT, the formed precipitate was filtered and washed with water and EA, dried to afford the crude compound 3 (20 g, 69% yield) as yellow oil.

Synthesis of Compound 4

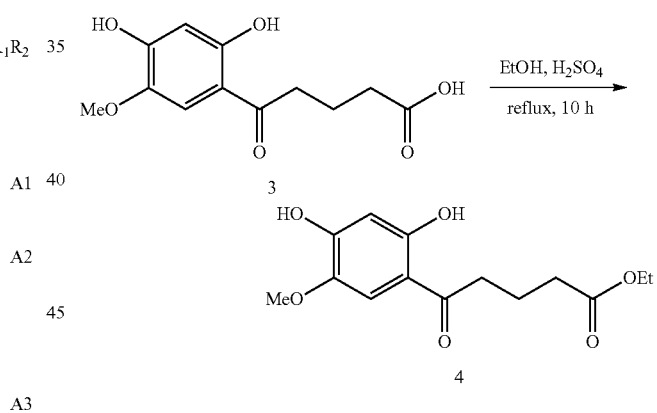

To a suspension of compound 3 (38 g, 0.15 mol) in EtOH (300 mL) was added H$_2$SO$_4$ (1 mL). The mixture was heated to reflux for 4 h. After cooling to RT, the reaction mixture was concentrated and purified by silica gel column to give compound 4 (30 g, 75% yield) as yellow oil.

Synthesis of Compound 5

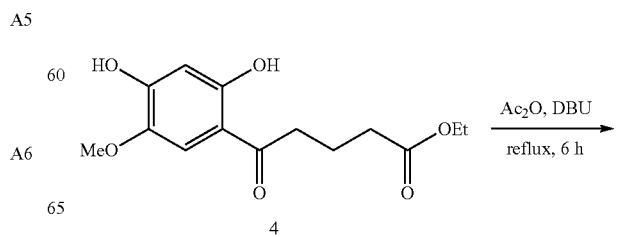

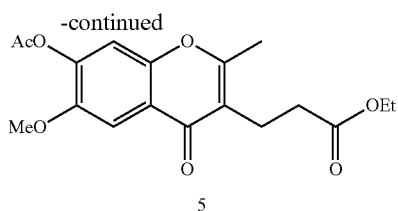

5

The mixture of compound 4 (30 g, 0.11 mol, Ac$_2$O (43.4 g, 0.42 mol) and DBU (15 g, 0.10 mol) was heated to reflux for 6 h. After cooled to RT, the reaction mixture was dissolved in DCM (400 mL), then the solution was washed with water, dried over Na$_2$SO$_4$ and concentrated to give the compound 5 (19 g, 50% yield). $^1$HNMR (CDCl$_3$, 400 MHz): δ 7.62 (s, 1H, ArH), 7.14 (s, 1H, ArH), 4.10 (q, 2H, J=7.2 Hz, CH$_2$), 3.91 (s, 3H, CH$_3$), 2.84 (t, 2H, J=7.6 Hz, CH$_2$), 2.60 (t, 2H, J=7.6 Hz, CH$_2$), 2.46 (s, 3H, CH$_3$), 1.57 (s, 3H, CH$_3$), 1.22 (t, 3H, J=7.2 Hz, CH$_3$).

Synthesis of Compound 6

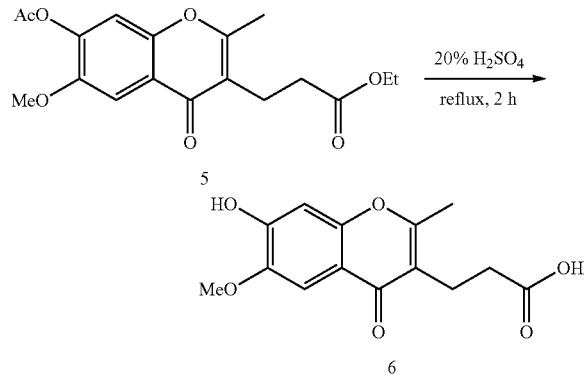

The suspension of compound 5 (19 g, 0.054 mol) in 20% H$_2$SO$_4$ (160 mL) was heated to reflux for 4 h, after cooling to RT, the formed precipitate was filtered, washed water and EA, dried to give compound 6 (12 g, 80%). $^1$HNMR (MeOD, 400 MHz): δ 7.43 (s, 1H, ArH), 6.84 (s, 1H, ArH), 3.93 (s, 3H, ArOCH$_3$), 2.81 (t, 2H, J=7.6 Hz, CH$_2$), 2.53 (q, 2H, J=7.6 Hz, CH$_2$), 2.47 (s, 3H, CH$_3$).

Synthesis of Compound 7

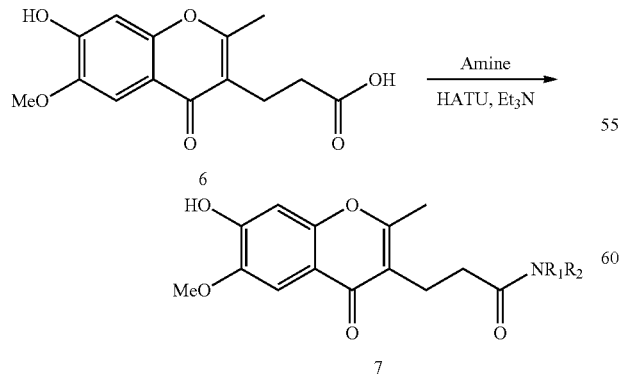

To the suspension of compound 6 (1 eq) and HATU (1.05 eq) in DMF was added Et$_3$N (1.1 eq) dropwise at RT. Then the mixture was stirred at RT for 1 h. Amine (1.1 eq) was added. The reaction mixture was stirred at RT for another 10 h. DMF was removed under vacuum. The residue was diluted with MeOH, the formed precipitate was filtered and washed with EA, dried to give compound 7.

Synthesis of Compound 8

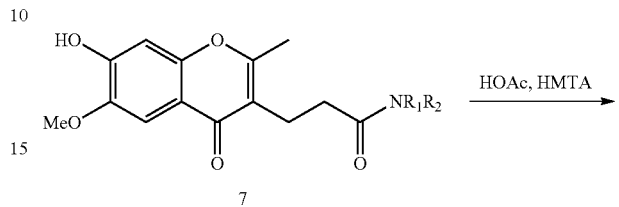

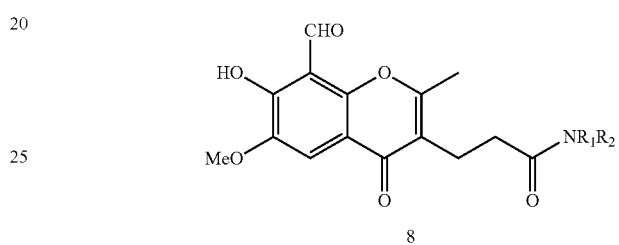

A mixture of compound 7 (1 eq) and HMTA (4 eq) in HOAc was heated at 120° C. under N$_2$ for 1.5 h. The reaction mixture was monitored by LCMS. After cooled to RT, the solvent was removed under vacuum; the residue was purified by prep-HPLC to give compound 8.

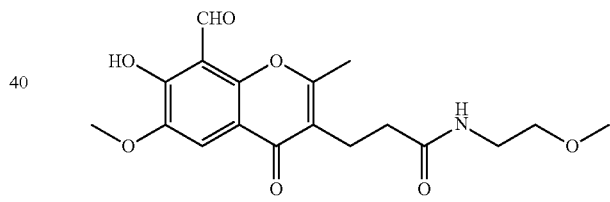

3-(8-Formyl-7-hydroxy-6-methoxy-2-methyl-4-oxo-4H-chromen-3-yl)-N-(2-methoxyethyl)propanamide was obtained by the above procedure from amine A1. 9% yield. $^1$HNMR (CDCl$_3$, 400 MHz): δ 12.78 (s, 1H, OH), 10.54 (s, 1H, CHO), 7.72 (s, 1H, ArH), 6.03 (br, 1H, NH), 4.00 (s, 3H, ArOCH$_3$), 3.42 (s, 4H, 2CH$_2$), 3.31 (s, 3H, OCH$_3$), 2.89 (t, J=6.8 Hz, 2H, CH$_2$), 2.55-2.51 (m, 5H). MS [ESI, MH$^+$]: 364.0.

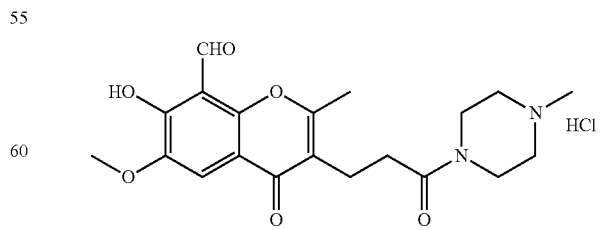

7-Hydroxy-6-methoxy-2-methyl-3-(3-(4-methylpiperazin-1-yl)-3-oxopropyl)-4-oxo-4H-chromene-8-carbaldehyde hydrochloride was obtained by the above procedure from amine A3. 13% yield. ¹HNMR (D₂O, 400 MHz): δ 10.12 (s, 1H, CHO), 7.15 (s, 1H, ArH), 4.62 (m, 1H), 4.28 (m, 1H), 3.82 (s, 3H, ArOCH₃), 3.63 (m, 3H), 3.24 (m, 1H), 3.12 (m, 2H, CH₂), 2.98 (s, 3H, NCH₃), 2.66 (m, 4H), 2.43 (s, 3H, CH₃). MS [ESI, MH⁺]: 389.3

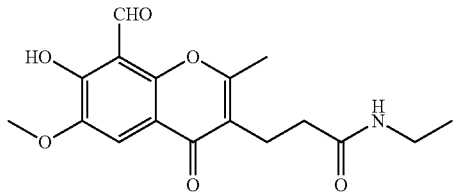 [SMILES: CCNC(=O)CCc1c(C)oc2c(C=O)c(O)c(OC)cc2c1=O]

N-Ethyl-3-(8-formyl-7-hydroxy-6-methoxy-2-methyl-4-oxo-4H-chromen-3-yl)propanamide was obtained by the above procedure from amine A4. 9% yield. ¹HNMR (CDCl₃, 400 MHz): δ 12.78 (s, 1H, OH), 10.51 (s, 1H, CHO), 7.67 (s, 1H, ArH), 6.21 (br, 1H, NH), 3.97 (s, 3H, ArOCH₃), 3.25 (q, J=7.2 Hz, 2H, CH₂), 2.86 (t, 2H, J=7.2 Hz, CH₂), 2.53 (m, 5H), 1.08 (t, 3H, J=7.2 Hz, CH₃). MS [ESI, MH⁺]: 334.1.

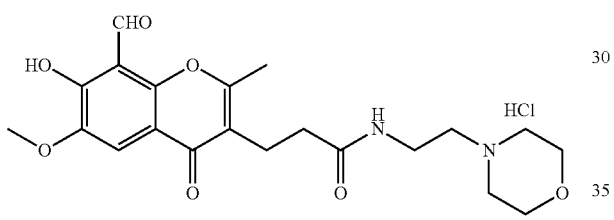

3-(8-Formyl-7-hydroxy-6-methoxy-2-methyl-4-oxo-4H-chromen-3-yl)-N-(2-morpholinoethyl)propanamide hydrochloride was obtained by the above procedure from amine A5. 12% yield. ¹HNMR (D₂O, 400 MHz): δ 10.07 (s, 1H, CHO), 7.10 (s, 1H, ArH), 4.13 (d, 2H, J=12.0 Hz, CH₂), 3.86 (d, 2H, J=12.0 Hz, CH₂), 3.78 (s, 3H, ArOCH₃), 3.62 (m, 4H, 2CH₂), 3.34 (t, 2H, J=6.0 Hz, CH₂), 3.23 (q, 2H, J=12.0 Hz, CH₂), 2.68 (t, 2H, J=8.0 Hz, CH₂), 2.43 (m, 5H). MS [ESI, MH⁺]: 419.2

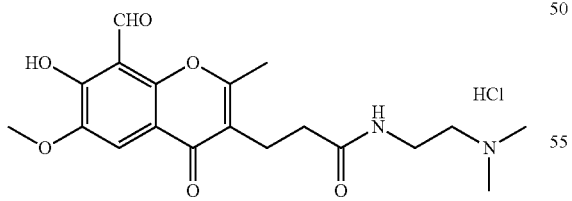

N-(2-(Dimethylamino)ethyl)-3-(8-formyl-7-hydroxy-6-methoxy-2-methyl-4-oxo-4H-chromen-3-yl)propanamide hydrochloride was obtained by the above procedure from amine A6. 11% yield. ¹HNMR (D₂O, 400 MHz): δ 10.10 (s, 1H, CHO), 7.15 (s, 1H, ArH), 3.80 (s, 3H, ArOCH₃), 3.58 (t, J=6.0 Hz, 2H, CH₂), 3.30 (t, 2H, J=6.0 Hz, CH₂), 2.94 (s, 6H, 2CH₃), 2.70 (t, 2H, J=6.8 Hz, CH₂), 2.41 (m, 5H). MS [ESI, MH⁺]: 377.1.

Example 71

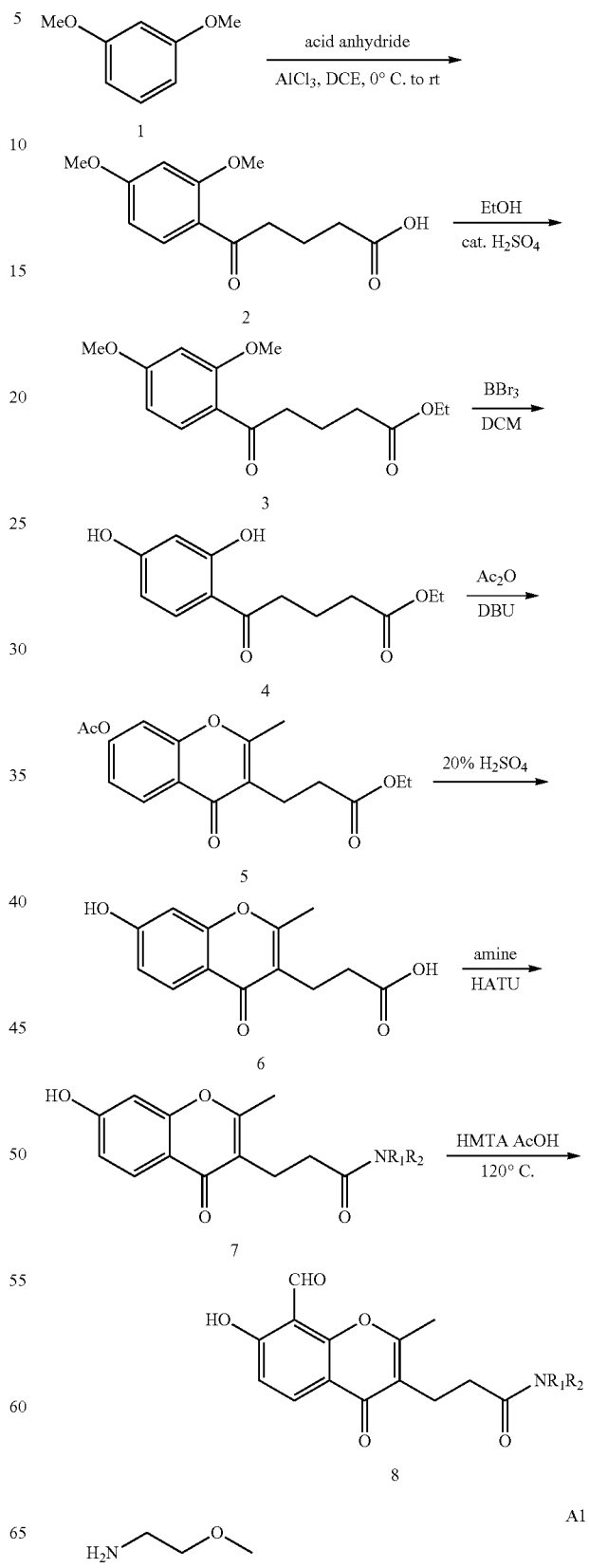

-continued

A2
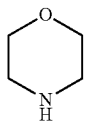

A3
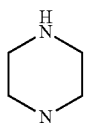

A4
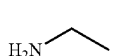

A5
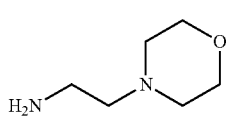

A6
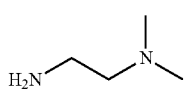

Synthesis of Compound 3

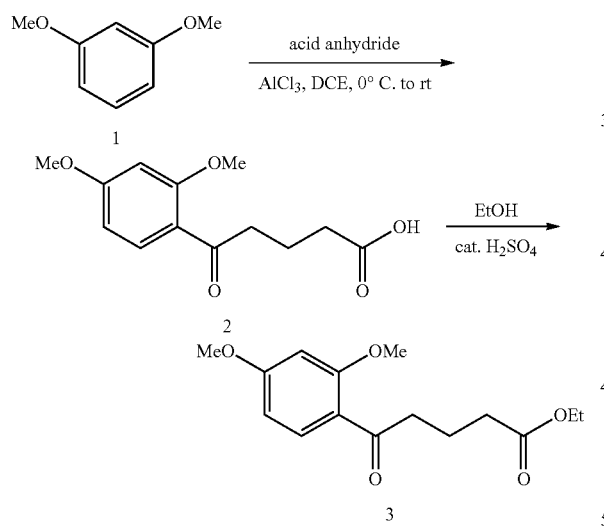

Glutaric anhydride dissolved in 3000 ml 1.2-DCE, the reaction mixture cooled to 0° C., AlCl$_3$ (138.3 g, 1.04 mol) added dropwise with stirring at 0° C., the above suspension added a solution of compound 1 (110.4 g, 0.8 mol) in 600 ml of 1,2-DCE from the dropping funnel over a period of 30 min. the mixture solution stirred at RT for 30 min, TLC (PE:EA=1:1) showed the starting material was consumed completely. The above solution poured into 1000 ml ice-water, the organic layers separated, the aqueous layer was extracted with DCM (500*3), the combined organic layers were washed with sat NaCl (500 ml*2), dried over Na$_2$SO$_4$, the solvent was removed to get the crude compound 2 and use at the next step directly.

The solution of the crude compound 2 in EtOH (1000 ml) and H$_2$SO$_4$(10 ml) was heated to refluxed for 2 h, LC-MS showed the starting material was consumed completely. after cooled, the solvent was removed, the solids was filtrated, washed with PE (300 ml) to give (160 g, 65%) compound 3 as white solid.

MS [ESI, MH$^+$]: 280.

Synthesis of Compound 4

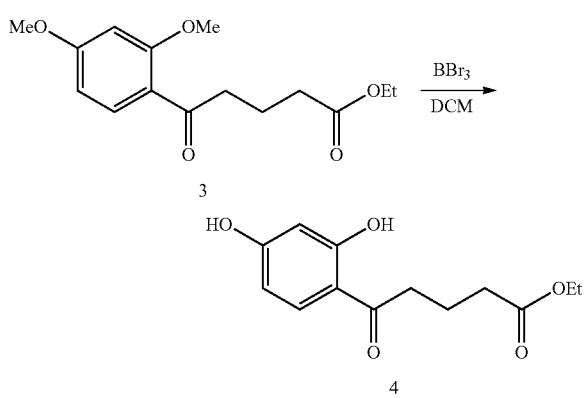

To a solution of compound 3(160 g, 0.57 mol) in dry DCM (1900 ml) was added BBr$_3$ (1142 g, 3.42 mol) in portions with stirring at −70° C., the reaction solution stirred at RT for 3 h, The reaction was quenched by addition of 1000 ml of ethanol at −70° C., the solvent was removed, the residue was chromatographed on silica gel (PE:EA=5:1) to give compound 4(80 g, 56%) as white solid. MS [ESI, MH$^+$]: 253.0.

Synthesis of Compound 5

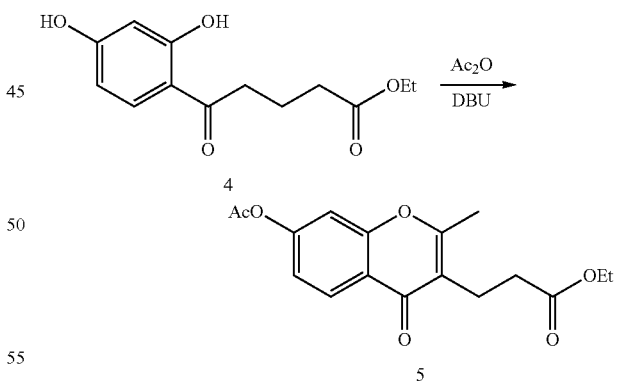

To a suspension of compound 4 (42.8 g, 0.17 mol) in AC$_2$O (69 g, 0.68 mol) was added DBU (20.7 g, 0.14 mol) in one portion. The solution stirred at 120° C. for 16 h, TLC (PE:EA=5:1) showed the starting material was consumed completely. After cooled, the residue poured into 500 ml ice-water, the reaction mixture was extracted with DCM (150*3). The combined organic layers dried, concentrated and chromatographed on silica gel (PE:EA=5:1) to give compound 5(40 g, 76%) as white solid.

Synthesis of Compound 6

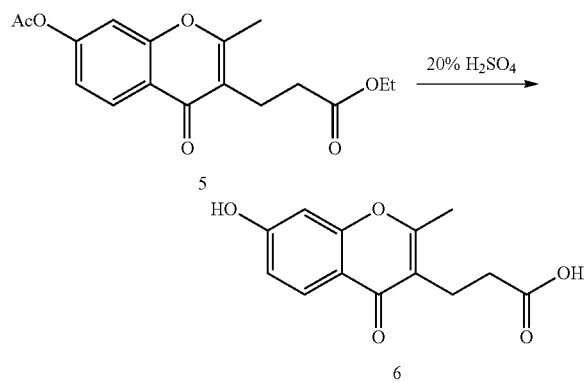

The compound 5 (33 g, 0.103 mol) in 20% $H_2SO_4$ (500 ml) were heated to 100° C. overnight, after cooled, the solids was filtrated, washed with DCM three times to give (20 g, 78%) compound 6 as white solid

Synthesis of Compound 7

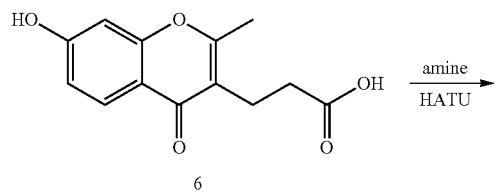

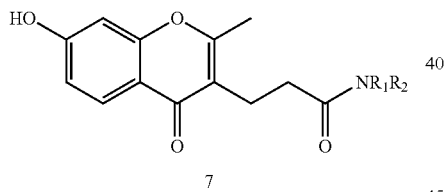

To the suspension of Compound 6 (1 eq) and HATU (1.05 eq) in DMF was added $Et_3N$ (1.1 eq) dropwise at RT, after the mixture was stirred at this temperature for 1 h, amine (1.1 eq) was added, the reaction mixture was stirred at RT for another 10 h, after DMF was eliminated, diluted with MeOH, the formed solid was filtered and washed with EA, dried to give Compound 7.

Synthesis of Compound 8

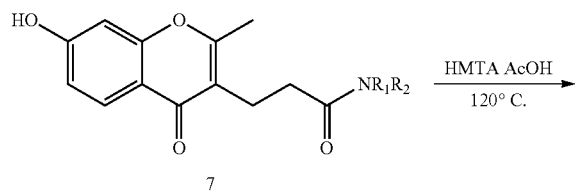

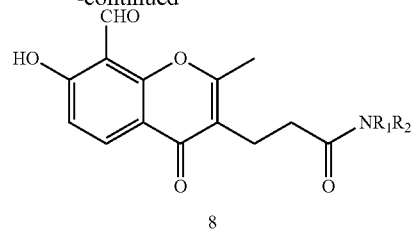

A mixture of compound 7 (1 eq) and HMTA (4 eq) in HOAc was heated at 120° C. under nitrogen for 1.5 h. The reaction mixture turned to dark-yellow in the period. LCMS indicated that the reaction was completed. After cooled to RT, the solvent was removed under reduced pressure, the product was purified by Prep-HPLC to give compound 8.

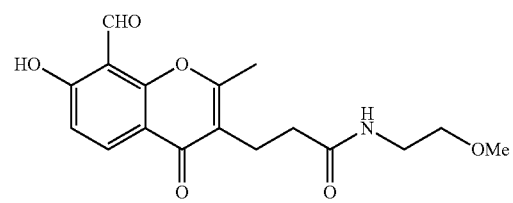 [SMILES: COCCNC(=O)CCc1c(C)oc2c(C=O)c(O)ccc2c1=O]

3-(8-Formyl-7-hydroxy-2-methyl-4-oxo-4H-chromen-3-yl)-N-(2-methoxyethyl)propanamide was obtained by the above procedure from amine A1. 4.1% yield. $^1$HNMR ($CDCl_3$, 400 MHz) δ 12.40 (s, 1H, OH), 10.51 (s, 1H, CHO), 8.26 (d, 1H, J=9.2 HZ, ArH), 6.93 (d, 1H, J=9.2 HZ, ArH), 5.95 (s, 1H, OH), 3.38.3.37 (m, 4H), 3.26 (s, 3H, $CH_3$), 2.83 (t, 2H, J=7.2 HZ, $CH_2$), 2.51 (s, 3H, $CH_3$), 2.47 (t, 2H, J=7.2 HZ, $CH_2$) MS [ESI, MH$^+$]: 334.0

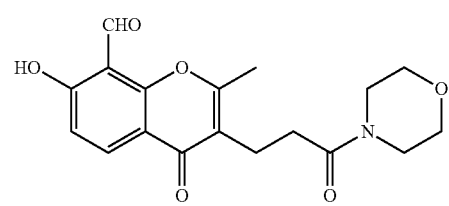 [SMILES: Cc1oc2c(C=O)c(O)ccc2c(=O)c1CCC(=O)N1CCOCC1]

7-Hydroxy-2-methyl-3-(3-morpholino-3-oxopropyl)-4-oxo-4H-chromene-8-carbaldehyde was obtained by the above procedure from amine A2. 3.6% yield. $^1$HNMR ($CDCl_3$, 400 MHz): δ 12.35 (s, 1H, OH), 10.46 (s, 1H, CHO), 8.20 (d, 1H, J=8.8 HZ, ArH), 6.89 (d, 1H, J=9.2 HZ, ArH), 3.60-3.47 (m, 8H), 2.76 (t, 2H, J=7.2 HZ, $CH_2$), 2.58 (t, 2H, J=7.2 HZ, $CH_2$), 2.50 (s, 3H, $CH_3$). MS [ESI, MH$^+$]: 346.0

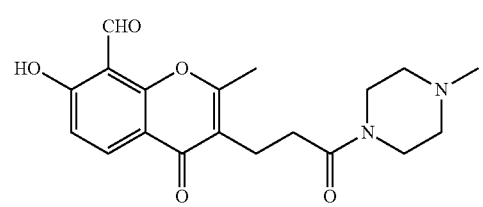 [SMILES: Cc1oc2c(C=O)c(O)ccc2c(=O)c1CCC(=O)N1CCN(C)CC1]

7-Hydroxy-2-methyl-3-(3-(4-methylpiperazin-1-yl)-3-oxopropyl)-4-oxo-4H-chromene-8-carbaldehyde was obtained by the above procedure from amine A3. 9.2% yield. ¹HNMR (MeOD, 400 MHz): δ 7.95 (d, 1H, J=8.8 HZ, ArH), 6.89 (d, 1H, J=8.8 HZ, ArH), 6.06 (s, 1H, CHO), 3.61 (br, 6H), 3.01 (s, 3H, CH₃), 2.81 (t, 2H, J=7.6 HZ, CH₂), 2.56 (t, 2H, J=3.2 HZ, CH₂), 2.51 (s, 3H, CH₃). MS [ESI, MH⁺]: 359.2

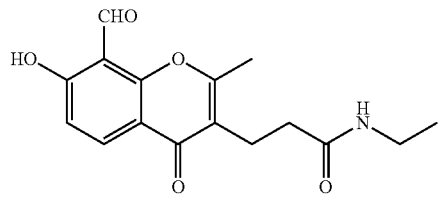 [SMILES: CCNC(=O)CCc1c(C)oc2c(C=O)c(O)ccc2c1=O]

N-Ethyl-3-(8-formyl-7-hydroxy-2-methyl-4-oxo-4H-chromen-3-yl)propanamide was obtained by the above procedure from amine A4. 4.5% yield. ¹HNMR (CDCl₃, 400 MHz) δ 12.36 (s, 1H, OH), 10.46 (s, 1H, CHO), 8.21 (d, 1H, J=9.2 HZ, ArH), 6.88 (d, 1H, J=9.2 HZ, ArH), 5.67 (d, 1H, J=10 HZ, OH), 3.17 (t, 2H, J=5.6 HZ, CH₂), 2.78 (t, 2H, J=5.6 HZ, CH₂), 2.47-2.39 (m, 5H), 1.03-0.99 (m, 3H, CH₃). MS [ESI, MH⁺]: 304.0

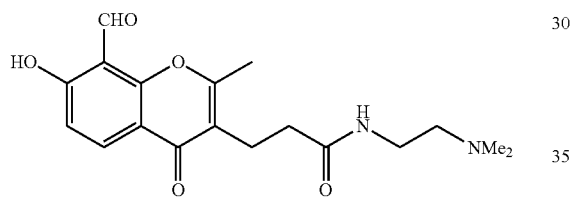

N-(2-(Dimethylamino)ethyl)-3-(8-formyl-7-hydroxy-2-methyl-4-oxo-4H-chromen-3-yl)propanamide was obtained by the above procedure from amine A5. 5.4% yield. ¹HNMR (D₂O, 400 MHz) δ 10.06 (s, 1H, CHO), 7.78 (d, 1H, J=8.8 HZ, ArH), 6.74 (d, 1H, J=8.8 HZ, ArH), 3.56 (t, 2H, J=6.0 HZ, CH₂), 3.29 (t, 2H, J=6.0 HZ, CH₂), 2.91 (s, 6H). 2.64 (t, 2H, J=7.2 HZ, CH₂), 2.40 (t, 2H, J=7.2 HZ, CH₂), 2.37 (s, 3H, CH₃). MS [ESI, MH⁺]: 347.0

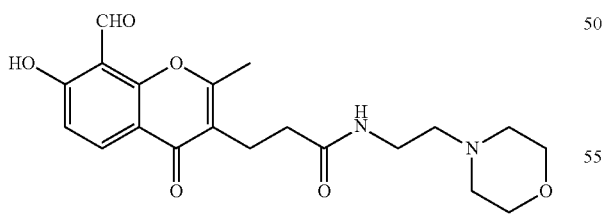

3-(8-Formyl-7-hydroxy-2-methyl-4-oxo-4H-chromen-3-yl)-N-(2-morpholinoethyl)propanamide was obtained by the above procedure from amine A6. 9.2% yield. ¹HNMR (D₂O, 400 MHz) δ 9.78 (s, 1H, CHO), 7.50 (d, 2H, J=8.8 HZ, ArH), 6.78 (d, 1H, J=9.2 HZ, ArH), 3.91 (d, 1H, J=13.2 HZ, CH₂), 3.62 (t, 2H, J=13.2 HZ, CH₂), 3.38 (t, 2H, J=14.4 HZ, CH₂), 3.12 (t, 4H, J=6.0 HZ, CH₂), 3.04-2.97 (m, 4H), 2.41-2.13 (m, 7H) MS [ESI, MH⁺]: 389.1.

Example 72

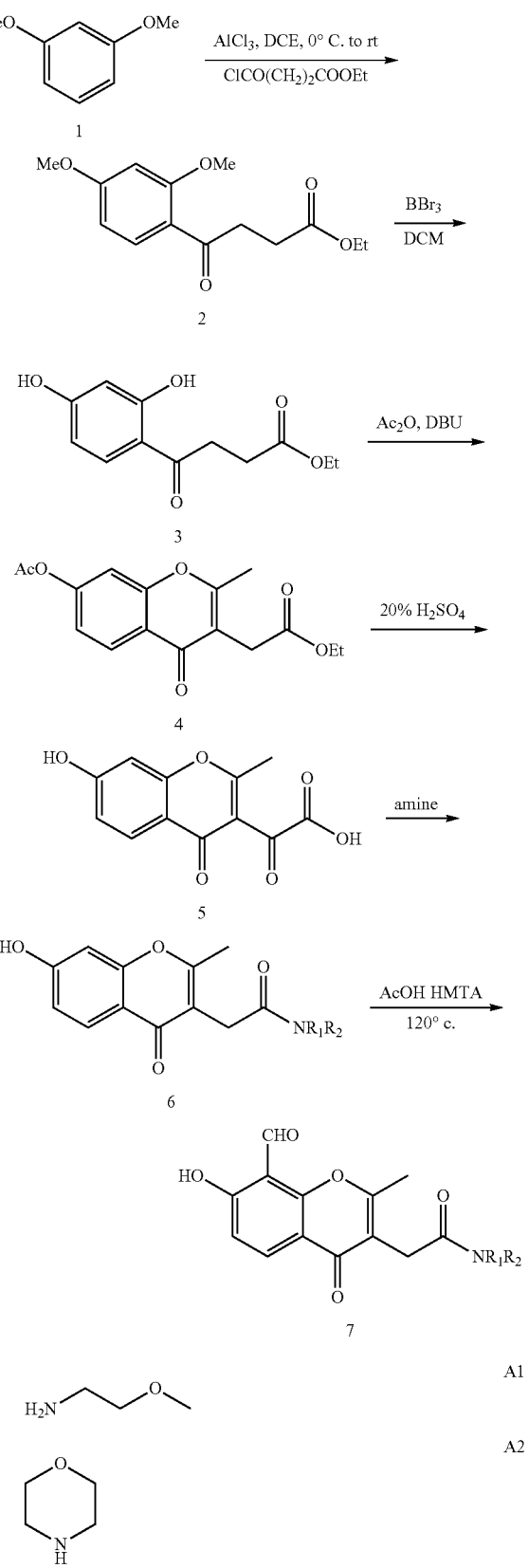

-continued

A3

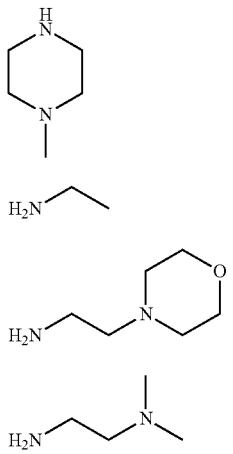

A4

A5

A6

Synthesis of Compound 2

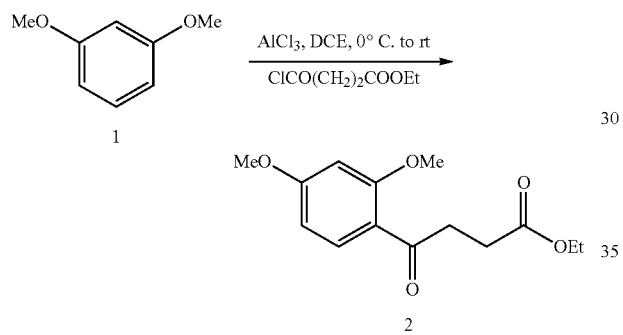

Ethyl succinyl chloride (18 g, 0.11 mol) dissolved in 1.2-DCE (1000 ml), the reaction mixture cooled to 0° C., AlCl$_3$ (17.3 g, 0.13 mol) added dropwise with stirring at 0° C., the above suspension added a solution of compound 1 (13.8 g, 0.1 mol) in 200 ml of 1,2-DCE from the dropping funnel over a period of 30 min, the mixture solution stirred at RT for 30 min, TLC (PE:EA=1:1) showed the starting material was consumed completely. The above solution poured into 1000 ml ice-water, the organic layers separated, the aqueous layer was extracted with DCM (500*3), the combined organic layers were washed with sat NaCl (500 ml*2), dried over Na$_2$SO$_4$, the solvent was removed to get the crude compound 2(16 g, 60%) and use at the next step directly. MS [ESI, MH$^+$]: 267.

Synthesis of Compound 3

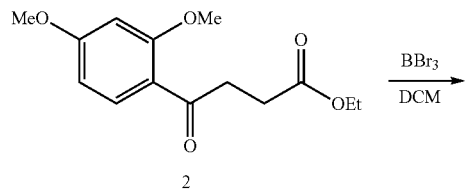

To a solution of compound 3(23 g, 0.086 mol) in dry DCM (1345 ml) was added BBr$_3$ (173 g, 0.692 mol) in portions with stirring at −70° C., the reaction solution stirred at RT for 3 h, The reaction was quenched by addition of 1000 ml of ethanol, the solvent was removed, the residue was chromatographed on silica gel (PE:EA=5:1) to give compound 4(12.2 g, 60%)) as white solid.

Synthesis of Compound 4

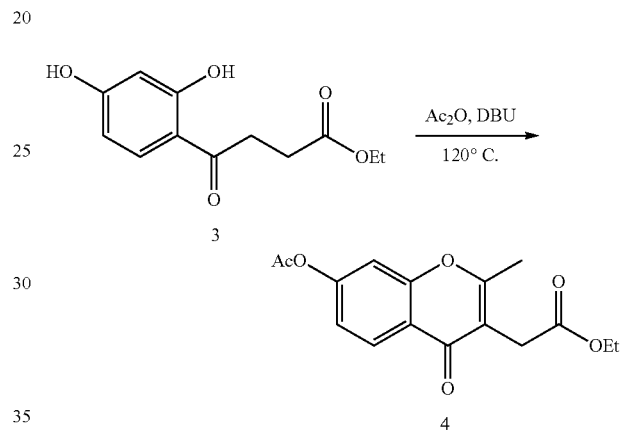

To a suspension of compound 3 (7.5 g, 0.032 mol) in Ac$_2$O (13 g, 0.13 mol) was added DBU (3.8 g, 0.025 mol) in one portion. The solution stirred at 120° C. for 16 h, TLC (PE:EA=1:1) showed the starting material was consumed completely. After cooled, the residue poured into 300 ml ice-water, the reaction mixture was extracted with DCM (150*3), The combined organic layers dried, concentrated and chromatographed on silica gel (PE:EA=5:1) to give compound 4(9 g, 92%) as white solid. MS [ESI, MH$^+$]: 305.2

Synthesis of Compound 5

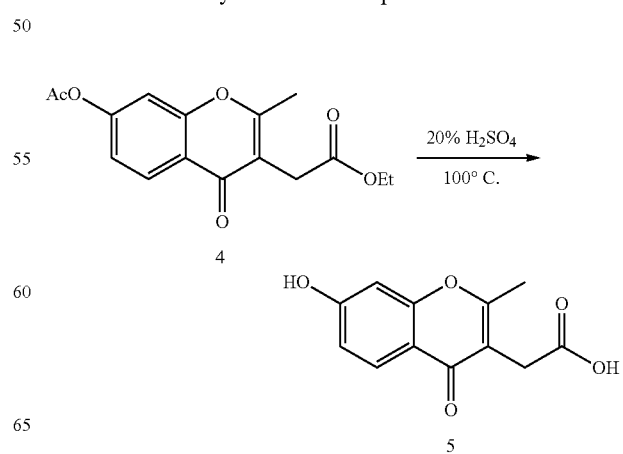

The compound 4 (9 g, 0.030 mol) in 20% H₂SO₄(200 ml) were heated to 100° C. overnight, after cooled, the solids was filtrated, washed with DCM three times to give (5 g, 70%) compound 5 and use at the next step directly. MS [ESI, MH⁺]: 234.8

Synthesis of Compound 6

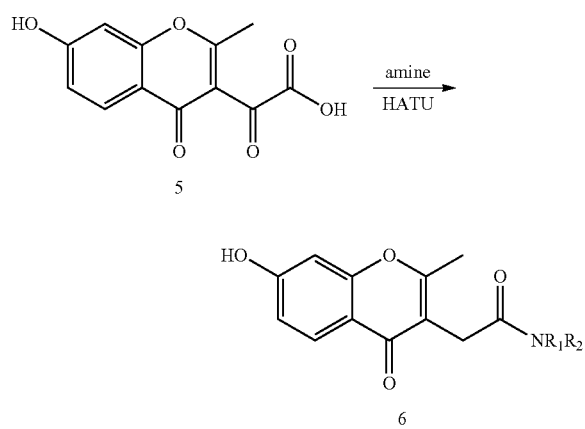

To the suspension of Compound 5 (1 eq) and HATU (1.05 eq) in DMF was added Et₃N (1.1 eq) dropwise at RT, after the mixture was stirred at this temperature for 1 h, amine (1.1 eq) was added, the reaction mixture was stirred at RT for another 10 h, after DMF was eliminated, diluted with MeOH, the formed solid was filtered and washed with EA, dried to give Compound 6.

Synthesis of Compound 7

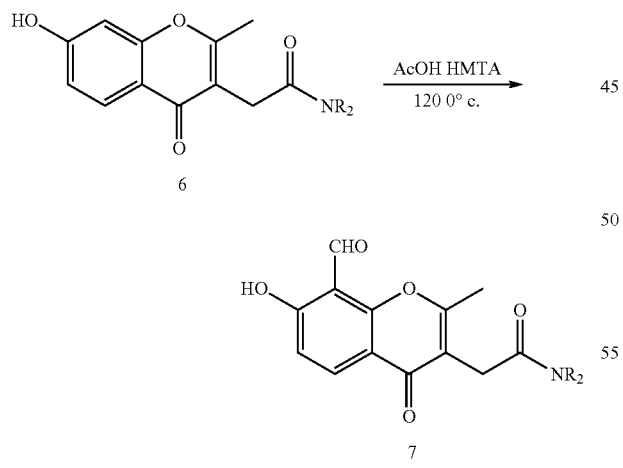

A mixture of compound 6 (1 eq) and HMTA (4 eq) in HOAc was heated at 120° C. under nitrogen for 1.5 h. The reaction mixture turned to dark-yellow in the period. LCMS indicated that the reaction was completed. After cooled to RT, the solvent was removed under reduced pressure; the product was purified by Prep-HPLC to give compound 7.

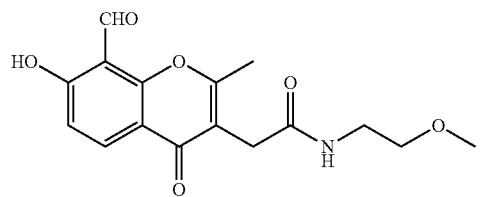 [SMILES: COCCNC(=O)Cc1c(C)oc2c(C=O)c(O)ccc2c1=O]

2-(8-Formyl-7-hydroxy-2-methyl-4-oxo-4H-chromen-3-yl)-N-(2-methoxyethyl)acetamide was obtained by the above procedure from amine A1. 9.12% yield. ¹HNMR (CDCl₃, 400 MHz): δ 12.38 (s, 1H, OH), 10.47 (s, 1H, CHO), 8.23 (d, 1H, J=9.2 Hz, ArH), 6.91 (d, 1H, J=9.2 Hz ArH), 3.38-3.29 (m, 6H), 3.26 (s, 3H, CH₃), 2.54 (s, 3H, CH₃) MS [ESI, MH⁺]: 320.0

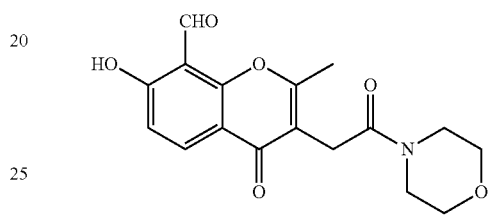

7-Hydroxy-2-methyl-3-(2-morpholino-2-oxoethyl)-4-oxo-4H-chromene-8-carbaldehyde was obtained by the above procedure from amine A2. 10% yield. ¹HNMR (CDCl₃, 400 MHz): δ 12.42 (br, 1H, OH), 10.54 (s, 1H, CHO), 8.28-8.25 (m, 1H, ArH), 6.97-6.94 (m, 1H, ArH), 3.74-3.58 (m, 10H), 2.54 (s, 3H, CH₃). MS [ESI, MH⁺]: 332.1

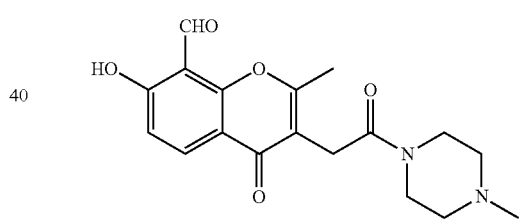

7-Hydroxy-2-methyl-3-(2-(4-methylpiperazin-1-yl)-2-oxoethyl)-4-oxo-4H-chromene-8-carbaldehyde was obtained by the above procedure from amine A3. 7.3% yield. ¹HNMR (MeOD, 400 MHz): δ 7.96 (d, 1H, J=8.8 Hz, ArH), 6.92 (d, 1H, J=8.8 Hz, ArH), 6.08 (s, 1H, CHO), 4.70-4.40 (m, 2H, CH₂), 3.79-3.30 (m, 8H), 2.96 (s, 3H, CH₃), 2.47 (s, 3H, CH₃). MS [ESI, MH⁺]: 345.1

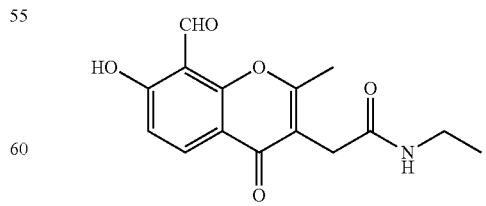

N-Ethyl-2-(8-formyl-7-hydroxy-2-methyl-4-oxo-4H-chromen-3-yl)acetamide was obtained by the above procedure from amine A4. 9.05% yield. ¹HNMR (CDCl₃, 400 MHz): δ 12.40 (br, 1H, OH), 10.48 (s, 1H, CHO), 8.22 (d, 1H, J=9.2 Hz, ArH), 6.92 (d, 1H, J=9.2 HZ, ArH), 6.43-6.36 (br, 1H, NH), 3.35 (s, 2H, CH$_3$), 3.16-313 (q, 2H, J=7.2 HZ, CH$_2$), 2.56 (s, 3H, CH$_3$), 1.03 (t, 3H, J=7.2 HZ CH$_3$), MS [ESI, MH$^+$]: 290.0.

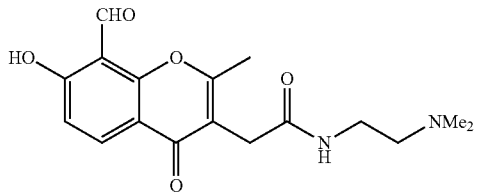 [SMILES: Cc1oc2c(C=O)c(O)ccc2c(=O)c1CC(=O)NCCN(C)C]

N-(2-(Dimethylamino)ethyl)-2-(8-formyl-7-hydroxy-2-methyl-4-oxo-4H-chromen-3-yl)acetamide hydrochloride was obtained by the above procedure from amine A5. 9.2% yield. $^1$HNMR (D$_2$O, 400 MHz): δ 10.02 (s, 1H, CHO), 7.72 (d, 1H, J=8.8 Hz ArH), 6.66 (d, 1H, J=8.8 Hz, ArH), 3.47 (m, 2H, CH$_2$), 3.26 (m, 2H, CH$_2$), 3.18 (m, 2H, CH$_2$), 2.79 (s, 6H), 2.28 (s, 3H, CH$_3$) MS [ESI, MH$^+$]: 333.1

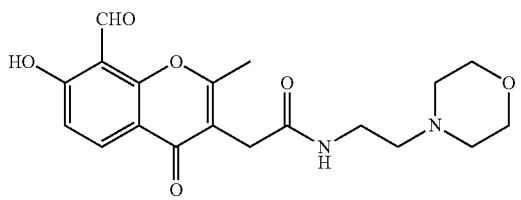 [SMILES: Cc1oc2c(C=O)c(O)ccc2c(=O)c1CC(=O)NCCN1CCOCC1]

2-(8-Formyl-7-hydroxy-2-methyl-4-oxo-4H-chromen-3-yl)-N-(2-morpholinoethyl)acetamide was obtained by the above procedure from amine A6. 18.6% yield $^1$HNMR (D$_2$O, 400 MHz): δ 10.32 (s, 1H, CHO), 8.00 (d, 1H, J=9.2 HZ, ArH), 6.90 (d, 1H, J=9.2 HZ, ArH), 4.10 (m, 2H, CH$_2$), 3.72 (m, 2H, CH$_2$) 3.55-3.09 (m, 8H), 2.40 (s, 3H, CH$_3$), MS [ESI, MH$^+$]: 375.

Example 73

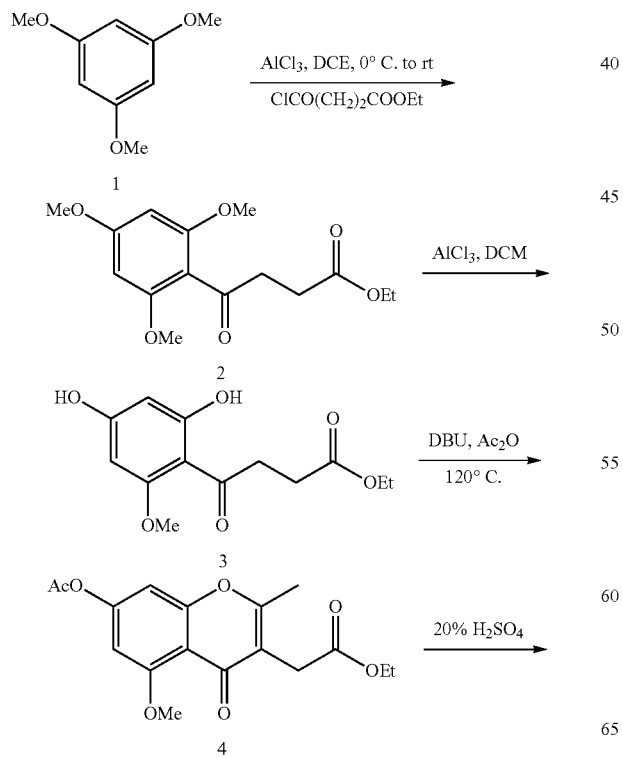

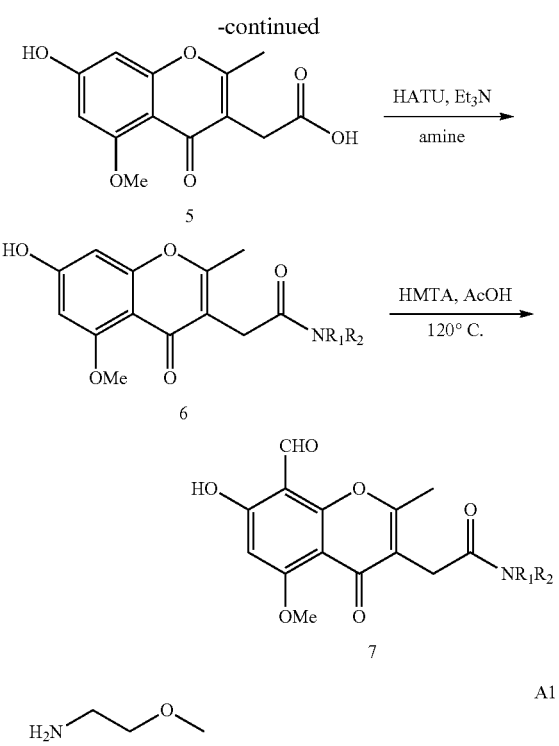

Synthesis of Compound 2

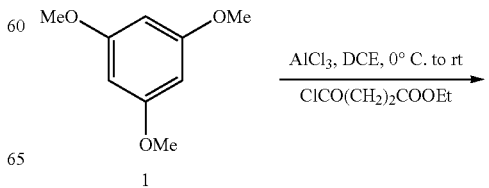

-continued

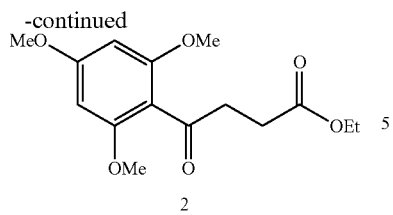

2

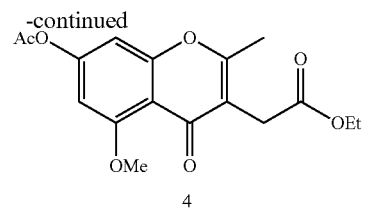

4

Ethyl succinyl chloride (13.2 g, 0.08 mol) dissolved in 1,2-DCE (270 ml), the reaction mixture cooled to 0° C., AlCl$_3$ (10.7 g, 0.08 mol) was added dropwise with stirring at 0° C., the above suspension added to a solution of compound 1 (9 g, 0.054 mol) in 1,2-DCE (30 ml) from the dropping funnel over a period of 30 min, the mixture solution stirred at RT for 30 min, TLC (PE:EA=1:1) showed the starting material was consumed completely. The above solution poured into ice-water (200 ml), the organic layers separated, the aqueous layer was extracted with DCM (500*3), the combined organic layers were washed with sat NaCl (500 ml*2), dried over Na$_2$SO$_4$ the solvent was removed to get the crude compound 2 and use at the next step directly. MS [ESI, MH$^+$]: 297.2.

Synthesis of Compound 3

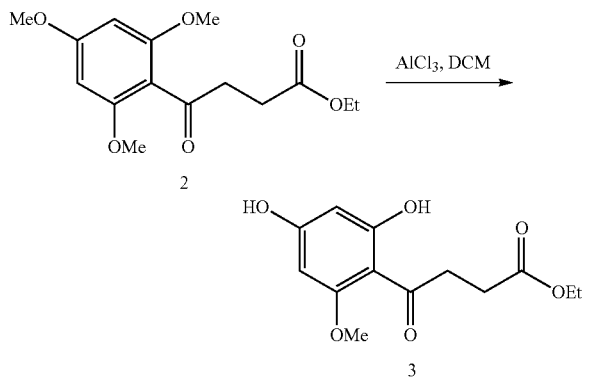

The compound 2 (46 g, 0.145 mol), AlCl$_3$ (43 g, 0.324 mol) in dry DCM (240 ml) was was heated to 60° C. for 15 min and additional AlCl$_3$ (43 g, 0.324 mol) was added followed by an additional 15 min. The reaction mixture heating at 60° C. for 2 h, LC-MS detected the starting material was consumed completely. The above suspension poured into ice-water (1000 ml), the organic layers separated, the aqueous layer was extracted with DCM (500 mL×3), The combined organic layers dried, concentrated and chromatographed on silica gel (PE:EA=5:1) to give compound 3(8 g, 21%) as white solid. MS [ESI, MH$^+$]: 269.2

Synthesis of Compound 4

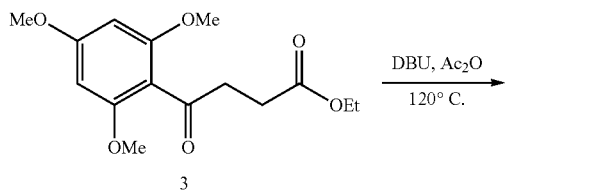

To a suspension of compound 3 (17 g, 0.063 mol) in Ac$_2$O (25.5 g, 0.25 mol) was added DBU (8.5 g, 0.056 mol) in one portion. The solution stirred at 120° C. for 16 h, TLC (PE:EA=1:1) showed the starting material was consumed completely. After cooled to RT, the residue poured into 300 ml ice-water, the reaction mixture was extracted with DCM (150*3), The combined organic layers dried, concentrated and chromatographed on silica gel (PE:EA=5:1) to give compound 4 (10 g, 47.5%) as white solid. MS [ESI, MH$^+$]: 334.8.

Synthesis of Compound 5

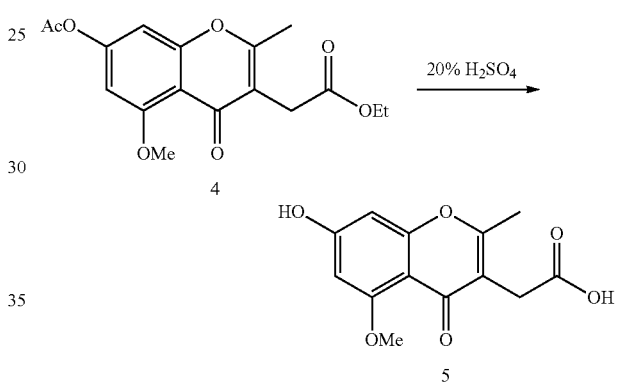

The compound 4 (10 g, 0.030 mol) in 20% H$_2$SO$_4$(200 ml) were heated to 100° C. overnight, after cooled, the solid was filtered, washed with DCM three times to give (5 g, 63%) compound 5 and use at the next step directly. MS [ESI, MH$^+$]: 265.2.

Synthesis of Compound 6

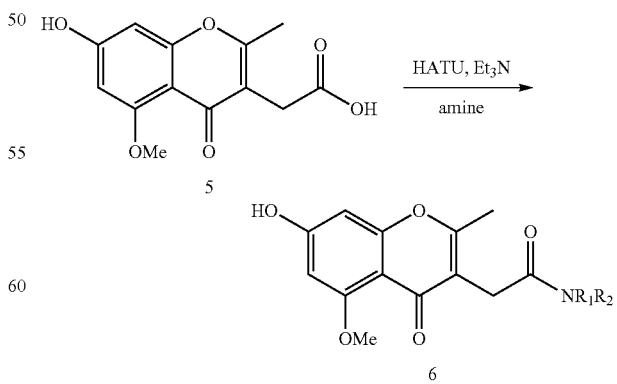

To the suspension of Compound 5 (1 eq) and HATU (1.05 eq) in DMF was added Et$_3$N (1.1 eq) dropwise at RT, after the mixture was stirred at this temperature for 1 h, amine (1.1 eq) was added, the reaction mixture was stirred at RT for another 10 h, after DMF was eliminated, diluted with MeOH, the formed solid was filtered and washed with EA, dried to give Compound 6.

Synthesis of Compound 7

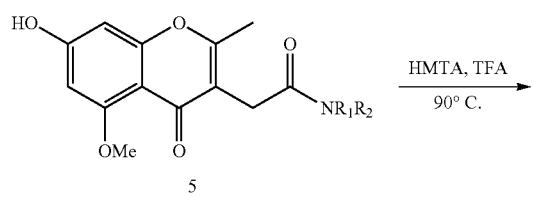

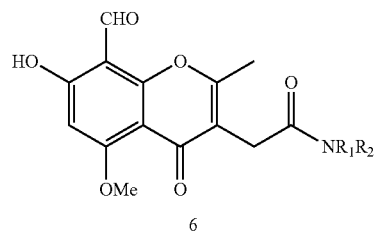

A mixture of compound 5 (1 eq) and HMTA (4 eq) in HOAc was heated at 120° C. under nitrogen for 1.5 h. The reaction mixture turned to dark-yellow in the period. LCMS indicated that the reaction was completed. After cooled to RT, the solvent was removed under reduced pressure; the product was purified by Prep-HPLC to give compound 6.

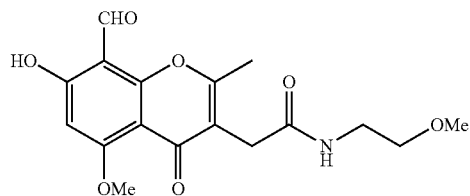 [SMILES: COCCNC(=O)Cc1c(C)oc2c(C=O)c(O)cc(OC)c2c1=O]

2-(8-Formyl-7-hydroxy-5-methoxy-2-methyl-4-oxo-4H-chromen-3-yl)-N-(2-methoxyethyl)acetamide was obtained by the above procedure from amine A1. 1.55% yield. $^1$HNMR (CDCl$_3$, 400 MHz): δ 12.80 (s, 1H, OH), 10.29 (s, 1H, CHO), 6.68 (br, 1H, NH), 6.29 (s, 1H, ArH), 4.00 (s, 3H, OCH$_3$), 3.40-3.30 (m, 9H), 2.53 (s, 3H, CH$_3$), MS [ESI, MH$^+$]: 350.2.

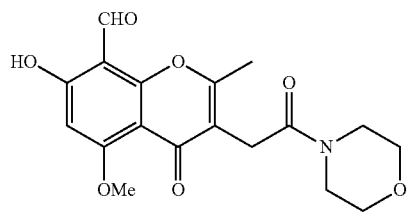 [SMILES: COc1cc(O)c(C=O)c2oc(C)c(CC(=O)N3CCOCC3)c(=O)c12]

7-Hydroxy-5-methoxy-2-methyl-3-(2-morpholino-2-oxo-ethyl)-4-oxo-4H-chromene-8-carbaldehyde was obtained by the above procedure from amine A2. 3.95% yield. $^1$HNMR (CDCl$_3$, 400 MHz): δ 12.85 (br, 1H, OH), 10.29 (s, 1H, CHO), 6.29 (s, 1H, ArH), 3.94 (s, 3H, OCH$_3$), 3.75-3.63 (m, 8H), 3.53 (s, 2H, CH$_2$), 2.47 (s, 3H, CH$_3$). MS [ESI, MH$^+$]: 362.2.

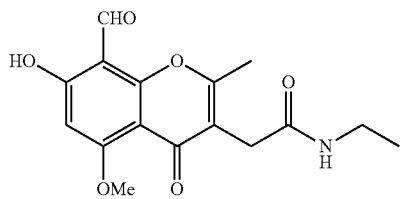 [SMILES: CCNC(=O)Cc1c(C)oc2c(C=O)c(O)cc(OC)c2c1=O]

N-Ethyl-2-(8-formyl-7-hydroxy-5-methoxy-2-methyl-4-oxo-4H-chromen-3-yl)acetamide was obtained by the above procedure from amine A4. 9.2% yield. $^1$HNMR (CDCl$_3$, 400 MHz): δ 12.83 (br, 1H, OH), 10.29 (s, 1H, CHO), 6.88 (br, 1H, NH), 6.31 (s, 1H, ArH), 4.00 (s, 3H, OCH$_3$), 3.37 (s, 2H, CH$_2$), 3.18 (q, 2H, J=7.2 Hz, CH$_2$), 2.55 (s, 3H, CH$_3$), 1.07 (t, 3H, J=7.2 Hz, CH$_3$), MS [ESI, MH$^+$]: 320.2.

Example 74

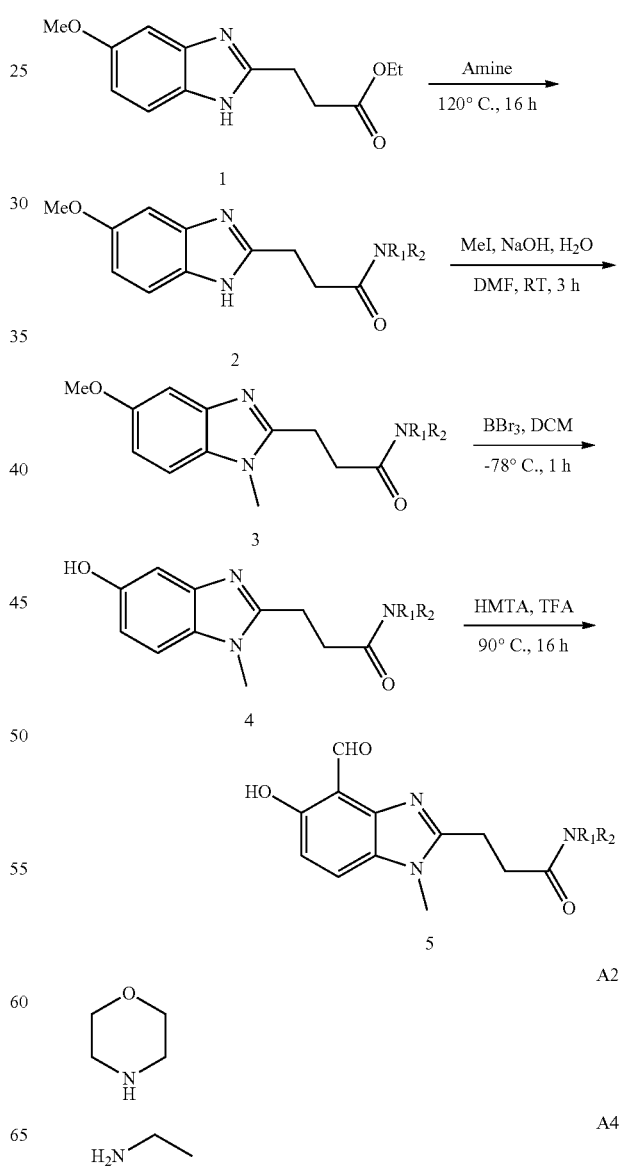

Synthesis of Compound 2

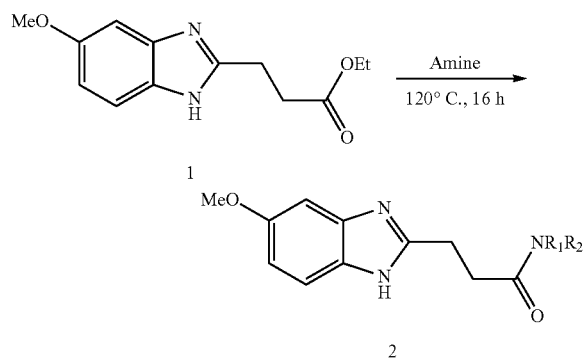

A mixture of compound 1 (1 eq) and amine was heated to 90° C. for 16 h. After cooling to room temperature, the reaction mixture was concentrated to give compound 2

Synthesis of Compound 3

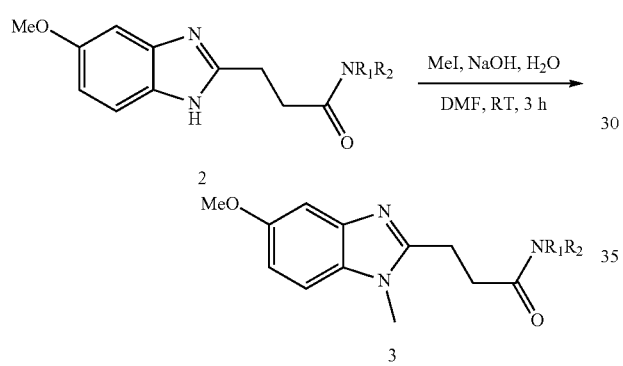

To a solution of compound 1(1.0 eq) in DMF/water (4:1) was added NaOH (2.0 eq) and MeI (1.2 eq) in turn. The reaction mixture was stirred at RT for 3 h, and then diluted with EtOAc (200 mL) and water (500 mL), extracted with EtOAc (200 mL×2), washed with brine (200 mL), dried over Na$_2$SO$_4$, concentrated to give the residue, and then purified by chromatography on silica gel to give compound 3

Synthesis of Compound 4

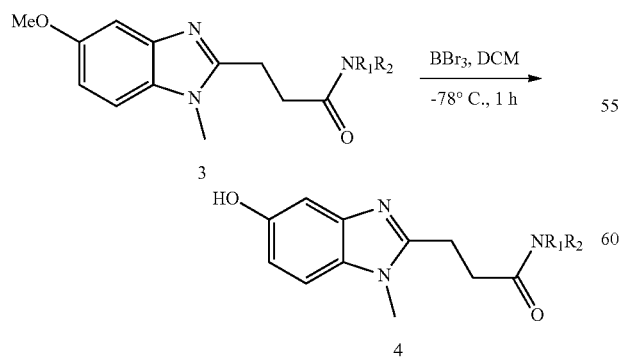

To a solution of compound 3 (1.0 eq) in DCM was added BBr$_3$ (2.0 eq) in DCM dropwise at −78° C. in 10 min and then warmed to RT and stirred for 1 h. The reaction mixture was quenched with MeOH at −78° C., concentrated to give the residue, and diluted with water (100 mL), washed with DCM. The aqueous layer was neutralized by 10% NaOH solution to pH=8-9, then extracted with EtOAc (200 mL×3), dried over Na$_2$SO$_4$, concentrated to give compound 4.

Synthesis of Compound 5

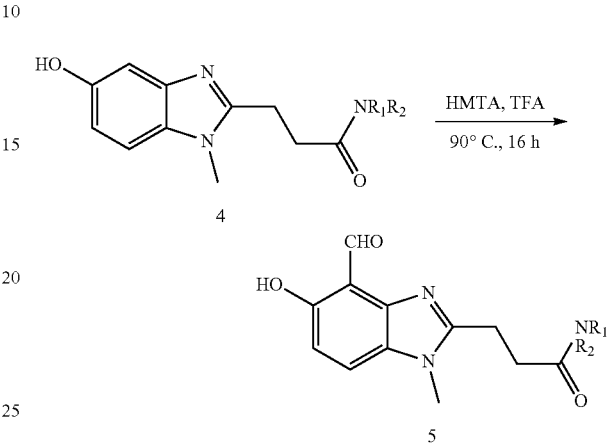

A solution of Compound 4 (1.0 eq) and HMTA (4.0 eq) in AcOH was heated to 90° C. for 16 h. After cooling to room temperature, the reaction mixture was concentrated to give the residue, and then purified by Prep-HPLC to give compound 5

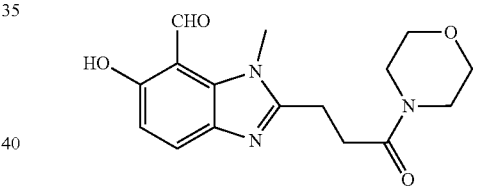

6-Hydroxy-1-methyl-2-(3-morpholino-3-oxopropyl)-1H-benzo[d]imidazole-7-carbaldehyde was obtained by the above procedure from amine A2. 7.4% yield. $^1$H NMR (D$_2$O, 400 MHz): δ 10.70 (s, 1H, CHO), 7.94 (d, J=9.2 Hz, 1H, ArH), 7.22 (d, J=8.8 Hz, 1H, ArH), 4.24 (s, 3H, NCH$_3$), 3.78 (t, J=4.8 Hz, 2H, CH$_2$), 3.73 (t, J=5.0 Hz, 2H, CH$_2$), 3.63 (t, J=4.8 Hz, 2H, CH$_2$), 3.57 (t, J=4.8 Hz, 2H, CH$_2$), 3.50 (t, J=6.8 Hz, 2H, CH$_2$), 3.18 (t, J=6.8 Hz, 2H, CH$_2$). MS [ESI, MH$^+$]: 318.2

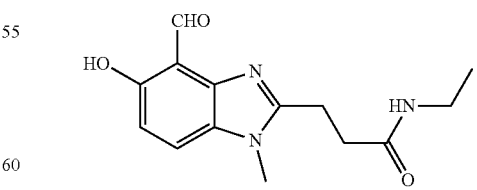

N-Ethyl-3-(4-formyl-5-hydroxy-1-methyl-1H-benzo[d]imidazol-2-yl)propanamide was obtained by the above procedure from amine A4. 2.0% yield. $^1$H NMR (MeOD, 400 MHz): δ 10.63 (s, 1H, CHO), 7.75 (d, J=9.2 Hz, 1H, ArH), 6.91 (d, J=9.2 Hz, 1H, ArH), 3.87 (s, 3H, NCH$_3$) 3.25 (t, J=7.2 Hz, 2H, CH$_2$), 3.19-3.14 (m, 2H, CH$_2$), 2.76 (t, J=4.8 Hz, 2H, CH$_2$), 1.06 (t, J=6.8 Hz, 3H, CH$_3$). MS [ESI, MH$^+$]: 276.2.

Example 75

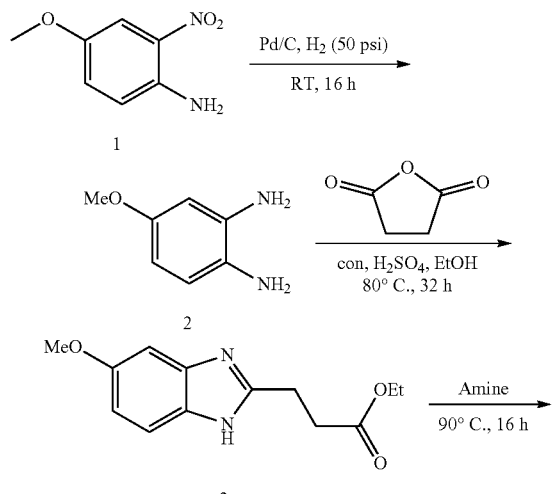

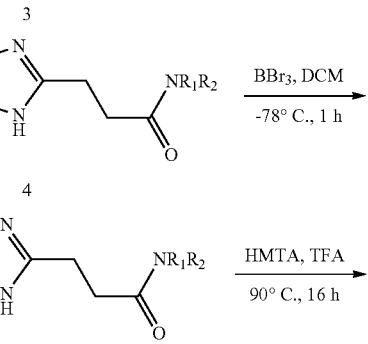

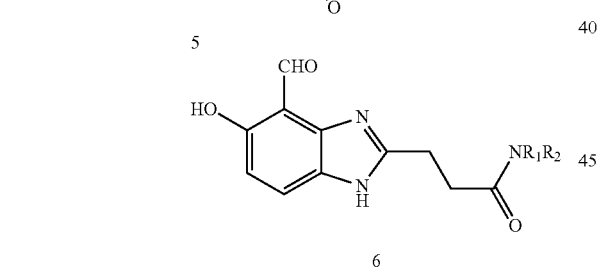

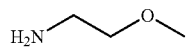
A1

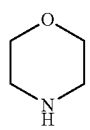
A2

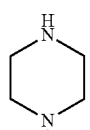
A3

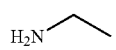
A4

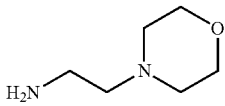
A5

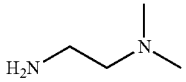
A6

Synthesis of Compound 2

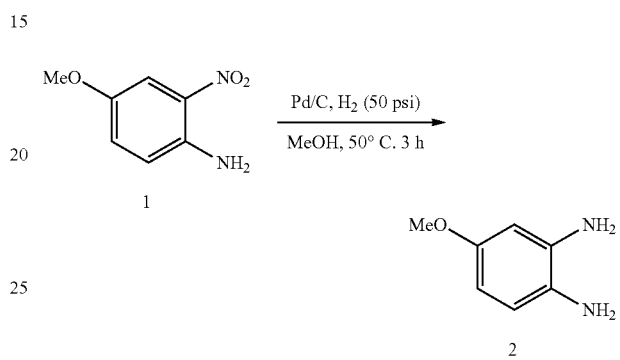

To a mixture of compound 1 (33.6 g, 0.020 mol) and Pd/C (6.72 g) in MeOH (400 mL) was hydrogenated under 50 psi of H$_2$ at 50° C. for 3 h. The catalyst was filtered off and the filtrate was concentrated to give the residue then purified by column chromatography on silica gel to give compound 2 (20 g, 72.5%) as reddish solid.

Synthesis of Compound 3

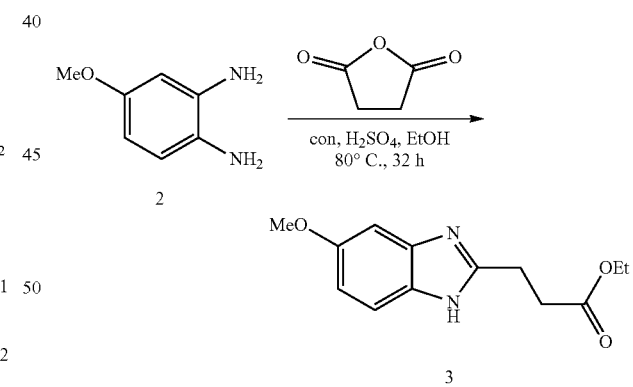

A mixture of compound 2 (11 g, 79.7 mmol) and succinic anhydride (9.57 g, 95.7 mmol) in dioxane (250 mL) was heated to 80° C. for 16 h. The reaction mixture was concentrated to give the residue, and then diluted with EtOH (300 mL) and added conc. H$_2$SO$_4$ (5 mL). The suspension was heated to 80° C. for 16 h. After cooling to RT, the reaction mixture was concentrated to give the residue, diluted with water (200 mL), neutralized by 1 M NaOH solution to pH=7-8, extracted with DCM (500×3), washed with water (100 mL), brine (100 mL), dried over Na$_2$SO$_4$ concentrated to give the residue, and then purified by chromatography on silica gel to give compound 3 as yellow solid (13 g, 65.7%). ¹H NMR (th02877-062-1D₂O, 400 MHz): δ 7.43 (d, J=8.4 Hz, 1H, ArH), 7.01 (d, J=2.4 Hz, 1H, ArH), 6.87-6.84 (m, 1H, ArH), 4.20-4.15 (m, 2H, CH₂), 3.83 (s, 3H, ArOCH₃), 3.19-3.16 (m, 2H, CH₂) 2.86-2.83 (m, 2H, CH₂) 1.26 (t, J=7.2 Hz, 4H, CH₂).

Synthesis of Compound 4

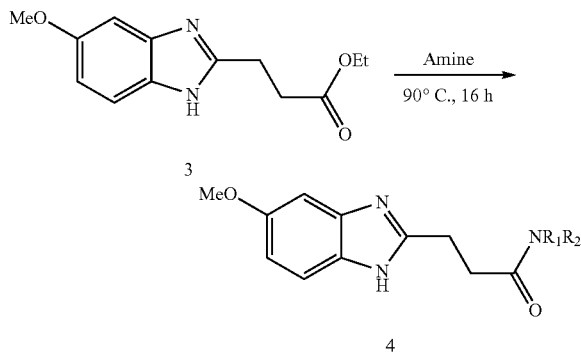

A mixture of compound 3 (1 eq) and amine was heated to 90° C. for 16 h. After cooling to RT, the reaction mixture was concentrated to give compound 4 (1.9 g, 95.4%).

Synthesis of Compound 5

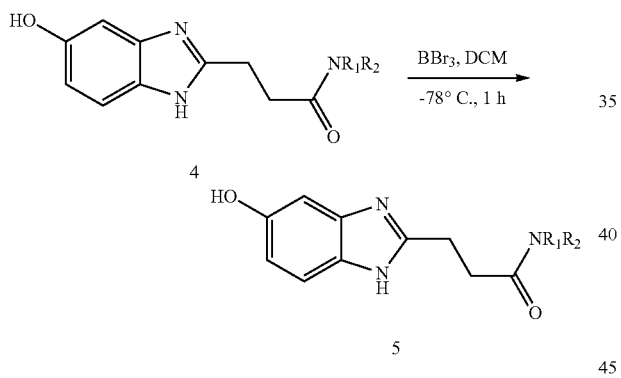

To a solution of Compound 4 (1 eq) in DCM was added BBr₃ (2.0 eq) dropwise at −78° C. over 10 min and then warmed to RT and stirred for 1. The reaction mixture was quenched with MeOH at −78° C., concentrated to give the residue, and diluted with water (100 mL), washed with DCM (50 mL×3). The aqueous layer was neutralized by 10% NaOH solution to pH=8-9, then extracted with EtOAc (200 mL×3), dried over Na₂SO₄, concentrated to give compound 5.

Synthesis of Compound 6

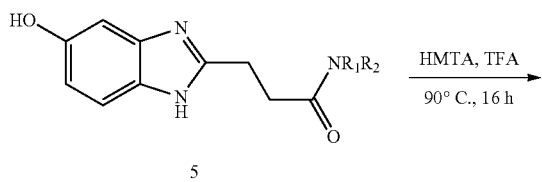

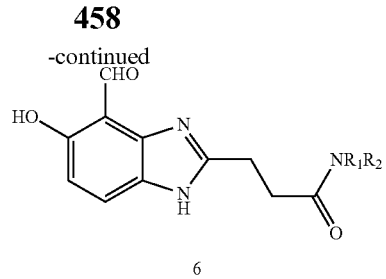

A solution of compound 5 (1 eq) and HMTA (4.0 eq) in TFA was heated to 90° C. for 1 h. After cooling to RT, the reaction mixture was concentrated to give the residue, and then purified by prep-HPLC to give compound 6.

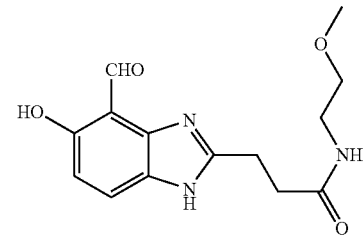 [SMILES: COCCNC(=O)CCc1nc2c(C=O)c(O)ccc2[nH]1]

3-(4-Formyl-5-hydroxy-1H-benzo[d]imidazol-2-yl)-N-(2-methoxyethyl)propanamide was obtained by the above procedure from amine A1. 15.4% yield. ¹H NMR (D₂O, 400 MHz): δ 10.33 (s, 1H, CHO), 7.82 (d, J=9.2 Hz, 1H, ArH), 7.11 (d, J=8.8 Hz, 1H, ArH), 3.50-3.44 (m, 4H, 2CH₂), 3.38 (d, J=5.2, Hz, CH₂), 3.27 (s, 3H, OCH₃), 2.92 (t, J=7.0 Hz, 2H, CH₂) MS [ESI, MH⁺]: 292.2

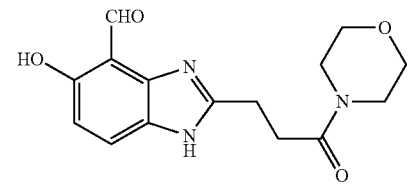 [SMILES: O=Cc1c(O)ccc2[nH]c(CCC(=O)N3CCOCC3)nc12]

5-Hydroxy-2-(3-morpholino-3-oxopropyl)-1H-benzo[d]imidazole-4-carbaldehyde was obtained by the above procedure from amine A2. 10.1% yield. ¹H NMR (DMSO, 400 MHz): δ 10.47 (s, 1H, CHO), 7.77 (d, J=8.8 Hz, 1H, ArH), 7.05 (d, J=8.8 Hz, 1H, ArH), 5.06 (br, 1H, NH), 3.54 (d, J=4.4, 4H, 2CH₂), 3.44 (t, J=4.6 Hz, 4H, 2CH₂), 3.24 (t, J=7.2 Hz, 2H, CH₂), 2.96 (t, J=7.2 Hz, 4H, CH₂) MS [ESI, MH⁺]: 304.2.

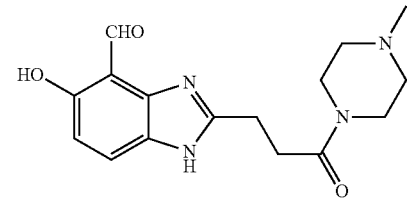 [SMILES: CN1CCN(C(=O)CCc2nc3c(C=O)c(O)ccc3[nH]2)CC1]

5-Hydroxy-2-(3-(4-methylpiperazin-1-yl)-3-oxopropyl)-1H-benzo[d]imidazole-4-carbaldehyde was obtained by the above procedure from amine A3.16% yield. ¹H NMR (D₂O, 400 MHz): δ 10.40 (s, 1H, CHO), 7.86 (d, J=8.8 Hz, 1H, ArH), 7.17 (d, J=9.2 Hz, 1H, ArH), 4.57 (d, J=7.0 Hz, 1H), 4.21 (d, J=15.6 Hz, 1H), 3.63-3.58 (m 3H, CH$_2$), 3.47 (t, J=6.6 Hz, 2H, CH$_2$), 3.21 (m, 3H, CH$_2$), 3.11-3.09 (m, 2H, CH$_2$), 2.95 (s, 3H, NCH$_3$); MS [ESI, MH$^+$]: 317.2.

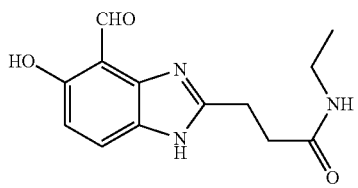 [SMILES: CCNC(=O)CCc1nc2c(C=O)c(O)ccc2[nH]1]

N-Ethyl-3-(4-formyl-5-hydroxy-1H-benzo[d]imidazol-2-yl)propanamide was obtained by the above procedure from amine A4. 7.2% yield. $^1$HNMR (M D$_2$O, 400 MHz): δ 10.38 (s, 1H, CHO), 7.85 (d, J=8.8 Hz, 1H, ArH), 7.16 (d, J=9.2 Hz, 1H, ArH), 3.45 (t, J=2.8 Hz, 2H, CH$_2$), 3.15 (t, J=7.2 Hz, 2H, CH$_2$), 2.86 (t, J=7.2 Hz, 2H, CH$_2$), 1.03-1.01 (t, J=7.2 Hz, 3H, CH$_3$); MS [ESI, MH$^+$]: 262.0.

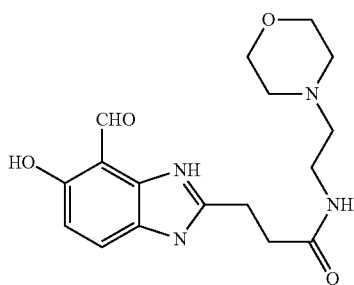 [SMILES: O=Cc1c(O)ccc2[nH]c(CCC(=O)NCCN3CCOCC3)nc12]

3-(7-Formyl-6-hydroxy-1H-benzo[d]imidazol-2-yl)-N-(2-morpholinoethyl)propanamide was obtained by the above procedure from amine A5. 14.0% yield. $^1$HNMR (D$_2$O, 400 MHz): δ 10.36 (s, 1H, CHO), 7.84 (d, J=9.2 Hz, 1H, ArH), 7.15 (d, J=9.2 Hz, 1H, ArH), 4.10 (d, J=13.6 Hz, 2H, CH$_2$), 3.81 (d, J=12.0 Hz, 2H, CH$_2$), 3.64-3.57 (m, 4H, CH$_2$), 3.46 (t, J=7.2 Hz, 2H, CH$_2$), 3.33 (t, J=6.2 Hz, 2H, CH$_2$), 3.22 (d, J=5.2 Hz, 2H, CH$_2$), 2.96 (t, J=7.0 Hz, 2H, CH$_2$); MS [ESI, MH$^+$]: 347.3.

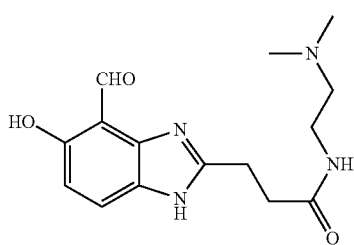 [SMILES: CN(C)CCNC(=O)CCc1nc2c(C=O)c(O)ccc2[nH]1]

N-(2-(Dimethylamino)ethyl)-3-(4-formyl-5-hydroxy-1H-benzo[d]imidazol-2-yl)propanamide was obtained by the above procedure from amine A6. 5.5% yield. $^1$H NMR (MeOD, 400 MHz): δ 7.54 (d, J=8.8 Hz, 1H, ArH), 7.07 (d, J=8.8 Hz, 1H, ArH), 5.89 (s, 1H, CONH), 3.58 (t, J=5.8 Hz, 2H, CH$_2$), 3.44 (t, J=7.0 Hz, 2H, CH$_2$), 3.29-3.27 (m, 2H, CH$_2$), 2.94 (t, J=4.8 Hz, 2H, CH$_2$), 2.92 (s, 6H, 2NCH$_3$); MS [ESI, MH$^+$]: 305.2.

Example 76

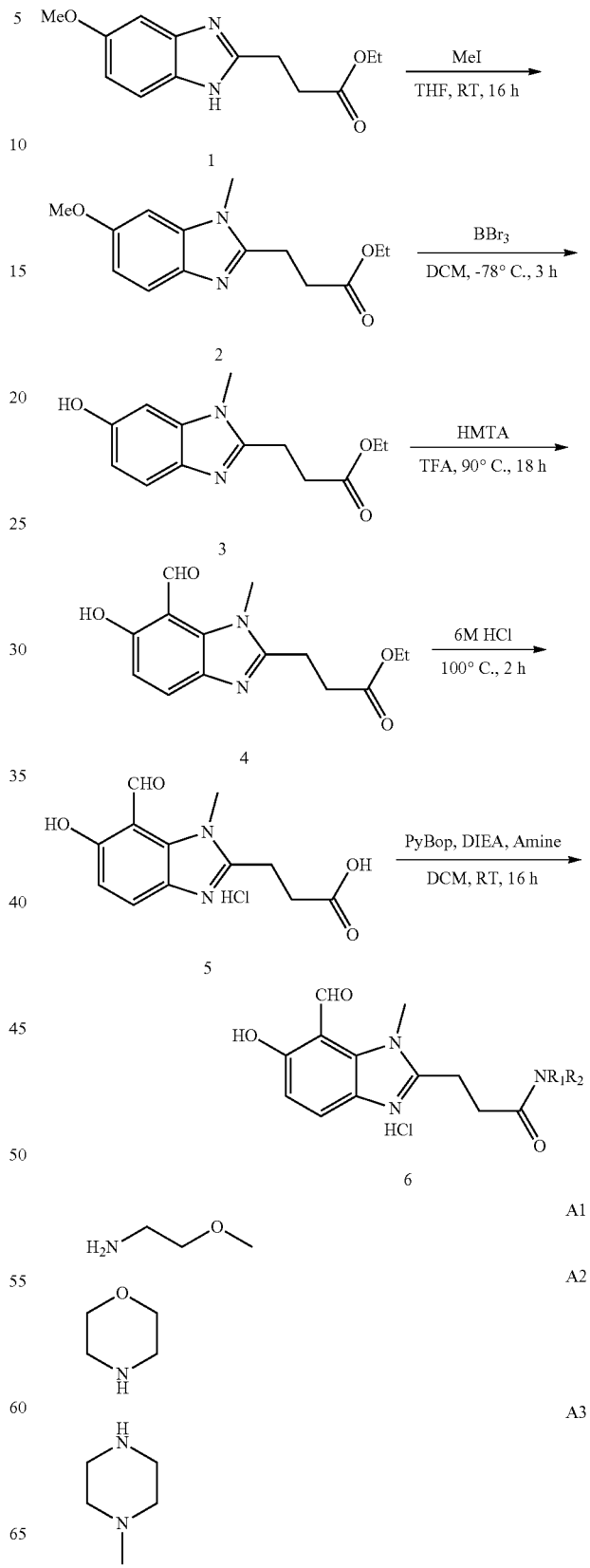

-continued

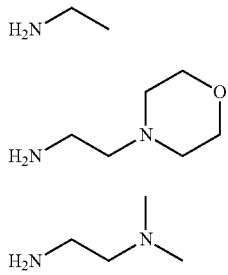

A4

A5

A6

Synthesis of Compound 2

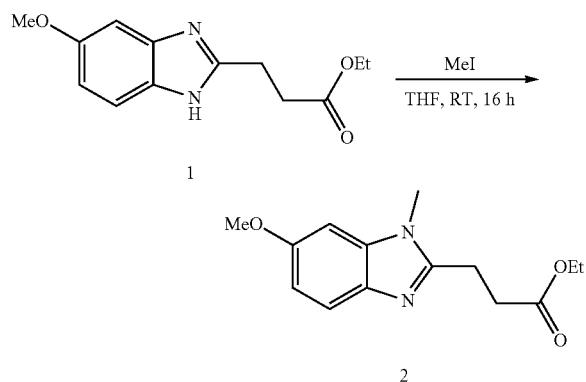

To a suspension of NaH (1.93 g, 48 mmol) in THF (100 mL) was added compound 1 (10 g, 40 mmol) in THF (100 mL) dropwise at 0° C. over 30 min. The reaction mixture was stirred at RT for 1 h, and MeI (6.81 g, 48 mmol) was added dropwise at 0° C. over 10 min. The mixture was stirred at RT for 16 h, then poured into ice water and extracted with EtOAc (1 L×3), washed with brine (100 mL×3), dried over Na$_2$SO$_4$, concentrated to give (9.8 g, 86%) compound 2 as yellow solid. MS [ESI, MH$^+$]: 263.1

Synthesis of Compound 3

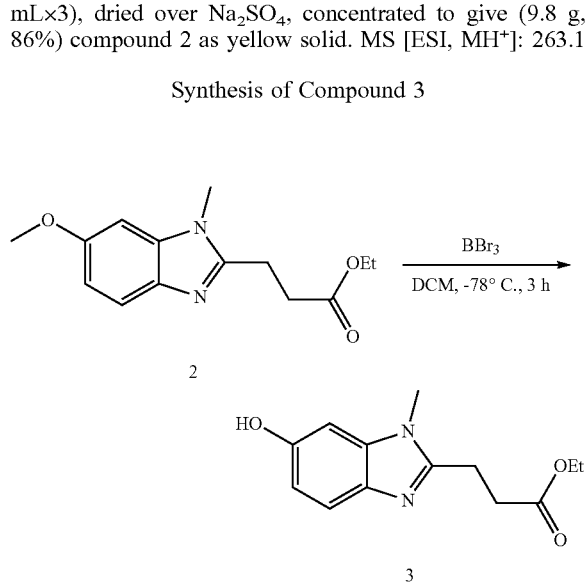

To a solution of compound 2 (10 g, 38 mmol) in DCM (150 mL) was added BBr$_3$ (19 g, 76 mmol) in DCM (50 mL) dropwise at −78° C. over 20 min. The reaction mixture was warmed to RT and stirred at RT for 2 h, then quenched with EtOH at −78° C. The mixture was diluted with water (50 mL), then neutralized by adding sat.NaHCO$_3$ to pH=7-8, extracted with DCM (300 mL×4), washed with brine (100 mL), dried over Na$_2$SO$_4$, concentrated to give the residue, and then purified by column chromatography on silica gel to give compound 3 (4.8 g, 51%) as yellow solid.

Synthesis of Compound 4

A mixture of compound 3 (2.47 g, 10 mmol) and HMTA (5.58 g, 40 mmol) in TFA (120 mL) was heated to 90° C. for 18 h. After cooling to RT, the reaction mixture was concentrated to give the residue, and then diluted with water (100 mL), extracted with EtOAc (500 mL×2), washed with brine (100 mL×2), dried over Na$_2$SO$_4$, concentrated to give the crude product, then purified by column chromatography on silica gel to give yellow solid and further purified by SFC to give compound 4 (0.5 g, 18%) as yellow solid.

Synthesis of Compound 5

A mixture of compound 4 (0.9 g, 3.26 mmol) and 6 M HCl (30 mL) solution was heated to 100° C. for 2 h. The solvent was removed under vacuum to give compound 5 (0.8 g, 86.5%) as reddish solid.

Synthesis of Compound 6

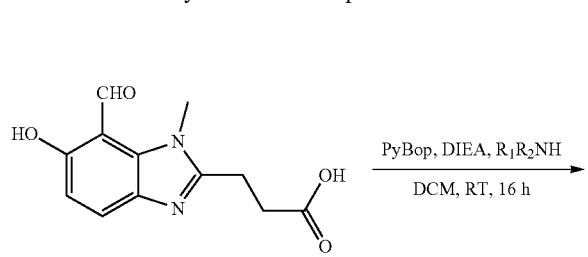

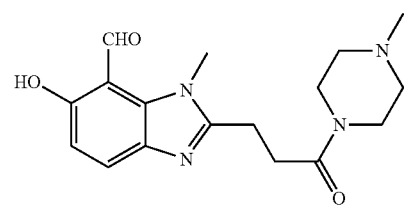

6-Hydroxy-1-methyl-2-(3-(4-methylpiperazin-1-yl)-3-oxopropyl)-1H-benzo[d]imidazole-7-carbaldehyde was obtained by the above procedure from amine A5. 14.1% yield. $^1$HNMR (M D$_2$O, 400 MHz): δ 10.69 (s, 1H, CHO), 7.93 (d, J=9.2 Hz, 1H, ArH), 7.20 (d, J=9.2 Hz, 1H, ArH), 4.53 (t, J=5.4 Hz, 1H), 4.22 (s, 4H), 3.69 (d, J=8.0 Hz, 3H, CH$_2$), 3.51 (t, J=6.2 Hz, 2H, CH$_2$), 3.21 (t, J=7.0 Hz, 3H, CH$_2$), 3.10 (t, J=5.2 Hz, 2H, CH$_2$), 2.95 (s, 3H, NCH$_3$); MS [ESI, MH$^+$]: 331.3.

To a suspension of of compound 5 (1.0 eq) in DCM was added PyBop (1.2 eq) and DIEA (2.5 eq). The mixture was stirred at RT for 30 min, and then added amine (1.2 eq). The reaction mixture was stirred at RT for 1 h. The solvent was removed to give the residue, purified by Prep-HPLC to give compound 6

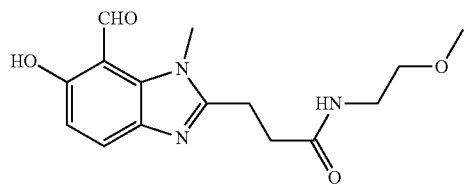 [SMILES: COCCNC(=O)CCc1nc2ccc(O)c(C=O)c2n1C]

3-(7-Formyl-6-hydroxy-1-methyl-1H-benzo[d]imidazol-2-yl)propanoic acid: $^1$HNMR (D$_2$O, 400 MHz): δ 10.60 (s, 1H, CHO), 7.86 (d, J=9.2 Hz, 1H, ArH), 7.11 (d, J=9.2 Hz, 1H, ArH), 4.17 (s, 3H, NCH$_3$), 3.48 (t, J=7.0 Hz, 2H, CH$_2$), 3.03 (t, J=7.0 Hz, 2H, CH$_2$); MS [ESI, MH$^+$]: 249.1.

3-(7-Formyl-6-hydroxy-1-methyl-1H-benzo[d]imidazol-2-yl)-N-(2-methoxyethyl)propanamide was obtained by the above procedure from amine A1 25% yield. $^1$HNMR (MeOD, 400 MHz): δ 10.68 (s, 1H, CHO), 7.73 (d, J=8.8 Hz, 1H, ArH), 6.81 (d, J=8.4 Hz, 1H, ArH), 4.02 (s, 3H, NCH$_3$), 3.43-3.40 (m, 2H, CH$_2$), 3.36-3.33 (m, 2H, CH$_2$), 3.31-3.29 (m, 3H, OCH$_3$), 3.19 (t, J=7.4 Hz, 2H, CH$_2$), 2.76 (t, J=7.6 Hz, 2H, CH$_2$) MS [ESI, MH$^+$]: 306.2

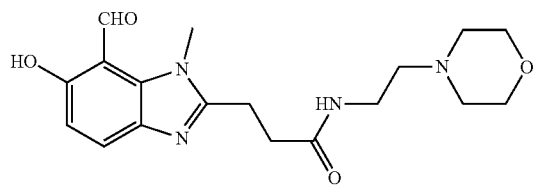 [SMILES: Cn1c(CCC(=O)NCCN2CCOCC2)nc2ccc(O)c(C=O)c21]

3-(7-Formyl-6-hydroxy-1-methyl-1H-benzo[d] imidazol-2-yl)-N-(2-morpholinoethyl)propanamide was obtained by the above procedure from amine A3. 28.6% yield. $^1$HNMR (D$_2$O, 400 MHz): δ 10.70 (s, 1H, CHO), 7.95 (d, J=9.2 Hz, 1H, ArH), 7.23 (d, J=8.8 Hz, 1H, ArH), 4.23 (s, 3H, NCH$_3$), 4.12 (d, J=6.4 Hz, 2H, CH$_2$), 3.81 (t, J=12.6 Hz, 2H, CH$_2$), 3.64 (m, 4H, 2CH$_2$), 3.58-3.51 (m, 2H, CH$_2$), 3.34 (t, J=6.2 Hz, 2H, CH$_2$), 3.26-3.20 (m, 2H, CH$_2$), 2.97 (t, J=7.4 Hz, 2H) MS [ESI, MH$^+$]: 361.1.

Example 77

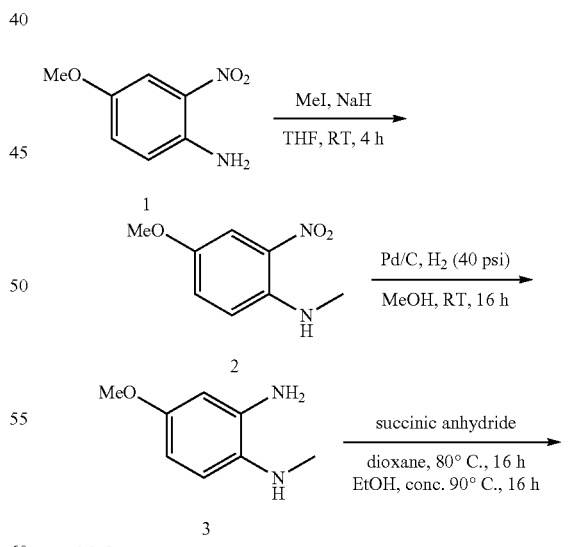

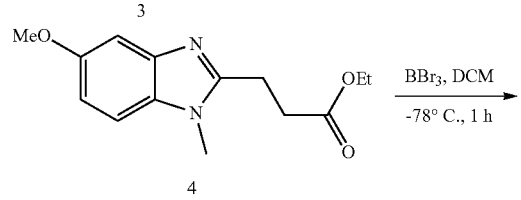

-continued

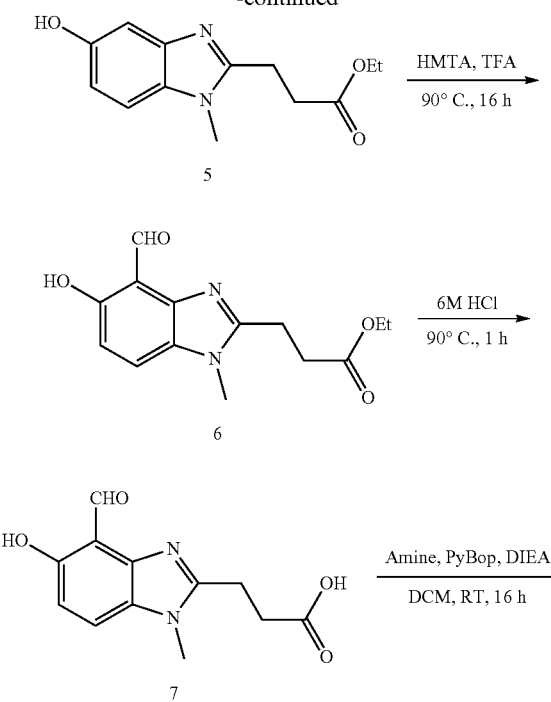

A1

H2N-CH2CH2-O-CH3

A2 morpholine (HN)

A3

1-methylpiperazine

A4

H2N-CH2CH3 (ethylamine)

A5

H2N-CH2CH2-N(morpholine)

A6

H2N-CH2CH2-N(CH3)2

Synthesis of Compound 2

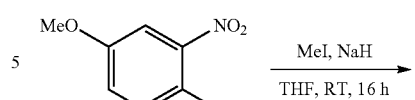

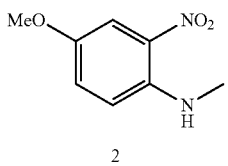

To a suspension of NaH (14.9 g, 0.373 mol) in DMF (1 L) was added compound 1 (50 g, 0.298 mol) in DMF (200 mL) dropwise at ° C. over 1 h. The reaction mixture was stirred at RT for 1 h, and then MeI (46.5 g, 0.328 mol) was added. The reaction mixture was stirred at RT for 16 h, and then poured into ice water. The mixture was concentrated to give the residue, diluted with DCM (3 L), washed with water (200 mL×2), brine (200 mL×2), dried over Na$_2$SO$_4$, concentrated to give compound 2 (50 g, 92.6%) as reddish solid.

Synthesis of Compound 3

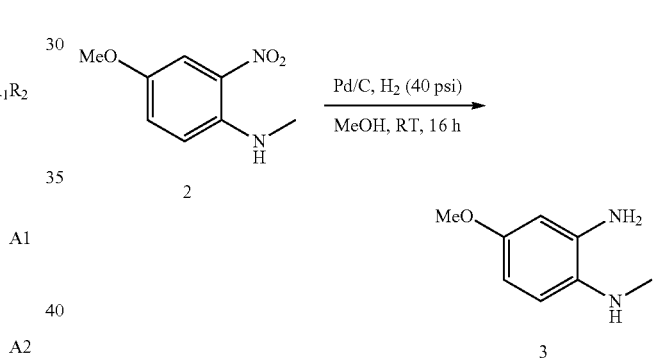

To a mixture of compound 2 (40 g, 0.22 mol) and Pd/C (9.0 g) in MeOH (1.0 L) was hydrogenated under 40 psi H$_2$ at 30° C. for 16 h. The catalyst was filtered off and the filtrate was concentrated to give the residue then purified by column chromatography on silica gel to give compound 3 (30 g, 91%) as brown solid.

Synthesis of Compound 4

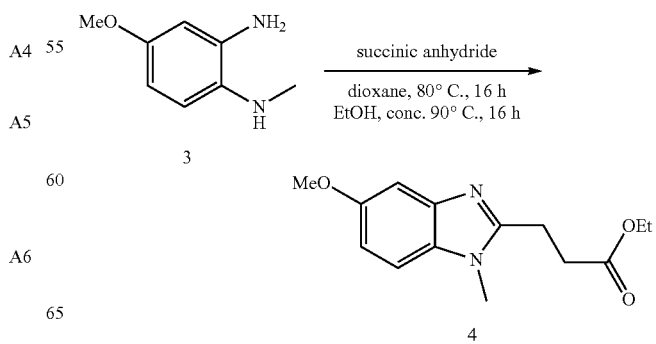

A mixture of compound 3 (30 g, 0.197 mol) and succinic anhydride (23.7 g, 0.237 mol) in dioxane (500 mL) was heated to 80° C. for 16 h. The reaction mixture was concentrated to give the residue. The residue was diluted with EtOH (500 mL) and added conc. $H_2SO_4$ (10 mL). The suspension was heated to 90° C. for 16 h. After cooling to RT, the reaction mixture was concentrated to give the residue, diluted with water (400 mL), neutralized by adding 1 M NaOH solution to pH=7-8, extracted with DCM (500 mL×3), washed with water (100 mL), brine (100 mL), dried over $Na_2SO_4$ concentrated to give the residue, and then purified by chromatography on silica gel to give compound 4 as yellow solid (23 g, 44%). MS [ESI, MH$^+$]: 263.2.

Synthesis of Compound 5

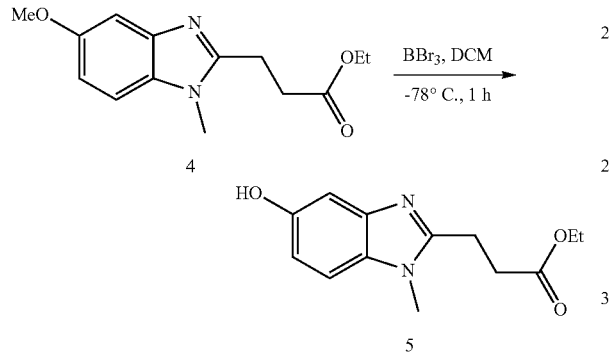

To a solution of compound 4 (22 g, 0.084 mol) in DCM (250 mL) was added $BBr_3$ (42 g, 0.168 mol) dropwise at −78° C. over 20 min and then warmed to RT and stirred for 1 h. The reaction mixture was quenched with MeOH at −78° C., concentrated to give the residue, neutralized by 10% NaOH solution to pH=8-9, then extracted with EtOAc (200 mL×3), dried over $Na_2SO_4$, concentrated to give compound 5 (5.0 g, 24%) as yellow solid. $^1$HNMR (MeOD, 400 MHz): δ 1 7.21 (d, J=8.4 Hz, 1H, ArH), 6.94 (d, J=2.0 Hz, 1H, ArH), 6.78-6.75 (m, 1H, ArH), 3.72 (s, 3H, NCH$_3$), 3.09 (t, J=7.2 Hz, 2H, CH$_2$), 2.88 (t, J=7.2 Hz, 2H, CH$_2$), 1.18 (t, J=7.0 Hz, 3H, CH$_3$).

Synthesis of Compound 6

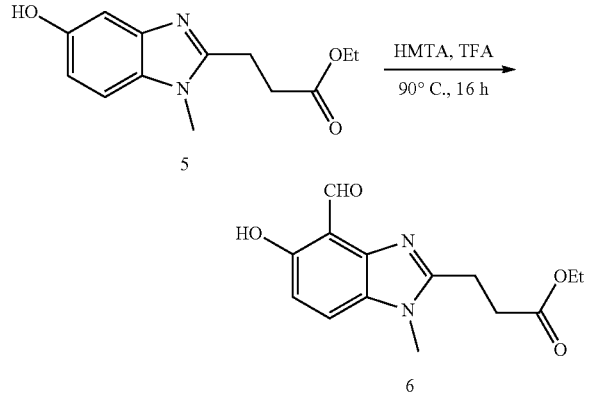

A solution of compound 5 (5.0 g, 0.020 mol) and HMTA (11.3 g, 0.080 mol) in TFA (150 mL) was heated to 90° C. for 16 h. After cooling to RT the reaction mixture was concentrated to give the residue, diluted with water (100 mL), and then extracted with EtOAc (500 mL), washed with water (50 mL×3), brine (100 mL), dried over Na$_2$SO4 to give the crude product and then purified by column chromatography on silica gel to give compound 6 (1.3 g, 23.6%) as yellow solid.

Synthesis of Compound 7

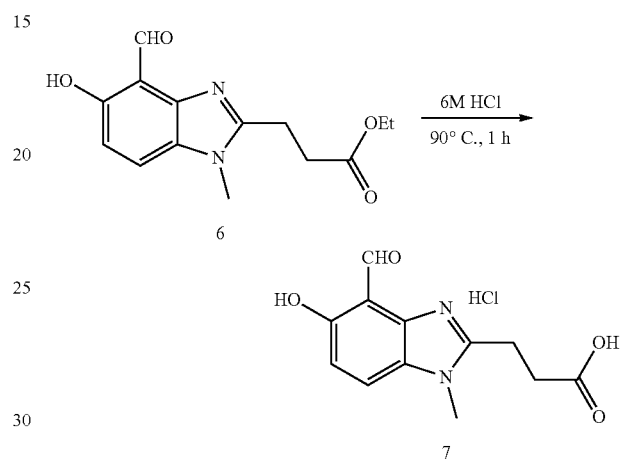

A mixture of compound 6 (1.3 g, 4.71 mmol) in 6 M HCl solution (40 mL) was heated to 90° C. for 1 h. The reaction mixture was concentrated to give the product (1.05 g, 68%) as red solid.

Synthesis of Compound 8

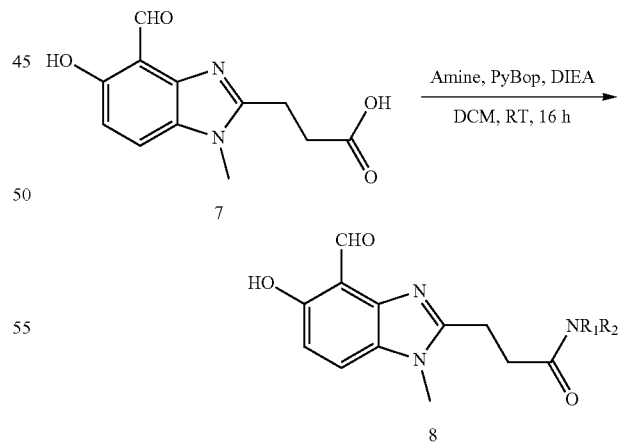

A suspension of compound 7 (1.0 eq), PyBop (1.2 eq) and DIEA (2.5 eq) in DCM (3 mL) was stirred at RT for 30 min, then added amine (1.0 eq). The mixture was stirred at RT for 16 h, diluted with DCM (200 mL), washed with water (20 mL×3), dried over Na$_2$SO$_4$, concentrated to give the residue, then purified by prep.TLC to give compound 8

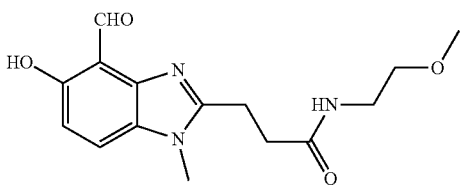 [SMILES: COCCNC(=O)CCc1nc2c(C=O)c(O)ccc2n1C]

3-(4-Formyl-5-hydroxy-1-methyl-1H-benzo[d]imidazol-2-yl)-N-(2-methoxyethyl)propanamide was obtained by the above procedure from amine A1. 18.5% yield. ¹H NMR (CDCl₃, 400 MHz): δ 11.45 (s, 1H, OH), 10.74 (s, 1H, CHO), 7.43 (d, J=8.8 Hz, 1H, ArH), 6.84 (d, J=8.4 Hz, 1H, ArH), 6.65 (br, 1H, NH), 3.76 (s, 3H, NCH₃), 3.41 (t, J=3.8 Hz, 2H, CH₂), 3.29 (s, 3H, OCH₃), 3.19 (t, J=6.8 Hz, 2H, CH₂), 2.88 (t, J=6.6 Hz, 2H, CH₂); MS [ESI, MH⁺]: 306.2.

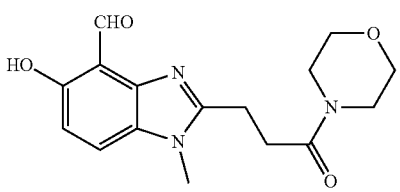 [SMILES: Cn1c(CCC(=O)N2CCOCC2)nc2c(C=O)c(O)ccc21]

5-Hydroxy-1-methyl-2-(3-morpholino-3-oxopropyl)-1H-benzo[d]imidazole-4-carbaldehyde was obtained by the above procedure from amine A2. 24.7% yield. ¹H NMR (DMSO, 400 MHz): δ 11.69 (s, 1H, OH), 10.46 (s, 1H, CHO), 8.09 (d, J=8.8 Hz, 1H, ArH), 7.28 (d, J=8.8 Hz, 1H, ArH), 3.98 (s, 3H, NCH₃), 3.56 (t, J=4.6 Hz, 2H, CH₂), 3.51 (t, J=5.0 Hz, 2H, CH₂), 3.39 (s, 4H, 2CH₂), 3.31 (t, 2H, J=5.2 Hz, CH₂), 2.98 (t, 2H, J=5.2 Hz, CH₂); MS [ESI, MH⁺]: 318.2.

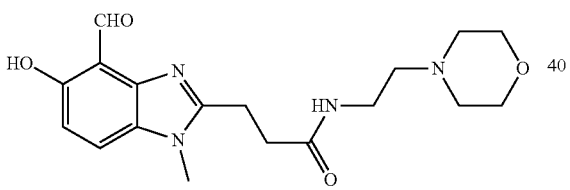

3-(4-Formyl-5-hydroxy-1-methyl-1H-benzo[d]imidazol-2-yl)-N-(2-morpholinoethyl)propanamide was obtained by the above procedure from amine A5. 12.6% yield. ¹H NMR (CDCl₃ 400 MHz): δ 11.42 (s, 1H, OH), 10.73 (s, 1H, CHO), 7.42 (d, J=8.8 Hz, 1H, ArH), 6.84 (d, J=8.8 Hz, 1H, ArH), 6.54-6.51 (br, 1H, NH), 3.77 (s, 3H, NCH₃), 3.68 (t, J=3.8 Hz, 4H, 2CH₂), 3.36 (d, J=5.6 Hz, 2H, CH₂), 3.20 (t, J=7.0 Hz, 2H, CH₂), 2.89 (d, J=7.2 Hz, 2H, CH₂), 2.45 (s, 6H); MS [ESI, MH⁺]: 361.3

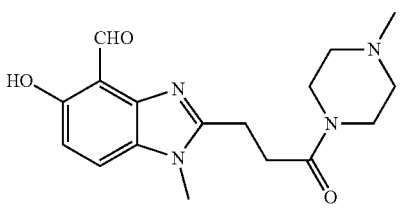 [SMILES: CN1CCN(C(=O)CCc2nc3c(C=O)c(O)ccc3n2C)CC1]

5-Hydroxy-1-methyl-2-(3-(4-methylpiperazin-1-yl)-3-oxopropyl)-1H-benzo[d]imidazole-4-carbaldehyde was obtained by the above procedure from amine A3. 6.9% yield. ¹H NMR (CDCl₃, 400 MHz): δ 11.45 (s, 1H, OH), 10.73 (s, 1H, CHO), 7.43 (d, J=8.8 Hz, 1H, ArH), 6.83 (d, J=9.2 Hz, 1H, ArH), 3.80 (s, 3H, NCH₃), 3.63-3.58 (m, 4H, 2CH₂), 3.21 (t, J=6.8 Hz, 2H, CH₂), 3.03 (d, J=7.0 Hz, 2H, CH₂), 2.44-2.38 (m, 4H, 2CH₂), 2.31 (s, 3H, NCH₃); MS [ESI, MH⁺]: 331.3.

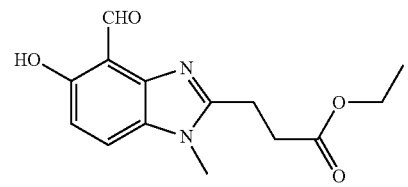 [SMILES: CCOC(=O)CCc1nc2c(C=O)c(O)ccc2n1C]

Ethyl 3-(4-formyl-5-hydroxy-1-methyl-1H-benzo[d]imidazol-2-yl)propanoate: ¹H NMR (CDCl₃, 400 MHz): δ 11.45 (s, 1H, OH), 10.72 (d, J=0.4 Hz 1H, CHO), 7.43 (d, J=8.8 Hz, 1H, ArH), 6.83 (d, J=8.8 Hz, 1H, ArH), 4.18-4.13 (m, 2H, CH₂), 3.77 (s, 3H, NCH₃), 3.16 (t, J=4.8 Hz, 2H, CH₂), 2.99 (t, J=4.8 Hz, 2H, CH₂), 1.24 (t, J=7.2 Hz, 3H, CH₃); MS [ESI, MH⁺]: =277.2

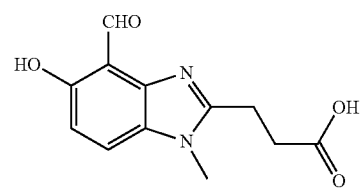 [SMILES: Cn1c(CCC(=O)O)nc2c(C=O)c(O)ccc21]

3-(4-Formyl-5-hydroxy-1-methyl-1H-benzo[d]imidazol-2-yl)propanoic acid: ¹H NMR (D₂O, 400 MHz): δ 10.35 (s, 1H, CHO), 7.91 (d, J=8.8 Hz, 1H, ArH), 7.19 (d, J=9.2 Hz, 1H, ArH), 4.03 (s, 3H, NCH₃), 3.49 (t, J=7.2 Hz, 2H, CH₂), 3.02 (t, J=7.0 Hz, 2H, CH₂); MS [ESI, MH⁺]: 249.2.

Example 78

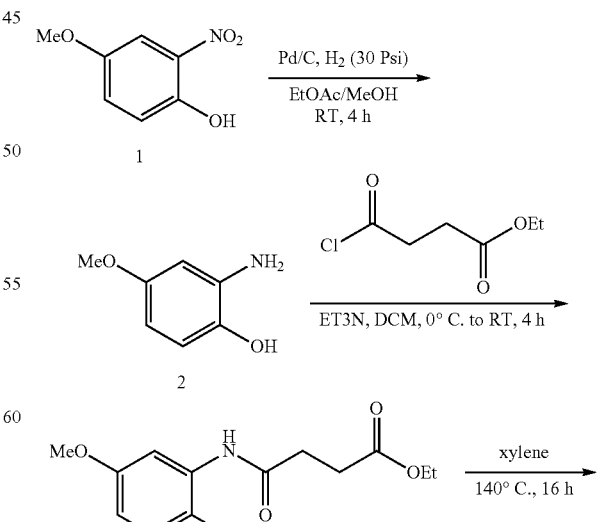

-continued

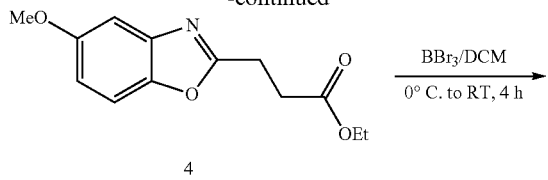
4

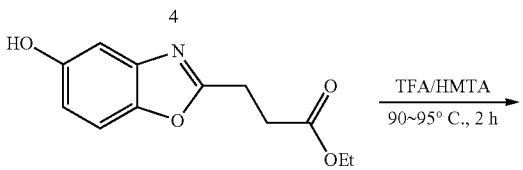
5

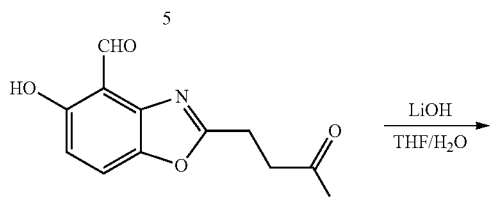
6

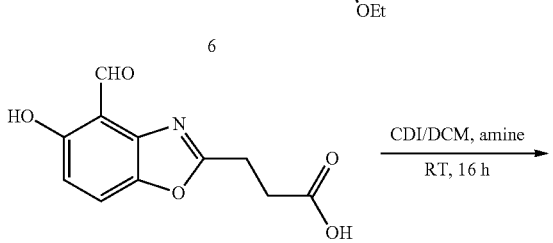
7

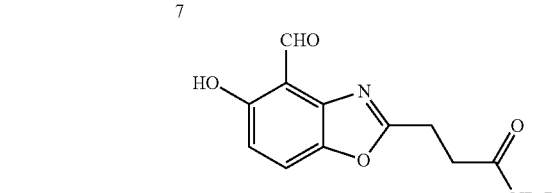
8

A1 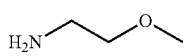

A2 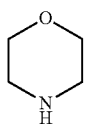

A3 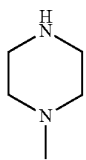

A4 

A5 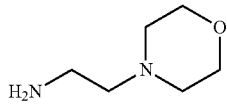

A6 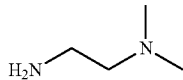

Synthesis of Compound 2

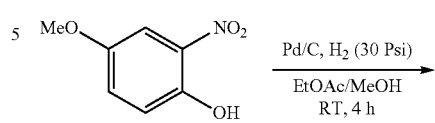

Compound 1 (60.0 g, 355.0 mmol) and Pd/C (8 g) were added to EA/MeOH (320 mL/480 mL). The reaction mixture was stirred at RT under H$_2$ (30 Psi) for 4 h and filtered through Celite pad. The filter was concentrated, afforded the crude product. The crude product was washed with MTBE (100 mL), dried, afforded compound 2 (45.0 g, 91.1%) as brown solid.

Synthesis of Compound 3

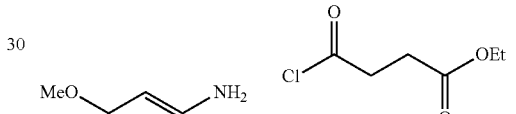

Compound 2 (32.5 g, 233.8 mmol) and Et$_3$N (23.6 g, 233.8 mmol) were added to DCM (650 mL). The solution of acylchloride (38.5 g, 234.7 mmol) in DCM (200 mL) was added dropwise. Then the mixture was warmed slowly to RT and stirred for 3 h. The reaction mixture was diluted with DCM (500 mL), washed with 1N HCl (100 mL) and brine ((200 mL×2). The DCM layer was dried over Na$_2$SO$_4$, filtered, concentrated, afforded crude compound 3 (52.0 g, ~40% purity) as brown oil.

Synthesis of Compound 4

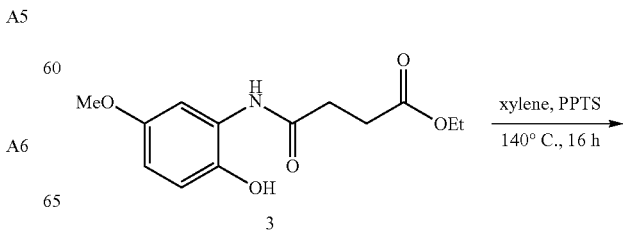

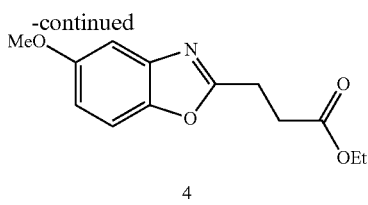

Compound 3 (40.0 g, 149.8 mmol) and PPTS (12.5 g, 49.8 mmol) were added to xylene (600 mL). The mixture was heated to 140° C. for 16 h. After cooled to RT, the reaction mixture was concentrated, purified by silica gel column (PE:EA=5:1), afforded compound 4 (10.0 g, 66.9%) as light red solid.

Synthesis of Compound 5

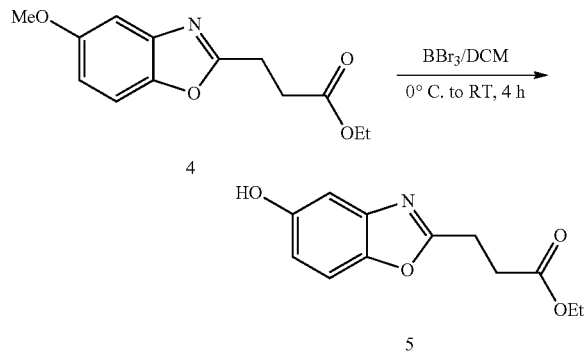

Compound 4 (12.6 g, 50.60 mmol) was dissolved in dry DCM (225 mL), cooled to −60° C. The solution of BBr$_3$ (75.6 g, 302.4 mmol) in DCM (225 mL) was added dropwise. Then the reaction mixture was warmed slowly to RT and stirred for another 2 h. The reaction was quenched with EtOH (17 mL) at −60° C. The reaction mixture was concentrated. The residue was diluted with H$_2$O (200 mL), extracted with EA (100 mL×3). The combined EA was washed with sat.NaHCO$_3$ (100 mL×2), dried over Na$_2$SO$_4$, filtered, concentrated, purified by silica gel column (PE:EA=3:1), afforded compound 5 (9.2 g, 77.3%) as light yellow solid.

Synthesis of Compound 6

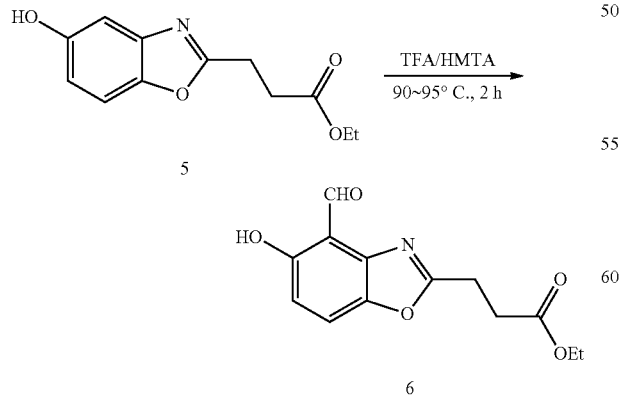

Compound 5 (4.0 g, 17.02 mmol) and HMTA (9.53 g, 68.07 mmol) were added to TFA (225 mL). The reaction mixture was heated to 90~95° C. for 2 h. The reaction mixture was concentrated. The residue was diluted with H$_2$O (100 mL), extracted with EA (80 mL×2). The combined EA was washed with sat. NaHCO$_3$, dried over Na$_2$SO$_4$, filtered, concentrated, purified by silica gel column (PE:EA=10:1), afforded compound 6 (2.0 g, 44.6%) as white solid. $^1$HNMR (CDCl$_3$, 400 MHz): δ 11.26 (s, 1H, OH), 10.57 (s, 1H, CHO), 7.61 (d, J=9.2 Hz, 1H, ArH), 6.89 (d, J=9.2 Hz, 1H, ArH), 4.17 (q, J=7.2 Hz, 2H, CH$_2$), 3.27 (t, J=7.2 Hz, 2H, CH$_2$), 2.94 (t, J=7.2 Hz, 2H, CH$_2$), 1.26 (t, J=7.2 Hz, 3H, CH$_3$). MS [ESI, MH$^+$]: 264.2

Synthesis of Compound 7

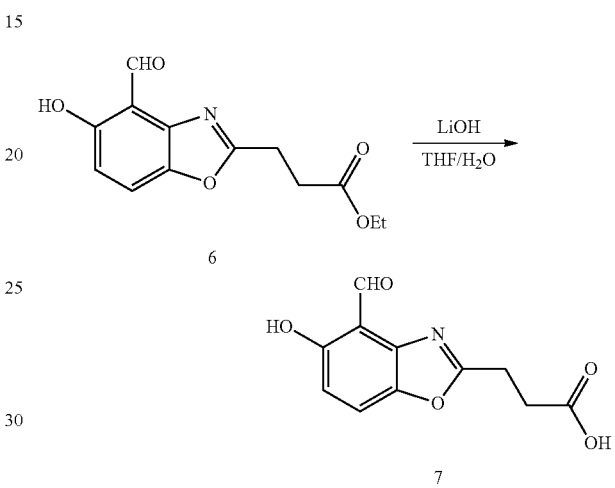

Compound 6 (2.0 g, 7.6 mmol) was added to THF/H$_2$O (25 mL/12 mL), LiOH.H$_2$O (1.16 g, 27.6 mmol) was added. The reaction mixture was stirred at RT for 30 min and quenched with 1N HCl (30 mL). Then the mixture was extracted with EA (15 mL×2). The combined EA was washed with brine, dried over Na$_2$SO$_4$, filtered, concentrated, afforded compound 7 (1.6 g, 89.4%) as white solid. $^1$HNMR (DMSO, 400 MHz): δ 12.39 (br, 1H, COOH), 10.92 (br, 1H, OH), 10.48 (s, 1H, —CHO), 7.90 (d, J=8.8 Hz, 1H, ArH), 6.94 (d, J=8.8 Hz, 1H, ArH), 3.17 (t, J=7.2 Hz, 2H, CH$_2$), 2.83 (t, J=7.2 Hz, 2H, CH$_2$). MS [ESI, MH$^+$]: 236.1

Synthesis of Compound 8

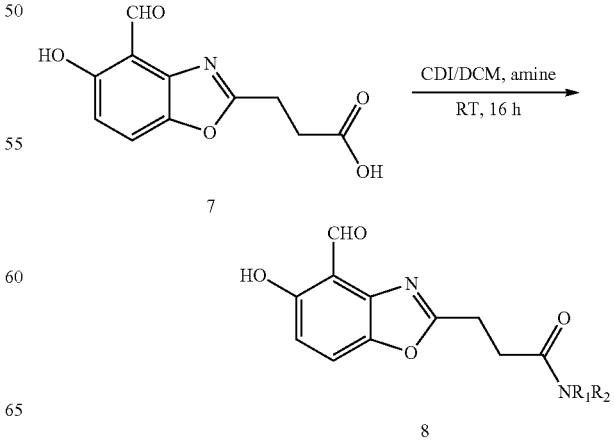

Compound 7 (1 eq) and CDI (1.1 eq) were added to dry DCM. The reaction mixture was stirred at RT for 0.5 h. The solution of amine (1 eq) in DCM was added dropwise at RT. Then the reaction mixture was stirred at RT for 16 h. LC-MS indicated that the reaction was completed. The mixture was diluted with DCM, washed with H$_2$O, dried over Na$_2$SO$_4$, concentrated. The crude product was purified by by silica gel column, afforded compound 8.

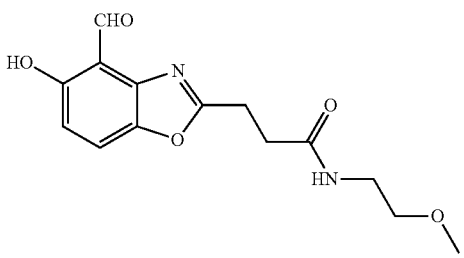 [SMILES: COCCNC(=O)CCc1nc2c(C=O)c(O)ccc2o1]

3-(4-Formyl-5-hydroxybenzo[d]oxazol-2-yl)-N-(2-methoxyethyl)propanamide was obtained by the above procedure from amine A1. 26.8% yield. $^1$HNMR (CDCl$_3$, 400 MHz): δ 11.25 (s, 1H, OH), 10.57 (s, 1H, CHO), 7.60 (d, J=9.2 Hz, 1H, ArH), 6.88 (d, J=9.2 Hz, 1H, ArH), 6.14 (br, 1H, NH), 3.45-3.43 (m, 4H, 2CH$_2$), 3.33 (s, 3H, OCH$_3$), 3.30 (t, J=7.2 Hz, 2H, CH$_2$), 2.81 (t, J=7.2 Hz, 2H, CH$_2$). MS [ESI, MH$^+$]: 293.2.

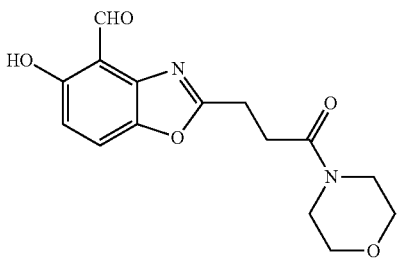 [SMILES: O=Cc1c(O)ccc2oc(CCC(=O)N3CCOCC3)nc12]

5-Hydroxy-2-(3-morpholino-3-oxopropyl)benzo[d]oxazole-4-carbaldehyde was obtained by the above procedure from amine A2. 42.6% yield. $^1$HNMR (CDCl$_3$, 400 MHz): δ 11.26 (s, 1H, OH), 10.57 (s, 1H, CHO), 7.61 (d, J=9.2 Hz, 1H, ArH), 3.73-3.63 (m, 4H, 2CH$_2$), 3.57-3.54 (m, 2H, CH$_2$), 3.34-3.30 (m, 2H, CH$_2$), 3.32 (t, J=7.2 Hz, 2H, CH$_2$), 2.96 (t, J=7.2 Hz, 2H, CH$_2$). MS [ESI, MH$^+$]: 305.2.

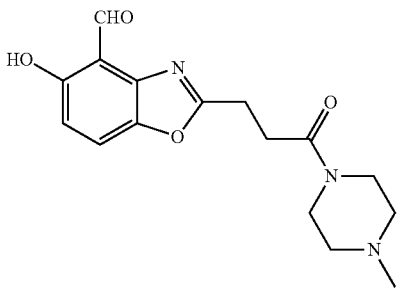 [SMILES: CN1CCN(C(=O)CCc2nc3c(C=O)c(O)ccc3o2)CC1]

5-Hydroxy-2-(3-(4-methylpiperazin-1-yl)-3-oxopropyl)benzo[d]oxazole-4-carbaldehyde was obtained by the above procedure from amine A3. 20% yield. $^1$HNMR (CDCl$_3$, 400 MHz): δ 10.56 (s, 1H, CHO), 7.59 (d, J=8.8 Hz, 1H, ArH), 6.86 (d, J=8.8 Hz, 1H, ArH), 3.66-3.63 (m, 2H, CH$_2$), 3.57-3.55 (m, 2H, CH$_2$), 3.30 (t, J=7.2 Hz, 2H, CH$_2$), 2.95 (t, J=7.2 Hz, 2H, CH$_2$), 2.45-2.44 (m, 2H, CH$_2$), 2.43-2.39 (m, 2H, CH$_2$), 2.31 (s, 3H, CH$_3$). MS [ESI, MH$^+$]: 318.2.

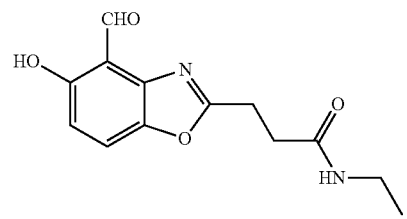 [SMILES: CCNC(=O)CCc1nc2c(C=O)c(O)ccc2o1]

N-Ethyl-3-(4-formyl-5-hydroxybenzo[d]oxazol-2-yl)propanamide was obtained by the above procedure from amine A4. 38.9% yield. $^1$HNMR (CDCl$_3$, 400 MHz): δ 10.56 (s, 1H, CHO), 7.77 (d, J=8.8 Hz, 1H, ArH), 6.93 (d, J=8.8 Hz, 1H, ArH), 3.32 (t, J=7.2 Hz, 2H, CH$_2$), 3.21 (q, J=7.2 Hz, 2H, CH$_2$), 2.81 (t, J=7.2 Hz, 2H, CH$_2$), 1.11 (t, J=7.2 Hz, 3H, CH$_3$). MS [ESI, MH$^+$]: 263.2.

3-(4-Formyl-5-hydroxybenzo[d]oxazol-2-yl)-N-(2-morpholinoethyl)propanamide was obtained by the above procedure from amine A5. 10.2% yield. $^1$HNMR (CDCl$_3$, 400 MHz): δ 11.24 (s, 1H, OH), 10.57 (s, 1H, CHO), 7.61 (d, J=8.8 Hz, 1H, ArH), 6.89 (d, J=8.8 Hz, 1H, ArH), 6.15 (br, 1H, NH), 3.70-3.67 (m, 4H, 2CH$_2$), 3.40-3.35 (m, 2H, CH$_2$), 3.31 (t, J=7.2 Hz, 2H, CH$_2$), 2.83 (t, J=7.2 Hz, 2H, CH$_2$), 2.48-2.43 (m, 6H, 3CH$_2$). MS [ESI, MH$^+$]: 348.2.

Example 79

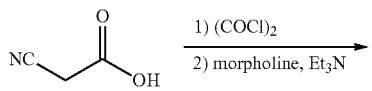

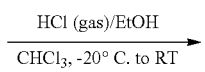

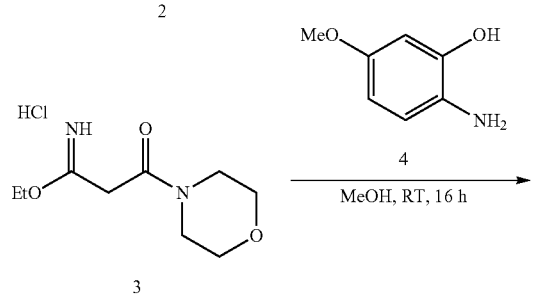

-continued

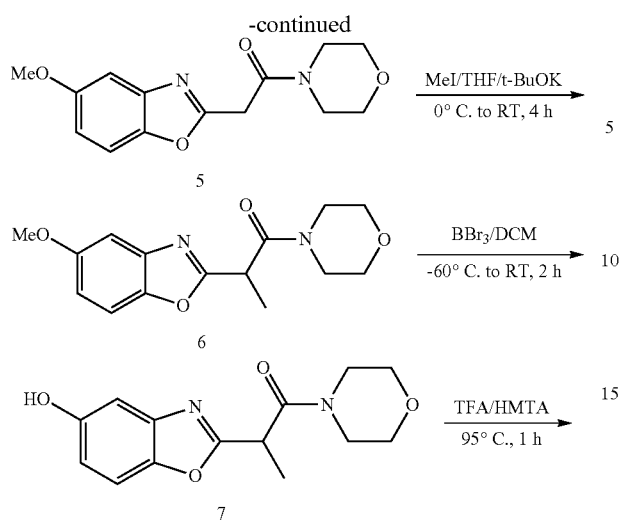

Synthesis of Compound 2

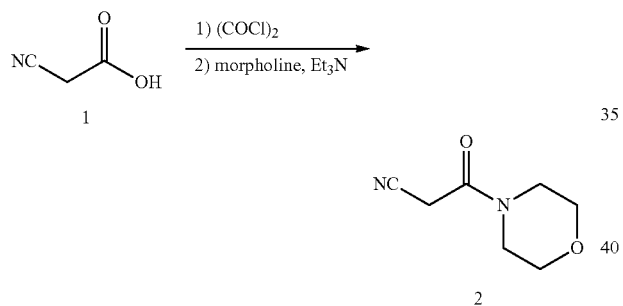

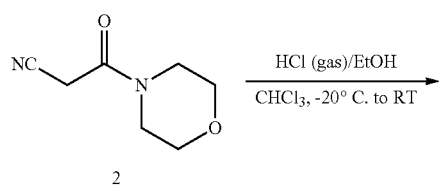

Compound 1 (25 g, 294.1 mmol) and DMF (0.5 mL) were suspended in DCM (250 mL). (COCl)₂ (41 g, 323.5 mmol) was added dropwise at 0° C. After that the reaction mixture was stirred at RT for 4 h. The reaction mixture was concentrate. The residue was dissolved in dry DCM (250 mL). The solution of acyl chloride was added dropwise to the solution morpholine (28.1 g, 323.5 mmol) and Et₃N (32.7 g, 323.5 mmol) in DCM (100 mL) at 0° C. Then the mixture was stirred at RT for 16 h and concentrated. The residue was purified by silica gel column (DCM:MeOH=20:1), afforded compound 2 (18.7 g, 41%) as white solid.

Synthesis of Compound 3

-continued

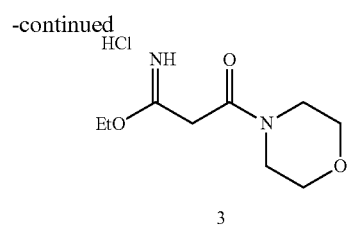

Compound 2 (18.5 g, 120.1 mmol) and EtOH (8.3 mmol) were added to CHCl₃ (120 mL), cooled to −20° C. HCl (gas) was bubble into the mixture for 1 h. Then the reaction mixture was stirred at RT for another 1.5 h. The solvent was removed under vacuum. The residue was washed with MTBE, afforded compound 3 (14.5 g, 51%) as white solid.

Synthesis of Compound 5

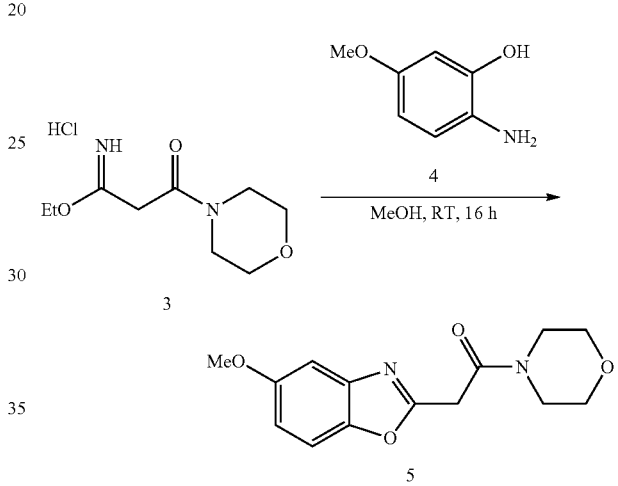

Compound 3 (12.2 g, 51.5 mmol) was dissolved in MeOH (105 mL), cooled to 0° C. The solution of compound 4 (6 g, 43.1 mmol) in MeOH (60 mL) was added dropwise. The reaction mixture was stirred at RT for 16 h. The reaction mixture was concentrated, purified by silica gel column (PE:EA=2:1), afforded compound 5 (8.7 g, 73.1%) as white solid.

Synthesis of Compound 6

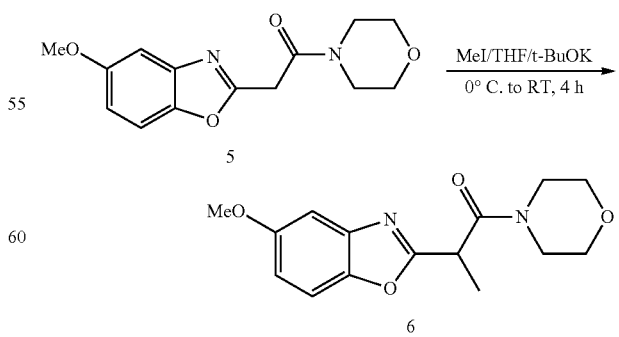

t-BuOK (4.2 g, 38.7 mmol) was suspended in THF (100 mL), cooled to 0° C. The solution of compound 5 (8.7 g, 32.2 mmol) in THF (75 mL) was added dropwise and stirred for 1 h. The solution of MeI (4.7 g, 33.8 mmol) in THF (25 mL) was added dropwise at 0° C., then stirred at RT for another 4 h. The reaction mixture was quenched with H2O, acidified by 2 N HCl to pH=4, extracted with EA, concentrated. The residue was purified by silica gel column (PE:EA=2:1), afforded compound 6 (7.3 g, 80.2%) as white solid.

Synthesis of Compound 7

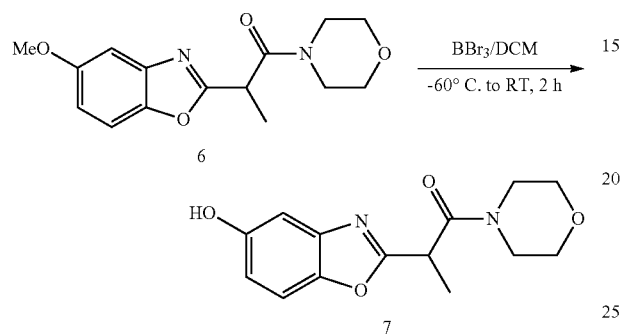

Compound 6 (5.8 g, 20 mmol) was dissolved in DCM (120 mL), cooled to −60° C. The solution of BBr$_3$ (30 g, 120 mmol) in DCM (40 mL) was added at −60° C. After that, the reaction mixture was stirred at RT for 1 h. Then the reaction was quenched with H2O, extracted with EA. The combined EA was dried over Na$_2$SO$_4$, filtered, concentrated. The residue was purified by silica gel column (PE:EA=1:2), afforded compound 7 (3.3 g, 47.8%) as white solid. $^1$HNMR (CDCl$_3$, 400 MHz): δ 7.28 (dd, J=8.8 Hz, 2.4 Hz, 1H, ArH), 7.16 (d, J=2.4 Hz, 1H, ArH), 6.82 (dd, J=8.8 Hz, 2.4 Hz, 1H, ArH), 4.30 (q, J=6.8 Hz, 1H, CH), 3.75-3.55 (m, 8H, 4CH$_2$), 1.70 (d, J=6.8 Hz, 3H, CH$_3$).

Synthesis of 5-hydroxy-2-(1-morpholino-1-oxopropan-2-yl)benzo[d]oxazole-4-carbaldehyde Compound 7 (1 g, 3.62 mmol) and HMTA (2.1 g, 14.5 mmol) were added to TFA (45 mL). The reaction mixture was heated to 95° C. for 1 h. The reaction mixture was concentrated. The residue was purified by prep-HPLC and prep-TLC successively, afforded 5-hydroxy-2-(1-morpholino-1-oxopropan-2-yl) benzo[d] oxazole-4-carbaldehyde (200 mg, 12.1%) as yellow solid. MS [ESI, MH$^+$]: 305.2.

Example 80

Compound 1 (100 g, 657 mmol) and NH$_2$OH.HCl (137 g, 1973 mmol) were added to EtOH (1.5 L). The reaction mixture was refluxed for 16 h. The reaction mixture was concentrated. The residue was recrystallized from DCM/PE (4:1), afforded compound 2 (95 g, 86.4% yield). $^1$HNMR (MeOD, 400 MHz): δ 6.88 (q, J=1.2 Hz, 1H, ArH), 6.688-6.682 (m, 2H), 2.25 (s, 3H).

Synthesis of Compound 3

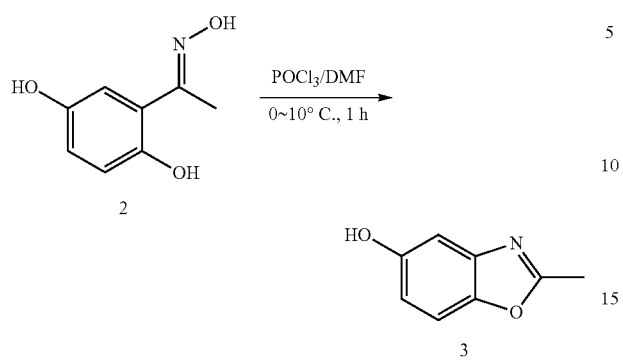

Compound 2 (20.0 g, 119.7 mmol) was dissolved in DMF (300 mL), cooled to 0° C. POCl$_3$ (20 g, 131.6 mmol) was added dropwise keeping the inner temperature below 10° C. Then the reaction mixture was stirred for another 1 h. H$_2$O (1 L) was added to the reaction mixture, extracted with EA (300 mL×3). The combined EA was concentrated. The residue was dissolved in MTBE (800 mL), washed with H$_2$O (200 mL×3). The organic layer was dried over Na$_2$SO$_4$, concentrated. The residue was washed with DCM/PE (4:1) (250 mL), afforded compound 3 (13.5 g, 75.6%). $^1$HNMR (MeOD, 400 MHz): δ 7.32 (d, J=8.8 Hz, 1H, ArH), 6.95 (s, 1H, ArH), 6.79 (d, J=8.8 Hz, 1H, ArH), 2.56 (s, 3H).

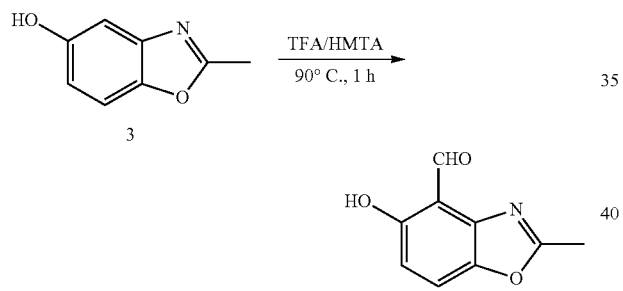

5-hydroxy-2-methylbenzo[d]oxazole-4-carbaldehyde 2: Compound 3 (1.5 g, 10.06 mmol) and HMTA (5.6 g, 40.0 mmol) were added to TFA (100 mL). The mixture was heated to 90° C. for 1 h. After cooled to RT, the reaction mixture was concentrated, purified by prep-HPLC and prep-TLC successively, afforded 5-hydroxy-2-methylbenzo[d]oxazole-4-carbaldehyde (20.0 mg, 1.1%) as yellow solid. $^1$HNMR (CDCl$_3$, 400 MHz): δ 11.27 (s, 1H, OH), 10.58 (s, 1H, CHO), 7.60 (d, J=8.8 Hz, 1H, ArH), 6.88 (d, J=8.8 Hz, 1H, ArH), 2.67 (s, 3H, CH$_3$). MS [ESI, MH$^+$]: 178.0.

Example 81

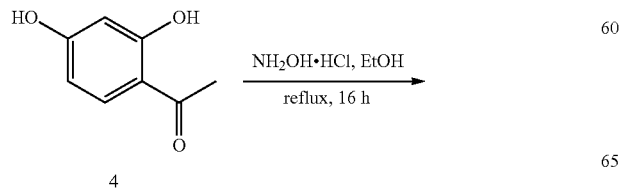

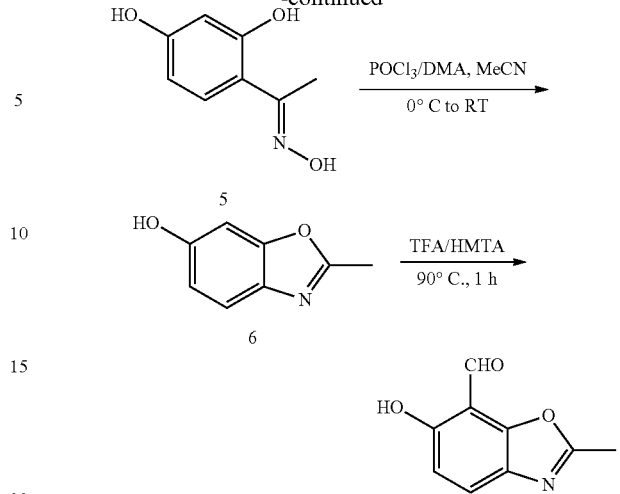

Synthesis of Compound 5

Compound 4 (33 g, 217 mmol) and NH$_2$OH.HCl (45.2 g, 650.3 mmol) were added to EtOH (500 mL). The reaction mixture was refluxed for 16 h. The reaction mixture was concentrated, purified by silica gel column (PE:EA=4:1), afforded compound 5 (5.2 g, 14.3%).

Synthesis of Compound 6

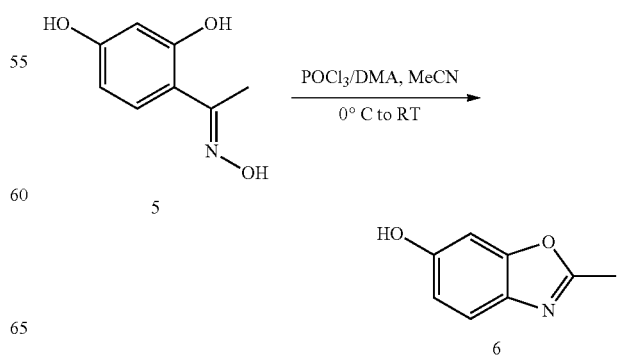

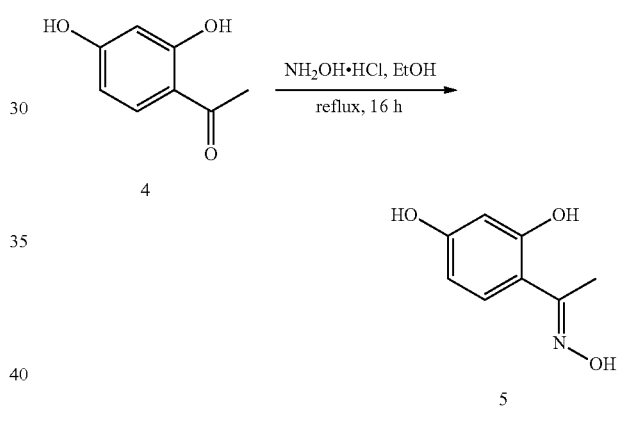

Compound 5 (5.2 g, 31.1 mmol) was dissolved in DMA/MeCN (6 mL/18 mL), cooled to 0° C. POCl₃ (5.2 g, 34.2 mmol) was added dropwise to keep the inner temperature below 10° C., then stirred at RT for 1 h. The reaction was monitored by TLC. The reaction mixture was poured into crush-ice (200 mL) containing NaOAc (7.5 g, 91.4 mmol), stirred for 5 min, then stand for 30 min. The precipitate was collected by filtration, dried, afforded compound 6 (2.9 g, 63%).

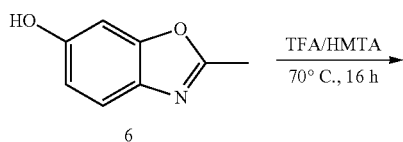

6-Hydroxy-2-methylbenzo[d]oxazole-7-carbaldehyde: Compound 6 (0.5 g, 3.3 mmol) and HMTA (1.88 g, 13.4 mmol) were added to TFA (40 mL). The mixture was heated to 70° C. for 16 h. After cooled to RT, the reaction mixture was concentrated, purified by prep-TLC, afforded 6-Hydroxy-2-methylbenzo[d]oxazole-7-carbaldehyde (40.0 mg, 6.7%) as yellow solid. ¹HNMR (CDCl₃, 400 MHz): δ 11.14 (s, 1H, OH), 10.41 (s, 1H, CHO), 7.77 (d, J=8.8 Hz, 1H, ArH), 6.91 (d, J=8.8 Hz, 1H, ArH), 2.66 (s, 3H, CH₃). MS [ESI, MH⁺]: 178.0.

Example 82

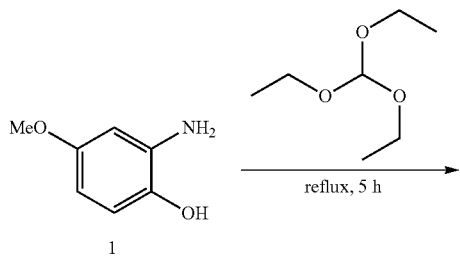

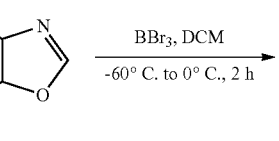

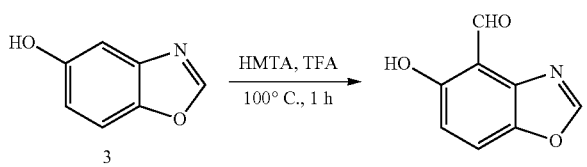

Synthesis of Compound 2

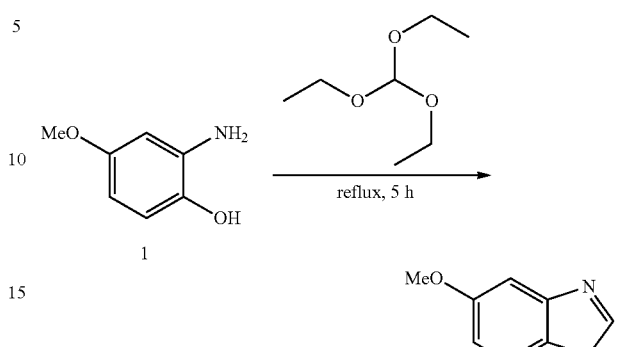

A mixture of compound 1 (3.0 g, 23.0 mmol) and triethyl orthoformate (50 mL) was refluxed for 5 h. After cooled to RT, triethyl orthoformate was removed under high vacuum. The residue was purified by silica gel column to give compound 2 (1.3 g, 38% yield) as white solid.

Synthesis of Compound 3

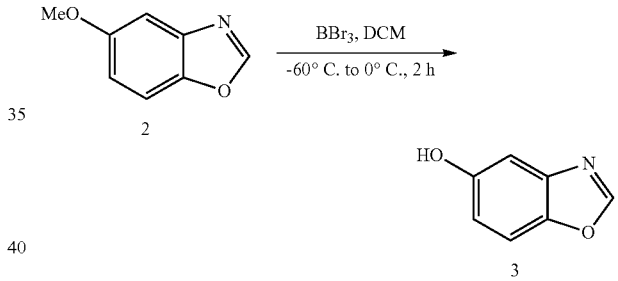

The solution of compound 2 (1.2 g, 8.0 mmol) in DCM (50 mL) was cooled to −60° C. The solution of BBr₃ (10.0 g, 40.0 mmol) in DCM (30 mL) was added dropwise keep temperature below −50° C. After stirred for another 2 h at RT, the reaction mixture was quenched with MeOH at −60° C. The reaction mixture was diluted with DCM (200 mL), and the solution was washed with sat.NaHCO₃, brine, dried over Na₂SO₄, concentrated to give compound 3 (0.6 g, 60% yield) as white solid. MS [ESI, MH⁺]: 136.2.

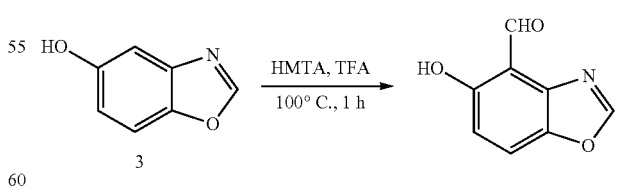

5-Hydroxybenzo[d]oxazole-4-carbaldehyde: A mixture of compound 3 (350 mg, 1.05 mmol) and HMTA (560 mg, 4 mmol) in AcOH (35 mL) was heated to 90° C. under N₂ for 1.5 h. The reaction was monitored by LCMS. After cooled to RT, the solvent was removed under vacuum. The residue was purified by prep-HPLC to give 5-hydroxybenzo[d]

oxazole-4-carbaldehyde (152 mg, 25% yield). ¹HNMR (DMSO, 400 MHz): δ 10.99 (s, 1H, OH), 10.53 (s, 1H, CHO), 8.86 (s, 1H, ArH), 8.00 (d, 1H, J=9.2 Hz, ArH), 7.05 (d, 1H, J=8.8 Hz, ArH). MS [ESI, MH⁺]: 164.1.

Example 83

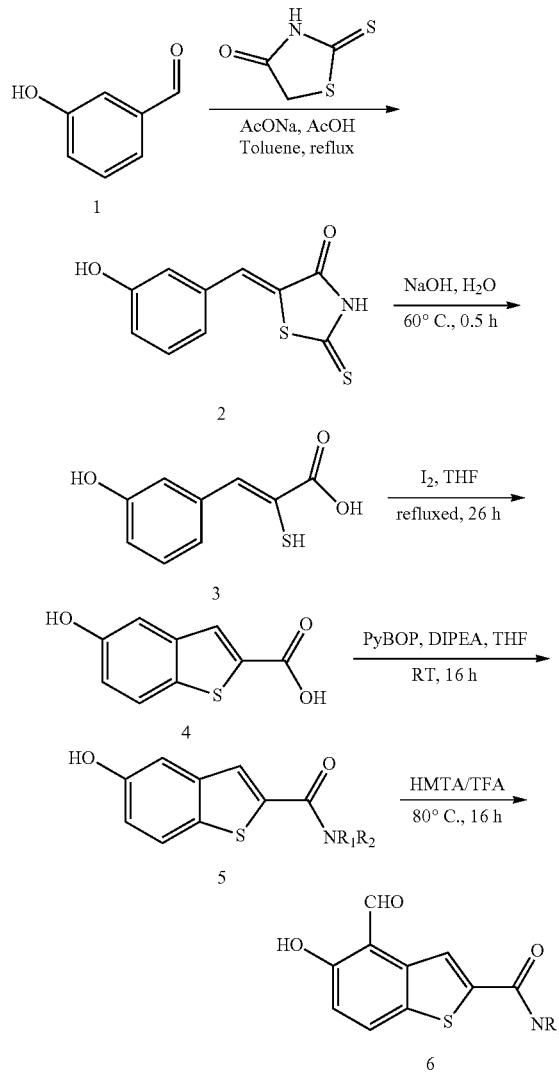

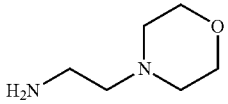
A5

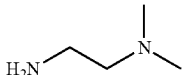
A6

Synthesis of Compound 2

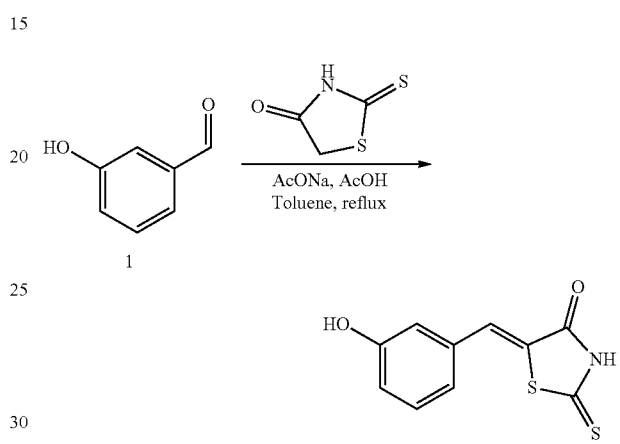

A stirred mixture of rhodanine (31 g, 232 mmol), sodium acetate (1.76 g, 21 mmol), compound 1 (28.2 g, 232 mmol), glacial acetic acid (5.3 mL) and toluene (300 mL) were heated to reflux for 4 hours in a round-bottomed flask equipped with a Dean and Stark water separator. During this time a total of 45 mL of water was collected and a yellow precipitate was resulted. After concentrating this mixture to approximately half of its volume, it was cooled to 5. The separated yellow solid was filtered and collected, afforded compound 2 (54.8 g, 100%), without further purification, go to next step directly.

Synthesis of Compound 3

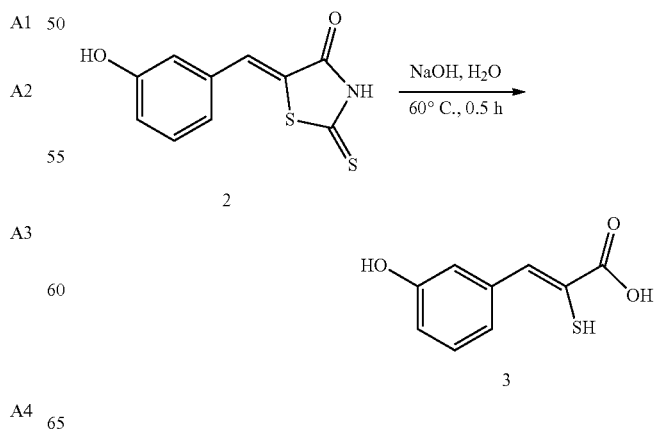

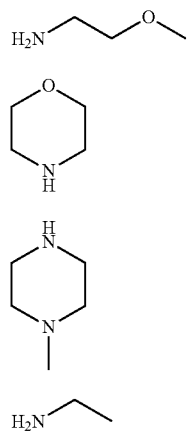

Compound 2 (54.8 g, 231 mmol) was dissolved in a solution of sodium hydroxide (46.2 g, 1155 mmol) in water (750 mL) and kept at 60-70° C. for 30 minutes. During the last 15 minutes, it was treated with charcoal and filtered. The filtrate was cooled to 5-10° C. and acidified under stirring by dropwise addition of concentrated HCl. The precipitated solid was collected, washed with water and dried in vacuum to give compound 3 (38.6 g, 85.7% yield) as yellow solid.

Synthesis of Compound 4

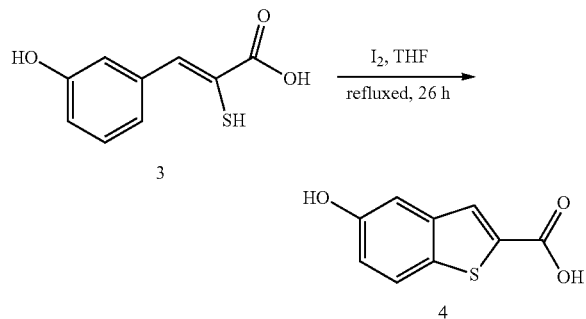

A stirred solution of compound 3 (38.6 g, 195.94 mmol) and iodine (62.5 g, 244.92 mmol) in dry THF was heated to reflux for 26 h. After removing almost of THF, the residue was poured into water. The pH was adjusted to 12 by progressively adding solid NaOH and the water phase was washed with EA for 3 times, then the water phase was acidified by conc.HCl to pH 2. The result precipitate was collected by filtration, washed by water, dried to give compound 4 (13.5 g, 35%) as light yellow solid.

Synthesis of Compound 5

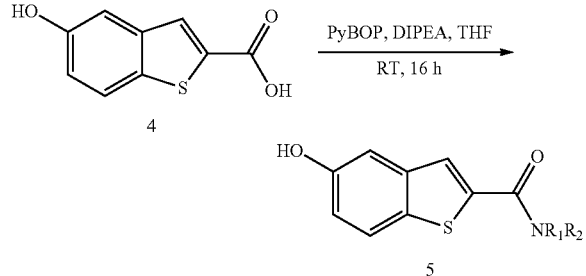

The mixture of compound 4 (1.0 eq), PyBOP (1.0 eq), amine (1.0 eq) and DIPEA (2.0 eq) were added to dry THF. The reaction mixture was stirred at RT for 16 h. The mixture was concentrated and purified by column chromatogram to give compound 5.

Synthesis of Compound 6

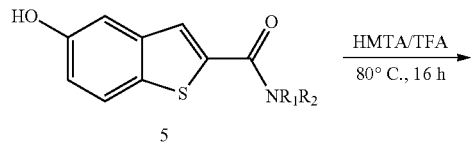

-continued

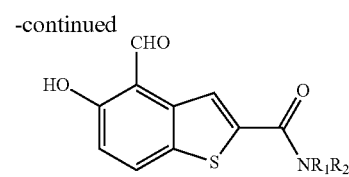

A mixture of compound 5 (1.0 eq) and HMTA (4.0 eq) in TFA was heated to 80° C. under nitrogen for 16 h. LC-MS indicated that the reaction was completed. After cooled to RT, the solvent was removed under vacuum. The residue was purified by prep-HPLC, afforded compound 6.

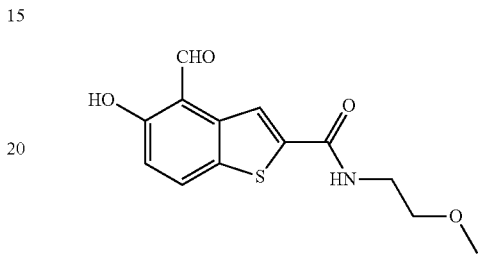

4-Formyl-5-hydroxy-N-(2-methoxyethyl)benzo[b]thiophene-2-carboxamide was obtained by the above procedure from amine A1. 10% yield. $^1$HNMR (DMSO, 400 MHz): δ 11.02 (s, 1H, OH), 10.56 (s, 1H, CHO), 9.00 (t, 1H, J=5.6 Hz, NH), 8.80 (d, 1H, J=0.4 Hz, ArH), 8.13 (dd, 1H, J=8.8, 0.4 Hz, ArH), 7.14 (d, 1H, J=8.8 Hz, ArH), 3.48-3.40 (m, 4H, CH$_2$), 3.28 (s, 3H, CH$_3$); MS [ESI, MH$^+$]: 280.1.

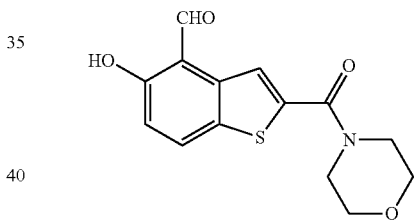

5-Hydroxy-2-(morpholine-4-carbonyl)benzo[b]thiophene-4-carbaldehyde was obtained by the above procedure from amine A2. 10% yield. $^1$HNMR (DMSO, 400 MHz): δ 11.15 (s, 1H, —OH), 10.56 (s, 1H, CHO), 8.34 (s, 1H, ArH), 8.16 (dd, 1H, J=9.2, 0.8 Hz) 7.14 (d, 1H, J=8.8 Hz, ArH), 3.64 (d, 8H, J=4.4 Hz, CH$_2$). MS [ESI, MH$^+$]: 292.1.

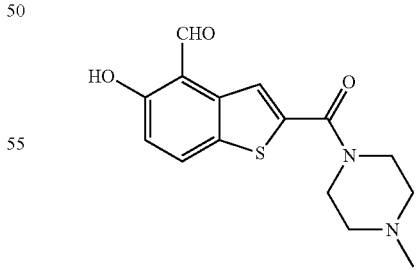

5-Hydroxy-2-(4-methylpiperazine-1-carbonyl)benzo[b]thiophene-4-carbaldehyde was obtained by the above procedure from amine A3. 10% yield. $^1$HNMR (DMSO, 400 MHz): δ 10.53 (s, 1H, CHO), 8.30 (s, 1H, ArH), 8.10 (d, 1H, J=8.8 Hz, ArH), 7.10 (d, 1H, J=8.8 Hz, ArH), 3.61 (t, 4H, J=4.4 Hz, CH$_2$), 2.32 (s, 4H, CH$_2$), 2.17 (s, 3H, CH$_3$). MS [ESI, MH$^+$]: 305.2.

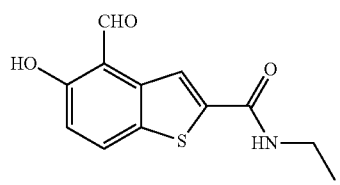

N-Ethyl-4-formyl-5-hydroxybenzo[b]thiophene-2-carboxamide was obtained by the above procedure from amine A4. 10% yield. $^1$HNMR (DMSO, 400 MHz): δ 11.00 (s, 1H, OH), 10.58 (s, 1H, CHO), 8.92 (t, 1H, J=5.6 Hz, NH), 8.77 (s, 1H, ArH), 8.12 (d, 1H, J=8.8 Hz, ArH), 7.14 (d, 1H, J=8.8 Hz, ArH), 3.29-3.24 (m, 2H, CH$_2$), 1.12 (t, 3H, J=7.2 Hz, CH$_3$). MS [ESI, MH$^+$]: 250.1.

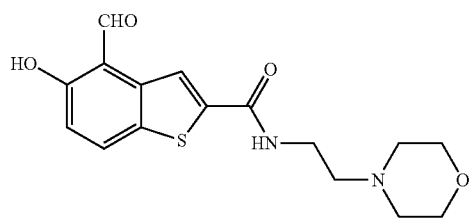

4-Formyl-5-hydroxy-N-(2-morpholinoethyl)benzo[b]thiophene-2-carboxamide was obtained by the above procedure from amine A5. 10% yield. $^1$HNMR (DMSO, 400 MHz): δ10.40 (s, 1H, CHO), 8.73-8.72 (m, 3H, ArH), 7.88 (d, 1H, J=9.2 Hz, ArH), 6.90 (d, 1H, J=9.2 Hz, ArH), 3.53 (t, 6H, J=4.4 Hz, CH$_2$), 2.38 (s, 6H, CH$_2$). MS [ESI, MH$^+$]: 335.2.

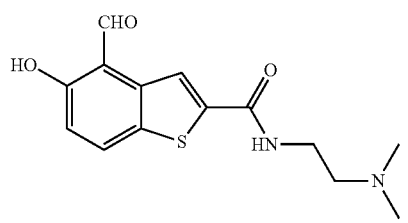 [SMILES: CN(C)CCNC(=O)c1cc2c(C=O)c(O)ccc2s1]

N-(2-(Dimethylamino)ethyl)-4-formyl-5-hydroxybenzo[b]thiophene-2-carboxamide was obtained by the above procedure from amine A6. 10% yield. $^1$HNMR (DMSO, 400 MHz): δ10.54 (s, 1H, CHO), 8.84 (t, 1H, J=5.6 Hz, NH), 8.75 (s, 3H, ArH), 8.09 (d, 1H, J=8.8 Hz, ArH), 7.12 (d, 1H, J=9.2 Hz, ArH), 3.35-3.30 (m, 2H, CH$_2$), 2.44-2.41 (m, 2H, CH$_2$), 2.18 (s, 6H, CH$_3$); MS [ESI, MH$^+$]: 293.2.

Example 84

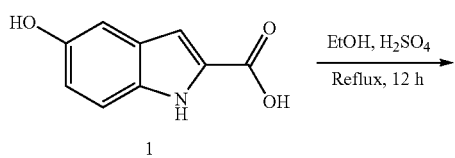

-continued

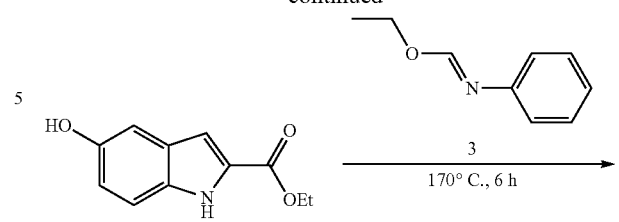

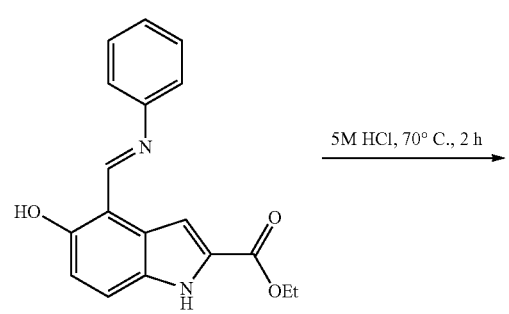

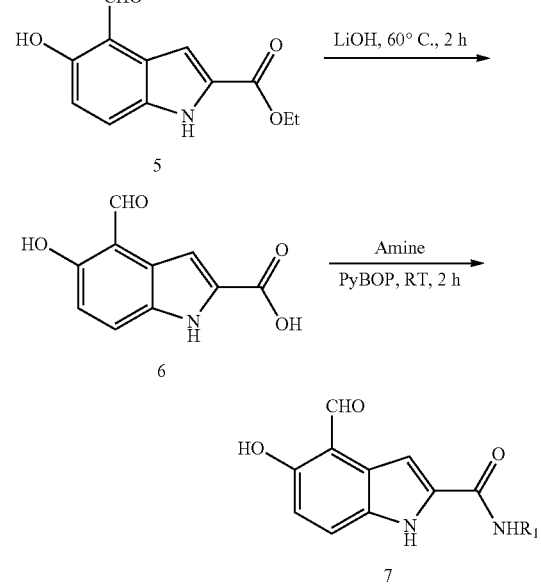

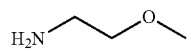 A1

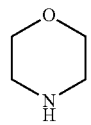 A2

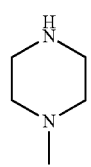 A3

 A4

-continued

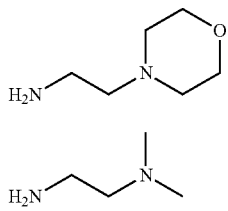

Synthesis of Compound 2

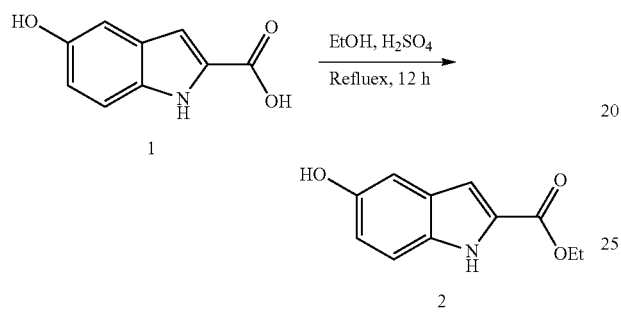

To the solution of compound 1 (5 g, 0.028 mol) in EtOH (250 mL) was added H₂SO₄ (0.5 mL). The mixture was heated to reflux for 12 h. After cooled to RT, the reaction mixture was concentrated and dissolved in DCM (100 mL). The DCM layer was washed with sat.NaHCO₃, dried over Na₂SO₄, concentrated to give compound 2 (5.0 g, 86% yield) as white solid.

Synthesis of Compound 4

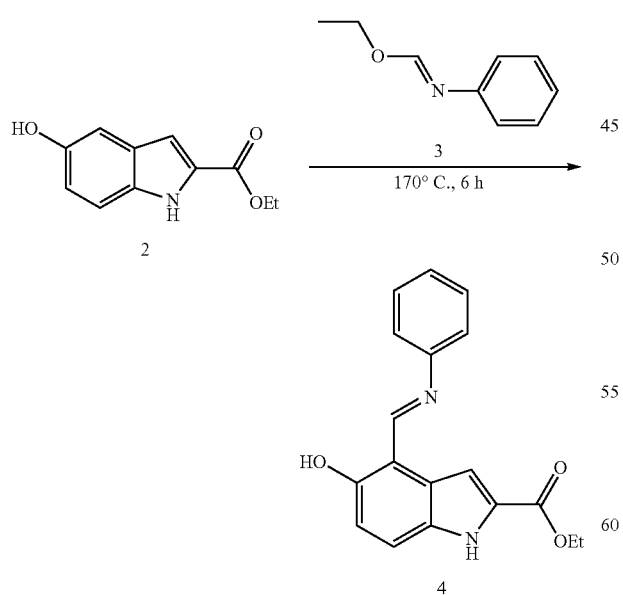

The mixture of compound 2 (5 g, 0.024 mol) and compound 3 (3.7 g, 0.024 mol) was heated to 160-180° C. under N₂ for 2 h. After cooled to RT, the reaction mixture was dissolved in MeOH (5 mL) at 70° C. Then the mixture was cooled to RT, the formed precipitate was filtered and washed with MeOH, dried to give compound 4 (3.0 g, 40% yield) as yellow solid.

Synthesis of Compound 5

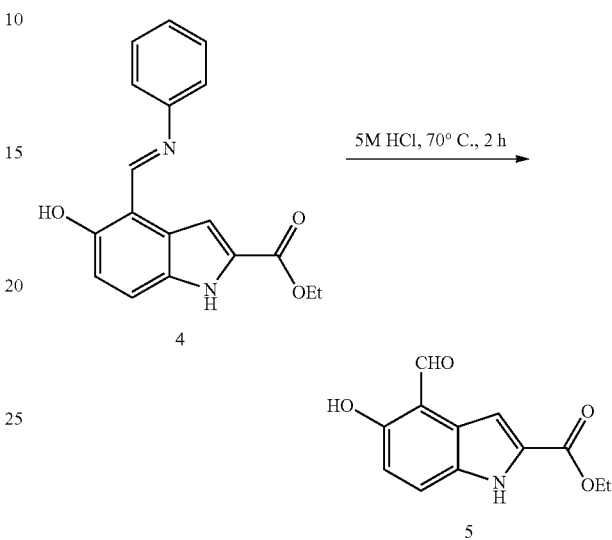

The suspension of compound 4 (3.0 g, 9.7 mmol) in 5M HCl (100 mL) was heated at 70° C. for 2 h. After cooled to RT, the reaction mixture was diluted with water (50 mL), the formed precipitate was filtered and washed with water, dried to give compound 5 (2.0 g, 90.5% yield). ¹H NMR (CDCl₃, 400 MHz): δ 11.72 (s, 1H, OH), δ 10.40 (s, 1H, CHO), 9.08 (br, 1H, NH), 7.58 (d, 1H, J=9.2 Hz, ArH), 7.44 (s, 1H, ArH), 6.97 (d, 1H, J=9.2 Hz, ArH), 4.41 (q, 2H, J=7.2 Hz, CH₂), 1.41 (t, 3H, J=7.2 Hz, CH₃).

Synthesis of Compound 6

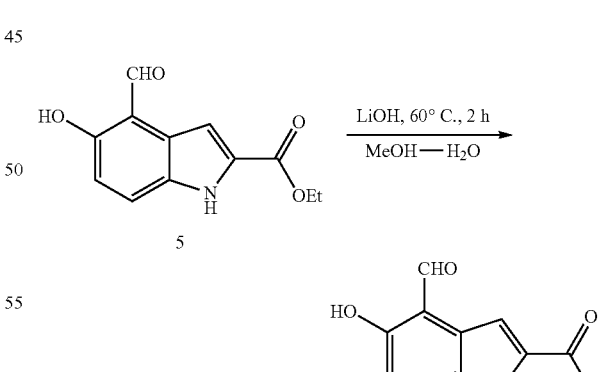

To the solution of compound 5 (2.0 g, 8.0 mmol) in MeOH (30 mL), the solution of LiOH—H₂O (0.5 g, 12.0 mmol) in H₂O (15 mL) was added. The mixture was heated to 60° C. for 2 h. After cooled to RT, the reaction mixture was concentrated, then acidified with 3 M HCl to pH=2. The formed precipitate was filtered and washed with water, dried to give compound 6 (1.6 g, 91.4% yield). MS [ESI, MH+]: 206.1.

Synthesis of Compound 7

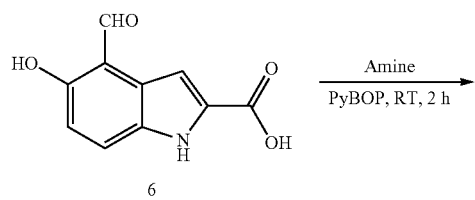
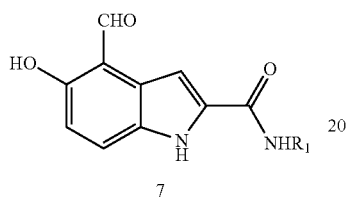

To the solution of compound 6 (1 eq), amine (1 eq) and PyBOP (1 eq) in DMF was added DIPEA (2 eq) dropwise at 0° C. Then the reaction mixture was stirred at RT overnight. LCMS showed that starting material was consumed completed, the reaction mixture was concentrated and purified by prep-HPLC to give compound 7.

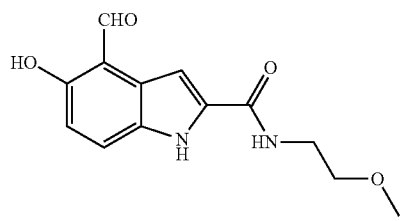 [SMILES: COCCNC(=O)c1cc2c(C=O)c(O)ccc2[nH]1]

4-Formyl-5-hydroxy-N-(2-methoxyethyl)-1H-indole-2-carboxamide was obtained by the above procedure from amine A1. 18% yield. $^1$H NMR (MeOD, 400 MHz): δ 10.45 (s, 1H, CHO), 7.60 (dd, 1H, J=0.8 Hz, J=8.8 Hz, ArH), 7.47 (d, 1H, J=1.2 Hz, ArH), 6.81 (d, 1H, J=9.2 Hz, ArH), 3.53 (m, 4H, 2CH$_2$), 3.34 (s, 3H, OCH$_3$);
MS [ESI, MH+]: 263.2.

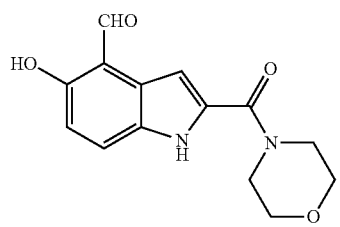

5-Hydroxy-2-(morpholine-4-carbonyl)-1H-indole-4-carbaldehyde was obtained by the above procedure from amine A2. 25% yield. $^1$HNMR (DMSO, 400 MHz): δ 11.80 (s, 1H, OH), 10.53 (s, 1H, CHO), 10.51 (s, 1H, NH), 7.59 (dd, 1H, J=0.8 Hz, J=8.8 Hz, ArH), 7.26 (dd, 1H, J=0.8 Hz, ArH), 6.87 (d, 1H, J=8.8 Hz, ArH), 3.73 (s, 4H, 2CH$_2$), 3.63 (m, 4H, 2CH$_2$). MS [ESI, MH+]: 275.2.

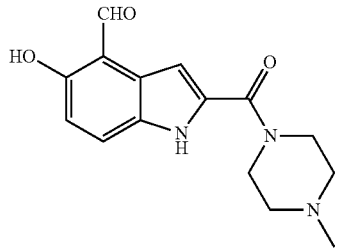 [SMILES: CN1CCN(C(=O)c2cc3c(C=O)c(O)ccc3[nH]2)CC1]

5-Hydroxy-2-(4-methylpiperazine-1-carbonyl)-1H-indole-4-carbaldehyde was obtained by the above procedure from amine A3. 23.6% yield. $^1$H NMR (D$_2$O, 400 MHz): δ 9.97 (s, 1H, CHO), 7.42 (d, 1H, J=9.2 Hz, ArH), 6.91 (s, 1H, ArH), 6.63 (d, 1H, J=9.2 Hz, ArH), 4.53 (d, 2H, J=14.8 Hz, CH$_2$), 3.55-3.41 (m, 4H), 3.09 (m, 2H, CH$_2$), 2.85 (s, 3H, NCH$_3$). MS [ESI, MH+]: 288.2.

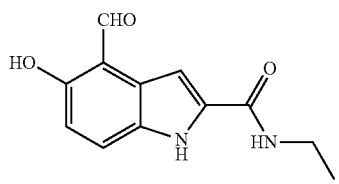 [SMILES: CCNC(=O)c1cc2c(C=O)c(O)ccc2[nH]1]

N-Ethyl-4-formyl-5-hydroxy-1H-indole-2-carboxamide was obtained by the above procedure from amine A4. 30% yield. $^1$H NMR (DMSO, 400 MHz): δ 11.68 (s, 1H, OH), δ 10.50 (s, 1H, CHO), δ 10.32 (s, 1H, NH), 8.56 (br, 1H, NH), 7.62 (d, 1H, J=1.6 Hz, ArH), 7.54 (d, 1H, J=4.8 Hz, ArH), 6.83 (d, 1H, J=4.8 Hz, ArH), 3.24 (m, 2H, CH$_2$), 1.09 (t, 3H, J=7.2 Hz, CH$_3$). MS [ESI, MH+]: 233.2.

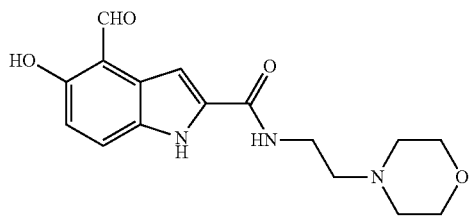 [SMILES: O=Cc1c(O)ccc2[nH]c(C(=O)NCCN3CCOCC3)cc12]

4-Formyl-5-hydroxy-N-(2-morpholinoethyl)-1H-indole-2-carboxamide was obtained by the above procedure from amine A5. 22% yield. $^1$H NMR (D$_2$O, 400 MHz): δ 9.93 (s, 1H, CHO), 7.37 (d, 1H, J=8.8 Hz, ArH), 6.96 (s, 1H, ArH), 6.63 (d, 1H, J=8.8 Hz, ArH), 4.03 (d, 2H, CH$_2$), 3.78-3.67 (m, 4H, 2CH$_2$), 3.56 (d, 2H, J=12.4 Hz, CH$_2$), 3.35 (t, 2H, J=6.0 Hz, CH$_2$), 3.17 (t, 2H, J=11.2 Hz, CH$_2$). MS [ESI, MH+]: 318.3.

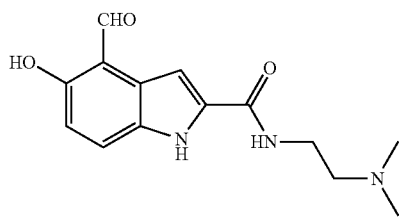

N-(2-(Dimethylamino)ethyl)-4-formyl-5-hydroxy-1H-indole-2-carboxamide was obtained by the above procedure from amine A6. 25% yield. $^1$H NMR (MeOD, 400 MHz): δ

10.49 (s, 1H, CHO), 7.64 (d, 1H, J=8.8 Hz, ArH), 7.52 (s, 1H, ArH), 6.85 (d, 1H, J=8.8 Hz, ArH), 3.55 (t, 2H, J=6.4 Hz, CH$_2$), 2.64 (t, 2H, J=6.4 Hz, CH$_2$), 2.36 (s, 6H, 2NCH$_3$). MS [ESI, MH$^+$]: 276.2.

Example 85

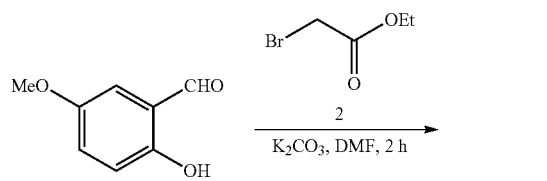
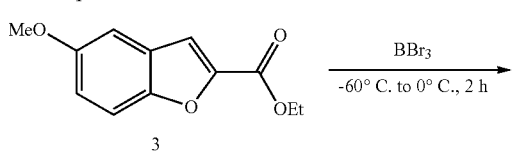
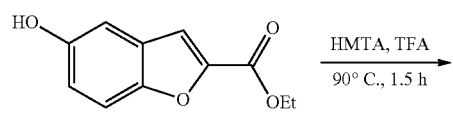
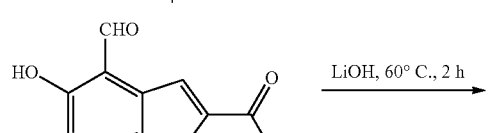
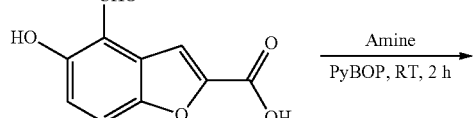
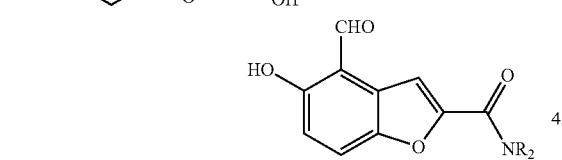

A1
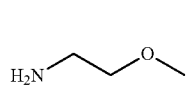

A2
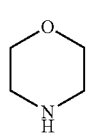

A3
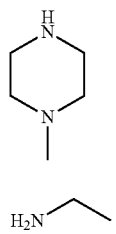

A4

A5
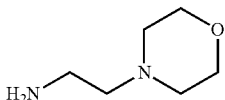

A6
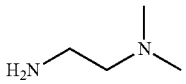

Synthesis of Compound 3

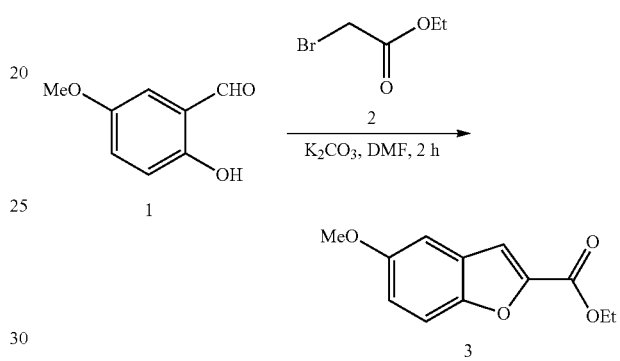

The mixture of compound 1 (15.2 g, 0.1 mol), compound 2 (16.6 g, 0.1 mol) and K$_2$CO$_3$ (27.6 g, 0.2 mol) in DMF (150 mL) was heated to reflux under N$_2$ for 2 h. After cooled to RT, the reaction mixture was concentrated and dissolved in DCM (100 mL), the solution washed with sat.NaHCO$_3$, brine, dried over Na$_2$SO$_4$, concentrated. The residue was purified by silica gel column to give compound 3 (11.8 g, 62% yield) as white solid.

Synthesis of Compound 4

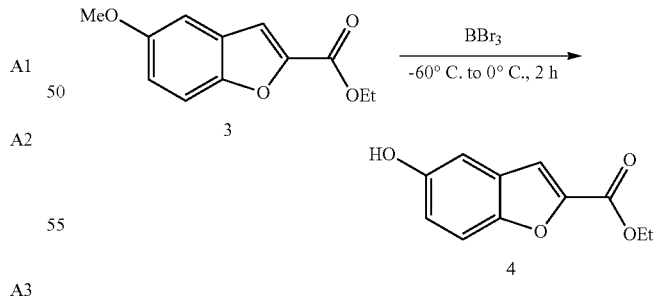

The solution of BBr$_3$ (40 g, 160.0 mmol) in DCM (100 mL) was added dropwise to the solution of compound 3 (9 g, 40.9 mmol) in DCM (300 mL) at −60° C. After that the reaction mixture was warmed slowly to 0° C. and stirred for another 1 h. The reaction mixture was quenched with EtOH (10 ml) slowly at −60° C. The reaction mixture was washed with water, brine, dried over Na$_2$SO$_4$, concentrated to give compound 4 (8.8 g, 100% yield). MS [ESI, MH$^+$]: 206.1.

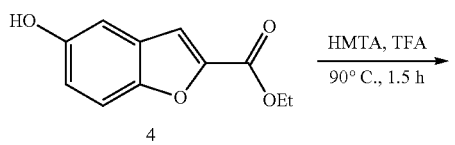

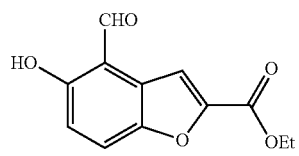

Ethyl 4-formyl-5-hydroxybenzofuran-2-carboxylate: The mixture of compound 4 (5.0 g, 24.3 mmol), and HMTA (13.5 g, 97.0 mmol) in TFA (500 mL) was heated to 100° C. under N₂ for 2 h. The reaction was monitored by LCMS. The reaction mixture was concentrated, diluted with H₂O (20 mL) and stirred for 30 min. The formed precipitate was filtered, washed with water, dried to give MNKD-227(3.0 g, 53.5% yield). ¹HNMR (CDCl₃, 400 MHz): δ 11.45 (s, 1H, OH), 10.26 (d, 1H, J=0.4 Hz, CHO), 7.72 (s, 1H, ArH), 7.68 (d, 1H, J=9.2 Hz, ArH), 7.02 (d, 1H, J=9.2 Hz, ArH), 4.40 (q, 2H, J=7.2 Hz, CH₂), 1.37 (t, 3H, J=7.2 Hz, CH₃). MS [ESI, MH⁺]: 235.1.

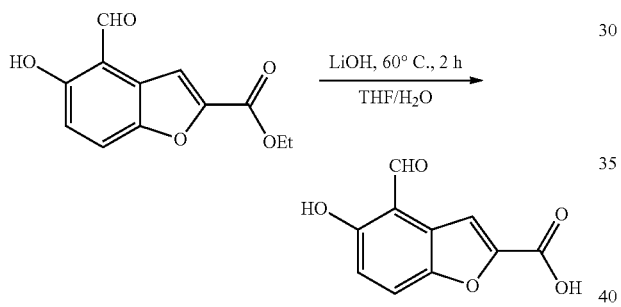

4-Formyl-5-hydroxybenzofuran-2-carboxylic acid: The solution of LiOH—H₂O (1.26 g, 60 mmol) in H₂O (15 mL) was added dropwise to the solution of ethyl 4-formyl-5-hydroxybenzofuran-2-carboxylate (4.6 g, 20 mmol) in THF (40 mL). The reaction mixture was heated to 50° C. for 2 h. After cooled to RT, the reaction mixture was concentrated, then acidified with 3 M HCl to pH=2. The formed precipitate was filtered and washed with water, dried to give 4-formyl-5-hydroxybenzofuran-2-carboxylic acid (4.1 g. 87.8% yield). ¹HNMR (DMSO, 400 MHz): δ 10.91 (s, 1H, OH), 10.47 (s, 1H, CHO), 7.92 (d, 1H, J=0.8 Hz, ArH), 7.87 (dd, 1H, J=9.2 Hz, 0.8 Hz, ArH), 7.13 (d, 1H, J=9.2 Hz, ArH); MS [ESI, MH⁺]: 207.1.

Synthesis of Compound 5

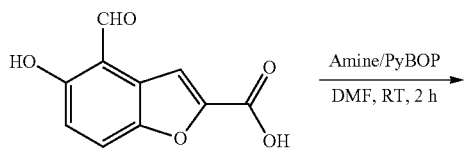

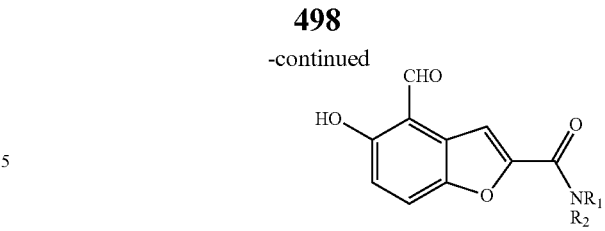

To the solution of 4-formyl-5-hydroxybenzofuran-2-carboxylic acid (1 eq), amine (1 eq) and PyBOP (1 eq) in DMF was added DIPEA (2 eq) dropwise keeping the inner temperature below 10° C. The reaction mixture was stirred at RT for 2 h. The reaction was monitored by LCMS. The reaction mixture was concentrated and purified by prep-HPLC to give compound 5.

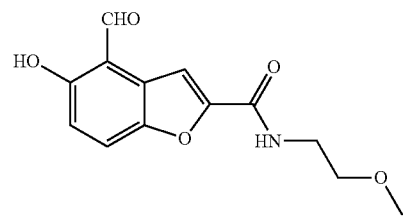

4-Formyl-5-hydroxy-N-(2-methoxyethyl)benzofuran-2-carboxamide was obtained by the above procedure from amine A1. 17.6% yield. ¹HNMR (DMSO, 400 MHz): δ 10.80 (s, 1H, OH), 10.47 (s, 1H, CHO), 8.77 (t, 1H, J=5.2 Hz, NH), 7.96 (d, 1H, J=0.8 Hz, ArH), 7.81 (dd, 1H, J=8.8 Hz, 0.8 Hz, ArH), 7.06 (d, 1H, J=8.8 Hz, ArH), 3.41 (m, 4H, 2CH₂), 3.24 (s, 3H, OCH₃). MS [ESI, MH⁺]: 264.1.

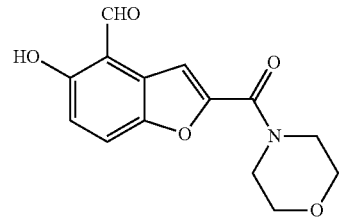

5-Hydroxy-2-(morpholine-4-carbonyl)benzofuran-4-carbaldehyde was obtained by the above procedure from amine A2. 21.7% yield. ¹HNMR (CDCl3, 400 MHz): δ 11.48 (s, 1H, OH), 10.31 (s, 1H, CHO), 7.65 (d, 1H, J=1.2 Hz, ArH), 7.03 (d, 1H, J=9.2 Hz, ArH), 3.87-3.78 (m, 8H); MS [ESI, MH⁺]: 276.2.

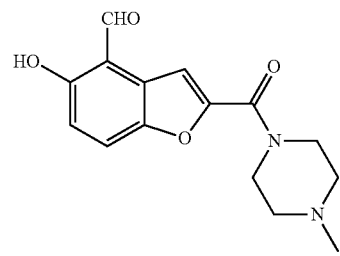 [SMILES: CN1CCN(C(=O)c2cc3c(C=O)c(O)ccc3o2)CC1]

5-Hydroxy-2-(4-methylpiperazine-1-carbonyl)benzofuran-4-carbaldehyde was obtained by the above procedure from amine A3. 30% yield. ¹HNMR (MeOD, 400 MHz): δ 7.63 (s, 1H, ArH), 7.41 (d, 1H, J=9.2 Hz, ArH), 6.97 (dd, 1H, J=8.8 Hz, 0.8 Hz, ArH), 5.87 (d, 1H, J=0.8 Hz, NH), 4.79 (d. 2H, J=14.8 Hz, CH$_2$), 3.63-3.48 (m, 4H, 2CH$_2$), 3.25-3.22 (m. 2H, CH$_2$), 2.96 (s, 3H, CH$_3$); MS [ESI, MH$^+$]: 289.2.

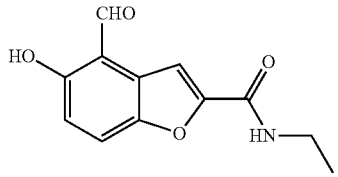

N-Ethyl-4-formyl-5-hydroxybenzofuran-2-carboxamide was obtained by the above procedure from amine A4. 18.7% yield. $^1$HNMR (DMSO, 400 MHz): δ 10.80 (s, 1H, OH), 10.47 (s, 1H, CHO), 8.77 (t, 1H, J=5.2 Hz, NH), 7.94 (s, 1H, ArH), 7.80 (dd, 1H, J=8.8 Hz, 0.8 Hz, ArH), 7.08 (d, 1H, J=8.8 Hz, ArH), 3.26 (m, 2H, CH$_2$), 1.10 (t, 3H, J=7.2 Hz, CH$_3$); MS [ESI, MH$^+$]: 234.2.

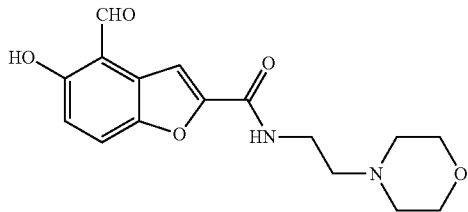

4-Formyl-5-hydroxy-N-(2-morpholinoethyl)benzofuran-2-carboxamide was obtained by the above procedure from amine A5. 21.7% yield. $^1$HNMR (MeOD, 400 MHz): δ 7.72 (d, 1H, J=1.2 Hz, ArH), 7.40 (dd, 1H, J=8.8 Hz, 1.2 Hz, ArH), 6.97 (d, 1H, J=8.8 Hz, ArH), 5.87 (s, 1H, NH), 4.08 (m. 2H, CH$_2$), 3.80 (t, 4H, J=5.6 Hz, 2CH$_2$), 3.68 (d. 2H, J=12.0 Hz, CH$_2$), 3.25-3.17 (m, 2H, CH$_2$); MS [ESI, MH$^+$]: 319.2.

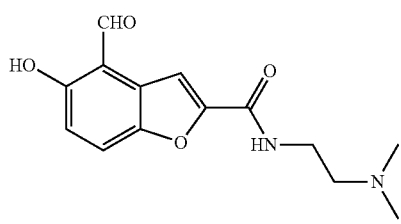

N-(2-(dimethylamino)ethyl)-4-formyl-5-hydroxybenzofuran-2-carboxamide was obtained by the above procedure from amine A6. 25% yield. $^1$HNMR (DMSO, 400 MHz): δ 10.89 (s, 1H, OH), 10.48 (s, 1H, CHO), 9.41 (br, 1H, NH), 8.97 (br, 1H, NH), 7.98 (s, 1H, ArH), 7.84 (d, 1H, J=8.8 Hz, ArH), 7.12 (d, 1H, J=9.2 Hz, ArH), 3.59 (d, 2H, J=6.4 Hz, CH$_2$), 3.24 (s, 2H, CH$_2$), 2.81 (s, 6H, 2CH$_3$); MS [ESI, MH$^+$]: 277.2.

---

The invention claimed is:

1. A compound, wherein the compound directly inhibits IRE-1α activity in vitro and is represented by structural formula (A-1):

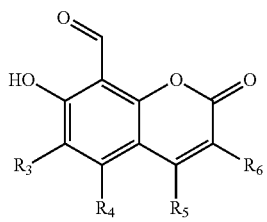

(A-1)

or a pharmaceutically acceptable salt thereof,
wherein

R3 is hydrogen, halogen; alkoxyl or alkylamino, wherein the alkoxyl and alkylamino is each optionally substituted with (1) a $C_1$-$C_6$ hydrocarbon chain containing an N or O atom and optionally substituted with a $C_1$-$C_3$ perfluoroalkyl, or (2) a cycloalkyl which optionally contains 1 or 2 heteroatoms selected from N, O, and S, and which is optionally substituted with a $C_1$-$C_3$ perfluoroalkyl;

R4 is hydrogen; halogen; alkyl, alkoxyl, or alkylamino, wherein the alkyl, alkoxyl and alkylamino is each optionally substituted with (1) a $C_1$-$C_6$ hydrocarbon chain containing an N or O atom and optionally substituted with a $C_1$-$C_3$ perfluoroalkyl, or (2) a cycloalkyl which optionally contains 1 or 2 heteroatoms selected from N, O, and S, and which is optionally substituted with a $C_1$-$C_3$ perfluoroalkyl;

R5 is hydrogen; halogen; —CN; an optionally substituted alkyl; or an optionally substituted alkoxyl and optional substituents for the alkyl and for the alkoxyl are (1) a $C_1$-$C_6$ hydrocarbon chain containing an N or O atom and optionally substituted with a $C_1$-$C_3$ perfluoroalkyl, and (2) a cycloalkyl which optionally contains 1 or 2 heteroatoms selected from N, O, and S, and which is optionally substituted with a $C_1$-$C_3$ perfluoroalkyl;

R6 is

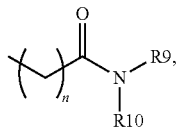

wherein n is 0, 1, or 2;

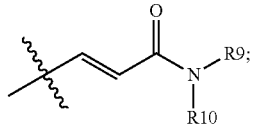

or alkyl, which is substituted with 1, 2 or 3 substituents independently selected from the group consisting of

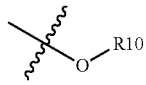

R9 and R10 are independently hydrogen; alkyl; alkoxylalkyl; perfluoroalkoxylalkyl; aryl, optionally substituted with 1, 2, or 3 substituents independently selected from members of R21; a 5- or 6-membered heterocycle, optionally substituted with 1, 2, or 3 substituents independently selected from members of R21; a 5- or 6-membered heteroaryl, optionally substituted with 1, 2, or 3 substituents independently selected from members of R21; or

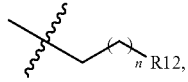

wherein n is 0, 1, 2, or 3; or

R9 and R10, together with the nitrogen atom to which they are attached, form a heterocycle containing 1, 2, 3, or 4 heteroatoms selected from N, O, and S, optionally substituted with 1, 2, or 3 substituents selected independently from members of R11;

R11 is hydrogen; alkyl; aryl; heteroaryl containing 1 or 2 heteroatoms selected from N, O, and S; arylalkyl; heteroarylalkyl in which the heteroaryl contains 1 or 2 heteroatoms selected from N, O, and S;

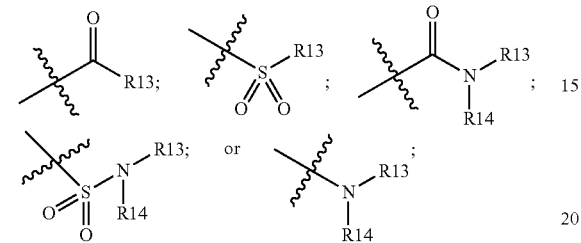

R12 is amino; alkoxy; aryl, optionally substituted with 1, 2, or 3 substituents selected independently from members of R11; a 5- or 6-membered heterocycle having 1, 2, or 3 heteroatoms selected from N, O, and S and optionally substituted with 1, 2, or 3 substituents selected independently from members of R11; or a 5- or 6-membered heteroaryl having 1, 2, or 3 heteroatoms selected from N, O, and S and optionally substituted with 1, 2, or 3 substituents selected independently from members of R11;

R13 is alkyl; alkoxylalkyl; perfluoroalkoxylalkyl; aryl, optionally substituted with 1, 2, or 3 substituents independently selected from members of R21; a 5- or 6-membered heterocycle, optionally substituted with 1, 2, or 3 substituents independently selected from members of R21; a 5- or 6-membered heteroaryl, optionally substituted with 1, 2, or 3 substituents independently selected from members of R21; or

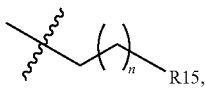

wherein n is 0, 1, 2, or 3; and R14 is hydrogen or R13; or

R13 and R14, together with the nitrogen to which they are attached, form a heterocycle containing 1, 2, or 3 heteroatoms selected independently from N, O, and S, optionally substituted with 1, 2, or 3 substituents selected independently from R16;

R15 is amino; alkoxy; aryl, optionally substituted with 1, 2, or 3 substituents selected independently from members of R21; a 5- or 6-membered heterocycle having 1, 2, or 3 heteroatoms selected from N, O, and S and optionally substituted with 1, 2, or 3 substituents selected from members of R21; or a 5- or 6-membered heteroaryl having 1, 2, or 3 heteroatoms selected from N, O, and S and optionally substituted with 1, 2, or 3 substituents selected from members of R21;

R16 is hydrogen; alkyl; aryl; heteroaryl containing 1 or 2 heteroatoms selected from N, O, and S; arylalkyl; heteroarylalkyl in which the heteroaryl contains 1 or 2 heteroatoms selected from N, O, and S;

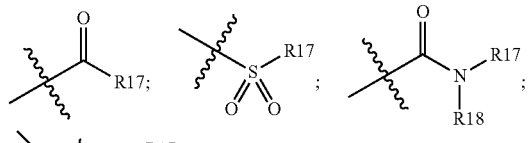

amino; or

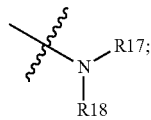

R17 is alkyl; alkoxylalkyl; perfluoroalkoxylalkyl; aryl, optionally substituted with 1, 2, or 3 substituents independently selected from members of R21; a 5- or 6-membered heterocycle, optionally substituted with 1, 2, or 3 substituents independently selected from members of R21; a 5- or 6-membered heteroaryl, optionally substituted with 1, 2, or 3 substituents independently selected from members of R21; or

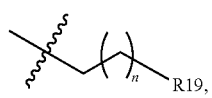

wherein n is 0, 1, 2, or 3; and R18 is hydrogen or R17; or

R17 and R18, together with the nitrogen to which they are attached, form a heterocycle containing 1, 2, 3, or 4 heteroatoms selected independently from N, O, and S, optionally substituted with 1, 2, or 3 substituents selected independently from members of R20;

R19 is alkoxy; aryl, optionally substituted with 1, 2, or 3 substituents selected independently from members of R21; a 5- or 6-membered heterocycle, optionally substituted with 1, 2, or 3 substituents independently selected from members of R21; or a 5- or 6-membered heteroaryl, optionally substituted with 1, 2, or 3 substituents independently selected from members of R21;

R20 is a 5- or 6-membered heterocycle having 1 or 2 heteroatoms selected from N, O, and S and optionally substituted with 1, 2, or 3 substituents selected independently from members of R21; a 5- or 6-membered heteroaryl, optionally substituted with 1, 2, or 3 substituents independently selected from members of R21; or R21; and R21 is perfluoroalkyl, perfluoroalkoxy, —CN, —CONH$_2$, —CON(CH$_3$)$_2$, alkyl, hydroxylalkyl, or alkoxylalkyl.

2. The compound or the pharmaceutically acceptable salt thereof of claim 1, wherein R3 is hydrogen; or alkoxyl, optionally substituted with (1) a C$_1$-C$_6$ hydrocarbon chain containing an N or O atom, or (2) a cycloalkyl which optionally contains 1 or 2 heteroatoms selected from N, and O.

3. The compound or the pharmaceutically acceptable salt thereof of claim 1, wherein R4 is hydrogen; or alkoxyl, optionally substituted with a C$_1$-C$_6$ hydrocarbon chain containing an N or O atom.

4. The compound or the pharmaceutically acceptable salt thereof of claim 1, wherein R5 is optionally substituted alkyl and optional substituents for the alkyl is a $C_1$-$C_6$ hydrocarbon chain containing an N or O atom.

5. The compound or the pharmaceutically acceptable salt thereof of claim 4, wherein the alkyl is methyl.

6. The compound or the pharmaceutically acceptable salt thereof of claim 1, wherein R6 is

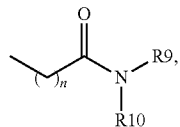

wherein n is 0, 1, or 2;

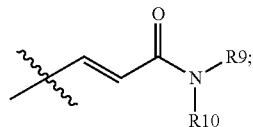

or alkyl independently substituted with 1, 2 or 3 of

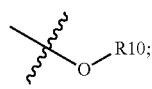

R9 and R10 are independently hydrogen; alkyl; or

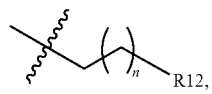

wherein n is 0, 1, 2, or 3; or

R9 and R10, together with the nitrogen atom to which they are attached, form a 6-membered heterocycle containing 1 or 2 heteroatoms selected from N and O, optionally substituted with 1, 2, or 3 substituents selected independently from alkyl; and R12 is alkoxy; or a 6-membered heterocycle having 1 or 2 heteroatoms selected from N and O, and optionally substituted with 1, 2, or 3 substituents selected independently from alkyl.

7. A compound selected from the group consisting of:

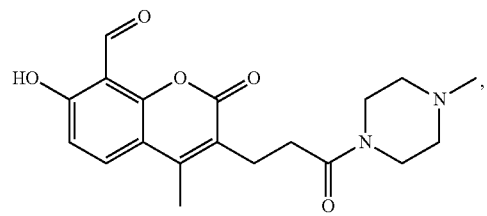

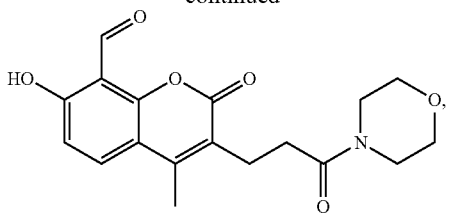

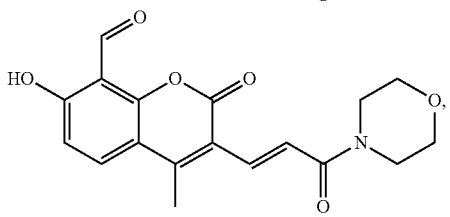

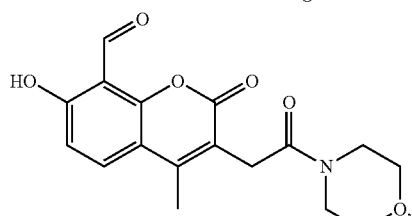

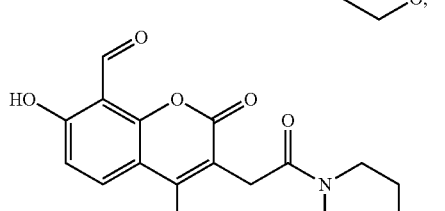

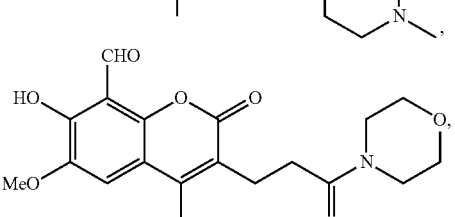

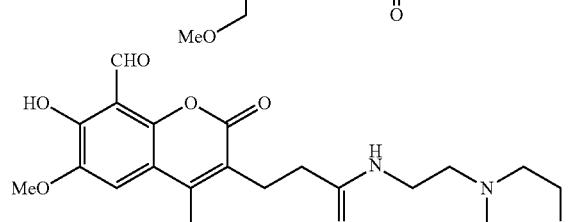

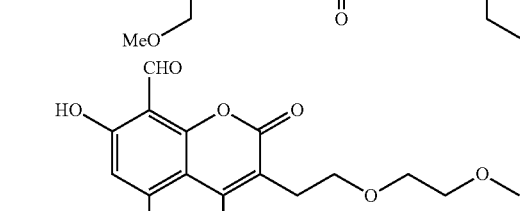

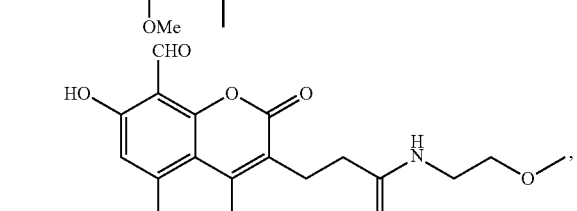

507
-continued
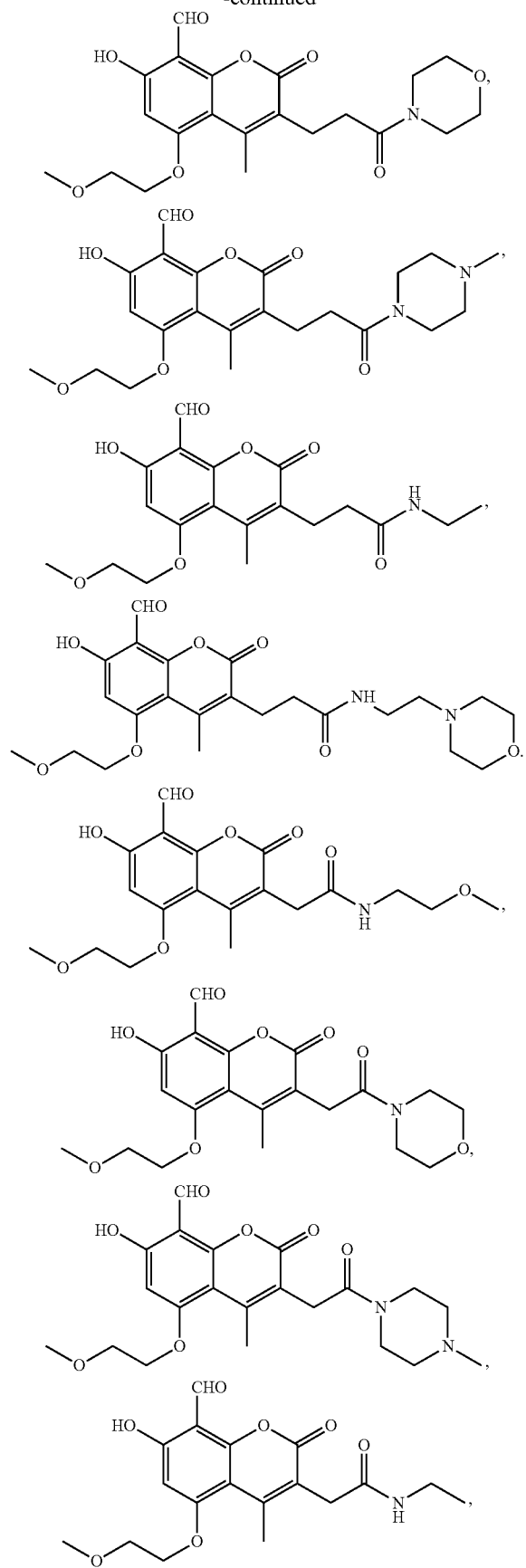
508
-continued
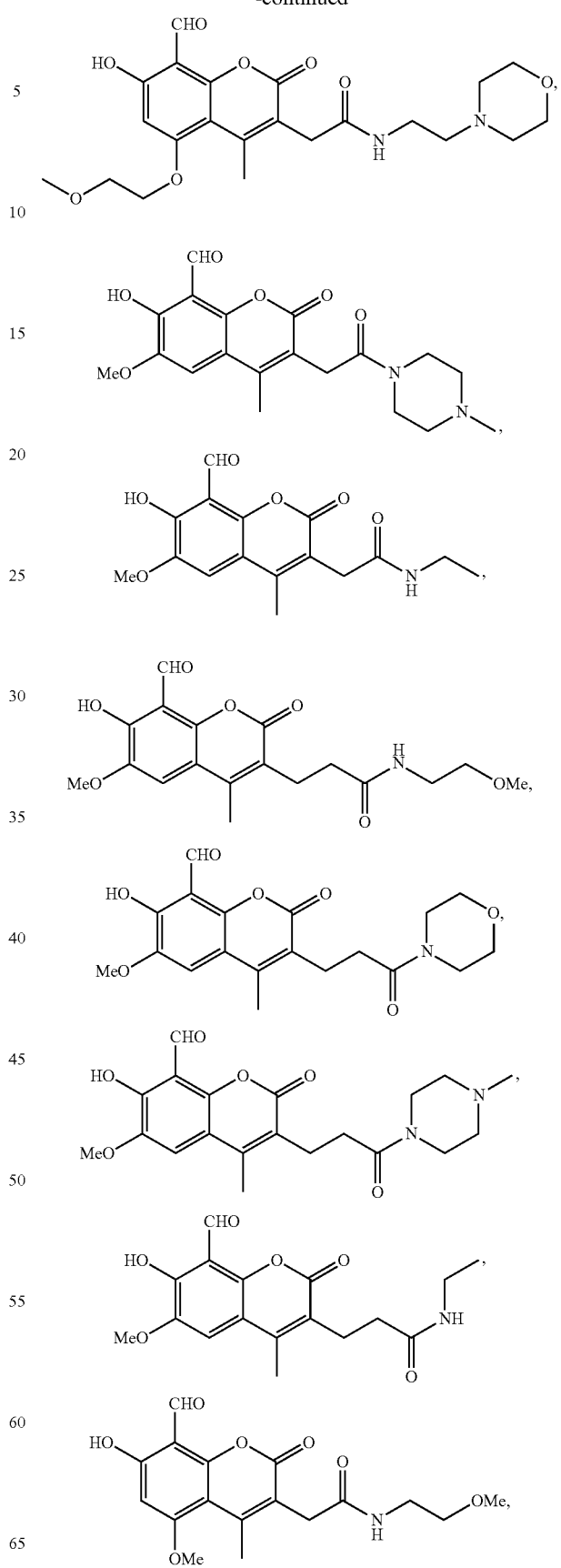

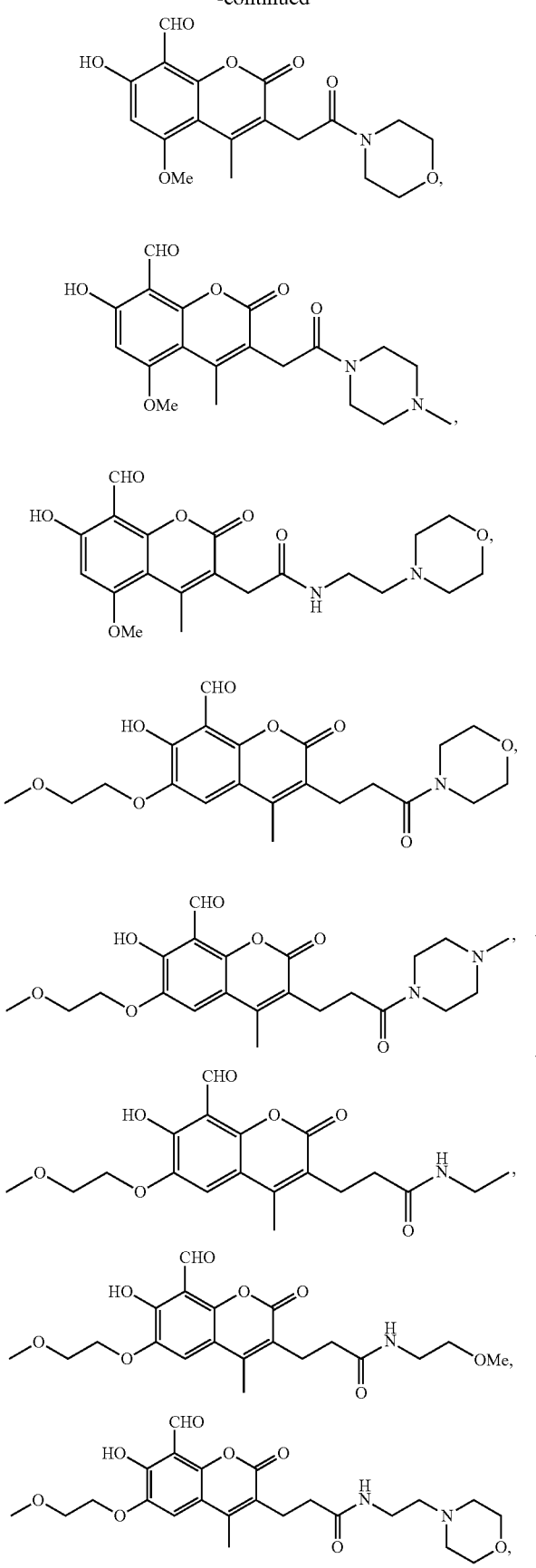
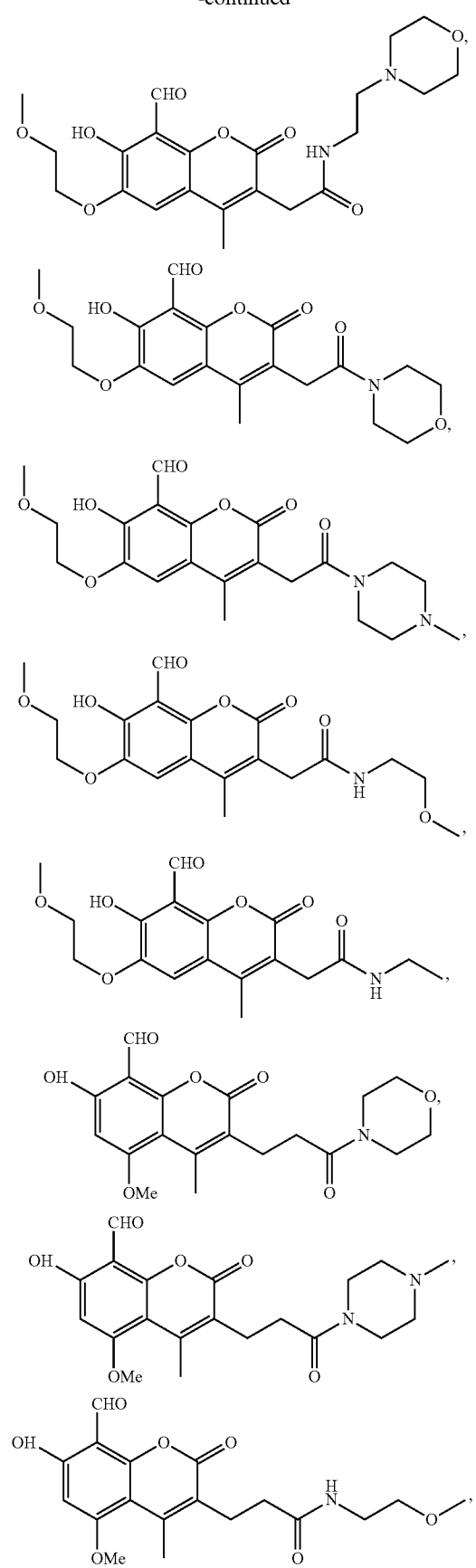

511
-continued
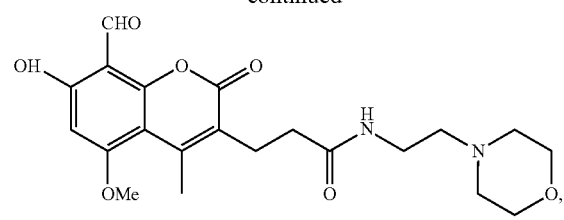
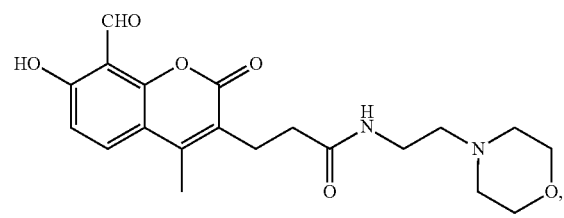
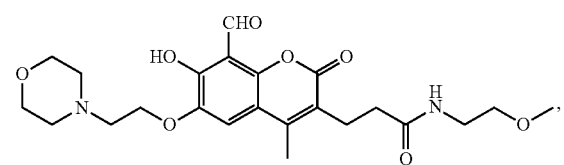
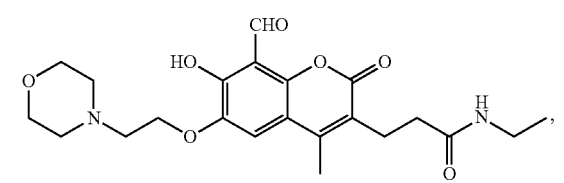
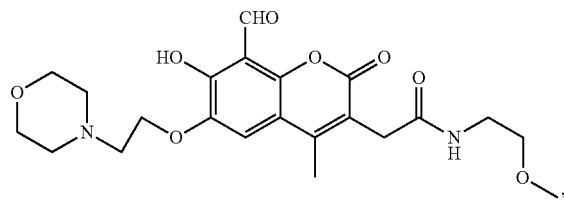
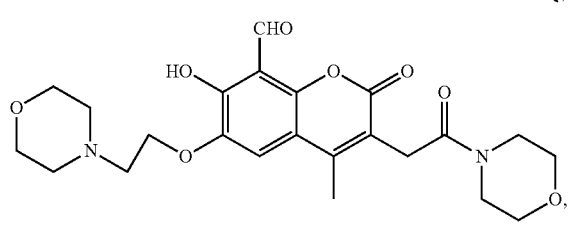
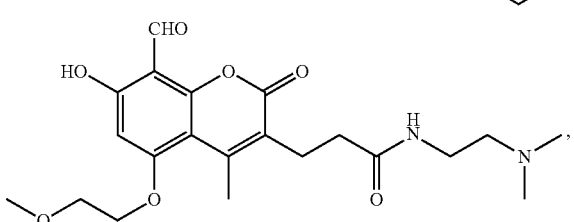
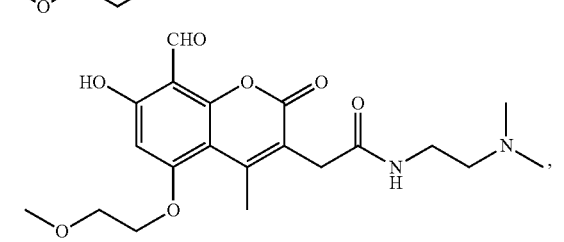
512
-continued
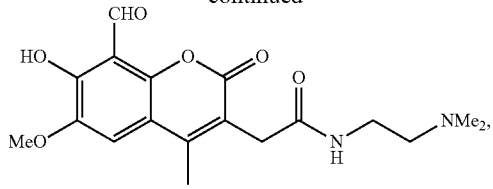
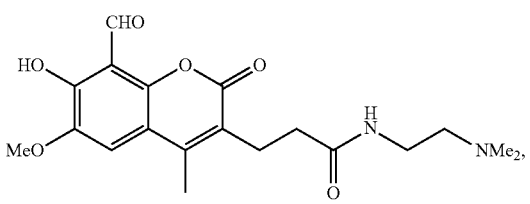
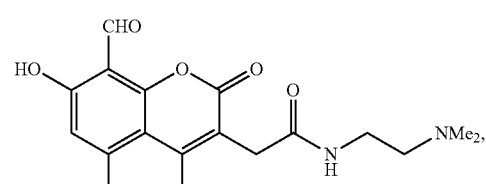
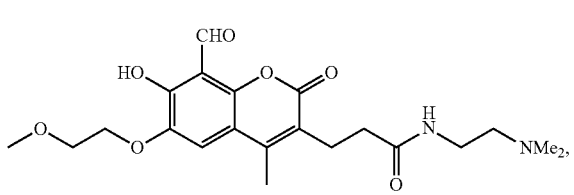
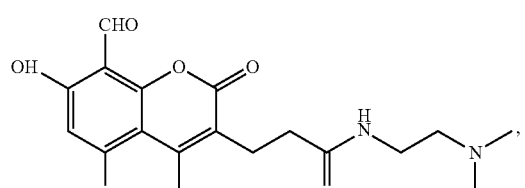
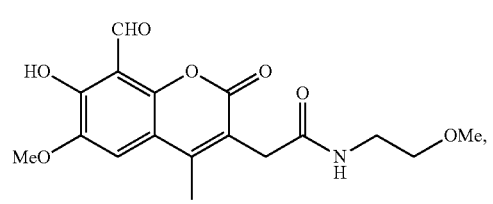
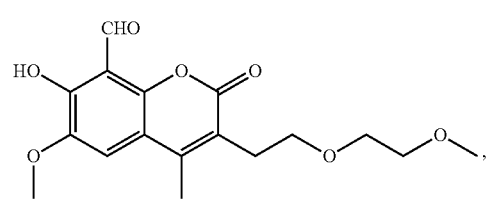
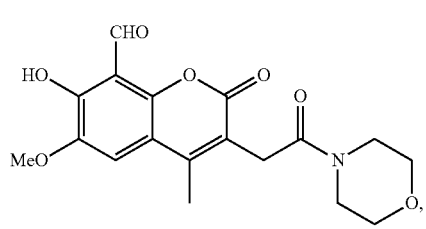

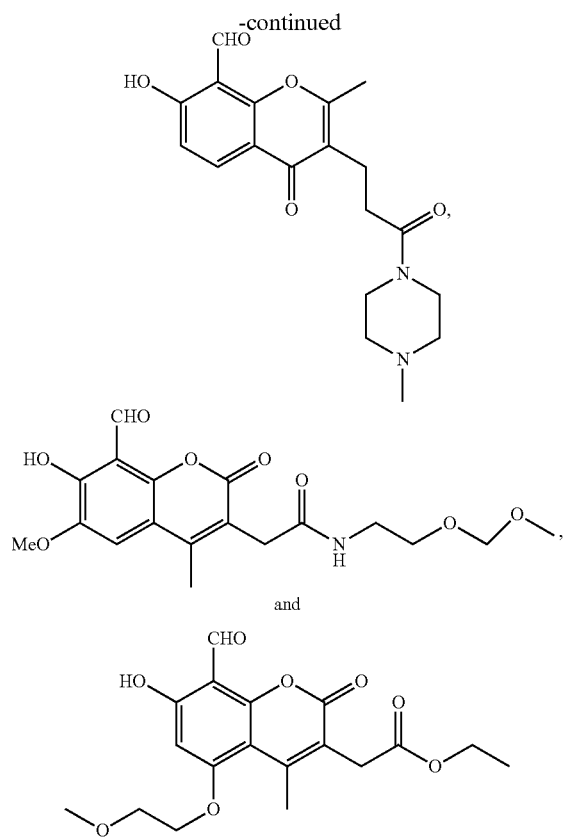

or a pharmaceutically acceptable salt thereof.

8. A pharmaceutical composition comprising the compound or the pharmaceutically acceptable salt thereof of claim 1 and a pharmaceutically acceptable vehicle.

9. A method for the treatment of a disorder associated with the unfolded protein response or a disorder associated with a target of regulated IRE-1α-dependent decay (RIDD) in a subject in need thereof, comprising administering to the subject the compound or the pharmaceutically acceptable salt thereof of claim 1.

10. A method of inhibiting IRE-1α activity, comprising contacting IRE-1α with the compound or the pharmaceutically acceptable salt thereof of claim 1.

11. A pharmaceutical composition comprising the compound or the pharmaceutically acceptable salt thereof of claim 7 and a pharmaceutically acceptable vehicle.

12. A method for the treatment of a disorder associated with the unfolded protein response or a disorder associated with a target of regulated IRE-1α-dependent decay (RIDD) in a subject in need thereof, comprising administering to the subject the compound or the pharmaceutically acceptable salt thereof of claim 7.

13. A method of inhibiting IRE-1α activity, comprising contacting IRE-1α with the compound or the pharmaceutically acceptable salt thereof of claim 7.

* * * * *

SEQUENCE LISTING

```
<160> NUMBER OF SEQ ID NOS: 6

<210> SEQ ID NO 1
<211> LENGTH: 15
<212> TYPE: RNA
<213> ORGANISM: Artificial Sequence
<220> FEATURE:
<223> OTHER INFORMATION: human mini-XBP-1 mRNA stem-loop substrate

<400> SEQUENCE: 1
caguccgcag gacug                                                   15

<210> SEQ ID NO 2
<211> LENGTH: 20
<212> TYPE: DNA
<213> ORGANISM: Homo sapiens

<400> SEQUENCE: 2
cctggttgct gaagaggagg                                              20

<210> SEQ ID NO 3
<211> LENGTH: 21
<212> TYPE: DNA
<213> ORGANISM: Homo sapiens

<400> SEQUENCE: 3
ccatggggag atgttctgga g                                            21

<210> SEQ ID NO 4
<211> LENGTH: 24
<212> TYPE: DNA
<213> ORGANISM: Homo sapiens
```

```
<400> SEQUENCE: 4
ccagttggtg taggagttga gacc                                          24

<210> SEQ ID NO 5
<211> LENGTH: 22
<212> TYPE: DNA
<213> ORGANISM: Homo sapiens

<400> SEQUENCE: 5
aggctatgac ctgaatggca ga                                            22

<210> SEQ ID NO 6
<211> LENGTH: 23
<212> TYPE: DNA
<213> ORGANISM: Homo sapiens

<400> SEQUENCE: 6
cagccaggac gagcagcagc ccg                                           23
```